US007232819B2

(12) United States Patent
Di Francesco et al.

(10) Patent No.: US 7,232,819 B2
(45) Date of Patent: Jun. 19, 2007

(54) DIHYDROXYPYRIMIDINE CARBOXAMIDE INHIBITORS OF HIV INTEGRASE

(75) Inventors: Maria E. Di Francesco, Rome (IT); Cristina Gardelli, Ariccia (IT); Steven Harper, Rome (IT); Victor G. Matassa, Hirschberg (DE); Ester Murgalia, Rome (IT); Emanuela Nizi, Siena (IT); Paola Pace, Rome (IT); Barbara Pacini, Rome (IT); Alessia Petrocchi, Rome (IT); Marco Poma, Porto S. Stefano (IT); Vincenzo Summa, Velletri (IT)

(73) Assignee: Istituto Di Ricerche Di Biologia P. Angeletti S.p.A., Rome (IT)

( * ) Notice: Subject to any disclaimer, the term of this patent is extended or adjusted under 35 U.S.C. 154(b) by 353 days.

(21) Appl. No.: 10/493,279

(22) PCT Filed: Oct. 21, 2002

(86) PCT No.: PCT/GB02/04742

§ 371 (c)(1),
(2), (4) Date: Apr. 20, 2004

(87) PCT Pub. No.: WO03/035076

PCT Pub. Date: May 1, 2003

(65) Prior Publication Data

US 2005/0075356 A1    Apr. 7, 2005

Related U.S. Application Data

(60) Provisional application No. 60/348,195, filed on Oct. 26, 2001.

(51) Int. Cl.
*C07D 239/54* (2006.01)
*A61K 31/515* (2006.01)
*C07D 209/14* (2006.01)

(52) U.S. Cl. ........................ 514/235.8; 514/252.14; 514/269; 544/123; 544/295; 544/319

(58) Field of Classification Search ................ 544/123, 544/295, 319; 514/235.8, 252.14, 269
See application file for complete search history.

(56) References Cited

U.S. PATENT DOCUMENTS

| | | | |
|---|---|---|---|
| 4,636,508 A * | 1/1987 | Brewer et al. ............... 514/274 |
| 5,420,129 A | 5/1995 | Breu et al. | |
| 5,654,311 A | 8/1997 | Kurtz et al. | |
| 6,306,891 B1 | 10/2001 | Selnick et al. | |
| 6,841,558 B2 | 1/2005 | Anthony et al. | |
| 6,919,351 B2 | 7/2005 | Anthony et al. | |
| 2003/0055071 A1 | 3/2003 | Anthony et al. | |
| 2004/0106627 A1 | 6/2004 | Gardelli et al. | |
| 2004/0110804 A1 | 6/2004 | Walker et al. | |
| 2004/0127708 A1 | 7/2004 | Fuji et al. | |
| 2004/0204498 A1 | 10/2004 | Walker et al. | |
| 2004/0229892 A1 | 11/2004 | Naidu et al. | |
| 2004/0229909 A1 | 11/2004 | Kiyama et al. | |
| 2005/0010048 A1 | 1/2005 | Zhuang et al. | |

FOREIGN PATENT DOCUMENTS

| | | |
|---|---|---|
| CA | 2339272 A1 | 3/2000 |
| EP | 1422218 A1 | 5/2004 |
| EP | 601886 A1 | 6/2004 |
| WO | WO 99/32117 A1 | 7/1999 |
| WO | WO 99/62520 A1 | 12/1999 |
| WO | WO 99/62897 A1 | 12/1999 |
| WO | WO 00/51990 A1 | 9/2000 |
| WO | WO 01/00578 A1 | 1/2001 |

(Continued)

OTHER PUBLICATIONS

Miles, Medline Abstract (Community Pract, vol. 78, Issue 8, pp. 292-294) Aug. 2005.*

(Continued)

*Primary Examiner*—Deepak Rao
(74) *Attorney, Agent, or Firm*—Kenneth R. Walton; Valerie J. Camara

(57) ABSTRACT

4,5-Dihydroxypyrimidine-6-carboxamides of formula (I); are described as inhibitors of HIV integrase and inhibitors of HIV replication, wherein $R^1$, $R^2$, $R^3$ and $R^4$ are defined herein. These compounds are useful in the prevention and treatment of infection by HIV and in the prevention, delay in the onset, and treatment of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines. Methods of preventing, treating or delaying the onset of AIDS and methods of preventing or treating infection by HIV are also described

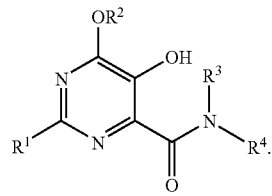

(I)

46 Claims, No Drawings

FOREIGN PATENT DOCUMENTS

| | | |
|---|---|---|
| WO | WO 01/85700 A2 | 11/2001 |
| WO | WO 02/02646 A1 | 1/2002 |
| WO | WO 02/06246 A1 | 1/2002 |
| WO | WO 2004/004657 A1 | 1/2004 |
| WO | WO 2004/062613 A2 | 7/2004 |

OTHER PUBLICATIONS van Heeswijk et al., PubMed Abstract (Antivir Ther. 6(4):201-29) Dec. 2001.☐☐*

Marcus et al., PubMed Abstract (Intervirology 45(4-6):260-6) 2002.*

Ratner, L., et al., "Complete Nucleotide Sequence of the AIDS Virus, HTLV-III", Nature, vol. 313, pp. 277-284, (1985).

Toh, H., et al., "Close Structural Resemblance Between Putative Polymerase of a Drosphila Transposable Genetic Element 17.6 and Pol Gene Product of Moloney Murine Leukemia Virus", EMBO Journal, vol. 4, No. 5, pp. 1267-1272, (1985).

Power, M.D., et al., "Nucleotide Sequence of SRV-1, a Type D Simian Acquired Immune Deficiency Syndrome Retrovirus", Science, vol. 231, pp. 1567-1572, (1986).

Pearl, L.H., et al., "A Structural Model for the Retroviral Proteases", Nature, vol. 329, pp. 351-354, (1987).

Ivin, B.A., et al., "Unsaturated Hydantoin Derivatives, XI.", vol. 10, No. 11, (1976).

Culbertson, Townley P., et al., "Synthesis of 5,6-Dihydroxy-2-phenyl-4-pyrimidinecarboxylic Acid, Methyl Ester, a Corrected Sturcture", Journal of Heterocyclic Chemistry, vol. 16, pp. 1423-1424, (1979).

CAPLUS No. 1992:571466. "Preparation of 2-Phenylpyrimidines as Agrochemical Fungicides", 1992, Abstract of DE4029654, plus compounds therein indexed in the CAS Registry File.

Derwent Abstract No. 2000-237546, "Antiviral Agent Containing New or Unknown Pyrazine, Pyrimidine, Pyridazine or Triazine Caboxamide", 2000, Abstract of WO 00/10569 (See Cite No. 13—CA2339272).

Derwent Abstract No. 2003-505255/47, "HIV Integrase Inhibitor Comprises New and Known Cyclic Compounds", 2003, Abstract of WO 03/47564.

Sunderland, C., et al., "6-Carboximido-5,4-Hydroxypyrimidinones: A New Class of Heterocyclic Ligands and Their Evaluation as Gadolinium Chelating Agents", Inorganic Chemistry, vol. 40, No. 26, pp. 6746-6756 (2001).

Mauss, S., et al., "Influence of HIV Protease Inhibitors on Hepatitis C Viral Load in Individuals with HIV and HCV Coinfection", Program and Abstracts of the Interscience Conference on Antimicrobial Agents and Chemotherapy, p. 218 (1997).

* cited by examiner

DIHYDROXYPYRIMIDINE CARBOXAMIDE INHIBITORS OF HIV INTEGRASE

This application is the National Stage of International Application No. PCT/GB02/004742, filed on Oct. 21, 2002, which claims the benefit under 35 U.S.C. 119(e) of U.S. Provisional Application No. 60/348,195 filed on Oct. 26, 2001.

FIELD OF THE INVENTION

The present invention is directed to 5,6-dihydroxypyrimidine-4-carboxamides and pharmaceutically acceptable salts thereof, their synthesis, and their use as inhibitors of the HIV integrase enzyme. The compounds and pharmaceutically acceptable salts thereof of the present invention are useful for preventing or treating infection by HIV and for treating or delaying the onset of AIDS.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3'termini of the linear proviral DNA; covalent joining of the recessed 3'OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhbitors such as indinavir and nelfinavir. The compounds of this invention are inhibitors of HIV integrase and inhibitors of HIV replication. The inhibition of integrase in vitro and HIV replication in cells is a direct result of inhibiting the strand transfer reaction catalyzed by the recombinant integrase in vitro in HIV infected cells. The particular advantage of the present invention is highly specific inhibition of HIV integrase and HIV replication.

SUMMARY OF THE INVENTION

The present invention is directed to novel dihydroxypyrimidine carboxamides. These compounds are useful in the inhibition of HIV integrase, the prevention of infection by HIV, the treatment of infection by HIV and in the prevention, treatment, and delay in the onset of AIDS, either as compounds or their pharmaceutically acceptable salts or hydrates (when appropriate), or as pharmaceutical composition ingredients, whether or not in combination with other HIV/AIDS antivirals, anti-infectives, immunomodulators, antibiotics or vaccines. More particularly, the present invention includes a compound of Formula (I):

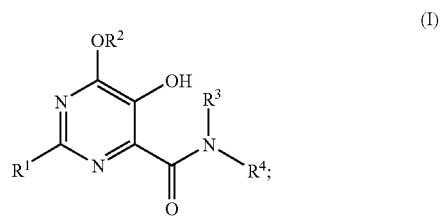

wherein
$R^1$ is
(1) —H,
(2) —$C_{1-6}$ alkyl, which is optionally substituted with one or more substituents each of which is independently halogen, —OH, —CN, —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —C(=O)—$C_{0-6}$ alkyl-N($R^aR^b$), N($R^a$)—C(=O)—$C_{0-6}$ alkyl-N($R^bR^c$), —$SO_2R^a$, —N($R^a$)$SO_2R^b$, —$SO_2$N($R^aR^b$), —N($R^a$)—C(=O)$R^b$,

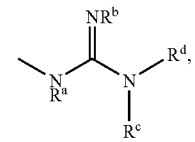

—N($R^a$)C(=O)N($R^bR^c$), —N($R^a$)C(=O)C(=O)N($R^bR^c$), or —N($R^a$)C(=O)O$R^b$,
(3) —O—$C_{1-6}$ alkyl, which is optionally substituted with one or more substituents each of which is independently halogen, —OH, —CN, —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —C(=O)—$C_{0-6}$ alkyl-N($R^aR^b$), N($R^a$)—C(=O)—$C_{0-6}$ alkyl-N($R^bR^c$), —$SO_2R^a$, —N($R^a$)$SO_2R^b$, —$SO_2$N($R^aR^b$), or —N($R^a$)—C($R^b$)=O,
(4) —$R^k$,
(5) —$C_{1-6}$ alkyl-$R^k$, wherein the alkyl is optionally substituted with one or more substituents each of which is independently halogen, —OH, —CN, —O—$C_{1-6}$ alkyl, —O—$C_{1-6}$ haloalkyl, —N($R^aR^b$), —N($R^a$)$CO_2R^b$, —N($R^a$)C(=O)—$C_{0-6}$ alkyl-N($R^bR^c$), or —N($R^a$)—$C_{2-6}$ alkyl-OH with the proviso that the —OH is not attached to the carbon alpha to N($R^a$),
(6) —$C_{2-5}$ alkenyl-$R^k$,
(7) —$C_{2-5}$ alkynyl-$R^k$,
(8) —$C_{0-6}$ alkyl-O—$C_{0-6}$ alkyl-$R^k$,
(9) —$C_{0-6}$ alkyl-S(O)$_n$—$C_{0-6}$ alkyl-$R^k$,
(10) —O—$C_{1-6}$ alkyl-O$R^k$,
(11) —O—$C_{1-6}$ alkyl-O—$C_{1-6}$ alkyl-$R^k$,
(12) —O—$C_{1-6}$ alkyl-S(O)$_n R^k$,
(13) —$C_{0-6}$ alkyl-N($R^a$)—$R^k$,
(14) —$C_{0-6}$ alkyl-N($R^a$)—$C_{1-6}$ alkyl-$R^k$,
(15) —$C_{0-6}$ alkyl-N($R^a$)—$C_{1-6}$ alkyl-O$R^k$,
(16) —$C_{0-6}$ alkyl-C(=O)—$R^k$,

(17) —$C_{0-6}$ alkyl-C(=O)N($R^a$)—$C_{0-6}$ alkyl-$R^k$,
(18) —$C_{0-6}$ alkyl-N($R^a$)C(=O)—$C_{0-6}$ alkyl-$R^k$,
(19) —$C_{0-6}$ alkyl-N($R^a$)C(=O)—O—$C^{0-6}$ alkyl-$R^k$,
(20) —$C_{1-6}$ alkyl which is:
  (i) substituted with aryl or —O-aryl, wherein the aryl is optionally substituted with one or more substituents each of which is independently halogen, —OH, —$C_{1-6}$ alkyl, —$C_{1-6}$ alkyl-$OR^a$, —$C_{1-6}$ haloalkyl, —O—$C_{1-6}$ alkyl, —O—$C_{1-6}$ haloalkyl, methylenedioxy attached to two adjacent carbon atoms, or aryl, or
  (ii) substituted with —$R^k$, —$C_{1-6}$ alkyl-$R^k$, —N($R_a$)—C(=O)—$C_{0-6}$ alkyl-$R^k$, —$C_{0-6}$ alkyl-N($R^a$)—$C_{0-6}$ alkyl-$R^k$, —$C_{0-6}$ alkyl-O—$C_{0-6}$ alkyl-$R^k$, or —$C_{0-6}$ alkyl-N($R^a$)—C(=O)—$C_{0-6}$ alkyl-$R^k$; and
  (iii) optionally substituted with one or more substituents each of which is independently halogen, —OH, —CN, —O—$C_{1-6}$ alkyl, —O—$C_{1-6}$ haloalkyl, or —N($R^aR^b$), or
(21) —$C_{1-6}$ alkyl, substituted with —O—$C_{1-6}$ alkyl, and with a substituent selected from the group consisting of —N($R^a$)C(=O)$R^k$ and —N($R^a$)$C_{1-6}$ alkyl-$R^k$, $R^2$ is —H or —$C_{1-6}$ alkyl which is optionally substituted with one or more substituents each of which is independently
  (1) halogen,
  (2) —OH,
  (3) —CN,
  (4) —O—$C_{1-6}$ alkyl,
  (5) —O—$C_{1-6}$ haloalkyl,
  (6) —C(=O)$R^a$,
  (7) —$CO_2R^a$,
  (8) —$SR^a$,
  (9) —S(=O)$R^a$,
  (10) —N($R^aR^b$),
  (11) —C(=O)N($R^aR^b$),
  (12) —N($R^a$)—C(=O)—$C_{1-6}$ alkyl-N($R^bR^c$),
  (13) —$SO_2R^a$,
  (14) —N($R^a$)$SO_2R^b$,
  (15) —$SO_2$N($R^aR^b$),
  (16) —N($R^a$)—C($R^b$)=O,
  (17) —$C_{3-8}$ cycloalkyl,
  (18) aryl, wherein the aryl is optionally substituted with one or more substituents each of which is independently halogen, —$C_{1-6}$ alkyl, —$C_{1-6}$ haloalkyl, —O—$C_{1-6}$ alkyl, —O—$C_{1-6}$ haloalkyl, —$C_{0-6}$ alkyl-N($R^aR^b$), or —$C_{1-6}$ alkyl substituted with a 5- or 6-membered saturated heterocyclic ring containing from 1 to 4 heteroatoms independently selected from N, O and S; wherein the saturated heterocyclic ring is optionally substituted with from 1 to 3 substituents each of which is independently —$C_{1-6}$ alkyl, oxo, or a 5- or 6-membered heteroaromatic ring containing from 1 to 4 heteroatoms independently selected from N, O and S; or
  (19) a 5- to 8-membered monocyclic heterocycle which is saturated or unsaturated and contains from 1 to 4 heteroatoms independently selected from N, O and S; wherein the heterocycle is optionally substituted with one or more substituents each of which is independently —$C_{1-6}$ alkyl, —O—$C_{1-6}$ alkyl, oxo, phenyl, or naphthyl;

$R^3$ is —H or —$C_{1-6}$ alkyl;
$R^4$ is
  (1) H,
  (2) $C_{1-6}$ alkyl which is optionally substituted with one or more substituents each of which is independently halogen, —OH, O—$C_{1-6}$ alkyl, —O—$C_{1-6}$ haloalkyl, —$NO_2$, —N($R^aR^b$), —C(=O)$R^a$, —$CO_2R^a$, —$SR^a$, —S(=O)$R^a$, —$SO_2R^a$, or —N($R^a$)$CO_2R^b$,
  (3) $C_{1-6}$ alkyl which is optionally substituted with one or more substituents each of which is independently halogen, —OH, or O—$C_{1-4}$ alkyl, and which is substituted with 1 or 2 substituents each of which is independently:
    (i) $C_{3-8}$ cycloalkyl,
    (ii) aryl,
    (iii) a fused bicyclic carbocycle consisting of a benzene ring fused to a $C_{5-7}$ cycloalkyl,
    (iv) a 5- or 6-membered saturated heterocyclic ring containing from 1 to 4 heteroatoms independently selected from N, O and S,
    (v) a 5- or 6-membered heteroaromatic ring containing from 1 to 4 heteroatoms independently selected from N, O and S, or
    (vi) a 9- or 10-membered fused bicyclic heterocycle containing from 1 to 4 heteroatoms independently selected from N, O and S, wherein at least one of the rings is aromatic,
  (4) $C_{2-5}$ alkynyl optionally substituted with aryl,
  (5) $C_{3-8}$ cycloalkyl optionally substituted with aryl,
  (6) aryl,
  (7) a fused bicyclic carbocycle consisting of a benzene ring fused to a $C_{5-7}$ cycloalkyl,
  (8) a 5- or 6-membered saturated heterocyclic ring containing from 1 to 4 heteroatoms independently selected from N, O and S,
  (9) a 5- or 6-membered heteroaromatic ring containing from 1 to 4 heteroatoms independently selected from N, O and S, or
  (10) a 9- or 10-membered fused bicyclic heterocycle containing from 1 to 4 heteroatoms independently selected from N, O and S, wherein at least one of the rings is aromatic;

wherein
  each aryl in (3)(ii) or the aryl (4), (5) or (6) or each fused carbocycle in (3)(iii) or the fused carbocycle in (7) is optionally substituted with one or more substituents each of which is independently halogen, —OH, —$C_{1-6}$ alkyl, —$C_{1-6}$ alkyl-$OR^a$, —$C_{1-6}$ haloalkyl, —O—$C_{1-6}$ alkyl, —O—$C_{1-6}$ haloalkyl, —CN, —$NO_2$, —N($R^aR^b$), —$C_{1-6}$ alkyl-N($R^aR^b$), —C(=O)N($R^aR^b$), —C(=O)$R^a$, —$CO_2R^a$, —$C_{1-6}$ alkyl-$CO_2R^a$, —$OCO_2R^a$, —$SR^a$, —S(=O)$R^a$, —$SO_2R^a$, —N($R^a$)$SO_2R^b$, —$SO_2$N($R^aR^b$), —N($R^a$)C(=O)$R^b$, —N($R^a$)$CO_2R^b$, —$C_{1-6}$ alkyl-N($R^a$)$CO_2R^b$, aryl, —$C_{1-6}$ alkyl-aryl, —O-aryl, or —$C_{0-6}$ alkyl-het wherein het is a 5- or 6-membered heteroaromatic ring containing from 1 to 4 heteroatoms independently selected from N, O and S, and het is optionally fused with a benzene ring, and is optionally substituted with one or more substituents each of which is independently —$C_{1-6}$ alkyl, —$C_{1-6}$ haloalkyl, —O—$C_{1-6}$ alkyl, —O—$C_{1-6}$ haloalkyl, oxo, or —$CO_2R^a$;

each saturated heterocyclic ring in (3)(iv) or the saturated heterocyclic ring in (8) is optionally substituted with one or more substituents each of which is independently halogen, —$C_{1-6}$ alkyl, —$C_{1-6}$ haloalkyl, —O—$C_{1-6}$ alkyl, —O—$C_{1-6}$ haloalkyl, oxo, aryl, or a 5- or 6-membered heteroaromatic ring containing from 1 to 4 heteroatoms independently selected from N, O and S; and each heteroaromatic ring in (3)(v) or the heteroaromatic ring in (9) or each fused bicyclic heterocycle in (3)(vi) or the fused bicyclic heterocycle in (10) is optionally substituted with one or more substituents each of which is independently halogen, —$C_{1-6}$ alkyl, —$C_{1-6}$ haloalkyl, —O—$C_{1-6}$ alkyl, —O—$C_{1-6}$ haloalkyl, oxo, aryl, or —$C_{1-6}$ alkyl-aryl;

or alternatively $R^3$ and $R^4$ together with the N to which both are attached form a $C_{3-7}$ azacycloalkyl which is optionally substituted with one or more substituents each of which is independently —$C_{1-6}$ alkyl or oxo;

each $R^a$, $R^b$, $R^c$, and $R^d$ is independently —H or —$C_{1-6}$ alkyl;

$R^k$ is carbocycle or heterocycle, wherein the carbocycle or heterocycle is optionally substituted with one or more substituents each of which is independently (1) halogen,
(2) —OH,
(3) —CN,
(4) —$C_{1-6}$ alkyl, which is optionally substituted with one or more substituents each of which is independently halogen, —OH, —CN, —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —C(=O)—($CH_2$)$_{0-2}$N($R^aR^b$), N($R^a$)—C(=O)—($CH_2$)$_{0-2}$N($R^bR^c$), —$SO_2R^a$, —N($R^a$)$SO_2R^b$, —$SO_2$N($R^aR^b$), or —N($R^a$)—C($R^b$)=O,
(5) —O—$C_{1-6}$ alkyl, which is optionally substituted with one or more substituents each of which is independently halogen, —OH, —CN, —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —C(=O)—($CH_2$)$_{0-2}$N($R^aR^b$), N($R^a$)—C(=O)—($CH_2$)$_{0-2}$N($R^bR^c$), —$SO_2R^a$, —N($R^a$)$SO_2R^b$, —$SO_2$N($R^aR^b$), or —N($R^a$)—C($R^b$)=O,
(6) —$NO_2$,
(7) oxo,
(8) ethylenedioxy, spiro substituted on a ring carbon in a saturated ring of $R^k$,
(9) —C(=O)$R^a$,
(10) —$CO_2R^a$,
(11) —$SR^a$,
(12) —S(=O)$R^a$,
(13) —N($R^aR^b$),
(14) —C(=O)N($R^aR^b$),
(15) —C(=O)—$C_{1-6}$ alkyl-N($R^aR^b$),
(16) —N($R^a$)C(=O)$R^b$,
(17) —$SO_2R^a$,
(18) —$SO_2$N($R^aR^b$),
(19) —N($R^a$)$SO_2R^b$,
(20) —$R^m$,
(21) —$C_{1-6}$ alkyl-$R^m$, wherein the alkyl is optionally substituted with one or more substituents each of which is independently halogen, —OH, —CN, —$C_{1-6}$ haloalkyl, —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —N($R^a$)$CO_2R^b$, —$SO_2R^a$, —N($R^a$)$SO_2R^b$, —$SO_2$N($R^aR^b$), or —N($R^a$)—C($R^b$)=O,
(22) —$C_{0-6}$ alkyl-N($R^a$)—$C_{0-6}$ alkyl-$R^m$,
(23) —$C_{0-6}$ alkyl-O—$C_{0-6}$ alkyl-$R^m$,
(24) —$C_{0-6}$ alkyl-S—$C_{0-6}$ alkyl-$R^m$,
(25) —$C_{0-6}$ alkyl-C(=O)—$C_{0-6}$ alkyl-$R^m$,
(26) —C(=O)—O—$C_{0-6}$ alkyl-$R^m$,
(27) —C(=O)N($R^a$)—$C_{0-6}$ alkyl-$R^m$,
(28) —N($R^a$)C(=O)—$R^m$,
(29) —N($R^a$)C(=O)—$C_{1-6}$ alkyl-$R^m$, wherein the alkyl is optionally substituted with one or more substituents each of which is independently halogen, —OH, —CN, —$C_{1-6}$ haloalkyl, —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —N($R^a$)$CO_2R^b$, —$SO_2R^a$, —N($R^a$)$SO_2R^b$, —$SO_2$N($R^aR^b$), or —N($R^a$)—C($R^b$)=O,
(30) —N($R^a$)—C(=O)—N($R^b$)—$C_{0-6}$ alkyl-$R^m$,
(31) —N($R^a$)—C(=O)—O—$C_{0-6}$ alkyl-$R^m$, or
(32) —N($R^a$)—C(=O)—N($R^b$)—$SO_2$—$C_{0-6}$ alkyl-$R^m$;

carbocycle in $R^k$ is (i) a $C_3$ to $C_8$ monocyclic, saturated or unsaturated ring, (ii) a $C_7$ to $C_{12}$ bicyclic ring system, or (iii) a $C_{11}$ to $C_{16}$ tricyclic ring system, wherein each ring in (ii) or (iii) is independent of or fused to the other ring or rings and each ring is saturated or unsaturated;

heterocycle in $R^k$ is (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of or fused to or bridged with or spiro to the other ring or rings and each ring is saturated or unsaturated; the monocyclic ring, bicyclic ring system, or tricyclic ring system contains from 1 to 6 heteroatoms selected from N, O and S and a balance of carbon atoms; and wherein any one or more of the nitrogen and sulfur heteroatoms is optionally be oxidized, and any one or more of the nitrogen heteroatoms is optionally quaternized;

each $R^m$ is independently $C_{3-8}$ cycloalkyl; aryl; a 5- to 8-membered monocyclic heterocycle which is saturated or unsaturated and contains from 1 to 4 heteroatoms independently selected from N, O and S; or a 9- to 10-membered bicyclic heterocycle which is saturated or unsaturated and contains from 1 to 4 heteroatoms independently selected from N, O and S; wherein any one or more of the nitrogen and sulfur heteroatoms in the monocyclic or bicyclic heterocycle is optionally oxidized and any one or more of the nitrogen heteroatoms is optionally quaternized; and wherein the cycloalkyl or the aryl is optionally substituted with one or more substituents each of which is independently halogen, —$C_{1-6}$ alkyl, —$C_{1-6}$ haloalkyl, —O—$C_{1-6}$ alkyl, —O—$C_{1-6}$ haloalkyl, —N($R^aR^b$), aryl, or —$C_{1-6}$ alkyl-aryl; and the monocyclic or bicyclic heterocycle is optionally substituted with one or more substituents each of which is independently halogen, —$C_{1-6}$ alkyl optionally substituted with —O—$C_{1-6}$ alkyl, —$C_{1-6}$ haloalkyl, —O—$C_{1-6}$ alkyl, —O—$C_{1-6}$ haloalkyl, oxo, aryl, —$C_{1-6}$ alkyl-aryl, —C(=O)-aryl, —$CO_2$-aryl, —$CO_2$—$C_{1-6}$ alkyl-aryl, a 5- or 6-membered saturated heterocyclic ring containing from 1 to 4 heteroatoms independently selected from N, O and S, or a 5- or 6-membered heteroaromatic ring containing from 1 to 4 heteroatoms independently selected from N, O and S; and each n is independently an integer equal to zero, 1 or 2;

or a pharmaceutically acceptable salt thereof.

An embodiment of the present invention is a compound of Formula (I) as originally defined above except that: (I) in the definition of $R^1$, $R^1$ is one of the groups (1) to (20), all of which are as defined above except that (2) of $R^1$ is —$C_{1-6}$ alkyl, which is optionally substituted with one or more substituents each of which is independently halogen, —OH, —CN, —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —C(=O)—$C_{0-6}$ alkyl-N($R^aR^b$), N($R^a$)—C(=O)—$C_{0-6}$ alkyl-N($R^bR^c$), —$SO_2R^a$, —N($R^a$)$SO_2R^b$, —$SO_2$N($R^aR^b$), —N($R^a$)—C(=O)$R^b$, or

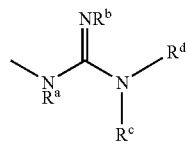

The present invention also includes pharmaceutical compositions containing a compound of the present invention and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes the dihydroxypyrimidine carboxamides of Formula (I) above. These compounds and pharmaceutically acceptable salts thereof are HIV integrase inhibitors.

An embodiment of the present invention is a compound of Formula (I) exactly as defined above, except that in the definition of $R^k$, $R^k$ is optionally substituted with one or more substituents each of which is independently one of the substituents (1) to (19), and is optionally mono-substituted with one of the substituents (20) to (32).

Another embodiment of the present invention is a compound of Formula (I), wherein $R^1$ is:

(1) —H,
(2) —$C_{1-6}$ alkyl, which is optionally substituted with from 1 to 5 substituents each of which is independently halogen, —OH, —CN, —O—$C_{1-4}$ alkyl, —O—$C_{1-4}$ haloalkyl, —C(=O)$R^a$, —$CO_2R^a$, —$SR^a$, —S(=O)$R^a$, —N($R^aR^b$), —C(=O)—$(CH_2)_{0-2}$N($R^aR^b$), N($R^a$)—C(=O)—$(CH_2)_{0-2}$N($R^bR^c$), —$SO_2R^a$, —N($R^a$)$SO_2R^b$, —$SO_2$N($R^aR^b$), —N($R^a$)—C(=O)$R^b$,

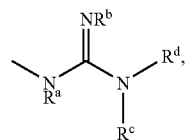

—N($R^a$)C(=O)N($R^bR^c$), —N($R^a$)C(=O)C(=O)N($R^bR^c$), or —N($R^a$)C(=O)O$R^b$,
(3) —$R^k$,
(4) —$C_{1-4}$ alkyl-$R^k$, wherein the alkyl is optionally substituted with 1 or 2 substituents each of which is independently halogen, —OH, —CN, —O—$C_{1-4}$ alkyl, —O—$C_{1-4}$ haloalkyl, —N($R^aR^b$), or —N($R^a$)—$(CH_2)_{2-4}$—OH,
(5) —O—$(CH_2)_{0-3}$—$R^k$,
(6) —$C_{1-4}$ alkyl-O—$(CH_2)_{0-3}$—$R^k$,
(7) —$(CH_2)_{0-3}$—S(O)$_n$—$(CH_2)_{0-3}$—$R^k$,
(8) —O—$(CH_2)_{1-3}$—O$R^k$,
(9) —O—$(CH_2)_{1-3}$—O—$(CH_2)_{1-3}$—$R^k$,
(10) —O—$(CH_2)_{1-3}$—S(O)$_n$$R^k$,
(11) —$(CH_2)_{0-3}$—N($R^a$)—$R^k$,
(12) —$(CH_2)_{0-3}$—N($R^a$)—$(CH_2)_{1-3}$—$R^k$,
(13) —$(CH_2)_{0-3}$—N($R^a$)—$(CH_2)_{1-3}$—O$R^k$,
(14) —$(CH_2)_{0-3}$—C(=O)—$R^k$,
(15) —$(CH_2)_{0-3}$—C(=O)N($R^a$)—$(CH_2)_{0-3}$—$R^k$,
(16) —$(CH_2)_{0-3}$—N($R^a$)C(=O)—$(CH_2)_{0-3}$—$R^k$,
(17) —$(CH_2)_{0-3}$—N($R^a$)C(=O)—O—$(CH_2)_{0-3}$—$R^k$,
(18) —$C_{1-6}$ alkyl which is:
  (i) substituted with aryl or —O-aryl, wherein the aryl is optionally substituted with from 1 to 3 substituents each of which is independently halogen, —OH, —$C_{1-4}$ alkyl, —$C_{1-4}$ alkyl-O$R^a$, —$C_{1-4}$ haloalkyl, —O—$C_{1-4}$ alkyl, —O—$C_{1-4}$ haloalkyl, methylenedioxy attached to two adjacent carbon atoms, or aryl;
  (ii) substituted with —$R^k$, —$(CH_2)_{1-3}$—$R^k$, —N($R^a$)—C(=O)—$(CH_2)_{0-3}$—$R^k$, —$(CH_2)_{0-3}$—N($R^a$)—$(CH_2)_{0-3}$—$R^k$, or —$(CH_2)_{0-3}$—O—$(CH_2)_{0-3}$—$R^k$ or —$(CH_2)_{0-3}$—N($R^a$)—C(=O)—$(CH_2)_{0-3}$—$R^k$; and
  (iii) optionally substituted with from 1 to 4 substituents each of which is independently halogen, —OH, —CN, —O—$C_{1-4}$ alkyl, —O—$C_{1-4}$ haloalkyl, or —N($R^aR^b$),
(19) —C($CH_3$)$_2$N($R^a$)C(=O)OCH$_2R^k$,
(20) —C($CH_3$)$_2$N($R^a$)CH$_2R^k$,
(21) —C($CH_3$)$_2$N($R^a$)C(=O)$R^k$, or
(22) —C($R^b$)(N($R^a$)C(=O)$R^k$)(CH$_2$O$R^c$),
(23) —C($R^b$)(N($R^a$)(CH$_2$)—$R^k$)(CH$_2$O$R^c$), and all other variables are as originally defined above;

or a pharmaceutically acceptable salt thereof.

Still another embodiment of the present invention is a compound of Formula (I) as defined in the immediately preceding embodiment, except that $R^1$ is one of the groups (1) to (18), wherein (2) of $R^1$ is $C_{1-6}$ alkyl, which is optionally substituted with from 1 to 5 substituents each of which is independently halogen, —OH, —CN, —O—$C_{1-4}$ alkyl, —O—$C_{1-4}$ haloalkyl, —C(=O)$R^a$, —$CO_2R^a$, —$SR^a$, —S(=O)$R^a$, —N($R^aR^b$), —C(=O)—$(CH_2)_{0-2}$N($R^aR^b$), N($R^a$)—C(=O)—$(CH_2)_{0-2}$N($R^bR^c$), —$SO_2R^a$, —N($R^a$)$SO_2R^b$, —$SO_2$N($R^aR^b$), —N($R^a$)—C(=O)$R^b$, or

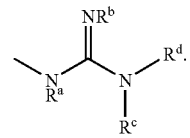

Another embodiment of the present invention is a compound of Formula (I), wherein $R^1$ is:

(1) —H,
(2) —$C_{1-4}$ alkyl, which is optionally substituted with from 1 to 3 substituents each of which is independently halogen, —OH, —CN, —O—$C_{1-4}$ alkyl, —O—$C_{1-4}$ haloalkyl, —C(=O)$R^a$, —$CO_2R^a$, —$SR^a$, —S(=O)$R^a$, —N($R^aR^b$), —C(=O)—$(CH_2)_{0-2}$N($R^aR^b$), N($R^a$)—C(=O)—$(CH_2)_{0-2}$N($R^bR^c$), —$SO_2R^a$, —N($R^a$)$SO_2R^b$, —$SO_2$N($R^aR^b$), —N($R^a$)—C(=O)$R^b$,

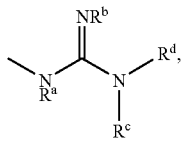

$N(R^a)C(=O)N(R^bR^c)$, —$N(R^a)C(=O)C(=O)N(R^bR^c)$, or —$N(R^a)C(=O)OR^b$, (3) —$R^k$,
(4) —$CH(CH_3)$—$R^k$,
(5) —$(CH_2)_{1-4}$—$R^k$, wherein the —$(CH_2)_{1-4}$— moiety is optionally substituted with one of —$N(R^aR^b)$ or —$N(R^a)$—$(CH_2)_2$—OH,
(6) —$(CH_2)_{1-2}$—O—$(CH_2)_{0-1}$—$R^k$,
(7) —$(CH_2)_{1-2}$—$S(O)_n$—$(CH_2)_{0-1}$—$R^k$,
(8) —O—$(CH_2)_{1-2}$—$OR^k$,
(9) —O—$(CH_2)_{1-2}$—O—$(CH_2)_{1-2}$—$R^k$,
(10) —O—$(CH_2)_{1-2}$—$S(O)_nR^k$,
(11) —$(CH_2)_{1-2}$—$N(R^a)$—$R^k$,
(12) —$(CH_2)_{1-2}$—$N(R^a)$—$(CH_2)_{1-3}$—$R^k$,
(13) —$(CH_2)_{1-2}$—$N(R^a)$—$(CH_2)_{1-3}$—$OR^k$,
(14) —$(CH_2)_{0-2}$—$C(=O)$—$R^k$,
(15) —$C(=O)N(R^a)$—$(CH_2)_{1-2}$—$R^k$,
(16) —$(CH_2)_{0-2}$—$C(=O)N(R^a)$—$(CH_2)_{0-2}$—$R^k$,
(17) —$(CH_2)_{1-2}$—$N(R^a)C(=O)$—$(CH_2)_{0-1}$—$R^k$,
(18) —$(CH_2)_{1-2}$—$N(R^a)C(=O)$—O—$(CH_2)_{0-1}$—$R^k$,
(19) —$C_{1-4}$ alkyl which is:
 (i) substituted with aryl or —O-aryl wherein the aryl is optionally substituted with from 1 to 3 substituents each of which is independently fluoro, chloro, —$C_{1-4}$ alkyl, —$C_{1-4}$ fluoroalkyl, —O—$C_{1-4}$ alkyl, —O—$C_{1-4}$ fluoroalkyl, methylenedioxy attached to two adjacent carbon atoms, or phenyl;
 (ii) substituted with —$R^k$, —$(CH_2)_{1-3}$—$R^k$, —$N(R^a)$—$C(=O)$—$(CH_2)_{0-3}$—$R^k$, —$N(R^a)$—$(CH_2)_{1-3}$—$R^k$, —O—$(CH_2)_{1-2}$—$R^k$, or —$N(R^a)$—$C(=O)$—$(CH_2)_{0-2}$—$R^k$; and
 (iii) optionally substituted with from 1 to 4 substituents each of which is independently halogen, —OH, —CN, —O—$C_{1-4}$ alkyl, —O—$C_{1-4}$ haloalkyl, or —$N(R^aR^b)$,
(20) —$C(CH_3)_2N(R^a)C(=O)OCH_2R^k$,
(21) —$C(CH_3)_2N(R^a)CH_2R^k$,
(22) —$C(CH_3)_2N(R^a)C(=O)R^k$,
(23) —$C(R^b)(N(R^a)C(=O)R^k)(CH_2OR^c)$, or
(24) —$C(R^b)(N(R^a)(CH_2)$—$R^k)(CH_2OR^c)$;

and all other variables are as originally defined above;

or a pharmaceutically acceptable salt thereof.

In an aspect of this embodiment, $R^1$ is
(1) —H,
(2) —$C_{1-4}$ alkyl, which is optionally substituted with from 1 to 3 substituents each of which is independently halogen, —OH, —CN, —O—$C_{1-4}$ alkyl, —O—$C_{1-4}$ haloalkyl, —$C(=O)R^a$, —$CO_2R^a$, —$SR^a$, —$S(=O)R^a$, —$N(R^aR^b)$, —$C(=O)$—$(CH_2)_{0-2}N(R^aR^b)$, $N(R^a)$—$C(=O)$—$(CH_2)_{0-2}N(R^bR^c)$, —$SO_2R^a$, —$N(R^a)SO_2R^b$, —$SO_2N(R^aR^b)$, —$N(R^a)$—$C(=O)R^b$, or

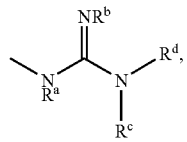

(3) —$R^k$,
(4) —$CH(CH_3)$—$R^k$,
(5) —$(CH_2)_{1-4}$—$R^k$, wherein the —$(CH_2)_{1-4}$— moiety is optionally substituted with one of —$N(R^aR^b)$ or —$N(R^a)$—$(CH_2)_2$—OH,
(6) —$(CH_2)_{1-2}$—O—$(CH_2)_{0-1}$—$R^k$,
(7) —$(CH_2)_{1-2}$—$S(O)_n$—$(CH_2)_{0-1}$—$R^k$,
(8) —O—$(CH_2)_{1-2}$—$OR^k$,
(9) —O—$(CH_2)_{1-2}$—O—$(CH_2)_{1-2}$—$R^k$,
(10) —O—$(CH_2)_{1-2}$—$S(O)_nR^k$,
(11) —$(CH_2)_{1-2}$—$N(R^a)$—$R^k$,
(12) —$(CH_2)_{1-2}$—$N(R^a)$—$(CH_2)_{1-3}$—$R^k$,
(13) —$(CH_2)_{1-2}$—$N(R^a)$—$(CH_2)_{1-3}$—$OR^k$,
(14) —$(CH_2)_{0-2}$—$C(=O)$—$R^k$,
(15) —$C(=O)N(R^a)$—$(CH_2)_{1-2}$—$R^k$,
(16) —$(CH_2)_{0-2}$—$C(=O)N(R^a)$—$(CH_2)_{0-2}$—$R^k$,
(17) —$(CH_2)_{1-2}$—$N(R^a)C(=O)$—$(CH_2)_{0-1}$—$R^k$,
(18) —$(CH_2)_{1-2}$—$N(R^a)C(=O)$—O—$(CH_2)_{0-1}$—$R^k$, or
(19) —$C_{1-4}$ alkyl which is:
 (i) substituted with aryl or —O-aryl wherein the aryl is optionally substituted with from 1 to 3 substituents each of which is independently fluoro, chloro, —$C_{1-4}$ alkyl, —$C_{1-4}$ fluoroalkyl, —O—$C_{1-4}$ alkyl, —O—$C_{1-4}$ fluoroalkyl, methylenedioxy attached to two adjacent carbon atoms, or phenyl;
 (ii) substituted with —$R^k$, —$(CH_2)_{1-3}$—$R^k$, —$N(R^a)$—$C(=O)$—$(CH_2)_{0-3}$—$R^k$, —$N(R^a)$—$(CH_2)_{1-3}$—$R^k$, —O—$(CH_2)_{1-2}$—$R^k$, or —$N(R^a)$—$C(=O)$—$(CH_2)_{0-2}$—$R^k$; and
 (iii) optionally substituted with from 1 to 4 substituents each of which is independently halogen, —OH, —CN, —O—$C_{1-4}$ alkyl, —O—$C_{1-4}$ haloalkyl, or —$N(R^aR^b)$.

Another embodiment of the present invention is a compound of Formula (I), wherein $R^k$ is $C_{3-8}$ cycloalkyl; aryl selected from phenyl and naphthyl; a bicyclic carbocycle selected from indanyl and tetrahydronaphthyl; a 5- or 6-membered saturated heterocyclic ring containing from 1 to 4 heteroatoms independently selected from N, O and S; a 5- or 6-membered heteroaromatic ring containing from 1 to 4 heteroatoms independently selected from N, O and S; or a bicyclic heterocycle which is a benzene ring fused to a 5- or 6-membered saturated or unsaturated heterocyclic ring containing from 1 to 3 heteroatoms independently selected from N, O and S;

wherein the cyloalkyl, aryl, bicyclic carbocycle, saturated heterocyclic ring, heteroaromatic ring, or bicyclic heterocycle is optionally substituted with from 1 to 4 substituents each of which is independently (1) halogen,
(2) —OH,
(3) —CN,
(4) —$C_{1-4}$ haloalkyl,
(5) —$C_{1-4}$ alkyl, which is optionally substituted with from 1 to 3 substituents each of which is independently —OH, —CN, —O—$C_{1-4}$ alkyl, —O—$C_{1-4}$ haloalkyl, —$C(=O)R^a$, —$CO_2R^a$, —$SR^a$, —$S(=O)R^a$, —N($R^a R^b$), —C(=O)—(CH$_2$)$_{0-2}$N($R^a R^b$), N($R^a$)—C(=O)—(CH$_2$)$_{0-2}$N($R^b R^c$), —SO$_2 R^a$, —N($R^a$)SO$_2 R^b$, —SO$_2$N($R^a R^b$), or —N($R^a$)—C($R^b$)=O, (6) —O—C$_{1-4}$ haloalkyl (7) —O—C$_{1-4}$ alkyl, which is optionally substituted with from 1 to 3 substituents each of which is independently —OH, —CN, —O—C$_{1-6}$ alkyl, —O—C$_{1-6}$ haloalkyl, —C(=O)$R^a$, —CO$_2 R^a$, —S$R^a$, —S(=O)$R^a$, —N($R^a R^b$), —C(=O)—(CH$_2$)$_{0-2}$N($R^a R^b$), N($R^a$)—C(=O)—(CH$_2$)$_{0-2}$N($R^b R^c$), —SO$_2 R^a$, —N($R^a$)SO$_2 R^b$, —SO$_2$N($R^a R^b$), or —N($R^a$)—C($R^b$)=O, (8) —NO$_2$,
(9) oxo,
(10) —C(=O)$R^a$,
(11) —CO$_2 R^a$,
(12) —S$R^a$,
(13) —S(=O)$R^a$,
(14) —N($R^a R^b$),
(15) —C(=O)N($R^a R^b$),
(16) —C(=O)—C$_{1-6}$ alkyl-N($R^a R^b$),
(17) —N($R^a$)C(=O)$R^b$,
(18) —SO$_2 R^a$,
(18) —SO$_2$N($R^a R^b$),
(19) —N($R^a$)SO$_2 R^b$,
(20) —$R^m$,
(21) —CH(CH$_3$)—$R^m$,
(22) —(CH$_2$)$_{1-4}$—$R^m$,
(23) —(CH$_2$)$_{0-2}$—N($R^a$)—(CH$_2$)$_{0-2}$—$R^m$,
(24) —(CH$_2$)$_{0-2}$—O—(CH$_2$)$_{0-2}$—$R^m$,
(25) —(CH$_2$)$_{0-2}$—S—(CH$_2$)$_{0-2}$—$R^m$,
(26) —(CH$_2$)$_{0-2}$—C(=O)—(CH$_2$)$_{0-2}$—$R^m$,
(27) —C(=O)—O—(CH$_2$)$_{0-2}$—$R^m$,
(28) —C(=O)N($R^a$)—$R^m$,
(29) —N($R^a$)C(=O)—$R^m$,
(30) —N($R^a$)C(=O)—(CH$_2$)$_{0-3}$—$R^m$, wherein the —(CH$_2$)$_{1-3}$— moiety is optionally substituted with one of —N($R^a R^b$), —N($R^a$)CO$_2 R^b$, —SO$_2 R^a$, —N($R^a$)SO$_2 R^b$, —SO$_2$N($R^a R^b$), or —N($R^a$)—C($R^b$)=O,
(31) —N($R^a$)—C(=O)—N($R^b$)—(CH$_2$)$_{1-2}$—$R^m$,
(32) —N($R^a$)—C(=O)—O—(CH$_2$)$_{1-2}$—$R^m$, or
(33) —N($R^a$)—C(=O)—N($R^b$)SO$_2$—$R^m$;

and all other variables are as originally defined above;

or a pharmaceutically acceptable salt thereof.

In an aspect of this embodiment, $R^k$ (i.e., the cycloalkyl, aryl, bicyclic carbocycle, saturated heterocyclic ring, heteroaromatic ring, or bicyclic heterocycle) is optionally substituted with from 1 to 4 substituents each of which is independently one of the substituents (1) to (19), and is optionally mono-substituted with one of the substituents (20) to (33). In a feature of this aspect, $R^k$ is optionally substituted with from 1 to 4 substituents each of which is independently one of the substituents (1) to (19), and is mono-substituted with one of the substituents (20) to (33).

In another aspect of this embodiment, each $R^m$ is independently C$_{5-7}$ cycloalkyl; aryl selected from phenyl and naphthyl; a 5- or 6-membered saturated heterocyclic ring containing from 1 to 4 heteroatoms independently selected from N, O and S; a 5- or 6-membered heteroaromatic ring containing from 1 to 4 heteroatoms independently selected from N, O and S; or a bicyclic heterocycle which is a benzene ring fused to a 5- or 6-membered, saturated or unsaturated heterocyclic ring containing from 1 to 3 heteroatoms selected from N, O and S; wherein the cycloalkyl or the aryl is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, —N($R^a R^b$), phenyl, or —(CH$_2$)$_{1-2}$-phenyl;

the saturated heterocyclic ring is optionally substituted with from 1 to 4 substituents each of which is independently —C$_{1-4}$ alkyl optionally substituted with —O—C$_{1-4}$ alkyl, —C$_{1-4}$ haloalkyl, —O—C$_{1-4}$ alkyl, —O—C$_{1-4}$ haloalkyl, oxo, phenyl, —(CH$_2$)$_{1-2}$-phenyl, —C(=O)phenyl, —CO$_2$-phenyl, —CO$_2$—(CH$_2$)$_{1-2}$-phenyl, a 5- or 6-membered saturated heterocyclic ring containing from 1 to 4 heteroatoms independently selected from N, O and S, or a 5- or 6-membered heteroaromatic ring containing from 1 to 4 heteroatoms independently selected from N, O and S; and the heteroaromatic ring or the bicyclic heterocycle is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, oxo, phenyl, or —(CH$_2$)$_{1-2}$-phenyl.

Another embodiment of the present invention is a compound of Formula (I), wherein $R^k$ is cycloalkyl selected from cyclopropyl, cyclopentyl and cyclohexyl; aryl selected from phenyl and naphthyl; a bicyclic carbocycle selected from indanyl and tetrahydronaphthyl; a 5- or 6-membered saturated heterocyclic ring selected from pyrrolidinyl, piperidinyl, piperazinyl, morpholinyl, pyranyl, tetrahydrofuranyl, imidazolidinyl, thiomorpholinyl, thiazolidinyl, isothiazolidinyl, oxazolidinyl, isooxazolidinyl, and pyrazolidinyl; a 5- or 6-membered heteroaromatic ring selected from thienyl, pyridyl, imidazolyl, pyrrolyl, pyrazolyl, thiazolyl, isothiazolyl, thiadiazolyl, oxopiperidinyl, oxazolyl, isooxazolyl, oxadiazolyl, pyrazinyl, pyrimidinyl, triazolyl, tetrazolyl, furanyl, and pyridazinyl; or a bicyclic heterocycle selected from indolyl, indolinyl, tetrahydroquinolinyl, quinolinyl, tetrahydroisoquinolinyl, isoquinolinyl, 1,4-dioxa-8-azaspiro[4.5]dec-8-yl, azabicyclo[2.2.1]hept-1-yl, azabicyclo[2.1.1]hex-1-yl, 2,3-dihydrobenzofuranyl, 2,3-dihydrobenzo-1,4-dioxinyl, and benzo-1,3-dioxolyl;

and all other variables are as originally defined above;

or a pharmaceutically acceptable salt thereof.

In an aspect of this embodiment, Rk is as just defined except that it excludes cyclopropyl, pyranyl, oxopiperidinyl, 1,4-dioxa-8-azaspiro[4.5]decyl, azabicyclo[2.2.1]heptyl, and azabicyclo[2.1.1]hexyl.

In another aspect of this embodiment, the cycloalkyl, aryl, bicyclic carbocycle, saturated heterocyclic ring, heteroaromatic ring, or bicyclic heterocycle is optionally substituted with from 1 to 3 substituents each of which is independently (1) fluoro,
(2) chloro,
(3) bromo,
(4) —CF$_3$,
(5) —C$_{1-4}$ alkyl, which is optionally substituted with 1 or 2 substituents each of which is independently —OH, —CN, —O—C$_{1-4}$ alkyl, —OCF$_3$, —N($R^a R^b$), —C(=O)N($R^a R^b$), or N($R^a$)—C(=O)—(CH$_2$)$_{0-2}$N($R^b R^c$),
(6) —OCF$_3$,
(7) —O—C$_{1-4}$ alkyl
(8) —NO$_2$,
(9) oxo,
(10) —C(=O)$R^a$,
(11) —CO$_2 R^a$,
(12) —S$R^a$,
(13) —S(=O)$R^a$,
(14) —N($R^a R^b$),

(15) —C(=O)N($R^aR^b$),
(16) —C(=O)—(CH$_2$)$_{1-2}$—N($R^aR^b$),
(17) —N($R^a$)C(=O)$R^b$,
(18) —SO$_2$$R^a$,
(19) —$R^m$,
(20) —CH(CH$_3$)—$R^m$,
(21) —CH$_2$—$R^m$,
(22) —(CH$_2$)$_{0-2}$—N($R^a$)—(CH$_2$)$_{0-2}$—$R^m$,
(23) —O—(CH$_2$)$_{1-2}$—$R^m$,
(24) —(CH$_2$)$_{0-1}$—S—(CH$_2$)$_{0-2}$—$R^m$,
(25) —(CH$_2$)$_{0-1}$—C(=O)—(CH$_2$)$_{0-2}$—$R^m$,
(26) —(CH$_2$)$_{0-1}$—C(=O)—O—(CH$_2$)$_{0-2}$—$R^m$,
(27) —C(=O)N($R^a$)—$R^m$,
(28) —N($R^a$)C(=O)—$R^m$,
(29) —N($R^a$)C(=O)—(CH$_2$)$_{1-2}$—$R^m$, wherein the —(CH$_2$)$_{1-2}$— moiety is optionally substituted with —N($R^aR^b$),
(30) —N($R^a$)—C(=O)—N($R^b$)—(CH$_2$)$_{1-2}$—$R^m$,
(31) —N($R^a$)—C(=O)—O—(CH$_2$)$_{1-2}$—$R^m$,
(32) —N($R^a$)—C(=O)—N($R^b$)SO$_2$—$R^m$, or
(33) —OH.

In another aspect of this embodiment, the substituents are selected from substituents (1) to (32) just defined.

In another aspect of this aspect, the cycloalkyl, aryl, bicyclic carbocycle, saturated heterocyclic ring, heteroaromatic ring, or bicyclic heterocycle is optionally substituted with from 1 to 3 substituents each of which is independently one of the substituents (1) to (18) as just defined in the preceding aspect, and is optionally mono-substituted with one of the substituents (19) to (32) as just defined in the preceding aspect.

In still another aspect of this embodiment, each $R^m$ is independently aryl selected from phenyl and naphthyl; a 5- or 6-membered saturated heterocyclic ring selected from pyrrolidinyl, imidazolidinyl, pyrazolidinyl, piperidinyl, piperazinyl, thiazolidinyl, and morpholinyl; or a 5- or 6-membered heteroaromatic ring selected from thienyl, pyridyl, imidazolyl, pyrrolyl, pyrazolyl, thiazolyl, isothiazolyl, oxazolyl, isooxazolyl, oxadiazolyl, thiadiazolyl, pyrazinyl, pyrimidinyl, triazolyl, tetrazolyl, furanyl, and pyridazinyl; wherein
  the aryl is optionally substituted with from 1 to 3 substituents each of which is independently halogen, —C$_{1-4}$ alkyl, —CF$_3$, —O—C$_{1-4}$ alkyl, —OCF$_3$, or —N($R^aR^b$);
  the saturated heterocyclic ring is optionally substituted with 1 or 2 substituents each of which is independently —C$_{1-4}$ alkyl, —CF$_3$, —O—C$_{1-4}$ alkyl, —OCF$_3$, oxo, phenyl, —(CH$_2$)$_{1-2}$-phenyl, —C(=O)-phenyl, —CO$_2$-phenyl, or —CO$_2$—CH$_2$-phenyl; and
  the heteroaromatic ring is optionally substituted with 1 or 2 substituents each of which is independently —C$_{1-4}$ alkyl, —CF$_3$, —O—C$_{1-4}$ alkyl, —OCF$_3$, oxo, phenyl, or —(CH$_2$)$_{1-2}$-phenyl.

In an aspect of this embodiment, the 5- or 6-membered saturated heterocyclic ring is selected from pyrrolidinyl, imidazolidinyl, pyrazolidinyl, piperidinyl, piperazinyl, and morpholinyl.

Another embodiment of the present invention is a compound of Formula (I), wherein $R^2$ is —H or —C$_{1-6}$ alkyl which is optionally substituted with one of:
(1) —N($R^aR^b$),
(2) phenyl which is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, or —C$_{0-6}$ alkyl-N($R^aR^b$), or
(3) a 5- or 6-membered saturated monocyclic heterocycle which contains from 1 to 4 heteroatoms independently selected from N, O and S; wherein the heterocycle is optionally substituted with from 1 to 4 substituents each of which is independently —C$_{1-6}$ alkyl, —O—C$_{1-6}$ alkyl, oxo, or phenyl;

and all other variables are as originally defined above;

or a pharmaceutically acceptable salt thereof.

In an aspect of the preceding embodiment, $R^2$ is
(1) —H,
(2) —C$_{1-4}$ alkyl,
(3) —(CH$_2$)$_{1-3}$—N($R^aR^b$),
(4) —(CH$_2$)$_{1-3}$-phenyl, wherein the phenyl is optionally substituted with from 1 to 3 substituents each of which is independently fluoro, chloro, bromo, —C$_{1-4}$ alkyl, —C$_{1-4}$ fluoroalkyl, —O—C$_{1-4}$ alkyl, —O—C$_{1-4}$ fluoroalkyl, or —(CH$_2$)$_{1-3}$—N($R^aR^b$); or
(5) —(CH$_2$)$_{1-3}$$R^t$, wherein $R^t$ is a 6-membered saturated heterocyclic ring containing from 1 to 3 heteroatoms independently selected from N, O and S.

Other embodiments of the present invention include a compound wherein $R^2$ is —H or methyl; or $R^2$ is —H; and all other variables are as originally defined above; or a pharmaceutically acceptable salt thereof.

Another embodiment of the present invention is a compound of Formula (I), wherein $R^3$ is —H or —C$_{1-4}$ alkyl;

and all other variables are as originally defined above;

or a pharmaceutically acceptable salt thereof.

In an aspect of this embodiment, $R^3$ is —H or methyl. In another aspect of this embodiment, $R^3$ is —H.

Another embodiment of the present invention is a compound of Formula (I), wherein $R^4$ is
(1) C$_{1-4}$ alkyl,
(2) C$_{1-4}$ alkyl substituted with from 1 to 3 substituents each of which is independently —OH, O—C$_{1-4}$ alkyl, or —O—C$_{1-4}$ haloalkyl,
(3) C$_{1-4}$ alkyl which is substituted with an aryl or with two aryls which are the same or different, and is optionally substituted with —OH,
(4) C$_{1-4}$ alkyl substituted with one of:
  (i) C$_{5-7}$ cycloalkyl,
  (ii) a fused bicyclic carbocycle consisting of a benzene ring fused to a C$_{5-7}$ cycloalkyl,
  (iii) a 5- or 6-membered saturated heterocyclic ring containing from 1 to 4 heteroatoms independently selected from N, O and S,
  (iv) a 5- or 6-membered heteroaromatic ring containing from 1 to 4 heteroatoms independently selected from N, O and S, or
  (v) a 9- or 10-membered fused bicyclic heterocycle containing from 1 to 4 heteroatoms independently selected from N, O and S, wherein at least one of the rings is aromatic;
(5) C$_{2-4}$ alkynyl optionally substituted with aryl,
(6) C$_{3-7}$ cycloalkyl optionally substituted with aryl,
(7) aryl,
(8) a fused bicyclic carbocycle consisting of a benzene ring fused to a C$_{5-7}$ cycloalkyl,
(9) a 5- or 6-membered saturated heterocyclic ring containing from 1 to 4 heteroatoms independently selected from N, O and S,
(10) a 5- or 6-membered heteroaromatic ring containing from 1 to 4 heteroatoms independently selected from N, O and S, or

(11) a 9- or 10-membered fused bicyclic heterocycle containing from 1 to 4 heteroatoms independently selected from N, O and S, wherein at least one of the rings is aromatic;

wherein each aryl in (3) or the aryl in (5), (6) or (7) or the fused carbocycle in (4)(ii) or (8) is optionally substituted with from 1 to 4 substituents each of which is independently halogen, —OH, —$C_{1-4}$ alkyl, —$C_{1-4}$ alkyl-OR$^a$, —$C_{1-4}$ haloalkyl, —O—$C_{1-4}$ alkyl, —O—$C_{1-4}$ haloalkyl, —CN, —NO$_2$, —N(R$^a$R$^b$), —$C_{1-4}$ alkyl-N(R$^a$R$^b$), —C(=O)N(R$^a$R$^b$), —C(=O)R$^a$, —CO$_2$R$^a$, —$C_{1-4}$ alkyl-CO$_2$R$^a$, —OCO$_2$R$^a$, —SR$^a$, —S(=O)R$^a$, —SO$_2$R$^a$, —N(R$^a$)SO$_2$R$^b$, —SO$_2$N(R$^a$R$^b$), —N(R$^a$)C(=O)R$^b$, —N(R$^a$)CO$_2$R$^b$, —$C_{1-4}$ alkyl-N(R$^a$)CO$_2$R$^b$, phenyl, —$C_{1-4}$ alkyl-phenyl, —O-phenyl, or —(CH$_2$)$_{0-2}$-het wherein het is a 5- or 6-membered heteroaromatic ring containing from 1 to 4 heteroatoms independently selected from N, O and S, and het is optionally fused with a benzene ring, and is optionally substituted with 1 or 2 substituents each of which is independently —$C_{1-4}$ alkyl, —$C_{1-4}$ haloalkyl, —O—$C_{1-4}$ alkyl, —O—$C_{1-4}$ haloalkyl, or —CO$_2$R$^a$;

the saturated heterocyclic ring in (4)(iii) or (9) is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, oxo, phenyl, or a 5- or 6-membered heteroaromatic ring containing from 1 to 4 heteroatoms independently selected from N, O and S; and the heteroaromatic ring in (4)(iv) or (10) or the fused bicyclic heterocycle in (4)(v) or (11) is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, oxo, or phenyl;

and all other variables are as originally defined above;

or a pharmaceutically acceptable salt thereof.

Another embodiment of the present invention is a compound of Formula (I), wherein R$^4$ is:

(1) $C_{1-3}$ alkyl substituted with 1 or 2 phenyls, and is optionally substituted with an —OH, (2) $C_{1-4}$ alkyl substituted with one of:
  (i) cyclohexyl,
  (ii) naphthyl,
  (iii) a fused bicyclic carbocycle selected from

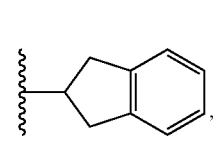,

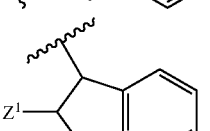, and

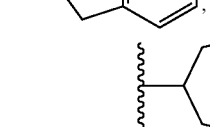;

(iv) a saturated heterocyclic ring containing from zero to 1 oxygen atoms and from 1 to 3 nitrogen atoms, (v) a 5- or 6-membered heteroaromatic ring containing from zero to 1 heteroatoms selected from O and S and from 1 to 3 nitrogen atoms, or (vi) a fused bicyclic heterocycle selected from

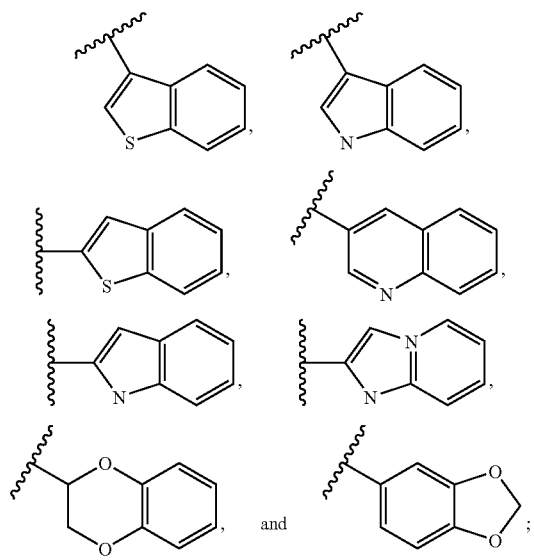

(3)

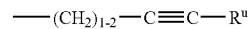

wherein R$^u$ is H or phenyl, (4) $C_{3-6}$ cycloalkyl optionally substituted with phenyl, (5) phenyl or naphthyl, (6) a fused bicyclic carbocycle selected from

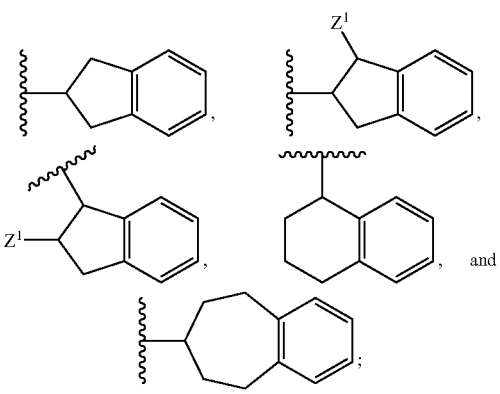

(7) a saturated heterocyclic ring containing from zero to 1 oxygen atoms and from 1 to 3 nitrogen atoms, (8) a 5- or 6-membered heteroaromatic ring containing from zero to 1 heteroatoms selected from O and S and from 1 to 3 nitrogen atoms, or (9) a fused bicyclic heterocycle selected from

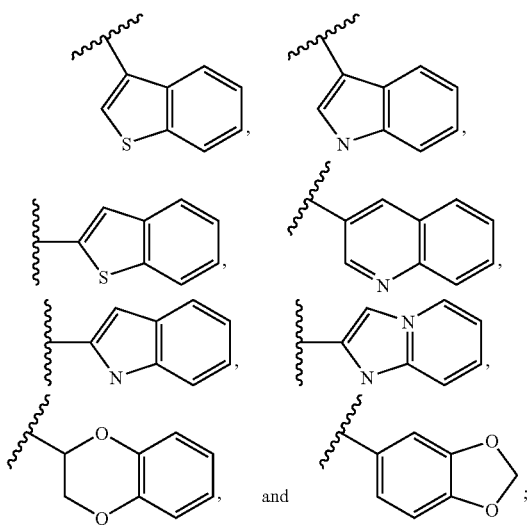

wherein $Z^1$ is —H or —OH;

each phenyl in (1) or the phenyl in (3) or (4) or (5) or the naphthyl in (2)(ii) or (5) is optionally substituted with from 1 to 3 substituents each of which is independently fluoro, bromo, chloro, —OH, —$C_{1-4}$ alkyl, —$CF_3$, —O—$C_{1-4}$ alkyl, —$OCF_3$, —CN, —$NO_2$, —$(CH_2)_{1-2}$—N($R^aR^b$), —C(=O)$R^a$, —$CO_2R^a$, —$SR^a$, —S(=O)$R^a$, —$SO_2R^a$, —N($R^a$)$SO_2R^b$, —$SO_2$N($R^aR^b$), or —N($R^a$)$CO_2R^b$; and is additionally and optionally mono-substituted with phenyl, —$(CH_2)_{1-2}$-phenyl, —O-phenyl, or —$(CH_2)_{0-2}$-het wherein het is thiadiazolyl or indolyl, and het is optionally substituted with —$C_{1-4}$ alkyl, —$CF_3$, —O—$C_{1-6}$ alkyl, —$OCF_3$, or —$CO_2R^a$;

the saturated heterocyclic ring in (2)(iv) or (7) is optionally substituted with from 1 to 3 substituents each of which is independently halogen, —$C_{1-4}$ alkyl, —$CF_3$, —O—$C_{1-4}$ alkyl, —$OCF_3$, oxo; and is additionally and optionally mono-substituted with phenyl or a heteroaromatic ring selected from pyridyl, pyrimidinyl, and pyrazinyl; and the heteroaromatic ring in (2)(v) or (8) is optionally substituted with from 1 to 3 substituents each of which is independently halogen, —$C_{1-4}$ alkyl, —$CF_3$, —O—$C_{1-4}$ alkyl, —$OCF_3$, or oxo; and is additionally and optionally mono-substituted with phenyl;

and all other variables are as originally defined above;

or a pharmaceutically acceptable salt thereof.

Another embodiment of the present invention is a compound of Formula (I), wherein $R^4$ is:

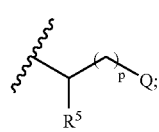

wherein
Q is
(1) ethynyl optionally substituted with aryl,
(2) $C_{5-7}$ cycloalkyl,
(3) aryl,
(4) a fused bicyclic carbocycle consisting of a benzene ring fused to a $C_{5-7}$ cycloalkyl,
(5) a 5- or 6-membered saturated heterocyclic ring containing from 1 to 4 heteroatoms independently selected from N, O and S,
(6) a 5- or 6-membered heteroaromatic ring containing from 1 to 4 heteroatoms independently selected from N, O and S, or
(7) a 9- or 10-membered fused bicyclic heterocycle containing from 1 to 4 heteroatoms independently selected from N, O and S, wherein at least one of the rings is aromatic;

wherein
aryl in (1) or (3) or the fused carbocycle in (4) is optionally substituted with from 1 to 4 substituents each of which is independently halogen, —OH, —$C_{1-4}$ alkyl, —$C_{1-4}$ alkyl-O$R^a$, —$C_{1-4}$ haloalkyl, —O—$C_{1-4}$ alkyl, —O—$C_{1-4}$ haloalkyl, —CN, —$NO_2$, —N($R^aR^b$), —$C_{1-4}$ alkyl-N($R^aR^b$), —C(=O)N($R^aR^b$), —C(=O)$R^a$, —$CO_2R^a$, —$C_{1-4}$ alkyl-$CO_2R^a$, —$OCO_2R^a$, —$SR^a$, —S(=O)$R^a$, —$SO_2R^a$, —N($R^a$)$SO_2R^b$, —$SO_2$N($R^aR^b$), —N($R^a$)C(=O)$R^b$, —N($R^a$)$CO_2R^b$, —$C_{1-4}$ alkyl-N($R^a$)$CO_2R^b$, phenyl, —$C_{1-4}$ alkyl-phenyl, —O-phenyl, or —$(CH_2)_{0-2}$-het wherein het is a 5- or 6-membered heteroaromatic ring containing from 1 to 4 heteroatoms independently selected from N, O and S, and het is optionally fused with a benzene ring, and is optionally substituted with —$C_{1-4}$ alkyl, —$C_{1-4}$ haloalkyl, —O—$C_{1-4}$ alkyl, —O—$C_{1-4}$ haloalkyl, or —$CO_2R^a$;

the saturated heterocyclic ring in (5) is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, oxo, phenyl, or a 5- or 6-membered heteroaromatic ring containing from 1 to 4 heteroatoms independently selected from N, O and S; and the heteroaromatic ring in (6) or the fused bicyclic heterocycle in (7) is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, oxo, or phenyl;

$R^5$ is H, methyl, or $CH_2OH$, with the proviso that when $R^5$ is $CH_2OH$, then Q is aryl; and p is an integer equal to zero, 1 or 2;

and all other variables are as originally defined above;

or a pharmaceutically acceptable salt thereof.

In an aspect of the preceding embodiment, Q is
(1) —C≡C—$R^u$ wherein $R^u$ is H or phenyl,
(2) phenyl or naphthyl,
(3) cyclopentyl or cyclohexyl,
(4) a fused bicyclic carbocycle selected from the group consisting of indanyl, tetrahydronaphthalenyl, and benzocycloheptyl,
(5) a saturated heterocyclic ring selected from the group consisting of tetrahydrofuranyl, pyrrolidinyl, imidazolidinyl, piperidinyl, piperazinyl, morpholinyl, thiomorpholinyl, thiazolidinyl, isothiazolidinyl, oxazolidinyl, isooxazolidinyl, and pyrazolidinyl,
(6) a heteroaromatic ring selected from the group consisting of thienyl, pyridyl, imidazolyl, pyrrolyl, pyrazolyl, thiazolyl, isothiazolyl, oxazolyl, isooxazolyl, oxadiazolyl, pyrazinyl, pyrimidinyl, triazolyl, tetrazolyl, furanyl, and pyridazinyl, or (7) a fused bicyclic heterocycle selected from the group consisting of benzothiophenyl, indolyl, pyridoimidazolyl, indazolyl, 2,3-dihydrobenzo-1,4-dioxinyl, dihydrobenzofuranyl, benzo-1,3-dioxolyl, quinolinyl, and isoquinolinyl;

wherein
the phenyl in (1) or the phenyl or naphthyl in (2) is optionally substituted with from 1 to 4 substituents each of which is independently halogen, —OH, —$C_{1-4}$ alkyl, —$C_{1-4}$ haloalkyl, —O—$C_{1-4}$ alkyl, —O—$C_{1-4}$ haloalkyl, —CN, —$NO_2$, —$C_{1-4}$ alkyl-N($R^a R^b$), —C(=O)$R^a$, —$CO_2 R^a$, —$C_{1-4}$ alkyl-$CO_2 R^a$, —$SR^a$, —S(=O)$R^a$, —$SO_2 R^a$, —N($R^a$)$SO_2 R^b$, —$SO_2$N($R^a R^b$), —N($R^a$)$CO_2 R^b$, —$C_{1-4}$ alkyl-N($R^a$)$CO_2 R^b$, phenyl, —$(CH_2)_{1-2}$-phenyl, —O-phenyl, or —$(CH_2)_{0-2}$-het wherein het is pyrrolyl, pyrazolyl, imidazolyl, triazolyl, thiazolyl, oxazolyl, isothiazolyl, isooxazolyl, pyridyl, pyrazinyl, thiadiazolyl or indolyl, and het is optionally substituted with —$C_{1-4}$ alkyl, —$CF_3$, —O—$C_{1-6}$ alkyl, —$OCF_3$, oxo, or —$CO_2 R^a$;

the fused carbocycle in (4) is optionally substituted with from 1 to 4 substituents each of which is independently halogen, —OH, —$C_{1-4}$ alkyl, —$C_{1-4}$ haloalkyl, —O—$C_{1-4}$ alkyl, —O—$C_{1-4}$ haloalkyl, —$C_{1-4}$ alkyl-N($R^a R^b$), —C(=O)$R^a$, —$CO_2 R^a$, —$SR^a$, —S(=O)$R^a$, —$SO_2 R^a$, —N($R^a$)$CO_2 R^b$, phenyl, —$(CH_2)_{1-2}$-phenyl, or —O-phenyl;

the saturated heterocyclic ring in (5) is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, oxo, phenyl, pyridyl, pyrazinyl, or pyrimidinyl; and the heteroaromatic ring in (6) or the fused bicyclic heterocycle in (7) is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, oxo, or phenyl.

In another aspect of the preceding embodiment, Q is phenyl, which is optionally substituted with from 1 to 3 substituents each of which is independently fluoro, bromo, chloro, —OH, —$C_{1-4}$ alkyl, —$C_{1-4}$ fluoroalkyl, —O—$C_{1-4}$ alkyl, —O—$C_{1-4}$ fluoroalkyl, —CN, —$SR^a$, —$(CH_2)_{1-2}$-N($R^a R^b$), —$SO_2 R^a$, —N($R^a$)$SO_2 R^b$, —$SO_2$N($R^a R^b$), —$(CH_2)_{0-2}$—$CO_2 R^{a*}$, —$(CH_2)_{0-2}$—N($R^a$)$CO_2 R^{b*}$, —$NO_2$, or phenyl;

each $R^a$ is independently H, methyl, or ethyl;
each $R^b$ is independently H, methyl, or ethyl; and
each $R^{a*}$ and $R^{b*}$ is independently H or —$C_{1-4}$ alkyl.

In another aspect of the preceding embodiment, the phenyl substituents are independently selected from the group consisting of fluoro, bromo, chloro, —OH, —$C_{1-4}$ alkyl, —$C_{1-4}$ fluoroalkyl, —O—$C_{1-4}$ alkyl, —O—$C_{1-4}$ fluoroalkyl, —CN, —$(CH_2)_{1-2}$—N($R^a R^b$), —$SO_2 R^a$, —N($R^a$)$SO_2 R^b$, —$SO_2$N($R^a R^b$), —$(CH_2)_{0-2}$—$CO_2 R^{a*}$, —$(CH_2)_{0-2}$—N($R^a$)$CO_2 R^{b*}$, —$NO_2$, and phenyl.

In still another aspect of the preceding embodiment, Q is phenyl which is optionally substituted with from 1 to 3 substituents, each of which is independently —F, —Br, —Cl, —OH, —$C_{1-4}$ alkyl, —$C_{1-4}$ fluoroalkyl, —O—$C_{1-4}$ alkyl, —O—$C_{1-4}$ fluoroalkyl, —CN, —$SR^a$ or —$SO_2 R^a$. In still another aspect of the preceding embodiment, Q is phenyl which is optionally substituted with from 1 to 3 substituents, each of which is independently —F, —Br, —Cl, —OH, —$C_{1-4}$ alkyl, —$C_{1-4}$ fluoroalkyl, —O—$C_{1-4}$ alkyl, —O—$C_{1-4}$ fluoroalkyl, —CN, or —$SO_2 R^a$.

In still another aspect of the preceding embodiment, Q is p-fluorophenyl or 2,3-dimethoxyphenyl. In still another aspect of the preceding embodiment, Q is p-fluorophenyl.

In yet another aspect of the preceding embodiment, and also a feature of each of the preceding aspects thereof, $R^5$ is H and p is zero.

A class of compounds of the present invention includes any compound of Formula (I), wherein
$R^1$ is —$R^k$;
$R^k$ is a 5- or 6-membered heteroaromatic ring containing from 1 to 3 heteroatoms independently selected from N, O and S;
wherein the heteroaromatic ring is optionally substituted with from 1 to 3 substituents each of which is independently
(1) halogen,
(2) —$C_{1-6}$ alkyl, which is optionally substituted with from 1 to 5 substituents each of which is independently halogen, —O—$C_{1-4}$ alkyl, —O—$C_{1-4}$ haloalkyl, —C(=O)$R^a$, —$CO_2 R^a$, —$SR^a$, —S(=O)$R^a$, —N($R^a R^b$), —C(=O)—$(CH_2)_{0-2}$N($R^a R^b$), N($R^a$)—C(=O)—$(CH_2)_{0-2}$N($R^b R^c$), —$SO_2 R^a$, —N($R^a$)$SO_2 R^b$, —$SO_2$N($R^a R^b$), or —N($R^a$)—C($R^b$)=O,
(3) —$NO_2$,
(4) oxo,
(5) —C(=O)$R^a$,
(6) —$CO_2 R^a$,
(7) —C(=O)N($R^a R^b$),
(8) —C(=O)—$C_{1-4}$ alkyl-N($R^a R^b$),
(9) —$R^m$,
(10) —$C_{1-6}$ alkyl-$R^m$, wherein the alkyl is optionally substituted with from 1 to 5 substituents each of which is independently halogen, —OH, —CN, —$C_{1-4}$ haloalkyl, —O—$C_{1-4}$ alkyl, —O—$C_{1-4}$ haloalkyl, —C(=O)$R^a$, —$CO_2 R^a$, —$SR^a$, —S(=O)$R^a$, —N($R^a R^b$), —N($R^a$)$CO_2 R^b$, —$SO_2 R^a$, —N($R^a$)$SO_2 R^b$, —$SO_2$N($R^a R^b$), or —N($R^a$)—C($R^b$)=O,
(11) —$C_{0-4}$ alkyl-N($R^a$)—$C_{0-4}$ alkyl-$R^m$,
(12) —$C_{0-4}$ alkyl-O—$C_{0-4}$ alkyl-$R^m$,
(13) —$C_{0-4}$ alkyl-S—$C_{0-4}$ alkyl-$R^m$,
(14) —$C_{0-4}$ alkyl-C(=O)—$C_{0-4}$ alkyl-$R^m$,
(15) —C(=O)—O—$C_{0-4}$ alkyl-$R^m$,
(16) —C(=O)N($R^a$)—$C_{0-4}$ alkyl-$R^m$,
(17) —N($R^a$)C(=O)—$R^m$,
(18) —N($R^a$)C(=O)—$C_{1-6}$ alkyl-$R^m$, wherein the alkyl is optionally substituted with from 1 to 5 substituents each of which is independently halogen, —OH, —CN, —$C_{1-4}$ haloalkyl, —O—$C_{1-4}$ alkyl, —O—$C_{1-4}$ haloalkyl, —C(=O)$R^a$, —$CO_2 R^a$, —$SR^a$, —S(=O)$R^a$, —N($R^a R^b$), —N($R^a$)$CO_2 R^b$, —$SO_2 R^a$, —N($R^a$)$SO_2 R^b$, —$SO_2$N($R^a R^b$), or —N($R^a$)—C($R^b$)=O,
(19) —N($R^a$)—C(=O)—N($R^b$)—$C_{0-4}$ alkyl-$R^m$,
(20) —N($R^a$)—C(=O)—O—$C_{0-4}$ alkyl-$R^m$, or
(21) —N($R^a$)—C(=O)—N($R^b$)$SO_2$—$C_{0-4}$ alkyl-$R^m$;
wherein each $R^m$ is independently aryl selected from phenyl and naphthyl or a 5- or 6-membered heteroaromatic ring containing from 1 to 3 heteroatoms independently selected from N, O and S; wherein
the aryl is optionally substituted with from 1 to 3 substituents each of which is independently halogen, —$C_{1-4}$ alkyl, —$CF_3$, —O—$C_{1-4}$ alkyl, —$OCF_3$, or —N($R^a R^b$); and
the heteroaromatic ring is optionally substituted with 1 or 2 substituents each of which is independently —$C_{1-4}$ alkyl or oxo; and each $R^a$ and $R^b$ is independently —H or —$C_{1-4}$ alkyl;

and all other variables are as originally defined above;

or a pharmaceutically acceptable salt thereof.

A sub-class of the preceding class of compounds of the present invention includes any compounds of Formula (I) exactly as defined in the class, except that in the definition of $R^k$, $R^k$ is optionally substituted with from 1 to 3 substituents each of which is independently one of the substituents (1) to (8), and is optionally mono-substituted with one of the substituents (9) to (21).

Another sub-class of the preceding class of compounds of the present invention includes any compounds of Formula (I), wherein $R^1$ is:

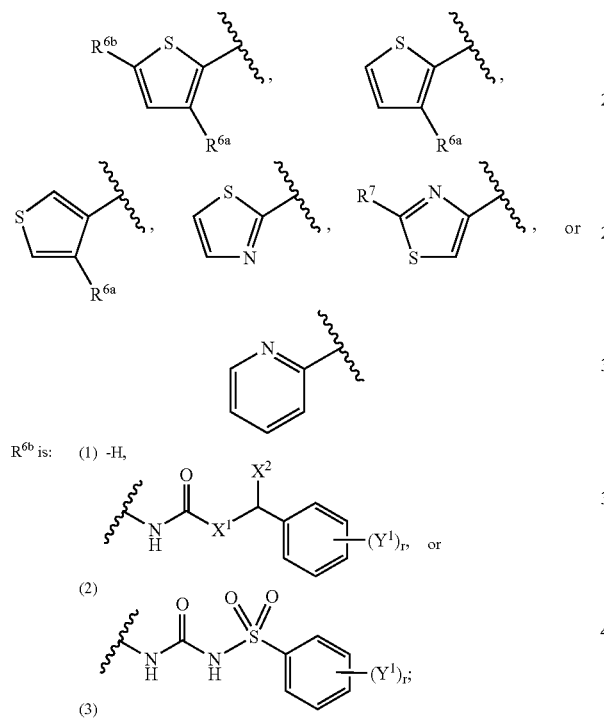

wherein $X^1$ is a single bond connecting the carbonyl carbon to the carbon substituted with $X^2$, —O—, or —NH—;

$X^2$ is —H, —$NH_2$, or —N(H)$CO_2R^a$;

$Y^1$ is —H, halo or —$C_{1-4}$ alkyl; and r is an integer equal to zero, 1 or 2; and $R^{6b}$ is —H or —$NO_2$; and $R^7$ is —H or —$C_{1-4}$ alkyl;

and all other variables are as defined in the class;

or a pharmaceutically acceptable salt thereof.

In a feature of this sub-class, $R^{6a}$ and $R^{6b}$ are both —H; and $R^7$ is —H or —$CH_3$.

Another class of compounds of the present invention includes any compound of Formula (I), wherein $R^1$ is —$R^k$;

$R^k$ is phenyl which is optionally substituted with from 1 to 3 substituents each of which is independently:

(1) halogen, (2) —$C_{1-6}$ alkyl, which is optionally substituted with from 1 to 5 substituents each of which is independently halogen, —OH, —O—$C_{1-4}$ alkyl, —O—$C_{1-4}$ haloalkyl, —C(=O)$R^a$, —$CO_2R^a$, —$SR^a$, —S(=O)$R^a$, —N($R^aR^b$), —C(=O)—$(CH_2)_{0-2}$N($R^aR^b$), N($R^a$)—C(=O)—$(CH_2)_{0-2}$N($R^bR^c$), —$SO_2R^a$, —N($R^a$)$SO_2R^b$, —$SO_2$N($R^aR^b$), or —N($R^a$)—C($R^b$)=O, (3) —$NO_2$, (4) —C(=O)$R^a$, (5) —$CO_2R^a$, (6) —C(=O)N($R^aR^b$), (7) —C(=O)—$C_{1-4}$ alkyl-N($R^aR^b$), (8) —$R^m$, (9) —$C_{1-6}$ alkyl-$R^m$, wherein the alkyl is optionally substituted with from 1 to 5 substituents each of which is independently halogen, —OH, —CN, —$C_{1-4}$ haloalkyl, —O—$C_{1-4}$ alkyl, —O—$C_{1-4}$ haloalkyl, —C(=O)$R^a$, —$CO_2R^a$, —$SR^a$, —S(=O)$R^a$, —N($R^aR^b$), —N($R^a$)$CO_2R^b$, —$SO_2R^a$, —N($R^a$)$SO_2R^b$, —$SO_2$N($R^aR^b$), or —N($R^a$)—C($R^b$)=O,

(10) —$C_{0-4}$ alkyl-N($R^a$)—$C_{0-4}$ alkyl-$R^m$,

(11) —$C_{0-4}$ alkyl-O—$C_{0-4}$ alkyl-$R^m$,

(12) —$C_{0-4}$ alkyl-S—$C_{0-4}$ alkyl-$R^m$,

(13) —$C_{0-4}$ alkyl-C(=O)—$C_{0-4}$ alkyl-$R^m$,

(14) —C(=O)—O—$C_{0-4}$ alkyl-$R^m$,

(15) —C(=O)N($R^a$)—$C_{0-4}$ alkyl-$R^m$,

(16) —N($R^a$)C(=O)—$R^m$,

(17) —N($R^a$)C(=O)—$C_{1-6}$ alkyl-$R^m$, wherein the alkyl is optionally substituted with from 1 to 5 substituents each of which is independently halogen, —OH, —CN, —$C_{1-4}$ haloalkyl, —O—$C_{1-4}$ alkyl, —O—$C_{1-4}$ haloalkyl, —C(=O)$R^a$, —$CO_2R^a$, —$SR^a$, —S(=O)$R^a$, —N($R^aR^b$), —N($R^a$)$CO_2R^b$, —$SO_2R^a$, —N($R^a$)$SO_2R^b$, —$SO_2$N($R^aR^b$), or —N($R^a$)—C($R^b$)=O,

(18) —N($R^a$)—C(=O)—N($R^b$)—$C_{0-4}$ alkyl-$R^m$,

(19) —N($R^a$)—C(=O)—O—$C_{0-4}$ alkyl-$R^m$, or

(20) —N($R^a$)—C(=O)—N($R^b$)$SO_2$—$C_{0-4}$ alkyl-$R^m$;

wherein each $R^m$ is independently aryl selected from phenyl and naphthyl; a 5- or 6-membered saturated heterocyclic ring containing from 1 to 3 heteroatoms independently selected from N, O and S; or a 5- or 6-membered heteroaromatic ring containing from 1 to 3 heteroatoms independently selected from N, O and S; wherein the aryl is optionally substituted with from 1 to 3 substituents each of which is independently halogen, —$C_{1-4}$ alkyl, —$CF_3$, —O—$C_{1-4}$ alkyl, —$OCF_3$, or —N($R^aR^b$);

the saturated heterocyclic ring is optionally substituted with from 1 to 3 substituents each of which is independently —$C_{1-4}$ alkyl or oxo, and is additionally optionally mono-substituted with phenyl, —$(CH_2)_{1-2}$-phenyl, —C(=O)-phenyl, —$CO_2$-phenyl, or —$CO_2$—$(CH_2)_{1-2}$-phenyl; and the heteroaromatic ring is optionally substituted with 1 or 2 substituents each of which is independently —$C_{1-4}$ alkyl or oxo;

and all other variables are as originally defined above;

or a pharmaceutically acceptable salt thereof.

A sub-class of the preceding class of compounds of the present invention includes any compounds of Formula (I) exactly as defined in the class, except that in the definition of $R^k$, $R^k$ is optionally substituted with from 1 to 3 substituents each of which is independently one of the substituents (1) to (8), and is optionally mono-substituted with one of the substituents (9) to (20).

Another sub-class of the preceding class of compounds of the present invention includes any compounds of Formula (I), wherein $R^1$ is phenyl which is mono-substituted (e.g., para-substituted) with one of:
(1) fluoro, chloro, or bromo,
(2) —$C_{1-4}$ alkyl, which is optionally substituted with 1 or 2 substituents each of which is independently —OH, —O—$C_{1-4}$ alkyl, —$OCF_3$, —C(=O)$R^a$, —$CO_2R^a$, —$SR^a$, —N($R^aR^b$), or —C(=O)N($R^aR^b$),
(3) —$NO_2$,
(4) —$C_{1-4}$ alkyl-$R^m$,
(5) —O—$(CH_2)_{1-2}$—$R^m$,
(6) —$(CH_2)_{0-2}$—S—$(CH_2)_{0-2}$—$R^m$,
(7) —N($R^a$)C(=O)—$R^m$,
(8) —N($R^a$)C(=O)—$(CH_2)_{1-2}$—$R^m$, wherein the $(CH_2)_{1-2}$ moiety is optionally mono-substituted with —N($R^aR^b$) or —N($R^a$)$CO_2R^b$, or
(9) —N($R^a$)—C(=O)—N($R^b$)—$(CH_2)_{1-2}$—$R^m$;
wherein $R^m$ is aryl selected from phenyl and naphthyl; a 5- or 6-membered saturated heterocyclic ring containing 1 or 2 heteroatoms independently selected from N and O; or a 5- or 6-membered heteroaromatic ring containing from 1 or 2 nitrogens; wherein
the aryl is optionally substituted with from 1 to 3 substituents each of which is independently halogen, —$C_{1-4}$ alkyl, —$CF_3$, —O—$C_{1-4}$ alkyl, —$OCF_3$, or —N($R^aR^b$); and
the saturated heterocyclic ring is optionally substituted with from 1 to 3 substituents each of which is independently —$C_{1-4}$ alkyl or oxo; and is additionally and optionally mono-substituted with phenyl, —$(CH_2)_{1-2}$-phenyl, —C(=O)-phenyl, —$CO_2$-phenyl, or —$CO_2$—$(CH_2)_{1-2}$-phenyl; and
the heteroaromatic ring is optionally substituted with 1 or 2 substituents each of which is independently —$C_{1-4}$ alkyl or oxo; and
each $R^a$ and $R^b$ is each independently —H or —$C_{1-4}$ alkyl;
and all other varaibles are as defined in the class;
or a pharmaceutically acceptable salt thereof.

Another class of compounds of the present invention includes any compound of Formula (I), wherein
$R^1$ is —$R^k$;
$R^k$ is a 5- or 6-membered saturated heterocyclic ring containing from 0 to 1 oxygen atoms and from 1 to 3 nitrogen atoms or a bicyclic heterocycle which is a benzene ring fused to a 5- or 6-membered saturated heterocyclic ring containing from 0 to 1 oxygen atoms and from 1 to 3 nitrogen atoms;
wherein the saturated heterocyclic ring or bicyclic heterocycle is optionally substituted with from 1 to 3 substituents each of which is independently
(1) halogen,
(2) —$C_{1-6}$ alkyl, which is optionally substituted with from 1 to 5 substituents each of which is independently halogen, —O—$C_{1-4}$ alkyl, —O—$C_{1-4}$ haloalkyl, —C(=O)$R^a$, —$CO_2R^a$, —$SR^a$, —S(=O)$R^a$, —N($R^aR^b$), —C(=O)—$(CH_2)_{0-2}$N ($R^aR^b$), N($R^a$)—C(=O)—$(CH_2)_{0-2}$N($R^bR^c$), —$SO_2R^a$, —N($R^a$)$SO_2R^b$, —$SO_2$N($R^aR^b$), or —N($R^a$)—C($R^b$)=O,
(3) —NO2,
(4) oxo,
(5) —C(=O)$R^a$,
(6) —$CO_2R^a$,
(7) —C(=O)N($R^aR^b$),
(8) —C(=O)—$C_{1-4}$ alkyl-N($R^aR^b$),
(9) —$SR^a$,
(10) —S(=O)$R^a$,
(11) —$SO_2R^a$,
(12) —N($R^aR^b$),
(13) —$R^m$,
(14) —$C_{1-6}$ alkyl-$R^m$, wherein the alkyl is optionally substituted with from 1 to 5 substituents each of which is independently halogen, —OH, —CN, —$C_{1-4}$ haloalkyl, —O—$C_{1-4}$ alkyl, —O—$C_{1-4}$ haloalkyl, —C(=O)$R^a$, —$CO_2R^a$, —$SR^a$, —S(=O)$R^a$, —N($R^aR^b$), —N($R^a$)$CO_2R^b$, —$SO_2R^a$, —N($R^a$)$SO_2R^b$, —$SO_2$N($R^aR^b$), or —N($R^a$)—C($R^b$)=O,
(15) —$C_{0-4}$ alkyl-N($R^a$)—$C_{0-4}$ alkyl-$R^m$,
(16) —$C_{0-4}$ alkyl-O—$C_{0-4}$ alkyl-$R^m$,
(17) —$C_{0-4}$ alkyl-S—$C_{0-4}$ alkyl-$R^m$,
(18) —$C_{0-4}$ alkyl-C(=O)—$C_{0-4}$ alkyl-$R^m$,
(19) —C(=O)—O—$C_{0-4}$ alkyl-$R^m$,
(20) —C(=O)N($R^a$)$C_{0-4}$ alkyl-$R^m$,
(21) —N($R^a$)C(=O)—$R^m$,
(22) —N($R^a$)C(=O)—$C_{1-6}$ alkyl-$R^m$, wherein the alkyl is optionally substituted with from 1 to 5 substituents each of which is independently halogen, —OH, —CN, —$C_{1-4}$ haloalkyl, —O—$C_{1-4}$ alkyl, —O—$C_{1-4}$ haloalkyl, —C(=O)$R^a$, —$CO_2R^a$, —$SR^a$, —S(=O)$R^a$, —N($R^aR^b$), —N($R^a$)$CO_2R^b$, —$SO_2R^a$, —N($R^a$)$SO_2R^b$, —$SO_2$N($R^aR^b$), or —N($R^a$)—C($R^b$)=O,
(23) —N($R^a$)—C(=O)—N($R^b$)—$C_{0-4}$ alkyl-$R^m$,
(24) —N($R^a$)—C(=O)—O—$C_{0-4}$ alkyl-$R^m$, or
(25) —N($R^a$)—C(=O)—N($R^b$)$SO_2$—$C_{0-4}$ alkyl-$R^m$;
wherein each $R^m$ is independently aryl selected from phenyl and naphthyl; a 5- or 6-membered saturated heterocyclic ring containing from 1 to 3 heteroatoms independently selected from N, O and S; a 5- or 6-membered heteroaromatic ring containing from 1 to 3 heteroatoms independently selected from N, O and S; or a 9- to 10-membered bicyclic heterocycle which is saturated or unsaturated and contains from 1 to 3 heteroatoms independently selected from N, O and S; wherein
the aryl is optionally substituted with from 1 to 3 substituents each of which is independently halogen, —$C_{1-4}$ alkyl, —$CF_3$, —O—$C_{1-4}$ alkyl, —$OCF_3$, or —N($R^aR^b$);
the saturated heterocyclic ring is optionally substituted with from 1 to 3 substituents each of which is independently —$C_{1-4}$ alkyl or oxo, and is additionally optionally mono-substituted with phenyl, —$(CH_2)_{1-2}$-phenyl, —C(=O)-phenyl, —$CO_2$-phenyl, or —$CO_2$-$(CH_2)_{1-2}$-phenyl; and
the heteroaromatic ring or the bicyclic heterocycle is optionally substituted with 1 or 2 substituents each of which is independently —$C_{1-4}$ alkyl or oxo;

and all other variables are as originally defined above;

or a pharmaceutically acceptable salt thereof.

A sub-class of the preceding class of compounds of the present invention includes any compounds of Formula (I) exactly as defined in the class, except that in the definition of $R^k$, $R^k$ is optionally substituted with from 1 to 3 substituents each of which is independently one of the substituents (1) to (12), and is optionally mono-substituted with one of the substituents (13) to (25).

Another subclass of the preceding class of compounds of the present invention includes any compounds of Formula (I), wherein $R^1$ is:

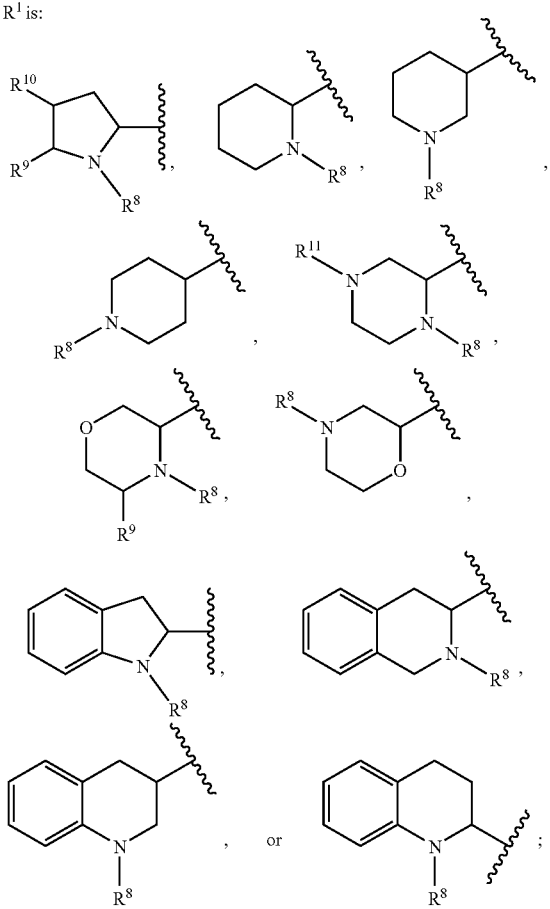

$R^8$ is:
(1) —H,
(2) —$C_{1-4}$ alkyl, which is optionally substituted with 1 or 2 substituents each of which is independently —OH, —O—$C_{1-4}$ alkyl, —$OCF_3$, —C(=O)$R^a$, —$CO_2R^a$, —$SR^a$, —N($R^aR^b$), or —C(=O)N($R^aR^b$),
(3) —C(=O)$R^a$,
(4) —$CO_2R^a$,
(5) —C(=O)—$(CH_2)_{1-2}$—N($R^aR^b$),
(6) —$SO_2R^a$,
(7) —$(CH_2)_{1-2}$—$R^m$,
(8) —$(CH_2)_{0-2}$—C(=O)—$(CH_2)_{0-2}$—$R^m$,
(9) —C(=O)—O—$(CH_2)_{0-2}$—$R^m$, or
(10) —C(=O)N($R^a$)—$(CH_2)_{0-2}$—$R^m$;
$R^9$ is —H, —$C_{1-4}$ alkyl, or oxo;
$R^{10}$ is —H, —OH, —$C_{1-4}$ alkyl, —O—$C_{1-4}$ alkyl, oxo, or —O—$(CH_2)_{1-2}$—$R^m$;
$R^{11}$ is
(1) —H,
(2) —$C_{1-4}$ alkyl, which is optionally substituted with 1 or 2 substituents each of which is independently —OH, —O—$C_{1-4}$ alkyl, —$OCF_3$, —C(=O)$R^a$, —$CO_2R^a$, —$SR^a$, —N($R^aR^b$), or —C(=O)N($R^aR^b$),
(3) —C(=O)$R^a$,
(4) —$CO_2R^a$,
(5) —C(=O)—$(CH_2)_{1-2}$—N($R^aR^b$)
(6) —$SO_2R^a$,
(7) —$(CH_2)_{1-2}$—$R^m$,
(8) —$(CH_2)_{0-2}$—C(=O)—$(CH_2)_{0-2}$—$R^m$,
(9) —C(=O)—O—$(CH_2)_{0-2}$—$R^m$, or
(10) —C(=O)N($R^a$)—$(CH_2)_{0-2}$—$R^m$;

with the proviso that when one of $R^8$ and $R^{11}$ is —$(CH_2)_{1-2}$—$R^m$, —$(CH_2)_{0-2}$—C(=O)—$(CH_2)_{0-2}$—$R^m$, —C(=O)—O—$(CH_2)_{0-2}$—$R^m$, or —C(=O)N($R^a$)—$(CH_2)_{0-2}$—$R^m$, then the other of $R^8$ and $R^{11}$ is other than —$(CH_2)_{1-2}$—$R^m$, —$(CH_2)_{0-2}$—C(=O)—$(CH_2)_{0-2}$—$R^m$, —C(=O)—O—$(CH_2)_{0-2}$—$R^m$, or —C(=O)N($R^a$)—$(CH_2)_{0-2}$—$R^m$;

$R^m$ is aryl selected from phenyl and naphthyl; a 5- or 6-membered saturated heterocyclic ring containing 1 or 2 heteroatoms independently selected from N and O; a 5- or 6-membered heteroaromatic ring containing from 1 to 3 heteroatoms selected from N, O and S; or a bicyclic heterocycle which is a benzene ring fused to a saturated or unsaturated heterocycle containing from 1 to 3 nitrogen atoms; wherein the aryl is optionally substituted with from 1 to 3 substituents each of which is independently halogen, —$C_{1-4}$ alkyl, —$CF_3$, —O—$C_{1-4}$ alkyl, —$OCF_3$, or —N($R^aR^b$); and the saturated heterocyclic ring is optionally substituted with from 1 to 3 substituents each of which is independently —$C_{1-4}$ alkyl or oxo; and is additionally and optionally mono-substituted with phenyl, —$(CH_2)_{1-2}$-phenyl, —C(=O)-phenyl, —$CO_2$-phenyl, or —$CO_2$—$(CH_2)_{1-2}$-phenyl; and the heteroaromatic ring or the bicyclic heterocycle is optionally substituted with 1 or 2 substituents each of which is independently —$C_{1-4}$ alkyl or oxo; and each $R^a$ and $R^b$ is independently —H or —$C_{1-4}$ alkyl;

and all other variables are as defined in the class;

or a pharmaceutically acceptable salt thereof.

Another embodiment of the present invention is a compound of Formula (I), wherein $R^2$ is —H or methyl;

$R^3$ is —H;

$R^4$ is —$CH_2$-Q; wherein Q is phenyl optionally substituted with from 1 to 3 substituents each of which is independently —F, —Cl, —Br, —OH, —$C_{1-4}$ alkyl, —$CF_3$, —O—$C_{1-4}$ alkyl, —$OCF_3$, —CN, —$SR^a$, or —$SO_2R^a$; and is additionally and optionally mono-substituted with methylenedioxy attached to two adjacent ring carbon atoms, phenyl, or —O-phenyl;

and all other variables are as originally defined above;

or a pharmaceutically acceptable salt thereof.

In an aspect of this embodiment, $R^4$ is —$CH_2$-Q; wherein Q is phenyl optionally substituted with from 1 to 3 substituents each of which is independently —F, —Cl, —Br, —OH, —$C_{1-4}$ alkyl, —$CF_3$, —O—$C_{1-4}$ alkyl, —$OCF_3$, —CN, or —$SO_2R^a$; and is additionally and optionally mono-substituted with methylenedioxy attached to two adjacent ring carbon atoms, phenyl, or —O-phenyl.

Aspects of this embodiment include a compound of Formula (I) in which $R^1$ is as defined in any of the preceding classes or sub-classes.

Another class of compounds of the present invention includes any compound of Formula (II):

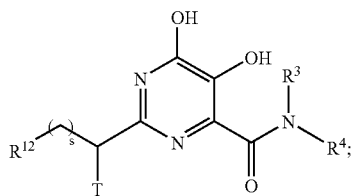

(II)

wherein T is:
(1) —H,
(2) —OH,
(3) —$C_{1-4}$ haloalkyl,
(4) —$C_{1-3}$ alkyl, optionally substituted with —OH or —O—$C_{1-4}$ alkyl,
(5) —O—$C_{1-4}$ haloalkyl,
(6) —O—$C_{1-4}$ alkyl
(7) —N($R^a R^b$),
(8) —N($R^a$)—($CH_2$)$_2$—OH,
(9) —N($R^a$)—$CO_2 R^b$,
(10) —N($R^a$)—C(=O)—($CH_2$)$_{1-2}$—N($R^a R^b$),
(11) —$R^k$,
(12) —($CH_2$)$_{1-4}$—$R^k$,
(13) —($CH_2$)$_{0-2}$—O—($CH_2$)$_{0-2}$—$R^k$,
(14) —($CH_2$)$_{0-2}$—N($R^a$)—($CH_2$)$_{0-3}$—$R^k$, or
(15) —($CH_2$)$_{0-2}$—N($R^a$)—C(=O)—($CH_2$)$_{0-2}$—$R^k$;

$R^k$ is aryl selected from phenyl and naphthyl; a 5- or 6-membered saturated heterocyclic ring containing from 1 to 3 heteroatoms independently selected from N, O and S; a 5- or 6-membered heteroaromatic ring containing from 1 to 3 heteroatoms independently selected from N, O and S; or a bicyclic heterocycle which is a benzene ring fused to a 5- or 6-membered saturated or unsaturated heterocyclic ring containing from 1 to 3 heteroatoms independently selected from N, O and S; wherein the aryl is optionally substituted with from 1 to 4 substituents each of which is independently halogen, —$C_{1-4}$ alkyl, —$C_{1-4}$ alkyl-$OR^a$, —$C_{1-4}$ haloalkyl, —O—$C_{1-4}$ alkyl, —O—$C_{1-4}$ haloalkyl, or —N($R^a R^b$); and the saturated heterocyclic ring is optionally substituted with from 1 to 4 substituents each of which is independently —$C_{1-4}$ alkyl; —$C_{1-4}$ alkyl-$OR^a$; —$C_{1-4}$ haloalkyl; —O—$C_{1-4}$ alkyl; —O—$C_{1-4}$ haloalkyl; —C(=O)$R^a$; oxo; ethylenedioxy spiro substituted on a ring carbon; phenyl; —$CH_2$-phenyl; a 5- or 6-membered saturated heterocyclic ring containing from 1 to 4 heteroatoms independently selected from N, O and S; —$CH_2$-saturated heterocycle which is a a 5- or 6-membered ring containing from 1 to 4 heteroatoms independently selected from N, O and S; or a 5- or 6-membered heteroaromatic ring containing from 1 to 4 heteroatoms independently selected from N, O and S;

the heteroaromatic ring is optionally substituted with from 1 to 4 substituents each of which is independently —$C_{1-4}$ alkyl, —$C_{1-4}$ alkyl-$OR^a$, —$C_{1-4}$ haloalkyl, —O—$C_{1-4}$ alkyl, —O—$C_{1-4}$ haloalkyl, or oxo; and the bicyclic heterocycle is optionally substituted with from 1 to 4 substituents each of which is independently —$C_{1-4}$ alkyl or oxo;

$R^{12}$ is phenyl which is optionally substituted with from 1 to 3 substituents each of which is independently —F, —Cl, Br, —$C_{1-4}$ alkyl, —$CF_3$, —O—$C_{1-4}$ alkyl, —$OCF_3$, methylenedioxy attached to two adjacent carbon atoms, or phenyl;

each $R^a$ and $R^b$ is independently —H or —$C_{1-4}$ alkyl; and
s is an integer equal to zero, 1, 2, or 3;

and all other variables are as originally defined above;

or a pharmaceutically acceptable salt thereof.

A sub-class of the preceding class of compounds of the present invention includes any compounds of Formula (II) exactly as defined in the class, except that s is zero, 1 or 2; and with the proviso that when s is 1 or 2, T is —H.

Another sub-class of the preceding class of compounds of the present invention includes any compounds of Formula (II), wherein $R^3$ is —H; and $R^4$ is —$CH_2$-Q; wherein Q is phenyl optionally substituted with from 1 to 3 substituents each of which is independently —F, —Cl, —Br, —OH, —$C_{1-4}$ alkyl, —$CF_3$, —O—$C_{1-4}$ alkyl, —$OCF_3$, —CN, —$SR^a$, or —$SO_2 R^a$; and is additionally and optionally mono-substituted with methylenedioxy attached to two adjacent ring carbon atoms, phenyl, or —O-phenyl;

and all other variables are as defined in the class;

or a pharmaceutically acceptable salt thereof.

In a feature of this sub-class, $R^4$ is —$CH_2$-Q; wherein Q is phenyl optionally substituted with from 1 to 3 substituents each of which is independently —F, —Cl, —Br, —OH, —$C_{1-4}$ alkyl, —$CF_3$, —O—$C_{1-4}$ alkyl, —$OCF_3$, —CN, or —$SO_2 R^a$; and is additionally and optionally mono-substituted with methylenedioxy attached to two adjacent ring carbon atoms, phenyl, or —O-phenyl;

Still another class of compounds of the present invention includes any compound of Formula (III):

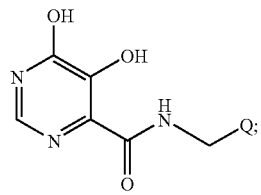

(III)

wherein Q is phenyl optionally substituted with from 1 to 3 substituents each of which is independently —F, —Cl, —Br, —OH, —$C_{1-4}$ alkyl, —$CF_3$, —O—$C_{1-4}$ alkyl, —$OCF_3$, —CN, —$SR^a$, or —$SO_2 R^a$; and is additionally and optionally mono-substituted with methylenedioxy attached to two adjacent ring carbon atoms, phenyl, or —O-phenyl;

each $R^a$ is independently —H or —$C_{1-4}$ alkyl or a pharmaceutically acceptable salt thereof. In a subclass of this class, Q is phenyl optionally substituted with from 1 to 3 substituents each of which is independently —F, —Cl, —Br, —OH, —$C_{1-4}$ alkyl, —$CF_3$, —O—$C_{1-4}$ alkyl, —$OCF_3$, —CN, or —$SO_2 R^a$.

Still another class of compounds of the present invention includes any compound of Formula (I), wherein $R^1$ is (1) —$C_{1-4}$ alkyl, which is optionally substituted with 1 to 3 substituents each of which is independently fluoro, chloro, —OH, —O—$C_{1-4}$ alkyl, —O—$C_{1-4}$ haloalkyl, —C(=O)$R^a$, —$CO_2 R^a$, —$SR^a$, —S(=O)$R^a$, —N($R^a R^b$), —C(=O)—($CH_2$)$_{0-2}$N($R^a R^b$), —N($R^a$)—C(=O)—($CH_2$)$_{1-2}$N($R^b R^c$), —$SO_2 R^a$, —N($R^a$)$SO_2 R^b$, —$SO_2 N(R^a R^b)$, —N($R^a$)—C($R^b$)=O,

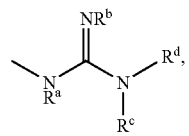

—N(R$^a$)C(=O)N(R$^b$R$^c$), —N(R$^a$)C(=O)C(=O)N(R$^b$R$^c$), or —N(R$^a$)C(=O)OR$^b$, (2) —(CH$_2$)$_{1-3}$—R$^k$,
(3) —(CH$_2$)$_{1-3}$—O—(CH$_2$)$_{0-2}$—R$^k$,
(4) —(CH$_2$)$_{1-3}$—N—(CH$_2$)$_{0-2}$—R$^k$,
(5) —(CH$_2$)$_{1-3}$—N(R$^a$)C(=O)—(CH$_2$)$_{0-2}$—R$^k$,
(6) —(CH$_2$)$_{1-3}$—N(R$^a$)C(=O)—O—(CH$_2$)$_{0-2}$—R$^k$,
(7) —(CH$_2$)$_{0-3}$—C(=O)N(R$^a$)—(CH$_2$)$_{0-2}$—R$^k$,
(8) —C(=O)—(CH$_2$)$_{0-2}$—R$^k$,
(9) —C(CH$_3$)$_2$N(R$^a$)C(=O)OCH$_2$R$^k$,
(10) —C(CH$_3$)$_2$N(R$^a$)CH$_2$R$^k$,
(11) —C(CH$_3$)$_2$N(R$^a$)C(=O)R$^k$, or
(12) —C(R$^b$)(N(R$^a$)C(=O)R$^k$)(CH$_2$OR$^c$),

R$^k$ is aryl selected from phenyl and naphthyl, with the proviso that when R$^1$ is —(CH$_2$)$_{1-3}$—R$^k$, then R$^k$ is not phenyl; a bicyclic carbocycle selected from indanyl and tetrahydronaphthyl; a 5- or 6-membered saturated heterocyclic ring containing from 1 to 4 heteroatoms independently selected from N, O and S; a 5- or 6-membered heteroaromatic ring containing from 1 to 4 heteroatoms independently selected from N, O and S; or a bicyclic heterocycle which is a benzene ring fused to a 5- or 6-membered saturated or unsaturated heterocyclic ring containing from 1 to 3 heteroatoms independently selected from N, O and S, with the proviso that the bicyclic heterocycle is not benzo-1,3-dioxolyl;

wherein the aryl, bicyclic carbocycle, saturated heterocyclic ring, heteroaromatic ring, or bicyclic heterocycle is optionally substituted with from 1 to 3 substituents each of which is independently (1) fluoro, chloro, or bromo,
(2) —OH,
(3) —CN,
(4) —CF$_3$,
(4) —C$_{1-4}$ alkyl, which is optionally substituted with 1 or 2 substituents each of which is independently —OH, —O—C$_{1-4}$ alkyl, —OCF$_3$, —C(=O)R$^a$, —CO$_2$R$^a$, —SR$^a$, or —N(R$^a$R$^b$),
(5) —OCF$_3$,
(5) —O—C$_{1-4}$ alkyl,
(8) oxo,
(9) methylenedioxy attached to two adjacent ring carbon atoms,
(10) —C(=O)R$^a$,
(11) —CO$_2$R$^a$,
(12) —SR$^a$,
(13) —S(=O)R$^a$,
(14) —N(R$^a$R$^b$),
(15) —(CH$_2$)$_{0-2}$—C(=O)N(R$^a$R$^b$),
(16) —C(=O)—(CH$_2$)$_{1-2}$—N(R$^a$R$^b$), or
(17) —SO$_2$R$^a$;

and all other variables are as originally defined above;

or a pharmaceutically acceptable salt thereof.

In a sub-class of this class, R$^1$ is
(1) —C$_{1-4}$ alkyl, which is optionally substituted with 1 to 3 substituents each of which is independently fluoro, chloro, —OH, —O—C$_{1-4}$ alkyl, —O—C$_{1-4}$ haloalkyl, —C(=O)R$^a$, —CO$_2$R$^a$, —SR$^a$, —S(=O)R$^a$, —N(R$^a$R$^b$), —C(=O)—(CH$_2$)$_{0-2}$N(R$^a$R$^b$), —N(R$^a$)—C(=O)—(CH$_2$)$_{1-2}$N(R$^b$R$^c$), —SO$_2$R$^a$, —N(R$^a$)SO$_2$R$^b$, —SO$_2$N(R$^a$R$^b$), —N(R$^a$)—C(R$^b$)=O, or

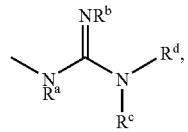

(2) —(CH$_2$)$_{1-3}$—R$^k$,
(3) —(CH$_2$)$_{1-3}$—O—(CH$_2$)$_{0-2}$—R$^k$,
(4) —(CH$_2$)$_{1-3}$—N—(CH$_2$)$_{0-2}$—R$^k$,
(5) —(CH$_2$)$_{1-3}$—N(R$^a$)C(=O)—(CH$_2$)$_{0-2}$—R$^k$,
(6) —(CH$_2$)$_{1-3}$—N(R$^a$)C(=O)—O—(CH$_2$)$_{0-2}$—R$^k$,
(7) —(CH$_2$)$_{0-3}$—C(=O)N(R$^a$)—(CH$_2$)$_{0-2}$—R$^k$, or
(8) —C(=O)—(CH$_2$)$_{0-2}$—R$^k$.

A sub-class of the preceding class of compounds of the present invention includes any compounds of Formula (I), wherein R$^2$ is —H; and
R$^4$ is —CH$_2$-Q; wherein Q is phenyl optionally substituted with from 1 to 3 substituents each of which is independently —F, —Cl, —Br, —OH, —C$_{1-4}$ alkyl, —CF$_3$, —O—C$_{1-4}$ alkyl, —OCF$_3$, —CN, —SR$^a$, or —SO$_2$R$^a$; and is additionally and optionally mono-substituted with methylenedioxy attached to two adjacent ring carbon atoms, phenyl, or —O-phenyl;

each R$^a$ and R$^b$ is independently —H or —C$_{1-4}$ alkyl;

R$^k$ is aryl selected from phenyl and naphthyl, with the proviso that when R$^1$ is —(CH$_2$)$_{1-3}$—R$^k$, then R$^k$ is not phenyl; a bicyclic carbocycle selected from indanyl and tetrahydronaphthyl; a 5- or 6-membered saturated heterocyclic ring containing from 1 to 4 heteroatoms independently selected from N, O and S; a 5- or 6-membered heteroaromatic ring containing from 1 to 4 heteroatoms independently selected from N, O and S; or a bicyclic heterocycle which is a benzene ring fused to a 5- or 6-membered saturated or unsaturated heterocyclic ring containing from 1 to 3 heteroatoms independently selected from N, O and S, with the proviso that the bicyclic heterocycle is not benzo-1,3-dioxolyl;

wherein the aryl, bicyclic carbocycle, saturated heterocyclic ring, heteroaromatic ring, or bicyclic heterocycle is optionally substituted with from 1 to 3 substituents each of which is independently (1) fluoro, chloro, or bromo,
(2) —OH,
(3) —CN,
(4) —CF$_3$,
(4) —C$_{1-4}$ alkyl, which is optionally substituted with 1 or 2 substituents each of which is independently —OH, —O—C$_{1-4}$ alkyl, —OCF$_3$, —C(=O)R$^a$, —CO$_2$R$^a$, —SR$^a$, or —N(R$^a$R$^b$),
(5) —OCF$_3$,
(5) —O—C$_{1-4}$ allyl,
(8) oxo,
(9) methylenedioxy attached to two adjacent ring carbon atoms,
(10) —C(=O)R$^a$,
(11) —CO$_2$R$^a$,
(12) —SR$^a$,
(13) —S(=O)R$^a$,
(14) —N(R$^a$R$^b$),

(15) —(CH$_2$)$_{0-2}$—C(=O)N(R$^a$R$^b$),
(16) —C(=O)—(CH$_2$)$_{1-2}$—N(R$^a$R$^b$), or
(17) —SO$_2$R$^a$;

and all other variables are as defined in the class;

or a pharmaceutically acceptable salt thereof.

In a feature of this sub-class, R$^4$ is —CH$_2$-Q; wherein Q is phenyl optionally substituted with from 1 to 3 substituents each of which is independently —F, —Cl, —Br, —OH, —C$_{1-4}$ alkyl, —CF$_3$, —O—C$_{1-4}$ alkyl, —OCF$_3$, —CN, or —SO$_2$R$^a$; and is additionally and optionally mono-substituted with methylenedioxy attached to two adjacent ring carbon atoms, phenyl, or —O-phenyl;

Still another class of compounds of the present invention includes any compound of Formula (IV):

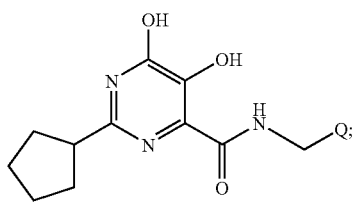

(IV)

wherein Q is phenyl optionally substituted with from 1 to 3 substituents each of which is independently —F, —Cl, —Br, —OH, —C$_{1-4}$ alkyl, —CF$_3$, —O—C$_{1-4}$ alkyl, —OCF$_3$, —CN, —SR$^a$, or —SO$_2$R$^a$; and is additionally and optionally mono-substituted with methylenedioxy attached to two adjacent ring carbon atoms, phenyl, or —O-phenyl;

each R$^a$ is independently —H or —C$_{1-4}$ alkyl or a pharmaceutically acceptable salt thereof.

In a sub-class of this class, Q is phenyl optionally substituted with from 1 to 3 substituents each of which is independently —F, Cl, —Br, —OH, —C$_{1-4}$ alkyl, —CF$_3$, —O—C$_{1-4}$ alkyl, —OCF$_3$, —CN, or —SO$_2$R$^a$.

Still another class of compounds of the present invention includes any compound of Formula (V):

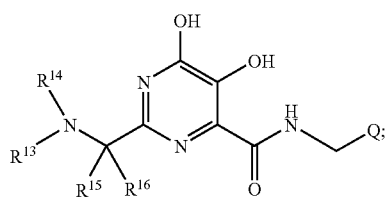

(V)

wherein
R$^{13}$ is —H or —C$_{1-6}$ alkyl;
R$^{14}$ is —H, —C$_{1-6}$ alkyl, —C(=O)—C$_{1-6}$ alkyl, —C(=O)—(CH$_2$)$_{0-2}$-J, or —C(=O)—O—(CH$_2$)$_{0-2}$-J; wherein J is aryl selected from phenyl and naphthyl; a 5- or 6-membered saturated heterocyclic ring containing from 1 to 4 heteroatoms independently selected from N, O and S; or a 5- or 6-membered heteroaromatic ring containing from 1 to 4 heteroatoms independently selected from N, O and S; and wherein the aryl is optionally substituted with from 1 to 3 substituents each of which is independently fluoro, chloro, bromo, —CF$_3$, —C$_{1-4}$ alkyl, —OCF$_3$, or —O—C$_{1-4}$ alkyl; and wherein the saturated heterocyclic ring or heteroaromatic ring is optionally substituted with from 1 to 3 substituents each of which is independently fluoro, chloro, bromo, —CF$_3$, —C$_{1-4}$ alkyl, —OCF$_3$, —O—C$_{1-4}$ alkyl, or oxo;

R$^{15}$ and R$^{16}$ are each independently —C$_{1-6}$ alkyl; or alternatively R$^{15}$ and R$^{16}$ together with the carbon atom to which they are both attached form C$_{3-8}$ cycloalkyl; and Q is phenyl optionally substituted with from 1 to 3 substituents each of which is independently —F, —Cl, —Br, —OH, —C$_{1-4}$ alkyl, —CF$_3$, —O—C$_{1-4}$ alkyl, —OCF$_3$, —CN, —SR$^a$, or —SO$_2$R$^a$; and is additionally and optionally mono-substituted with methylenedioxy attached to two adjacent ring carbon atoms, phenyl, or —O-phenyl;

each R$^a$ is independently —H or —C$_{1-4}$ alkyl or a pharmaceutically acceptable salt thereof.

In a sub-class of this class, Q is phenyl optionally substituted with from 1 to 3 substituents each of which is independently —F, —Cl, —Br, —OH, —C$_{1-4}$ alkyl, —CF$_3$, —O—C$_{1-4}$ alkyl, —OCF$_3$, —CN, or —SO$_2$R$^a$; and is additionally and optionally mono-substituted with methylenedioxy attached to two adjacent ring carbon atoms, phenyl, or —O-phenyl.

A sub-class of the preceding class of compounds of the present invention includes any compounds of Formula (V), wherein R$^{15}$ and R$^{16}$ are both methyl; or alternatively R$^{15}$ and R$^{16}$ together with the carbon atom to which they are both attached form cyclohexyl;

and all other variables are as defined in the class;

or a pharmaceutically acceptable salt thereof.

It is to be understood that additional embodiments of the present invention include, but are not limited to, compounds of Formula I wherein each of two or three or more of R$^1$, R$^2$, R$^3$, R$^4$, R$^a$, R$^b$, R$^c$, R$^d$, R$^k$ and R$^m$ is independently defined in accordance with its definition in one of the embodiments or an aspect thereof as set forth above, or in accordance with its definition in one of the foregoing classes set forth above or a sub-class or feature thereof. Any and all possible combinations of these variables in Formula I are additional embodiments within the scope of the present invention.

An aspect of the present invention is a compound selected from the group consisting of
4-fluorobenzyl)-5,6-dihydroxy-2-[1-methyl-1-(methylamino)ethyl]pyrimidine-4-carboxamide;
N-(4-fluorobenzyl)-5,6-dihydroxy-2-(4-methylmorpholin-3-yl)pyrimidine-4-carboxamide;
2-[1-benzoyl-4-(N,N-dimethylglycyl)piperazin-2-yl]-N-(4-fluorobenzyl)-5,6-dihydroxypyrimidine-4-carboxamide;
2-(1-benzoyl-4-methylpiperazin-2-yl)-N-(4-fluorobenzyl)-5,6-dihydroxypyrimidine-4-carboxamide;
N-(4-fluorobenzyl)-5,6-dihydroxy-2-(1-methylpiperidin-2-yl)pyrimidine-4-carboxamide;
N-(4-fluorobenzyl)-5,6-dihydroxy-2-[1-(pyridin-2-ylcarbonyl)-1,2,3,4-tetrahydroquinolin-2-yl]pyrimidine-4-carboxamide;
N-(4-fluorobenzyl)-5,6-dihydroxy-2-[4-methyl-1-(pyridin-2-ylcarbonyl)piperazin-2-yl]pyrimidine-4-carboxamide;
N-(4-fluorobenzyl)-5,6-dihydroxy-2-[1-methyl-4-(pyridin-2-ylcarbonyl)piperazin-2-yl]pyrimidine-4-carboxamide;
2-(1-ethylpiperidin-2-yl)-N-(4-fluorobenzyl)-5,6-dihydroxypyrimidine-4-carboxamide;

N-(4-fluorobenzyl)-5,6-dihydroxy-2-(4-isopropyl-1-methylpiperazin-2-yl)pyrimdine-4-carboxamide;
2-[1-(acetylamino)cyclohexyl]-N-(4-fluorobenzyl)-5,6-dihydroxypyrimidine-4-carboxamide;
N-(4-fluorobenzyl)-5,6-dihydroxy-2-[1-(morpholin-4-ylacetyl)piperidin-2-yl]pyrimidine-4-carboxamide;
N-(4-fluorobenzyl)-5,6-dihydroxy-2-(pyrrolidin-1-ylmethyl)pyrimidine-4-carboxamide;
N-(4-fluorobenzyl)-5,6-dihydroxy-2-(1-methylpyrrolidin-2-yl)pyrimidine-4-carboxamide;
2-[1-(N,N-dimethylglycyl)piperidin-2-yl]-N-(4-fluorobenzyl)-5,6-dihydroxypyrimidine-4-carboxamide;
N-(4-fluorobenzyl)-5,6-dihydroxy-2-{1-methyl-1-[(pyridin-2-lcarbonyl)amino]ethyl}pyrimidine-4-carboxamide;
2-[1-(dimethylamino)-2-phenylethyl]-N-(4-fluorobenzyl)-5,6-dihydroxypyrimidine-4-carboxamide;
2-{1-[(2,4-dimethyl-1,3-thiazol-5-yl)carbonyl]piperidin-2-yl}-N-(4-fluorobenzyl)-5,6-dihydroxypyrimidine-4-carboxamide;
2-[1-(3-chlorobenzoyl)-4-methylpiperazin-2-yl]-N-(4-fluorobenzyl)-5,6-dihydroxypyrimidine-4-carboxamide;
N-(4-fluorobenzyl)-5,6-dihydroxy-2-[1-methyl-4-(methylsulfonyl)piperazin-2-yl]pyrimidine-4-carboxamide;
N-(4-fluorobenzyl)-5,6-dihydroxy-2-(1-isopropyl-4-methylpiperazin-2-yl)pyrimdine-4-carboxamide;
N-(3-bromo-4-fluorobenzyl)-2-[1-(dimethylamino)-1-methylethyl]-5,6-dihydroxypyrimidine-4-carboxamide;
2-[1-(dimethylamino)cyclohexyl]-N-(4-fluorobenzyl)-5,6-dihydroxypyrimidine-4-carboxamide;
N-(4-fluorobenzyl)-5,6-dihydroxy-2-{1-[(pyridin-2-ylcarbonyl)amino]cyclohexyl}pyrimidine-4-carboxamide;
2-(4-benzyl-methylpiperazin-2-yl)-N-(4-fluorobenzyl)-5,6-dihydroxypyrimidine-4-carboxamide;
N-(2,3-dimethoxybenzyl)-5,6-dihydroxy-2-[4-(1-piperidin-1-ylethyl)phenyl]pyrimidine-4-carboxamide;
N-(4-fluorobenzyl)-5,6-dihydroxy-2-(2-methyl-1,2,3,4-tetrahydroisoquinolin-3-yl)pyrimidine-4-carboxamide;
N-(2,3-dimethoxybenzyl)-2-[1-(N,N-dimethylglycyl)piperidin-2-yl]-5,6-dihydroxypyrimidine-4-carboxamide;
2-[1-(anilinocarbonyl)piperidin-2-yl]-N-(4-fluorobenzyl)-5,6-dihydroxypyrimidine-4-carboxamide;
2-[(2S,4R)-1-benzoyl-4-(benzyloxy)pyrrolidin-2-yl]-N-(4-fluorobenzyl)-5,6-dihydroxypyrimidine-4-carboxamide;
N-(4-fluorobenzyl)-5,6-dihydroxy-2-[1-(pyridin-2-ylcarbonyl)piperidin-2-yl]pyrimidine-4-carboxamide;
N-(4-fluorobenzyl)-5,6-dihydroxy-2-[2-(morpholin-4-ylacetyl)-1,2,3,4-tetrahydroisoquinolin-3-yl]pyrimidine-4-carboxamide;
N-(4-fluorobenzyl)-5,6-dihydroxy-2-{2-phenyl-1-[(pyridin-2-lcarbonyl)amino]ethyl}pyrimidine-4-carboxamide;
2-(1-benzoylpiperidin-2-yl)-N-(4-fluorobenzyl)-5,6-dihydroxypyrimidine-4-carboxamide;
2-(1-benzylpiperidin-2-yl)-N-(4-fluorobenzyl)-5,6-dihydroxypyrimidine-4-carboxamide;
2-(1-benzoylpyrrolidin-2-yl)-N-(4-fluorobenzyl)-5,6-dihydroxypyrimidine-4-carboxamide;
N-(4-fluorobenzyl)-5,6-dihydroxy-2-(1-isonicotinoylpiperidin-2-yl)pyrimidine-4-carboxamide;
N-(2,3-dimethoxybenzyl)-5,6-dihydroxy-2-(1-isonicotinoylpiperidin-2-yl)pyrimidine-4-carboxamide;
N-(4-fluorobenzyl)-5,6-dihydroxy-2-[1-(methylsulfonyl)piperidin-2-yl]pyrimidine-4-carboxamide;
2-(1-benzoyl-1,2,3,4-tetrahydroquinolin-2-yl)-N-(4-fluorobenzyl)-5,6-dihydroxypyrimidine-4-carboxamide;
2-{1-[(N,N-dimethylglycyl)amino]-2-phenylethyl}-N-(4-fluorobenzyl)-5,6-dihydroxypyrimidine-4-carboxamide;
N-(2,3-dimethoxybenzyl)-5,6-dihydroxy-2-[4-(piperidin-1-ylmethyl)phenyl]pyrimidine-4-carboxamide;
2-{4-[(diethylamino)methyl]phenyl}-N-(2,3-dimethoxybenzyl)-5,6-dihydroxypyrimidine-4-carboxamide;
N-(4-fluorobenzyl)-5,6-dihydroxy-2-[1-(pyridin-4-ylmethyl)piperidin-2-yl]pyrimidine-4-carboxamide;
2-(1-benzoylpyrrolidin-2-yl)-N-(2,3-dimethoxybenzyl)-5,6-dihydroxypyrimidine-4-carboxamide;
tert-butyl 2-(4-{[(4-fluorobenzyl)amino]carbonyl}-5,6-dihydroxypyrimidin-2-yl)morpholine-4-carboxylate;
N-(4-fluorobenzyl)-5,6-dihydroxy-2-[1-(pyridin-3-ylcarbonyl)piperidin-2-yl]pyrimidine-4-carboxamide;
2-[2-N,N-dimethylglycyl)-1,2,3,4-tetrahydroisoquinolin-3-yl]-N-(4-fluorobenzyl)-5,6-dihydroxypyrimidine-4-carboxamide;
2-(1-benzoyl-2,3-dihydro-1H-indol-2-yl)-N-(4-fluorobenzyl)-5,6-dihydroxypyrimidine-4-carboxamide;
2-(2-benzoyl-1,2,3,4-tetrahydroisoquinolin-3-yl)-N-(4-fluorobenzyl)-5,6-dihydroxypyrimidine-4-carboxamide;
2-(1-amino-2-phenylethyl)-N-(4-fluorobenzyl)-5,6-dihydroxypyrimidine-4-carboxamide;
2-(4-benzylmorpholin-3-yl)-N-(4-fluorobenzyl)-5,6-dihydroxypyrimidine-4-carboxamide;
N-(4-fluorobenzyl)-5,6-dihydroxy-2-{1-[(1-methyl-1H-imidazol-2-yl)carbonyl]piperidin-2-yl}pyrimidine-4-carboxamide;
N-(2,3-dimethoxybenzyl)-5,6-dihydroxy-2-[4-(morpholin-4-ylmethyl)phenyl]pyrimidine-4-carboxamide;
N-(4-fluorobenzyl)-5,6-dihydroxy-2-(morpholin-4-ylmethyl)pyrimidine-4-carboxamide;
N-(4-Fluorobenzyl)-5,6-dihydroxypyrimidine-4-carboxamide;
2-{4-[({[(2-chlorophenyl)sulfonyl]amino}carbonyl)amino]thien-3-yl}-N-(2,3-dimethoxybenzyl)-5,6-dihydroxypyrimidine-4 carboxamide;
$N^4$-(4-fluorobenzyl)-5,6-dihydroxy-$N^2$-(pyridin-2-ylmethyl)pyrimidine-2,4-dicarboxamide;
2-Benzyl-N-(4-fluorobenzyl)-5-hydroxy-6-(2-morpholin-1-ylethoxy)pyrimidine-4-carboxamide;

and pharmaceutically acceptable salts thereof.

Another aspect of the present invention is a compound selected from the group consisting of
N-(4-fluorobenzyl)-5,6-dihydroxy-2-(1-methylpiperidin-2-yl)pyrimidine-4-carboxamide;
2-[1-(dimethylamino)-1-methylethyl]-N-(4-fluorobenzyl)-5,6-dihydroxypyrimidine-4-carboxamide;
N-(4-fluorobenzyl)-5,6-dihydroxy-2-(4-methylmorpholin-3-yl)pyrimidine-4-carboxamide;
2-[(dimethylamino)(phenyl)methyl]-N-(4-fluorobenzyl)-5,6-dihydroxypyrimidine-4-carboxamide;
2-{4-[(diethylamino)methyl]phenyl}-N-(2,3-dimethoxybenzyl)-5,6-dihydroxypyrimidine-4-carboxamide;
N-benzyl-5,6-dihydroxy-2-(3-phenylpropyl)pyrimidine-4-carboxamide;
N-(4-fluorobenzyl)-5,6-dihydroxy-2-[1-(pyridin-2-ylcarbonyl)-1,2,3,4-tetrahydroquinolin-2-yl]pyrimidine-4-carboxamide;

and pharmaceutically acceptable salts thereof.

Another aspect of the present invention is a compound selected from the group consisting of
benzyl 1-[4-({[4-fluoro-2-(methylsulfonyl)benzyl]amino}carbonyl)-5,6-dihydroxypyrimidin-2-yl]-1-methylethylcarbamate;
2-(1-amino-1-methylethyl)-N-[4-fluoro-2-(methylsulfonyl)benzyl]-5,6-dihydroxypyrimidine-4-carboxamide;

2-[1-(dimethylamino)-1-methylethyl]-N-[4-fluoro-2-(methylsulfonyl)benzyl]-5,6-dihydroxypyrimidine-4-carboxamide;
2-(1-aminocyclopropyl)-N-(4-fluorobenzyl)-5,6-dihydroxypyrimidine-4-carboxamide;
2-[1-(dimethylamino)cyclopropyl]-N-(4-fluorobenzyl)-5,6-dihydroxypyrine-4-carboxamide;
N-(4-fluorobenzyl)-5,6-dihydroxy-2-{1-[(pyrazin-2-ylcarbonyl)amino]cyclopropyl}pyrimidine-4-carboxamide;
benzyl 1-(4-{[(4-fluorobenzyl)amino]carbonyl}-5,6-dihydroxypyrimidin-2-yl)cyclopentylcarbamate;
2-(1-aminocyclopentyl)-N-(4-fluorobenzyl)-5,6-dihydroxypyrimidine-4-carboxamide;
2-[1-(dimethylamino)cyclopentyl]-N-(4-fluorobenzyl)-5,6-dihydroxypyrimidine-4-carboxamide;
2-(1-{[(ethylamino)carbonyl]amino}-1-methylethyl)-N-(4-fluorobenzyl)-5,6-dihydroxypyrimidine-4-carboxamide;
2-[1-(benzylamino)-1-methylethyl]-N-(4-fluorobenzyl)-5,6-dihydroxypyrimidine-4-carboxamide;
2-[1-(benzoylamino)-1-methylethyl]-N-(4-fluorobenzyl)-5,6-dihydroxypyrimidine-4-carboxamide;
2-{1-[benzyl(methyl)amino]-1-methylethyl}-N-(4-fluorobenzyl)-5,6-dihydroxypyrimdine-4-carboxamide;
2-[1-(dimethylamino)-1-methylethyl]-N-(2-ethoxybenzyl)-5,6-dihydroxypyrimidine-4-carboxamide;
N-(2-chlorobenzyl)-2-[1-(dimethylamino)-1-methylethyl]-5,6-dihydroxypyrimidine-4-carboxamide;
N-(2-chlorobenzyl)-2-[1-(dimethylamino)-1-methylethyl]-5,6-dihydroxypyrimidine-4-carboxamide;
N-(5-chloro-2-methylbenzyl)-2-[1-(dimethylamino)-1-methylethyl]-5,6-dihydroxypyrimidine-4-carboxamide;
N-(4-fluorobenzyl)-5,6-dihydroxy-2-{1-methyl-1-[(pyrazin-2-ylcarbonyl)amino]ethyl}pyrimidine-4-carboxamide;
2-[1-(diethylamino)-1-methylethyl]-N-(4-fluorobenzyl)-5,6-dihydroxypyrimdine-4-carboxamide;
N-(4-fluorobenzyl)-5,6-dihydroxy-2-(1-methyl-1-morpholin-4-ylethyl)pyrimidine-4-carboxamide;
N-(4-fluorobenzyl)-5,6-dihydroxy-2-(1-methyl-1-piperidin-1-ylethyl)pyrimidine-4-carboxamide;
N-(4-fluorobenzyl)-5,6-dihydroxy-2-(1-methyl-1-pyrrolidin-1-ylethyl)pyrimidine-4-carboxamide;
N-(4-fluorobenzyl)-5,6-dihydroxy-2-{1-methyl-1-[methyl(pyridin-4-ylmethyl)amino]ethyl}pyrimidine-4-carboxamide;
2-[1-(dimethylamino)-1-methylethyl]-5,6-dihydroxy-N-[2-(methylthio)benzyl]pyrimidine-4-carboxamide;
N$^1$,N$^1$-diethyl-N~2~-[1-(4-{[(4-fluorobenzyl)amino]carbonyl}-5,6-dihydroxypyrimidin-2-yl)-1-methylethyl]ethanediamide;
2-[1-(1,4-dioxa-8-azaspiro[4.5]dec-8-yl)-1-methylethyl]-N-(4-fluorobenzyl)-5,6-dihydroxypyrimidine-4-carboxamide;
N-(4-fluorobenzyl)-5,6-dihydroxy-2-(1-methyl-1-{[(1-methyl-1H-imidazol-2-yl)carbonyl]amino}ethyl)pyrimidine-4-carboxamide;
N-(4-fluorobenzyl)-5,6-dihydroxy-2-[1-methyl-1-(4-oxopiperidin-1-yl)ethyl]pyrimidine-4-carboxamide;
N-(4-fluorobenzyl)-5,6-dihydroxy-2-{1-methyl-1-[methyl(pyridin-2-ylmethyl)amino]ethyl}pyrimidine-4-carboxamide;
N-[1-(4-{[(4-fluorobenzyl)amino]carbonyl}-5,6-dihydroxypyrimidin-2-yl)-1-methylethyl]-4-methylmorpholine-2-carboxamide;
2-{1-[acetyl(methyl)amino]-1-methylethyl}-N-(4-fluorobenzyl)-5,6-dihydroxypyrimidine-4-carboxamide;
2-[1-(acetylamino)-1-methylethyl]-N-(4-fluorobenzyl)-5,6-dihydroxypyrimidine-4-carboxamide;
2-{1-[4-(dimethylamino)piperidin-1-yl]-1-methylethyl}-N-(4-fluorobenzyl)-5,6-dihydroxypyrimidine-4-carboxamide;
N-(2,3-dimethoxybenzyl)-2-[1-(dimethylamino)-1-methylethyl]-5,6-dihydroxypyrimidine-4-carboxamide;
2-[4-(dimethylamino)tetrahydro-2H-pyran-4-yl]-N-(4-fluorobenzyl)-5,6-dihydroxypyrimidine-4-carboxamide;
N-(4-fluorobenzyl)-5,6-dihydroxy-2-(7-methyl-7-azabicyclo[2.2.1]hept-1-yl)pyrimidine-4-carboxamide;
2-(7-acetyl-7-azabicyclo[2.2.1]hept-1-yl)-N-(4-fluorobenzyl)-5,6-dihydroxypyrimidine-4-carboxamide;
2-(2-acetyl-2-azabicyclo[2.1.1]hex-1-yl)-N-(4-fluorobenzyl)-5,6-dihydroxypyrimidine-4-carboxamide;
N-(4-fluorobenzyl)-5,6-dihydroxy-2-(2-methyl-2-azabicyclo[2.1.1]hex-1-yl)pyrimidine-4-carboxamide;
tert-butyl (2S,4R)-4-(benzyloxy)-2-(4-{[(4-fluorobenzyl)amino]carbonyl}-5,6-dihydroxypyrimidin-2-yl)piperidine-1-carboxylate;
2-[(2S,4R)-4-(benzyloxy)piperidin-2-yl]-N-(4-fluorobenzyl)-5,6-dihydroxypyrimidine-4-carboxamide;
2-[(2S,4R)-4-(benzyloxy)-1-methylpiperidin-2-yl]-N-(4-fluorobenzyl)-5,6-dihydroxypyrimidine-4-carboxamide;
N-(4-fluorobenzyl)-5,6-dihydroxy-2-[(2S,4R)-4-hydroxy-1-methylpiperidin-2-yl]pyrimidine carboxamide;
2-[1-acetyl-4-(benzyloxy)piperidin-2-yl]-N-(4-fluorobenzyl)-5,6-dihydroxypyrimidine-4-carboxamide;
2-(1-ethyl-4-methylpiperazin-2-yl)-N-(4-fluorobenzyl)-5,6-dihydroxypyrimidine-4-carboxamide;
N-(4-fluorobenzyl)-5,6-dihydroxy-2-[4-methyl-1-(pyrazin-2-ylcarbonyl)piperazin-2-yl]pyrimidine-4-carboxamide;
tert-butyl 3-(4-{[(4-fluorobenzyl)amino]carbonyl}-5,6-dihydroxypyrimidin-2-yl)thiomorpholine-4-carboxylate;
N-(4-fluorobenzyl)-5,6-dihydroxy-2-thiomorpholin-3-ylpyrimidine-4-carboxamide;
N-(4-fluorobenzyl)-5,6-dihydroxy-2-(4-methylthiomorpholin-3-yl)pyrimidine-4-carboxamide;
N-(4-fluorobenzyl)-5,6-dihydroxy-2-[4-(pyridin-2-ylcarbonyl)thiomorpholin-3-yl]pyrimidine-4-carboxamide;
2-(4-acetylthiomorpholin-3-yl)-N-(4-fluorobenzyl)-5,6-dihydroxypyrimidine-4-carboxamide;
tert-butyl 1-(4-{[(4-fluorobenzyl)amino]carbonyl}-5,6-dihydroxypyrimidin-2-yl)-2-methoxyethylcarbamate;
2-[1-(dimethylamino)-2-methoxyethyl]-N-(4-fluorobenzyl)-5,6-dihydroxypyrimidine-4-carboxamide;
2-[1-(acetylamino)-2-methoxyethyl]-N-(4-fluorobenzyl)-5,6-dihydroxypyrimidine-4-carboxamide;
2-(1-amino-2-methoxyethyl)-N-(4-fluorobenzyl)-5,6-dihydroxypyrimidine-4-carboxamide;
N-(4-fluorobenzyl)-5,6-dihydroxy-2-{2-methoxy-1-[(pyridin-2-ylcarbonyl)amino]ethyl}pyrimidine-4-carboxamide;
N-(4-fluorobenzyl)-2-[1-(formylamino)-2-methoxyethyl]-5,6-dihydroxypyrimidine-4-carboxamide;
N-(4-fluorobenzyl)-5,6-dihydroxy-2-[2-methoxy-1-(methylamino)ethyl]pyrimidine-4-carboxamide;
2-{1-[acetyl(methyl)amino]-2-methoxyethyl}-N-(4-fluorobenzyl)-5,6-dihydroxypyrimidine-4-carboxamide;
N-(4-fluorobenzyl)-5,6-dihydroxy-2-{2-methoxy-1-[methyl(pyridin-2-ylcarbonyl)amino]ethyl}pyrimidine-4-carboxamide;
N-(4-fluorobenzyl)-5,6-dihydroxy-2-[(4R)-3-(pyridin-2-ylcarbonyl-1,3-thiazolidin-4-yl]pyrimidine-4-carboxamide;
N-(4-fluorobenzyl)-5,6-dihydroxy-2-[(4R)-1,3-thiazolidin-4-yl]pyrimidine-4-carboxamide;

N-(4-fluorobenzyl)-5,6-dihydroxy-2-[(4R)-3-methyl-1,3-thiazolidinyl]pyrimidine-4-carboxamide;

2-(3-acetyl-1,3-thiazolidin-2-yl)-N-(4-fluorobenzyl)-5,6-dihydroxypyrimidine-4-carboxamide;

N-(4-fluorobenzyl)-5,6-dihydroxy-2-(3-methyl-1,3-thiazolidin-2-yl)pyrimidine-4-carboxamide;

N-(4-fluorobenzyl)-5,6-dihydroxy-2-(1,2,4-trimethylpiperazin-2-yl)pyrimidine-4-carboxamide;

2-[2,4-dimethyl-1-(pyrazin-2-ylcarbonyl)piperazin-2-yl]-N-(4-fluorobenzyl)-5,6-dihydroxypyrimidine-4-carboxamide;

2-(1-acetyl-2,4-dimethylpiperazin-2-yl)-N-(4-fluorobenzyl)-5,6-dihydroxypyrimidine-4-carboxamide;

tert-butyl 1-(4-{[(4-fluorobenzyl)amino]carbonyl}-5,6-dihydroxypyrimidin-2-yl)-2-methoxy-1-methylethylcarbamate;

2-(1-amino-2-methoxy-1-methylethyl)-N-(4-fluorobenzyl)-5,6-dihydroxypyrimidine-4-carboxamide;

2-[1-(acetylamino)-2-methoxy-1-methylethyl]-N-(4-fluorobenzyl)-5,6-dihydroxypyrimidine-4-carboxamide;

2-[1-(dimethylamino)-2-methoxy-1-methylethyl]-N-(4-fluorobenzyl)-5,6-dihydroxypyrimidine-4-carboxamide;

N-(4-fluorobenzyl)-5,6-dihydroxy-2-[2-methoxy-1-methyl-1-(methylamino)ethyl]pyrimidine-4-carboxamide;

N-(4-fluorobenzyl)-5,6-dihydroxy-2-{2-methoxy-1-methyl-1-[(pyridin-2-ylcarbonyl)amino]ethyl}pyrimidine-4-carboxamide;

2-(1,2-dimethylpiperidin-2-yl)-N-(4-fluorobenzyl)-5,6-dihydroxypyrimidine-4-carboxamide;

2-{1-[acetyl(methyl)amino]-2-methoxy-1-methylethyl}-N-(4-fluorobenzyl)-5,6-dihydroxypyrimidine-4-carboxamide;

N-(4-fluorobenzyl)-5,6-dihydroxy-2-{2-methoxy-1-methyl-1-[methyl(pyridin-2-ylcarbonyl)amino]ethyl}pyrimidine-4-carboxamide;

2-{1-[(cyclohexylmethyl)(methyl)amino]-2-methoxy-1-methylethyl}-N-(4-fluorobenzyl)-5,6-dihydroxypyrimidine-4-carboxamide;

2-{1-[(cyclohexylmethyl)amino]-2-methoxy-1-methylethyl}-N-(4-fluorobenzyl)-5,6-dihydroxypyrimidine-4-carboxamide;

2-{1-[(cyclohexylmethyl)amino]-2-methoxy-1-methylethyl}-N-(4-fluorobenzyl)-5,6-dihydroxypyrimidine-4-carboxamide;

2-(4-acetyl-1,2-dimethylpiperazin-2-yl)-N-(4-fluorobenzyl)-5,6-dihydroxypyrimidine-4-carboxamide;

2-(1-acetyl-2-methylpiperidin-2-yl)-N-(4-fluorobenzyl)-5,6-dihydroxypyrimidine-4-carboxamide;

N-(4-fluorobenzyl)-5,6-dihydroxy-2-[2-methyl-1-(pyrazin-2-ylcarbonyl)piperidin-2-yl]pyrimidine-4-carboxamide;

N-(2,3-dimethoxybenzyl)-2-(1,2-dimethylpiperidin-2-yl)-5,6-dihydroxypyrimidine-4-carboxamide;

N-(4-fluorobenzyl)-5,6-hydroxy-2-[2-methyl-1-(pyridin-2-ylcarbonyl)piperidin-2-yl]pyrimidine-4-carboxamide;

2-{1-[(2,4-dimethyl-1,3-thiazol-5-yl)carbonyl]-2-methylpiperidin-2-yl}-N-(4-fluorobenzyl)-5,6-dihydroxypyrimidine-4-carboxamide;

2-[(2S)-1-acetyl-2-methylpyrrolidin-2-yl]-N-(4-fluorobenzyl)-5,6-dihydroxypyrimidine-4-carboxamide;

and pharmaceutically acceptable salts thereof.

Other embodiments of the present invention include the following:

(a) A pharmaceutical composition comprising a compound of Formula (I) and a pharmaceutically acceptable carrier.

(b) A pharmaceutical composition which comprises the product prepared by combining (e.g., mixing) an effective amount of a compound of Formula (I) and a pharmaceutically acceptable carrier.

(c) The pharmaceutical composition of (a) or (b), further comprising a therapeutically effective amount of an HIV infection/AIDS treatment agent selected from the group consisting of HIV/AIDS antiviral agents, immunomodulators, and anti-infective agents.

(d) The pharmaceutical composition of (c), wherein the HIV infection/AIDS treatment agent is an antiviral selected from the group consisting of HIV protease inhibitors, non-nucleoside HIV reverse transcriptase inhibitors, and nucleoside HIV reverse transcriptase inhibitors.

(e) A combination useful for inhibiting HIV integrase, for treating or preventing infection by HIV, or for preventing, treating or delaying the onset of AIDS, which is a therapeutically effective amount of a compound of Formula (I) and a therapeutically effective amount of an HIV infection/AIDS treatment agent selected from the group consisting of HIV/AIDS antiviral agents, immunomodulators, and anti-infective agents.

(f) The combination of (e), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject a therapeutically effective amount of a compound of Formula (I).

(h) A method of preventing or treating infection by HIV in a subject in need thereof which comprises administering to the subject a therapeutically effective amount of a compound of Formula (I).

(i) The method of (h), wherein the compound of Formula (I) is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.

(j) A method of preventing, treating or delaying the onset of AIDS in a subject in need thereof which comprises administering to the subject a therapeutically effective amount of a compound of Formula (I).

(k) The method of (j), wherein the compound is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors (l) A method of inhibiting HIV integrase in a subject in need thereof which comprises administering to the subject the pharmaceutical composition of (a), (b), (c) or (d) or the combination of (e) or (f).

(m) A method of preventing or treating infection by HIV in a subject in need thereof which comprises administering to the subject the pharmaceutical composition of (a), (b), (c) or (d) or the combination of (e) or (f).

(n) A method of preventing, treating or delaying the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) inhibiting HIV protease, (b) preventing or treating infection by HIV, or (c) preventing, treating or delaying the onset of AIDS. In these uses, the compounds of the present invention can optionally be employed in combination with one or more HIV/AIDS treatment agents selected from HIV/AIDS antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt.

As used herein, the term "$C_{1-6}$ alkyl" (or "$C_1$-$C_6$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "$C_0$" as employed in expressions such as "$C_{0-6}$ alkyl" means a direct covalent bond. For example, when $R^1$ in Compound I is —$C_{0-6}$ alkyl-O—$C_{0-6}$ alkyl-$R^k$, then $R^1$ is —O—$R^k$ when both alkyl groups are $C_0$ alkyl. Similarly, when an integer defining the presence of a certain number of atoms in a group is equal to zero, it means that the atoms adjacent thereto are connected directly by a bond. For example, when $R^4$ is

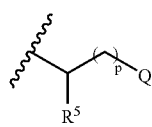

wherein p is an integer equal to zero, 1 or 2, then $R^4$ has the following structure when p is zero:

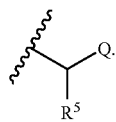

The term "—$C_{1-6}$ alkyl-" refers to a $C_1$ to $C_6$ linear or branched alkyl group as just defined which is bivalent. It can alternatively be referred to as "$C_{1-6}$ alkylene" or "$C_{1-6}$ alkanediyl". A class of alkylenes of particular interest with respect to the invention is —$(CH_2)_{1-6}$—, and subclasses of particular interest include —$(CH_2)_{1-4}$—, —$(CH_2)_{1-3}$—, —$(CH_2)_{1-2}$—, and —$CH_2$—.

The term "$C_{2-5}$ alkenyl" (or "$C_2$-$C_5$ alkenyl") means linear or branched chain alkenyl groups having from 2 to 5 carbon atoms and includes all of the pentenyl isomers as well as 1-butenyl, 2-butenyl, 3-butenyl, isobutenyl, 1-propenyl, 2-propenyl, and ethenyl (or vinyl). Similar terms such as "$C_{2-3}$ alkenyl" have an analogous meaning.

The term "—$C_{2-5}$ alkenyl-" refers to a $C_2$ to $C_5$ linear or branched alkenyl group as just defined which is bivalent. It can alternatively be referred to as "$C_{2-5}$ alkenylene" or "$C_{2-5}$ alkenediyl".

The term "$C_{2-5}$ alkynyl" (or "$C_2$-$C_5$ alkynyl") means linear or branched chain alkynyl groups having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "$C_{2-3}$ alkynyl" have an analogous meaning.

The term "—$C_{2-5}$ alkynyl-" refers to a $C_2$ to $C_5$ linear or branched alkenyl group as just defined which is bivalent. It can alternatively be referred to as "$C_{2-5}$ alkynylene" or "$C_{2-5}$ alkynediyl".

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "$C_{3-7}$ azacycloalkyl" (or "$C_3$-$C_7$ azacycloalkyl") means a saturated cyclic ring consisting of one nitrogen and from three to seven carbon atoms (i.e., azetidinyl, pyrrolidinyl, piperidinyl, or azepanyl).

The term "halogen" (or "halo") refers to fluorine, chlorine, bromine and iodine (alternatively referred to as fluoro, chloro, bromo, and iodo).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein refers to (i) a $C_3$ to $C_8$ monocyclic, saturated or unsaturated ring, (ii) a $C_7$ to $C_{12}$ bicyclic ring system, or (iii) a $C_{11}$ to $C_{16}$ tricyclic ring system, wherein each ring in (ii) or (iii) is independent of or fused to the other ring or rings and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. Fused tricyclic carbocycles have an analogous meaning. A subset of the fused bicyclic carbocycles are those bicyclic carbocycles in which one ring is a benzene ring and the other ring is saturated or unsaturated, with attachment via any carbon atom that results in a stable compound. Representative examples of this subset include the following:

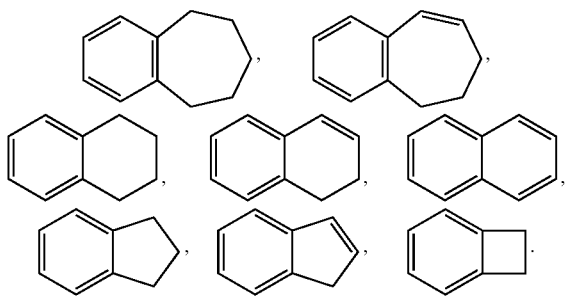

The term "aryl" refers to aromatic mono- and polycarbocyclic ring systems, wherein the individual carbocyclic rings in the polyring systems are fused or attached to each other via a single bond. Suitable aryl groups include phenyl, naphthyl, and biphenylenyl.

The term "heterocycle" (and variations thereof such as "heterocyclic" or "heterocyclyl") broadly refers to (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of or fused to, or bridged with, or spiro to the other ring or rings and each ring is saturated or unsaturated, and the monocyclic ring, bicyclic ring system, or tricyclic ring system contains one or more heteroatoms (e.g., from 1 to 6 heteroatoms, or from 1 to 4 heteroatoms) selected from N, O and S and a balance of carbon atoms (the monocylic ring typically contains at least one carbon atom and the ring systems typically contain at least two carbon atoms); and wherein any one or more of the nitrogen and sulfur heteroatoms is optionally be oxidized, and any one or more of the nitrogen heteroatoms is optionally quaternized. The heterocyclic ring may be attached at any heteroatom or carbon atom, provided that attachment results in the creation of a stable structure. When the heterocyclic ring has substituents, it is understood that the substituents may be attached to any atom in the ring, whether a heteroatom or a carbon atom, provided that a stable chemical structure results.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring which consists of carbon atoms and one or more heteroatoms selected from N, O and S. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 7-azabicyclo[2.2.1]heptyl (e.g.,

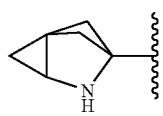

), 1,4-dioxa-8-azaspiro[4.5]decyl (e.g.,

), azabicyclo[2.1.1]hexyl, (e.g.,

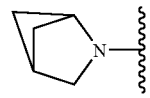

), 2,3-dihydrobenzo-1,4-dioxinyl (i.e.,

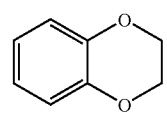

), and benzo-1,3-dioxolyl (i.e.,

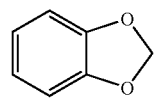

). In certain contexts herein,

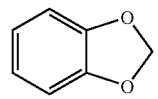

is alternatively referred to as phenyl having as a substituent methylenedioxy attached to two adjacent carbon atoms.

Representative examples of tricyclic heterocycles include phenothiazinyl, carbazolyl, beta-carbolinyl, tetrahydro-beta-carbolinyl, acridinyl, phenazinyl, and phenoxazinyl.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable (e.g., $R^a$, $R^b$, $R^c$, $R^k$, etc.) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

Substituted ring systems, which systems are themselves substituents bonded to a non-substituent atom, include, but are not limited to, moieties in which the atom bearing the ring substituent and the atom bonded to the non-substituent atom are the same. For example, the substituent represented by

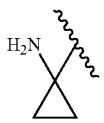

is a substituted cyclopropyl ring, wherein the cyclopropyl ring substituent is an amino group.

The compounds of the present invention may have asymmetric centers and may occur, except when specifically noted, as mixtures of stereoisomers or as individual diastereomers, or enantiomers, with all isomeric forms being included in the present invention.

The dihydroxypyrimidine compounds of the present invention (i.e., compounds of Formula I wherein $R^2$=H) may also occur as tautomers thereof. Tautomers include, but are not limited to:

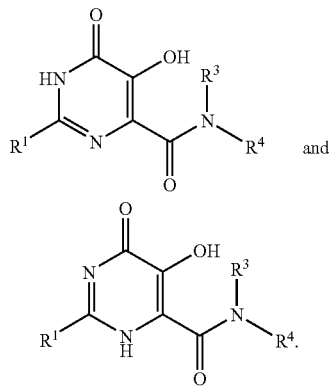

It is understood that the present invention includes all tautomers of the dihydroxy compounds embraced by Formula I, both singly and in mixtures.

The compounds of the present inventions are useful in the inhibition of HIV integrase, the prevention or treatment of infection by human immunodeficiency virus (HIV) and the prevention, treatment or the delay in the onset of consequent pathological conditions such as AIDS. Preventing AIDS, treating AIDS, delaying the onset of AIDS, or preventing or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

Compounds representative of the present invention have been tested for inhibition in an assay for the strand transfer activity of integrase. The assay is conducted in accordance with Wolfe, A. L. et al., *J. Virol.* 1996, 70: 1424-1432, for recombinant integrase, except that: (i) the assay uses preassembled integrase strand transfer complexes; (ii) the strand transfer reaction is performed in the presence of inhibitor in 2.5 mM $MgCl_2$ using 0.5 to 5 nM of a 3' FITC labeled target DNA substrate as described in WO 02/30930, the disclosure of which is hereby incorporated by reference, and (iii) strand transfer products are detected using an alkaline phosphatase conjugated anti-FITC antibody and a chemiluminescent alkaline phosphatase substrate. Representative compounds (e.g., the compounds set forth in Tables 1-25 below) tested in the integrase assay demonstrated $IC_{50}$'s of about 5 micromolar or less.

Further description on conducting the assay using preassembled complexes is found in Hazuda et al., *J. Virol.* 1997, 71: 7005-7011; Hazuda et al., *Drug Design and Discovery* 1997, 15: 17-24; and Hazuda et al., *Science* 2000, 287: 646-650.

Certain compounds representative of the present invention have also been tested in an assay for inhibition of acute HIV infection of T-lymphoid cells, conducted in accordance with Vacca, J. P. et al., *Proc. Natl. Acad. Sci. USA* 1994, 91: 4096. These compounds demonstrated $IC_{95}$'s of about 10 micromolar or less.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. When the compounds of the invention carry an acidic moiety, suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

For the purpose of preventing or treating HIV infection or preventing, treating or delaying the onset of AIDS, the compounds of the present invention may be administered orally, parenterally (including subcutaneous injections, intravenous, intramuscular, intrasternal injection or infusion techniques), by inhalation spray, or rectally, in the form of a unit dosage of a pharmaceutical composition containing a therapeutically effective amount of the compound and conventional non-toxic pharmaceutically-acceptable carriers, adjuvants and vehicles.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HIV infection or AIDS), "administration" and its variants are each understood to include concurrent and sequential provision of the compound or prodrug and other agents.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated. When the active compound (i.e., active ingredient) is administered as the salt, references to the amount of active ingredient are to the free acid or free base form of the compound.

The pharmaceutical compositions may be in the form of orally-administrable suspensions or tablets or capsules, nasal sprays, sterile injectible preparations, for example, as sterile injectible aqueous or oleagenous suspensions or suppositories. These compositions can be prepared by methods and contain excipients which are well known in the art. Suitable methods and ingredients are described in *Remington's Pharmaceutical Sciences*, 18$^{th}$ edition, edited by A. R. Gennaro, Mack Publishing Co., 1990, which is herein incorporated by reference in its entirety.

The compounds of this invention can be administered orally in a dosage range of 0.001 to 1000 mg/kg of mammal (e.g., human) body weight in divided doses. One preferred dosage range is 0.01 to 500 mg/kg body weight orally in divided doses. Another preferred dosage range is 0.1 to 100 mg/kg body weight orally in divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of the HIV integrase inhibitor compounds of the present invention with one or more agents useful in the treatment of HIV infection or AIDS. For example, the compounds of this invention may be effectively administered, whether at periods of pre-exposure and/or post-exposure, in combination with effective amounts of one or more of the HIV/AIDS antivirals, imunomodulators, antiinfectives, or vaccines useful for treating HIV infection or AIDS. Suitable antiviral agents include those listed in the following Table:

| Drug Name | Manufacturer (Tradename and/or Location) | Indication (Activity) |
|---|---|---|
| abacavir GW 1592 1592U89 | Glaxo Welcome (ZIAGEN ®) | HIV infection, AIDS, ARC (nRTI) |
| abacavir + lamivudine + zidovudine | GlaxoSmithKline (TRIZIVIR ®) | HIV infection, AIDS, ARC (nnRTI) |
| acemannan | Carrington Labs (Irving, TX) | ARC |
| ACH 126443 | Achillion Pharm. | HIV infections, AIDS, ARC (nucleoside reverse transcriptase inhibitor) |
| acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| adefovir dipivoxil GS 840 | Gilead | HIV infection, AIDS, ARC (RTI) |
| AL-721 | Ethigen (Los Angeles, CA) | ARC, PGL, HIV positive, AIDS |
| alpha interferon | Glaxo Wellcome | Kaposi's sarcoma, HIV, in combination w/Retrovir |
| AMD3100 | AnorMed | HIV infection, AIDS, ARC (CXCR4 antagonist) |
| amprenavir 141 W94 GW 141 VX478 (Vertex) | Glaxo Wellcome (AGENERASE ®) | HIV infection, AIDS, ARC (PI) |

-continued

ANTIVIRALS

| Drug Name | Manufacturer (Tradename and/or Location) | Indication (Activity) |
|---|---|---|
| ansamycin LM 427 | Adria Laboratories (Dublin, OH) Erbamont (Stamford, CT) | ARC |
| antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| atazanavir (BMS 232632) | Bristol-Myers-Squibb (ZRIVADA ®) | HIV infection, AIDS, ARC (PI) |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (PI) |
| BMS-234475 (CGP-61755) | Bristol-Myers Squibb/ Novartis | HIV infection, AIDS, ARC (PI) |
| capravirine (AG-1549, S-1153) | Pfizer | HIV infection, AIDS, ARC (nnRTI) |
| CI-1012 | Warner-Lambert | HIV-1 infection |
| cidofovir | Gilead Science | CMV retinitis, herpes, papillomavirus |
| curdlan sulfate | AJI Pharma USA | HIV infection |
| cytomegalovirus immune globin | MedImmune | CMV retinitis |
| cytovene ganciclovir | Syntex | sight threatening CMV peripheral CMV retinitis |
| delavirdine | Pharmacia-Upjohn (RESCRIPTOR ®) | HIV infection, AIDS, ARC (nnRTI) |
| dextran Sulfate | Ueno Fine Chem. Ind. Ltd. (Osaka, Japan) | AIDS, ARC, HIV positive asymptomatic |
| ddC (zalcitabine, dideoxycytidine) | Hoffman-La Roche (HIVID ®) | HIV infection, AIDS, ARC (nRTI) |
| ddI Dideoxyinosine | Bristol-Myers Squibb (VIDEX ®) | HIV infection, AIDS, ARC; combination with AZT/d4T (nRTI) |
| DPC 681 & DPC 684 | DuPont | HIV infection, AIDS, ARC (PI) |
| DPC 961 & DPC 083 | DuPont | HIV infection AIDS, ARC (nnRTRI) |
| emvirine | Triangle Pharmaceuticals (COACTINON ®) | HIV infection, AIDS, ARC (non-nucleoside reverse transcriptase inhibitor) |
| EL10 | Elan Corp, PLC (Gainesville, GA) | HIV infection |
| efavirenz (DMP 266) | DuPont (SUSTIVA ®) Merck (STOCRIN ®) | HIV infection, AIDS, ARC (nnRTI) |
| famciclovir | Smith Kline | herpes zoster, herpes simplex |
| emtricitabine FTC | Triangle Pharmaceuticals (COVIRACIL ®) Emory University | HIV infection, AIDS, ARC (nRTI) |
| emvirine | Triangle Pharmaceuticals (COACTINON ®) | HIV infection, AIDS, ARC (non-nucleoside reverse transcriptase inhibitor) |
| HBY097 | Hoechst Marion Roussel | HIV infection, AIDS, ARC (nnRTI) |
| hypericin | VIMRx Pharm. | HIV infection, AIDS, ARC |
| recombinant human interferon beta | Triton Biosciences (Almeda, CA) | AIDS, Kaposi's sarcoma, ARC |
| interferon alfa-n3 | Interferon Sciences | ARC, AIDS |
| indinavir | Merck (CRIXIVAN ®) | HIV infection, AIDS, ARC, asymptomatic HIV positive, also in combination with AZT/ddI/ddC (PI) |
| ISIS 2922 | ISIS Pharmaceuticals | CMV retinitis |
| JE2147/AG1776 | Agouron | HIV infection, AIDS, ARC (PI) |

ANTIVIRALS -continued

| Drug Name | Manufacturer (Tradename and/or Location) | Indication (Activity) |
|---|---|---|
| KNI-272 | Nat'l Cancer Institute | HIV-assoc. diseases |
| lamivudine, 3TC | Glaxo Wellcome (EPIVIR ®) | HIV infection, AIDS, ARC; also with AZT (nRTI) |
| lobucavir | Bristol-Myers Squibb | CMV infection |
| lopinavir (ABT-378) | Abbott | HIV infection, AIDS, ARC (PI) |
| lopinavir + ritonavir (ABT-378/r) | Abbott (KALETRA ®) | HIV infection, AIDS, ARC (PI) |
| mozenavir (DMP-450) | AVID (Camden, NJ) | HIV infection, AIDS, ARC (PI) |
| nelfinavir | Agouron (VIRACEPT ®) | HIV infection, AIDS, ARC (PI) |
| nevirapine | Boeheringer Ingleheim (VIRAMUNE ®) | HIV infection, AIDS, ARC (nnRTI) |
| novapren | Novaferon Labs, Inc. (Akron, OH) | HIV inhibitor |
| pentafusaide T-20 | Trimeris | HIV infection, AIDS, ARC (fusion inhibitor) |
| peptide T octapeptide sequence | Peninsula Labs (Belmont, CA) | AIDS |
| PRO 542 | Progenics | HIV infection, AIDS, ARC (attachment inhibitor) |
| PRO 140 | Progenics | HIV infection, AIDS, ARC (CCR5 co-receptor inhibitor) |
| trisodium phosphonoformate | Astra Pharm. Products, Inc | CMV retinitis, HIV infection, other CMV infections |
| PNU-140690 | Pharmacia Upjohn | HIV infection, AIDS, ARC (PI) |
| probucol | Vyrex | HIV infection, AIDS |
| RBC-CD4 | Sheffield Med. Tech (Houston TX) | HIV infection, AIDS, ARC |
| ritonavir (ABT-538) | Abbott (RITONAVIR ®) | HIV infection, AIDS, ARC (PI) |
| saquinavir | Hoffmann-LaRoche (FORTOVASE ®) | HIV infection, AIDS, ARC (PI) |
| stavudine; d4T didehydrodeoxy-thymidine | Bristol-Myers Squibb (ZERIT ®) | HIV infection, AIDS, ARC (nRTI) |
| T-1249 | Trimeris | HIV infection, AIDS, ARC (fusion inhibitor) |
| TAK-779 | Takeda | HIV infection, AIDS, ARC (injectable CCR5 receptor antagonist) |
| tenofovir | Gilead (VIREAD ®) | HIV infection, AIDS, ARC (nRTI) |
| tipranavir (PNU-140690) | Boehringer Ingelheim | HIV infection, AIDS, ARC (PI) |
| TMC-120 & TMC-125 | Tibotec | HIV infections, AIDS, ARC (nnRTI) |
| TMC-126 | Tibotec | HIV infection, AIDS, ARC (PI) |
| valaciclovir | Glaxo Wellcome | genital HSV & CMV infections |
| virazole ribavirin | Viratek/ICN (Costa Mesa, CA) | asymptomatic HIV positive, LAS, ARC |
| zidovudine; AZT | Glaxo Wellcome (RETROVIR ®) | HIV infection, AIDS, ARC, Kaposi's sarcoma in combination with other therapies (nRTI) |

PI = protease inhibitor
nnRTI = non-nucleoside reverse transcriptase inhibitor
nRTI = nucleoside reverse transcriptase inhibitor A compound of the present invention can also be administered in combination with another HIV integrase inhibitor such as a compound described in WO 99/62513, WO 99/62520, or WO 99/62897. A compound of the present invention can also be administered in combination with a CCR5 receptor antagonist, such as a compound described in WO 99/04794, WO 99/09984, WO 99/38514, WO 00/59497, WO 00/59498, WO 00/59502, WO 00/59503, WO 00/76511, WO 00/76512, WO 00/76513, WO 00/76514, WO 00/76792, or WO 00/76793. The compounds of this invention may be effectively administered, whether at periods of pre-exposure and/or post-exposure, in combination with effective amounts of one or more HIV/AIDS antivirals, immunomodulators, antiinfectives, or vaccines useful for treating HIV infection or AIDS disclosed in the Table in WO 01/38332, which is herein incorporated by reference in its entirety.

It will be understood that the scope of combinations of the compounds of this invention with HIV/AIDS antivirals, immunomodulators, anti-infectives or vaccines is not limited to the list in the above-referenced Table in WO 01/38332, but includes in principle any combination with any pharmaceutical composition useful for the treatment of AIDS. The HIV/AIDS antivirals and other agents will typically be employed in these combinations in their conventional dosage ranges and regimens as reported in the art, including the dosages described in the *Physicians' Desk Reference*, 54$^{th}$ edition, Medical Economics Company, 2000. The dosage ranges for a compound of the invention in these combinations are the same as those set forth above.

Abbreviations used in the instant specification, particularly the Schemes and Examples, include the following:
AIDS=acquired immunodeficiency syndrome
ARC=AIDS related complex
BOC or Boc=t-butyloxycarbonyl The compounds of the present invention can be readily prepared according to the following reaction schemes and examples, or modifications thereof, using readily available starting materials and reagents. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

The compounds of the present invention can be prepared by coupling suitable alkyl 2-substituted-5,6 dihydroxypyrimidine-4-carboxylates (or the corresponding carboxylic acids or acid derivatives such as acid halides) with the appropriate amines, as represented by General Scheme below. In the scheme, $P^1$ and $P^2$ are H or protective groups, typically esters (e.g., benzoate or pivalate) that are normally removed under the conditions employed to convert the —COOR$^\wedge$ ester to the amide. The ester protective groups are typically used to purify the 2-substituted-5,6 dihydroxypyrimidine-4-carboxylates after their synthesis when the unprotected product cannot be crystallized from the reaction crude and/or for synthetic reasons.

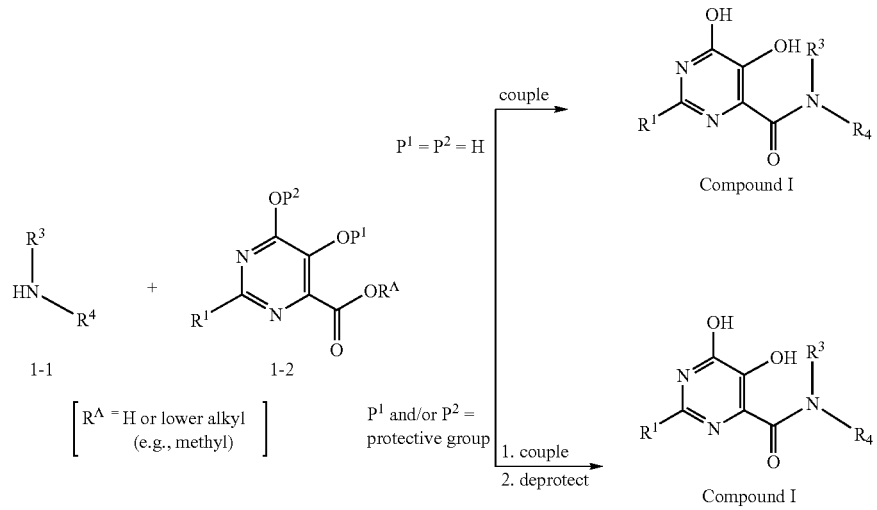

General Scheme

Bn=benzyl
Bz=benzoyl
CBZ or Cbz=carbobenzoxy (alternatively, benzyloxycarbonyl)
DMAD=dimethylacetylenedicarboxylate
DMF=N,N-dimethylformamide
Et=ethyl
FIA-MS=flow injection analysis mass spectrometry
HIV=human immunodeficiency virus
BPLC=high performance liquid chromatography
Me=methyl
NMP=N-methyl pyrrolidinone
NMR=nuclear magnetic resonance
Ph=phenyl
TFA=trifluoroacetic acid
THF=tetrahydrofuran Methods for coupling carboxylic acid derivatives with amines to form carboxamides are well known in the art. Suitable methods are described, for example, in Jerry March, *Advanced Organic Chemistry*, 3rd edition, John Wiley & Sons, 1985, pp. 370-376. Amines of formula 1-1 can be prepared using the methods described in Richard Larock, *Comprehensive Organic Transformations*, VCH Publishers Inc, 1989, pp 385-438, or routine variations thereof. Methyl-2-sustituted-5,6-dihydroxypyrimidine-4-carboxylate of formula 1-2 can be prepared using methods described in Culbertson et al., *J Heterocycl. Chem.* 1979, 16 (7): 1423-24. The procedures and schemes below illustrate and expand upon the chemistry portrayed in the General Scheme.

Scheme A depicts the synthesis of 2-substituted-5,6-dihydroxypyrimidine-4-carboxamide (2-3). The methyl-5,6-dihydroxypyrimidine-4-carboxylate 2-2 can be obtained by reacting the appropriate amidoxime 2-1 with dimethylacetylenedicarboxylate, followed by cyclization at high temperature in appropriate solvent. The methyl ester 2-2 can be reacted with the amine in solvents like DMF, methanol, ethanol, toluene, NMP, at the appropriate temperature to give the final compound 2-3. Amidoximes 2-1 can be prepared from the corresponding nitrites by chemistry described herein (see Example 5, Step 4 or Example 6, Step 1). Nitriles can be prepared from carboxylic acids by various procedures, including, for example, conversion to carboxamides by the procedure of Pozdnev, *Tetrahedron Lett.* 1989, 30: 5193), and dehydration by the procedure of Waldmann, *Tetrahedron* 1994, 50: 11865) (see Example 5, Step 3). Compound 2-2 can be recovered by precipitation and filtration from the cooled reaction mixture. Scheme A is exemplified in Example 1 below.

SCHEME A:

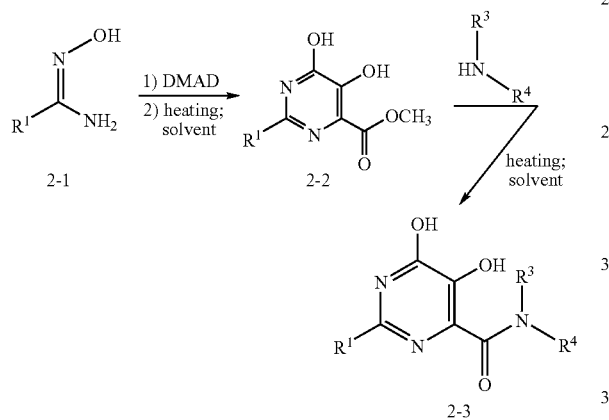

Part 1 of Scheme B depicts a general synthesis of compounds bearing a nucleophilic group (e.g., an amine) in the 2-substituent. After bromination of a —CH$_2$Br (or —CH$_2$Cl) group using standard chemistry, the bromo (or chloro) derivative 3-1 can be treated with a nucleophile ("Nu"; e.g., an amine, thiol, or alcoholate) and, without isolation of the nucleophile-substituted ester intermediate 3-2, then with the amine 1-1 to give the final product 3-3. Part 1 of Scheme B is exemplified in Example 2 below. Part 2 of Scheme B shows a variation of Part 1, wherein the site of nucleophilic substitution is —CHBr— (or —CHCl—). Scheme B, Part 2 is exemplified in Example 3 below.

Scheme B

Part 1

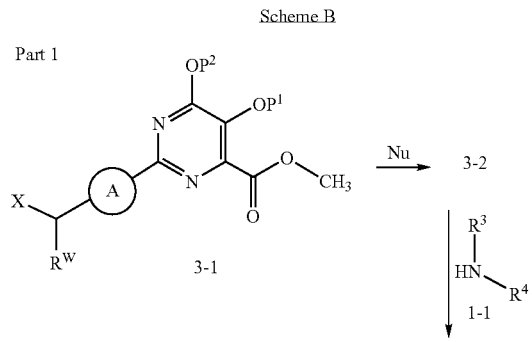

-continued

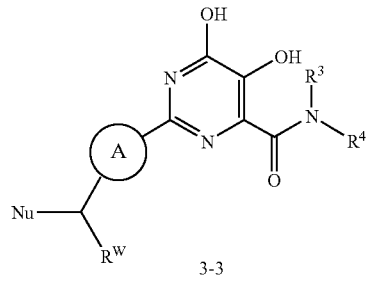

[ A = carbocycle, heterocycle, or alkyl
P$^1$, P$^2$ = H or protective group
X = Cl or Br
Nu = nucleophile
R$^W$ = H or alkyl ]

Part 2

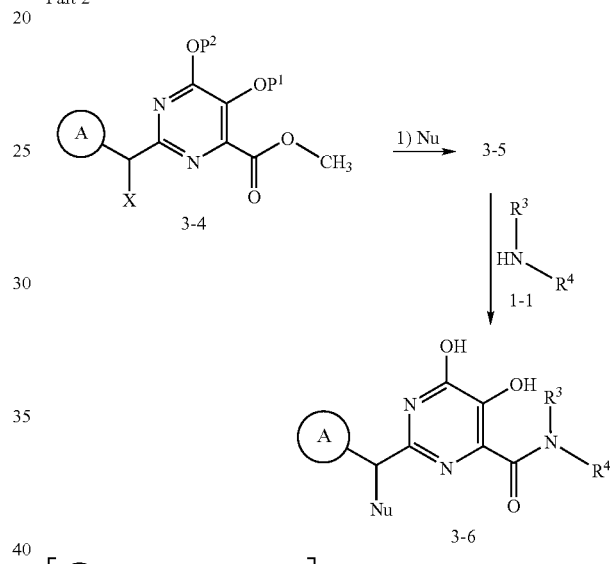

[ A = carbocycle, heterocycle, or alkyl
P$^1$, P$^2$ = H or protective group
X = Cl or Br
Nu = nucleophile ]

Scheme C shows a method for preparing compounds of the present invention that contain an alkylated aliphatic amine in the substituent at the 2 position. Nitrogen alkylation is achieved via a reductive amination. There are two equivalent synthetic strategies within the scope of Scheme C: reductive alkylation on the pyrimidine methyl ester followed by synthesis of the carboxamide or, alternatively, synthesis of the carboxamide followed by reductive amination. A deprotection step can be employed as needed. Example 4 below illustrates the application of Scheme C for preparing a compound with an acyclic aliphatic amine in the 2-position, wherein the CBZ-protected pyrimidine derivative was converted to the corresponding benzylic amide. Example 5 below describes the preparation of a compound with a cyclic amne in the 2 position in which Scheme C was used in the final two steps. Example 6 below illustrates the application of Scheme C to the preparation of a compound with a pyrrolidine in the 2-position. Example 7 describes the alkylation of a compound with a piperazine in the 2-position.

Scheme C

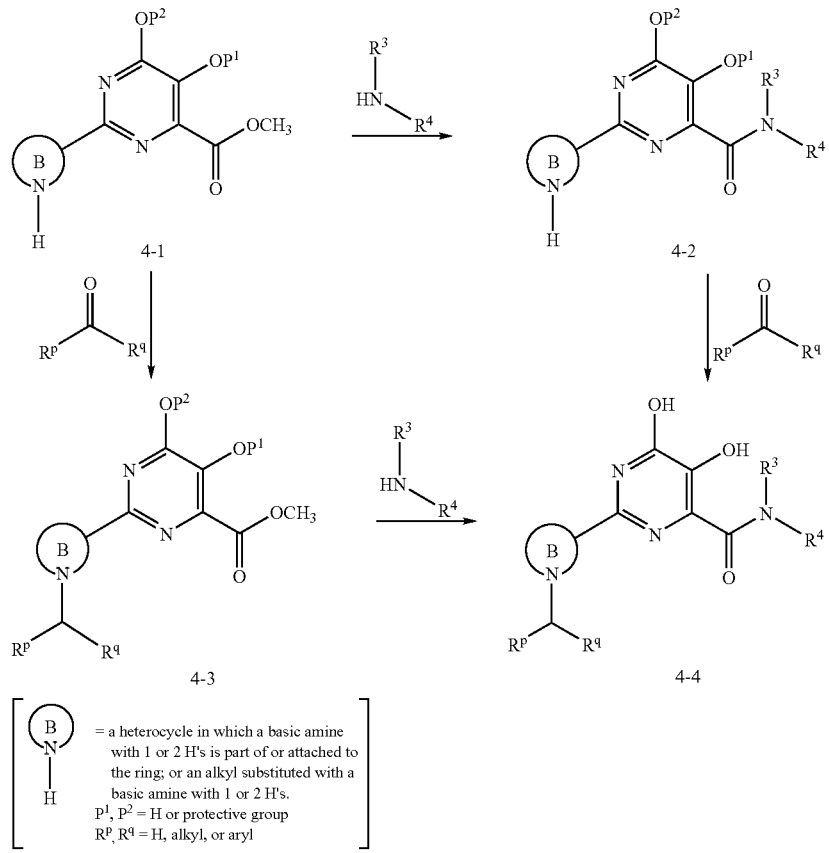

Scheme D presents an alternative approach to the preparation of compounds bearing a cyclic aliphatic tertiary amine as 2-substituents of the pyrimidine core, wherein the alkylation of the secondary amine with an alkyl halide is followed by synthesis of the benzylic amide with concomitant deprotection of the benzoate ester. Scheme D is exemplified in Example 8 below.

-continued

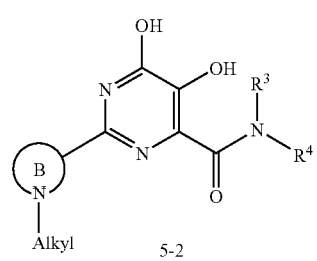

Scheme E shows the preparation of compounds of the present invention of formula 6-2 by reaction of aldehydes or ketones 6-1 with suitable amines under reductive alkylation conditions. Scheme E is exemplified in Example 9 below.

Scheme D

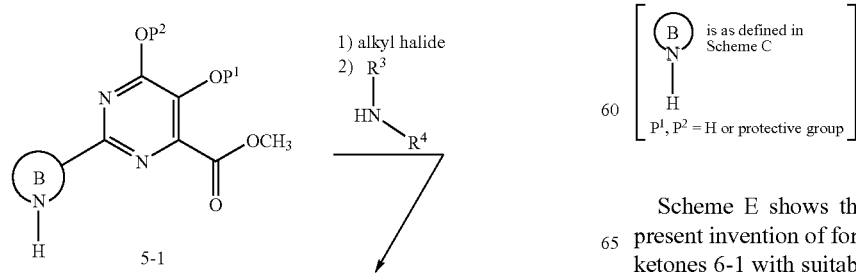

Scheme E

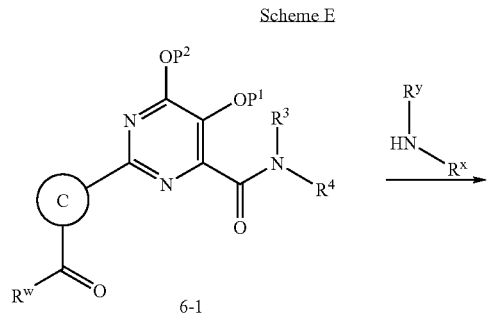

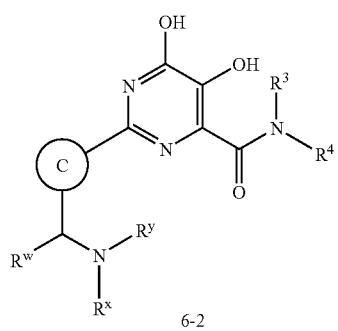

[
C = absent, alkyl, or aryl
P¹, P² = H or protective group
$R^w$ = H, alkyl, or aryl
$R^x$ = H, alkyl, or aryl
$R^y$ = alkyl, or aryl
or $R^x$ and $R^y$ together with the N to which they are attached form an N-containing heterocycle
]

Scheme F shows a procedure for preparing compounds of the present invention which are unsubstituted in the 2 position. The pyrimidine monocarboxylic acid 7-1 can be decarboxylated in acid solution to the 2-unsubstitued pyrimidine 7-2, which can be further elaborated to the amide 7-3. Scheme F is exemplifed in Example 10 below.

Scheme F

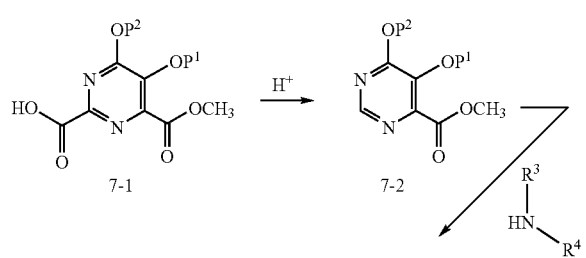

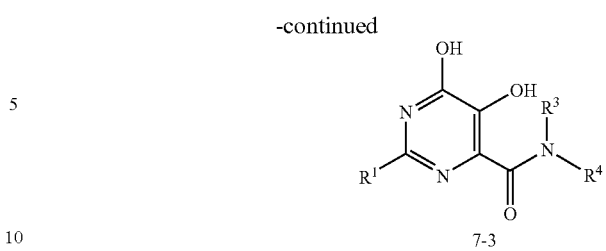

Synthesis of compounds of general formula 8-3 can be achieved as depicted in Scheme G. The synthetic strategy is based on the reaction of a pyrimidine bearing an aminoaromatic system in the 2 position (8-1) with an isocyanate in the presence of a base and the resulting urea 8-2 can then be converted into the final amide 8-3. Scheme G is exemplifed in Example 11 below.

Scheme G

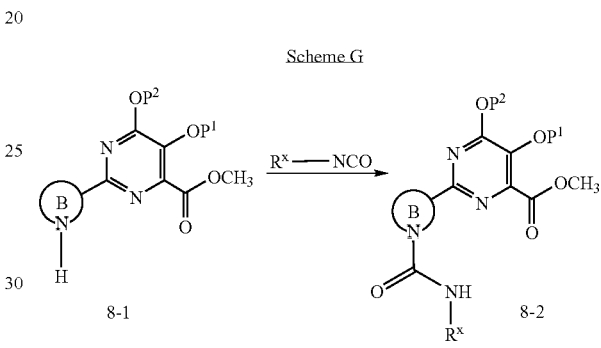

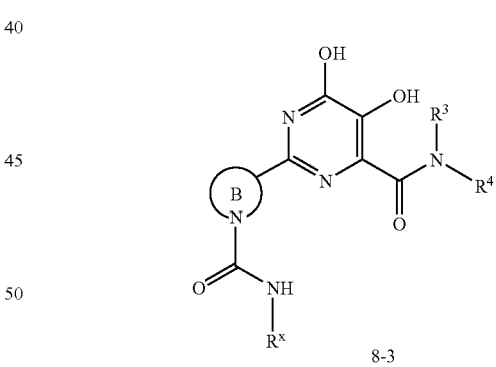

[
B–N–H = is as defined in Scheme C
$R^x$ = alkyl, aryl, or heteroaryl
]

The preparation of compounds that feature a carboxamide at the 2 position of the pyrimidine core can be achieved as shown in Scheme H. Reaction of 4-ethyl-2-methyl-5,6-dihydroxypyrimidine-2,4 dicarboxylate (9-1) with a suitable amine affords regioselectively the 4-carboxamide (9-2), which can subsequently be converted into the 2,4-dicarboxamide derivative (9-3) by further reaction with an amine. Scheme H is exemplifed in Example 12 below.

Scheme H

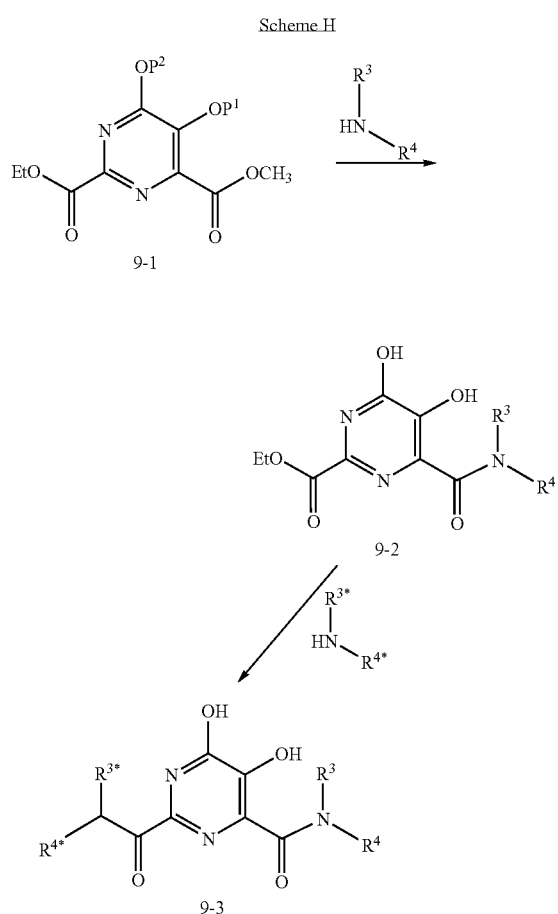

Compounds of the present invention with general formula 10-3 containing an acylated nitrogen or sulfonylated nitrogen in the substituent at the 2-position, can be prepared following Scheme I. Acylation or sulfonylation of the nitrogen in the 2-substituent of the pyrimidine core provides compound 10-2, which can be elaborated into the final amide 10-3. Scheme I is exemplified in Examples 13 and 14 below.

Scheme I

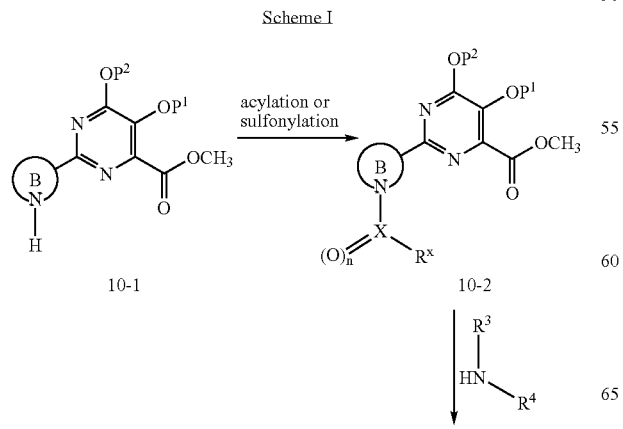

-continued

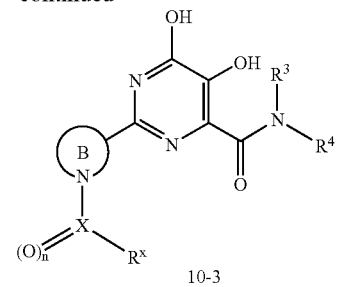

[
= is as defined in Scheme C

X = C or S
n = 1 if X is C
n = 2 if X is S
R$^x$ = alkyl, arlyl, or heteroaryl
]

Compounds of the present invention bearing an alkoxy substituent on the 6 position of the pyrimidine core can be synthesized as shown in Scheme J. The synthetic pathway is based on the reaction of pyrimidine 11-1, suitably protected on the 5-hydroxyl group, with an alkylating agent (such as an halide or a sulphate). Intermediate 11-2 can be further elaborated into the amide 11-3 following the usual chemistry. Scheme J is exemplified in Example 15 below.

Scheme J

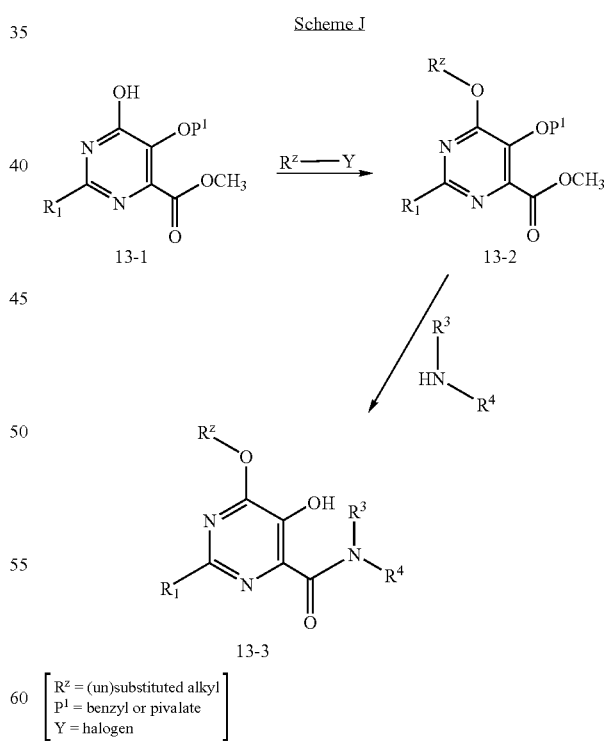

[
R$^z$ = (un)substituted alkyl
P$^1$ = benzyl or pivalate
Y = halogen
]

Compounds of the present invention with general formula 14-1 containing a tertiary amine at the 2-position of the pyrimidine core can be prepared according to general procedure describe in scheme K. The N,N dimethyl amine present at the two position of C-4 can be replace with another amine by mixing and heating the substrate and regent in appropriate solvent to afford the desired product 14-1. Scheme K is exemplified in Example 16 reported below.

Scheme K:

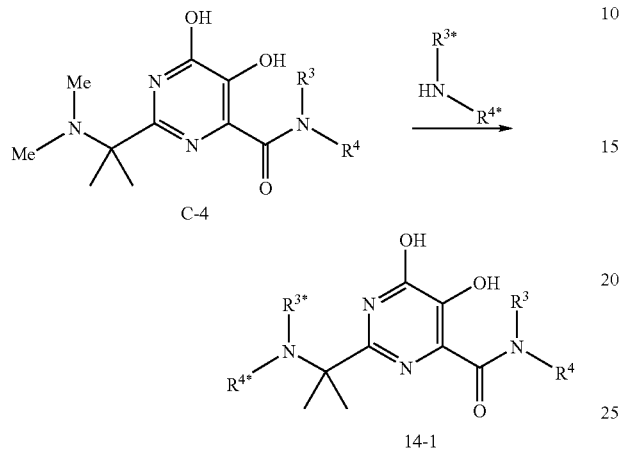

In the processes for preparing compounds of the present invention set forth in the foregoing schemes and exemplified in the examples below, functional groups in various moieties and substituents may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 1991. The protecting groups can be removed at a convenient subsequent stage using methods known in the art. For example, in preparing the compounds of the invention it is sometimes necessary to protect one or more amino groups (e.g., amino groups present in substituents at the 2-position of the pyrimidine ring) with, for example, a Boc or Cbz group; or to protect hydroxy (e.g., the 5,6-dihydroxy groups on the pyrimidine ring) with, for example, a benzoyl, benzyl, or pivaloyl group. The Boc group can be removed by acid treatment (e.g., TFA) either before or after formation of the final amide at C-4 of the pyrimidine nucleus. The Cbz and benzyl groups are typically removed by catalytic hydrogenation or under strong acid conditions, either prior to or following formation of the final amide. The benzoyl or pivaloyl group can be removed concurrently with the formation of the final amide. Examples 4 and 6 below illustrate the use of a Cbz protective group and of Boc and benzoyl protective groups in the preparation of compounds of the invention.

The following examples serve only to illustrate the invention and its practice. The examples are not to be construed as limitations on the scope or spirit of the invention.

EXAMPLE 1

N-(4-fluorobenzyl)-5,6-dihydroxy-2-thien-2-ylpyrimidine-4-carboxamide

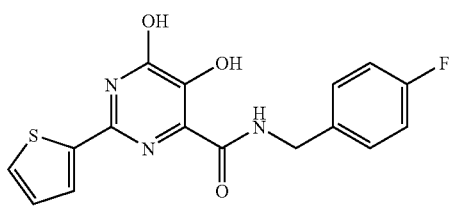

Step 1: Methyl 5,6-dihydroxy-2-thien-2-ylpyrimidine-4-carboxylate (A-2)

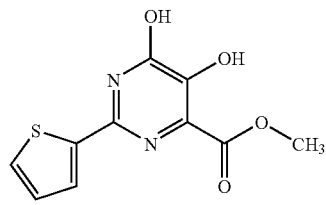

N'-hydroxythiophene-2-carboximidamide (A-1) (amidoxine synthesis is exemplified below—see compounds C-8 and C-14) was suspended in chloroform and refluxed overnight in the presence of 1.0 eq. of dimethylacetylenedicarboxylate. After cooling to room temperature, volatiles were evaporated and the residue was refluxed in xylene for 3 hr. The mixture was cooled to room temperature to allow the formation of a precipitate. The title product (A-2) was collected by filtration and washed with diethyl ether several times.

$^1$H NMR (DMSO-$d_6$, 300 MHz) δ 13.0 (bs, 1 H), 8.08 (d, J=3.2 Hz, 1 H), 7.85 (d, J=4.4 Hz, 1 H), 7.25 (dd, J=4.9 Hz, J=3.9 Hz, 1 H), 3.93 (s, 3 H).

Step 2: N-(4-fluorobenzyl)-5,6-dihydroxy-2-thien-2-ylpyrimidine-4-carboxamide (A-3)

Methyl 5,6-dihydroxy-2-thien-2-ylpyrimidine-4-carboxylate (A-2) was dissolved in DMF and 2.0 eq. of 4-fluorobenzylamine were added to the stirred solution. Reaction mixture was left overnight at 90° C. After cooling to room temperature 1 N HCl was added and a solid precipitated from the mixture. This solid was collected by filtration, washed with ethyl ether and dried under vacuum to afford the compound (A-3).

$^1$H NMR (DMSO-$d_6$, 300 MHz) δ 13.0 (s, 1 H), 12.5 (s, 1H), 9.18 (bs, 1 H), 8.03 (d, J=3.0 Hz, 1 H), 7.81 (d, J=4.8 Hz, 1 H), 7.39 (dd, J=5.7 Hz, J=8.4 Hz, 2 H), 7.19-7.2 (m, 3 H), 4.51 (d, J=6.3 Hz, 2 H). MS m/z 346 (M+H)$^+$.

EXAMPLE 2

2-{4-[(Diethylamino)methyl]phenyl}-N-(2,3-dimethoxybenzyl)-5,6-dihydroxypyrimidine-4-carboxamide

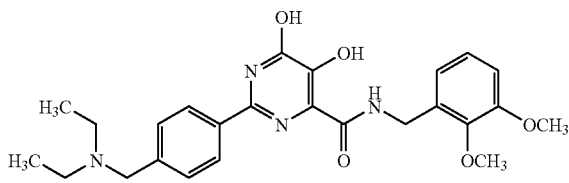

Step 1: Methyl 5,6-bis(benzoyloxy)-2-(4-methylphenyl)pyrimidine-4-carboxylate (B-2)

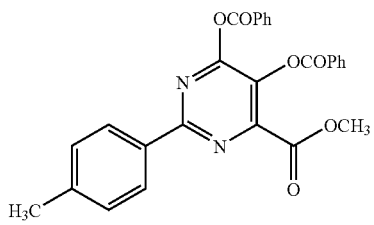

A mixture of dihydroxypyrimidine methylcarboxylate (B-1) (prepared from 4-methylbenzonitrile by procedures similar to those set forth in Scheme A), 4 eq. of benzoylchloride and 8 eq. of dry pyridine was stirred in dry dichloromethane at room temperature over night. The reaction mixture was diluted with EtOAc and the organic layer was washed twice with 1N HCl, once with brine. The organic layer was dried over anhydrous sodium sulfate, filtered and concentrated in vacuo. The solid residue was triturated with diethyl ether to give product (B-2).

$^1$H-NMR (CDCl$_3$, 400 MHz) δ 8.38 (d, J=8.2 Hz, 2 H), 8.14 (d, J=7.44 Hz, 2 H), 8.10 (d, J=7.44 Hz, 2 H), 7.62 (m, 2 H), 7.45 (m, 4 H), 7.3 (d, J=8.06 Hz, 2 H), 3.93 (s, 3 H), 2.44 (s, 3 H).

Step 2: Methyl 5,6-bis(benzoyloxy)-2-[4-(bromomethyl)phenyl]pyrimidine-4-carboxylate (B-3)

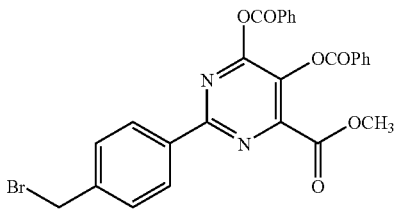

A suspension of methyl ester (B-2), an equimolar amount of N-bromosuccinimide and 5% of dibenzoylhydroperoxide in carbon tetrachloride was heated at 95° C. The reaction mixture was refluxed for 2 hrs, then allowed to cool at room temperature. Succinimide was filtered off and volatiles were removed in vacuo to give the desired product (B-3) as a white solid after treatment with petroleum ether.

$^1$H-NMR (CDCl$_3$, 400 MHz) δ 8.47 (d, J=8.25 Hz, 2 H), 8.14 (d, J=7.56 Hz, 2 H), 8.10 (d, J=7.50 Hz, 2 H), 7.63 (m, 2 H), 7.53 (d, J=8.23 Hz, 2 H), 7.46 (m, 4 H), 4.56 (s, 2 H), 3.94 (s, 3 H).

Step 3: 2-{4-[(Diethylamino)methyl]phenyl}-N-(2,3-dimethoxybenzyl)-5,6-dihydroxypyrimidine-4-carboxamide (B-4)

A mixture of the benzylic bromide (B-3) and diethylamine (4 eq.) in THF was allowed to stir at room temperature overnight. The volatiles were then removed in vacuo, the residue was taken up in DMF and after the addition of a slight excess of 2,3-dimethoxybenzylamine the reaction mixture was stirred at 90° C. over night. 1N HCl was then added to the reaction mixture and the crude product was purified by preparative HPLC (C18, CH$_3$CN/H$_2$O, 0.1% trifluoroacetic acid) to obtain title compound (B-4) as the trifluoroacetate salt.

$^1$H-NMR (DMSO-d$_6$, 400 MHz) δ 13.01 (bs, 1 H), 12.57 (s, 1 H), 9.53 (bs, 1 H), 9.36 (bs, 1 H), 8.34 (d, J=8.32 Hz, 2 H), 7.63 (d, J=8.27 Hz, 2 H), 7.08-6.96 (m, 2 H), 6.80 (m, 1 H), 4.52 (d, J=6.36 Hz, 2 H), 4.37 (d, J=4.35 Hz, 2 H), 3.82 (s, 3 H), 3.80 (s,3 H), 3.08 (m, 4 H), 1.22 (t, J=7.20 Hz, 6 H). MS m/z 467 (M+H)$^+$.

EXAMPLE 3

2-[(Dimethylamino)(phenyl)methyl]-N-(4-fluorobenzyl)-5,6-dihydroxypyrimidine-4-carboxamide

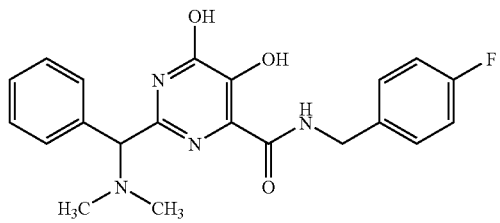

Step 1: Methyl-5,6-bis(benzoyloxy)-2-benzylpyrimidine-4-carboxylate (B-6)

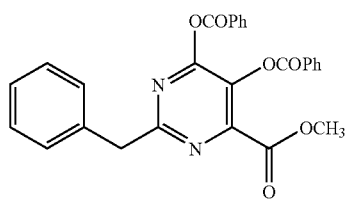

To a stirred solution of methyl-2-benzyl-5,6-dihydroxypyrimidine-4-carboxylate (B-5) (1.0 eq.) (prepared from phenylacetonitrile by procedures similar to those set forth in Scheme A) in anhydrous pyridine, benzoyl chloride (5.0 eq.) was added dropwise with external cooling and the reaction was stirred overnight at room temperature. The mixture was poured into 1N HCl and extracted with EtOAc. The organic phase was washed with a saturated solution of NaHCO$_3$ and with brine, dried (Na$_2$SO$_4$), filtered and concentrated under vacuum. The residue was purified by flash column chromatography (SiO$_2$, 80/20 v/v petroleum ether/ ethyl acetate as eluent) to give the title compound (B-6) as a colorless oil.

$^1$H NMR (CDCl$_3$) δ 8.07 (t, J=9.0 Hz, 4 H), 7.62-7.57 (m, 2 H), 7.48-7.40 (m, 6 H), 7.31 (t, J=8.9 Hz, 2 H), 7.28 (d, J=8.9 Hz, 1 H), 4.41 (s, 2 H), 3.91 (s, 3 H).

Step 2: Methyl-5,6-bis(benzoyloxy)-2-[bromo(phenyl)methyl]pyrimidine-4-carboxylate (B-7)

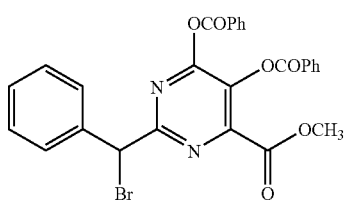

A solution of methyl-5,6-bis(benzoyloxy)-2-benzylpyrimidine-4-carboxylate (B-6) (1.0 eq.) in carbon tetrachloride was heated up to 90° C. under nitrogen; N-bromosuccinimide (1.0 eq.) and benzoyl peroxide (0.1 eq.) were added as dry powder and mixture was refluxed for 3 h. After cooling, succinimide was removed by filtration and the filtrate was concentrated and purified by flash column chromatography (SiO$_2$, 85/15 v/v petroleum ether/ ethyl acetate as eluent) to give the title product (B-7).

$^1$H NMR (CDCl$_3$) δ 8.11 (d, J=8.6 Hz, 2 H), 8.05 (d, J=8.6 Hz, 2 H), 7.79 (d, J=8.9 Hz, 2 H), 7.56-7.49 (m, 2 H), 7.50-7.30 (m, 7 H), 6.30 (s, 1 H), 3.90 (s, 3 H).

Step 3: 2-[(Dimethylamino)(phenyl)methyl]-N-(4-fluorobenzyl)-5,6-dihydroxypyrimidine-4-carboxamide (B-8)

Methyl-5,6-bis(benzoyloxy)-2-[bromo(phenyl)methyl] pyrimidine-4-carboxylate (B-7) was added to 2.0 M solution of dimethylamine in THF. After stirring the mixture for 10 min at room temperature, volatiles were evaporated by bubbling N$_2$ through the solution and 4 eq. of 4-fluorobenzylamine in DMF were added. Reaction mixture was stirred at 90° C. for 1 h. After cooling to room temperature, title compound (B-8) was obtained by RP-HPLC (C18, acetonitrile /water containing 0.1% of trifluoroacetic acid as eluant) as its trifluoroacetate salt.

$^1$H NMR (DMSO-d$_6$, 600 MHz) δ 13.42 (bs, 1 H), 12.34 (s, 1 H), 10.06 (bs, 1 H), 9.64 (t, J=5.9 Hz, 1 H), 7.52 (s, 5 H), 7.43 (dd, J=8.4 Hz, J=5.6 Hz, 2 H), 7.23 (t, J=8.8 Hz, 2 H), 5.28 (s, 1 H), 4.67 (dd, J=15.4 Hz, J=6.6 Hz, 1 H), 4.59 (dd, J=15.5 Hz, J=6.0 Hz, 1 H), 3.02 (s, 3 H), 2.06 (s, 3 H). $^{13}$C NMR (DMSO-d$_6$, 600 MHz) δ 168.25, 161.32 (d, J=242.9 Hz), 148.41, 144.29, 134.30, 130.89, 130.61, 129.40, 129.24, 129.00 (d, J=8.2 Hz), 125.95, 115.56 (d, J=21.4 Hz), 68.90, 43.30, 41.20, 40.80. MS m/z 397 (M+H)$^+$.

EXAMPLE 4

2-[1-(Dimethylamino)-1-methylethyl]-N-(4-fluorobenzyl)-5,6-dihydroxypyrimidine-4-carboxamide

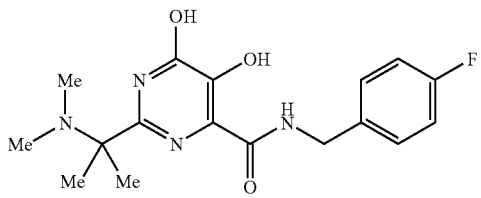

Step 1: Benzyl 1-(4-{[(4-fluorobenzyl)amino]carbonyl}-5,6-dihydroxypyrimidin-2-yl)-1-methylethyl carbamate (C-2)

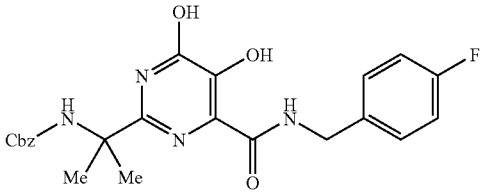

A methanol solution of methyl 2-(1-{[(benzyloxy)carbonyl]amino}-1-methylethyl)-5,6-dihydroxypyrimidine-4-carboxylate (C-1) (prepared from N-[(benzyloxy)carbonyl]-2-methylalanine by procedures similar to those set forth in Scheme A) was treated with 2 eq. of 4-fluorobenzylamine and refluxed overnight. After evaporation of the solvent, the residue was poured into EtOAc and extracted with 1N HCl and brine. The organic phase was dried over Na$_2$SO$_4$, filtered and concentrated under vacuum. The solid residue was triturated with diethyl ether to give the product (C-2).

$^1$H NMR (DMSO-d$_6$, 400 MHz) δ 12.4 (bs, 1 H), 12.3 (bs, 1 H), 9.2 (bs, 1 H) 7.5-7.25 (m, 7 H), 7.16 (t, J=8.8 Hz, 2 H), 4.97 (s, 2 H), 4.48 (d, J=6.4 Hz, 2 H), 1.51 (s, 6 H).

Step 2: 2-(1-Amino-1-methylethyl)-N-(4-fluorobenzyl)-5,6-dihydroxypyrimidine-4-carboxamide(C-3)

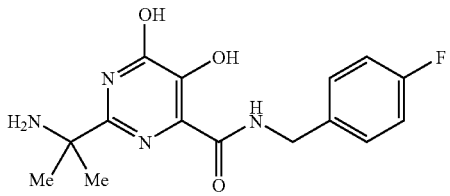

To a solution of benzyl 1-(4-{[(4-fluorobenzyl)amino] carbonyl}-5,6-dihydroxypyrimidin-2-yl)-1-methylethylcarbamate (C-2) in methanol 10% Pd/C (10% by weight) was added. The flask was evacuated, then filled with hydrogen and stirred under an hydrogen atmosphere at room temperature for 1 h. The catalyst was filtered off, washed with methanol, the filtrate was evaporated to dryness and the residue was triturated with Et$_2$O to obtain (C-3) as a pale yellow solid.

$^1$H NMR (DMSO-$_6$, 400 MHz) δ 7.36 (t, J=8.2 Hz, 2 H), 7.16 (t, J=8.8 Hz, 2 H), 4.46 (d, J=6.2 Hz, 2 H), 1.43 (s, 6 H).

Step 3: 2-[1-(Dimethylamino)-1-methylethyl]-N-(4-fluorobenzyl)-5,6-dihydroxypyrimidine-4-carboxamide (C-4)

To a stirred solution of (C-3) in methanol about 11 eq. of acetic acid were added and subsequently NaBH$_3$CN (8 eq.) and formaldehyde (37% solution, 2.5 eq.). The mixture was stirred at room temperature for 5 days, concentrated by rotary evaporation and subjected to RP-HPLC (C18, water/acetonitrile with 0.1% of trifluoroacetic acid as eluant). Collection and liophilization of appropriate fractions afforded the product (C-4) as its trifluoroacetate salt. The white powder was dissolved in 1N HCl and lyophilized again to be converted into the corresponding hydrochloride salt.

$^1$H NMR (DMSO-d$_6$, 300 MHz) δ 12.4 (s, 1 H) 10.2 (bs, 2 H), 7.41 (dd, J=8.3 Hz, J=6.9 Hz, 2 H), 7.16 (t, J=8.3 Hz, 2 H), 4.50 (d, J=5.9 Hz, 2 H), 2.73 (s, 6 H), 1.60 (s, 6H). MS m/z 349 (M+H)$^+$.

EXAMPLE 5

N-(4-fluorobenzyl)-5,6-dihydroxy-2-(4-methylmorpholin-3-yl)-pyrimidine-4-carboxamide

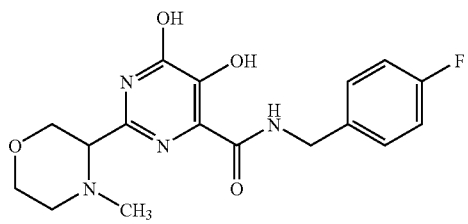

Step 1:
4-(tert-butoxycarbonyl)morpholine-3-carboxylic acid (C-5)

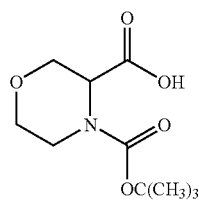

To a vigorously stirred solution of 3-morpholinecarboxylic acid and triethylamine (1.11 eq.) in MeOH at 50° C. was added di-t-butyl dicarbonate (2 eq.). Stirring was continued at 50° C. for 5 min and at room temperature overnight. The reaction mixture was then concentrated to obtain an oily residue and suspended between EtOAc and saturated NaHCO$_3$. The organic layer was extracted with saturated NaHCO$_3$ and H$_2$O. The combined aqueous layers were brought to pH=2.0 with 3 M HCl and immediately extracted with EtOAc. The combined organic layers were washed with dilute HCl, dried, filtered and evaporated to give C-5 as a pale yellow oil, a 1:1 mixture of rotamers by NMR.

δ $^1$H NMR (400 MHz, DMSO-d6) 12.93 (bs, 1 H), 4.32 (s, 0.5 H), 4.29 (s, 0.5 H), 4.2-4.1 (m, 1 H), 3.83-3.74 (m,1 H), 3.58-3.52 (m, 2 H), 3.36-3.31 (m, 1 H), 3.16 (t, J=11.4 Hz, 0.5 H), 3.00 (t, J=11.4 Hz, 0.5 H), 1.40 (s, 4.5 H), 1.36 (s, 4.5 H). MS m/z 232 (M+H)$^+$.

Step 2: tert-Butyl 3-(aminocarbonyl)morpholine-4-carboxylate-(C-6)

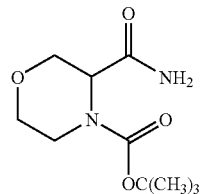

To a stirred solution of compound C-5 (1 eq.), pyridine (0.6 eq.) and di-t-butyl dicarbonate (1.3 eq.) in dioxane, NH$_4$HCO$_3$ (1.26 eq.) was added and the mixture was stirred at room temperature for 20 hours. Mixture was concentrated, taken up in EtOAc and washed with water and brine. Organics were dried over Na$_2$SO$_4$ and evaporated giving C-6 as an oil which crystallized at room temperature.

$^1$H-NMR (DMSO-d$_6$, 300 MHz) δ 7.35 (bs, 1 H), 7.06 (bs, 1 H), 4.15 (bs, 2 H), 3.76 (bs, 1 H), 3.57-3.51 (m, 2H), 3.28 (m, 1 H), 3.18 (m, 1 H), 1.36 (s, 9 H). MS m/z 231 (M+H)$^+$.

Step 3: tert-Butyl 3-cyanomorpholine-4-carboxylate-(C-7)

A solution of C-6 (1 eq.) and triethylamine (2.1 eq.) in CH$_2$Cl$_2$ was cooled to 0° C. and trifluoroacetic anhydride (1.1 eq.) added dropwise under nitrogen. Stirring was continued 3.5 hours more at room temperature and volatiles removed in vacuo. Residues taken in EtOAc were washed with water, brine and dried over Na$_2$SO$_4$. Evaporation gave the title compound as a brown solid.

$^1$H NMR (DMSO-d$_6$, 400 MHz) δ 5.04 (d, J=2.7 Hz, 1 H), 3.96 (d, J=12.2 Hz, 1 H), 3.86 (dd, J=11.5, 2.6 Hz, 1 H), 3.69 (d, J=12.4 Hz, 1 H), 3.56 (dd, J=12.2, 3.2 Hz, 1 H), 3.40 (td, J=11.9, 2.89 Hz, 1 H), 2.97 (m, 1 H), 1.43 (s, 9 H). MS m/z 213 (M+H)$^+$.

Step 4: tert-Butyl 3-[(Z)-amino(hydroxyimino)methyl]morpholine-4-carboxylate-(C-8)

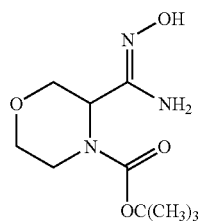

A solution of C-7 (1 eq.), hydroxylamine hydrochloride (1.4 eq.) and triethylamine (1.7 eq.) in EtOH was refluxed under nitrogen for 5 hours. Mixture was concentrated and residues taken up in EtOAc and washed with water and brine. Combined organics were dried over $Na_2SO_4$ and evaporated giving C-8 as yellow solid.

$^1$H NMR (DMSO-$d_6$, 400 MHz) δ 9.16 (bs, 1 H), 5.32 (bs, 2 H), 4.30 (bs, 1 H), 4.08 (d, J=11.6 H, 1 H), 3.75 (d, J=6.8 Hz, 1 H), 3.50-3.33 (m, 4 H), 1.38 (s, 9 H) MS: m/z 246 (M+H)$^+$.

Step 5: Dimethyl-2-({2-amino-2-[4-(tert-butoxycarbonyl)morpholin-3-yl]ethenyl}oxy)but-2-enedioate-(C-9)

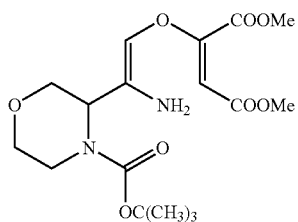

A solution of C-8 (1 eq.) and dimethylacetylenedicarboxylate (1.2 eq.) in $CHCl_3$ was refluxed for 1 hour under nitrogen and solution concentrated. Residue was purified by flash chromatography on silica gel, eluents petroleum ether/EtOAc 7:3→1:1, to give the desired product as a mixture of two isomers E/Z (76:14).

$^1$H NMR (DMSO-$d_6$, 400 MHz, 300K) δ 6.60 and 6.20 (2 bs, 2 H), 5.58 and 5.41 (2s, 1 H), 4.36 (bs, 1 H), 4.04 (bs, 1 H), 3.8 (bs, 1 H), 3.76 and 3.72 (2 s, 3 H), 3.63 and 3.58 (2 s, 3 H), 3.53 (td, J=13.6, 3.7 Hz, 1 H), 3.44 (t, J=10.4 Hz, 1 H), 3.31 (m, 2 H), (s, 9 H). MS m/z 388 (M+H)$^+$.

Step 6: tert-Butyl-3-[4,5-dihydroxy-6-(methoxycarbonyl)pyrimidin-2-yl]morpholine-4-carboxylate-(C-10)

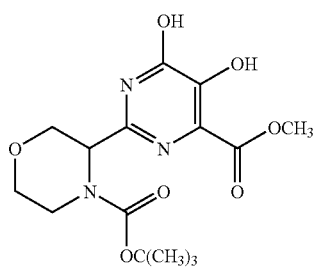

The adducts C-9 were refluxed in xylenes for 24 hours. Then the reaction was cooled and concentrated in vacuo. Ethyl ether was added until precipitation of a solid that was filtered, washed with ethyl ether and dried to give the pyrimidine C-10 as an orange solid.

$^1$H NMR (DMSO-$d_6$, 400 MHz, 340 K) δ 4.62 (s, 1H), 4.15 (d, J=12 Hz, 1H), 3.84 (bs,1H), 3.82 (s, 3H), 3.70 (dd, J=12.3, 4 Hz, 1H), 3.61 (dd, J=12.2, 3.8 Hz, 1H), 3.56 (t, J=13 Hz, 1H), 3.43 (td, J=11.5, 3.4 Hz, 1H), 1.35 (s, 9H). MS m/z 356 (M+H)$^+$.

Step 7: Methyl 5,6-dihydroxy-2-morpholin-3-ylpyrimidine-4-carboxylate (C-11)

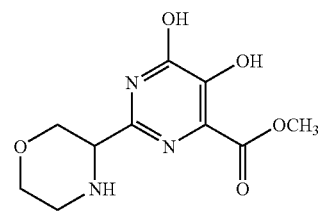

The methyl ester A was treated with a mixture of TFA:dichloromethane:$H_2O$ (65:35:10) at room temperature for 15 minutes. The reaction mixture was concentrated and the residue was taken up in $Et_2O$ and evaporated several times in order to remove excess trifluoroacetic acid. A solid residue was obtained after filtration.

$^1$H NMR (DMSO-$d_6$, 400 MHz, 300K) δ 13.24 (bs, 1 H), 10.54 (bs, 1H), 9.54 (bs, 2H), 4.34 (d, J=6.9 Hz, 1 H), 4.24 (dd, J=12.2, 3.2 Hz, 1H), 3.93 (d, J=11.2 Hz, 1H), 3.84 (s, 3H), 3.75 (t, J=10.3 Hz, 1H), 3.58 (t, J=10.5 Hz, 1H), 3.32 (d, J=12.8 Hz, 1H), 3.20 (td, J=11, 3.7 Hz, 1H). MS: m/z 256 (M+H)$^+$.

Step 8: N-(4-fluorobenzyl)-5,6-dihydroxy-2-morpholin-3-ylpyrimidine-4-carboxamide (C-12)

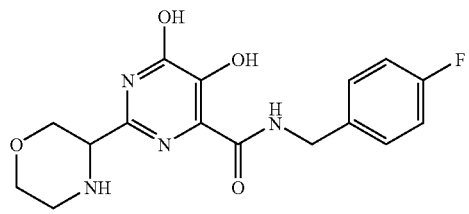

The methyl ester C-11 in dry MeOH was treated with 4-fluorobenzyl amine (2.0 eq.) at 90° C. for 1 hour. The reaction mixture was concentrated and the residue triturated with $Et_2O$. A solid residue was obtained. Title compound was isolated by RP-HPLC as its trifluoroacetate salt (C18 column, eluants water/acetonitrile containing 0.1% TFA).

$^1$H NMR (DMSO-$d_6$+TFA, 400 MHz, 300 K) δ 9.63 (bs, 1 H), 9.4 (t, J=6.07 Hz, 1 H), 9.2 (bs, 1 H), 7.39 (dd, J=8.31, J=5.76 Hz, 2 H), 7.18 (t, J=8.84 Hz, 2 H), 4.59 (dd, J=15.53, J=6.80 Hz, 1 H), 4.53 (dd, J=15.36, J=6.24 Hz, 1 H), 4.37 (bs, 1 H), 4.24 (dd, J=12.41, J=3.24 Hz, 1 H), 3.99 (d, J=12.04 Hz, 1 H), 3.74-3.62 (m, 2 H), 3.41 (d, J=13.09 Hz, 1 H), 3.40 (bs, 1 H). MS m/z 349 (M+H)$^+$.-

Step 9: N-(4-fluorobenzyl)-5,6-dihydroxy-2-(4-methylmorpholin-3-yl)-pyrimidine-4-carboxamide (C-13)

To a solution of C-12 (1 eq.) in MeOH were added 37% HCOH (6 eq.), NaBH₃CN (5.2 eq.) and AcONa (5.8 eq.). Mixture was stirred at room temperature under nitrogen for 12 hours, then concentrated and title compound C-13 was obtained by RP-HPLC purification on a C18 column (eluants water/acetonitrile containing 0.1% TFA) as its trifluoacetate salt.

¹H NMR (DMSO-d₆+TFA, 400 MHz, 330 K) δ 9.2 (bt, 1 H), 7.40 (dd, J=8.38, J=5.75 Hz, 2 H), 7.16 (t, J=8.84 Hz, 2 H), 4.57 (d, J=6.34 Hz, 2 H), 4.27 (dd, J=10.03, J=3.55 Hz, 1 H), 4.22 (dd, J=12.82, J=3.22 Hz, 1 H), 4.10 (d, J=13.73 Hz, 1 H), 3.77 (t, J=11.84 Hz, 1 H), 3.65-3.60 (m, 2 H), 3.41 (td, J=12.54, J=3.67 Hz, 1 H), 2.87 (s, 3 H). MS m/z 363 (M+H)⁺.

EXAMPLE 6

N-(4-fluorobenzyl)-5,6-dihydroxy-2-(1-methylpyrrolidin-2-yl)pyrimidine-4-carboxamide

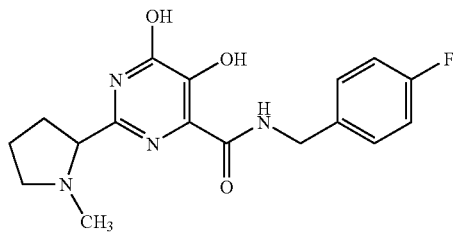

Step 1: Tert-butyl-2-[amino(hydroxyimino)methyl]pyrrolidine-1-carboxylate (C-14)

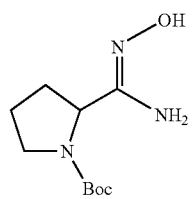

A solution of hydroxylamine hydrochloride (1.0 eq.) in MeOH was added at 0° C. to a solution of KOH (1.0 eq.) in MeOH. The resulting reaction mixture was filtered and added to a solution of tert-butyl-2-cyanopyrrolidine-1-carboxylate (1.0 eq.) in methanol and stirred at 40° C. for 2 h. The solvent was removed in vacuo and the residue treated with water, the solid was filtered and washed with a mixture of Et₂O: Petroleum Ether 1:1 to afford the title compound C-14 as a white solid.

¹H-NMR (DMSO-d₆, 400 MHz) δ 8.92 (s, 1 H), 5.35 (s,1 H), 5.15 (s, 1 H), 4.25 (bs, 0.5 H), 4.10 (s, 0.5 H), 3.40-3.30 (m, 1 H), 2.10-1-70 (m, 4 H), 1.40 (s, 4.5 H),1.35 (s, 4.5 H), one signal is obscured by water.

Step 2: Methyl 5-(benzoyloxy)-2-[1-(tert-butoxycarbonyl)pyrrolidin-2-yl]-6-hydroxypyrimidine-4-carboxylate (C-15)

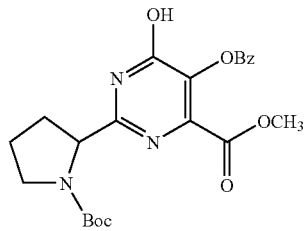

A solution of C-14 (1.0 eq.) and dimethyl acetylenedicarboxylate (1.05 eq.) in CHCl₃ was refluxed for 3 h. The reaction mixture was concentrated and the crude product was used directly in the next step without further purification. The crude product was dissolved in xylene and refluxed for 24 h. The solvent was removed in vacuo and the crude was dissolved in pyridine. Benzoic anhydride was added (1.5 eq.). The reaction mixture was stirred at room temperature until the starting material was consumed as determined by MS analysis. The reaction mixture concentrated, the resulting oil was diluted with ethyl acetate and washed with 1N HCl solution, saturated NaHCO₃ solution, brine. The crude oil obtained after organic solvent evaporation was purified by flash chromatography to obtain C-15 as a yellow solid.

¹H-NMR (CDCl₃, 400 MHz) δ 12.08 (bs, 1 H), 8.18 (d, J=7.6 Hz, 2 H), 7.64 (t, J=7.6 Hz, 1 H), 7.50 (t, J=7.6 Hz, 2 H), 4.80-4.60 (m, 1 H), 3.82 (s, 3 H), 3.60-3.50 (m, 1 H), 3.40-3.20 (m, 1 H), 2.50-2.10 (m, 2 H), 2.00-1.70 (m, 2 H), 1.50 (s, 9 H). MS m/z 444 (M+H)⁺.

Step 3: Methyl 5-(benzoyloxy)-6-hydroxy-2-pyrrolidin-2-ylpyrimidine-4-carboxylate (C-16)

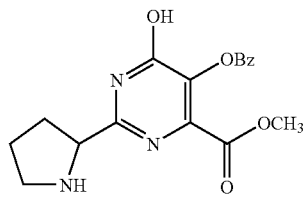

Methyl 5-(benzoyloxy)-2-[1-(tert-butoxycarbonyl)pyrrolidin-2-yl]-6-hydroxypyridine-4-carboxylate C-15 was treated with TFA:CH₂Cl₂ (3:7) at 0° C. The solution was warmed to room temperature and the progress of the reaction was monitored by MS analysis. After 1 h the reaction was complete and the solvent was removed under reduced pressure using a rotatory evaporator. The product C-16 was precipitated with Et₂O and collected by filtration.

¹H NMR (CDCl₃, 400 MHz) δ 8.14 (d, J=7.5 Hz, 2 H), 7.67 (t, J=7.6 Hz, 1 H), 7.50 (dd, J=7.6, 7.6 Hz, 2 H), 4.99 (dd, J=14.9, J=7.3 Hz, 1 H), 3.78 (s, 3 H), 3.60-3.40 (m, 2 H), 2.60-2.45 (m, 1 H), 2.40-2.30 (m, 1 H), 2.20-2.10 (m, 2 H). MS m/z 344 (M+H)⁺.-

Step 4: N-(4-fluorobenzyl)-5,6-dihydroxy-2-pyrrolidin-2-ylpyrimidine-4-carboxamide (C-17)

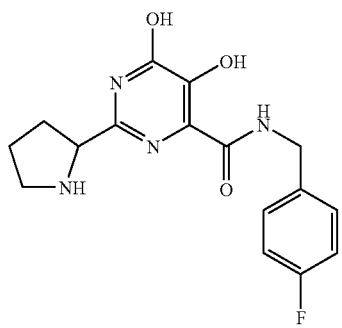

A solution of methyl 5-(benzoyloxy)-6-hydroxy-2-pyrrolidin-2-ylpyrimidine-4-carboxylate (C-16) (1.0 eq.) in MeOH was treated with 4-fluorobenzylamine (3.0 eq.). The solution was stirred at reflux until the starting material was consumed as determined by MS analysis. The reaction was concentrated and the product (C-17) was precipitated with MeOH and collected by filtration.

$^1$H NMR (DMSO-d$_6$, 400 MHz) δ 9.55 (bs, 1 H), 7.35 (dd, J=13.7, J=7.8 Hz, 2 H), 7.16 (dd, J=17.5, J=8.8 Hz, 2 H), 4.60-4.40 (m, 2 H), 4.06 (dd, J=14.0, J=6.9 Hz, 1 H), 3.15-3.10 (m, 1 H), 3.00-2.90 (m, 1 H), 2.20-2.10 (m, 1 H), 1.90-1.70 (m, 3 H). MS m/z 333 (M+H)$^+$.

Step 5: N-(4-fluorobenzyl)-5,6-dihydroxy-2-(1-methylpyrrolidin-2-yl)pyrimidine-4-carboxamide (C-18)

To a stirred solution of N-(4-fluorobenzyl)-5,6-dihydroxy-2-pyrrolidin-2-ylpyrimidine-4-carboxamide (C-17) (1.0 eq.) in MeOH, Et$_3$N (1.0 eq.) was added followed by the addition of AcONa (1.6 eq.), AcOH glacial (1.6 eq.), 37% HCOH (2.0 eq.) and NaBH(AcO)$_3$ (1.4 eq.). The mixture was stirred at room temperature until the reactants were consumed as determined by MS analysis. The reaction mixture was quenched by adding aqueous NaHCO$_3$, and the product extracted with EtOAc. The organic layer was dried over anhydrous Na$_2$SO$_4$, filtered and concentrated under reduced pressure using a rotatory evaporator. A portion of the mixture was purified by RP-HPLC (C18, water/acetonitrile with 0.1% of trifluoroacetic acid as eluant) to give the title compound C-18 as its trifluoroacetate salt.

$^1$H NMR δ (DMSO-d$_6$, 400 MHz) δ 13.20 (bs, 1 H), 12.50 (bs, 1 H), 10.0-9.70, (m, 1 H), 9.63 (bs, 1 H), 7.35 (dd, J=13.8 Hz, J=8.2 Hz, 2 H), 7.18 (dd, J=17.5 Hz, J=8.8 Hz, 2 H), 4.54 (m, 2 H), 4.40 (dd, J=15.7 Hz, J=7.7 Hz, 1 H), 3.82-3.70 (m, 1 H), 3.40-3.20 (m, 1 H), 2.94 (s, 3 H), 2.60-2.50 (m, 1 H), 2.20-1.80 (m, 3 H). MS m/z 347 (M+H)$^+$.

EXAMPLE 7

2-(1,4-dimethylpiperazin-2-yl)-N-(4-fluorobenzyl)-5,6-dihydroxypyrimidine-4-carboxamide

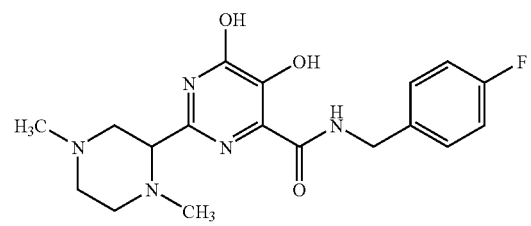

Step 1: Preparation of Compound C-20

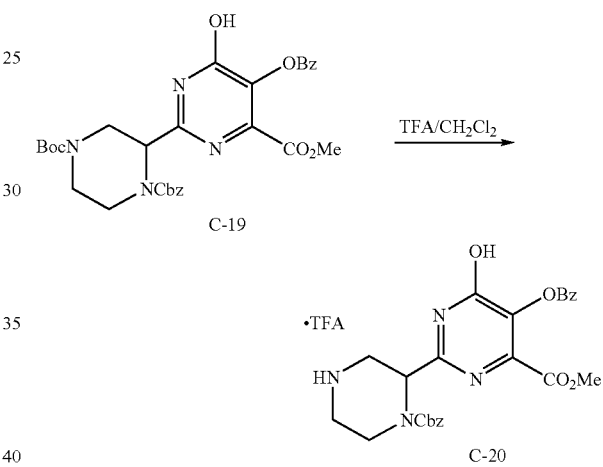

Compound C-19 (which was prepared from 1-[(benzyloxy)carbonyl]-4-(tert-butoxycarbonyl)piperazine-2-carboxylic acid (Bigge et al, *Tetrahedron Lett.* 1989, 30: 5193) using procedures similar to those set forth in Scheme A) was deprotected with TFA/dichloromethane 1:1. After 1.5 h the solution was evaporated to obtain the crude product C-20.

Step 2: Preparation of Compound C-21

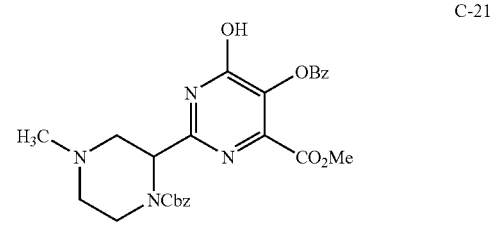

To the crude C-20 dissolved in MeOH, NaCNBH$_3$ (1.4 eq.), AcONa (1.6 eq.) and HCHO 37% (2 eq.) were added. After 1 h the mixture was evaporated to obtain crude C-21.

Step 3: Preparation of Compound C-22

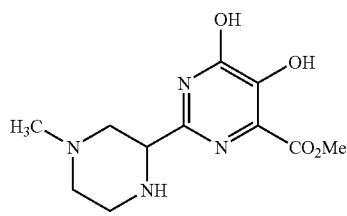

Crude C-21 dissolved in MeOH and hydrogenated at atmospheric pressure on 10% Pd/C overnight. After filtration and evaporation of the filtrate crude C-22 was obtained.

Step 4: Preparation of Compound C-23

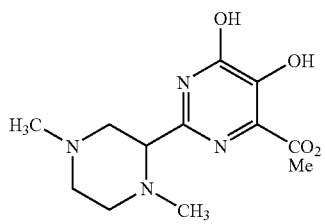

Crude C-22 was dissolved in MeOH and NaCNBH$_3$ (1.4 eq.), AcONa (1.6 eq.) and HCHO 37% (2 eq.) were added. After 2.5 h the mixture was evaporated to obtain crude product C-23.

Step 5: 2-(1,4-dimethylpiperazin-2-yl)-N-(4-fluorobenzyl)-5,6-dihydroxypyrimidine-4-carboxamide C-24

Crude C-23 was dissolved in NMP (6 ml/mmol) and 4-fluorobenzylamine (3 eq.) added. The mixture was stirred at 90° C. overnight. Part of the crude material was purified by preparative HPLC (C18, gradient of CH$_3$CN/H$_2$O+ 0.01% TFA) to obtain the title product (C-24) as its trifluoroacetate salt.

$^1$H NMR (DMSO d$_6$+TFA, 300 K, 400 MHz) δ 12.5 (bs, 1 H), 9.30 (t, J=6.4 H, 1 H), 7.38 (dd, J=5.8, 8.8 Hz, 2 H), 7.17 (t, J=8.8 H, 2 H), 4.58-4.4 (m, 2 H), 3.66 (bs, 1 H), 3.55-3.35 (m, 3 H), 3.20 (d, J=13.3 Hz, 1 H), 3.03, (t, J=11.7 Hz, 1 H), 2.79 (s, 3 H), 2.85-2.70 (m, 1 H), 2.33 (bs, 3 H). MS m/z 376 (M+H)$^+$.

EXAMPLE 4A

2-[4-(dimethylamino)tetrahydro-2H-pyran-4-yl]-N-[4-fluoro-2-(methylsulfonyl)benzyl]-5,6-dihydroxy-pyrimidine-4-carboxamide

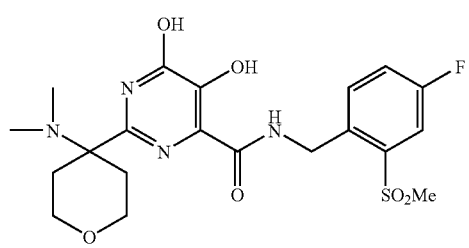

Step 1: tert-Butyl 4-(aminocarbonyl)tetrahydro-2H-pyran-4-yl-carbamate (C-25)

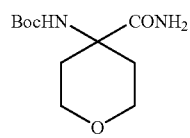

To a stirred solution of the commercially available 4-[(tert-butoxycarbonyl)amino]tetrahydro-2H-pyran-4-carboxylic acid in dioxane, pyridine (0.6 eq.), di-butyl dicarbonate (1.3 eq) and ammonium bicarbonate (1.26 eq) were added and the mixture was stirred at room temperature for 20 hours. Dioxane was concentrated and the residue dissolved in ethyl acetate and washed with HCl 1N, saturated aqueous NaHCO$_3$ solution and brine, dried over Na$_2$SO$_4$, filtered and evaporated in vacuo to obtain the solid compound (C-25).

$^1$H NMR (CDCl$_3$, 300 MHz, 300 K) δ 6.82 (bs,1H), 5.37 (bs, 1H), 4.80 (bs, 1H), 3.88 (t, J=4.4 Hz, 1H), 3.84 (t, J=4.4 Hz, 1H), 3.72-3.64 (m, 2H), 2.30-2.21 (m, 2H), 1.98-1.94 (m, 2H), 1.48 (s, 9H). MS: m/z 245 (M+H)$^+$.

Step 2: tert-Butyl 4-cyanotetrahydro-2H-pyran-4-yl-carbamate (C-26)

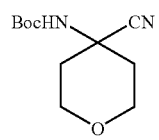

A solution of tert-butyl 4-(aminocarbonyl)tetrahydro-2H-pyran-4-yl-carbamate (C-25) and triethylamine (2.1 eq.) in dichloromethane was cooled to 0° C. and trifluoroacetic anhydride (1.1 eq.) was added dropwise under nitrogen. Stirring was continued for 1 hour allowing the mixture to reach room temperature. Volatiles were removed in vacuo and residue was taken up in ethyl acetate, washed with HCl 1N, brine and dried over Na$_2$SO$_4$. Evaporation gave a crude which was purified by flash chromatography on silica gel (eluent:petroleum ether:ethyl acetate=7:3) to give the title compound (C-26), colorless oil, as a 8:2 mixture of two rotamers by $^1$H NMR.

¹H NMR (CDCl₃, 300 MHz, 300 K) δ 4.71 (bs, 1H), 3.96 (t, J=3.5 Hz, 1H), 3.93 (t, J=4.1 Hz, 1H ), 3.79-3.76 (m, 2H), 2.37-2.34 (m, 2H), 1.89-1.82 (m, 2H), 1.50 (s, 7H), 1.47 (s, 2H). MS: m/z 227 (M+H)⁺.

Step 3: tert-Butyl-4-[amino(hydroxyimino)methyl]tetrahydro-2H-pyran-4-yl-carbamate (C-27)

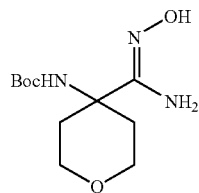

A solution of free hydroxylamine in ethanol was obtained by dissolving separately hydroxylamine hydrochloride (1.1 eq) and potassium hydroxide (1.1 eq) in ethanol. The two solutions were mixed together, the potassium chloride filtered off and the resulting ethanolic solution was used to treat a solution of tert-butyl-4-cyanotetrahydro-2H-pyran-4-yl-carbamate (C-26) in ethanol at 45° C. for 5 hours. Mixture was concentrated to obtain the title compound (C-27) as a crude solid that was used in the next step without further purification.

MS: m/z 260 (M+H)⁺.

Step 4: Dimethyl-2-{[(amino{4-[(tert-butoxycarbonyl)amino]tetrahydro-2H-pyran-4-yl}methylidene)amino]oxy}but-2-enedioate (C-28)

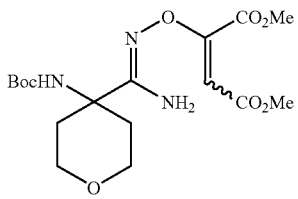

A solution of tert-butyl-4-[amino(hydroxyimino)methyl]tetrahydro-2H-pyran-4-yl-carbamate (C-27) and dimethylacetylendicarboxylate (1.2 eq.) in chloroform was refluxed for 1 hour under nitrogen and the solution was concentrated. Residue was purified by flash chromatography on silica gel (eluent:petroleum ether:ethyl acetate=7:3) to give the desired product (C-28) as a mixture of isomers in ratio 7:3.

¹H-NMR (CDCl₃, 300 MHz, 300 K) δ 5.91 (bs, 1H), 5.83 (s, 0.7H), 5.75 (s, 0.3H), 5.67 (bs, 1H), 4.67 (s, 0.7H), 4.63 (s, 0.3H), 3.93 (s, 2.1H), 3.86 (s,0.9H), 3.84-3.63 (m, 4H), 3.76 (s, 0.9H), 3.73 (s, 2.1H), 2.32-2.17 (m, 2H), 2.14-1.98 (m, 2H), 1.47 (s, 9H). MS: m/z 402 (M+H)⁺.

Step 5: Methyl 2-{4-[(tert-butoxycarbonyl)amino]-tetrahydro-2H-pyran-4-yl}-5,6-dihydroxypyrimidine-4-carboxylate (C-29)

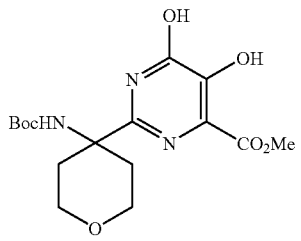

A solution of dimethyl-2-{[(amino{4-[(tert-butoxycarbonyl)amino]tetrahydro-2H-pyran-4-yl}methylidene)amino]oxy}but-2-enedioate (C-28) in o-xylene was refluxed for 6 hours. Then the reaction was cooled down and concentrated. Ethyl ether was added until precipitation of a solid that was filtered, washed with other ethyl ether and dried to give the title compound (C-29)as a brown solid.

MS: m/z 370 (M+H)⁺.

The reaction mother liquor was concentrated and used for the next step.

Step 6: Methyl 5-(benzoyloxy)-2-{4-[(tert-butoxycarbonyl)amino]tetrahydro-2H-pyran-4-yl}-6-hydroxypyrimidine-4-carboxylate (C-30)

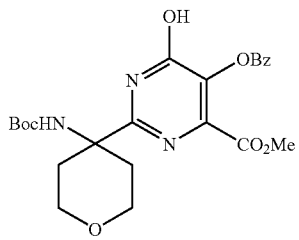

The concentrated mother liquor containing methyl 2-{4-[(tert-butoxycarbonyl)amino]-tetrahydro-2H-pyran-4-yl}-5,6-dihydroxypyrimidine-4-carboxylate (C-29), dissolved in dry pyridine was treated with benzoic anhydride (2 eq.) overnight at room temperature.

The mixture was evaporated, taken up in ethyl acetate and washed with HCl 1N and brine. Organics were dried over Na₂SO₄, filtered and evaporated the resulting crude oil was purified by flash chromatography on silica gel (eluent:ethyl acetate:petroleum ether=7:3) to obtain methyl 5-(benzoyloxy)-2-{4-[(tert-butoxycarbonyl)amino]tetrahydro-2H-pyran-4-yl}-6-hydroxypyrimidine-4-carboxylate (C-30).

¹H NMR (DMSO-d₆, 300 MHz, 300 K) δ 13.20 (bs, 1H), 8.09 (d, J=7.3 Hz, 2H), 7.79 (t, J=7.5 Hz, 1H), 7.63 (t, J=8.01 Hz, 2H), 3.76 (s, 3H), 3.75-3.60 (m, 4H), 2.22-2.15 (m, 2H), 2.00-1.87 (m, 2H), 1.34 (bs, 9H). MS: m/z 474 (M+H)⁺.-

Step 7: tert-Butyl-4-[4-({[4-fluoro-2-(methylsulfonyl)benzyl]amino}carbonyl)-5,6-dihydroxypyrimidin-2-yl]tetrahydro-2H-pyran-4-yl-carbamate (C-31)

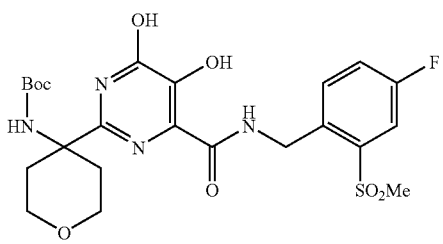

Methyl-5-(benzoyloxy)-2-{4[(tert-butoxycarbonyl) amino]tetrahydro-2H-pyran-4-yl}-6-hydroxypyrimidine-4-carboxylate (C-30) in dry MeOH was treated with 4-fluoro-2-(methylsulfonyl)benzylamine (2.5 eq.) at reflux for 2 hours. Solvent was removed in vacuo and the residue was taken up in ethyl acetate, washed with HCl 1N, brine, dried over Na$_2$SO$_4$. The filtrate was concentrated in vacuo and triturated with ethyl ether to obtain the crude title compound (C-31).
MS: m/z 541 (M+H)$^+$.

Step 8: 2-(4-Aminotetrahydro-2H-pyran-4-yl)-N-[4-fluoro-2-(methylsulfonyl)benzyl]-5,6-dihydroxypyrimidine-4-carboxamide trifluoroacetate (C-32)

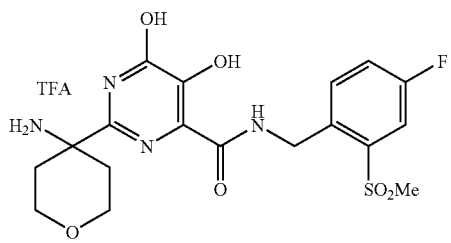

A solution of tert-butyl-4-[4-({[4-fluoro-2-(methylsulfonyl)benzyl]amino}carbonyl)-5,6-dihydroxypyrimidin-2-yl]tetrahydro-2H-pyran-4-yl-carbamate (C-31) in dichloromethane was treated with an excess of trifluoroacetic acid for 3 hours at room temperature. The acid in excess was removed in vacuo to obtain the crude title compound (C-32) as a pale yellow solid, after trituration with ethyl ether.
MS: m/z 441 (M+H)$^+$.

Step 9: 2-[4-(dimethylamino)tetrahydro-2H-pyran-4-yl]-N-[4-fluoro-2-(methylsulfonyl)benzyl]-5,6-dihydroxypyrimidine-4-carboxamide (C-33)

A solution of 2-(4-aminotetrahydro-2H-pyran-4-yl)-N-[4-fluoro-2-(methylsulfonyl)benzyl]-5,6-dihydroxypyrimidine-4-carboxamide trifluoroacetate (C-32) in MeOH was treated with triethylamine (1 eq.), sodium acetate (1.6 eq.), formaldehyde 37% w/w aq. soln. (3 eq.), and sodium cyanoborohydride (1.43 eq.). The mixture was left stirring at room temperature for 1 h. Trifluoroacetic acid (3 eq) and sodium cyanoborohydride (0.5 eq) were added, left stirring overnight. The reaction mixture was concentrated and the title compound (C-33) as trifluoro acetate salt was obtained by preparative HPLC purification (C$_{18}$, eluting with water and acetonitrile containing 0.1% trifluoroacetic acid in gradient).
$^1$H NMR (DMSO-d$_6$+TFA, 300 MHz, 300 K) δ 10.90 (bs, 1H), 9.42 (bt, 1H), 7.76 (d, J=8.5 Hz, 1H), 7.61 (d, J=5.6 Hz, 2H), 4.90 (d, J=6.3 Hz, 2H), 3.93 (d, J=6.3 Hz, 2H), 3.44 (s, 3H), 3.21-3.06 (m, 4H), 2.72 (s, 6H), 1.90-1.82 (m, 2H). MS: m/z 469(M+H)$^+$.

EXAMPLE 6A

N-(4-fluorobenzyl)-5,6-dihydroxy-2-(7-methyl-7-azabicyclo[2.2.1]hept-1-yl)pyrimidine-4-carboxamide

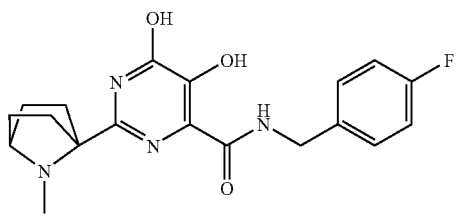

Step 1: 7-[(benzyloxy)carbonyl]-7-azabicyclo[2.2.1]heptane-1-carboxylic acid (C-35)

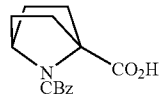

7-benzyl 1-tert-butyl 7-azabicyclo[2.2.1]heptane-1,7-dicarboxylate (C-34)(synthesized following the procedure reported in J.O.C, 1996, 61, 6313-6325) was stirred in TFA/DCM/H$_2$O (95/5/5, 0.3 M) for 10 minutes. Evaporation of the solvent afforded the titled compound (C-35).
$^1$H-NMR (DMSOd$_6$, 300K, 300 MHz) δ: 12.5 (bs, 1H), 7.45-7.30 (m, 5H), 5.06 (s, 2H), 4.27 (t, J=4.6 Hz, 1H), 2.00-1.92 (m, 2H), 1.76-1.65 (m, 4H), 1.55-1.43 (m, 2H). MS (EI+) m/z 276 (M+H)$^+$.

Step 2: benzyl 1-(aminocarbonyl)-7-azabicyclo[2.2.1]heptane-7-carboxylate (C-36)

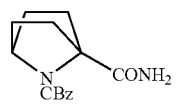

A stirred solution of 7-[(benzyloxy)carbonyl]-7-azabicyclo[2.2.1]heptane-1-carboxylic acid (C-35) in dioxane was treated with pyridine (0.8 eq.) and Boc$_2$O (1.5 eq.), then ammonium bicarbonate (1.46 eq.) was added and the mixture was stirred at room temperature for 15 hours. Dioxane was concentrated and the residue was taken up in ethyl acetate, washed with HCl 1N and brine and dried over Na$_2$SO$_4$ to give, after filtration and concentration, the titled compound (C-36).

¹H-NMR (DMSOd₆, 300K, 300 MHz) δ 7.42-7.28 (m, 5H), 7.18 (bs, 1H), 7.00 (bs, 1H), 5.05 (s, 2H), 4.28 (t, J=4.5 Hz, 1H), 2.00-1.90 (m, 2H), 1.77-1.60 (m, 4H), 1.52-1.40 (m, 2H). MS (EI+) m/z 275 (M+H)⁺.

Step 3: benzyl 1-cyano-7-azabicyclo[2.2.1]heptane-7-carboxylate (C-37)

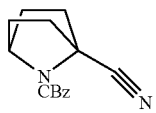

Benzyl 1-(aminocarbonyl)-7-azabicyclo[2.2.1]heptane-7-carboxylate (C-36) in dichloromethane was treated at 0° C. with Et₃N (2.1 eq.) and trifluoroacetic anhydride (1.1 eq.) was added dropwise. The reaction mixture was stirred at 0° C. for 30 minutes. Then, it was diluted with dichloromethane, washed with saturated NaHCO₃ solution, H₂O, brine and dried over Na₂SO₄. Filtration and evaporation afforded the titled compound (C-37).

¹H-NMR (DMSOd₆, 300K, 300 MHz) δ 7.42-7.30 (m, 5H), 5.14 (s, 2H), 4.32 (t, J=5.0 Hz, 1H), 2.2-1.98 (m, 4H), 1.90-1.70 (m, 2H), 1.62-1.45 (m, 2H). MS (EI+) m/z 257 (M+H)⁺.

Step 4: dimethyl-2-{[(amino{7-[(benzyloxy)carbonyl]-7-azabicyclo[2.2.1]hept-1-yl}methylidene)amino]oxy}but-2-enedioate (C-38).

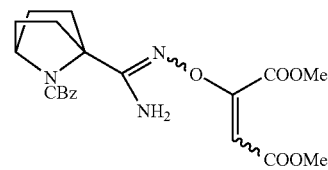

Triethyl amine (1.5 eq.), hydroxylamine hydrochloride (1.3 eq.) were added to a solution of benzyl 1-cyano-7-azabicyclo[2.2.1]heptane-7-carboxylate (C-37) in absolute methanol. The mixture was stirred at room temperature overnight. The solvent was removed under reduced pressure, the residue was dissolved in chloroform and treated with dimethylacetylene dicarboxylate (2 eq.) for 14 hours at 60° C. The reaction mixture was then concentrated and the resulting crude oil was purified by flash chromatography (petroleum ether/EtOAc 1:1) to give the titled compound (C-38) as a mixture of isomers.

¹H-NMR (DMSOd₆, 300K, 300 MHz δ: 7.41-7.25 (m, 5H), 6.57 (bs, 1.3 H), 6.17 (bs,0.7 H), 5.66 (s,0.65 H), 5.61 (s, 0.35 H), 5.04 (s, 2H), 4.35-4.30 (m, 1H), 3.79 (s, 1.95H), 3.75 (s, 1.05H), 3.63 (s,1.05H), 3.60 (s,1.95H), 2.15-1.92 (m, 2H), 1.80-1.45 (m, 6H). MS (EI+) m/z 432 (M+H)⁺.

Step 5: benzyl 1-[5-(benzoyloxy)-4-hydroxy-6-(methoxycarbonyl)pyrimidin-2-yl]-7-azabicyclo[2.2.1]heptane-7-carboxylate (C-39)

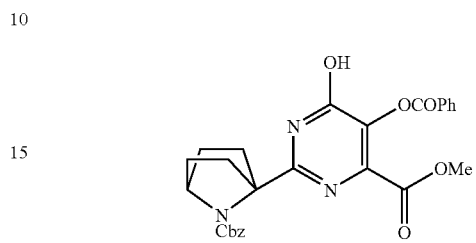

Dimethyl-2-{[(amino{7-[(benzyloxy)carbonyl]-7-azabicyclo[2.2.1]hept-1-yl}methylidene)amino]oxy}but-2-enedioate (C-38) was dissolved ortho-xylene and refluxed for 14 hours. Solvent was evaporated after cooling at room temperature and the resulting crude oil was dissolved in pyridine, treated with benzoic anhydride (2 eq.). The reaction mixture was stirred at room temperature for 3 hours. Reaction mixture was concentrated and the residue was taken up in ethyl acetate and washed with HCl 1N and saturated NaHCO₃ solution. The organic phase was dried over Na₂SO₄, filtered and after concentration and purification by flash chromatography the titled compound was obtained.

¹H-NMR (DMSOd₆, 300K, 300 MHz) δ 13.38 (s, 1H), 8.09 (d, J=7.5 Hz, 2H), 7.80 (t, J=7.5 Hz, 1H), 7.64 (t, J=7.5 Hz, 2H), 7.40-7.22 (m, 5H), 5.00 (s, 2H), 4.40 (t, J=4.3 Hz, 1H), 3.76 (s, 3H), 2.32-1.117 (m, 2H), 1.95-1.79 (m, 4H), 1.66-1.51 (m, 2H). MS (EI+) m/z 504 (M+H)⁺.

Step 6: N-(4-fluorobenzyl)-5,6-dihydroxy-2-(7-methyl-7-azabicyclo[2.2.1]hept-1-yl)pyrimidine-4-carboxamide (C-40)

Benzyl 1-[5-(benzoyloxy)-4-hydroxy-6-(methoxycarbonyl) pyrimidin-2-yl]-7-azabicyclo[2.2.1]heptane-7-carboxylate (C-39) in methanol was hydrogenated under H₂ atmosphere in presence of Pd/C 10% (10% w/w) at room temperature for 2 hours. After filtration and evaporation, the crude was dissolved in MeOH and p-fluorobenzylamine (3.5 eq.) added. After being refluxed overnight, the residue was washed with Et₂O/EP. The solid was dissolved in MeOH and NaCNBH₃ (1.4 eq.), AcONa (1.6 eq.), HCHO 37% (1 eq.) were added. The reaction mixture was stirred at room temperature overnight. The product was purified by preparative HPLC (C18, gradient CH₃CN/H₂O+0.01% TFA) to obatine the title compound (C-40) as trifluoro acetate salt.

¹H-NMR (DMSOd₆, 300K, 400 MHz) δ 12.9 (bs, 1H), 12.2 (s, 1H), 10.95 (bs, 1H), 9.66 (bs, 1H), 7.47-7.40 (m, 2H), 7.21-7.12 (m, 2H), 4.50 (d, J=6.0 Hz, 2H), 4.17 (bs, 1H), 2.67 (s, 3H), 2.45-2.1 (m, 6H), 1.95-1.80 (m, 2H). MS (EI+) m/z 373 (M+H)⁺.

EXAMPLE 7B

N-(4-fluorobenzyl)-5,6-dihydroxy-2-(1,2,4-trimethylpiperazin-2-yl)pyrimidine-4-carboxamide

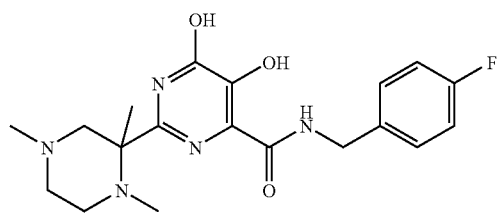

Step 1: 1-benzyl 4-tert-butyl 2-cyano-2-methylpiperazine-1,4-dicarboxylate (C-41)

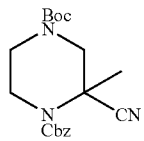

To a cooled (−75° C.) solution of LDA 2M in heptane/THF (1.5 eq) in THF, a solution of 1-[(benzyloxy)carbonyl]-4-(tert-butoxycarbonyl)piperazine-2-carboxylic acid (Bigge et al, *Tetrahedron Lett.* 1989, 30: 5193) in THF was added dropwise at −75° C. After being stirred for 1 hour at −75° C., MeI (1.5 eq) was added. After 2 hours at −75° C. the reaction mixture was left warming to r.t., evaporated, diluted with AcOEt, washed with NaHCO$_3$, water, brine and dried over Na$_2$SO$_4$. The crude was purified by flash chromatography on silica gel (petroleum ether/AcOEt, 85:15) to obtain the title compound (C-41).

$^1$H NMR (DMSOd$_6$, 340K, 300 MHz) δ 7.45-7.30 (m, 5H), 5.19 (AA' system, J=13 Hz, 2H), 4.05 (d, J=14 Hz, 1H), 3.87-3.78 (m, 1H), 3.66 (d, J=14 Hz, 1H), 3.62-3.35 (m, 3H), 1.66 (s, 3H), 1.45 (s, 9H). MS (EI+) m/z 360 (M+H)$^+$.

Step 2: 1-benzyl 4-tert-butyl 2-[(Z)-amino({[(1E)-3-methoxy-1-(methoxycarbonyl)-3-oxoprop-1-enyl]oxy}imino)methyl]-2-methylpiperazine-1,4-dicarboxylate (C-42)

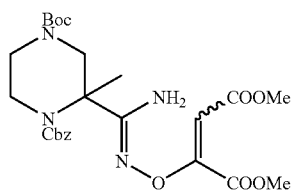

A solution of 1-benzyl 4-tert-butyl 2-cyano-2-methylpiperazine-1,4-dicarboxylate (C-41) in EtOH was added to a solution of Et$_3$N (3.2 eq) and NH$_2$OH HCl (3 eq) in EtOH. The mixture stirred 2 hr at 40° C. After evaporation of the solvent, the residue was diluted with AcOEt, washed with water, dried over Na$_2$SO$_4$, filtered and concentrated. The residue was further dissolved in chloroform and dimethylacetylenedicarboxylate (1.5 eq) added to the stirred solution. Reaction was refluxed over night. The mixture was evaporated and the residue was purified by flash chromatography on silica gel (petroleum ether/AcOEt, 65:35) affording (C-42).

$^1$H NMR (DMSOd$_6$, 340K, 300 MHz). Two sets of signals were observed due to the presence of the geometric isomers: δ 7.48-7.25 (m, 5H), 6.31, 6.01 (bs, 2H), 5.63, 5.55 (s, 1H), 5.12-5.02 (m, 2), 3.85-3.60 (m, 9H, at 3.79, 3.76 (s), at 3.66, 3.61 (s)), 3.60-3.45 (m, 2H), 3.45-3.31 (m, 1H), 1.51, 1.45 (s, 3H), 1.41 (s, 9H). MS (EI+) m/z 535 (M+H)$^+$.

Step 3: 1-benzyl 4-tert-butyl 2-[5-(benzoyloxy)-4-hydroxy-6-(methoxycarbonyl) pyrimidin-2-yl]-2-methylpiperazine-1,4-dicarboxylate (C-43)

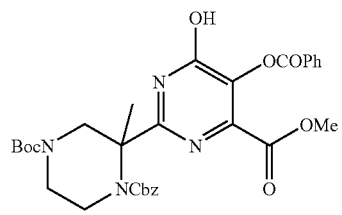

1-benzyl 4-tert-butyl 2-[(Z)-amino({[(1E)-3-methoxy-1-(methoxycarbonyl)-3-oxoprop-1-enyl]oxy}imino)methyl]-2-methylpiperazine-1,4-dicarboxylate (C-42) was dissolved in xylene and stirred at 155° C. for 8 h. After evaporation of the solvent, the residue was dissolved in pyridine and benzoic anhydride (1.5 eq) was added. The reaction mixture was stirred at room temperature over night, then pyridine was evaporated. The residue was diluted with AcOEt, the organic phase washed with HCl 1N, dried (Na$_2$SO$_4$) and evaporated. The product (C-43) was purified by flash chromatography (eluent:petroleum ether/AcOEt 70/30).

$^1$H-NMR (DMSOd$_6$, 340K, 400 MHz) δ 12.96 (bs, 1H), 8.11-8.04 (m, 2H), 7.79-7.73 (m, 1H), 7.66-7.58 (m, 2H), 7.37-7.22 (m, 5H), 5.03 (s, 2H), 4.00-3.91 (m, 1H), 3.80-3.52 (m, 7H, at 3.75 (s)), 3.47-3.40 (m, 1H), 1.65 (s, 3H), 1.35 (s, 9H). MS (EI+) m/z 607 (M+H)$^+$.

Step 4: Methyl 5-(benzoyloxy)-2-[4-(tert-butoxycarbonyl)-2-methylpiperazin-2-yl]-6-hydroxypyrimidine-4-carboxylate (C-44)

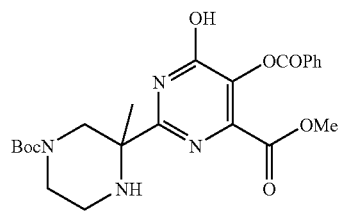

1-benzyl 4-tert-butyl 2-[5-(benzoyloxy)-4-hydroxy-6-(methoxycarbonyl)pyrimidin-2-yl]-2-methylpiperazine-1,4-dicarboxylate (C-43) was dissolved in AcOEt and hydrogenated at 1 atm on 10% (w/w) Pd/C over night. After filtration of the catalyst, solvent was evaporated to give the crude title compound (C-44).

¹H-NMR (DMSOd6+TFA, 340K, 400 MHz) δ: 8.11-8.04 (m, 2H), 7.81-7.74 (m, 1H), 7.66-7.58 (m, 2H), 4.22 (d, J=14.4 Hz, 1H), 3.80 (s, 3H), 3.75-3.67 (m, 2H), 3.63-3.44 (m, 2H), 3.32-3.24 (m, 1H) 1.68 (s, 3H), 1.38 (s, 9H). MS (EI+) m/z 473 (M+H)⁺.

Step 5: methyl 2-[4-(tert-butoxycarbonyl)-1,2-dimethylpiperazin-2-yl]-5,6-dihydroxypyrimidine-4-carboxylate (C-45)

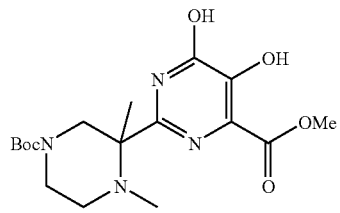

Crude material methyl 5-(benzoyloxy)-2-[4-(tert-butoxycarbonyl)-2-methylpiperazin-2-yl]-6-hydroxypyrimidine-4-carboxylate (C-44) obtained in step 1 was dissolved in MeOH, and NaCNBH₃ (2.8 eq), AcONa (3.2 eq) and HCHO (37% in H₂O, 4 eq) were added. The reaction mixture was stirred at room temperature. After 30', the solvent was evaporated and the crude solid (C-45) obtained washed with Et₂O.
MS (EI+) m/z 383 (M+H)⁺.

Step 6: tert-butyl 3-(4-{[(4-fluorobenzyl)amino]carbonyl}-5,6-dihydroxypyrimidin-2-yl)-3,4-dimethylpiperazine-1-carboxylate (C-46)

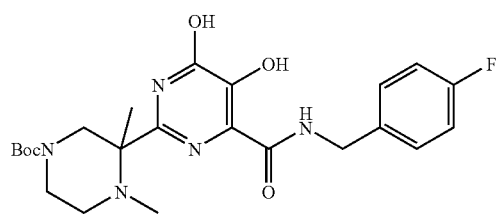

Crude material obtained methyl 2-[4-(tert-butoxycarbonyl)-1,2-dimethylpiperazin-2-yl]-5,6-dihydroxypyrimidine-4-carboxylate (C-45) was dissolved in MeOH and p-fluorobenzylamine (5.0 eq) was added. The mixture was refluxed till the consumption of the starting material was completed; then solvent was evaporated and the crude solid (C-46) obtained washed with Et₂O.
MS (EI+) m/z 476 (M+H)⁺.

Step 7: 2-(1,2-dimethylpiperazin-2-yl)-N-(4-fluorobenzyl)-5,6-dihydroxypyrimidine-4-carboxamide (C-47)

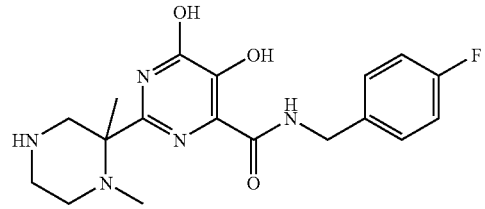

Crude material tert-butyl 3-(4-{[(4-fluorobenzyl)amino]carbonyl}-5,6-dihydroxypyrimdin-2-yl)-3,4-dimethylpiperazine-1-carboxylate (C-46) was stirred in DCM/TFA (1:1) for 1 hour. Evaporation of the solvent afforded the crude title compound (C47).
MS (EI+) m/z 376 (M+H)⁺.

Step 8: N-(4-fluorobenzyl)-5,6-dihydroxy-2-(1,2,4-trimethylpiperazin-2-yl)pyrimidine-4-carboxamide hydrochloride (C-48) (6)

Crude material obtained in step 2-(1,2-dimethylpiperazin-2-yl)-N-(4-fluorobenzyl)-5,6-dihydroxypyrimidine-4-carboxamide (C-47) was dissolved MeOH and Et₃N (2.2 eq) was added. Then NaCNBH3 (2.8 eq), AcONa (3.2 eq) and HCHO (37% in H₂O, 4 eq) were added. The reaction mixture was stirred at room temperature over night.
The reaction mixture was evaporated and the residue purified by preparative HPLC (C18, gradient of CH₃CN/H₂O+0.01% TFA) to give the title product (C-48) as trifluoroacetate salt.
¹H-NMR (CD₃CN+TFA, 280K, 600 MHz) δ: 7.50-7.38 (m, 2H), 7.13-7.07 (m, 2H), 4.66-4.51 (m, 2H), 4.00-3.72 (m, 4.3H), 3.60-3.56 (t, J=12.7 Hz, 0.7 H), 3.49-3.44 (t, J=15.5 Hz, 1 H), 3.04 (s, 2H), 2.91 (s, 1H), 2.73 (s, 1H), 2.69 (s b, 2H), 2.05 (s,1H) 1.95 (2H obscured by solvent). MS (EI+) m/z 390 (M+H)⁺.

EXAMPLE 8

N-(4-Fluorobenzyl)-5,6-dihydroxy-2-(1-methylpiperidin-2-yl)pyrimidine-4-carboxamide (D-2)

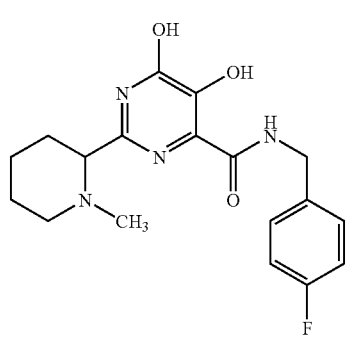

Methyl 5-(benzoyloxy)-6-hydroxy-2-piperidin-2-ylpyrimidine-4-carboxylate (D-1)(prepared from 1-[(benzyloxy)carbonyl]piperidine-2-carboxylic acid by procedures similar to those set forth in Scheme A) was dissolved in the minimal amount of chloroform. To the stirred solution were added tetrahydrofuran, triethylamine (5 eq.) and methyl iodide (3 eq.), and the reaction was stirred at 40° C. After 30 min, triethylamine (3 eq.) and methyl iodide (2 eq.) were added and mixture was stirred for 30 min at 40° C. After evaporation of volatiles, the residue was taken up into N-methylpyrrolidinone and treated with 3 eq. of 4-fluorobenzylamine at 95° C. for 15 min. The title product (D-2) was isolated as its trifluroacetate salt by RP-HPLC (C18, water/acetonitrile with 0.1% of trifluoroacetic acid as eluant).

$^1$H NMR (DMSO d$_6$, 400 MHz) δ 13.1 (bs, 1 H), 12.2 (s, 1 H), 9.45 (bs, 1 H), 9.34 (t, J=6.4 Hz, 1 H), 7.37 (dd, J=5.6 Hz, J=8.4 Hz, 2 H), 7.18 (t, J=8.8 Hz, 2 H), 4.57 (d, J=6.4 Hz, 2 H), 4.05 (bs, 1 H), 3.61 (bd, J=12.4 Hz, 1 H), 3.52-3.50 (m, 1 H), 2.78 (bs, 3 H), 2.16 (d, J=13.6 Hz, 1 H), 1.92-1.80 (m, 2 H), 1.65-1.46 (m, 3 H). MS m/z 361 (M+H)$^+$.

EXAMPLE 9

N-(4-Fluorobenzyl)-5,6-dihydroxy-2-(morpholin-4-ylmethyl)pyrimidine-4-carboxamide

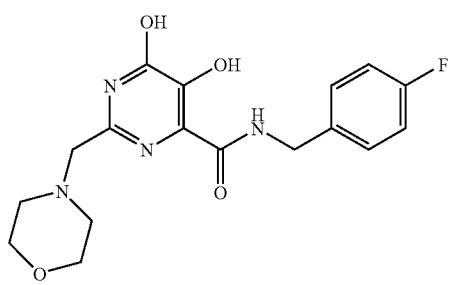

Step 1: 2-(Diethoxymethyl)-N-(4-fluorobenzyl)-5,6-dihydroxypyrimidine-4-carboxamide (E-2)

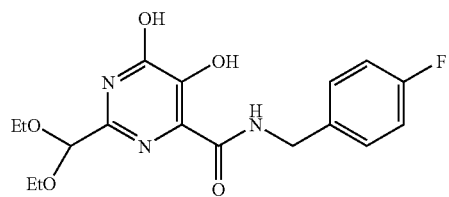

To a solution of methyl 2-(diethoxymethyl)-5,6-dihydroxypyrimidine-4-carboxylate E-1 (prepared from diethoxyacetonitrile by procedures similar to those set forth in Scheme A) (1.0 eq.) in dry MeOH was added 4-F-benzylamine (3 eq.), stirring at reflux overnight. Solvent was removed in vacuo and the solid residue washed with Et$_2$O and dried. This material dissolved in CHCl$_3$ was washed with 2N HCl, brine and dried over Na$_2$SO$_4$. Evaporation of solvents gave E-2 as a brown powder.

$^1$H NMR (300 MHz, DMSO-d$_6$) δ 12.62 (bs, 1 H), 12.51 (bs, 1 H), 9.22 (t, J=6.2 Hz, 1 H), 7.36 (dd, J=8.5, 5.7 Hz, 2 H), 7.14 (t, J=8.9 Hz, 2H), 5.12 (s, 1 H), 4.45 (d, J=6.3 Hz, 2 H), 3.71-3.41 (m, 4 H), 1.15 (t, J=7.0 Hz, 6 H). MS m/z 366 (M+H)$^+$.

Step 2: N-(4-Fluorobenzyl)-2-formyl-5,6-dihydroxypyrimidine-4-carboxamide (E-3)

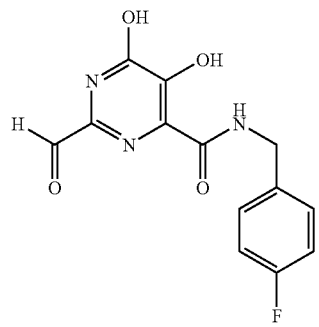

A solution of E-2 in 100% formic acid was stirred at 50° C. for 1.5 hours. Volatiles were removed in vacuo and solid residue triturated with Et$_2$O obtaining after drying E-3 as a white solid.

$^1$H NMR (300 MHz, DMSO) δ 13.19 (bs, 2 H), 9.62 (t, J=6.3 Hz, 1 H), 9.41 (s, 1 H), 7.40 (dd, J=8.5, 5.7 Hz, 2 H), 7.17 (t, J=8.8 Hz, 2 H), 4.49 (d, J=6.4 Hz, 2 H). MS m/z 292 (M+H)$^+$.

Step 3: N-(4-Fluorobenzyl)-5,6-dihydroxy-2-(morpholin-4-ylmethyl)pyrimidine-4-carboxamide (E4)

To a solution of E-3 in dry dichloroethane was added morpholine (1 eq.), stirring at room temperature for 30 minutes. NaB(OAc)$_3$H (1.4 eq.) was added and the reaction stirred at room temperature one more hour. Volatiles were removed in vacuo and solid residue purified by RP-HPLC on a C18 column, eluents water/acetonitrile+0.1% TFA, to give E-4 as its trifluoroacetate salt.

$^1$H NMR (300 MHz, DMSO-d6, 330 K) δ 9.05 (bt, 1 H), 7.38 (dd, J=8.5, 5.6 Hz, 2 H), 7.15 (t, J=8.8 Hz, 2 H), 4.51 (d, J=6.3 Hz, 2 H), 3.85 (bs, 2 H), 3.74 (t, J=4.6 Hz, 4 H), 2.98 (bs, 4 H). MS m/z 363 (M+H)$^+$.

EXAMPLE 10

N-(4-Fluorobenzyl)-5,6-dihydroxypyrimidine-4-carboxamide

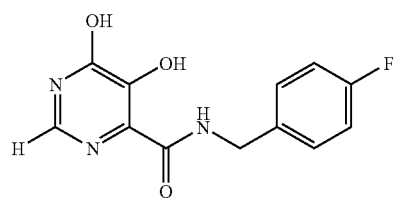

Step 1: 4,5-Dihydroxy-6-(methoxycarbonyl)pyrimidine-2-carboxylic acid (F-2)

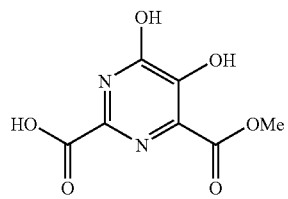

2-Ethoxycarbonyl-4,5-dihydroxy-6-(methoxycarbonyl) pyrimidine (F-1) [obtained from ethyl amino(hydroxyimino) ethanoate (Branco et al., *Tetrahedron* 1992, 40: 6335) by procedures similar to those set forth in Scheme A] was suspended in dioxane/THF 2:1 and 1N NaOH was added. After 20 min the mixture was acidified with 1N HCl, concentrated and filtered to give F-2.

$^1$H NMR (DMSO-d$_6$, 300 K, 400 MHz) δ 13.10 (bs, 1 H), 11.11 (bs, 1 H), 3.82 (s, 3 H). MS m/z 213 (M−H)$^-$.

Step 2: Methyl 5,6-dihydroxypyrimidine-4-carboxylate (F-3)

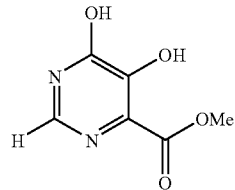

A solution of F-2 in HCl 1N was stirred for 6 hours at 90° C. The reaction mixture was filtered and the solid washed with HCl 1N. Evaporation of the filtrate afforded F-3 as a solid.

$^1$H NMR (DMSO d$_6$, 300 K, 400 MHz) δ 7.75 (s, 1 H), 3.82 (s, 3 H).

Step 3: N-(4-Fluorobenzyl)-5,6-dihydroxypyrimidine-4-carboxamide (F-4)

F-3 was dissolved in DMF and 4-fluorobenzylamine (3 eq.) was added. After 2 hours at 90° C. the mixture was evaporated. The title product F-4 was purified by preparative HPLC (C18, 5 μm, gradient of CH$_3$CN/H$_2$O+0.01% TFA).

$^1$H NMR (DMSO d$_6$, 300 K, 400 MHz) δ 12.72 (bs, 1 H), 12.54 (bs, 1H), 9.48 (bs, 1 H), 7.77 (s, 1 H), 7.36 (t, J=8.0 Hz, 2 H), 7.14 (t, J=8.8 Hz, 2 H), 4.43 (d, J=6.3 Hz, 2 H). MS m/z 262 (M−H)$^-$.

EXAMPLE 11

2-{4-[({[(2-chlorophenyl)sulfonyl]amino}carbonyl) amino]thien-3-yl}-N-(2,3-dimethoxybenzyl)-5,6-dihydroxypyrimidine-4 carboxamide

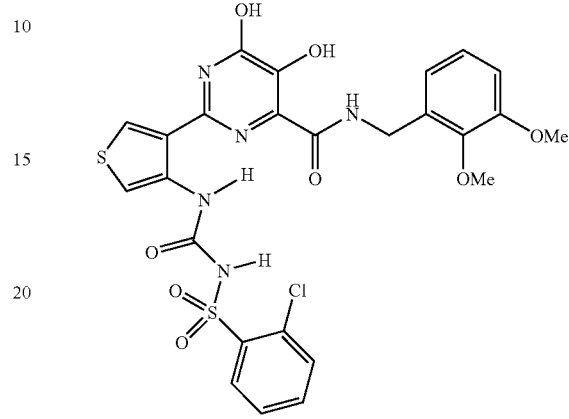

Step 1: Methyl 2-{4-[({[(2-chlorophenyl)sulfonyl] amino}carbonyl)amino]-thien-3-yl}-N-(2,3-dimethoxybenzyl)-5,6-dihydroxypyrimidine-4 carboxylate (G-2)

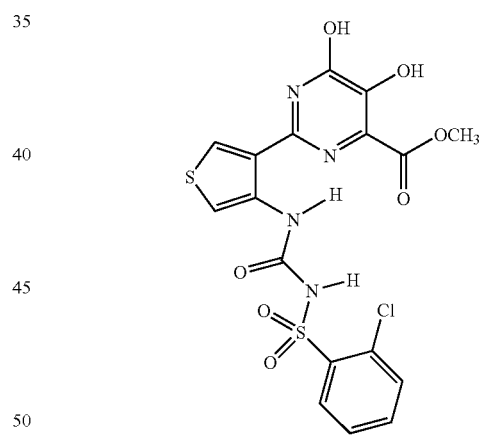

A solution of methyl 2-(4-aminothien-3-yl)5,6-dihydroxypyrimidine-4-carboxylate trifluoroacetate (1 eq.) G-1 (obtained from the deprotection of the corresponding Boc protected compound) and 2-chlorobenzensulfonylisocyanate (1.02 eq.) in pyridine was stirred at room temperature for 12 h. Pyridine was removed by concentration under reduced pressure. 1N HCl was added to the residue and the resulting solid was collected by filtration. The solid was triturated with H$_2$O and then Et$_2$O to give the title compound.

$^1$H NMR (400 MHz, DMSO) δ 13.17 (bs, 1 H), 11.70 (bs, 1 H), 10.91 (bs, 1 H), 10.80 (bs, 1 H), 8.35 (d, J=3.35 Hz, 1 H), 8.11 (d, J=7.33 Hz, 1 H), 7.77 (m, 2 H), 7.63-7.57 (m, 1 H), 7.58 (d, J=3.35 Hz, 1 H), 3.88 (s, 3 H). MS m/z 485 (M+H)$^+$.

Step 2: 2-{4-[({[(2-chlorophenyl)sulfonyl]amino}carbonyl)amino]thien-3-yl}-N-(2,3-dimethoxybenzyl)-5,6-dihydroxypyrimidine-4 carboxamide (G-3)

A solution of G-2 (1 eq.) and 2,3-dimethoxybenzylamine (1 eq.) in DMF was stirred at 50° C. for 12 h. DMF was removed by concentration under reduced pressure. 1N HCl was added to the residue. After filtration a solid was obtained which was triturated with water and then $Et_2O$. The title product G-3 was obtained by HPLC purification (Nucleosil, gradient: MeCN/$H_2O$ 30%-90% in 10 min) to give the title compound as a solid.

$^1$H NMR (400 MHz, DMSO) δ 13.03 (bs, 1 H), 12.65 (bs, 1 H), 11.60 (bs, 1 H), 9.47 (bs, 1 H), 9.20 (bs, 1 H), 8.11 (d, J=7.88 Hz, 1 H), 8.05 (m, 1 H), 7.68 (m, 2 H), 7.59 (m, 2 H), 7.07 (app. t, J=7.94 Hz, 1 H), 6.96 (m, 2 H), 4.57 (s, 1 H), 4.56 (s, 1 H), 3.80 (s, 6 H). MS m/z 620 (M+H)$^+$.

EXAMPLE 12

$N^4$-(4-fluorobenzyl)-5,6-dihydroxy-$N^2$-(pyridin-2-ylmethyl)pyrimidine-2,4-dicarboxamide

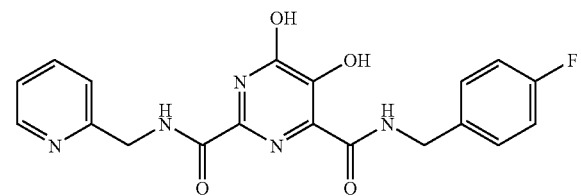

2-Ethoxycarbonyl-4,5-dihydroxy-6-(methoxycarbonyl)pyrimidine (F-1) was dissolved in DMF and 4-fluorobenzylamine (2.1 eq.) added. After stirring for 5 h at 90° C., a further addition of 4-fluorobenzylamine (0.61 eq.) was done and the mixture was stirred at the same temperature overnight. To this mixture, containing N-(4-fluorobenzyl)-2-ethoxycarbonyl-5,6-dihydroxy-pyrimidine-4-carboxamide (H-2), 2-picolylamine (3 eq.) was added and the reaction was stirred at 90° C. for 3 h. The product was purified by preparative RP-HPLC (gradient of $CH_3CN/H_2O$+0.01% TFA), to give the title compound (H-3) as its trifluoroacetate salt $^1$H NMR (DMSO-$d_6$, 300K, 400 MHz) δ 12.90 (bs, 1 H), 12.74 (bs, 1 H), 9.81 (t, J=6.7 Hz, 1 H), 9.74 (t, J=6.7 Hz, 1 H), 8.54 (d, J=4.8 Hz, 1 H), 7.82 (t, J=6.9 Hz, 1 H), 7.40-7.30 (m, 4 H), 7.18 (t, J=8.8 Hz, 2 H), 4.61 (d, J=6.4 Hz, 2 H), 4.56 (d, J=6.4 Hz, 2 H). MS m/z 398 (M+H)$^+$.

EXAMPLE 13

2-(1-benzoyl-2,3-dihydro-1H-indol-2-yl)-N-(4-fluorobenzyl)-5,6-dihydroxypyrimidine-4-carboxamide

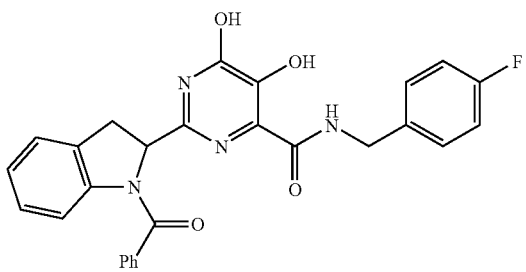

Step 1: Preparation of Compound I-2

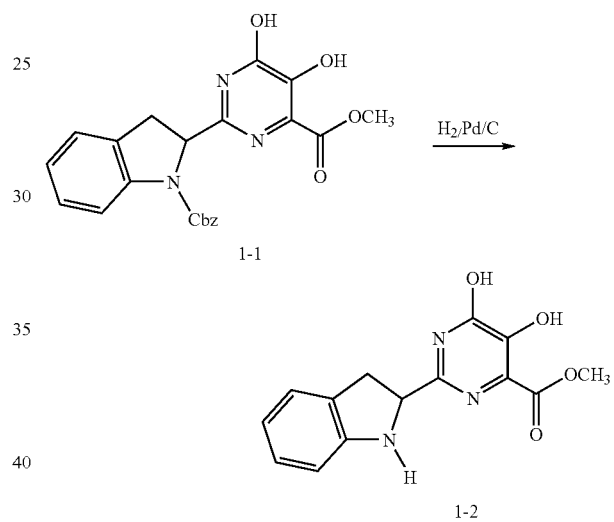

Compound I-1 (prepared from indoline-2-carboxylic acid by protection of the nitrogen and following procedures similar to those set forth in Scheme A) was dissolved in MeOH/EtOAc (1:4) and hydrogenated at atmospheric pressure on 10% Pd/C overnight, crude product I-2 was obtained after filtration and evaporation.

Step 2: Preparation of Compound I-3

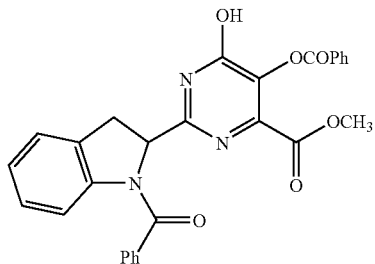

Crude product I-2 was dissolved in THF, followed by pyridine (8 eq.), and PhCOCl (4 eq.). Crude product I-3 was obtained after being stirred at room temperature overnight and solvent evaporation.

Step 3: 2-(1-benzoyl-2,3-dihydro-1H-indol-2-yl)-N-(4-fluorobenzyl)-5,6-dihydroxypyrimidine-4-carboxamide (I-4)

The crude I-3 dissolved in DMF and 4-fluorobenzylamine (4 eq.) added. The mixture was stirred at 90° C. for 4 hours. The title product I-4 was purified by preparative RP-HPLC (C18, gradient of CH$_3$CN/H$_2$O+0.01% TFA).

$^1$H NMR (DMSO d$_6$, 340 K, 300 MHz) δ 12.63 (bs, 1 H), 11.92 (bs, 1 H), 8.26 (bs, 1 H), 7.45-6.96 (m, 13 H), 5.38 (dd, J=4.5 Hz, J=10.0 Hz, 1H), 4.48-4.36 (m, 2H), 3.60 (dd, J=10.2 Hz, J=16.4 Hz, 1 H), 3.19 (dd, J=16.4 Hz, J=4.4 Hz, 1 H). MS m/z 485 (M+H)$^+$.

EXAMPLE 14

N-(4-fluorobenzyl)-5,6-dihydroxy-2-[1-(pyridin-2-ylcarbonyl)-1,2,3,4-tetrahydroquinolin-2-yl]pyrimidine-4-carboxamide

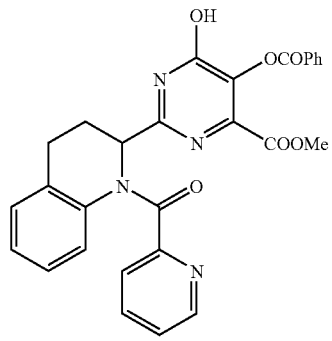

Step 1: Preparation of Compound I-6

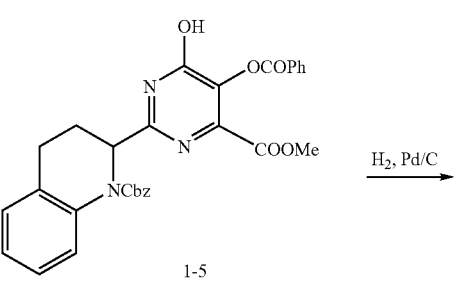 

1-5

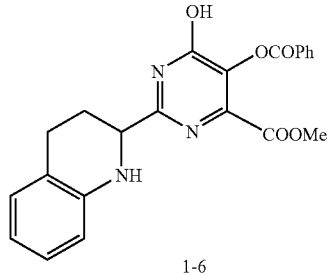

1-6

The benzoyl protected pyrimidine I-5 [prepared from tetrahydroquinoline-2-carboxylic acid (Robl et al, Tetrahedron Letters, 1995, 36, 1593) by protection of the nitrogen and following procedures similar to those set forth in Scheme A] was dissolved in EtOAc and hydrogenated at atmospheric pressure on 10% Pd/C at room temperature overnight. I-6 was obtained after filtration and evaporation of the organic solvent.

Step 2: Preparation of Compound I-7

The residue was dissolved in dichloromethane and picolinic acid (1.1 eq.), 1-(3-dimethylaminopropyl)-3-ethylcarbodiimide hydrochloride (1.3 eq.), hydroxybenzotriazole (1.3 eq.), and diethylisopropylamine (1.3 eq.) were added. Further additions of the reactants were made until complete consumption of the starting material. Mixture was evaporated to give crude I-7.

Step 3: N-(4-fluorobenzyl)-5,6-dihydroxy-2-[1-(pyridin-2-ylcarbonyl)-1,2,3,4-tetrahydroquinolin-2-yl] pyrimidine-4-carboxamide (I-8)

The crude I-7 product was dissolved in MeOH and 4-fluorobenzylamine (3 eq.) was added The reaction mixture was refluxed overnight. The product was purified by preparative RP-HPLC (C18 gradient of CH$_3$CN/H$_2$O+0.01% TFA), to give I-8 as its trifluoroacetate salt.

$^1$H-NMR (DMSO-d$_6$, 400 MHz, 340 K) δ 12.65 (bs, 1 H), 11.81 (bs, 1 H), 8.37 (d, J=4.4 Hz, 1 H), 7.92 (bt, 1 H), 7.82 (t, J=7.0 Hz, 1 H), 7.54 (d, J=7.6 Hz, 1 H), 7.38 (t, J=5.4 Hz, 1 H), 7.27 (t, J=5.4 Hz, 2 H), 7.14-7.10 (m, 3 H), 6.91 (t, J=6.7, 1 H), 6.70-6.50 (m, 2 H), 5.45 (t, J=7.2 Hz, 1 H), 4.45-4.35 (m, 2 H), 2.70-2.80 (m, 2 H), 2.05 (bs, 1 H), one proton obscured by DMSO MS m/z 500 (M+H$^+$).

EXAMPLE 15

2-Benzyl-N-(4-fluorobenzyl)-5-hydroxy-6-(2-morpholin-4-ylethoxy)pyrimidine-4-carboxamide

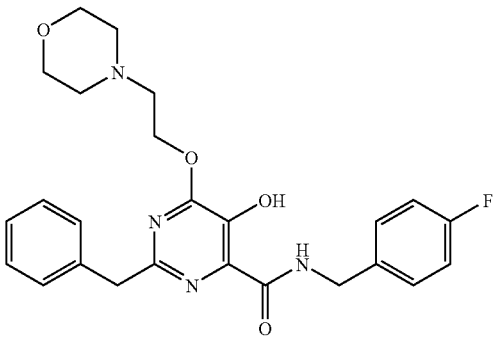

Step 1: Methyl 2-benzyl-5-[(tert-butoxycarbonyl)oxy]-6-(2-morpholin-4-ylethoxy)pyrimidine-4-carboxylate (N-2)

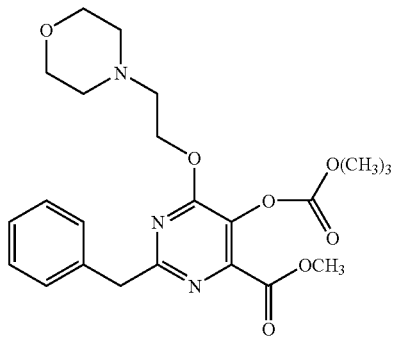

To a stirred solution of methyl 2-benzyl-5-[(tert-butoxycarbonyl)oxy]-6-hydroxypyrimidine-4-carboxylate (N-1) (prepared from B-5 in Example 3, Step 1 by protection of the 5-hydroxyl group with pivaloyl chloride using a procedure similar to those set forth in Example 6, Step 2) in THF, CsCO₃ (2 eq.) and 4-(2-chloroethyl)morpholine (1.5 eq.) hydrochloride were added and mixture reacted at 60° C. for 1 h. Further addition of 4-(2-chloroethyl)morpholine (1 eq.) allowed the complete consumption of starting material after 2 h. The mixture was then allowed to cool to room temperature, poured into EtOAc, extracted with brine, dried (Na₂SO₄), filtered and concentrated.

Step 2: 2-Benzyl-N-(4-fluorobenzyl)-5-hydroxy-6-(2-morpholin-4-ylethoxy)pyrimidine-4-carboxamide (N-3)

The oily residue containing N-2 was taken into DMF and treated with 3 eq. of 4-fluorobenzylamine at 90° C. for 1 h. The title compound (N-3) was isolated as its trifluoroacetate salt by RP-HPLC (C18, water/acetonitrile with 0.1% of TFA as eluant).

$^1$H NMR (DMSO-$d_6$, 400 MHz) δ 12.15 (bs, 1 H), 9.95 (bs, 1 H), 9.75 (t, J=6.4 Hz, 1 H), 7.38 (dd, J=8.5 Hz, J=5.7 Hz, 2 H), 7.34-7.27 (m, 4 H), 7.23-7.14 (m, 3 H), 4.67 (bs, 2 H), 4.49 (d, J=6.4 Hz, 2 H), 4.07 (s, 2 H), 4.00-3.90 (m, 2 H), 3.70-3.40 (m, 6 H), 3.25-3.10 (m, 2 H). MS m/z 467 (M+H$^+$).

EXAMPLE 16

N-(4-fluorobenzyl)-5,6-dihydroxy-2-(1-methyl-1-morpholin-4-ylethyl)pyrimidine-4-carboxamide

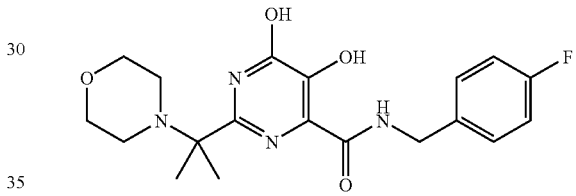

Step 1

To a stirred solution of 2-[1-(dimethylamino)-1-methylethyl]-N-(4-fluorobenzyl)-5,6-dihydroxypyrimidine-4-carboxamide hydrochloride (prepared as described in example 4) in NMP an excess of morpholine (10 eq.) was added and mixture was stirred over night at 100° C. After cooling to room temperature, title product was isolated by RP HPLC (MeCN/H₂O containing 0.1% TFA as eluant).

$^1$H NMR (DMSO-$d_6$) δ 12.33 (bs, 1 H), 9.41 (t, J=6.0 Hz, 1H), 7.39 (dd, J=8.6 Hz, J=5.5 Hz, 2 H), 7.19 (t, J=9.1 Hz, 2 H), 4.56 (d, J=6.0 Hz, 2H), 3.88 (bs, 2 H), 3.29 (bs, 2 H), 1.68 (s, 6 H). MS m/z (M$^+$+1) 391

Tables 1 to 25 below list compounds of the present invention which have been prepared. The Tables provide the structure and name of each compound, the mass of its molecular ion plus 1 (M$^+$) or molecular ion minus 1 (M$^-$) as determined via FIA-MS, and the synthetic scheme employed to prepare the compound. When the compound was prepared as a salt, the identity of the salt is included with the compound name. The synthetic scheme identified as "A*" in the Tables is identical to Scheme A above, except for an additional deprotection step to remove Boc, Cbz, or benzyl present from the substituent in the 2-position of the pyrimidine ring.

TABLE 1

| Exp | Structure | Name | M+ | Scheme |
|---|---|---|---|---|
| 1 | 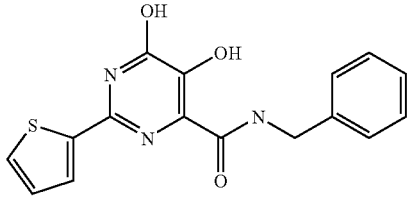 | N-benzyl-5,6-dihydroxy-2-thien-2-ylpyrimidine-4-carboxamide | 328 | A |
| 2 | 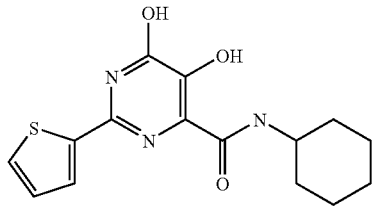 | N-cyclohexyl-5,6-dihydroxy-2-thien-2-ylpyrimidine-4-carboxamide | 320 | A |
| 3 | 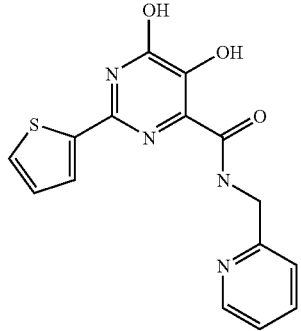 | 5,6-dihydroxy-N-(pyridin-2-ylmethyl)-2-thien-2-ylpyrimidine-4-carboxamide (HCl salt) | 329 | A |
| 4 | 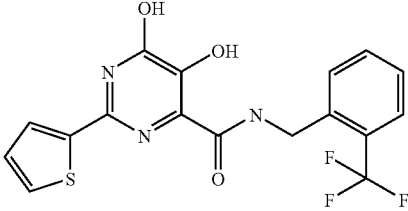 | 5,6-dihydroxy-2-thien-2-yl-N-[2-(trifluoromethyl)benzyl]pyrimidine-4-carboxamide | 396 | A |
| 5 | 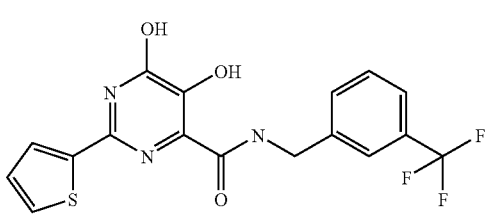 | 5,6-dihydroxy-2-thien-2-yl-N-[3-(trifluoromethyl)benzyl]pyrimidine-4-carboxamide | 396 | A |
| 6 | 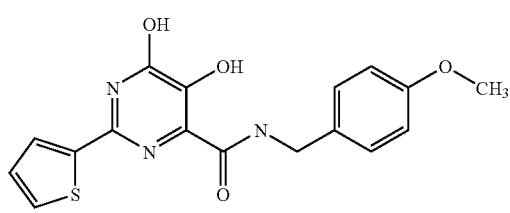 | 5,6-dihydroxy-N-(4-methoxybenzyl)-2-thien-2-ylpyrimidine-4-carboxamide | 358 | A |

TABLE 1-continued

| Exp | Structure | Name | M+ | Scheme |
|---|---|---|---|---|
| 7 | 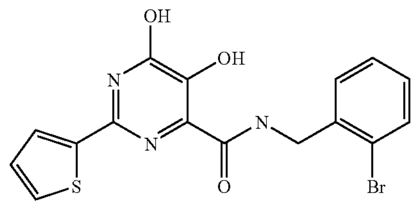 | N-(2-bromobenzyl)-5,6-dihydroxy-2-thien-2-ylpyrimidine-4-carboxamide | 407 | A |
| 8 | 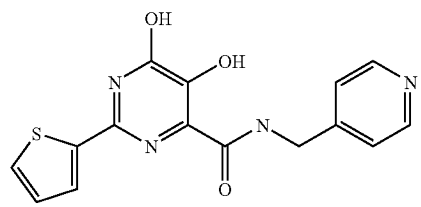 | 5,6-dihydroxy-N-(pyridin-4-ylmethyl)-2-thien-2-ylpyrimidine-4-carboxamide (HCl salt) | 329 | A |
| 9 | 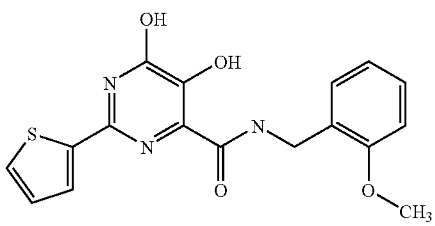 | 5,6-dihydroxy-N-(2-methoxybenzyl)-2-thien-2-ylpyrimidine-4-carboxamide | 358 | A |
| 10 | 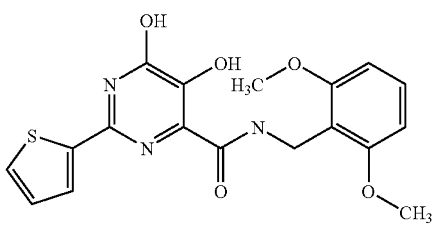 | N-(2,6-dimethoxybenzyl)-5,6-dihydroxy-2-thien-2-ylpyrimidine-4-carboxamide | 388 | A |
| 11 | 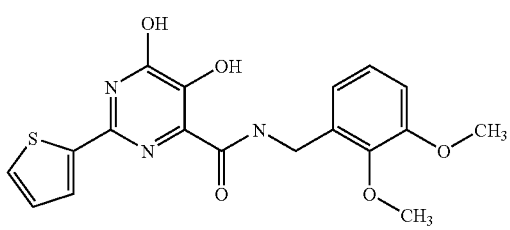 | N-(2,3-dimethoxybenzyl)-5,6-dihydroxy-2-thien-2-ylpyrimidine-4-carboxamide | 388 | A |
| 12 | 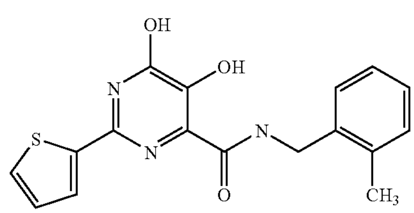 | 5,6-dihydroxy-N-(2-methylbenzyl)-2-thien-2-ylpyrimidine-4-carboxamide | 342 | A |
| 13 | 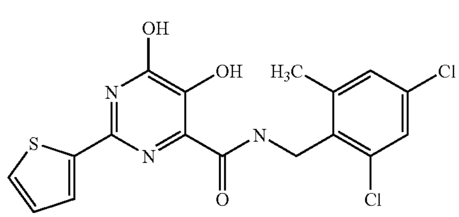 | N-(2,4-dichloro-6-methylbenzyl)-5,6-dihydroxy-2-thien-2-ylpyrimidine-4-carboxamide | 411 | A |

TABLE 1-continued

| Exp | Structure | Name | M+ | Scheme |
|---|---|---|---|---|
| 14 | 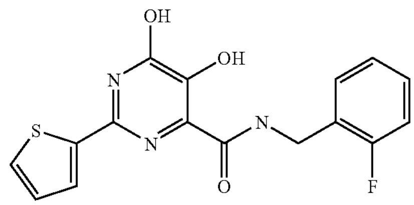 | N-(2-fluorobenzyl)-5,6-dihydroxy-2-thien-2-ylpyrimidine-4-carboxamide | 346 | A |
| 15 | 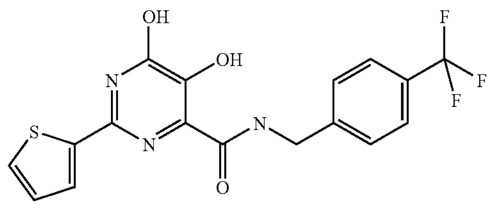 | 5,6-dihydroxy-2-thien-2-yl-N-[4-(trifluoromethyl)benzyl]pyrimidine-4-carboxamide | 396 | A |
| 16 | 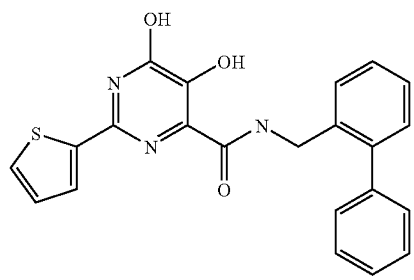 | N-(1,1'-biphenyl-2-ylmethyl)-5,6-dihydroxy-2-thien-2-ylpyrimidine-4-carboxamide | 404 | A |
| 17 | 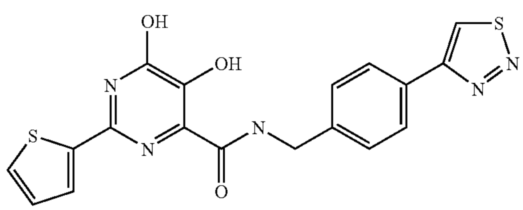 | 5,6-dihydroxy-N-[4-(1,2,3-thiadiazol-4-yl)benzyl]-2-thien-2-ylpyrimidine-4-carboxamide | 412 | A |
| 18 | 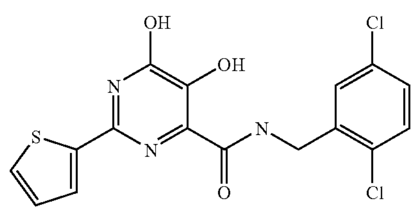 | N-(2,5-dichlorobenzyl)-5,6-dihydroxy-2-thien-2-ylpyrimidine-4-carboxamide | 397 | A |
| 19 | 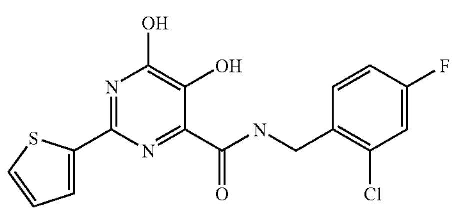 | N-(2-chloro-4-fluorobenzyl)-5,6-dihydroxy-2-thien-2-ylpyrimidine-4-carboxamide | 380 | A |
| 20 | 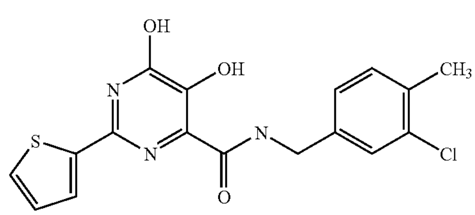 | N-(3-chloro-4-methylbenzyl)-5,6-dihydroxy-2-thien-2-ylpyrimidine-4-carboxamide | 376 | A |

TABLE 1-continued

| Exp | Structure | Name | M+ | Scheme |
|---|---|---|---|---|
| 21 | 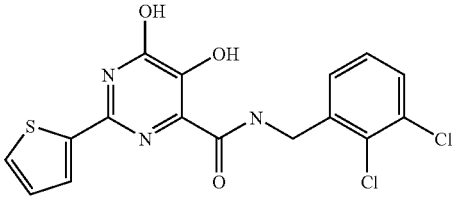 | N-(2,3-dichlorobenzyl)-5,6-dihydroxy-2-thien-2-ylpyrimidine-4-carboxamide | 397 | A |
| 22 | 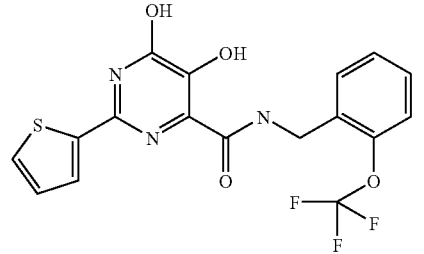 | 5,6-dihydroxy-2-thien-2-yl-N-[2-(trifluoromethoxy)benzyl]pyrimidine-4-carboxamide | 412 | A |
| 23 | 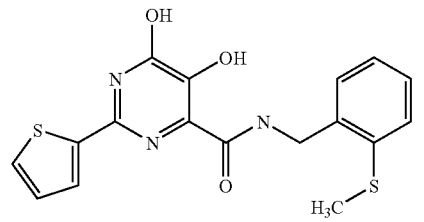 | 5,6-dihydroxy-N-[2-(methylthio)benzyl]-2-thien-2-ylpyrimidine-4-carboxamide | 374 | A |
| 24 | 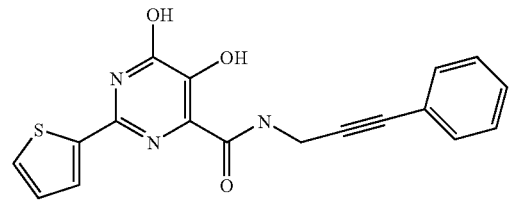 | 5,6-dihydroxy-N-(3-phenylprop-2-ynyl)-2-thien-2-ylpyrimidine-4-carboxamide | 352 | A |
| 25 | 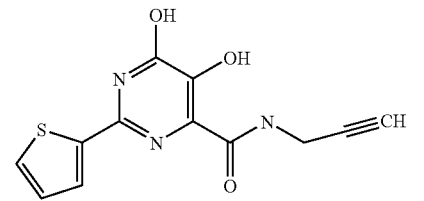 | 5,6-dihydroxy-N-prop-2-ynyl-2-thien-2-ylpyrimidine-4-carboxamide | 276 | A |
| 26 | 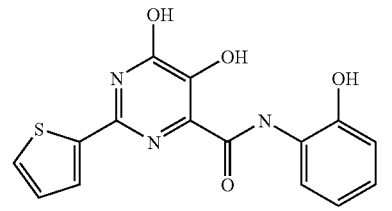 | 5,6-dihydroxy-N-(2-hydroxyphenyl)-2-thien-2-ylpyrimidine-4-carboxamide | 330 | A |
| 27 | 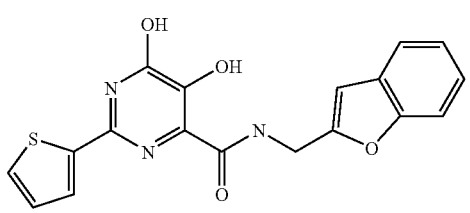 | N-(1-benzofuran-2-ylmethyl)-5,6-dihydroxy-2-thien-2-ylpyrimidine-4-carboxamide | 368 | A |

TABLE 1-continued

| Exp | Structure | Name | M+ | Scheme |
|---|---|---|---|---|
| 28 | 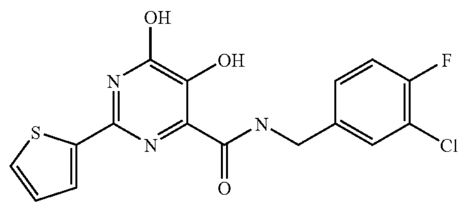 | N-(3-chloro-4-fluorobenzyl)-5,6-dihydroxy-2-thien-2-ylpyrimidine-4-carboxamide | 380 | A |
| 29 | 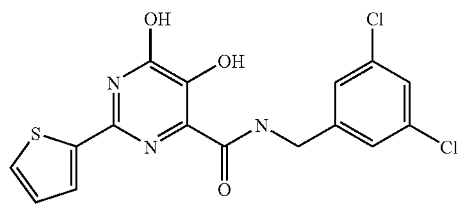 | N-(3,5-dichlorobenzyl)-5,6-dihydroxy-2-thien-2-ylpyrimidine-4-carboxamide | 397 | A |
| 30 | 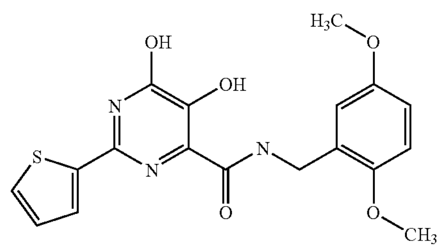 | N-(2,5-dimethoxybenzyl)-5,6-dihydroxy-2-thien-2-ylpyrimidine-4-carboxamide | 388 | A |
| 31 | 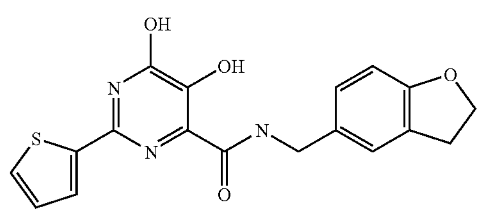 | N-(2,3-dihydro-1-benzofuran-5-ylmethyl)-5,6-dihydroxy-2-thien-2-ylpyrimidine-4-carboxamide | 370 | A |
| 32 | 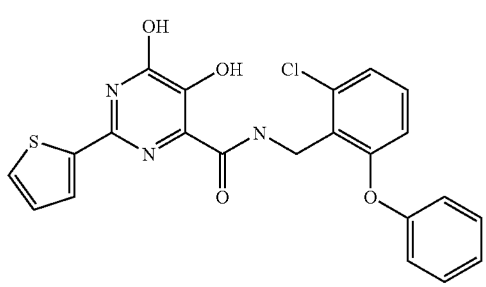 | N-(2-chloro-6-phenoxybenzyl)-5,6-dihydroxy-2-thien-2-ylpyrimidine-4-carboxamide | 454 | A |
| 33 | 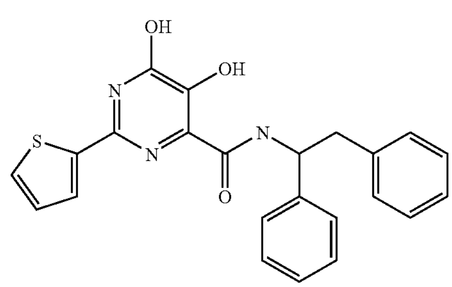 | N-(1,2-diphenylethyl)-5,6-dihydroxy-2-thien-2-ylpyrimidine-4-carboxamide | 418 | A |

TABLE 1-continued

| Exp | Structure | Name | M+ | Scheme |
|---|---|---|---|---|
| 34 | 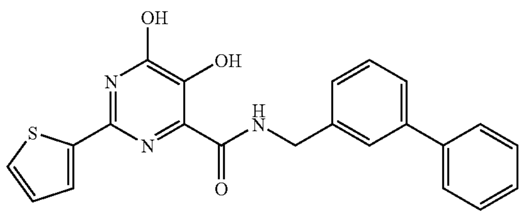 | N-(1,1'-biphenyl-3-ylmethyl)-5,6-dihydroxy-2-thien-2-ylpyrimidine-4-carboxamide | 404 | A |
| 35 | 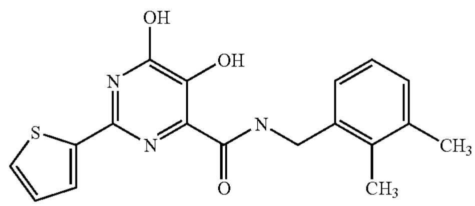 | N-(2,3-dimethylbenzyl)-5,6-dihydroxy-2-thien-2-ylpyrimidine-4-carboxamide | 356 | A |
| 36 | 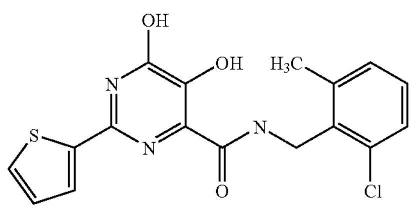 | N-(2-chloro-6-methylbenzyl)-5,6-dihydroxy-2-thien-2-ylpyrimidine-4-carboxamide | 376 | A |
| 37 | 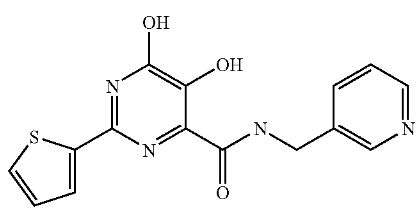 | 5,6-dihydroxy-N-(pyridin-3-ylmethyl)-2-thien-2-ylpyrimidine-4-carboxamide (HCl salt) | 329 | A |
| 38 | 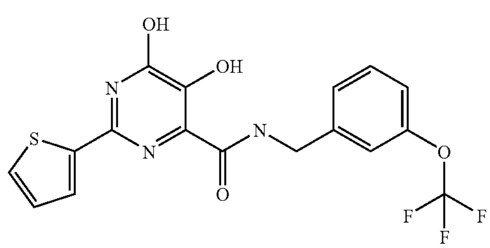 | 5,6-dihydroxy-2-thien-2-yl-N-[3-(trifluoromethoxy)benzyl]pyrimidine-4-carboxamide | 412 | A |
| 39 | 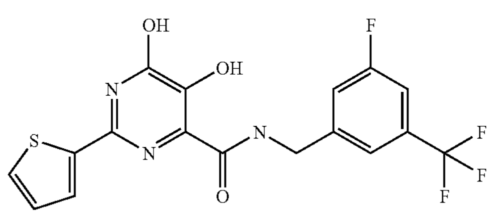 | N-[3-fluoro-5-(trifluoromethyl)benzyl]-5,6-dihydroxy-2-thien-2-ylpyrimidine-4-carboxamide | 414 | A |
| 40 | 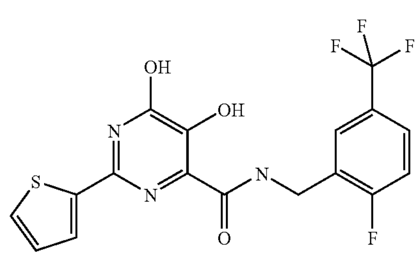 | N-[2-fluoro-5-(trifluoromethyl)benzyl]-5,6-dihydroxy-2-thien-2-ylpyrimidine-4-carboxamide | 414 | A |

TABLE 1-continued

| Exp | Structure | Name | M+ | Scheme |
|---|---|---|---|---|
| 41 | 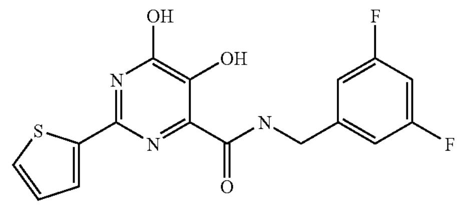 | N-(3,5-difluorobenzyl)-5,6-dihydroxy-2-thien-2-ylpyrimidine-4-carboxamide | 364 | A |
| 42 | 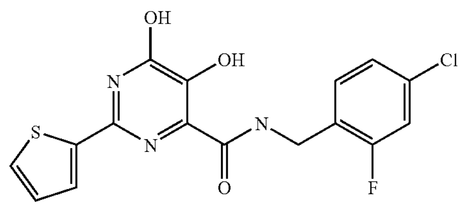 | N-(4-chloro-2-fluorobenzyl)-5,6-dihydroxy-2-thien-2-ylpyrimidine-4-carboxamide | 380 | A |
| 43 | 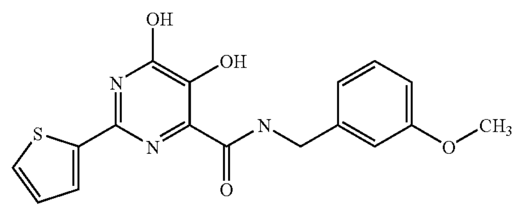 | 5,6-dihydroxy-N-(3-methoxybenzyl)-2-thien-2-ylpyrimidine-4-carboxamide | 358 | A |
| 44 | 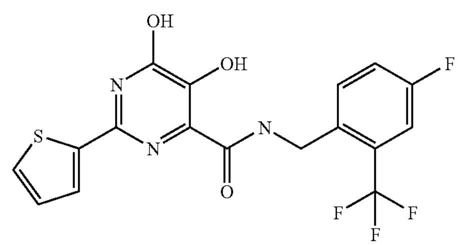 | N-[4-fluoro-2-(trifluoromethyl)benzyl]-5,6-dihydroxy-2-thien-2-ylpyrimidine-4-carboxamide | 414 | A |
| 45 | 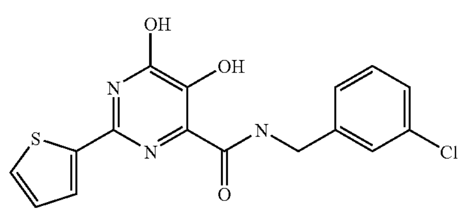 | N-(3-chlorobenzyl)-5,6-dihydroxy-2-thien-2-ylpyrimidine-4-carboxamide | 362 | A |
| 46 | 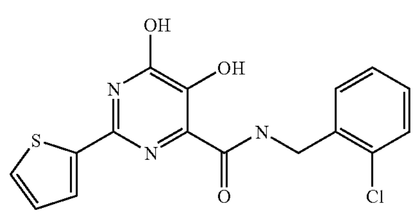 | N-(2-chlorobenzyl)-5,6-dihydroxy-2-thien-2-ylpyrimidine-4-carboxamide | 362 | A |
| 47 | 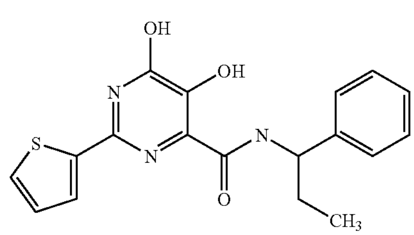 | 5,6-dihydroxy-N-(1-phenylpropyl)-2-thien-2-ylpyrimidine-4-carboxamide | 356 | A |

TABLE 1-continued

| Exp | Structure | Name | M+ | Scheme |
|---|---|---|---|---|
| 48 | 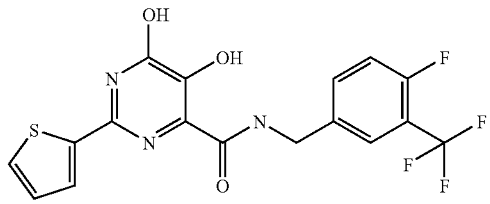 | N-[4-fluoro-3-(trifluoromethyl)-benzyl]-5,6-dihydroxy-2-thien-2-ylpyrimidine-4-carboxamide | 414 | A |
| 49 | 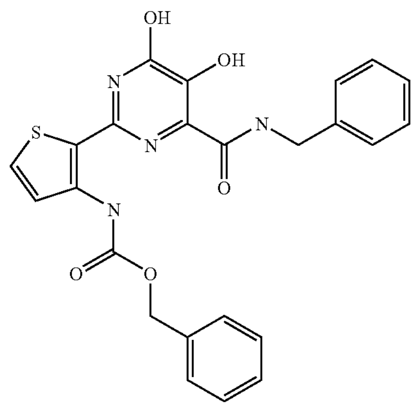 | benzyl 2-{4-[(benzylamino)carbonyl]-5,6-dihydroxy-pyrimidin-2-yl}thien-3-ylcarbamate | 477 | A |
| 50 | 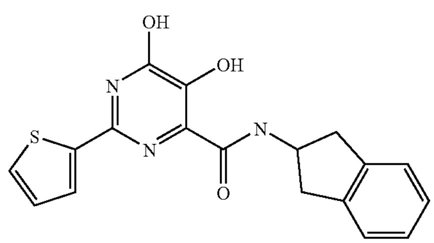 | N-(2,3-dihydro-1H-inden-2-yl)-5,6-dihydroxy-2-thien-2-ylpyrimidine-4-carboxamide | 354 | A |
| 51 | 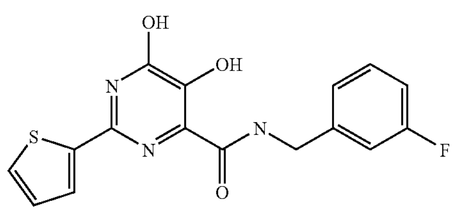 | N-(3-fluorobenzyl)-5,6-dihydroxy-2-thien-2-ylpyrimidine-4-carboxamide | 346 | A |
| 52 | 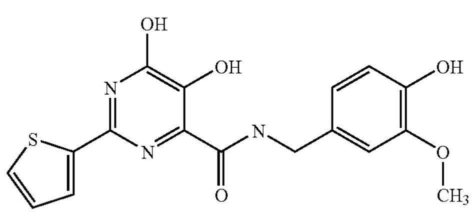 | 5,6-dihydroxy-N-(4-hydroxy-3-methoxybenzyl)-2-thien-2-ylpyrimidine-4-carboxamide | 374 | A |
| 53 | 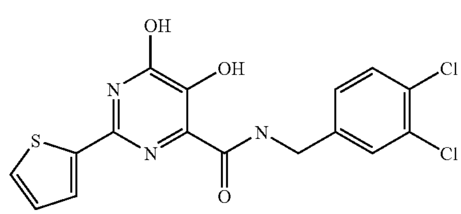 | N-(3,4-dichlorobenzyl)-5,6-dihydroxy-2-thien-2-ylpyrimidine-4-carboxamide | 397 | A |

TABLE 1-continued

| Exp | Structure | Name | M+ | Scheme |
|---|---|---|---|---|
| 54 | 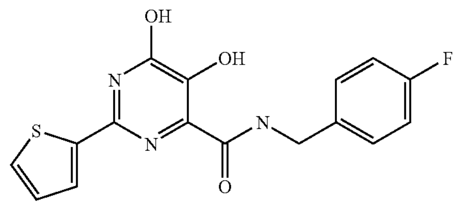 | N-(4-fluorobenzyl)-5,6-dihydroxy-2-thien-2-ylpyrimidine-4-carboxamide | 346 | A |
| 55 | 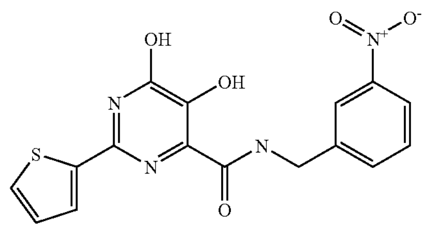 | 5,6-dihydroxy-N-(3-nitrobenzyl)-2-thien-2-ylpyrimidine-4-carboxamide | 373 | A |
| 56 | 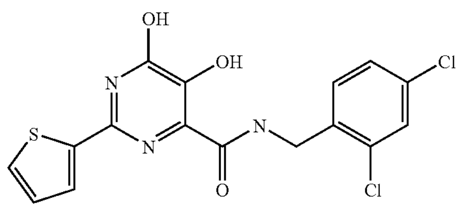 | N-(2,4-dichlorobenzyl)-5,6-dihydroxy-2-thien-2-ylpyrimidine-4-carboxamide | 397 | A |
| 57 | 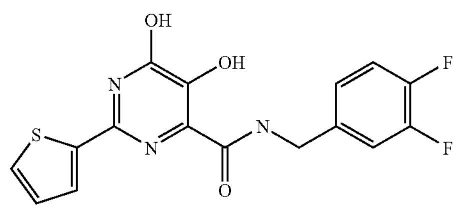 | N-(3,4-difluorobenzyl)-5,6-dihydroxy-2-thien-2-ylpyrimidine-4-carboxamide | 364 | A |
| 58 | 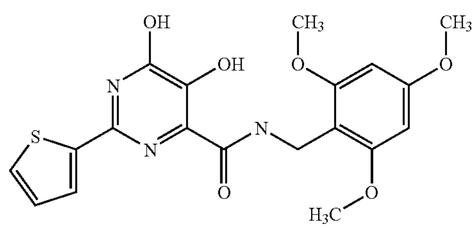 | 5,6-dihydroxy-2-thien-2-yl-N-(2,4,6-trimethoxybenzyl)pyrimidine-4-carboxamide | 418 | A |
| 59 | 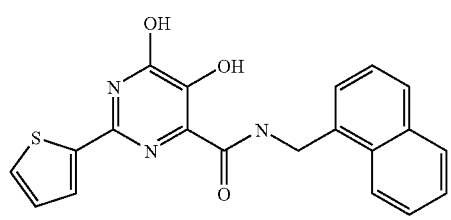 | 5,6-dihydroxy-N-(1-naphthylmethyl)-2-thien-2-ylpyrimidine-4-carboxamide | 378 | A |
| 60 | 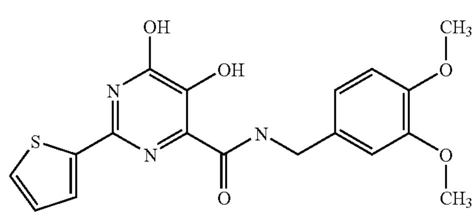 | N-(3,4-dimethoxybenzyl)-5,6-dihydroxy-2-thien-2-ylpyrimidine-4-carboxamide | 388 | A |

TABLE 1-continued

| Exp | Structure | Name | M+ | Scheme |
|---|---|---|---|---|
| 61 | 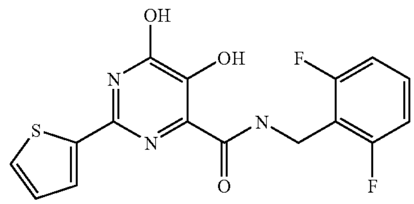 | N-(2,6-difluorobenzyl)-5,6-dihydroxy-2-thien-2-ylpyrimidine-4-carboxamide | 364 | A |
| 62 | 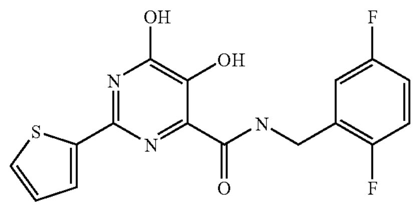 | N-(2,5-difluorobenzyl)-5,6-dihydroxy-2-thien-2-ylpyrimidine-4-carboxamide | 364 | A |
| 63 | 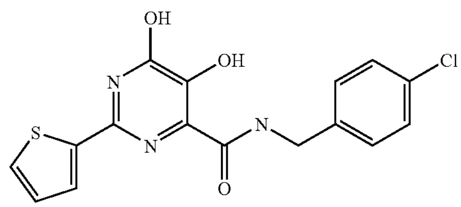 | N-(4-chlorobenzyl)-5,6-dihydroxy-2-thien-2-ylpyrimidine-4-carboxamide | 362 | A |
| 64 | 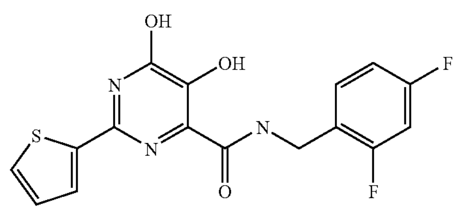 | N-(2,4-difluorobenzyl)-5,6-dihydroxy-2-thien-2-ylpyrimidine-4-carboxamide | 364 | A |
| 65 | 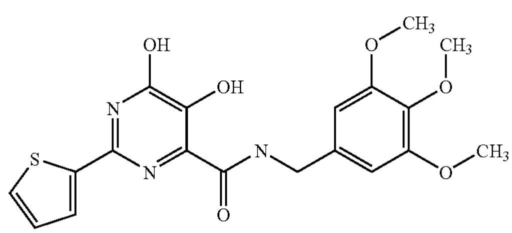 | 5,6-dihydroxy-2-thien-2-yl-N-(3,4,5-trimethoxybenzyl)pyrimidine-4-carboxamide | 418 | A |
| 66 | 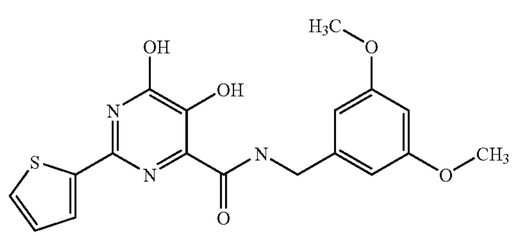 | N-(3,5-dimethoxybenzyl)-5,6-dihydroxy-2-thien-2-ylpyrimidine-4-carboxamide | 388 | A |
| 67 | 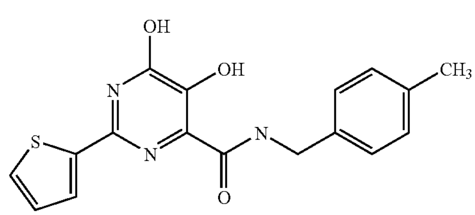 | 5,6-dihydroxy-N-(4-methylbenzyl)-2-thien-2-ylpyrimidine-4-carboxamide | 342 | A |

TABLE 1-continued

| Exp | Structure | Name | M+ | Scheme |
|---|---|---|---|---|
| 68 | 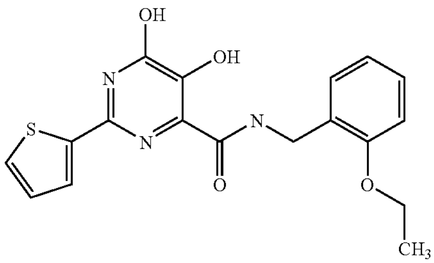 | N-(2-ethoxybenzyl)-5,6-dihydroxy-2-thien-2-ylpyrimidine-4-carboxamide | 372 | A |
| 69 | 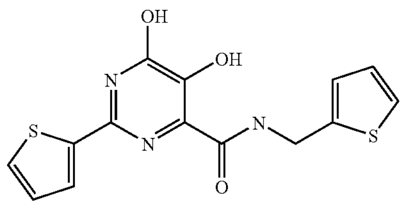 | 5,6-dihydroxy-2-thien-2-yl-N-(thien-2-ylmethyl)pyrimidine-4-4-carboxamide | 334 | A |
| 70 | 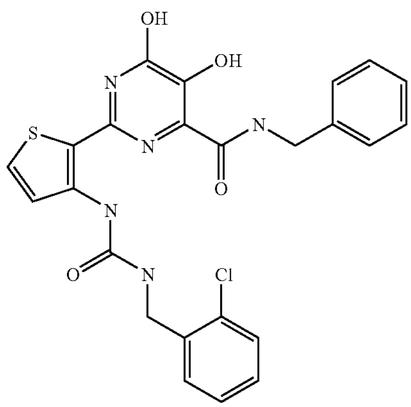 | N-benzyl-2-[3-({[(2-chlorobenzyl)amino]carbonyl}amino)thien-2-yl]-5,6-dihydroxypyrimidine-4-carboxamide | 08 (M−1 | A |
| 71 | 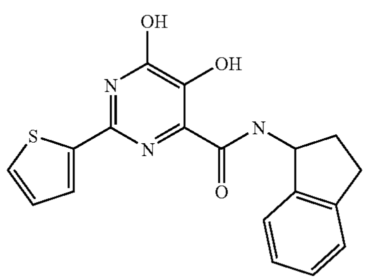 | N-(2,3-dihydro-1H-inden-1-yl)-5,6-dihydroxy-2-thien-2-ylpyrimidine-4-carboxamide | 354 | A |
| 72 | 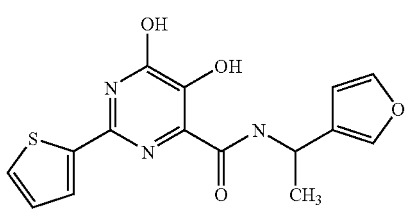 | N-[1-(3-furyl)ethyl]-5,6-dihydroxy-2-thien-2-ylpyrimidine-4-carboxamide | 332 | A |
| 73 | 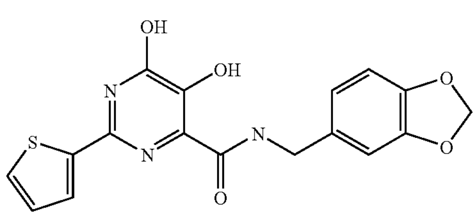 | N-(1,3-benzodioxol-5-ylmethyl)-5,6-dihydroxy-2-thien-2-ylpyrimidine-4-carboxamide | 372 | A |

TABLE 1-continued

| Exp | Structure | Name | M+ | Scheme |
|---|---|---|---|---|
| 74 | 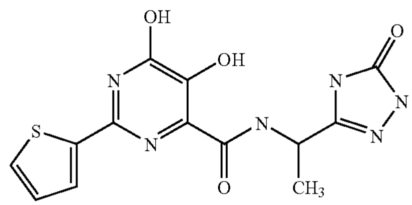 | 5,6-dihydroxy-N-[1-(5-oxo-4,5-dihydro-1H-1,2,4-triazol-3-yl)ethyl]-2-thien-2-ylpyrimidine-4-carboxamide | 349 | A |
| 75 | 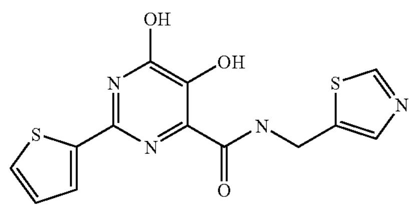 | 5,6-dihydroxy-N-(1,3-thiazol-5-ylmethyl)-2-thien-2-ylpyrimidine-4-carboxamide | 335 | A |
| 76 | 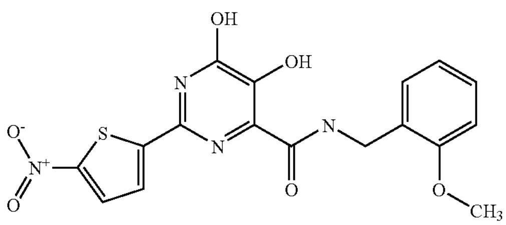 | 5,6-dihydroxy-N-(2-methoxybenzyl)-2-(5-nitrothien-2-yl)pyrimidine-4-carboxamide | 403 | A |
| 77 | 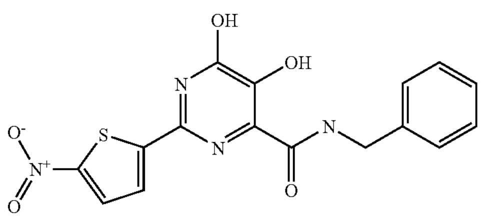 | N-benzyl-5,6-dihydroxy-2-(5-nitrothien-2-yl)pyrimidine-4-carboxamide | 373 | A |
| 78 | 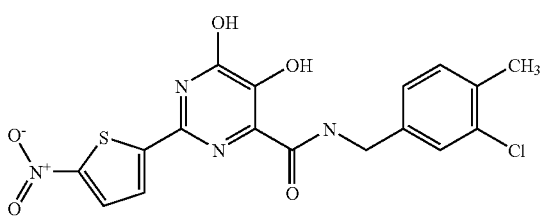 | N-(3-chloro-4-methylbenzyl)-5,6-dihydroxy-2-(5-nitrothien-2-yl)pyrimidine-4-carboxamide | 421 | A |
| 79 | 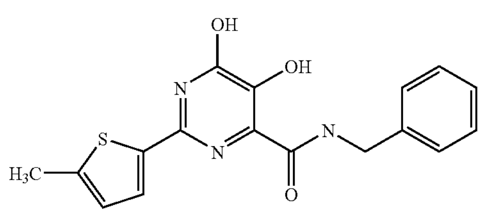 | N-benzyl-5,6-dihydroxy-2-(5-methylthien-2-yl)pyrimidine-4-carboxamide | 342 | A |
| 80 | 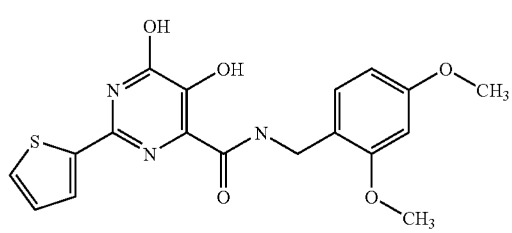 | N-(2,4-dimethoxybenzyl)-5,6-dihydroxy-2-thien-2-ylpyrimidine-4-carboxamide | 388 | A |

TABLE 1-continued

| Exp | Structure | Name | M+ | Scheme |
|---|---|---|---|---|
| 81 | 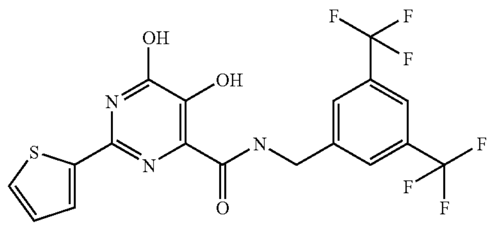 | N-[3,5-bis(trifluoromethyl)benzyl]-5,6-dihydroxy-2-thien-2-ylpyrimidine-4-carboxamide | 464 | A |
| 82 | 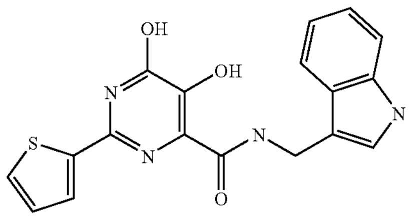 | 5,6-dihydroxy-N-(1H-indol-3-ylmethyl)-2-thien-2-ylpyrimidine-4-carboxamide | 367 | A |
| 83 | 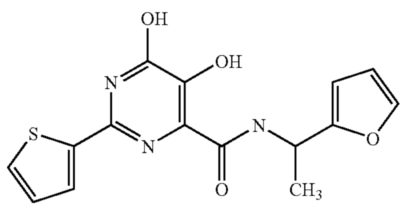 | N-[1-(2-furyl)ethyl]-5,6-dihydroxy-2-thien-2-ylpyrimidine-4-carboxamide | 332 | A |
| 84 | 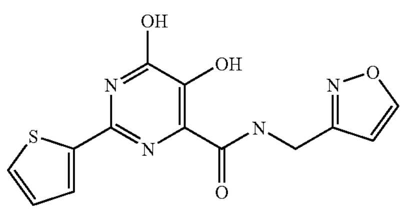 | 5,6-dihydroxy-N-(isoxazol-3-ylmethyl)-2-thien-2-ylpyrimidine-4-carboxamide | 319 | A |
| 85 | 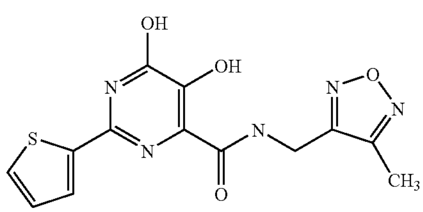 | 5,6-dihydroxy-N-[(4-methyl-1,2,5-oxadiazol-3-yl)methyl]-2-thien-2-ylpyrimidine-4-carboxamide | 334 | A |
| 86 | 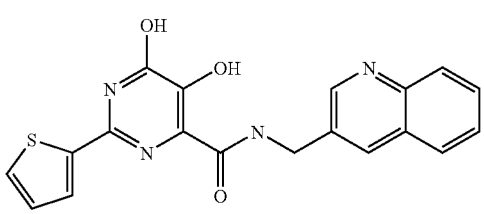 | 5,6-dihydroxy-N-(quinolin-3-ylmethyl)-2-thien-2-ylpyrimidine-4-carboxamide | 379 | A |
| 87 | 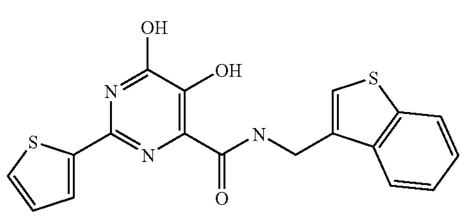 | N-(1-benzothien-3-ylmethyl)-5,6-dihydroxy-2-thien-2-ylpyrimidine-4-carboxamide | 384 | A |

TABLE 1-continued

| Exp | Structure | Name | M+ | Scheme |
|---|---|---|---|---|
| 88 | 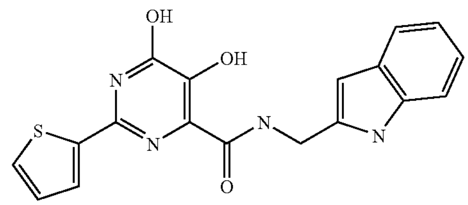 | 5,6-dihydroxy-N-(1H-indol-2-ylmethyl)-2-thien-2-ylpyrimidine-4-carboxamide | 367 | A |
| 89 | 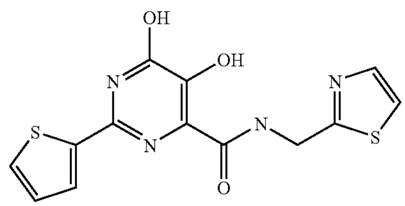 | 5,6-dihydroxy-N-(1,3-thiazol-2-ylmethyl)-2-thien-2-ylpyrimidine-4-carboxamide | 335 | A |
| 90 | 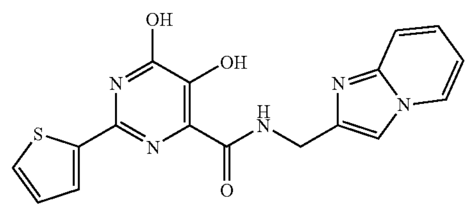 | 5,6-dihydroxy-N-(imidazo[1,2-a]pyridin-2-ylmethyl)-2-thien-2-ylpyrimidine-4-carboxamide | 368 | A |
| 91 | 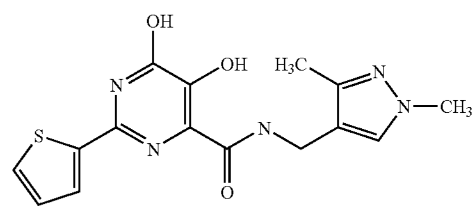 | N-[(1,3-dimethyl-1H-pyrazol-4-yl)methyl]-5,6-dihydroxy-2-thien-2-ylpyrimidine-4-carboxamide | 346 | A |
| 92 | 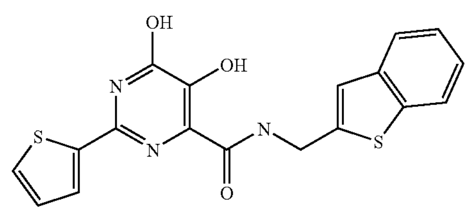 | N-(1-benzothien-2-ylmethyl)-5,6-dihydroxy-2-thien-2-ylpyrimidine-4-carboxamide | 384 | A |
| 93 | 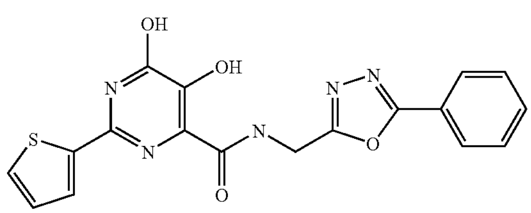 | 5,6-dihydroxy-N-[(5-phenyl-1,3,4-oxadiazol-2-yl)methyl]-2-thien-2-ylpyrimidine-4-carboxamide | 396 | A |
| 94 | 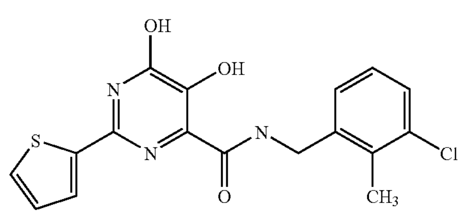 | N-(3-chloro-2-methylbenzyl)-5,6-dihydroxy-2-thien-2-ylpyrimidine-4-carboxamide | 376 | A |

TABLE 1-continued

| Exp | Structure | Name | M+ | Scheme |
|---|---|---|---|---|
| 95 | 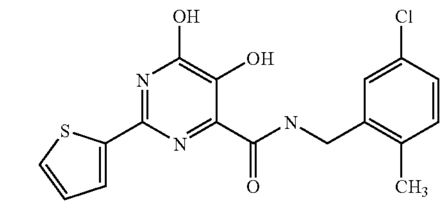 | N-(5-chloro-2-methylbenzyl)-5,6-dihydroxy-2-thien-2-ylpyrimidine-4-carboxamide | 376 | A |
| 96 | 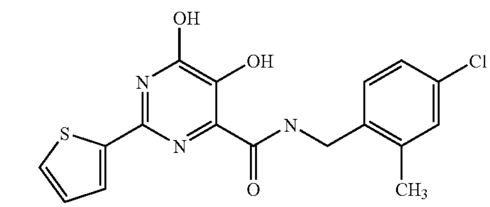 | N-(4-chloro-2-methylbenzyl)-5,6-dihydroxy-2-thien-2-ylpyrimidine-4-carboxamide | 376 | A |
| 97 | 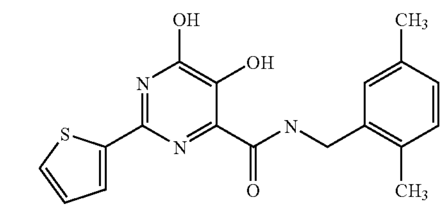 | N-(2,5-dimethylbenzyl)-5,6-dihydroxy-2-thien-2-ylpyrimidine-4-carboxamide | 356 | A |
| 98 | 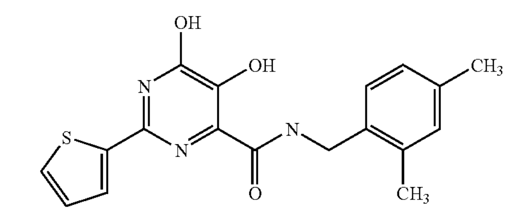 | N-(2,4-dimethylbenzyl)-5,6-dihydroxy-2-thien-2-ylpyrimidine-4-carboxamide | 356 | A |
| 99 | 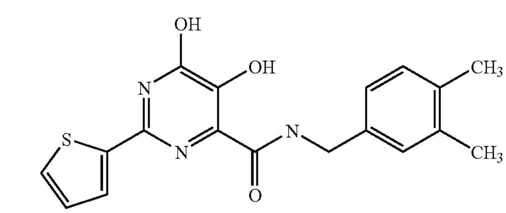 | N-(3,4-dimethylbenzyl)-5,6-dihydroxy-2-thien-2-ylpyrimidine-4-carboxamide | 356 | A |
| 100 | Chiral | N-[(1R)-2,3-dihydro-1H-inden-1-yl]-5,6-dihydroxy-2-thien-2-ylpyrimidine-4-carboxamide | 354 | A |
| 101 | 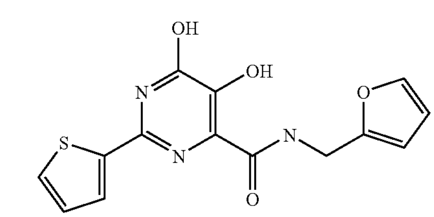 | N-(2-furylmethyl)-5,6-dihydroxy-2-thien-2-ylpyrimidine-4-carboxamide | 318 | A |

TABLE 1-continued

| Exp | Structure | Name | M+ | Scheme |
|---|---|---|---|---|
| 102 | 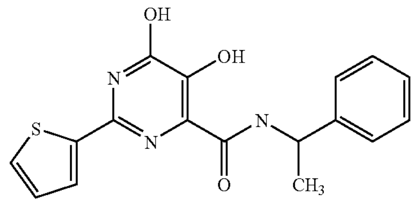 | 5,6-dihydroxy-N-(1-phenylethyl)-2-thien-2-ylpyrimidine-4-carboxamide | 342 | A |
| 103 | Chiral | 5,6-dihydroxy-N-[(1S)-1-phenylethyl]-2-thien-2-ylpyrimidine-4-carboxamide | 342 | A |
| 104 | Chiral | 5,6-dihydroxy-N-[(1R)-1-phenylethyl]-2-thien-2-ylpyrimidine-4-carboxamide | 342 | A |
| 105 | 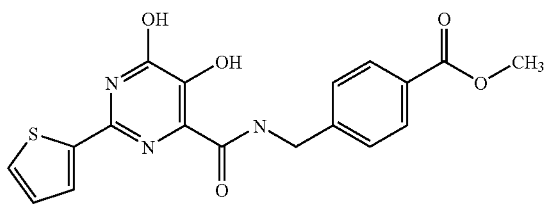 | methyl 4-({[(5,6-dihydroxy-2-thien-2-ylpyrimidin-4-yl)carbonyl]amino}methyl)benzoate | 386 | A |
| 106 | 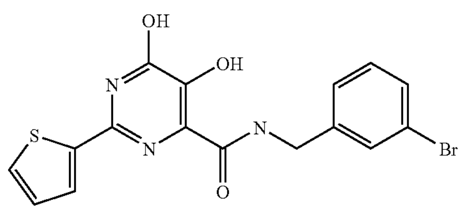 | N-(3-bromobenzyl)-5,6-dihydroxy-2-thien-2-ylpyrimidine-4-carboxamide | 407 | A |
| 107 | 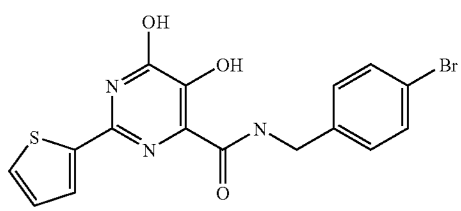 | N-(4-bromobenzyl)-5,6-dihydroxy-2-thien-2-ylpyrimidine-4-carboxamide | 407 | A |
| 108 | 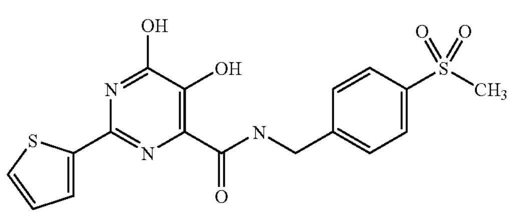 | 5,6-dihydroxy-N-[4-(methylsulfonyl)benzyl]-2-thien-2-ylpyrimidine-4-carboxamide | 406 | A |

TABLE 1-continued

| Exp | Structure | Name | M+ | Scheme |
|---|---|---|---|---|
| 109 | 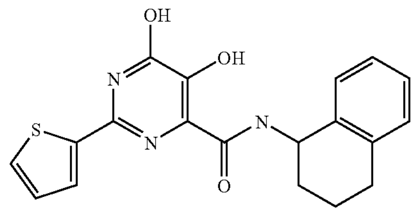 | 5,6-dihydroxy-N-(1,2,3,4-tetrahydronaphthalen-1-yl)-2-thien-2-ylpyrimidine-4-carboxamide | 368 | A |
| 110 | Chiral | N-[(1S)-2,3-dihydro-1H-inden-1-yl]-5,6-dihydroxy-2-thien-2-ylpyrimidine-4-carboxamide | 354 | A |
| 111 | 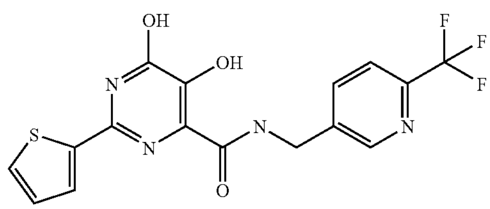 | 5,6-dihydroxy-2-thien-2-yl-N-{[6-(trifluoromethyl)pyridin-3-yl]methyl}pyrimidine-4-carboxamide (HCl salt) | 397 | A |
| 112 | 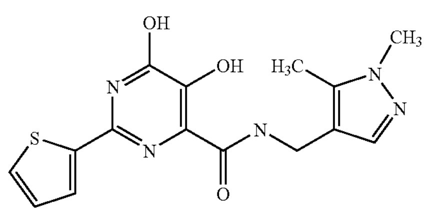 | N-[(1,5-dimethyl-1H-pyrazol-4-yl)methyl]-5,6-dihydroxy-2-thien-2-ylpyrimidine-4-carboxamide | 346 | A |
| 113 | 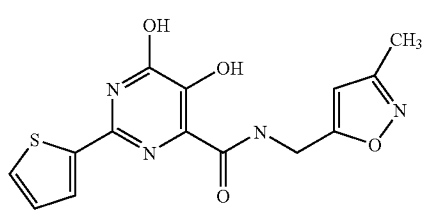 | 5,6-dihydroxy-N-[(3-methylisoxazol-5-yl)methyl]-2-thien-2-ylpyrimidine-4-carboxamide | 333 | A |
| 114 | 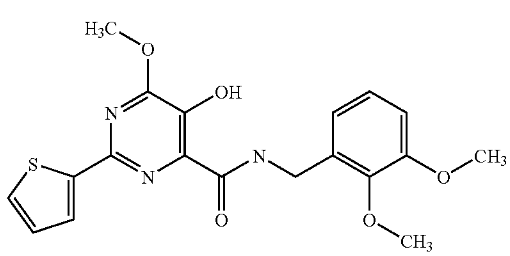 | N-(2,3-dimethoxybenzyl)-5-hydroxy-6-methoxy-2-thien-2-ylpyrimidine-4-carboxamide | 402 | A |

TABLE 1-continued

| Exp | Structure | Name | M+ | Scheme |
|---|---|---|---|---|
| 115 | 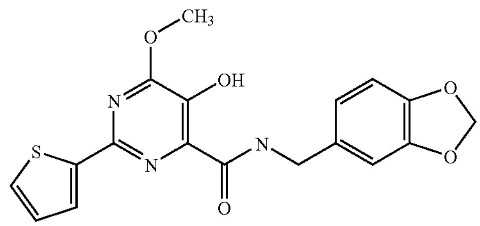 | N-(1,3-benzodioxol-5-ylmethyl)-5-hydroxy-6-methoxy-2-thien-2-ylpyrimidine-4-carboxamide | 386 | A |
| 116 | 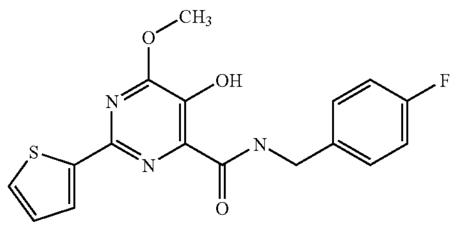 | N-(4-fluorobenzyl)-5-hydroxy-6-methoxy-2-thien-2-ylpyrimidine-4-carboxamide | 360 | A |
| 117 | 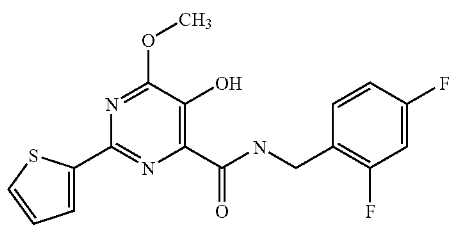 | N-(2,4-difluorobenzyl)-5-hydroxy-6-methoxy-2-thien-2-ylpyrimidine-4-carboxamide | 378 | A |
| 118 | 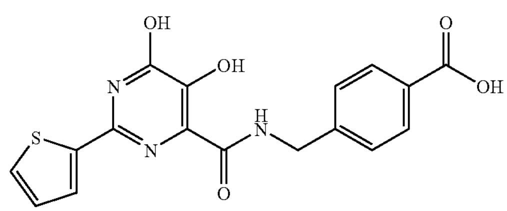 | 4-({[(5,6-dihydroxy-2-thien-2-ylpyrimidin-4-yl)carbonyl]-amino}methyl)benzoic acid | 372 | A |
| 119 | 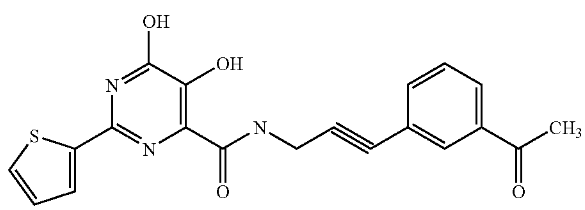 | N-[3-(3-acetylphenyl)prop-2-ynyl]-5,6-dihydroxy-2-thien-2-ylpyrimidine-4-carboxamide | 394 | A |
| 120 | 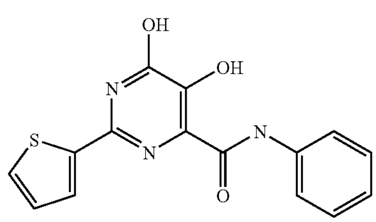 | 5,6-dihydroxy-N-phenyl-2-thien-2-ylpyrimidine-4-carboxamide | 314 | A |
| 121 | 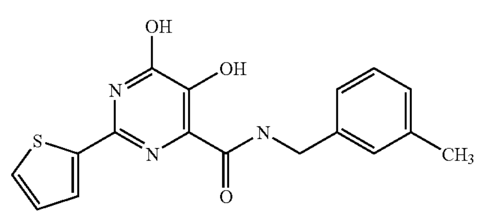 | 5,6-dihydroxy-N-(3-methylbenzyl)-2-thien-2-ylpyrimidine-4-carboxamide | 342 | A |

TABLE 1-continued

| Exp | Structure | Name | M+ | Scheme |
|---|---|---|---|---|
| 122 | 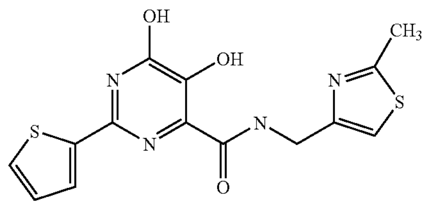 | 5,6-dihydroxy-N-[(2-methyl-1,3-thiazol-4-yl)methyl]-2-thien-2-ylpyrimidine-4-carboxamide (HCl salt) | 349 | A |
| 123 | 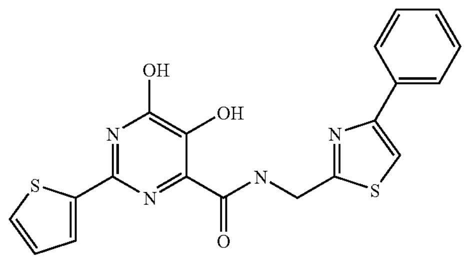 | 5,6-dihydroxy-N-[(4-pbenyl-1,3-thiazol-2-yl)methyl]-2-thien-2-ylpyrimidine-4-carboxamide (HCl salt) | 411 | A |
| 124 | 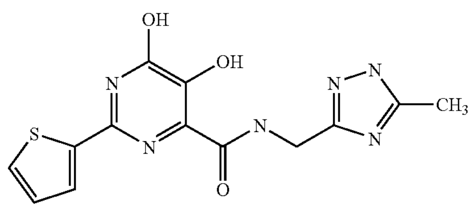 | 5,6-dihydroxy-N-[(5-methyl-1H-1,2,4-triazol-3-yl)methyl]-2-thien-2-ylpyrimidine-4-carboxamide (HCl salt) | 333 | A |
| 125 | 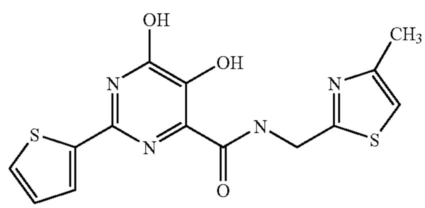 | 5,6-dihydroxy-N-[(4-methyl-1,3-thiazol-2-yl)methyl]-2-thien-2-ylpyrimidine-4-carboxamide (HCl salt) | 349 | A |
| 126 | 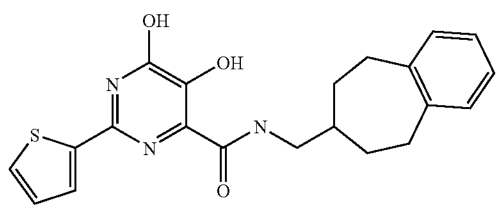 | 5,6-dihydroxy-N-(6,7,8,9-tetrahydro-5H-benzo[7]annulen-7-ylmethyl)-2-thien-2-ylpyrimidine-4-carboxamide | 396 | A |
| 127 | 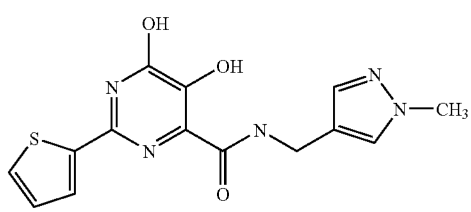 | 5,6-dihydroxy-N-[(1-methyl-1H-pyrazol-4-yl)methyl]-2-thien-2-ylpyrimidine-4-carboxamide (TFA salt) | 332 | A |
| 128 | 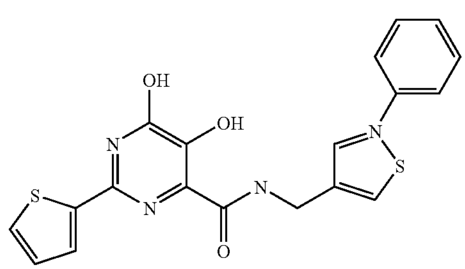 | 5,6-dihydroxy-N-[(2-phenyl-1,3-thiazol-4-yl)methyl]-2-thien-2-ylpyrimidine-4-carboxamide (TFA salt) | 411 | A |

TABLE 1-continued

| Exp | Structure | Name | M+ | Scheme |
|---|---|---|---|---|
| 129 | 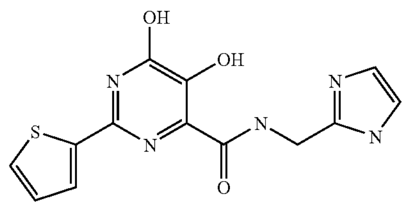 | 5,6-dihydroxy-N-(1H-imidazol-2-ylmethyl)-2-thien-2-ylpyrimidine-4-carboxamide (TFA salt) | 318 | A |
| 130 | 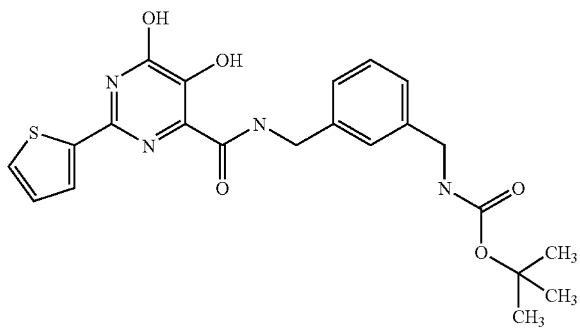 | tert-butyl 3-({[(5,6-dihydroxy-2-thien-2-ylpyrimidin-4-yl)carbonyl]amino}methyl)benzylcarbamate | 457 | A |
| 131 | 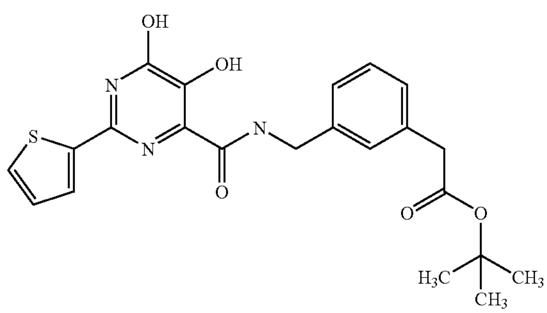 | tert-butyl [3-({[(5,6-dihydroxy-2-thien-2-ylpyrimidin-4-yl)carbonyl]amino}methyl)phenyl]acetate | 442 | A |
| 132 | 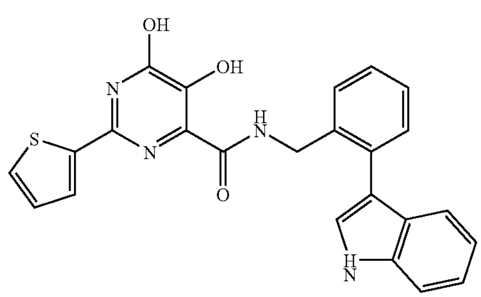 | 5,6-dihydroxy-N-[2-(1H-indol-3-yl)benzyl]-2-thien-2-ylpyrimidine-4-carboxamide | 443 | A |
| 133 | 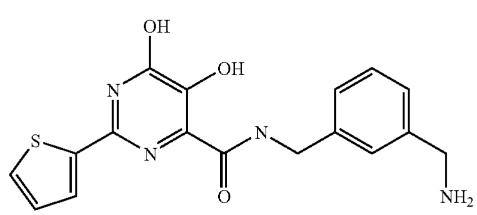 | N-[3-(aminomethyl)benzyl]-5,6-dihydroxy-2-thien-2-ylpyrimidine-4-carboxamide (TFA salt) | 357 | A |

TABLE 1-continued

| Exp | Structure | Name | M+ | Scheme |
|---|---|---|---|---|
| 134 | 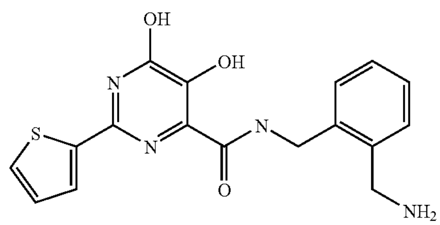 | N-[2-(aminomethyl)benzyl]-5,6-dihydroxy-2-thien-2-ylpyrimidine-4-carboxamide | 357 | A |
| 135 | 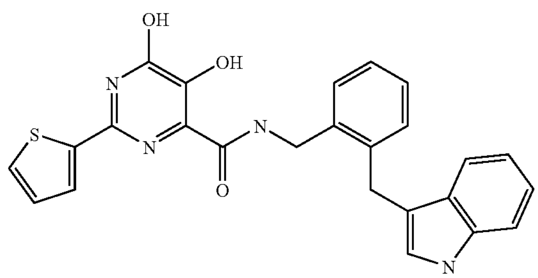 | 5,6-dihydroxy-N-[2-(1H-indol-3-ylmethyl)benzyl]-2-thien-2-ylpyrimidine-4-carboxamide | 457 | A |
| 136 | 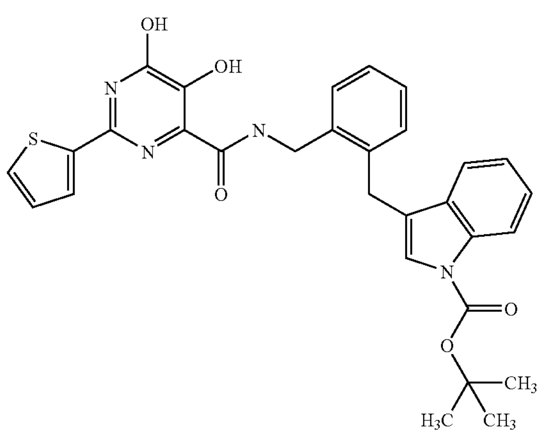 | tert-butyl 3-[2-({[(5,6-dihydroxy-2-thien-2-ylpyrimidin-4-yl)carbonyl]amino}methyl)benzyl]-1H-indole-1-carboxylate | 557 | A |
| 137 | 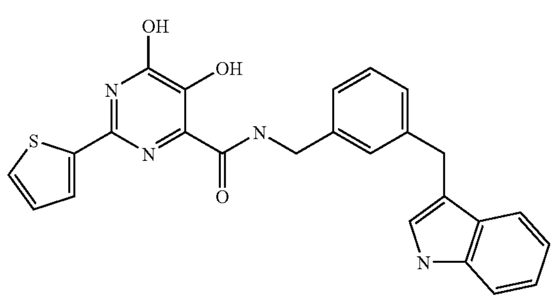 | 5,6-dihydroxy-N-[3-(1H-indol-3-ylmethyl)benzyl]-2-thien-2-ylpyrimidine-4-carboxamide | 457 | A |

TABLE 1-continued

| Exp | Structure | Name | M+ | Scheme |
|---|---|---|---|---|
| 138 | 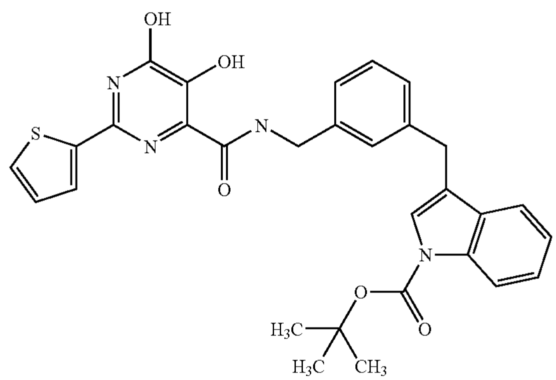 | tert-butyl 3-[3-({[(5,6-dihydroxy-2-thien-2-ylpyrimidin-4-yl)carbonyl]amino}methyl)benzyl]-1H-indole-1-carboxylate | 557 | A |
| 139 | 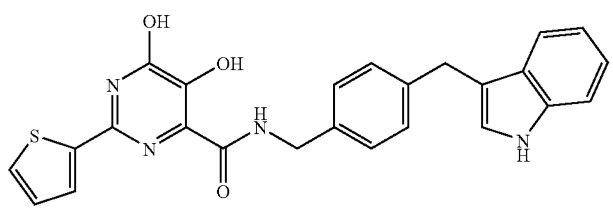 | 5,6-dihydroxy-N-[4-(1H-indol-3-ylmethyl)benzyl]-2-thien-2-ylpyrimidine-4-carboxamide | 457 | A |
| 140 | 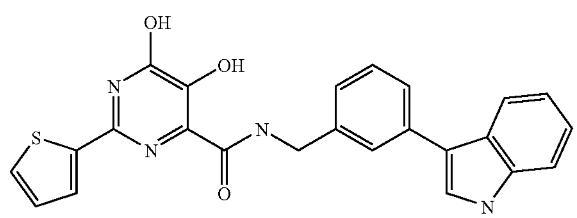 | 5,6-dihydroxy-N-[3-(1H-indol-3-yl)benzyl]-2-thien-2-ylpyrimidine-4-carboxamide | 443 | A |
| 141 | 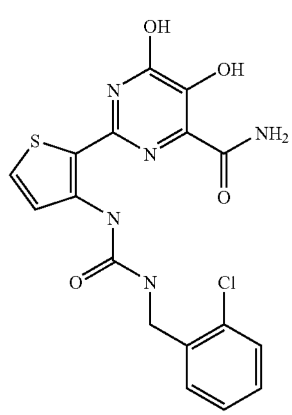 | 2-[3-({[(2-chlorobenzyl)amino]carbonyl}amino)thien-2-yl]-5,6-dihydroxypyrimidine-4-carboxamide | 420 | A |

TABLE 1-continued

| Exp | Structure | Name | M+ | Scheme |
|---|---|---|---|---|
| 142 | 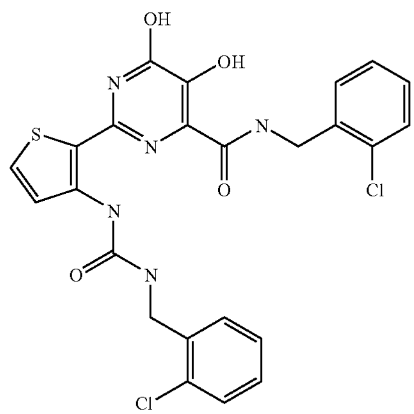 | N-(2-chlorobenzyl)-2-[3-({[(2-chlorobenzyl)amino]carbonyl}amino)thien-2-yl]-5,6-dihydroxy-pyrimidine-4-carboxamide | 642 (M−1) | A |
| 143 | 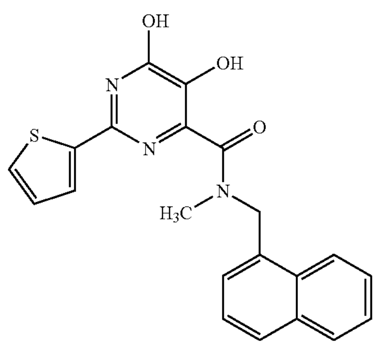 | 5,6-dihydroxy-N-methyl-N-(1-naphthylmethyl)-2-thien-2-ylpyrimidine-4-carboxamide | 392 | A |
| 144 | Chiral | 5,6-dihydroxy-N-[(1R)-1-(1-naphthyl)ethyl]-2-thien-2-ylpyrimidine-4-carboxamide | 392 | A |
| 145 | Chiral | 5,6-dihydroxy-N-[(1S)-1-(1-naphthyl)ethyl]-2-thien-2-ylpyrimidine-4-carboxamide | 392 | A |

TABLE 1-continued

| Exp | Structure | Name | M+ | Scheme |
|---|---|---|---|---|
| 146 | Chiral | 5,6-dihydroxy-N-[(1R)-2-hydroxy-1-phenylethyl]-2-thien-2-ylpyrimidine-4-carboxamide | 358 | A |
| 147 | 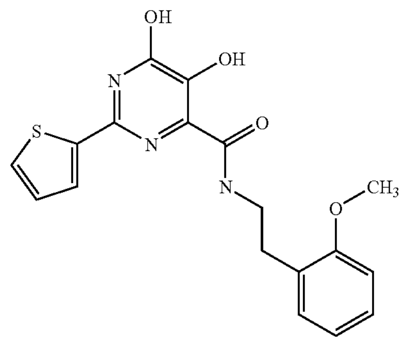 | 5,6-dihydroxy-N-[2-(2-methoxyphenyl)ethyl]-2-thien-2-ylpyrimidine-4-carboxamide | 372 | A |
| 148 | 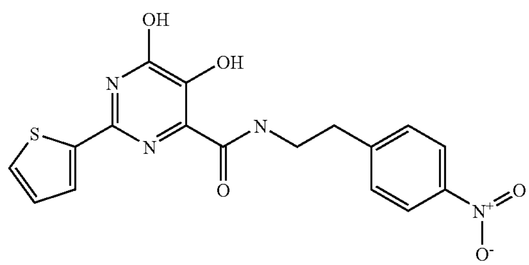 | 5,6-dihydroxy-N-[2-(4-nitrophenyl)ethyl]-2-thien-2-ylpyrimidine-4-carboxamide | 387 | A |
| 149 | 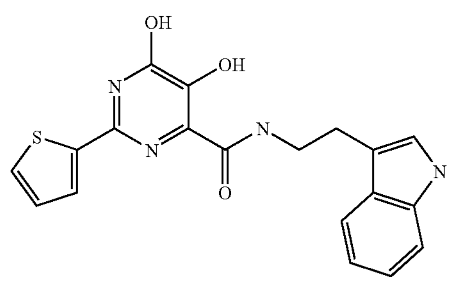 | 5,6-dihydroxy-N-[2-(1H-indol-3-yl)ethyl]-2-thien-2-ylpyrimidine-4-carboxamide | 381 | A |
| 150 | 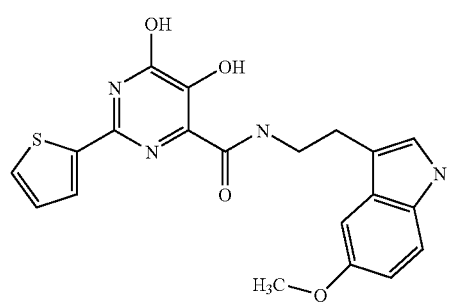 | 5,6-dihydroxy-N-[2-(5-methoxy-1H-indol-3-yl)ethyl]-2-thien-2-ylpyrimidine-4-carboxamide | 411 | A |

TABLE 1-continued

| Exp | Structure | Name | M+ | Scheme |
|---|---|---|---|---|
| 151 | 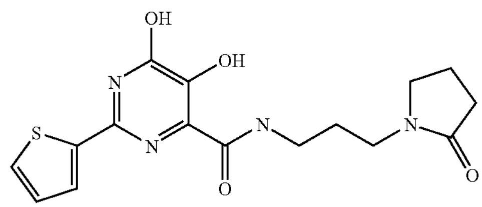 | 5,6-dihydroxy-N-[3-(2-oxopyrrolidin-1-yl)propyl]-2-thien-2-ylpyrimidine-4-carboxamide | 363 | A |
| 152 | Chrial | 5,6-dihydroxy-N-[(1R)-1-(4-methoxyphenyl)ethyl]-2-thien-2-ylpyrimidine-4-carboxamide | 372 | A |
| 153 | 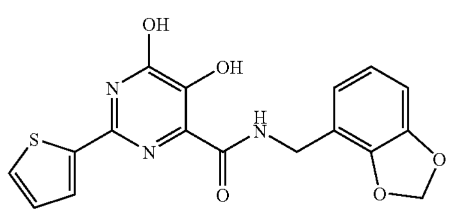 | N-(1,3-benzodioxol-4-ylmethyl)-5,6-dihydroxy-2-thien-2-ylpyrimidine-4-carboxamide | 372 | A |
| 154 | 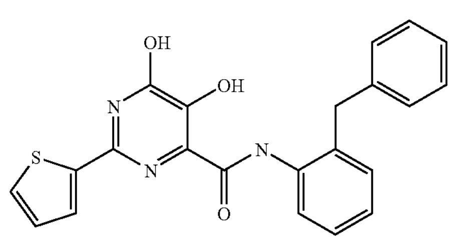 | N-(2-benzylphenyl)-5,6-dihydroxy-2-thien-2-ylpyrimidine-4-carboxamide | 404 | A |
| 155 | 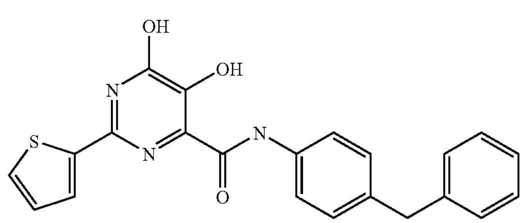 | N-(4-benzylphenyl)-5,6-dihydroxy-2-thien-2-ylpyrimidine-4-carboxamide | 404 | A |

TABLE 1-continued

| Exp | Structure | Name | M+ | Scheme |
|---|---|---|---|---|
| 156 | 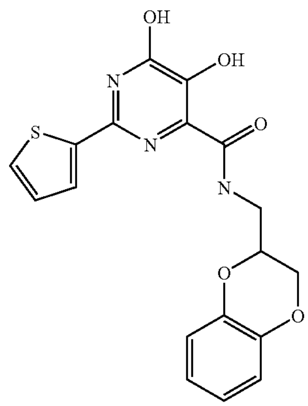 | N-(2,3-dihydro-1,4-benzodioxin-2-ylmethyl)-5,6-dihydroxy-2-thien-2-ylpyrimidine-4-carboxamide | 386 | A |
| 157 | 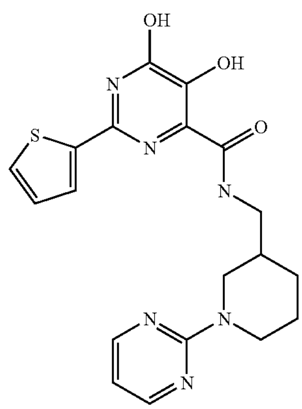 | 5,6-dihydroxy-N-[(1-pyrimidin-2-ylpiperidin-3-yl)methyl]-2-thien-2-ylpyrimidine-4-carboxamide (TFA salt) | 413 | A |
| 158 | 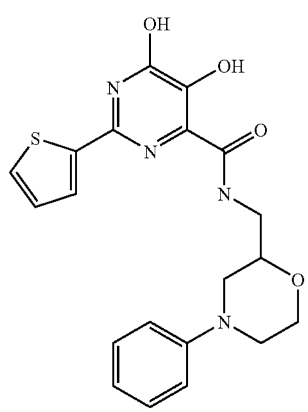 | 5,6-dihydroxy-N-[(4-phenyl-morpholin-2-yl)methyl]-2-thien-2-ylpyrimidine-4-carboxamide (TFA salt) | 413 | A |
| 159 | 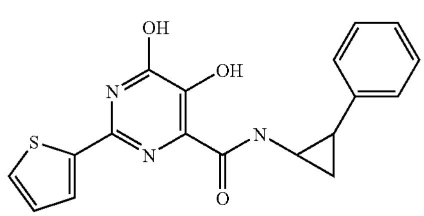 | 5,6-dihydroxy-N-(2-phenyl-cyclopropyl)-2-thien-2-ylpyrimidine-4-carboxamide | 354 | A |

TABLE 1-continued

| Exp | Structure | | Name | M+ | Scheme |
|---|---|---|---|---|---|
| 160 | 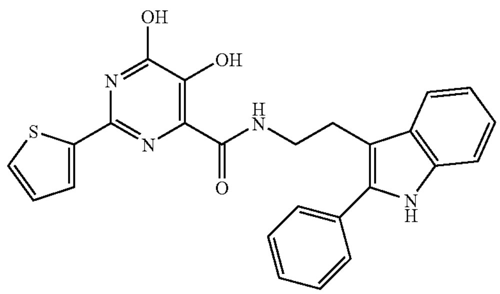 | | 5,6-dihydroxy-N-[2-(2-phenyl-1H-indol-3-yl)ethyl]-2-thien-2-ylpyrimidine-4-carboxamide | 457 | A |
| 161 | 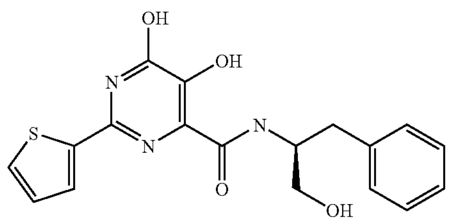 | Chiral | N-[(1S)-1-benzyl-2-hydroxyethyl]-5,6-dihydroxy-2-thien-2-ylpyrimidine-4-carboxamide | 372 | A |
| 162 | 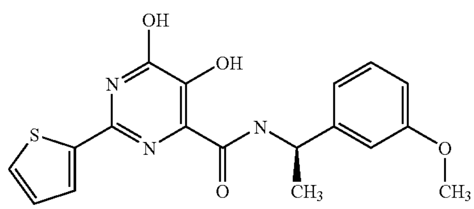 | Chiral | 5,6-dihydroxy-N-[(1R)-1-(3-methoxyphenyl)ethyl]-2-thien-2-ylpyrimidine-4-carboxamide | 372 | A |
| 163 | 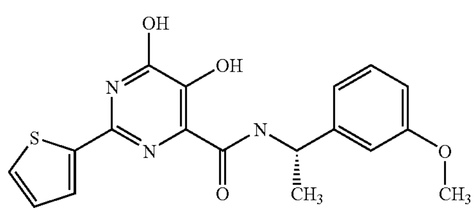 | Chiral | 5,6-dihydroxy-N-[(1S)-1-(3-methoxyphenyl)ethyl]-2-thien-2-ylpyrimidine-4-carboxamide | 372 | A |
| 164 | 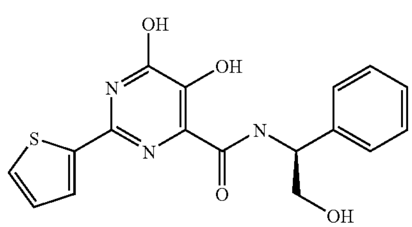 | Chiral | 5,6-dihydroxy-N-[(1S)-2-hydroxy-1-phenylethyl]-2-thien-2-ylpyrimidine-4-carboxamide | 358 | A |
| 165 | 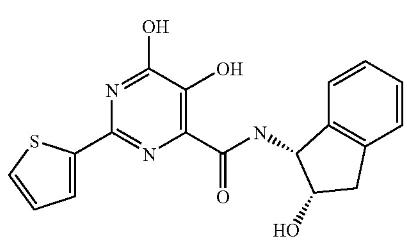 | Chiral | 5,6-dihydroxy-N-[(1R,2S)-2-hydroxy-2,3-dihydro-1H-inden-1-yl]-2-thien-2-ylpyrimidine-4-carboxamide | 370 | A |

TABLE 1-continued
| Exp | Structure | Name | M+ | Scheme |
|---|---|---|---|---|
| 166 | 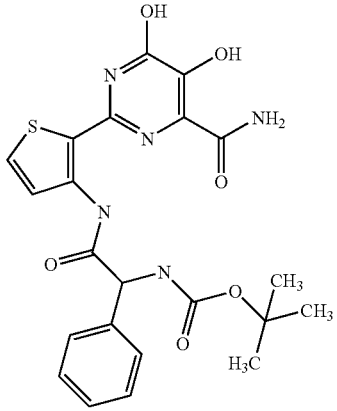 | tert-butyl 2-({2-[4-(aminocarbonyl)-5,6-dihydroxypyrimidin-2-yl]thien-3-yl}amino)-2-oxo-1-phenylethylcarbamate | 486 | A |
| 167 | 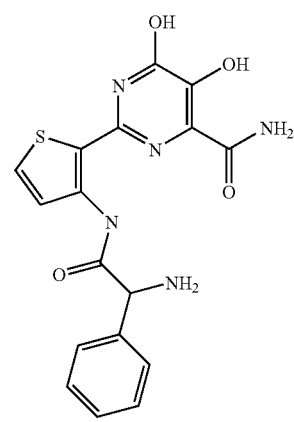 | 2-(3-{[amino(phenyl)acetyl]amino}thien-2-yl)-5,6-dihydroxy-pyrimidine-4-carboxamide (TFA salt) | 386 | A |
| 168 | 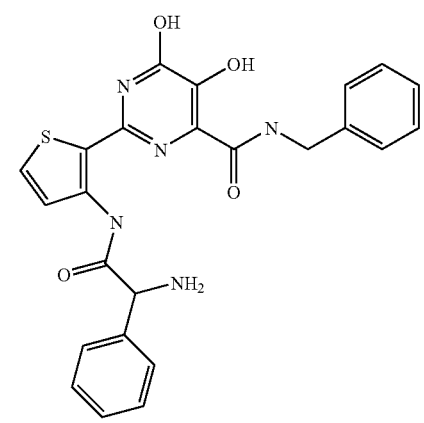 | 2-(3-{[amino(phenyl)acetyl]amino}thien-2-yl)-N-benzyl-5,6-dihydroxypyrimidine-4-carboxamide (TFA salt) | 476 | A |

TABLE 2

| # | Structure | Name | | |
|---|---|---|---|---|
| 1 | 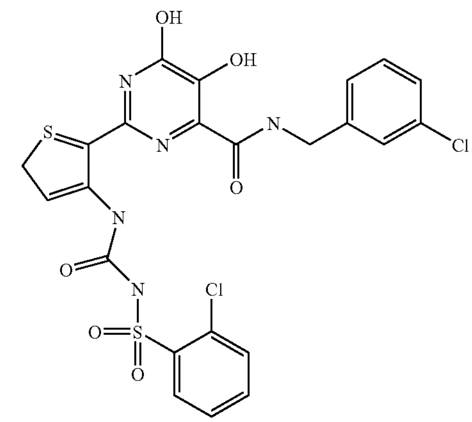 | N-(3-chlorobenzyl)-2-{4-[({[(2-chlorophenyl)sulfonyl]amino}carbonyl)amino]thien-3-yl}-5,6-dihydroxypyrimidine-4-carboxamide | 594 | G |
| 2 | 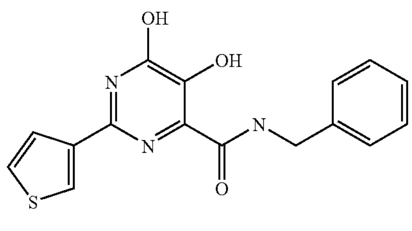 | N-benzyl-5,6-dihydroxy-2-thien-3-ylpyrimidine-4-carboxamide | 328 | A |
| 3 | 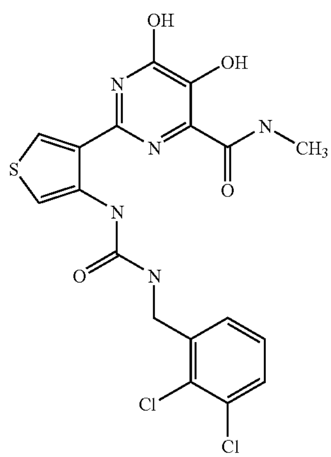 | 2-[4-({[(2,3-dichlorobenzyl)amino]carbonyl}amino)thien-3-yl]-5,6-dihydroxy-N-methylpyrimidine-4-carboxamide | 468 | G |
| 4 | 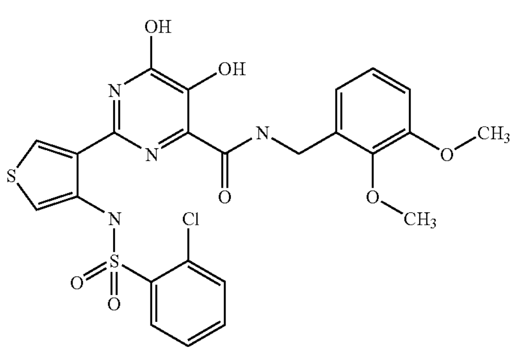 | 2-{4-[({[(2-chlorophenyl)sulfonyl]amino}carbonyl)amino]thien-3-yl}-N-(2,3-dimethoxybenzyl)-5,6-dihydroxypyrimidine-4-carboxamide | 620 | G |

TABLE 2-continued

| | | | | |
|---|---|---|---|---|
| 5 | *(structure)* | N-benzyl-2-(4-{[(benzylamino)carbonyl]amino}-3-thienyl)-5,6-dihydroxy-4-pyrimidinecarboxamide | 476 | G |
| 6 | *(structure)* | 2-{4-[({[(2-chlorophenyl)sulfonyl]amino}carbonyl)amino]thien-3-yl}-5,6-dihydroxy-N-(2-phenylethyl)pyrimidine-4-carboxamide | 574 | G |
| 7 | *(structure)* | 2-{4-[({[(2-chlorophenyl)sulfonyl]amino}carbonyl)-amino]thien-3-yl}5,6-dihydroxy-N-methylpyrimidine-4-carboxamide | 484 | G |
| 8 | *(structure)* | N-benzyl-5,6-dihydroxy-2-[4-({[(thien-2-ylmethyl)amino]carbonyl}amino)thien-3-yl]-pyrimidine-4-carboxamide | 482 | G |

TABLE 2-continued

| # | Structure | Name | | |
|---|---|---|---|---|
| 9 | 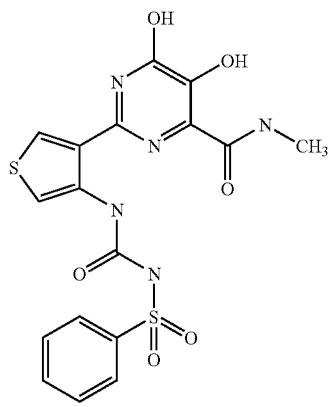 | 5,6-dihydroxy-N-methyl-2-[4-({[(phenylsulfonyl)amino]carbonyl}amino)thien-3-yl]pyrimidine-4-carboxamide | 450 | G |

TABLE 3

| # | Structure | Name | | |
|---|---|---|---|---|
| 1 | 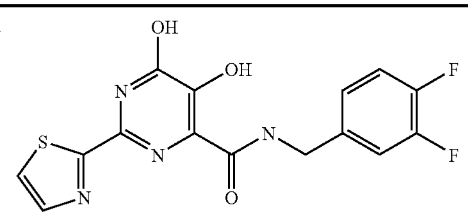 | N-(3,4-difluorobenzyl)-5,6-dihydroxy-2-(1,3-thiazol-2-yl)pyrimidine-4-carboxamide | 365 | A |
| 2 | 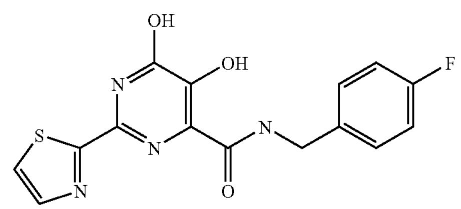 | N-(4-fluorobenzyl)-5,6-dihydroxy-2-(1,3-thiazol-2-yl)pyrimidine-4-carboxamide | 347 | A |
| 3 | 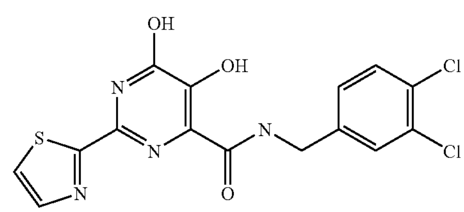 | N-(3,4-dichlorobenzyl)-5,6-dihydroxy-2-(1,3-thiazol-2-yl)pyrimidine-4-carboxamide | 397 | A |
| 4 | 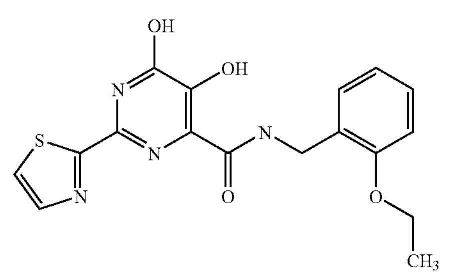 | N-(2-ethoxybenzyl)-5,6-dihydroxy-2-(1,3-thiazol-2-yl)pyrimidine-4-carboxamide | 373 | A |
| 5 | 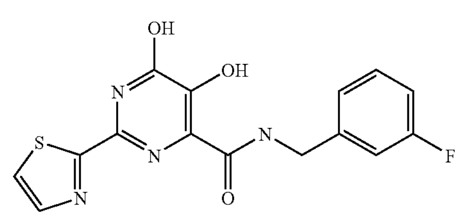 | N-(3-fluorobenzyl)-5,6-dihydroxy-2-(1,3-thiazol-2-yl)pyrimidine-4-carboxamide | 347 | A |

TABLE 3-continued

| | Structure | Name | MW | Activity |
|---|---|---|---|---|
| 6 | 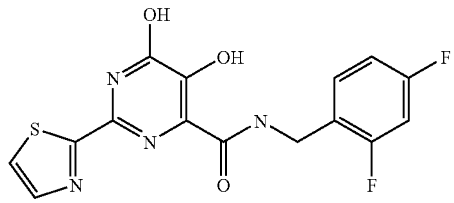 | N-(2,4-difluorobenzyl)-5,6-dihydroxy-2-(1,3-thiazol-2-yl)pyrimidine-4-carboxamide | 365 | A |
| 7 | 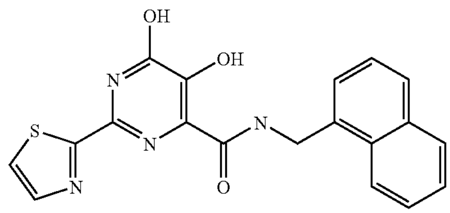 | 5,6-dihydroxy-N-(1-naphthylmethyl)-2-(1,3-thiazol-2-yl)pyrimidine-4-carboxamide | 379 | A |
| 8 | 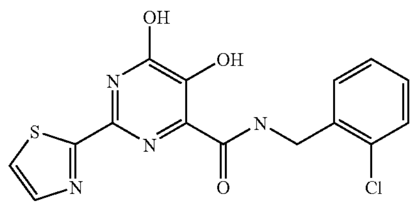 | N-(2-chlorobenzyl)-5,6-dihydroxy-2-(1,3-thiazol-2-yl)pyrimidine-4-carboxamide | 363 | A |
| 9 | 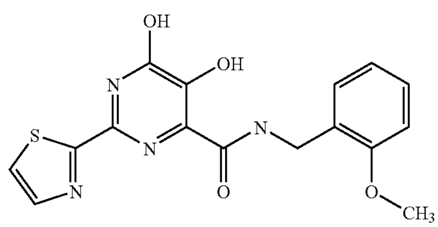 | 5,6-dihydroxy-N-(2-methoxy-benzyl)-2-(1,3-thiazol-2-yl)pyrimidine-4-carboxamide | 363 | A |
| 10 | 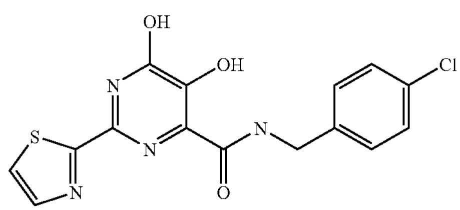 | N-(4-chlorobenzyl)-5,6-dihydroxy-2-(1,3-thiazol-2-yl)pyrimidine-4-carboxamide | 363 | A |
| 11 | 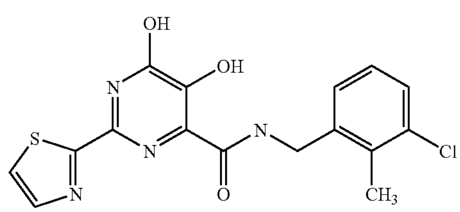 | N-(3-chloro-2-methylbenzyl)-5,6-dihydroxy-2-(1,3-thiazol-2-yl)pyrimidine-4-carboxamide | 377 | A |
| 12 | 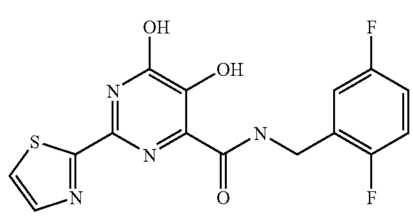 | N-(2,5-difluorobenzyl)-5,6-dihydroxy-2-(1,3-thiazol-2-yl)pyrimidine-4-carboxamide | 365 | A |

TABLE 3-continued

| # | Structure | Name | MW | Act |
|---|---|---|---|---|
| 13 | 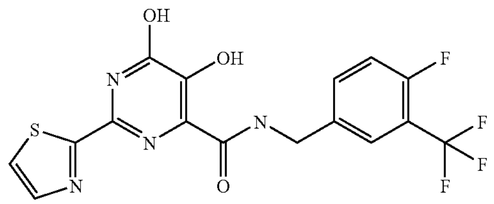 | N-[4-fluoro-3-(trifluoromethyl)benzyl]-5,6-dihydroxy-2-(1,3-thiazol-2-yl)pyrimidine-4-carboxamide | 415 | A |
| 14 | 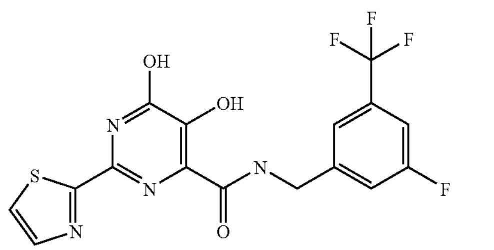 | N-[3-fluoro-5-(trifluoromethyl)benzyl]-5,6-dihydroxy-2-(1,3-thiazol-2-yl)pyrimidine-4-carboxamide | 415 | A |
| 15 | 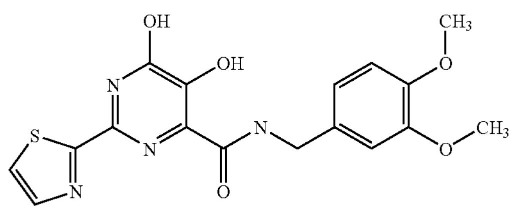 | N-(3,4-dimethoxybenzyl)-5,6-dihydroxy-2-(1,3-thiazol-2-yl)pyrimidine-4-carboxamide | 389 | A |
| 16 | 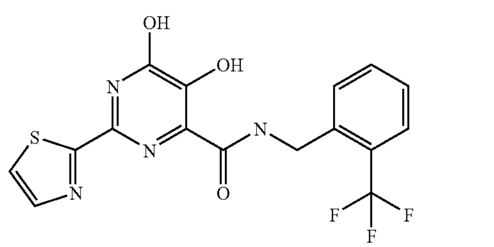 | 5,6-dihydroxy-2-(1,3-thiazol-2-yl)-N-[2-(trifluoromethyl)benzyl]pyrimidine-4-carboxamide | 397 | A |
| 17 | 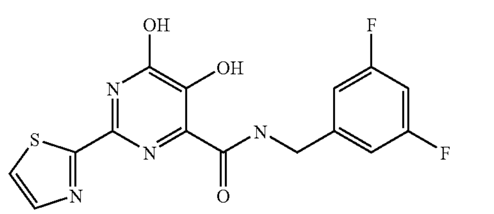 | N-(3,5-difluorobenzyl)-5,6-dihydroxy-2-(1,3-thiazol-2-yl)pyrimidine-4-carboxamide | 365 | A |
| 18 | 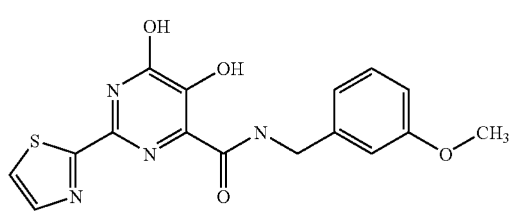 | 5,6-dihydroxy-N-(3-methoxybenzyl)-2-(1,3-thiazol-2-yl)pyrimidine-4-carboxamide | 359 | A |
| 19 | 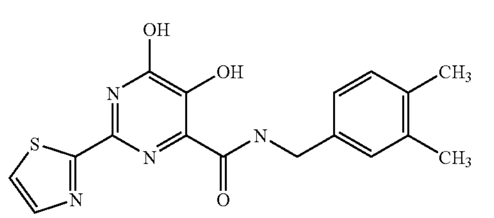 | N-(3,4-dimethylbenzyl)-5,6-dihydroxy-2-(1,3-thiazol-2-yl)pyrimidine-4-carboxamide | 357 | A |

TABLE 3-continued

| | | | | |
|---|---|---|---|---|
| 20 | (structure) | N-benzyl-5,6-dihydroxy-2-(1,3-thiazol-2-yl)pyrimidine-4-carboxamide | 329 | A |
| 21 | (structure) | N-(1-benzothien-3-ylmethyl)-5,6-dihydroxy-2-(1,3-thiazol-2-yl)pyrimidine-4-carboxamide | 385 | A |
| 22 | (structure) | N-(2,3-dihydro-1H-inden-1-yl)-5,6-dihydroxy-2-(1,3-thiazol-2-yl)pyrimidine-4-carboxamide | 355 | A |
| 23 | (structure) | N-(2,3-dihydro-1H-inden-2-yl)-5,6-dihydroxy-2-(1,3-thiazol-2-yl)pyrimidine-4-carboxamide | 355 | A |
| 24 | (structure) | 5,6-dihydroxy-N-(4-methoxy-benzyl)-2-(1,3-thiazol-2-yl)pyrimidine-4-carboxamide | 359 | A |
| 25 | (structure) | N-(3-chloro-4-methylbenzyl)-5,6-dihydroxy-2-(1,3-thiazol-2-yl)pyrimidine-4-carboxamide | 377 | A |
| 26 | (structure) | N-[4-fluoro-2-(trifluoromethyl)benzyl]-5,6-dihydroxy-2-(1,3-thiazol-2-yl)pyrimidine-4-carboxamide | 415 | A |

TABLE 3-continued

| | | | | |
|---|---|---|---|---|
| 27 | 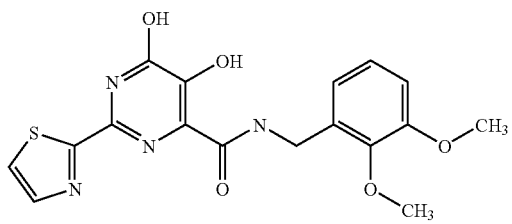 | N-(2,3-dimethoxybenzyl)-5,6-dihydroxy-2-(1,3-thiazol-2-yl)pyrimidine-4-carboxamide | 389 | A |
| 28 | 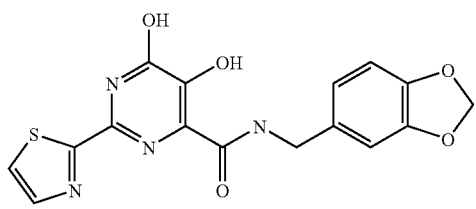 | N-(1,3-benzodioxol-5-ylmethyl)-5,6-dihydroxy-2-(1,3-thiazol-2-yl)pyrimidine-4-carboxamide | 373 | A |
| 29 | 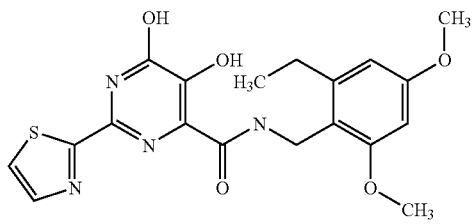 | 5,6-dihydroxy-2-(1,3-thiazol-2-yl)-N-(2,4,6-trimethoxybenzyl)pyrimidine-4-carboxamide | 419 | A |
| 30 | 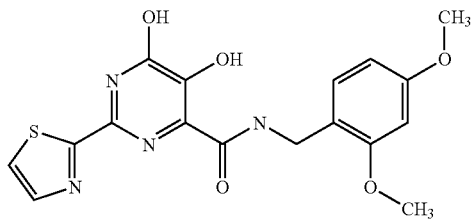 | N-(2,4-dimethoxybenzyl)-5,6-dihydroxy-2-(1,3-thiazol-2-yl)pyrimidine-4-carboxamide | 389 | A |
| 31 | 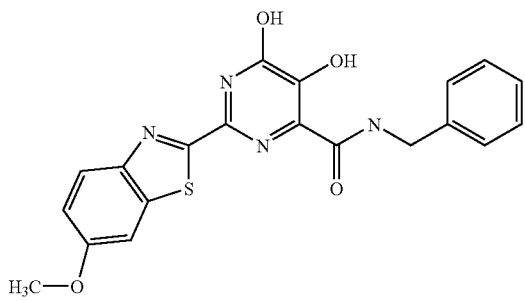 | N-benzyl-5,6-dihydroxy-2-(6-methoxy-1,3-benzothiazol-2-yl)pyrimidine-4-carboxamide | 409 | A |

TABLE 4

| | | | | |
|---|---|---|---|---|
| 1 | 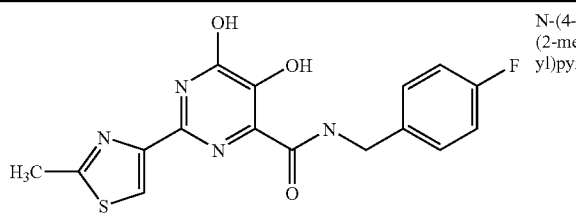 | N-(4-fluorobenzyl)-5,6-dihydroxy-2-(2-methyl-1,3-thiazol-4-yl)pyrimidine-4-carboxamide | 361 | A |

TABLE 4-continued

| # | Structure | Name | MW | Class |
|---|---|---|---|---|
| 2 | 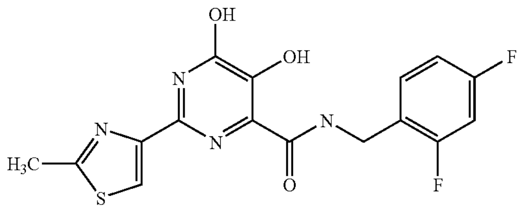 | N-(2,4-difluorobenzyl)-5,6-dihydroxy-2-(2-methyl-1,3-thiazol-4-yl)pyrimidine-4-carboxamide | 379 | A |
| 3 | 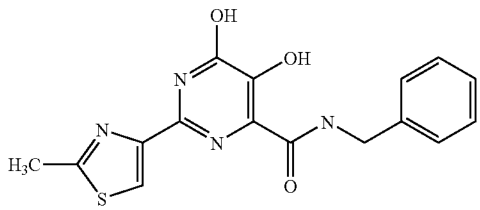 | N-benzyl-5,6-dihydroxy-2-(2-methyl-1,3-thiazol-4-yl)pyrimidine-4-carboxamide | 343 | A |
| 4 | 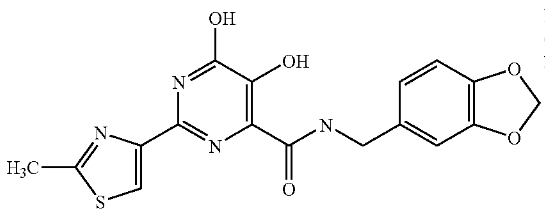 | N-(1,3-benzodioxol-5-ylmethyl)-5,6-dihydroxy-2-(2-methyl-1,3-thiazol-4-yl)pyrimidine-4-carboxamide | 387 | A |
| 5 | 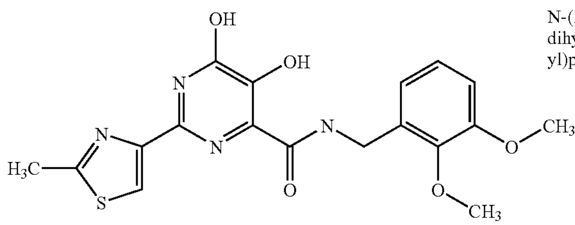 | N-(2,3-dimethoxybenzyl)-5,6-dihydroxy-2-(2-methyl-1,3-thiazol-4-yl)pyrimidine-4-carboxamide | 403 | A |

TABLE 5

| # | Structure | Name | MW | Class |
|---|---|---|---|---|
| 1 | 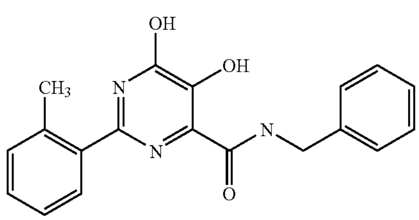 | N-benzyl-5,6-dihydroxy-2-(2-methylphenyl)pyrimidine-4-carboxamide | 336 | A |
| 2 | 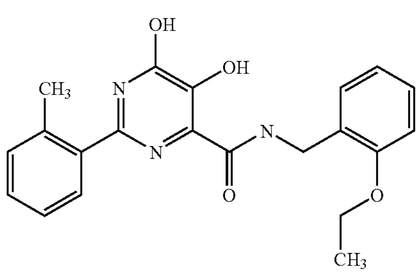 | N-(2-ethoxybenzyl)-5,6-dihydroxy-2-(2-methylphenyl)pyrimidine-4-carboxamide | 380 | A |

TABLE 5-continued

| | | | | |
|---|---|---|---|---|
| 3 | 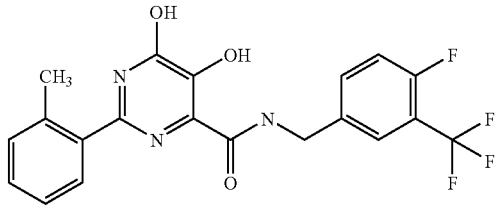 | N-[4-fluoro-3-(trifluoromethyl)benzyl]-5,6-dihydroxy-2-(2-methylphenyl)pyrimidine-4-carboxamide | 422 | A |
| 4 | 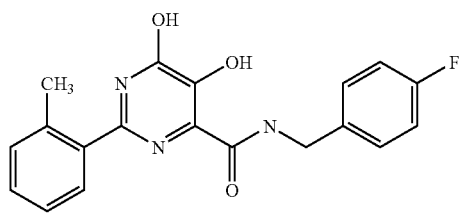 | N-(4-fluorobenzyl)-5,6-dihydroxy-2-(2-methylphenyl)pyrimidine-4-carboxamide | 354 | A |
| 5 | 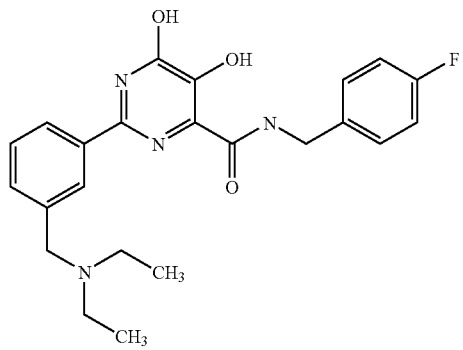 | N-(2,3-dimethoxybenzyl)-5,6-dihydroxy-2-(2-methylphenyl)pyrimidine-4-carboxamide | 396 | A |
| 6 | 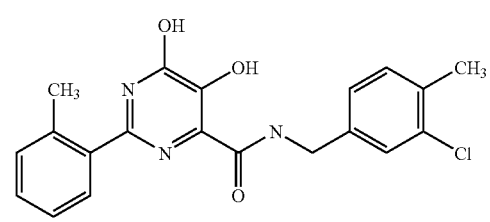 | N-(3-chloro-4-methylbenzyl)-5,6-dihydroxy-2-(2-methylphenyl)pyrimidine-4-carboxamide | 384 | A |
| 7 | 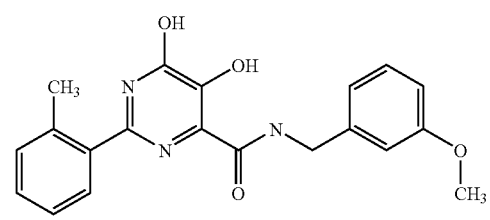 | 5,6-dihydroxy-N-(3-methoxybenzyl)-2-(2-methylphenyl)pyrimidine-4-carboxamide | 366 | A |
| 8 | 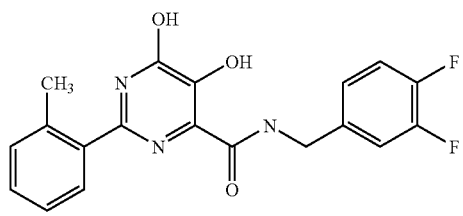 | N-(3,4-difluorobenzyl)-5,6-dihydroxy-2-(2-methylphenyl)pyrimidine-4-carboxamide | 372 | A |

TABLE 5-continued

| 9 | [structure] | N-(2,4-difluorobenzyl)-5,6-dihydroxy-2-(2-methylphenyl)pyrimidine-4-carboxamide | 372 | A |
| 10 | [structure] | N-benzyl-5,6-dihydroxy-2-phenylpyrimidine-4-carboxamide | 322 | A |
| 11 | [structure] | N-(2,3-dimethoxybenzyl)-5,6-dihydroxy-2-{2-[(pyridin-2-ylcarbonyl)amino]phenyl}pyrimidine-4-carboxamide | 502 | I |
| 12 | [structure] | N-[4-fluoro-2-(trifluoromethyl)benzyl]-5,6-dihydroxy-2-(2-methylphenyl)pyrimidine-4-carboxamide | 422 | A |
| 13 | [structure] | N-(2,3-dihydro-1H-inden-2-yl)-5,6-dihydroxy-2-phenylpyrimidine-4-carboxamide | 348 | A |
| 14 | [structure] | N-(2,3-dimethoxybenzyl)-5,6-dihydroxy-2-phenylpyrimidine-4-carboxamide | 382 | A |

TABLE 5-continued
| | | | | |
|---|---|---|---|---|
| 15 | 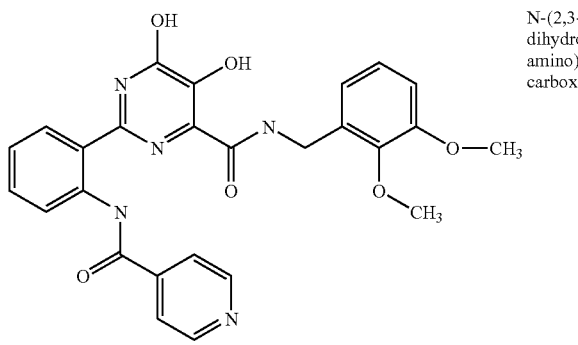 | N-(2,3-dimethoxybenzyl)-5,6-dihydroxy-2-[2-(isonicotinoyl-amino)phenyl]pyrimidine-4-carboxamide (HCL salt) | 502 | I |
| 16 | 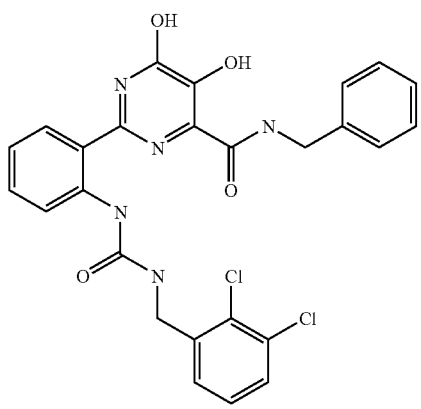 | N-benzyl-2-[2-({[(2,3-dichlorobenzyl)amino]carbonyl}amino)phenyl]-5,6-dihydroxypyrimidine-4-carboxamide | 538 | G |
| 17 | 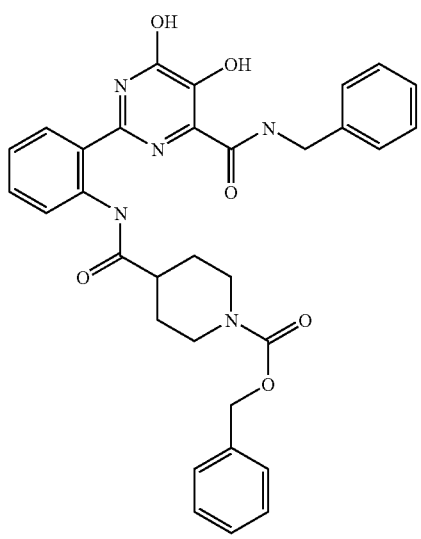 | benzyl 4-{[(2-{4-[(benzylamino)carbonyl]-5,6-dihydroxypyrimidin-2-yl}phenyl)amino]carbonyl}piperidine-1-carboxylate | 582 | I |

TABLE 5-continued
| 18 | 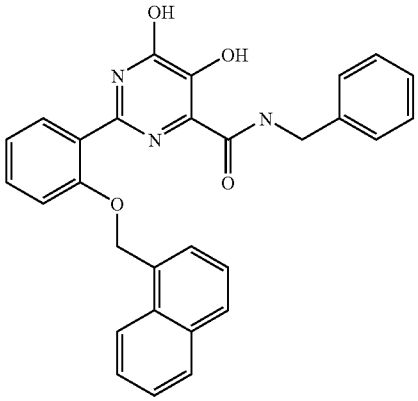 | N-benzyl-5,6-dihydroxy-2-[2-(1-naphthylmethoxy)phenyl]pyrimidine-4-carboxamide | 478 | A |
| 19 | 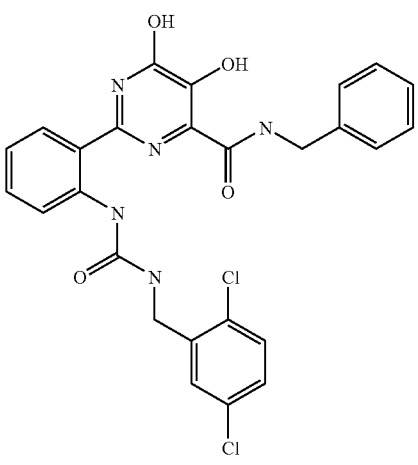 | N-benzyl-2-[2-({[(2,5-dichlorobenzyl)amino]carbonyl}amino]phenyl]-5,6-dihydroxypyrimidine-4-carboxamide | 538 | G |
| 20 | 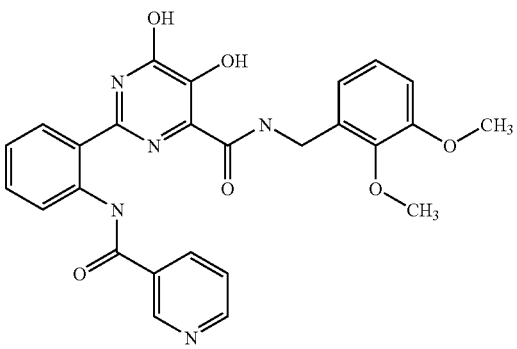 | N-(2,3-dimethoxybenzyl)-5,6-dihydroxy-2-{2-[(pyridin-3-yl-carbonyl)amino]phenyl}pyrimidine-4-carboxamide (TFA salt) | 502 | I |
| 21 | 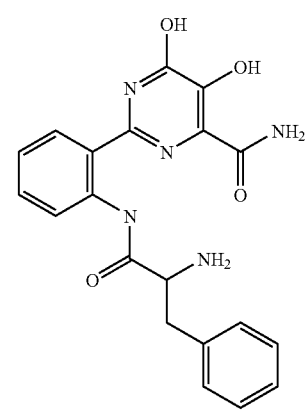 | N-{2-[4-(aminocarbonyl)-5,6-dihydroxypyrimidin-2-yl]phenyl}phenylalaninamide (TFA salt) | 394 | A* |

TABLE 5-continued

| | | | | |
|---|---|---|---|---|
| 22 | 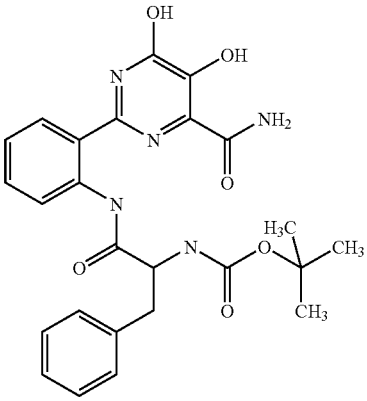 | tert-butyl 3-({3-[4-(aminocarbonyl)-5,6-dihydroxypyrimidin-2-yl]phenyl}amino)-3-oxo-1-phenylprop-2-ylcarbamate | 494.2 | I |

TABLE 6

| | | | | |
|---|---|---|---|---|
| 1 | 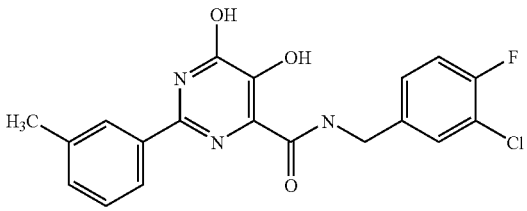 | N-(3-chloro-4-fluorobenzyl)-5,6-dihydroxy-2-(3-methylphenyl)-pyrimidine-4-carboxamide | 388 | A |
| 2 | 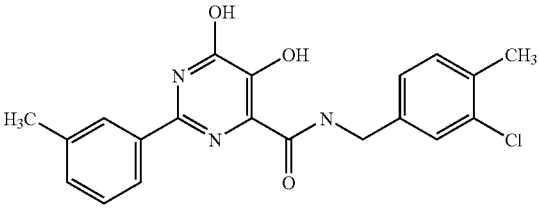 | N-(3-chloro-4-methylbenzyl)-5,6-dihydroxy-2-(3-methylphenyl)pyrimidine-4-carboxamide | 384 | A |
| 3 | 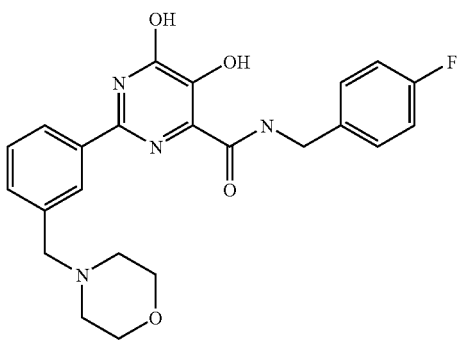 | N-(4-fluorobenzyl)-5,6-dihydroxy-2-[3-(morpholin-4-ylmethyl)phenyl]pyrimidine-4-carboxamide (TFA salt) | 439 | B |
| 4 | 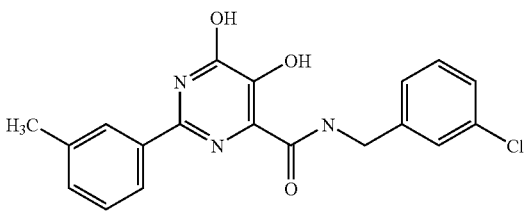 | N-(3-chlorobenzyl)-5,6-dihydroxy-2-(3-methylphenyl)pyrimidine-4-carboxamide | 370 | A |

TABLE 6-continued

| | | | | |
|---|---|---|---|---|
| 5 | 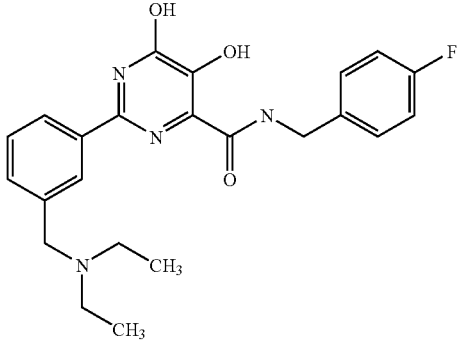 | 2-{3-[(diethylamino)methyl]phenyl}-N-(4-fluorobenzyl)-5,6-dihydroxy-pyrimidine-4-carboxamide (TFA salt) | 425 | B |
| 6 | 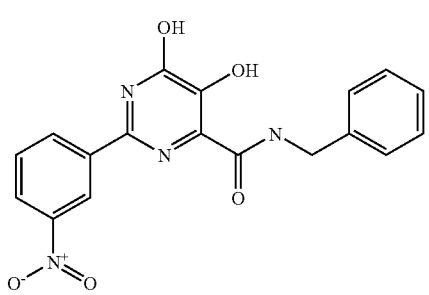 | N-benzyl-5,6-dihydroxy-2-(3-nitrophenyl)pyrimidine-4-carboxamide | 367 | A |
| 7 | 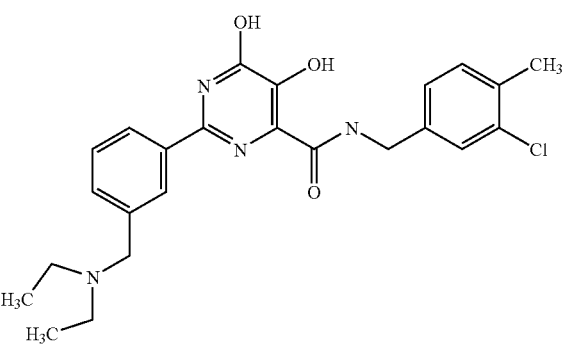 | N-(3-chloro-4-methylbenzyl)-2-{3-[(diethylamino)methyl]phenyl}-5,6-dihydroxypyrimidine-4-carboxamide (HCl salt) | 455 | B |
| 8 | 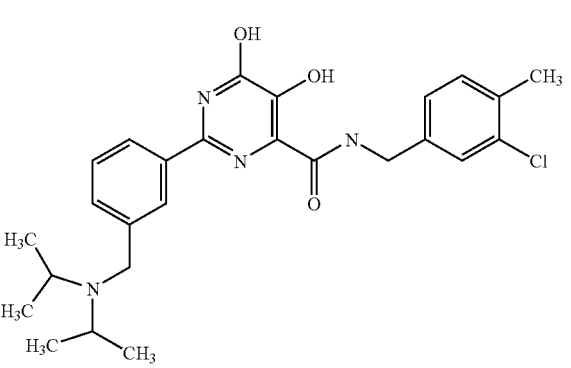 | N-(3-chloro-4-methylbenzyl)-2-{3-[(diisopropylamino)methyl]phenyl}-5,6-dihydroxypyrimidine-4-carboxamide (HCl salt) | 483 | B |
| 9 | 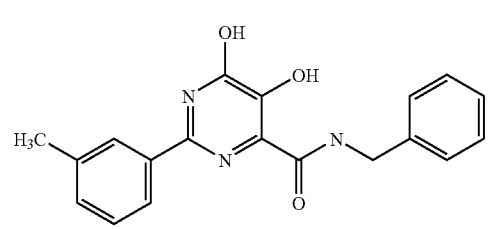 | N-benzyl-5,6-dihydroxy-2-(3-methylphenyl)pyrimidine-4-carboxamide | 336 | A |

TABLE 6-continued

| # | Structure | Name | MW | Class |
|---|---|---|---|---|
| 10 | 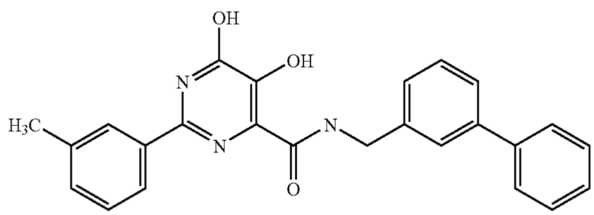 | N-(1,1'-biphenyl-3-ylmethyl)-5,6-dihydroxy-2-(3-methylphenyl)pyrimidine-4-carboxamide | 412 | A |
| 11 | 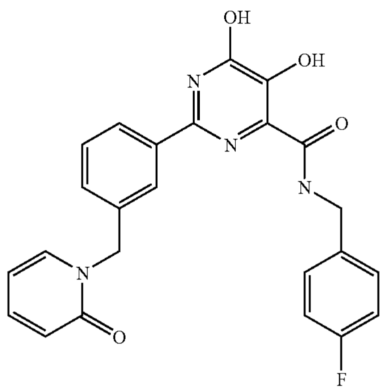 | N-(4-fluorobenzyl)-5,6-dihydroxy-2-{3-[(2-oxopyridin-1(2H)-yl)methyl]phenyl}pyrimidine-4-carboxamide | 447 | A |
| 12 | 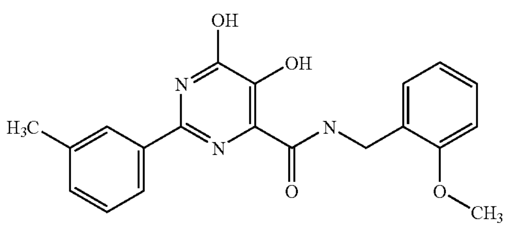 | 5,6-dihydroxy-N-(2-methoxybenzyl)-2-(3-methylphenyl)pyrimidine-4-carboxamide | 366 | A |
| 13 | 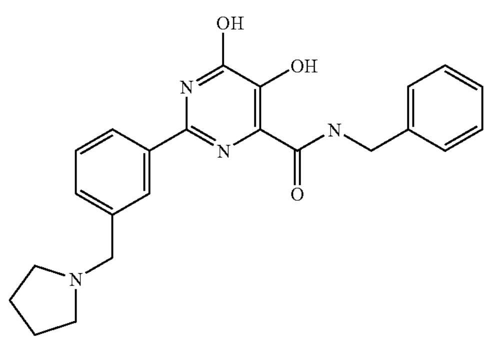 | N-benzyl-5,6-dihydroxy-2-[3-(pyrrolidin-1-ylmethyl)phenyl]-pyrimidine-4-carboxamide (HCl salt) | 405 | B |
| 14 | 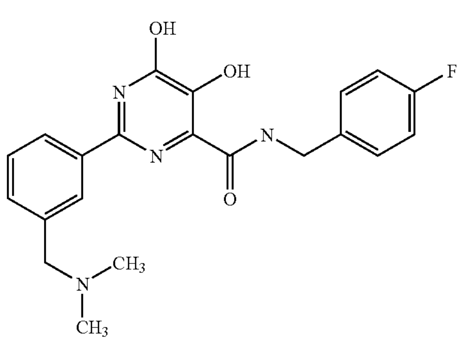 | 2-{3-[(dimethylamino)methyl]phenyl}-N-(4-fluorobenzyl)-5,6-dihydroxy-pyrimidine-4-carboxamide (TFA salt) | 397 | B |

TABLE 6-continued

| 15 | 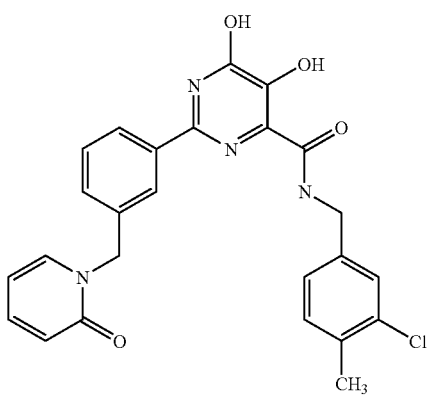 | N-(3-chloro-4-methylbenzyl)-5,6-dihydroxy-2-{3-[(2-oxopyridin-1(2H)-yl)methyl]phenyl}pyrimidine-4-carboxamide | 477 | A |
| --- | --- | --- | --- | --- |
| 16 | 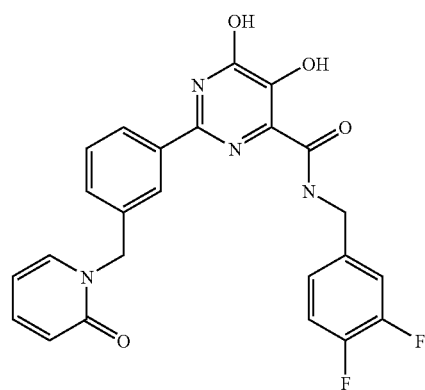 | N-(3,4-difluorobenzyl)-5,6-dihydroxy-2-{3-[(2-oxopyridin-1(2H)-yl)methyl]phenyl}pyrimidine-4-carboxamide | 465 | A |
| 17 | 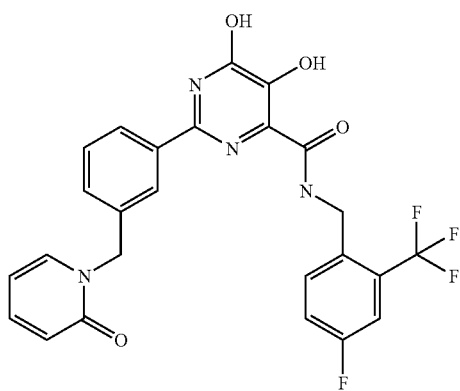 | N-[4-fluoro-2-(trifluoromethyl)benzyl]-5,6-dihydroxy-2-{3-[(2-oxopyridin-1(2H)-yl)methyl]phenyl}pyrimidine-4-carboxamide | 515 | A |
| 18 | 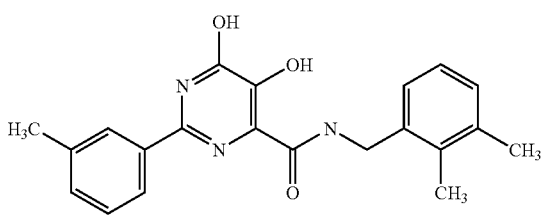 | N-(2,3-dimethylbenzyl)-5,6-dihydroxy-2-(3-methylphenyl)pyrimidine-4-carboxamide | 364 | A |

TABLE 6-continued

| | | | | |
|---|---|---|---|---|
| 19 | (structure) | 2-(3-bromophenyl)-N-(2,3-dihydro-1H-inden-2-yl)-5,6-dihydroxy-pyrimidine-4-carboxamide | 426 | A |
| 20 | (structure) | N-(4-fluorobenzyl)-5,6-dihydroxy-2-{3-[(4-methylpiperazin-1-yl)methyl]phenyl}pyrimidine-4-carboxamide (TFA salt) | 452 | B |
| 21 | (structure) | N-(4-fluorobenzyl)-5,6-dihydroxy-2-[3-(piperidin-1-ylmethyl)phenyl]pyrimidine-4-carboxamide (TFA salt) | 437 | B |
| 22 | (structure) | N-(1,3-benzodioxol-5-ylmethyl)-5,6-dihydroxy-2-{3-[(2-oxopyridin-1(2H)-yl)methyl]phenyl}pyrimidine-4-carboxamide | 473 | A |

| | | | | |
|---|---|---|---|---|
| 23 | 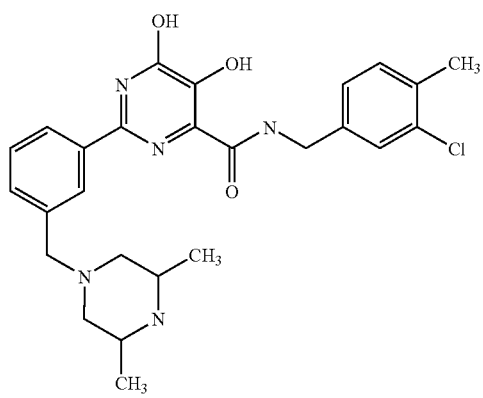 | N-(3-chloro-4-methylbenzyl)-2-{3-[(3,5-dimethylpiperazin-1-yl)methyl]phenyl}-5,6-dihydroxypyrimidine-4-carboxamide (TFA salt) | 496 | B |
| 24 | 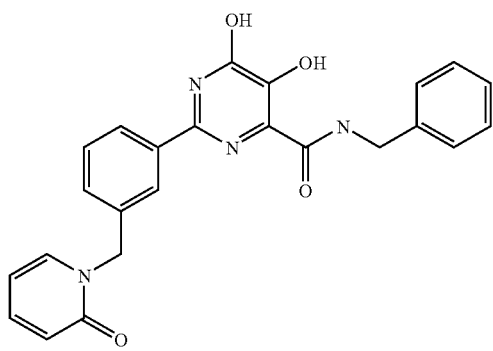 | N-benzyl-5,6-dihydroxy-2-{3-[(2-oxopyridin-1(2H)-yl)methyl]phenyl}pyrimidine-4-carboxamide | 429 | A |
| 25 | 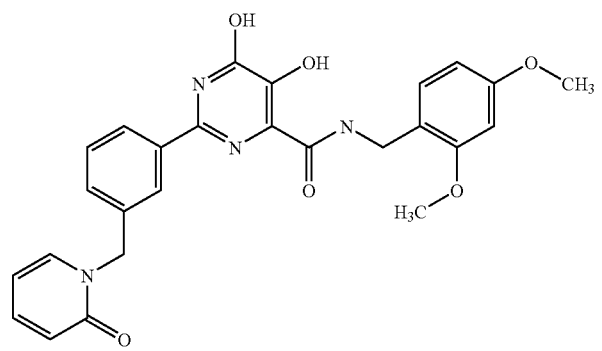 | N-(2,4-dimethoxybenzyl)-5,6-dihydroxy-2-{3-[(2-oxopyridin-1(2H)-yl)methyl]phenyl}pyrimidine-4-carboxamide | 489 | A |
| 26 | 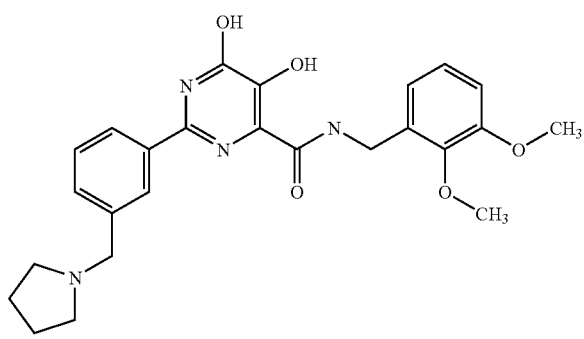 | N-(2,3-dimethoxybenzyl)-5,6-dihydroxy-2-[3-(pyrrolidin-1-ylmethyl)phenyl]pyrimidine-4-carboxamide (TFA salt) | 465 | B |

TABLE 6-continued

| # | Structure | Name | Value | Grade |
|---|---|---|---|---|
| 27 | 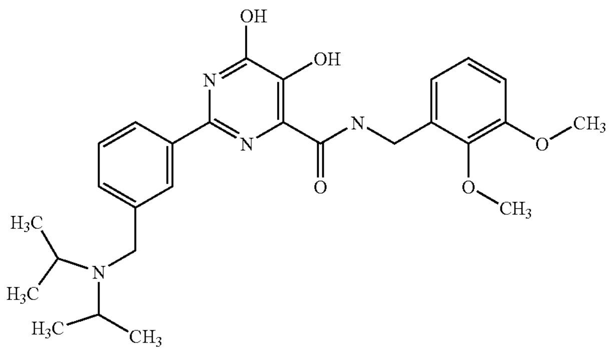 | 2-{3-[(diisopropylamino)methyl]phenyl}-N-(2,3-dimethoxybenzyl)-5,6-dihydroxypyrimidine-4-carboxamide (TFA salt) | 495 | B |
| 28 | 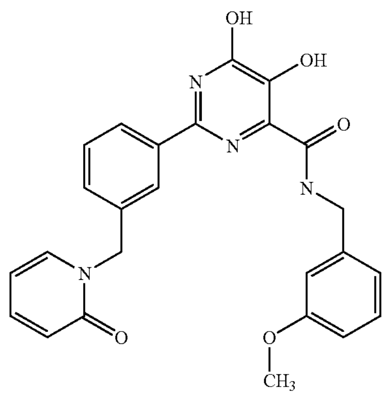 | 5,6-dihydroxy-N-(3-methoxybenzyl)-2-{3-[(2-oxopyridin-1(2H)-yl)methyl]phenyl}pyrimidine-4-carboxamide | 459 | A |
| 29 | 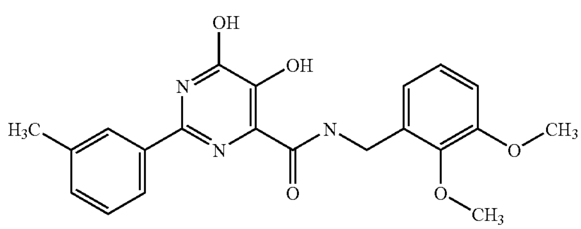 | N-(2,3-dimethoxybenzyl)-5,6-dihydroxy-2-(3-methylphenyl)pyrimidine-4-carboxamide | 396 | A |
| 30 | 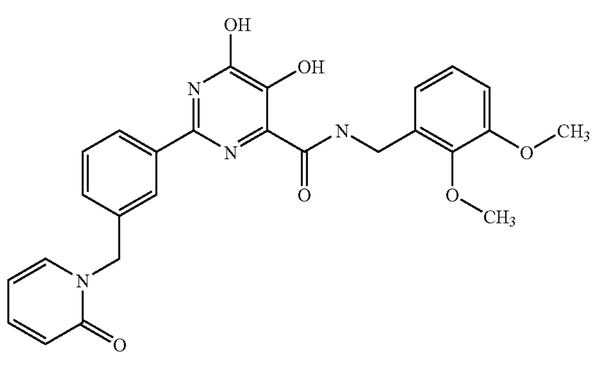 | N-(2,3-dimethoxybenzyl)-5,6-dihydroxy-2-{3-[(2-oxopyridin-1(2H)-yl)methyl]phenyl}pyrimidine-4-carboxamide | 489 | A |
| 31 | 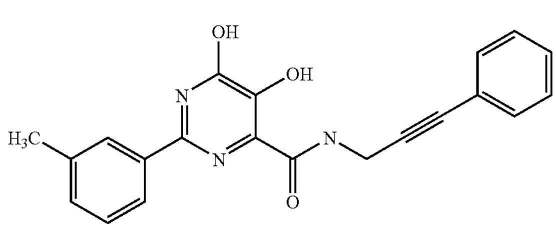 | 5,6-dihydroxy-2-(3-methylphenyl)-N-(3-phenylprop-2-ynyl)pyrimidine-4-carboxamide | 360 | A |

TABLE 6-continued

| 32 | 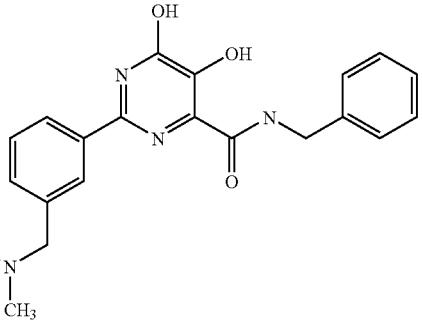 | N-benzyl-2-{3-[(dimethylamino)methyl]phenyl}-5,6-dihydroxypyrimidine-4-carboxamide (TFA salt) | 379 | B |
| 33 | 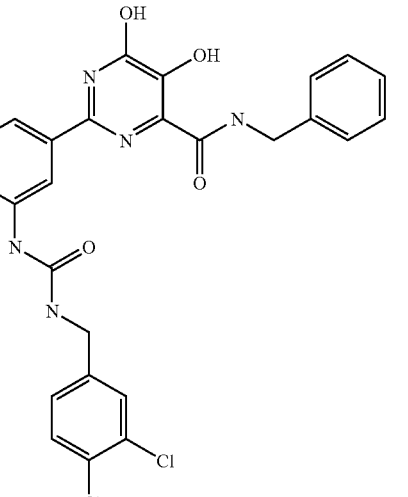 | N-benzyl-2-[3-({[(3,4-dichlorobenzyl)amino]carbonyl}amino)phenyl]-5,6-dihydroxy-pyrimidine-4-carboxamide | 539 | G |
| 34 | 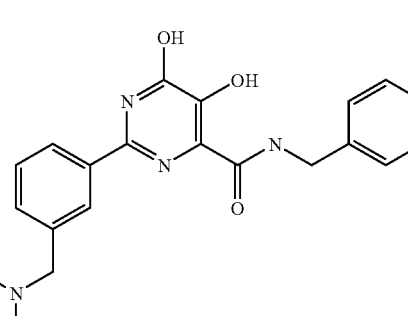 | N-benzyl-5,6-dihydroxy-2-[3-(piperidin-1-ylmethyl)phenyl]pyrimidine-4-carboxamide (TFA salt) | 419 | B |
| 35 | 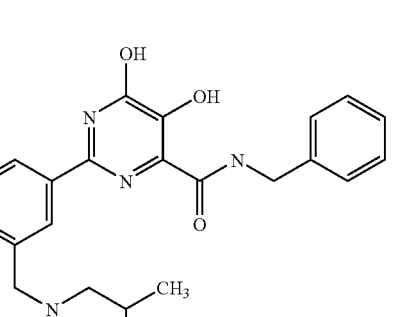 | N-benzyl-2-{3-[(3,5-dimethylpiperazin-1-yl)methyl]phenyl}-5,6-dihydroxypyrimidine-4-carboxamide (TFA salt) | 448 | B |

TABLE 6-continued

| | | | | |
|---|---|---|---|---|
| 36 | 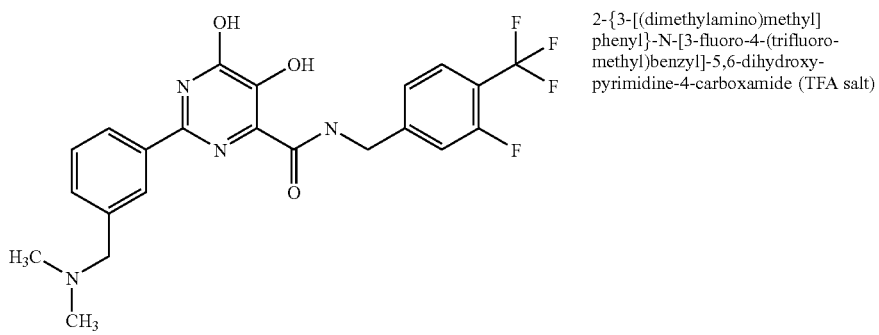 | 2-{3-[(dimethylamino)methyl]phenyl}-N-[3-fluoro-4-(trifluoromethyl)benzyl]-5,6-dihydroxy-pyrimidine-4-carboxamide (TFA salt) | 465 | B |
| 37 | 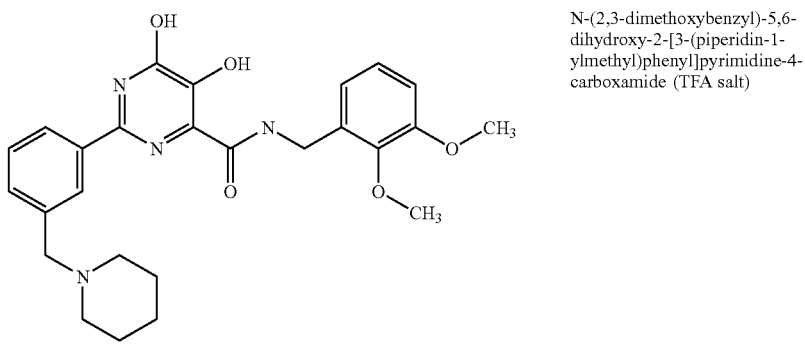 | N-(2,3-dimethoxybenzyl)-5,6-dihydroxy-2-[3-(piperidin-1-ylmethyl)phenyl]pyrimidine-4-carboxamide (TFA salt) | 479 | B |
| 38 | 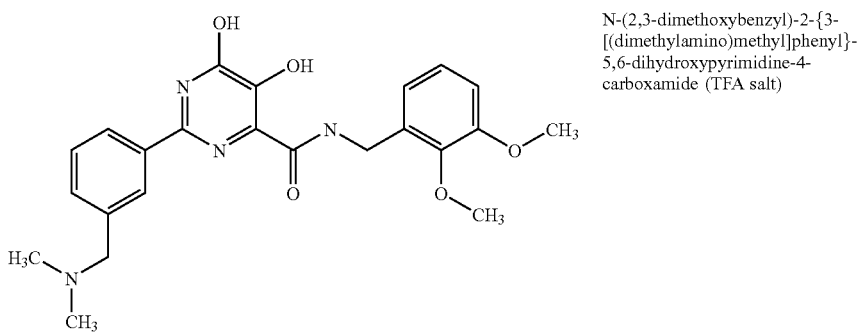 | N-(2,3-dimethoxybenzyl)-2-{3-[(dimethylamino)methyl]phenyl}-5,6-dihydroxypyrimidine-4-carboxamide (TFA salt) | 439 | B |
| 39 | 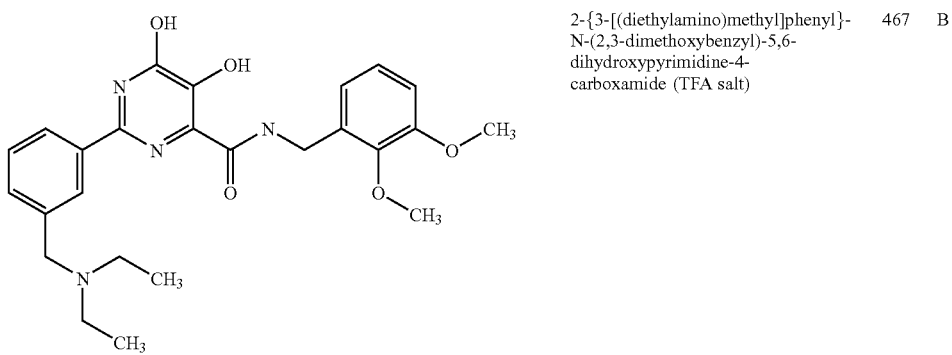 | 2-{3-[(diethylamino)methyl]phenyl}-N-(2,3-dimethoxybenzyl)-5,6-dihydroxypyrimidine-4-carboxamide (TFA salt) | 467 | B |

TABLE 6-continued

| | Structure | Name | MW | Class |
|---|---|---|---|---|
| 40 | (structure) | N-(2,3-dimethoxybenzyl)-5,6-dihydroxy-2-(3-{[(2,4,5-trichlorophenyl)thio]methyl}phenyl)pyrimidine-4-carboxamide | 607 | B |
| 41 | (structure) | 5,6-dihydroxy-2-(3-nitrophenyl)-N-prop-2-ynylpyrimidine-4-carboxamide | 315 | A |

TABLE 7

| | Structure | Name | MW | Class |
|---|---|---|---|---|
| 1 | (structure) | N-(4-fluorobenzyl)-5,6-dihydroxy-2-(4-methylphenyl)pyrimidine-4-carboxamide | 354 | A |
| 2 | (structure) | N-(2,4-difluorobenzyl)-5,6-dihydroxy-2-(4-methylphenyl)pyrimidine-4-carboxamide | 372 | A |
| 3 | (structure) | 5,6-dihydroxy-2-(4-methylphenyl)-N-[2-(trifluoromethyl)benzyl]pyrimidine-4-carboxamide | 404 | A |

TABLE 7-continued

| | | | | |
|---|---|---|---|---|
| 4 | 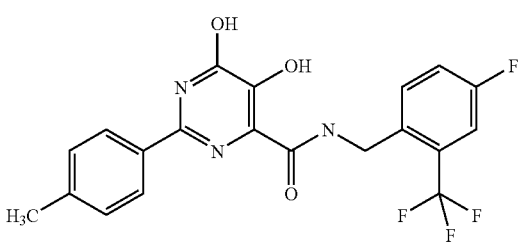 | N-[4-fluoro-2-(trifluoromethyl)-benzyl]-5,6-dihydroxy-2-(4-methylphenyl)pyrimidine-4-carboxamide | 422 | A |
| 5 | 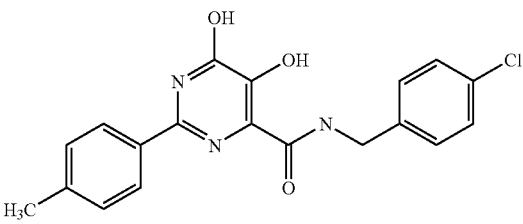 | N-(4-chlorobenzyl)-5,6-dihydroxy-2-(4-methylphenyl)pyrimidine-4-carboxamide | 370 | A |
| 6 | 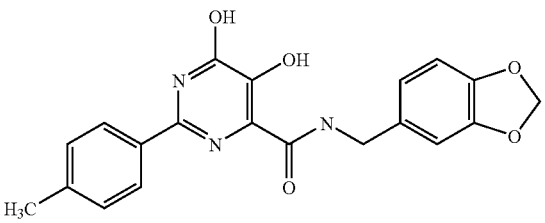 | N-(1,3-benzodioxol-5-ylmethyl)-5,6-dihydroxy-2-(4-methylphenyl)pyrimidine-4-carboxamide | 380 | A |
| 7 | 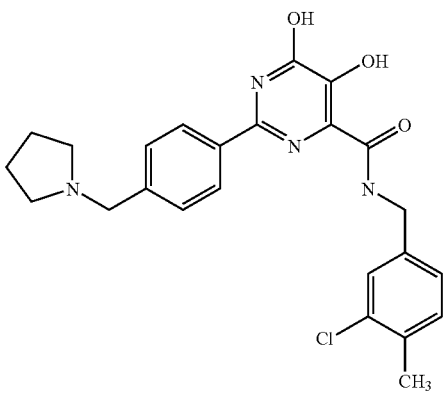 | N-(3-chloro-4-methylbenzyl)-5,6-dihydroxy-2-[4-(pyrrolidin-1-ylmethyl)phenyl]pyrimidine-4-carboxamide (TFA salt) | 453 | B |
| 8 | 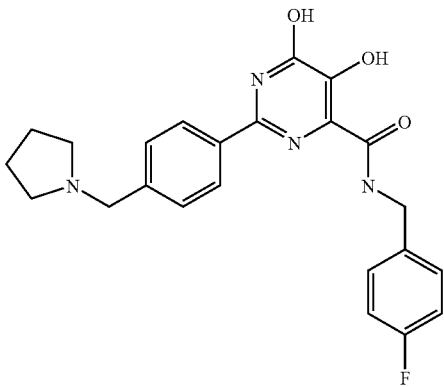 | N-(4-fluorobenzyl)-5,6-dihydroxy-2-[4-(pyrrolidin-1-ylmethyl)-phenyl]pyrimidine-4-carboxamide (TFA salt) | 423 | B |

TABLE 7-continued

| 9 | 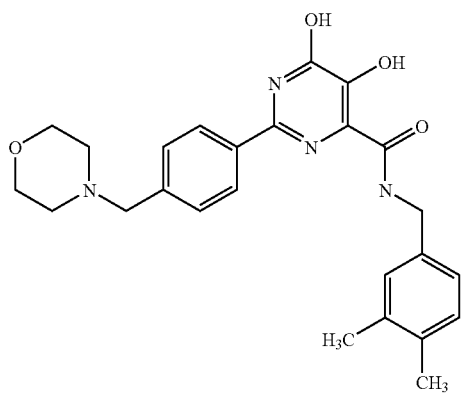 | N-(3,4-dimethylbenzyl)-5,6-dihydroxy-2-[4-(morpholin-4-ylmethyl)phenyl]pyrimidine-4-carboxamide (TFA salt) | 449 | B |
| 10 | 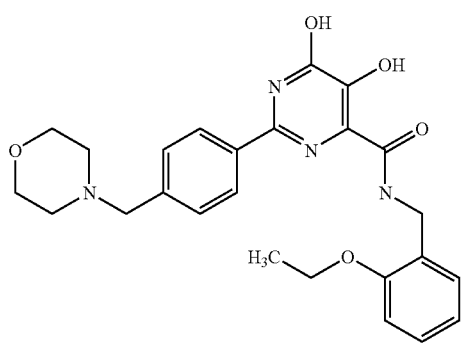 | N-(2-ethoxybenzyl)-5,6-dihydroxy-2-[4-(morpholin-4-ylmethyl)phenyl]pyrimidine-4-carboxamide (TFA salt) | 465 | B |
| 11 | 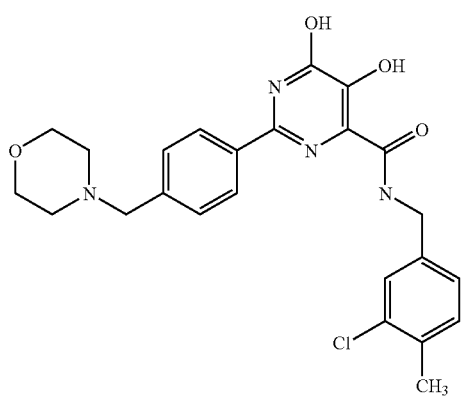 | N-(3-chloro-4-methylbenzyl)-5,6-dihydroxy-2-[4-(morpholin-4-ylmethyl)phenyl]pyrimidine-4-carboxamide (TFA salt) | 469 | B |
| 12 | 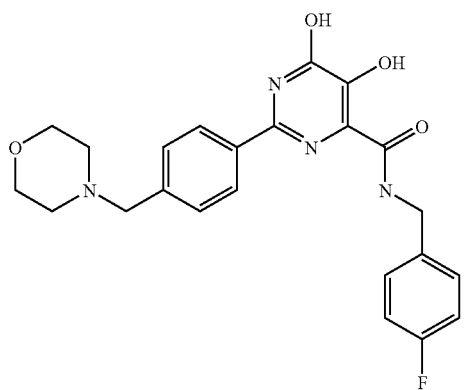 | N-(4-fluorobenzyl)-5,6-dihydroxy-2-[4-(morpholin-4-ylmethyl)phenyl]pyrimidine-4-carboxamide (TFA salt) | 439 | B |

TABLE 7-continued
| | | | | |
|---|---|---|---|---|
| 13 | 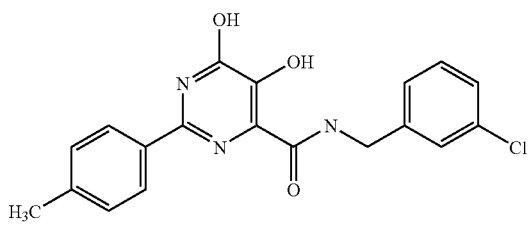 | N-(3-chlorobenzyl)-5,6-dihydroxy-2-(4-methylphenyl)pyrimidine-4-carboxamide | 370 | A |
| 14 | 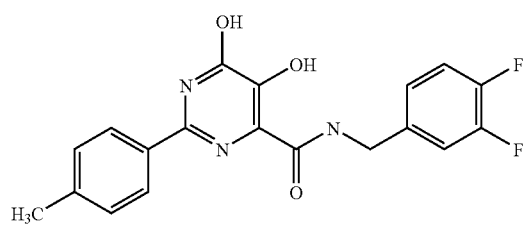 | N-(3,4-difluorobenzyl)-5,6-dihydroxy-2-(4-methylphenyl)pyrimidine-4-carboxamide | 372 | A |
| 15 | 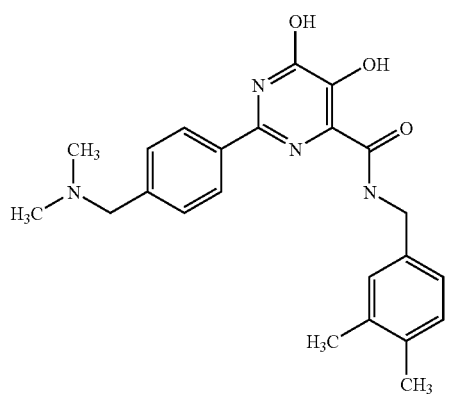 | 2-{4-[(dimethylamino)methyl]phenyl}-N-(3,4-dimethylbenzyl)-5,6-dihydroxypyrimidine-4-carboxamide (TFA salt) | 407 | B |
| 16 | 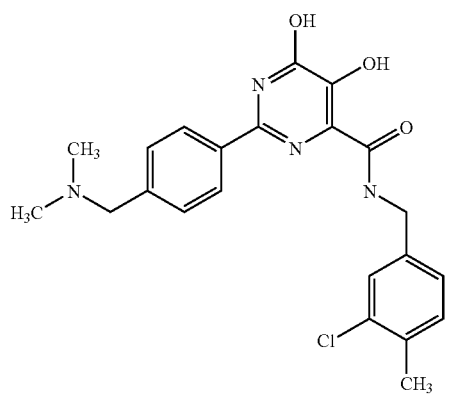 | N-(3-chloro-4-methylbenzyl)-2-{4-[(dimethylamino)methyl]phenyl}-5,6-dihydroxypyrimidine-4-carboxamide (TFA salt) | 427 | B |

TABLE 7-continued

| 17 | [structure] | N-(3-chloro-4-methylbenzyl)-2-{4-[(diethylamino)methyl]phenyl}-5,6-dihydroxypyrimidine-4-carboxamide (TFA salt) | 455 | B |
| 18 | [structure] | 2-{4-[(diethylamino)methyl]phenyl}-N-(4-fluorobenzyl)-5,6-dihydroxy-pyrimidine-4-carboxamide (TFA salt) | 425 | B |
| 19 | [structure] | N-(3-chloro-4-methylbenzyl)-5,6-dihydroxy-2-[4-(piperidin-1-ylmethyl)phenyl]pyrimidine-4-carboxamide (TFA salt) | 467 | B |
| 20 | [structure] | N-(4-fluorobenzyl)-5,6-dihydroxy-2-[4-(piperidin-1-ylmethyl)phenyl]pyrimidine-4-carboxamide (TFA salt) | 437 | B |

TABLE 7-continued

| 21 | (structure) | N-(1,1'-biphenyl-3-ylmethyl)-5,6-dihydroxy-2-(4-methylphenyl)pyrimidine-4-carboxamide | 412 | A |
| 22 | (structure) | N-(2,3-dimethoxybenzyl)-5,6-dihydroxy-2-[4-(morpholin-4-ylmethyl)phenyl]pyrimidine-4-carboxamide (TFA salt) | 481 | B |
| 23 | (structure) | N-(2-ethoxybenzyl)-5,6-dihydroxy-2-(4-methylphenyl)pyrimidine-4-carboxamide | 380 | A |
| 24 | (structure) | N-[4-fluoro-3-(trifluoromethyl)benzyl]-5,6-dihydroxy-2-(4-methylphenyl)pyrimidine-4-carboxamide | 422 | A |
| 25 | (structure) | 5,6-dihydroxy-N-(3-methoxybenzyl)-2-(4-methylphenyl)pyrimidine-4-carboxamide | 366 | A |
| 26 | (structure) | N-(2-ethoxybenzyl)-5,6-dihydroxy-2-{4-[(4-methylpiperazin-1-yl)methyl]phenyl}pyrimidine-4-carboxamide (TFA salt) | 478 | B |

TABLE 7-continued

| | | | | |
|---|---|---|---|---|
| 27 | 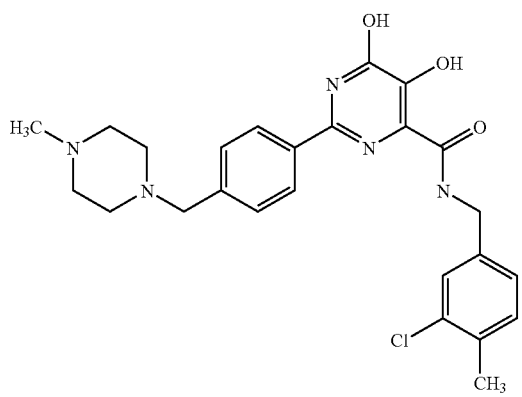 | N-(3-chloro-4-methylbenzyl)-5,6-dihydroxy-2-{4-[(4-methylpiperazin-1-yl)methyl]phenyl}pyrimidine-4-carboxamide (TFA salt) | 482 | B |
| 28 | 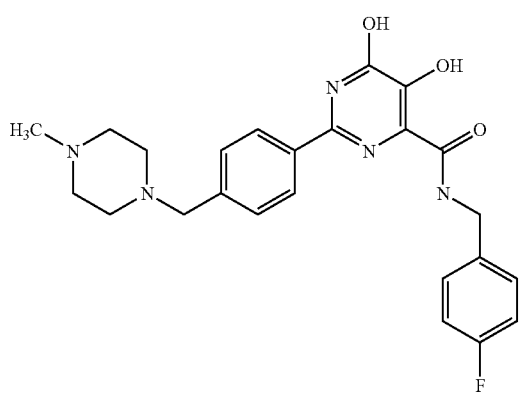 | N-(4-fluorobenzyl)-5,6-dihydroxy-2-{4-[(4-methylpiperazin-1-yl)methyl]phenyl}pyrimidine-4-carboxamide (TFA salt) | 452 | B |
| 29 | 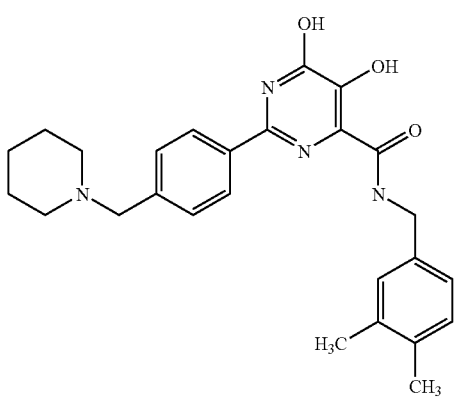 | N-(3,4-dimethylbenzyl)-5,6-dihydroxy-2-[4-(piperidin-1-ylmethyl)phenyl]pyrimidine-4-carboxamide (TFA salt) | 447 | B |
| 30 | 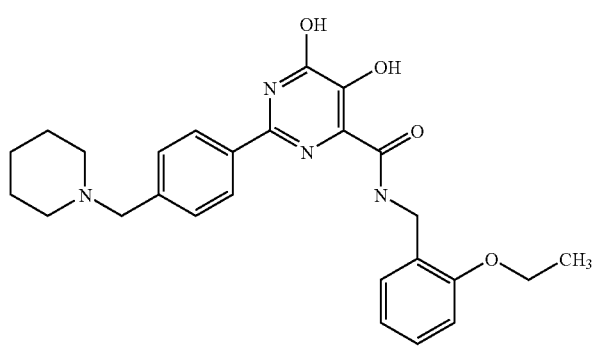 | N-(2-ethoxybenzyl)-5,6-dihydroxy-2-[4-(piperidin-1-ylmethyl)phenyl]pyrimidine-4-carboxamide (TFA salt) | 463 | B |

TABLE 7-continued

| | | | |
|---|---|---|---|
| 31 | 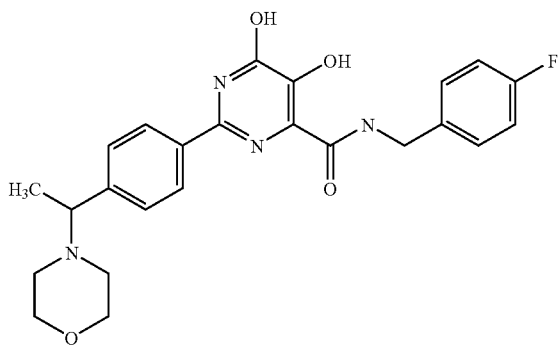 | N-(4-fluorobenzyl)-5,6-dihydroxy-2-[4-(1-morpholin-4-ylethyl)phenyl]pyrimidine-4-carboxamide (TFA salt) | 453 B |
| 32 | 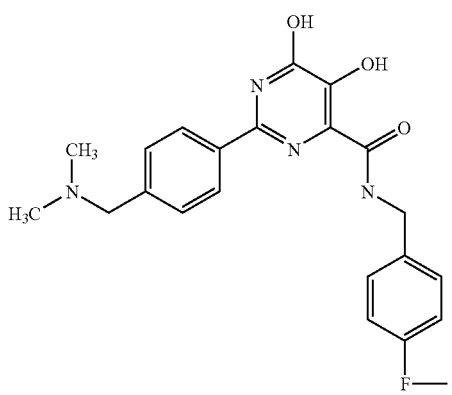 | 2-{4-[(dimethylamino)methyl]phenyl}-N-(4-fluorobenzyl)-5,6-dihydroxypyrimidine-4-carboxamide (TFA salt) | 397 B |
| 33 | 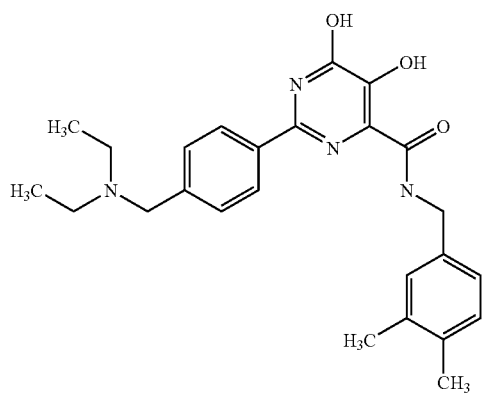 | 2-{4-[(diethylamino)methyl]phenyl}-N-(3,4-dimethylbenzyl)-5,6-dihydroxypyrimidine-4-carboxamide (TFA salt) | 435 B |
| 34 | 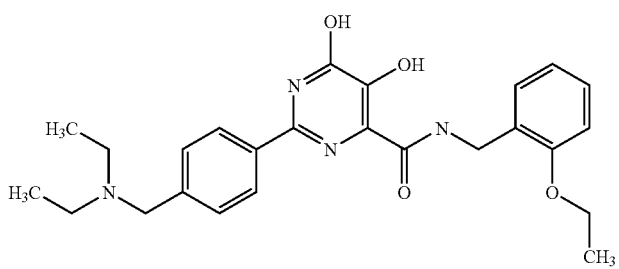 | 2-{4-[(diethylamino)methyl]phenyl}-N-(2-ethoxybenzyl)-5,6-dihydroxy-pyrimidine-4-carboxamide (TFA salt) | 451 B |

TABLE 7-continued

| | | | | |
|---|---|---|---|---|
| 35 | 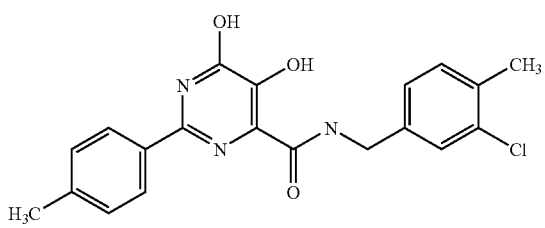 | N-(3-chloro-4-methylbenzyl)-5,6-dihydroxy-2-(4-methylphenyl)pyrimidine-4-carboxamide | 384 | A |
| 36 | 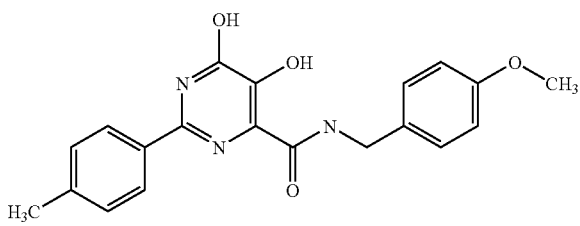 | 5,6-dihydroxy-N-(4-methoxybenzyl)-2-(4-methylphenyl)pyrimidine-4-carboxamide | 366 | A |
| 37 | 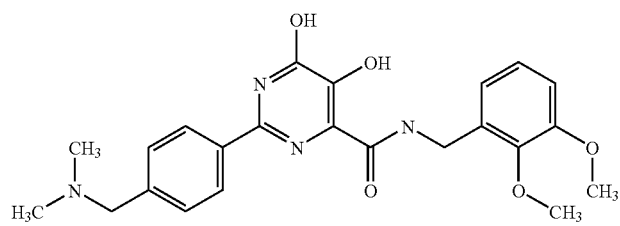 | N-(2,3-dimethoxybenzyl)-2-{4-[(dimethylamino)methyl]phenyl}-5,6-dihydroxypyrimidine-4-carboxamide (TFA salt) | 439 | B |
| 38 | 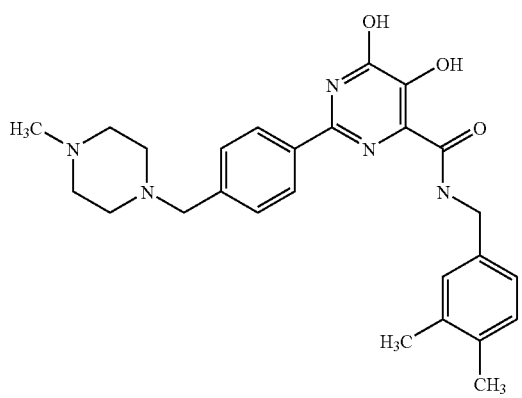 | N-(3,4-dimethylbenzyl)-5,6-dihydroxy-2-{4-[(4-methylpiperazin-1-yl)methyl]phenyl}pyrimidine-4-carboxamide (TFA salt) | 462 | B |
| 39 | 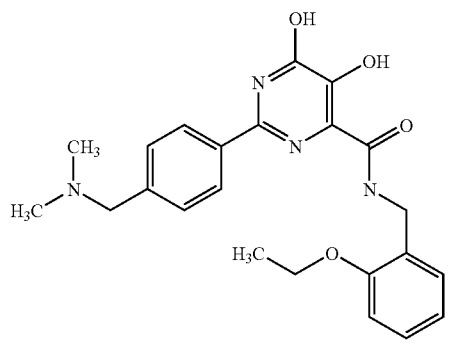 | 2-{4-[(dimethylamino)methyl]phenyl}-N-(2-ethoxybenzyl)-5,6-dihydroxypyrimidine-4-carboxamide (TFA salt) | 423 | B |

TABLE 7-continued

| | | | | |
|---|---|---|---|---|
| 40 | 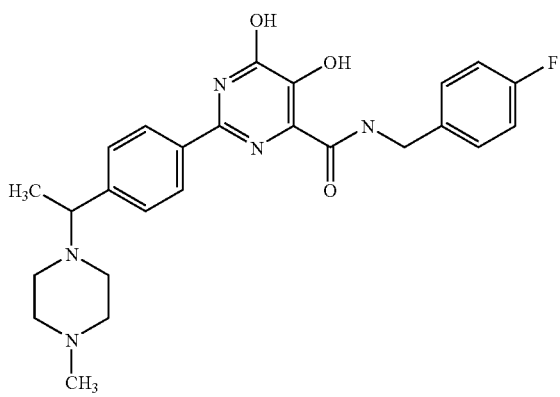 | N-(4-fluorobenzyl)-5,6-dihydroxy-2-{4-[1-(4-methylpiperazin-1-yl)ethyl]phenyl}pyrimidine-4-carboxamide (TFA salt) | 466 | B |
| 41 | 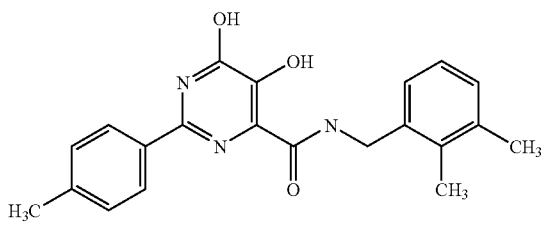 | N-(2,3-dimethylbenzyl)-5,6-dihydroxy-2-(4-methylphenyl)pyrimidine-4-carboxamide | 364 | A |
| 42 | 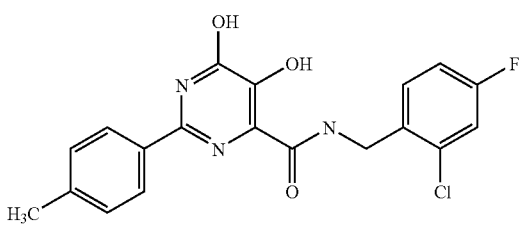 | N-(2-chloro-4-fluorobenzyl)-5,6-dihydroxy-2-(4-methylphenyl)pyrimidine-4-carboxamide | 388 | A |
| 43 | 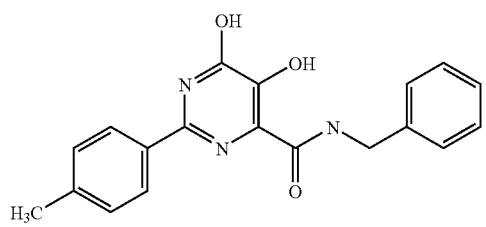 | N-benzyl-5,6-dihydroxy-2-(4-methylphenyl)pyrimidine-4-carboxamide | 336 | A |
| 44 | 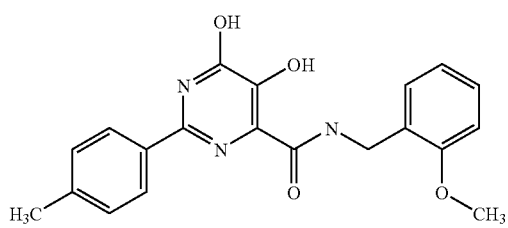 | 5,6-dihydroxy-N-(2-methoxybenzyl)-2-(4-methylphenyl)pyrimidine-4-carboxamide | 366 | A |

TABLE 7-continued

| 45 | 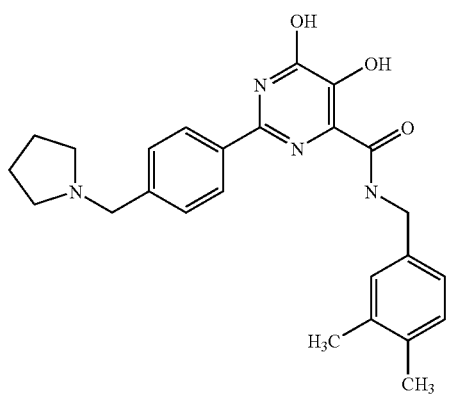 | N-(3,4-dimethylbenzyl)-5,6-dihydroxy-2-[4-(pyrrolidin-1-ylmethyl)phenyl]pyrimidine-4-carboxamide (TFA salt) | 433 | B |
| --- | --- | --- | --- | --- |
| 46 | 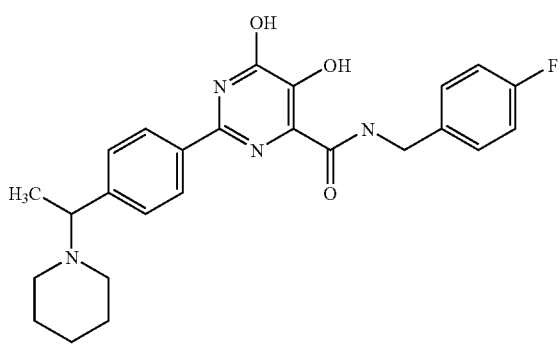 | N-(4-fluorobenzyl)-5,6-dihydroxy-2-[4-(1-piperidin-1-ylethyl)phenyl]pyrimidine-4-carboxamide (TFA salt) | 451 | B |
| 47 | 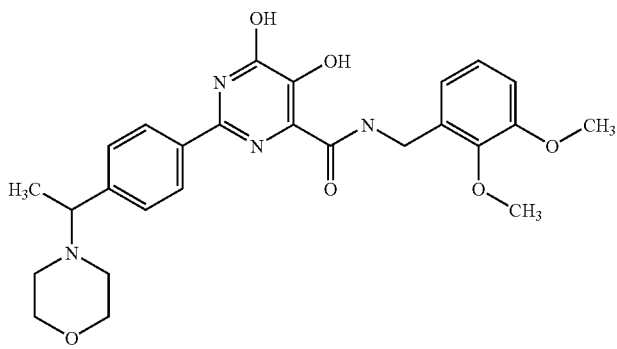 | N-(2,3-dimethoxybenzyl)-5,6-dihydroxy-2-[4-(1-morpholin-4-ylethyl)phenyl]pyrimidine-4-carboxamide (TFA salt) | 495 | B |
| 48 | 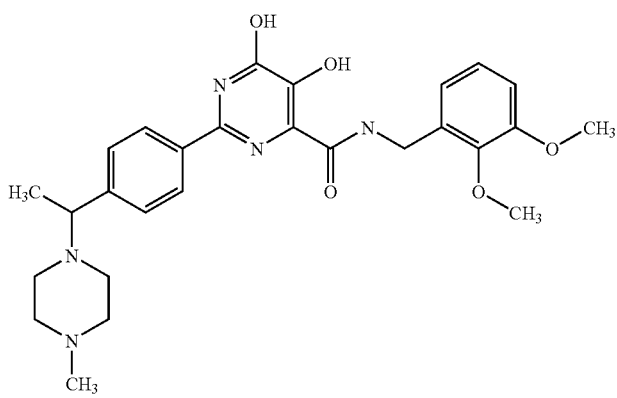 | N-(2,3-dimethoxybenzyl)-5,6-dihydroxy-2-{4-[1-(4-methyl-piperazin-1-yl)ethyl]phenyl}pyrimidine-4-carboxamide (TFA salt) | 508 | B |

TABLE 7-continued

| 49 | 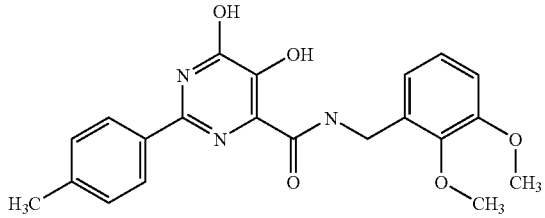 | N-(2,3-dimethoxybenzyl)-5,6-dihydroxy-2-(4-methylphenyl)pyrimidine-4-carboxamide | 396 | A |
| 50 | 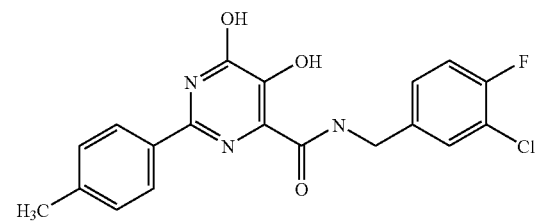 | N-(3-chloro-4-fluorobenzyl)-5,6-dihydroxy-2-(4-methylphenyl)pyrimidine-4-carboxamide | 388 | A |
| 51 | 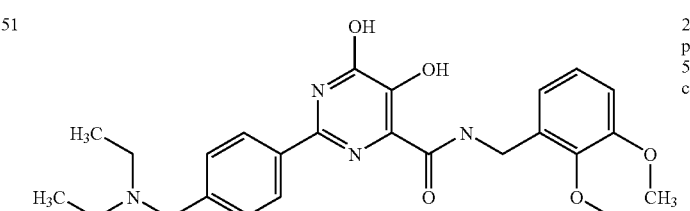 | 2-{4-[(diethylamino)methyl]phenyl}-N-(2,3-dimethoxybenzyl)-5,6-dihydroxypyrimidine-4-carboxamide (TFA salt) | 467 | B |
| 52 | 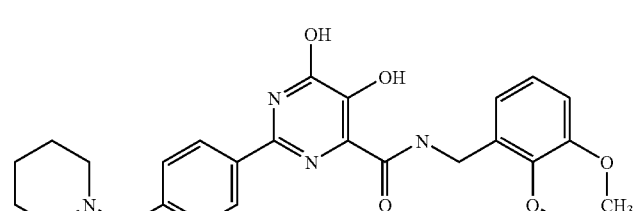 | N-(2,3-dimethoxybenzyl)-5,6-dihydroxy-2-[4-(piperidin-1-ylmethyl)phenyl]pyrimidine-4-carboxamide (TFA salt) | 479 | B |
| 53 | 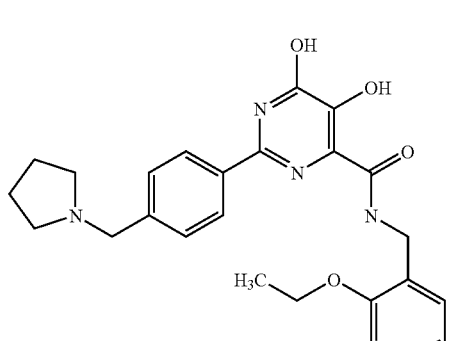 | N-(2-ethoxybenzyl)-5,6-dihydroxy-2-[4-(pyrrolidin-1-ylmethyl)phenyl]pyrimidine-4-carboxamide (TFA salt) | 449 | B |
| 54 | 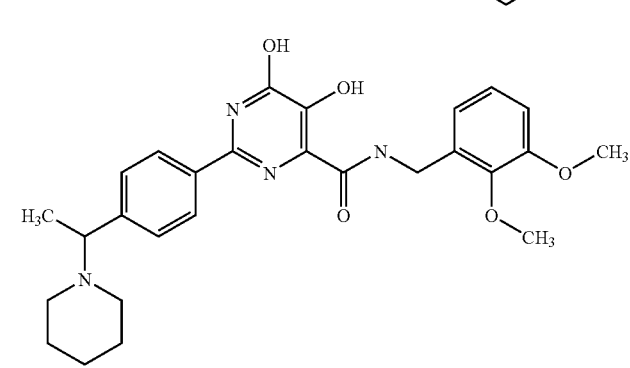 | N-(2,3-dimethoxybenzyl)-5,6-dihydroxy-2-[4-(1-piperidin-1-ylethyl)phenyl]pyrimidine-4-carboxamide (TFA salt) | 493 | B |

TABLE 7-continued

| 55 | 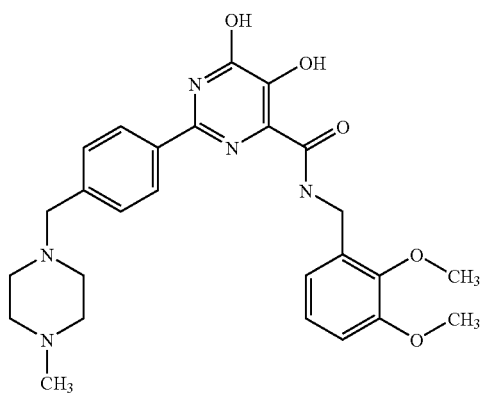 | N-(2,3-dimethoxybenzyl)-5,6-dihydroxy-2-{4-[4-methylpiperazin-1-yl)methyl]phenyl}pyrimidine-4-carboxamide (TFA salt) | 494 | B |
| --- | --- | --- | --- | --- |
| 56 | 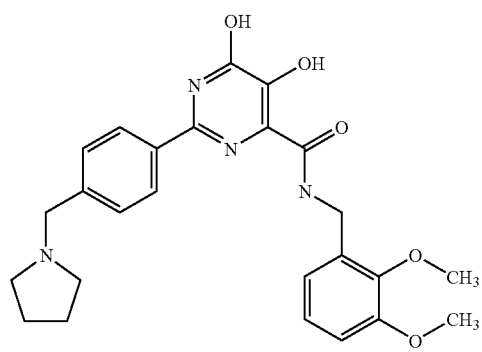 | N-(2,3-dimethoxybenzyl)-5,6-dihydroxy-2-[4-(pyrrolidin-1-ylmethyl)phenyl]pyrimidine-4-carboxamide (TFA salt) | 465 | B |

TABLE 8

| 1 | 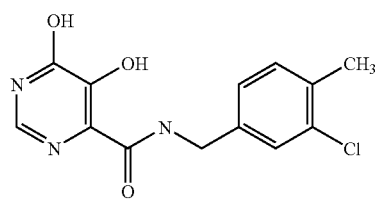 | N-(3-chloro-4-methylbenzyl)-5,6-dihydroxypyrimidine-4-carboxamide | 292 (M−) | F |
| --- | --- | --- | --- | --- |
| 2 | 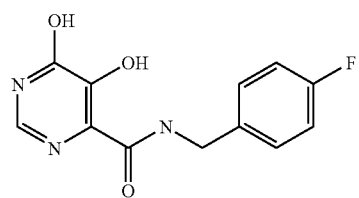 | N-(4-fluorobenzyl)-5,6-dihydroxypyrimidine-4-carboxamide | 262 (M−) | F |
| 3 | 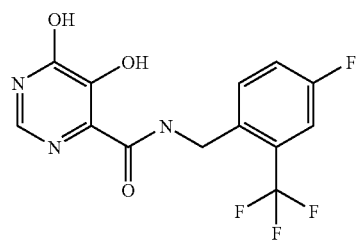 | N-[4-fluoro-2-(trifluoromethyl)-benzyl]-5,6-dihydroxypyrimidine-4-carboxamide | 332 | F |

TABLE 8-continued

| # | Structure | Name | MS | |
|---|---|---|---|---|
| 4 | 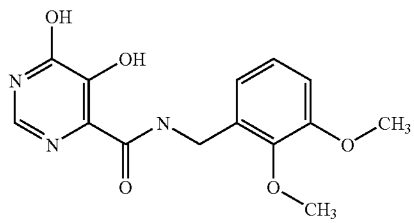 | N-(2,3-dimethoxybenzyl)-5,6-dihydroxypyrimidine-4-carboxamide | 304 (M−) | F |
| 5 | 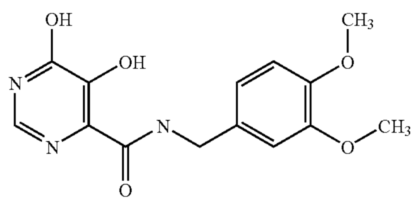 | N-(3,4-dimethoxybenzyl)-5,6-dihydroxypyrimidine-4-carboxamide | 306 | F |

TABLE 9

| # | Structure | Name | MS | |
|---|---|---|---|---|
| 1 | 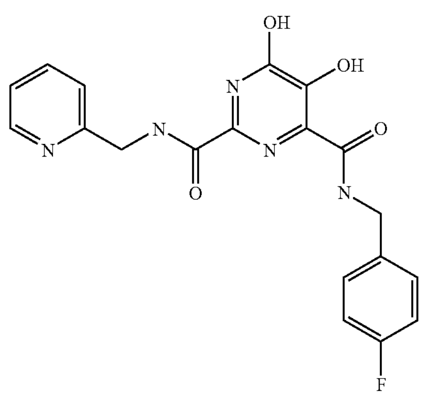 | N4-(4-fluorobenzyl)-5,6-dihydroxy-N2-(pyridin-2-ylmethyl)pyrimidine-2,4-dicarboxamide (TFA salt) | 396 (M−) | H |
| 2 | 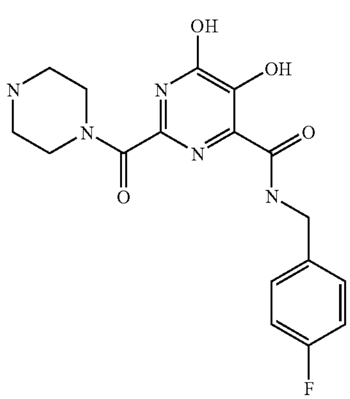 | N-(4-fluorobenzyl)-5,6-dihydroxy-2-(piperazin-1-ylcarbonyl)pyrimidine-4-carboxamide (TFA salt) | 376 | H |
| 3 | 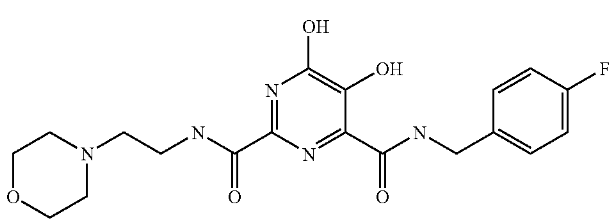 | N4-(4-fluorobenzyl)-5,6-dihydroxy-N2-(2-morpholin-4-ylethyl)pyrimidine-2,4-dicarboxamide (TFA salt) | 420 | H |

TABLE 9-continued

| | Structure | Name | MW | Activity |
|---|---|---|---|---|
| 4 | (structure) | N,N'-dibenzyl-5,6-dihydroxy-pyrimidine-2,4-dicarboxamide | 379 | H |
| 5 | (structure) | N2-(4-fluorobenzyl)-5,6-dihydroxy-N4-(2-morpholin-4-ylethyl)pyrimidine-2,4-dicarboxamide (TFA salt) | 420 | H |

TABLE 10

| | Structure | Name | MW | Activity |
|---|---|---|---|---|
| 1 | (structure) | 2-benzyl-N-(2,4-difluorobenzyl)-5,6-dihydroxypyrimidine-4-carboxamide | 372 | A |
| 2 | (structure) | 2-(benzyloxycarbonylaminomethyl)-N-(2,4-difluorobenzyl)-5,6-dihydroxy-pyrimidine-4-carboxamide | 445 | A |
| 3 | (structure) | N-[(4-{[(4-fluorobenzyl)amino]carbonyl}-5,6-dihydroxypyrimidin-2-yl)methyl]morpholine-4-carboxamide | 406 | G |
| 4 | (structure) | 2-(benzyloxycarbonylaminomethyl)-N-(4-fluorobenzyl)-5,6-dihydroxy-pyrimidine-4-carboxamide | 427 | A |

TABLE 10-continued

| | | | | |
|---|---|---|---|---|
| 5 | 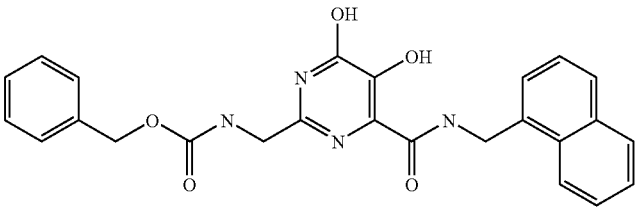 | 2-(benzyloxycarbonylaminomethyl)-N-(1-naphthylmethyl)-5,6-dihydroxy-pyrimidine-4-carboxamide | 459 | A |
| 6 | 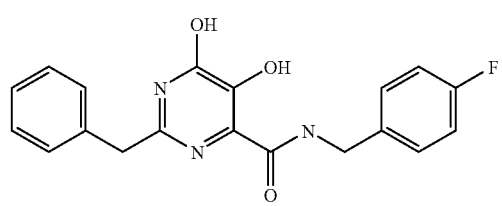 | 2-benzyl-N-(4-fluorobenzyl)-5,6-dihydroxypyrimidine-4-carboxamide | 354 | A |
| 7 | 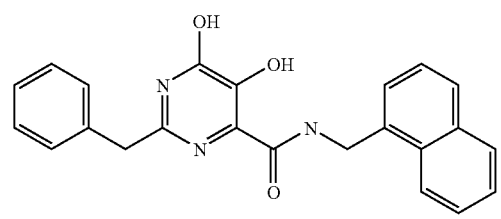 | 2-benzyl-5,6-dihydroxy-N-(1-naphthylmethyl)pyrimidine-4-carboxamide | 386 | A |
| 8 | 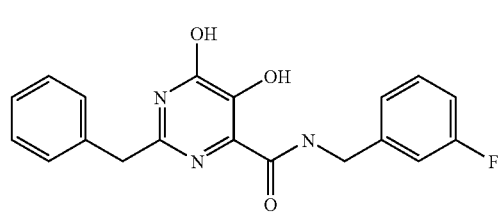 | 2-benzyl-N-(3-fluorobenzyl)-5,6-dihydroxypyrimidine-4-carboxamide | 354 | A |
| 9 | 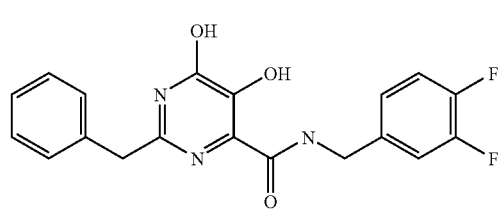 | 2-benzyl-N-(3,4-difluorobenzyl)-5,6-dihydroxypyrimidine-4-carboxamide | 372 | A |
| 10 | 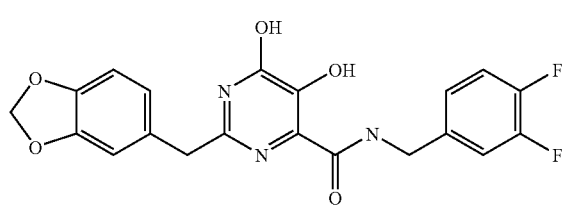 | 2-(1,3-benzodioxol-5-ylmethyl)-N-(3,4-difluorobenzyl)-5,6-dihydroxy-pyrimidine-4-carboxamide | 416 | A |
| 11 | 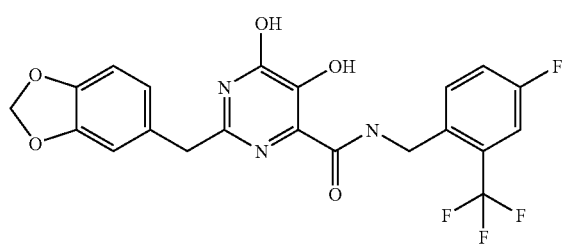 | 2-(1,3-benzodioxol-5-ylmethyl)-N-[4-fluoro-2-(trifluoromethyl)benzyl]-5,6-dihydroxypyrimidine-4-carboxamide | 466 | A |

TABLE 10-continued

| | Structure | Name | MW | Class |
|---|---|---|---|---|
| 12 | 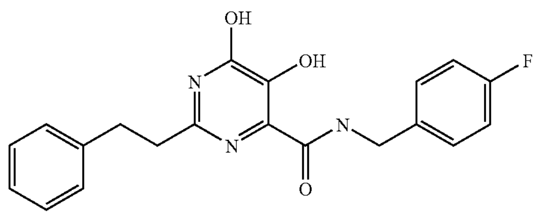 | N-(4-fluorobenzyl)-5,6-dihydroxy-2-(2-phenylethyl)pyrimidine-4-carboxamide | 368 | A |
| 13 | 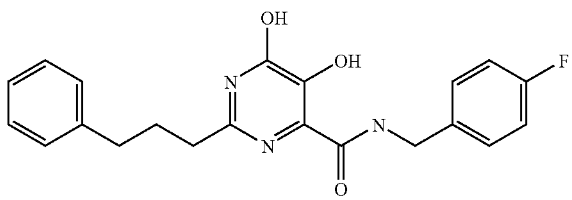 | N-(4-fluorobenzyl)-5,6-dihydroxy-2-(3-phenylpropyl)pyrimidine-4-carboxamide | 382 | A |
| 14 | 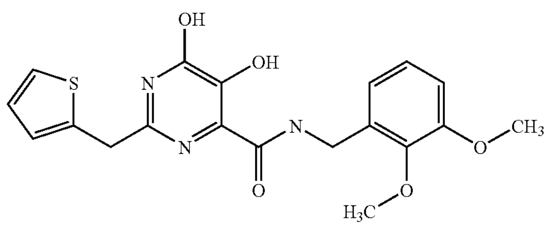 | N-(2,3-dimethoxybenzyl)-5,6-dihydroxy-2-(thien-2-ylmethyl)pyrimidine-4-carboxamide | 402 | A |
| 15 | 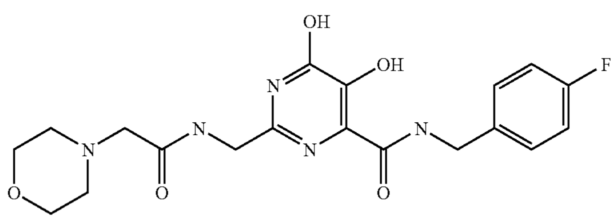 | N-(4-fluorobenzyl)-5,6-dihydroxy-2-{[(morpholin-4-ylacetyl)amino]methyl}pyrimidine-4-carboxamide (TFA salt) | 420 | I |
| 16 | 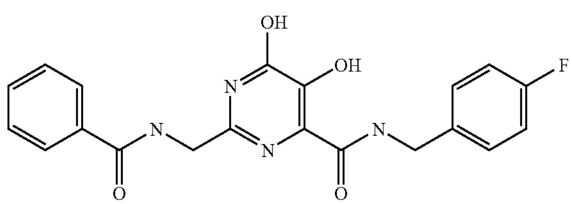 | 2-[(benzoylamino)methyl]-N-(4-fluorobenzyl)-5,6-dihydroxy-pyrimidine-4-carboxamide | 397 | I |
| 17 | 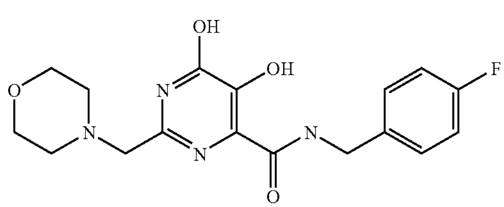 | N-(4-fluorobenzyl)-5,6-dihydroxy-2-(morpholin-4-ylmethyl)pyrimidine-4-carboxamide (TFA salt) | 363 | E |
| 18 | 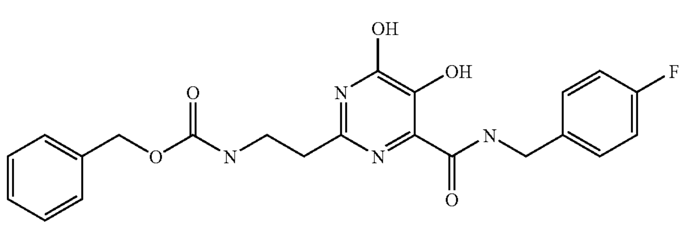 | benzyl 2-(4-{[(4-fluorobenzyl)amino]carbonyl}-5,6-dihydroxy-pyrimidin-2-yl)ethylcarbamate | 441 | A |

TABLE 10-continued

| | | | | |
|---|---|---|---|---|
| 19 | 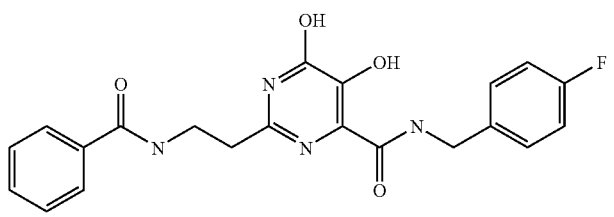 | 2-[2-(benzoylamino)ethyl]-N-(4-fluorobenzyl)-5,6-dihydroxy-pyrimidine-4-carboxamide | 411 | I |
| 20 | 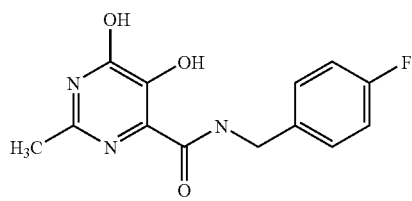 | N-(4-fluorobenzyl)-5,6-dihydroxy-2-methylpyrimidine-4-carboxamide | 278 | A |
| 21 | 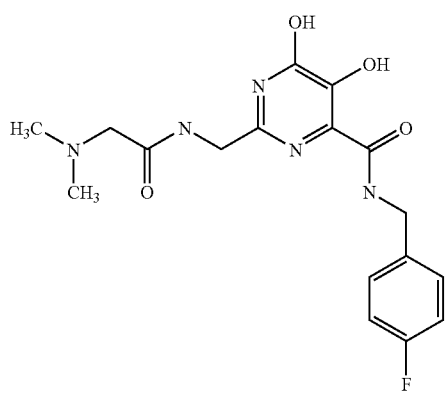 | 2-{[(N,N-dimethylglycyl)amino]methyl}-N-(4-fluorobenzyl)-5,6-dihydroxypyrimidine-4-carboxamide (TFA salt) | 378 | I |
| 22 | 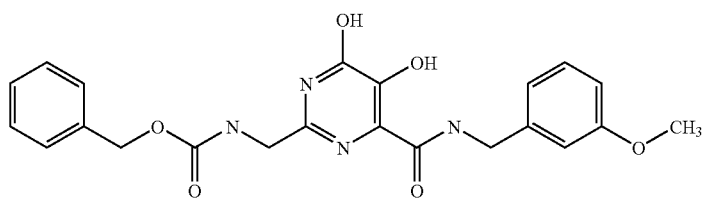 | 2-(benzyloxycarbonylamino-methyl)-N-(3-methoxybenzyl)-5,6-dihydroxypyrimidine-4-carboxamide | 439 | A |
| 23 | 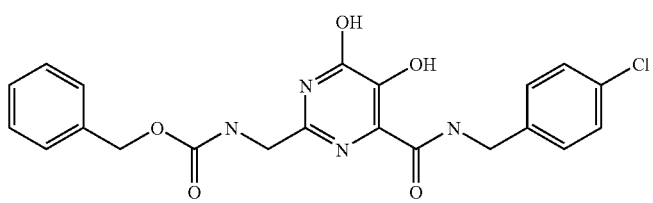 | 2-(benzyloxycarbonylamino-methyl)-N-(4-chlorobenzyl)-5,6-dihydroxypyrimidine-4-carboxamide | 443 | A |
| 24 | 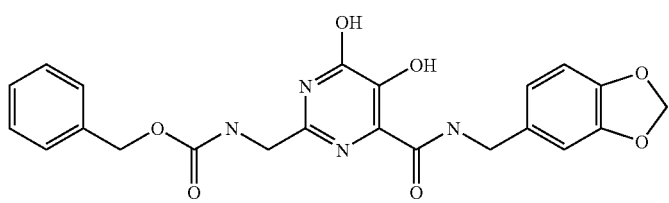 | 2-(benzyloxycarbonylamino-methyl)-N-(1,3-benzodioxol-5-yl-methyl)-5,6-dihydroxypyrimidine-4-carboxamide | 453 | A |

TABLE 10-continued

| # | Structure | Name | MW | Act |
|---|---|---|---|---|
| 25 | 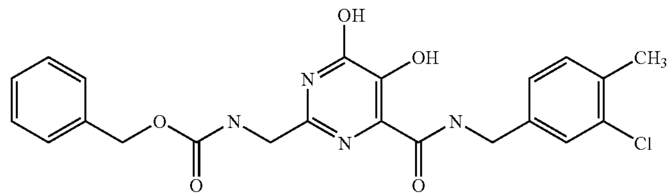 | 2-(benzyloxycarbonylaminomethyl)-N-(3-chloro-4-methylbenzyl)-5,6-dihydroxypyrimidine-4-carboxamide | 457 | A |
| 26 | 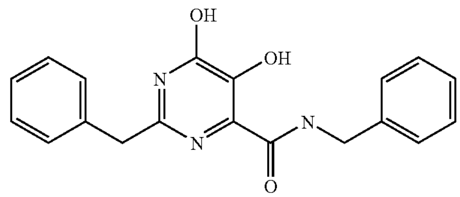 | N,2-dibenzyl-5,6-dihydroxy-pyrimidine-4-carboxamide | 336 | A |
| 27 | 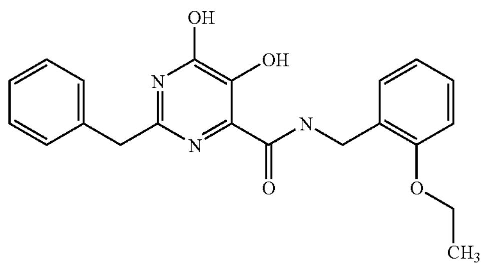 | 2-benzyl-N-(2-ethoxybenzyl)-5,6-dihydroxypyrimidine-4-carboxamide | 380 | A |
| 28 | 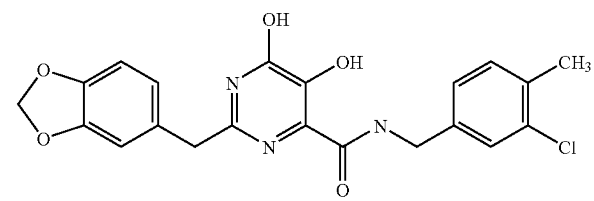 | 2-(1,3-benzodioxol-5-ylmethyl)-N-(3-chloro-4-methylbenzyl)-5,6-dihydroxypyrimidine-4-carboxamide | 428 | A |
| 29 | 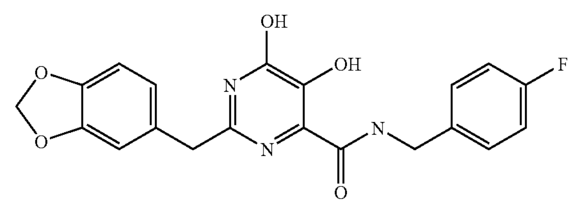 | 2-(1,3-benzodioxol-5-ylmethyl)-N-(4-fluorobenzyl)-5,6-dihydroxypyrimidine-4-carboxamide | 398 | A |
| 30 | 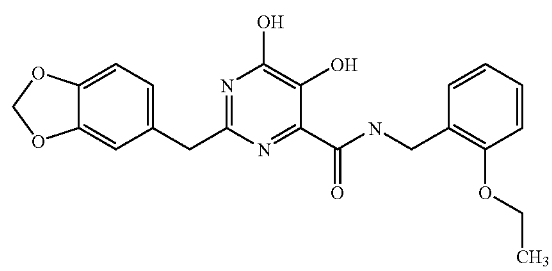 | 2-(1,3-benzodioxol-5-ylmethyl)-N-(2-ethoxybenzyl)-5,6-dihydroxypyrimidine-4-carboxamide | 424 | A |
| 31 | 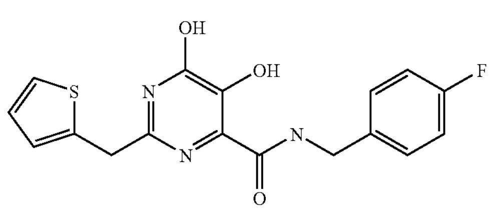 | N-(4-fluorobenzyl)-5,6-dihydroxy-2-(thien-2-ylmethyl)pyrimidine-4-carboxamide | 360 | A |

TABLE 10-continued
| 32 | 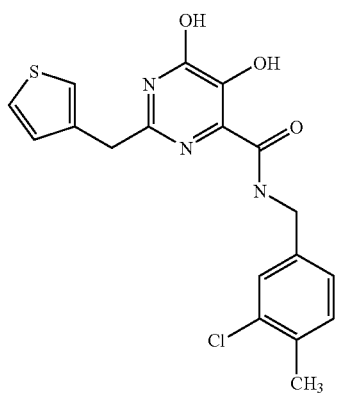 | N-(3-chloro-4-methylbenzyl)-5,6-dihydroxy-2-(thien-3-ylmethyl)pyrimidine-4-carboxamide | 390 | A |
| 33 | 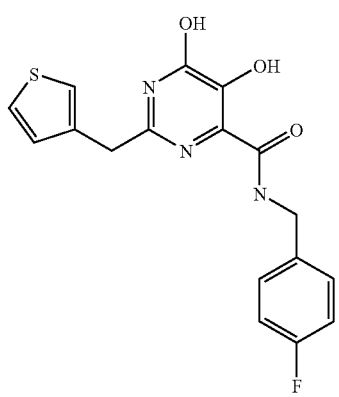 | N-(4-fluorobenzyl)-5,6-dihydroxy-2-(thien-3-ylmethyl)pyrimidine-4-carboxamide | 360 | A |
| 34 | 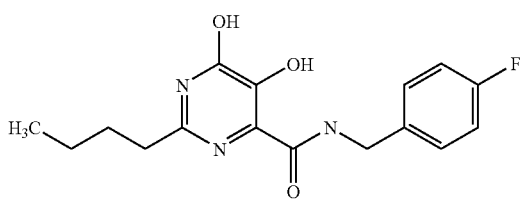 | 2-butyl-N-(4-fluorobenzyl)-5,6-dihydroxypyrimidine-4-carboxamide | 320 | A |
| 35 | 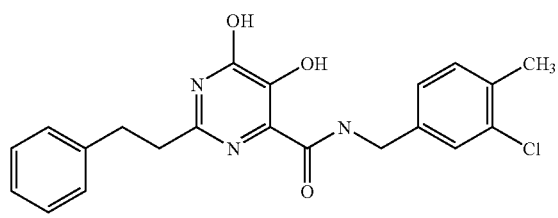 | N-(3-chloro-4-methylbenzyl)-5,6-dihydroxy-2-(2-phenylethyl)pyrimidine-4-carboxamide | 398 | A |
| 36 | 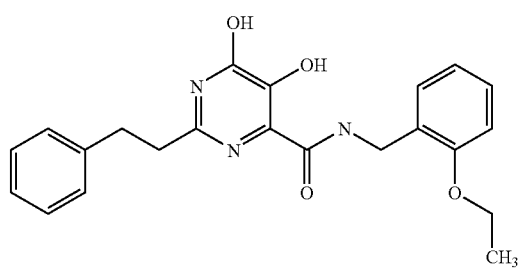 | N-(2-ethoxybenzyl)-5,6-dihydroxy-2-(2-phenylethyl)pyrimidine-4-carboxamide | 394 | A |

TABLE 10-continued

| | | | | |
|---|---|---|---|---|
| 37 | 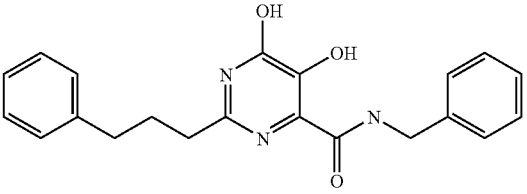 | N-benzyl-5,6-dihydroxy-2-(3-phenylpropyl)pyrimidine-4-carboxamide | 364 | A |
| 38 | 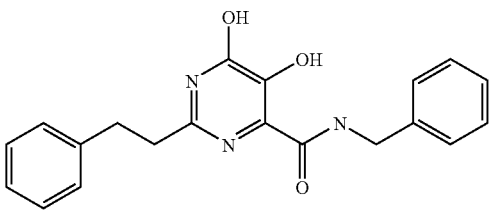 | N-benzyl-5,6-dihydroxy-2-(2-phenylethyl)pyrimidine-4-carboxamide | 350 | A |
| 39 | 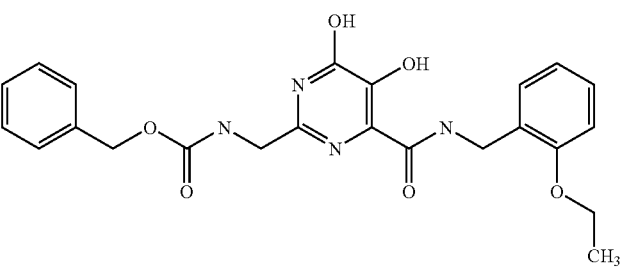 | 2-(benzyloxycarbonylaminomethyl)-N-(2-ethoxybenzyl)-5,6-dihydroxy-pyrimidine-4-carboxamide | 453 | A |
| 40 | 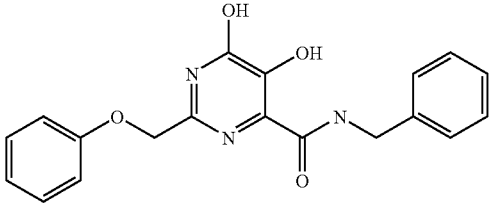 | N-benzyl-5,6-dihydroxy-2-(phenoxymethyl)pyrimidine-4-carboxamide | 352 | A |
| 41 | 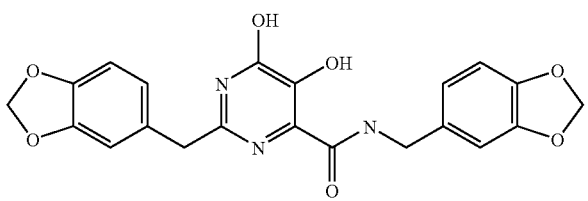 | N,2-bis(1,3-benzodioxol-5-ylmethyl)-5,6-dihydroxypyrimidine-4-carboxamide | 424 | A |
| 42 | 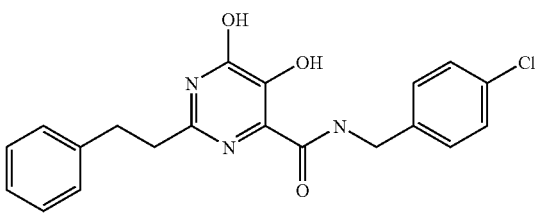 | N-(4-chlorobenzyl)-5,6-dihydroxy-2-(2-phenylethyl)pyrimidine-4-carboxamide | 384 | A |
| 43 | 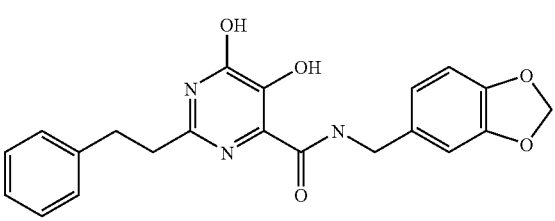 | N-(1,3-benzodioxol-5-ylmethyl)-5,6-dihydroxy-2-(2-phenylethyl)pyrimidine-4-carboxamide | 394 | A |

TABLE 10-continued

| | Structure | Name | MW | Class |
|---|---|---|---|---|
| 44 | 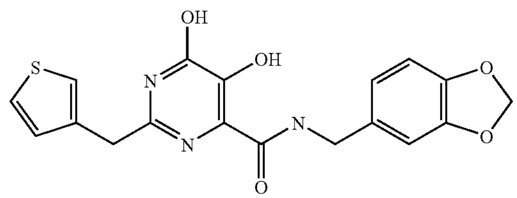 | N-(1,3-benzodioxol-5-ylmethyl)-5,6-dihydroxy-2-(thien-3-yl-methyl)pyrimidine-4-carboxamide | 386 | A |
| 45 | 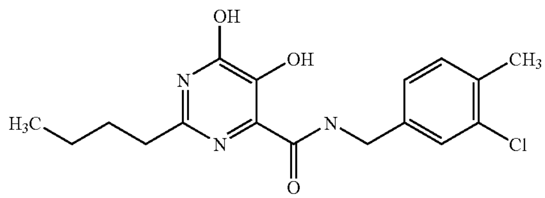 | 2-butyl-N-(3-chloro-4-methyl-benzyl)-5,6-dihydroxypyrimidine-4-carboxamide | 350 | A |
| 46 | 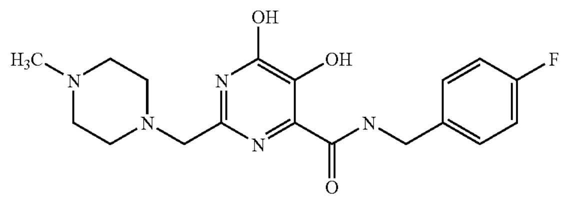 | N-(4-fluorobenzyl)-5,6-dihydroxy-2-[(4-methylpiperazin-1-yl)methyl]pyrimidine-4-carboxamide (TFA salt) | 376 | E |
| 47 | 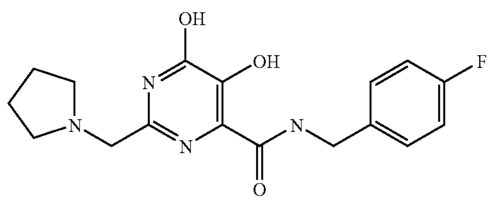 | N-(4-fluorobenzyl)-5,6-dihydroxy-2-(pyrrolidin-1-ylmethyl)pyrimidine-4-carboxamide (TFA salt) | 347 | E |
| 48 | 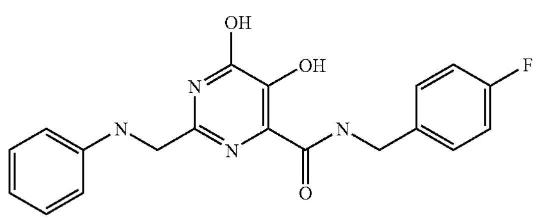 | 2-(anilinomethyl)-N-(4-fluoro-benzyl)-5,6-dihydroxypyrimidine-4-carboxamide (TFA salt) | 369 | E |
| 49 | 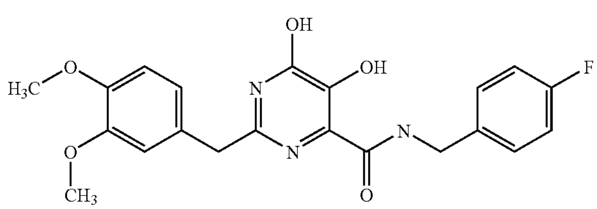 | 2-(3,4-dimethoxybenzyl)-N-(4-fluorobenzyl)-5,6-dihydroxy-pyrimidine-4-carboxamide | 414 | A |
| 50 | 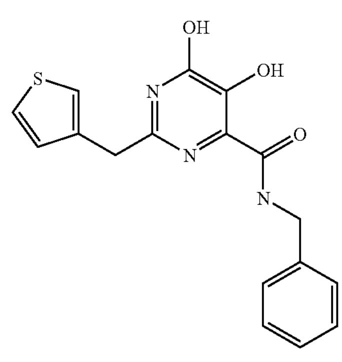 | N-benzyl-5,6-dihydroxy-2-(thien-3-ylmethyl)pyrimidine-4-carboxamide | 342 | A |

TABLE 10-continued

| 51 | 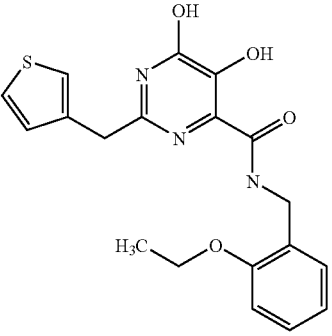 | N-(2-ethoxybenzyl)-5,6-dihydroxy-2-(thien-3-ylmethyl)pyrimidine-4-carboxamide | 386 | A |
| 52 | 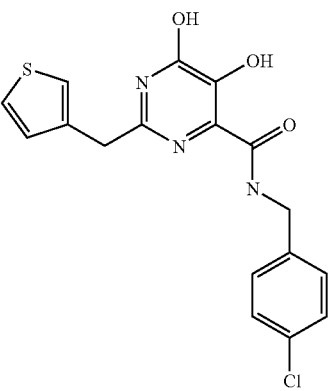 | N-(4-chlorobenzyl)-5,6-dihydroxy-2-(thien-3-ylmethyl)pyrimidine-4-carboxamide | 376 | A |
| 53 | 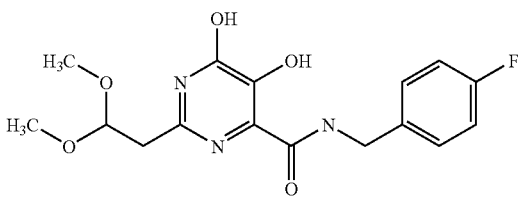 | 2-(2,2-dimethoxyethyl)-N-(4-fluorobenzyl)-5,6-dihydroxy-pyrimidine-4-carboxamide | 352 | A |
| 54 | 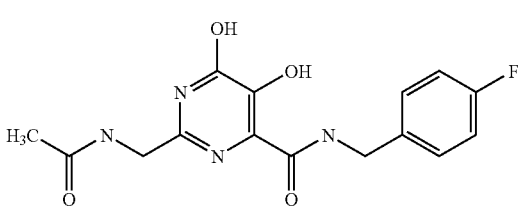 | 2-((acetylamino)methyl]-N-(4-fluorobenzyl)-5,6-dihydroxy-pyrimidine-4-carboxamide | 335 | I |
| 55 | 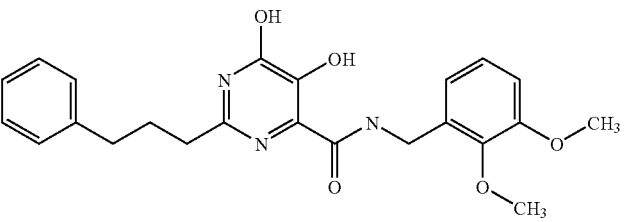 | N-(2,3-dimethoxybenzyl)-5,6-dihydroxy-2-(3-phenylpropyl)pyrimidine-4-carboxamide | 424 | A |
| 56 | 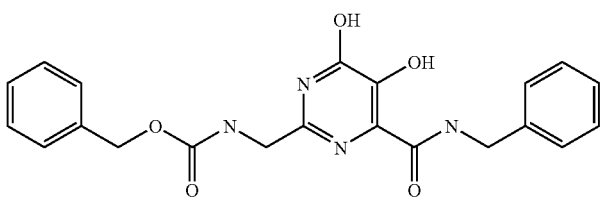 | 2-(benzyloxycarbonylaminomethyl)-N-benzyl-5,6-dihydroxypyrimidine-4-carboxamide | 409 | A |

TABLE 10-continued

| | | | | |
|---|---|---|---|---|
| 57 | | 2-(benzyloxycarbonylaminomethyl)-N-(2-methoxybenzyl)-5,6-dihydroxypyrimidine-4-carboxamide | 439 | A |
| 58 | | 2-(benzyloxycarbonylaminomethyl)-N-(2-trifluoromethylbenzyl)-5,6-dihydroxypyrimidine-4-carboxamide | 477 | A |
| 59 | | 2-benzyl-N-(2,3-dimethoxybenzyl)-5,6-dihydroxypyrimidine-4-carboxamide | 396 | A |
| 60 | | N-(1,3-benzodioxol-5-ylmethyl)-2-benzyl-5,6-dihydroxypyrimidine-4-carboxamide | 380 | A |
| 61 | | N-benzyl-2-(3,4-dimethoxybenzyl)-5,6-dihydroxypyrimidine-4-carboxamide | 396 | A |
| 62 | | N-(3-chloro-4-methylbenzyl)-2-(3,4-dimethoxybenzyl)-5,6-dihydroxy-pyrimidine-4-carboxamide | 444 | A |
| 63 | | 2-(3,4-dimethoxybenzyl)-N-(2-ethoxybenzyl)-5,6-dihydroxy-pyrimidine-4-carboxamide | 440 | A |

TABLE 10-continued

| | Structure | Name | MW | Class |
|---|---|---|---|---|
| 64 | 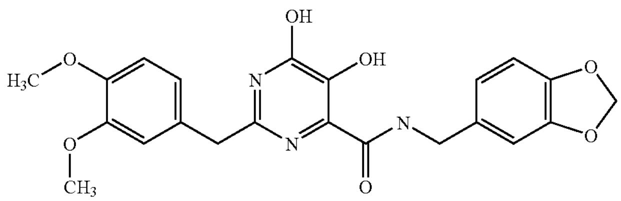 | N-(1,3-benzodioxol-5-ylmethyl)-2-(3,4-dimethoxybenzyl)-5,6-dihydroxypyrimidine-4-carboxamide | 440 | A |
| 65 | 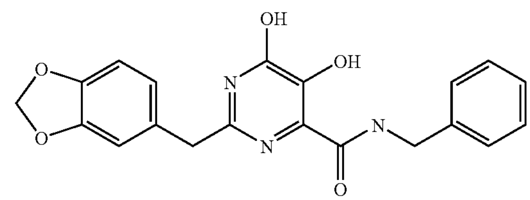 | 2-(1,3-benzodioxol-5-ylmethyl)-N-benzyl-5,6-dihydroxypyrimidine-4-carboxamide | 380 | A |
| 66 | 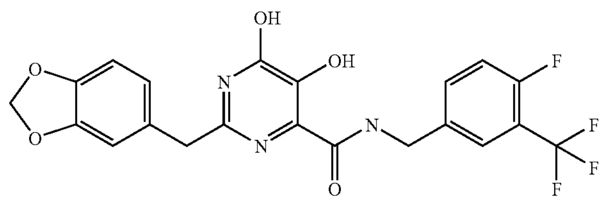 | 2-(1,3-benzodioxol-5-ylmethyl)-N-[4-fluoro-3-(trifluoromethyl)benzyl]-5,6-dihydroxypyrimidine-4-carboxamide | 466 | A |
| 67 | 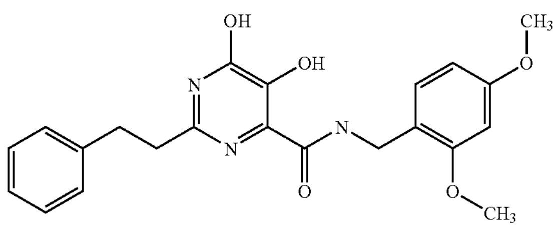 | N-(2,4-dimethoxybenzyl)-5,6-dihydroxy-2-(2-phenylethyl)-pyrimidine-4-carboxamide | 410 | A |
| 68 | 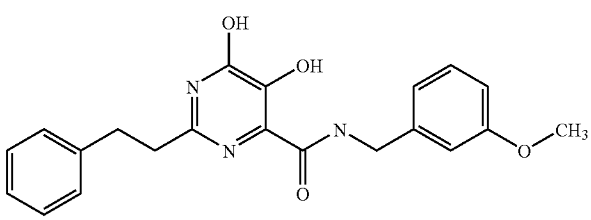 | 5,6-dihydroxy-N-(3-methoxybenzyl)-2-(2-phenylethyl)pyrimidine-4-carboxamide | 380 | A |
| 69 | 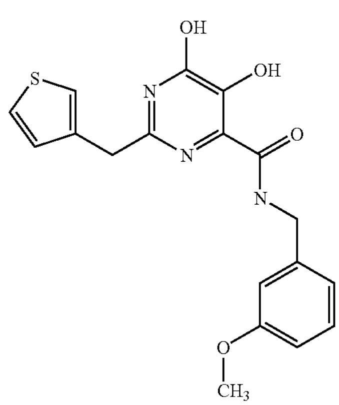 | 5,6-dihydroxy-N-(3-methoxybenzyl)-2-(thien-3-ylmethyl)pyrimidine-4-carboxamide | 372 | A |

TABLE 10-continued

| # | Structure | Name | MW | Class |
|---|---|---|---|---|
| 70 | 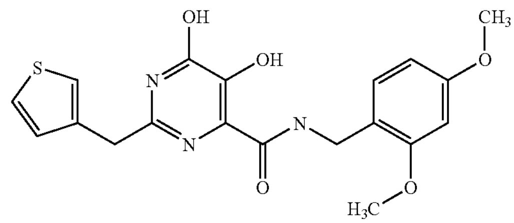 | N-(2,4-dimethoxybenzyl)-5,6-dihydroxy-2-(thien-3-ylmethyl)pyrimidine-4-carboxamide | 402 | A |
| 71 | 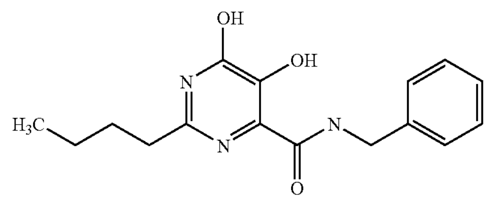 | N-benzyl-2-butyl-5,6-dihydroxypyrimidine-4-carboxamide | 302 | A |
| 72 | 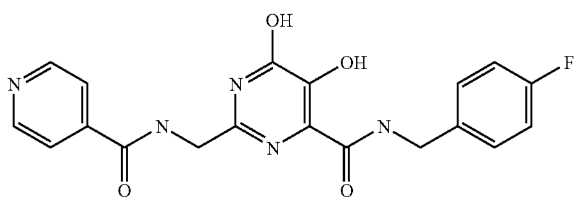 | N-(4-fluorobenzyl)-5,6-dihydroxy-2-[(isonicotinoylamino)methyl]pyrimidine-4-carboxamide (TFA salt) | 398 | I |
| 73 | 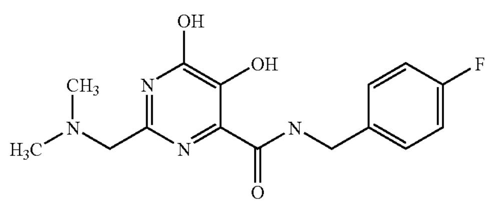 | 2-[(dimethylamino)methyl]-N-(4-fluorobenzyl)-5,6-dihydroxy-pyrimidine-4-carboxamide (TFA salt) | 321 | C |
| 74 | 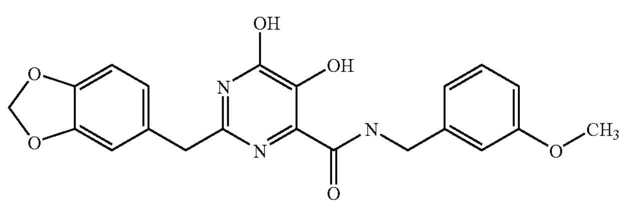 | 2-(1,3-benzodioxol-5-ylmethyl)-5,6-dihydroxy-N-(3-methoxybenzyl)pyrimidine-4-carboxmide | 410 | A |
| 75 | 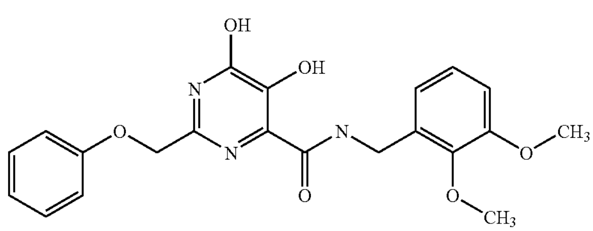 | N-(2,3-dimethoxybenzyl)-5,6-dihydroxy-2-(phenoxymethyl)-pyrimidine-4-carboxamide | 412 | A |
| 76 | 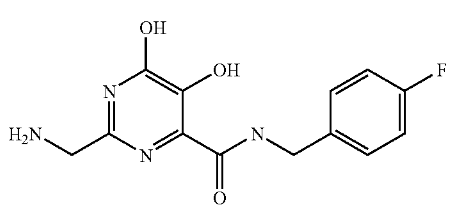 | 2-(aminomethyl)-N-(4-fluorobenzyl)-5,6-dihydroxypyrimidine-4-carboxamide (HCl salt) | 293 | A* |

TABLE 10-continued

| | | | | |
|---|---|---|---|---|
| 77 | [structure] | 2-(benzyloxycarbonylaminomethyl)-N-(2,3-dimethoxybenzyl)-5,6-dihydroxypyrimidine-4-carboxamide | 469 | A |
| 78 | [structure] | 2-(1,3-benzodioxol-5-ylmethyl)-N-(2,3-dimethoxybenzyl)-5,6-dihydroxypyrimidine-4-carboxamide | 440 | A |
| 79 | [structure] | N-(2,3-dimethoxybenzyl)-5,6-dihydroxy-2-(2-phenylethyl)pyrimidine-4-carboxamide | 410 | A |
| 80 | [structure] | N-(2,3-dimethoxybenzyl)-5,6-dihydroxy-2-(thien-3-ylmethyl)pyrimidine-4-carboxamide | 402 | A |
| 81 | [structure] | 2-(aminomethyl)-N-benzyl-5,6-dihydroxypyrimidine-4-carboxamide (TFA salt) | 275 | M |
| 82 | [structure] | 2-butyl-N-(2,3-dimethoxybenzyl)-5,6-dihydroxypyrimidine-4-carboxamide | 362 | A |

TABLE 10-continued

| | | | | |
|---|---|---|---|---|
| 83 | 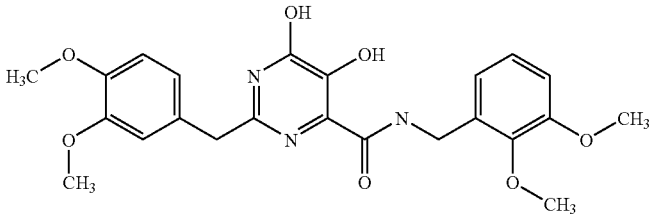 | N-(2,3-dimethoxybenzyl)-2-(3,4-dimethoxybenzyl)-5,6-dihydroxy-pyrimidine-4-carboxamide | 456 | A |
| 84 | 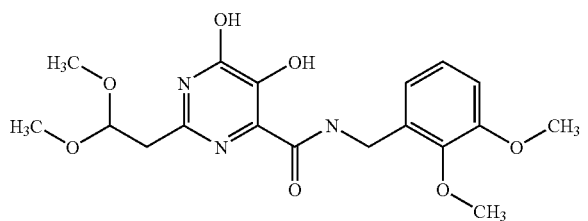 | N-(2,3-dimethoxybenzyl)-2-(2,2-dimethoxyethyl)-5,6-dihydroxy-pyrimidine-4-carboxamide | 394 | A |
| 85 | 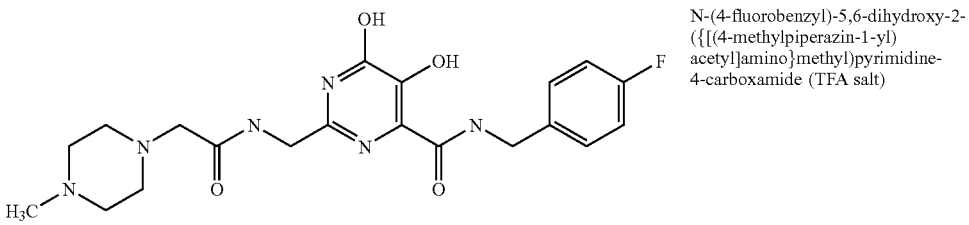 | N-(4-fluorobenzyl)-5,6-dihydroxy-2-({[(4-methylpiperazin-1-yl)acetyl]amino}methyl)pyrimidine-4-carboxamide (TFA salt) | 433 | I |
| 86 | 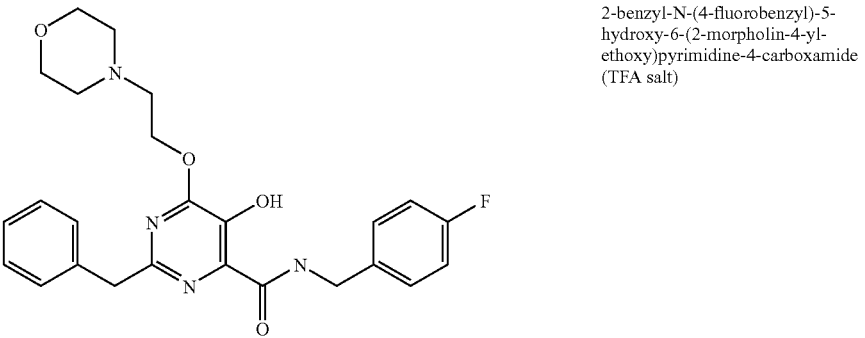 | 2-benzyl-N-(4-fluorobenzyl)-5-hydroxy-6-(2-morpholin-4-yl-ethoxy)pyrimidine-4-carboxamide (TFA salt) | 467 | J |
| 87 | 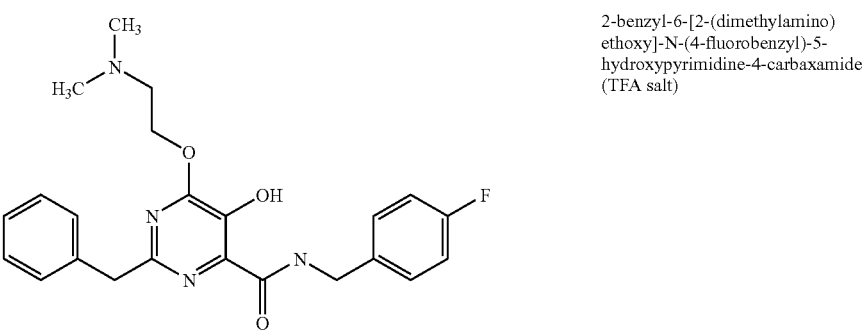 | 2-benzyl-6-[2-(dimethylamino)ethoxy]-N-(4-fluorobenzyl)-5-hydroxypyrimidine-4-carbaxamide (TFA salt) | 425 | J |

TABLE 11

| | | | | |
|---|---|---|---|---|
| 1 | | N-(4-fluorobenzyl)-5,6-dihydroxy-2-(4-methylmorpholin-2-yl)pyrimidine-4-carboxamide (TFA salt) | 363 | C |
| 2 | | 2-[4-(N,N-dimethylglycyl)morpholin-2-yl]-N-(4-fluorobenzyl)-5,6-dihydroxypyrimidine-4-carboxamide (TFA salt) | 434 | I |
| 3 | | 2-(diethoxymethyl)-N-(4-fluorobenzyl)-5,6-dihydroxypyrimidine-4-carboxamide | 366 | A |
| 4 | | N-benzyl-5,6-dihydroxy-2-[methoxy(phenyl)methyl]pyrimidine-4-carboxamide | 366 | A |
| 5 | | 5,6-dihydroxy-N-(3-methoxybenzyl)-2-[methoxy(phenyl)methyl]pyrimidine-4-carboxamide | 396 | A |

TABLE 11-continued

| 6 | 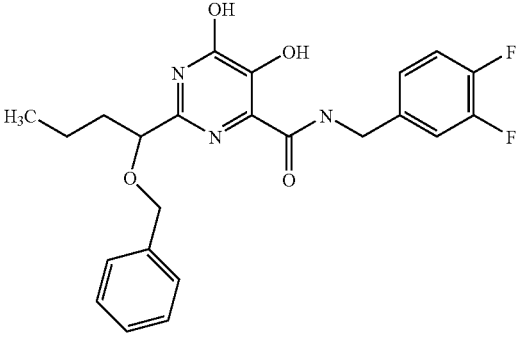 | 2-[1-(benzyloxy)butyl]-N-(3,4-difluorobenzyl)-5,6-dihydroxypyrimidine-4-carboxamide | 444 | A |
| 7 | 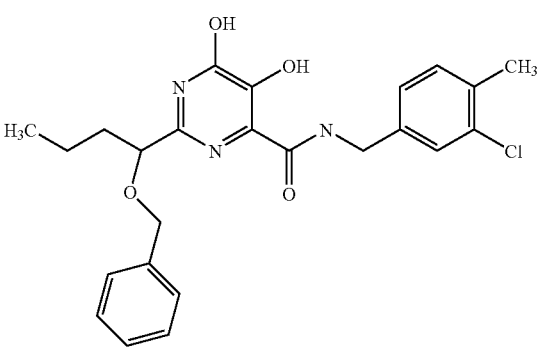 | 2-[1-(benzyloxy)butyl]-N-(3-chloro-4-methylbenzyl)-5,6-dihydroxypyrimidine-4-carboxamide | 456 | A |
| 8 | 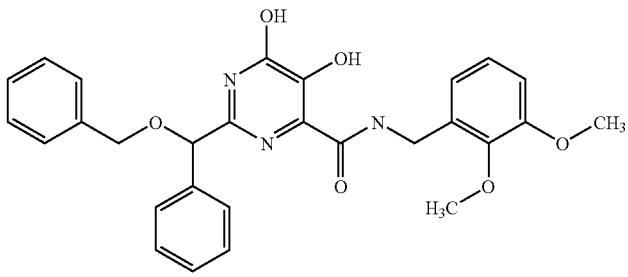 | 2-[(benzyloxy)(phenyl)methyl]-N-(2,3-dimethoxybenzyl)-5,6-dihydroxypyrimidine-4-carboxamide | 502 | A |
| 9 | 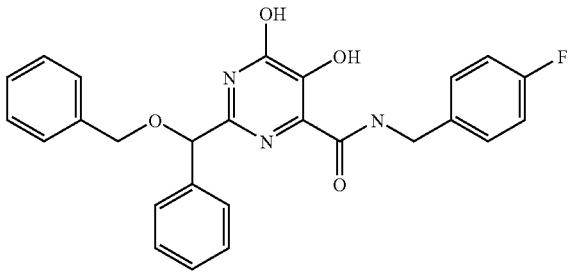 | 2-[(benzyloxy)(phenyl)methyl]-N-(4-fluorobenzyl)-5,6-dihydroxypyrimidine-4-carboxamide | 460 | A |
| 10 | 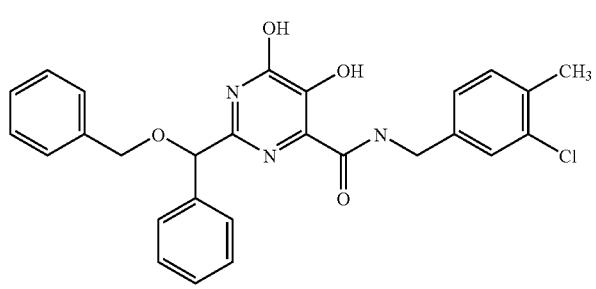 | 2-[(benzyloxy)(phenyl)methyl]-N-(3-chloro-4-methylbenzyl)-5,6-dihydroxypyrimidine-4-carboxamide | 490 | A |

TABLE 11-continued

| | | | | |
|---|---|---|---|---|
| 12 | 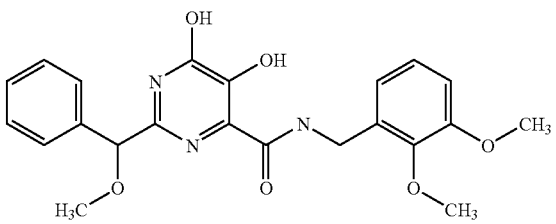 | N-(2,3-dimethoxybenzyl)-5,6-dihydroxy-2-[methoxy(phenyl)methyl]pyrimidine-4-carboxamide | 426 | A |
| 13 | 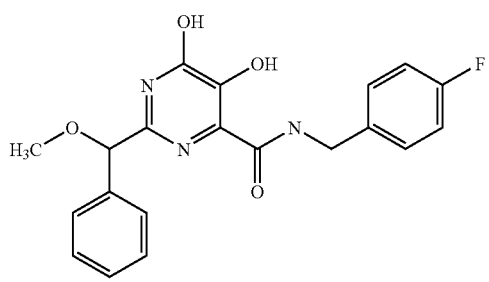 | N-(4-fluorobenzyl)-5,6-dihydroxy-2-[methoxy(phenyl)methyl]pyrimidine-4-carboxamide | 384 | A |
| 14 | 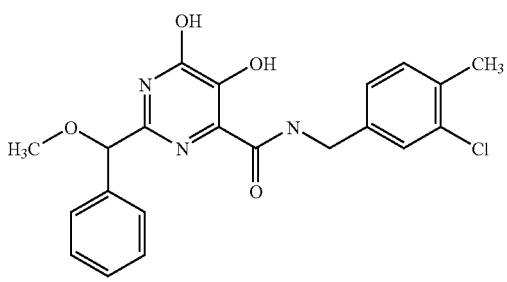 | N-(3-chloro-4-methylbenzyl)-5,6-dihydroxy-2-[methoxy(phenyl)methyl]pyrimidine-4-carboxamide | 414 | A |
| 15 | 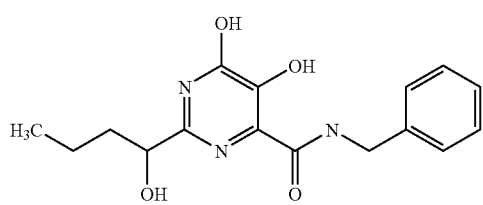 | N-benzyl-5,6-dihydroxy-2-(1-hydroxybutyl)pyrimidine-4-carboxamide | 318 | A* |
| 16 | 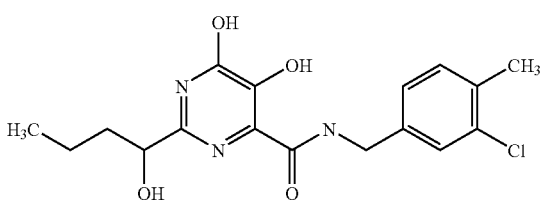 | N-(3-chloro-4-methylbenzyl)-5,6-dihydroxy-2-(1-hydroxybutyl)-pyrimidine-4-carboxamide | 366 | A* |
| 17 | 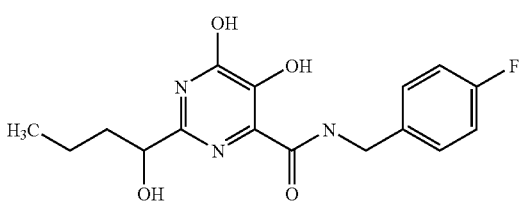 | N-(4-fluorobenzyl)-5,6-dihydroxy-2-(1-hydroxybutyl)pyrimidine-4-carboxamide | 336 | A* |

TABLE 11-continued

| | | | | |
|---|---|---|---|---|
| 18 | 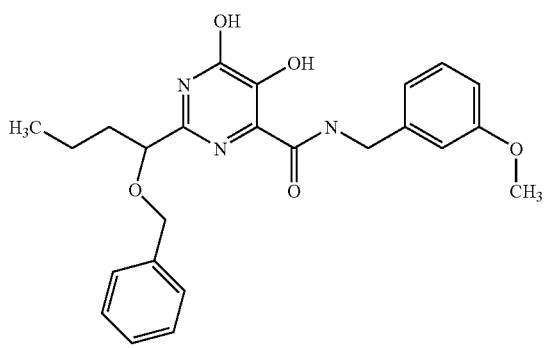 | 2-[1-(benzyloxy)butyl]-5,6-dihydroxy-N-(3-methoxybenzyl)pyrimidine-4-carboxamide | 438 | A |
| 19 | 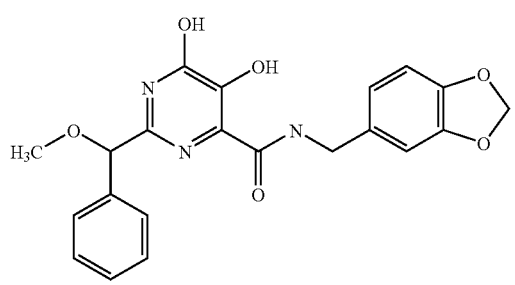 | N-(1,3-benzodioxol-5-ylmethyl)-5,6-dihydroxy-2-[methoxy(phenyl)methyl]pyrimidine-4-carboxamide | 410 | A |
| 20 | 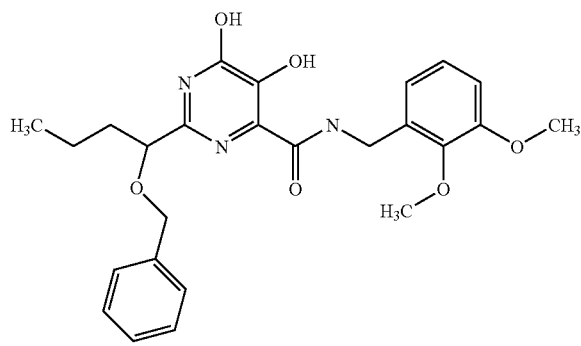 | 2-[1-(benzyloxy)butyl]-N-(2,3-dimethoxybenzyl)-5,6-dihydroxypyrimidine-4-carboxamide | 468 | A |
| 21 | 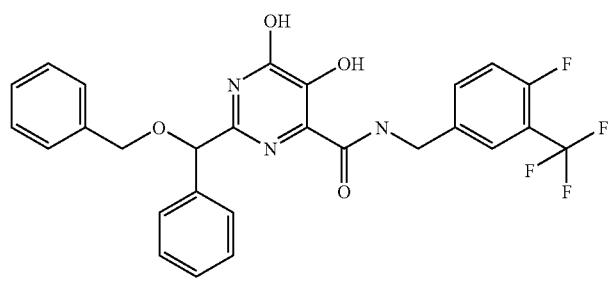 | 2-{(benzyloxy)(phenyl)methyl]-N-[4-fluoro-3-(trifluoromethyl)benzyl]-5,6-dihydroxypyrimidine-4-carboxamide | 528 | A |
| 22 | 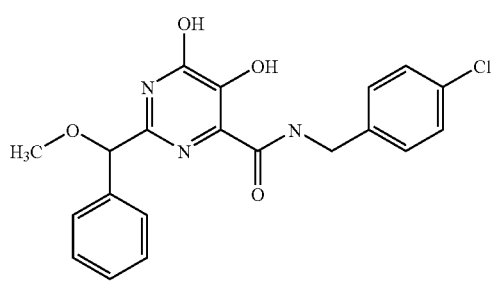 | N-(4-chlorobenzyl)-5,6-dihydroxy-2-[methoxy(phenyl)methyl]pyrimidine-4-carboxamide | 400 | A |

TABLE 11-continued

| | | | | |
|---|---|---|---|---|
| 23 | 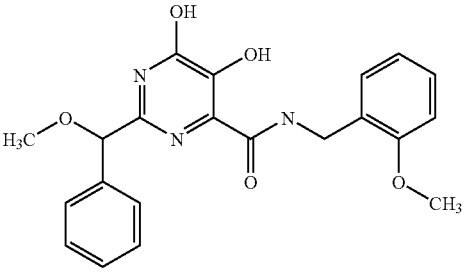 | 5,6-dihydroxy-N-(2-methoxy-benzyl)-2-[methoxy(phenyl)methyl]-pyrimidine-4-carboxamide | 396 | A |
| 24 | 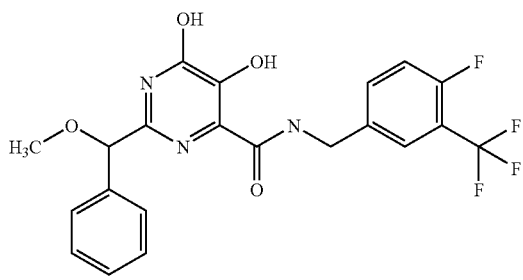 | N-[4-fluoro-3-(trifluoromethyl)benzyl]-5,6-dihydroxy-2-[methoxy(phenyl)methyl]pyrimidine-4-carboxamide | 452 | A |
| 25 | 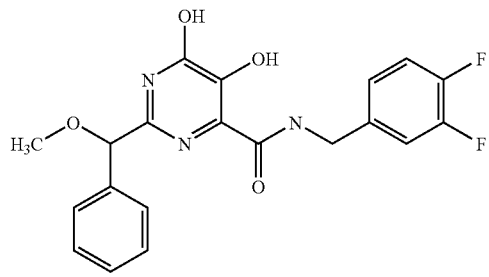 | N-(3,4-difluorobenzyl)-5,6-dihydroxy-2-[methoxy(phenyl)methyl]pyrimidine-4-carboxamide | 402 | A |
| 26 | 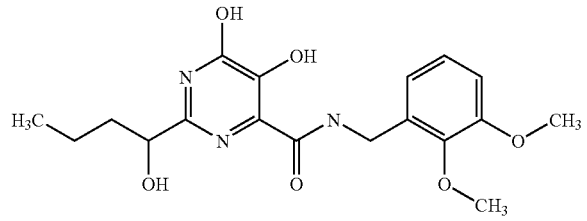 | N-(2,3-dimethoxybenzyl)-5,6-dihydroxy-2-(1-hydroxybutyl)pyrimidine-4-carboxamide | 378 | A* |
| 27 | 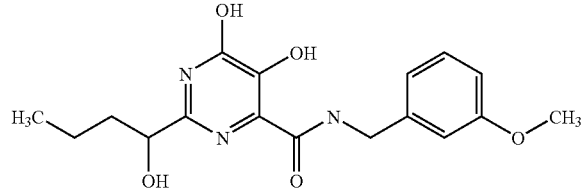 | 5,6-dihydroxy-2-(1-hydroxybutyl)-N-(3-methoxybenzyl)pyrimidine-4-carboxamide | 348 | A* |
| 28 | 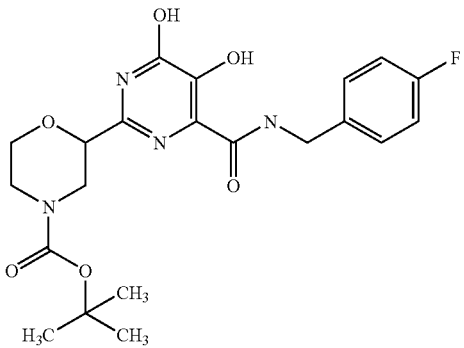 | tert-butyl 2-(4-{[(4-fluorobenzyl)amino]carbonyl}-5,6-dihydroxypyrimidin-2-yl)morpholine-4-carboxylate | 449 | A |

TABLE 11-continued

| 29 | 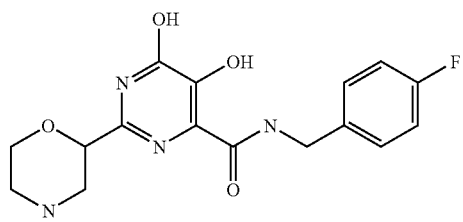 | N-(4-fluorobenzyl)-5,6-dihydroxy-2-morpholin-2-ylpyrimidine-4-carboxamide (TFA salt) | 349 | A* |
| --- | --- | --- | --- | --- |
| 30 | 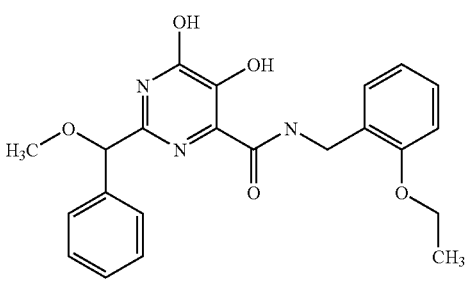 | N-(2-ethoxybenzyl)-5,6-dihydroxy-2-[methoxy(phenyl)methyl]pyrimidine-4-carboxamide | 410 | A |
| 31 | 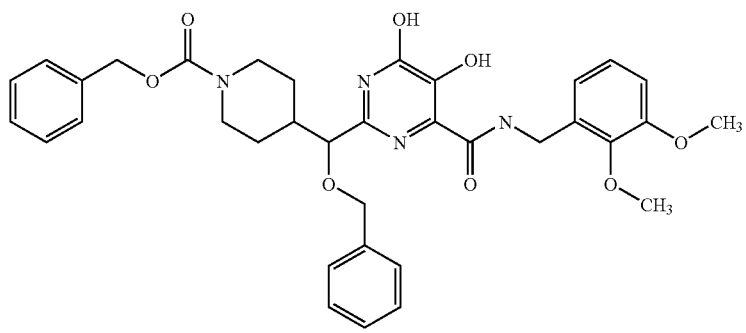 | benzyl 4-[(benzyloxy)(4-{[(2,3-dimethoxybenzyl)amino]carbonyl}-5,6-dihydroxy-pyrimidin-2-yl)methyl]piperidine-1-carboxylate | 643 | A |
| 32 | 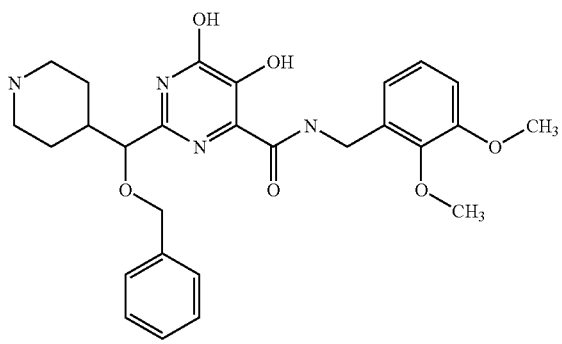 | 2-[(benzyloxy)(piperidin-4-yl)methyl]-N-(2,3-dimethoxy-benzyl)-5,6-dihydroxypyrimidine-4-carboxamide (TFA salt) | 509 | A* |

TABLE 12

| 1 | 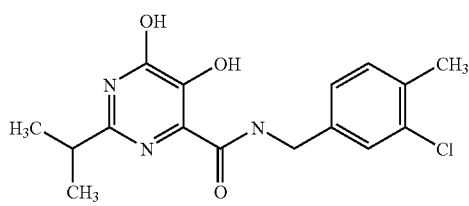 | N-(3-chloro-4-methylbenzyl)-5,6-dihydroxy-2-isopropylpyrimidine-4-carboxamide | 336 | A |
| --- | --- | --- | --- | --- |

TABLE 12-continued

| | Structure | Name | | |
|---|---|---|---|---|
| 2 | 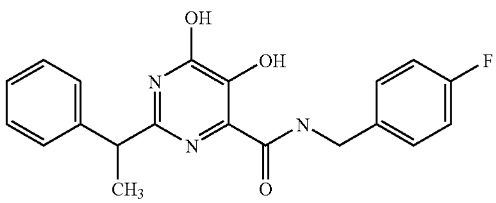 | N-(4-fluorobenzyl)-5,6-dihydroxy-2-(1-phenylethyl)pyrimidine-4-carboxamide | 368 | A |
| 3 | 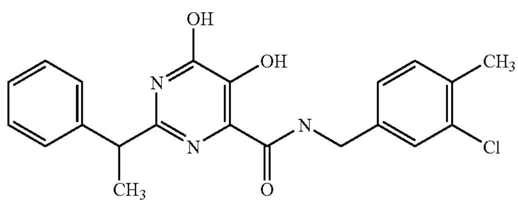 | N-(3-chloro-4-methylbenzyl)-5,6-dihydroxy-2-(1-phenylethyl)pyrimidine-4-carboxamide | 398 | A |
| 4 | 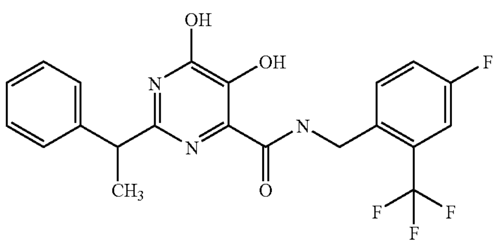 | N-[4-fluoro-2-(trifluoromethyl)benzyl]-5,6-dihydroxy-2-(1-phenylethyl)pyrimidine-4-carboxamide | 436 | A |
| 5 | 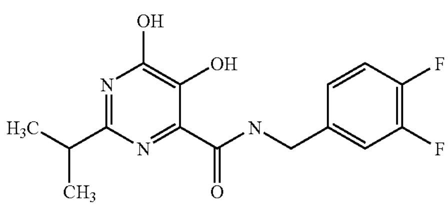 | N-(3,4-difluorobenzyl)-5,6-dihydroxy-2-isopropylpyrimidine-4-carboxamide | 324 | A |
| 6 | 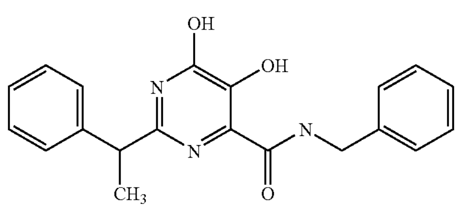 | N-benzyl-5,6-dihydroxy-2-(1-phenylethyl)pyrimidine-4-carboxamide | 350 | A |
| 7 | 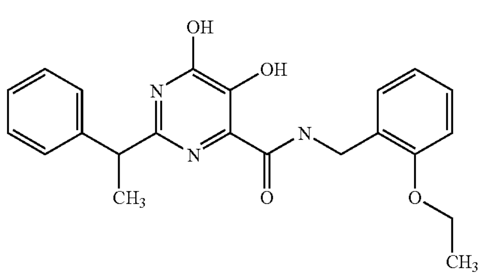 | N-(2-ethoxybenzyl)-5,6-dihydroxy-2-(1-phenylethyl)pyrimidine-4-carboxamide | 394 | A |
| 8 | 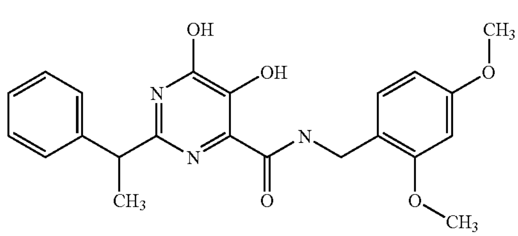 | N-(2,4-dimethoxybenzyl)-5,6-dihydroxy-2-(1-phenylethyl)pyrimidine-4-carboxamide | 410 | A |

TABLE 12-continued

| # | Structure | Name | MW | Act |
|---|---|---|---|---|
| 9 | 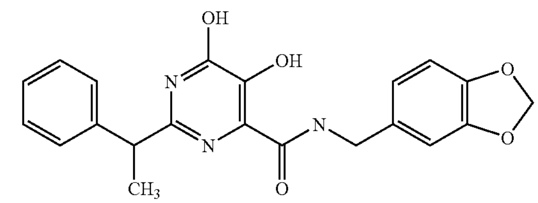 | N-(1,3-benzodioxol-5-ylmethyl)-5,6-dihydroxy-2-(1-phenylethyl)pyrimidine-4-carboxamide | 394 | A |
| 10 | 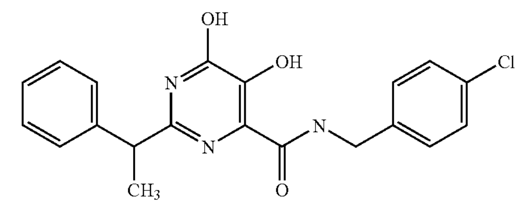 | N-(4-chlorobenzyl)-5,6-dihydroxy-2-(1-phenylethyl)pyrimidine-4-carboxamide | 384 | A |
| 11 | 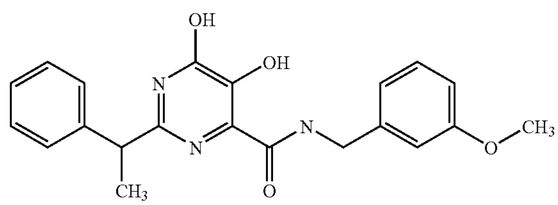 | 5,6-dihydroxy-N-(3-methoxybenzyl)-2-(1-phenylethyl)pyrimidine-4-carboxamide | 380 | A |
| 12 | 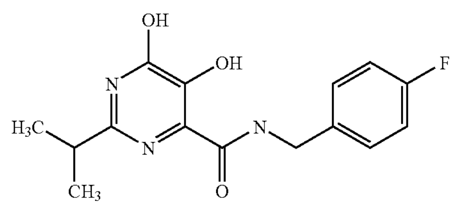 | N-(4-fluorobenzyl)-5,6-dihydroxy-2-isopropylpyrimidine-4-carboxamide | 306 | A |
| 13 | 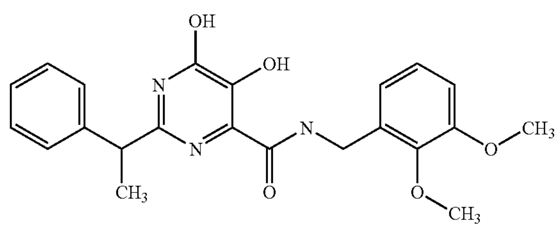 | N-(2,3-dimethoxybenzyl)-5,6-dihydroxy-2-(1-phenylethyl)pyrimidine-4-carboxamide | 410 | A |
| 14 | 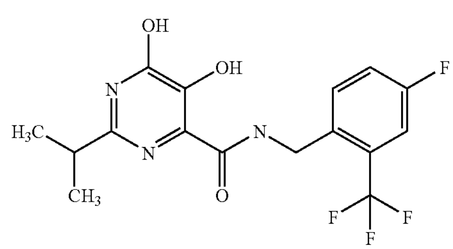 | N-[4-fluoro-2-(trifluoromethyl)benzyl]-5,6-dihydroxy-2-isopropylpyrimidine-4-carboxamide | 374 | A |
| 15 | 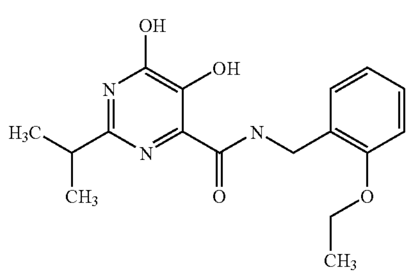 | N-(2-ethoxybenzyl)-5,6-dihydroxy-2-isopropylpyrimidine-4-carboxamide | 332 | A |

TABLE 12-continued

| 16 | [structure] | N-(2,3-dimethoxybenzyl)-5,6-dihydroxy-2-isopropylpyrimidine-4-carboxamide | 348 | A |
| 17 | [structure] | N-(1,3-benzodioxol-5-ylmethyl)-5,6-dihydroxy-2-isopropylpyrimidine-4-carboxamide | 332 | A |
| 18 | [structure] | N-benzyl-5,6-dihydroxy-2-isopropylpyrimidine-4-carboxamide | 288 | A |
| 19 | [structure] | N-[4-fluoro-3-(trifluoromethyl)benzyl]-5,6-dihydroxy-2-isopropylpyrimidine-4-carboxamide | 374 | A |
| 20 | [structure] | N-(2,4-dimethoxybenzyl)-5,6-dihydroxy-2-isopropylpyrimidine-4-carboxamide | 348 | A |

TABLE 13

| 1 | [structure] | N-benzyl-2-cyclopentyl-5,6-dihydroxypyrimidine-4-carboxamide | 314 | A |

TABLE 13-continued

| | | | | |
|---|---|---|---|---|
| 2 | 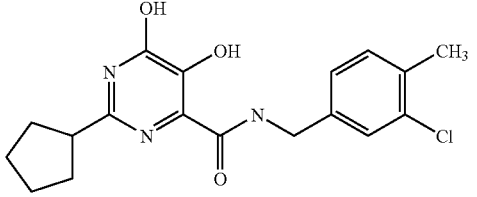 | N-(3-chloro-4-methylbenzyl)-2-cyclopentyl-5,6-dihydroxypyrimidine-4-carboxamide | 362 | A |
| 3 | 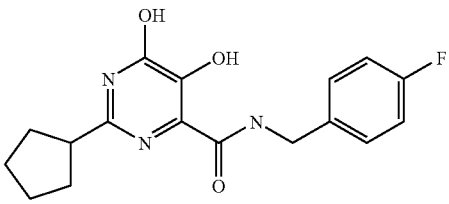 | 2-cyclopentyl-N-(4-fluorobenzyl)-5,6-dihydroxypyrimidine-4-carboxamide | 332 | A |
| 4 | 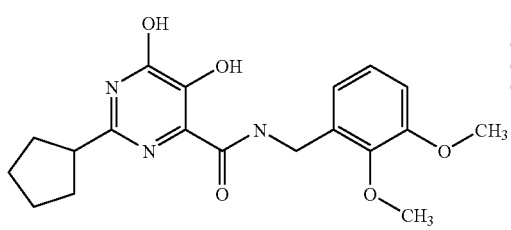 | 2-cyclopentyl-N-(2,3-dimethoxybenzyl)-5,6-dihydroxypyrimidine-4-carboxamide | 374 | A |
| 5 | 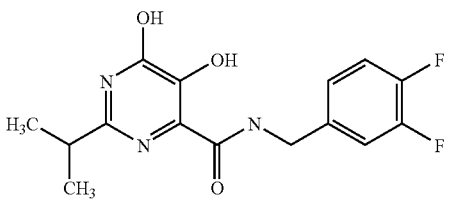 | 2-cyclopentyl-N-(2-ethoxybenzyl)-5,6-dihydroxypyrimidine-4-carboxamide | 358 | A |
| 6 | 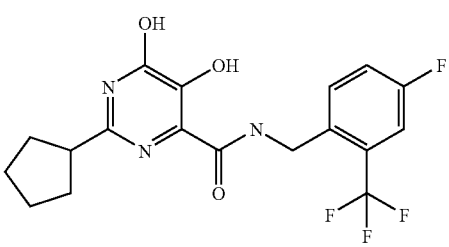 | 2-cyclopentyl-N-[4-fluoro-2-(trifluoromethyl)benzyl]-5,6-dihydroxypyrimidine-4-carboxamide | 400 | A |
| 7 | 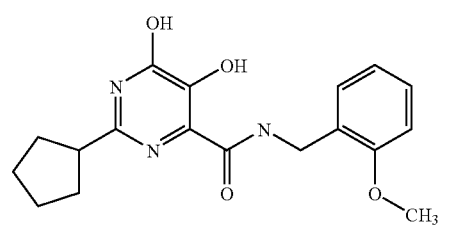 | 2-cyclopentyl-5,6-dihydroxy-N-(2-methoxybenzyl)pyrimidine-4-carboxamide | 344 | A |
| 8 | 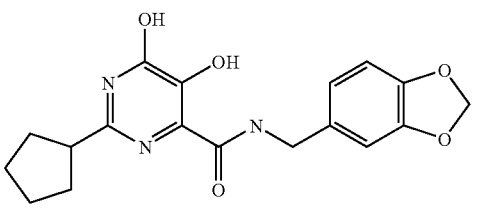 | N-(1,3-benzodioxol-5-ylmethyl)-2-cyclopentyl-5,6-dihydroxypyrimidine-4-carboxamide | 358 | A |

TABLE 13-continued

| | | | | |
|---|---|---|---|---|
| 9 | 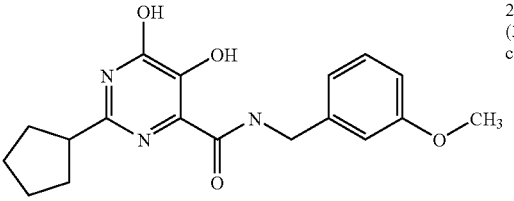 | 2-cyclopentyl-5,6-dihydroxy-N-(3-methoxybenzyl)pyrimidine-4-carboxamide | 344 | A |
| 10 | 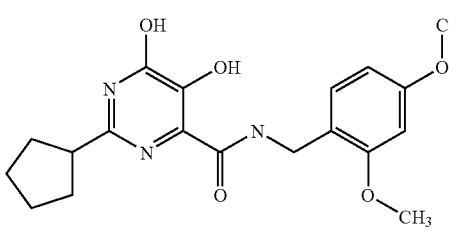 | 2-cyclopentyl-N-(2,4-dimethoxybenzyl)-5,6-dihydroxypyrimidine-4-carboxamide | 374 | A |

TABLE 14

| | | | | |
|---|---|---|---|---|
| 1 | 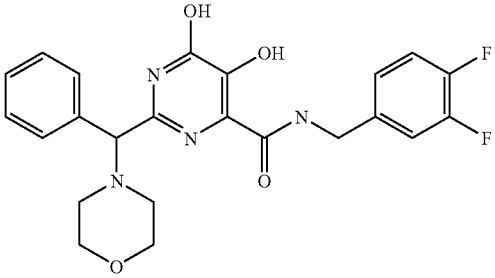 | N-(3,4-difluorobenzyl)-5,6-dihydroxy-2-[morpholin-4-yl(phenyl)methyl]pyrimidine-4-carboxamide (TFA salt) | 457 | B |
| 2 | 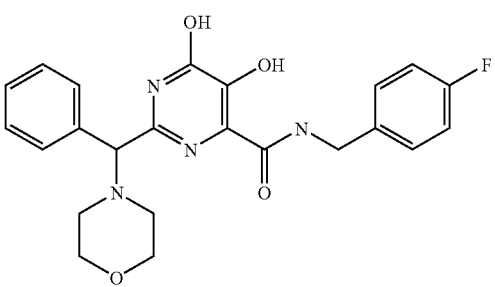 | N-(4-fluorobenzyl)-5,6-dihydroxy-2-[morpholin-4-yl(phenyl)methyl]pyrimidine-4-carboxamide (TFA salt) | 439 | B |
| 3 | 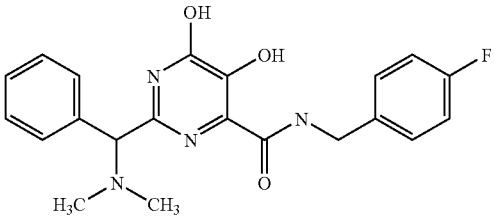 | 2-[(dimethylamino)(phenyl)methyl]-N-(4-fluorobenzyl)-5,6-dihydroxypyrimidine-4-carboxamide | 397 | B |
| 4 | 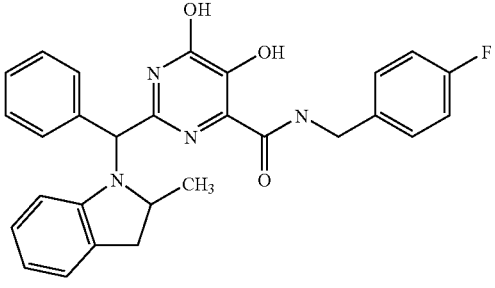 | N-(4-fluorobenzyl)-5,6-dihydroxy-2-[(2-methyl-2,3-dihydro-1H-indol-1-yl)(phenyl)methyl]pyrimidine-4-carboxamide (TFA salt) | 485 | B |

TABLE 14-continued

| | | | | |
|---|---|---|---|---|
| 5 | 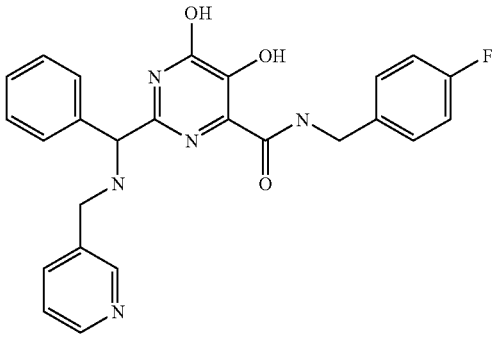 | N-(4-fluorobenzyl)-5,6-dihydroxy-2-{phenyl[(pyridin-3-yl-methyl)amino]methyl}pyrimidine-4-carboxamide (TFA salt) | 460 | B |
| 6 | 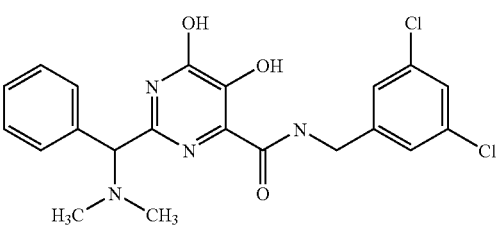 | N-(3,5-dichlorobenzyl)-2-[(dimethylamino)(phenyl)methyl]-5,6-dihydroxypyrimidine-4-carboxamide (TFA salt) | 447 | B |
| 7 | 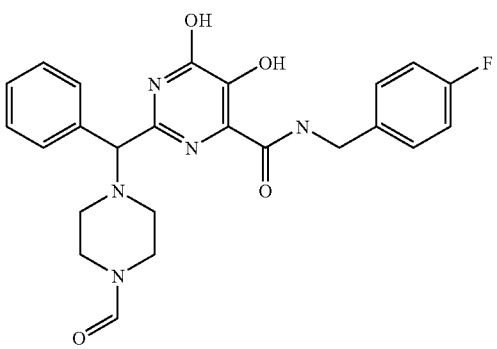 | N-(4-fluorobenzyl)-2-[(4-formylpiperazin-1-yl)(phenyl)methyl]-5,6-dihydroxypyrimidine-4-carboxamide (TFA salt) | 466 | B |
| 8 | 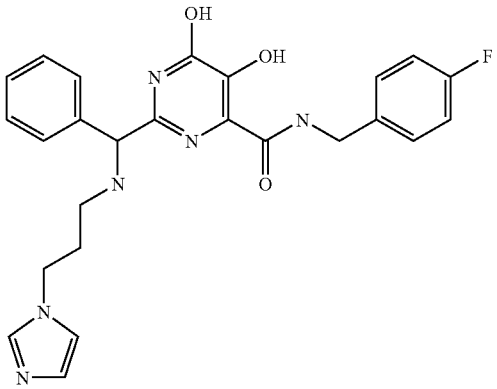 | N-(4-fluorobenzyl)-5,6-dihydroxy-2-[{[3-(1H-imidazol-1-yl)propyl]amino}(phenyl)methyl]pyrimidine-4-carboxamide (TFA salt) | 477 | B |

TABLE 14-continued

| # | Structure | Name | MW | Class |
|---|---|---|---|---|
| 9 | 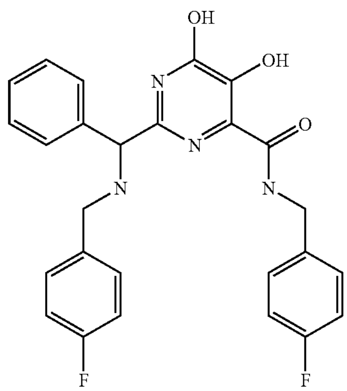 | N-(4-fluorobenzyl)-2-[[(4-fluorobenzyl)amino](phenyl)methyl]-5,6-dihydroxypyrimidine-4-carboxamide (TFA salt) | 477 | B |
| 10 | 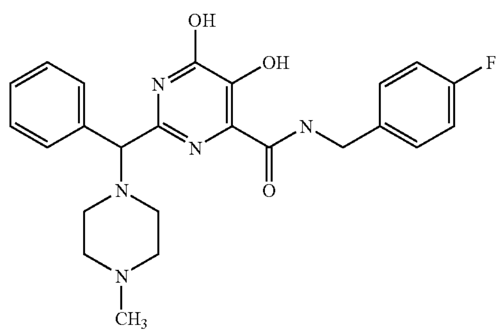 | N-(4-fluorobenzyl)-5,6-dihydroxy-2-[(4-methylpiperazin-1-yl)(phenyl)methyl]pyrimidine-4-carboxamide (TFA salt) | 452 | B |
| 11 | 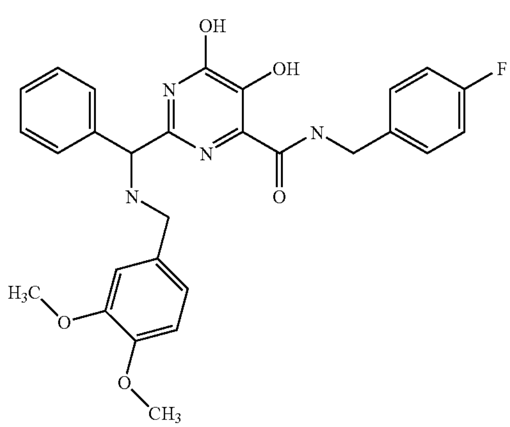 | 2-[[[(3,4-dimethoxybenzyl)amino](phenyl)methyl]-N-(4-fluorobenzyl)-5,6-dihydroxy-pyrimidine-4-carboxamide (TFA salt) | 519 | B |
| 12 | 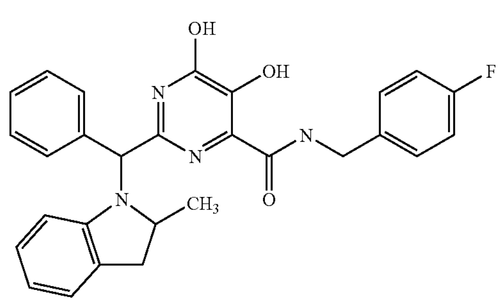 | N-(4-fluorobenzyl)-5,6-dihydroxy-2-[(2-methyl-2,3-dihydro-1H-indol-1-yl)(phenyl)methyl]pyrimidine-4-carboxamide (TFA salt) | 485 | B |

TABLE 14-continued

| | | | | |
|---|---|---|---|---|
| 13 | 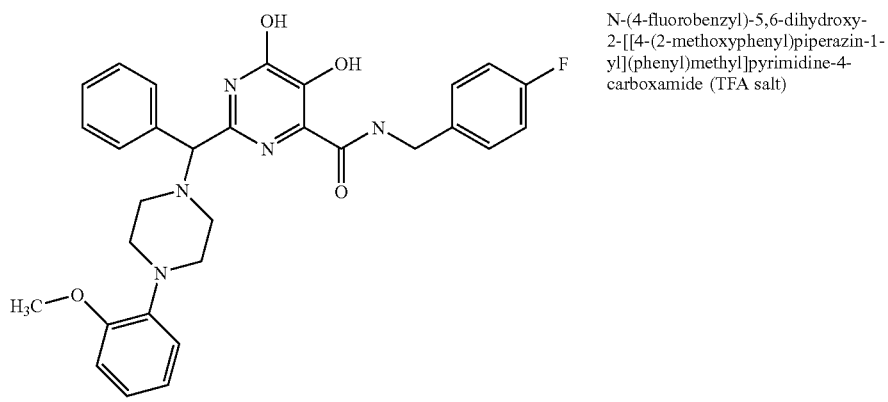 | N-(4-fluorobenzyl)-5,6-dihydroxy-2-[[4-(2-methoxyphenyl)piperazin-1-yl](phenyl)methyl]pyrimidine-4-carboxamide (TFA salt) | 544 | B |
| 14 | 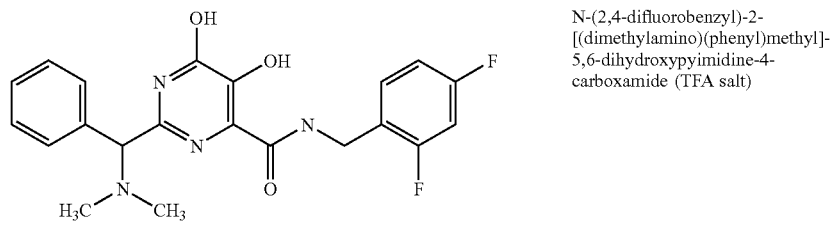 | N-(2,4-difluorobenzyl)-2-[(dimethylamino)(phenyl)methyl]-5,6-dihydroxypyrimidine-4-carboxamide (TFA salt) | 415 | B |
| 15 | 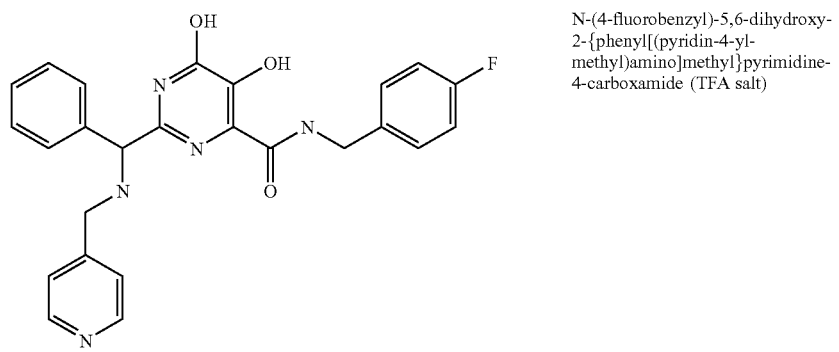 | N-(4-fluorobenzyl)-5,6-dihydroxy-2-{phenyl[(pyridin-4-yl-methyl)amino]methyl}pyrimidine-4-carboxamide (TFA salt) | 460 | B |
| 16 | 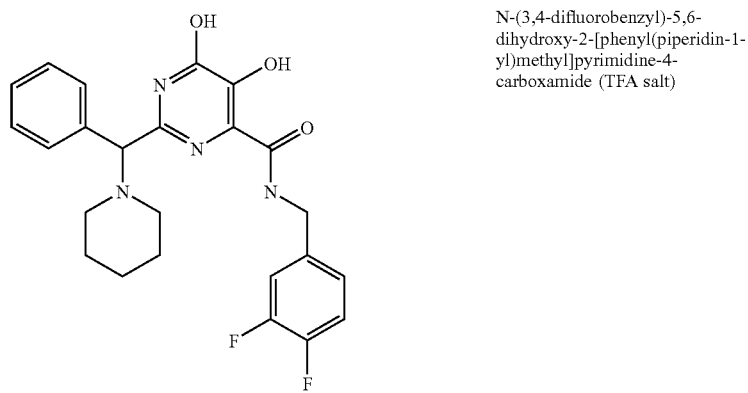 | N-(3,4-difluorobenzyl)-5,6-dihydroxy-2-[phenyl(piperidin-1-yl)methyl]pyrimidine-4-carboxamide (TFA salt) | 455 | B |

TABLE 14-continued

| | | | | |
|---|---|---|---|---|
| 17 | | N-(4-fluorobenzyl)-5,6-dihydroxy-2-[phenyl(piperidin-1-yl)methyl]pyrimidine-4-carboxamide (TFA salt) | 437 | B |
| 18 | | 2-[(dimethylamino)(phenyl)methyl]-N-(4-fluorobenzyl)-5,6-dihydroxypyimidine-4-carboxamide | 397 | B |
| 19 | | N-(4-fluorobenzyl)-5,6-dihydroxy-2-[{[3-(2-oxopyrrolidin-1-yl)propyl]amino}(phenyl)methyl]pyrimidine-4-carboxamide (TEA salt) | 494 | B |
| 20 | | N-(4-fluorobenzyl)-5,6-dihydroxy-2-[{[2-(1H-indol-3-yl)ethyl]amino}(phenyl)methyl]pyrimidine-4-carboxamide (TFA salt) | 512 | B |
| 21 | | 2-[[benzyl(methyl)amino]-(phenyl)methyl]-N-(4-fluorobenzyl)-5,6-dihydroxypyrimidine-4-carboxamide (TFA salt) | 473 | B |

TABLE 14-continued

| | | | | |
|---|---|---|---|---|
| 22 | 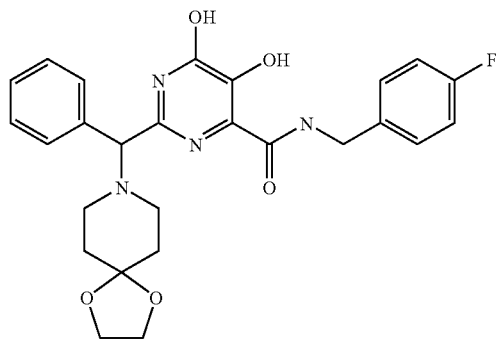 | 2-[1,4-dioxa-8-azaspiro[4.5]-dec-8-yl(phenyl)methyl]-N-(4-fluorobenzyl)-5,6-dihydroxypyrimidine-4-carboxamide (TFA salt) | 495 | B |
| 23 | 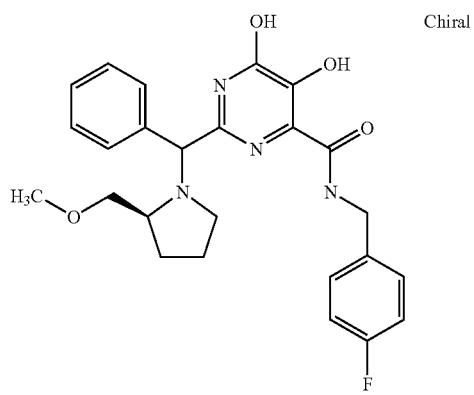 Chiral | N-(4-fluorobenzyl)-5,6-dihydroxy-2-[[(2S)-2-(methoxymethyl)pyrrolidin-1-yl](phenyl)methyl]pyrimidine-4-carboxamide (TFA salt) | 467 | B |
| 24 | 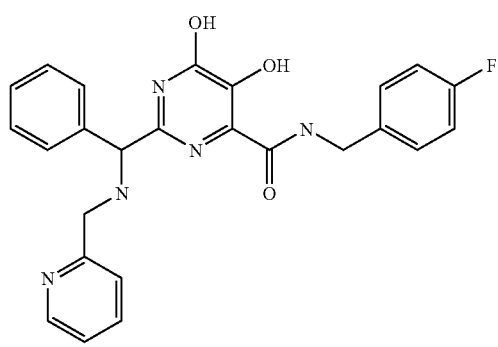 | N-(4-fluorobenzyl)-5,6-dihydroxy-2-{phenyl[(pyridin-2-ylmethyl)amino]methyl}pyrimidine-4-carboxamide (TFA salt) | 460 | B |
| 25 | 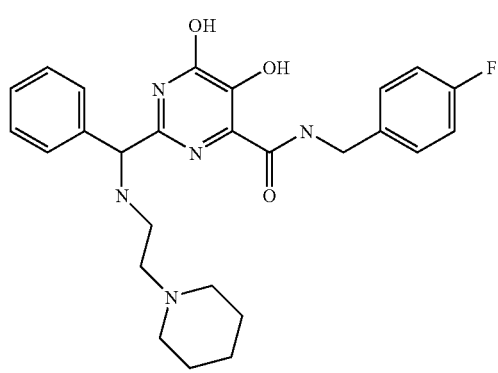 | N-(4-fluorobenzyl)-5,6-dihydroxy-2-{phenyl[(2-piperidin-1-yl-ethyl)amino]methyl}pyrimidine-4-carboxamide (TFA salt) | 480 | B |

TABLE 14-continued

| | | | | |
|---|---|---|---|---|
| 26 | 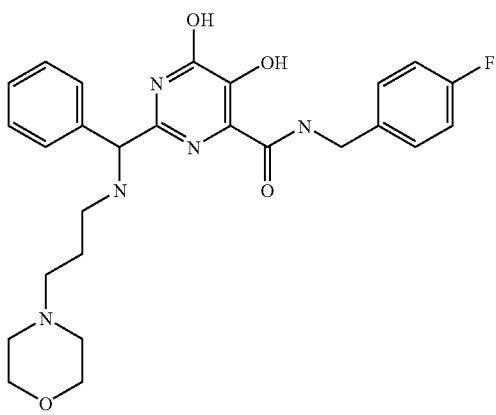 | N-(4-fluorobenzyl)-5,6-dihydroxy-2-[[(3-morpholin-4-ylpropyl)amino](phenyl)methyl]pyrimidine-4-carboxamide (TFA salt) | 496 | B |
| 27 | 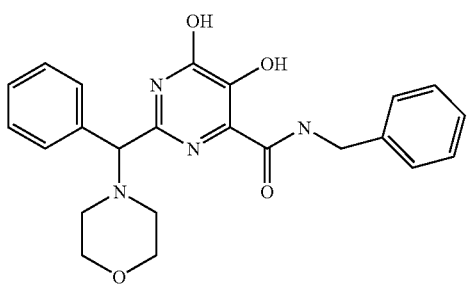 | N-benzyl-5,6-dihydroxy-2-[morpholin-4-yl(phenyl)methyl]pyrimidine-4-carboxamide (TFA salt) | 421 | B |
| 28 | 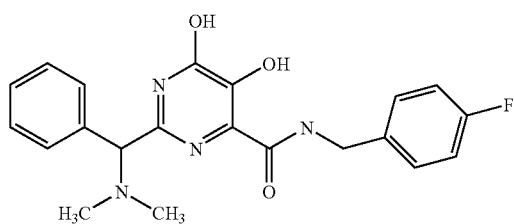 | 2-[(dimethylamino)(phenyl)methyl]-N-(4-fluorobenzyl)-5,6-dihydroxypyrimidine-4-carboxamide (TFA salt) | 397 | B |
| 29 | 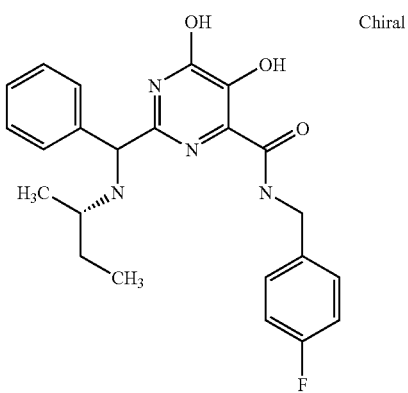 | N-(4-fluorobenzyl)-5,6-dihydroxy-2-[{[(1S)-1-methylpropyl]amino}(phenyl)methyl]pyrimidine-4-carboxamide (TFA salt) | 425 | B |

TABLE 14-continued

| | | | | |
|---|---|---|---|---|
| 30 | 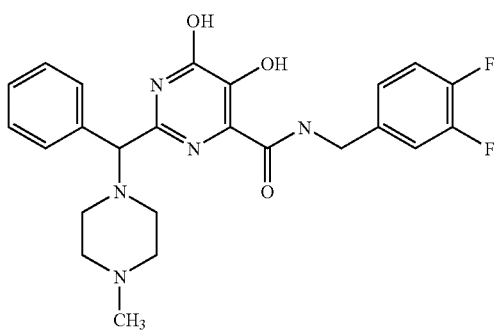 | N-(3,4-difluorobenzyl)-5,6-dihydroxy-2-[(4-methylpiperazin-1-yl)(phenyl)methyl]pyrimidine-4-carboxamide (TFA salt) | 470 | B |
| 31 | 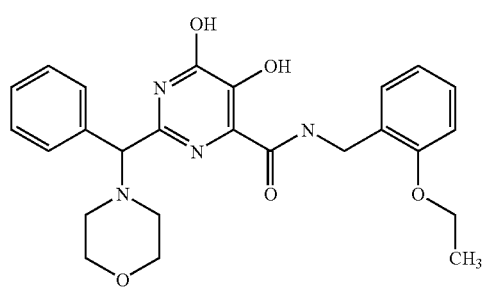 | N-(2-ethoxybenzyl)-5,6-dihydroxy-2-[morpholin-4-yl(phenyl)methyl]pyrimidine-4-carboxamide (TFA salt) | 465 | B |
| 32 | 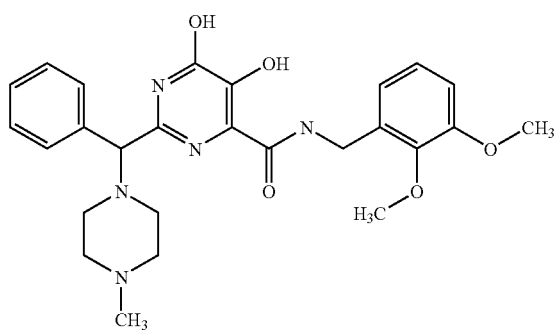 | N-(2,3-dimethoxybenzyl)-5,6-dihydroxy-2-[(4-methylpiperazin-1-yl)(phenyl)methyl]pyrimidine-4-carboxamide (TFA salt) | 494 | B |
| 33 | 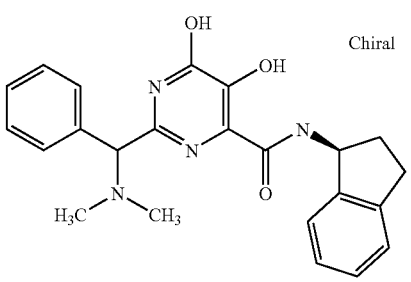 | N-[(1S)-2,3-dihydro-1H-inden-1-yl]-2-[(dimethylamino)(phenyl)methyl]-5,6-dihydroxypyrimidine-4-carboxamide (TFA salt) | 405 | B |
| 34 | 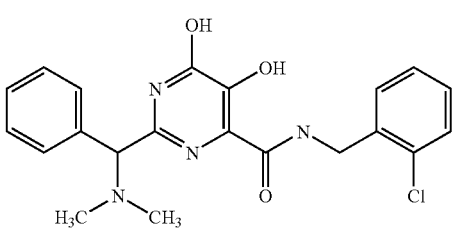 | N-(2-chlorobenzyl)-2-[(dimethylamino)(phenyl)methyl]-5,6-dihydroxypyrimidine-4-carboxamide (TFA salt) | 413 | B |

TABLE 14-continued

| 35 | 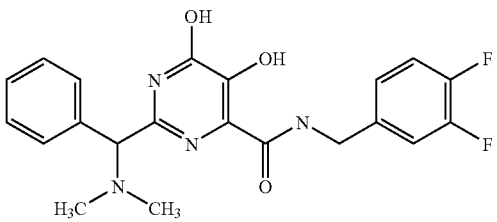 | N-(3,4-difluorobenzyl)-2-[(dimethylamino)(phenyl)methyl]-5,6-dihydroxypyrimidine-4-carboxamide (TFA salt) | 415 | B |
| --- | --- | --- | --- | --- |
| 36 | 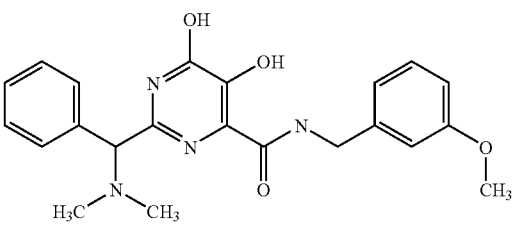 | 2-[(dimethylamino)(phenyl)methyl]-5,6-dihydroxy-N-(3-methoxybenzyl)pyrimidine-4-carboxamide (TFA salt) | 409 | B |
| 37 | 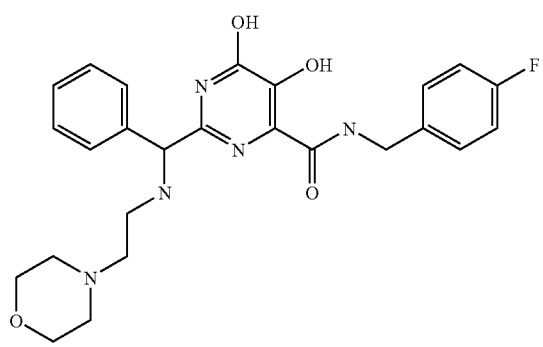 | N-(4-fluorobenzyl)-5,6-dihydroxy-2-[[(2-morpholin-4-ylethyl)amino](phenyl)methyl]pyrimidine-4-carboxamide (TFA salt) | 482 | B |
| 38 | 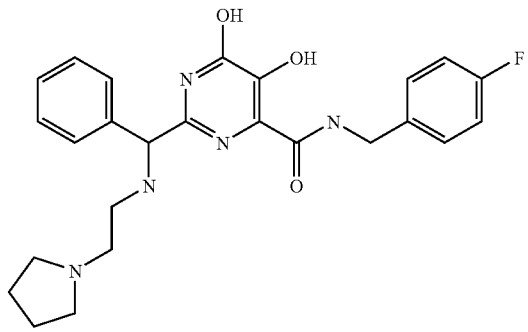 | N-(4-fluorobenzyl)-5,6-dihydroxy-2-{phenyl[(2-pyrrolidin-1-ylethyl)amino]methyl}pyrimidine-4-carboxamide (TFA salt) | 466 | B |
| 39 | 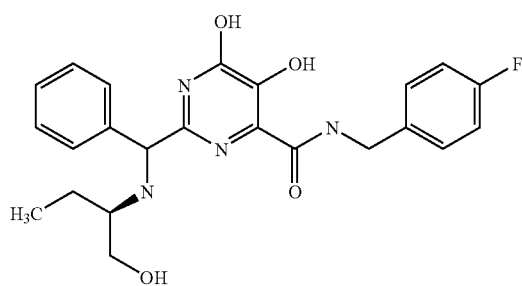 Chiral | N-(4-fluorobenzyl)-5,6-dihydroxy-2-[{[(1R)-1-(hydroxymethyl)propyl]amino}(phenyl)methyl]-pyrimidine-4-carboxamide (TFA salt) | 441 | B |

TABLE 14-continued

| | | | |
|---|---|---|---|
| 40 | *[structure]* | 2-[(diethylamino)(phenyl)methyl]-N-(3,4-difluorobenzyl)-5,6-dihydroxypyrimidine-4-carboxamide (TFA salt) | 443 B |
| 41 | *[structure]* | 2-{(diethylamino)(phenyl)methyl]-N-(4-fluorobenzyl)-5,6-dihydroxypyrimidine-4-carboxamide (TFA salt) | 425 B |
| 42 | *[structure]* | 2-[(4-benzylpiperazin-1-yl)(phenyl)methyl]-N-(4-fluorobenzyl)-5,6-dihydroxypyrimidine-4-carboxamide (TFA salt) | 528 B |
| 43 | *[structure]* | N-benzyl-2-[(dimethylamino)-(phenyl)methyl]-5,6-dihydroxy-pyrimidine-4-carboxamide (TFA salt) | 379 B |
| 44 | *[structure]* | N-(4-fluorobenzyl)-5,6-dihydroxy-2-[[methyl(1-methylpiperidin-4-yl)amino](phenyl)methyl]pyrimidine-4-carboxamide (TFA salt) | 480 B |

TABLE 14-continued

| # | Structure | Name | MW | |
|---|---|---|---|---|
| 45 | 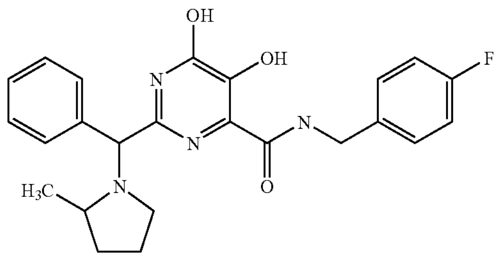 | N-(4-fluorobenzyl)-5,6-dihydroxy-2-[(2-methylpyrrolidin-1-yl)(phenyl)methyl]pyrimidine-4-carboxamide (TFA salt) | 437 | B |
| 46 | 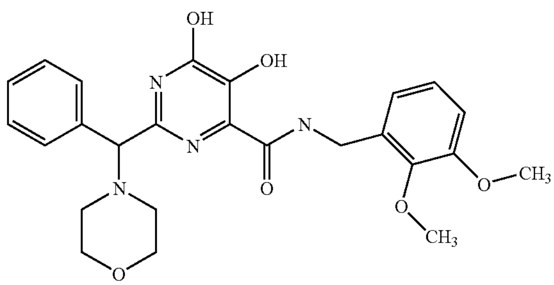 | N-(2,3-dimethoxybenzyl)-5,6-dihydroxy-2-[morpholin-4-yl(phenyl)methyl]pyrimidine-4-carboxamide (TFA salt) | 481 | B |
| 47 | 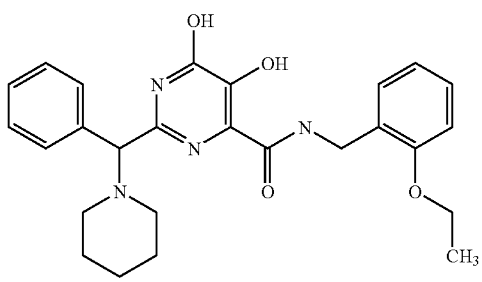 | N-(2-ethoxybenzyl)-5,6-dihydroxy-2-[phenyl(piperidin-1-yl)methyl]pyrimidine-4-carboxamide (TFA salt) | 463 | B |
| 48 | 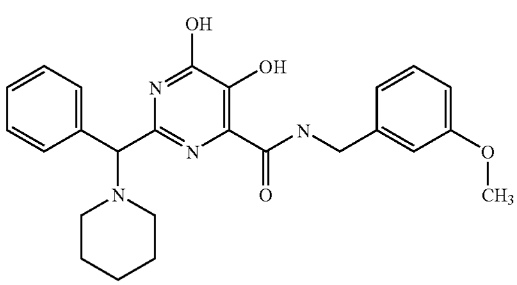 | 5,6-dihydroxy-N-(3-methoxybenzyl)-2-[phenyl(piperidin-1-yl)methyl]pyrimidine-4-carboxamide (TFA salt) | 449 | B |
| 49 | 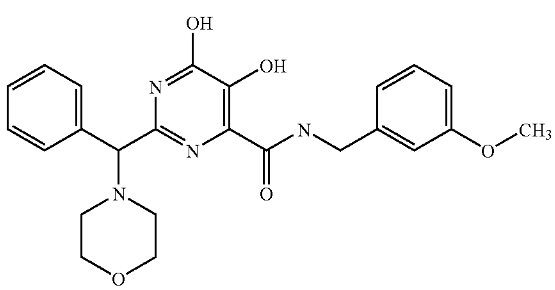 | 5,6-dihydroxy-N-(3-methoxybenzyl)-2-[morpholin-4-yl(phenyl)methyl]pyrimidine-4-carboxamide (TFA salt) | 451 | B |

TABLE 14-continued

| # | Structure | | Name | MS | Cat |
|---|---|---|---|---|---|
| 50 | (structure) | Chiral | N-(4-fluorobenzyl)-5,6-dihydroxy-2-{phenyl[(2S)-2-(pyrrolidin-1-ylmethyl)pyrrolidin-1-yl]methyl}pyrimidine-4-carboxamide (TFA salt) | 506 | B |
| 51 | (structure) | | N-(2,3-dimethoxybenzyl)-5,6-dihydroxy-2-[phenyl(piperidin-1-yl)methyl]pyrimidine-4-carboxamide (TFA salt) | 479 | B |
| 52 | (structure) | | 5,6-dihydroxy-N-(3-methoxybenzyl)-2-[(4-methylpiperazin-1-yl)(phenyl)methyl]pyrimidine-4-carboxamide (TFA salt) | 464 | B |
| 53 | (structure) | | 2-[[(4-fluorobenzyl)amino](phenyl)methyl]-5,6-dihydroxy-N-(pyridin-2-ylmethyl)pyrimidine-4-carboxamide (TFA salt) | 460 | B |
| 54 | (structure) | | N-(2,3-dimethoxybenzyl)-2-[(dimethylamino)(phenyl)methyl]-5,6-dihydroxypyrimidine-4-carboxamide (TFA salt) | 439 | B |

TABLE 14-continued

| | | | | |
|---|---|---|---|---|
| 55 | | 2-[[(4-fluorobenzyl)amino](phenyl)methyl]-5,6-dihydroxy-N-(pyridin-3-ylmethyl)pyrimidine-4-carboxamide (TFA salt) | 460 | B |
| 56 | | 5,6-dihydroxy-2-{phenyl[(pyridin-2-ylmethyl)amino]methyl}-N-(pyridin-2-ylmethyl)pyrimidine-4-carboxamide (TFA salt) | 443 | B |
| 57 | | 2-[(diethylamino)(phenyl)methyl]-N-(2,3-dimethoxybenzyl)-5,6-dihydroxypyrimidine-4-carboxamide (TFA salt) | 467 | B |

TABLE 15

| | | | | |
|---|---|---|---|---|
| 1 | | N-(4-fluorobenzyl)-5,6-dihydroxy-2-{1-methyl-1-[(pyridin-2-ylcarbonyl)amino]ethyl}pyrimidine-4-carboxamide (TFA salt) | 426 | I |
| 2 | | N-(4-fluorobenzyl)-5,6-dihydroxy-2-{1-[(pyridin-2-ylcarbonyl)amino]cyclohexyl}pyrimidine-4-carboxamide (TFA salt) | 466 | I |

TABLE 15-continued

| | Structure | Name | MW | Class |
|---|---|---|---|---|
| 3 | 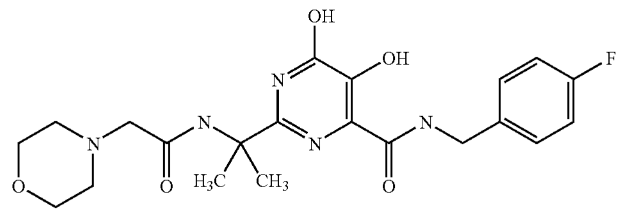 | N-(4-fluorobenzyl)-5,6-dihydroxy-2-{1-methyl-1-[(morpholin-4-ylacetyl)amino]ethyl}pyrimidine-4-carboxamide (TFA salt) | 448 | I |
| 4 | 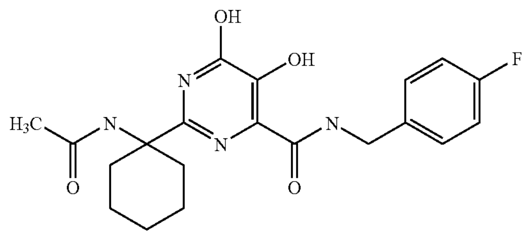 | 2-[1-(acetylamino)cyclohexyl]-N-(4-fluorobenzyl)-5,6-dihydroxy-pyrimidine-4-carboxamide | 403 | I |
| 5 | 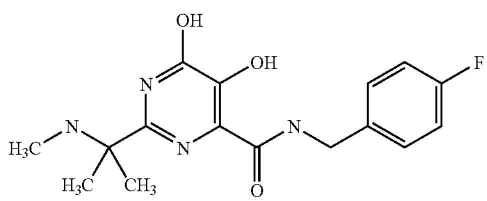 | N-(4-fluorobenzyl)-5,6-dihydroxy-2-[1-methyl-1-(methylamino)ethyl]-pyrimidine-4-carboxamide | 335 | C |
| 6 | 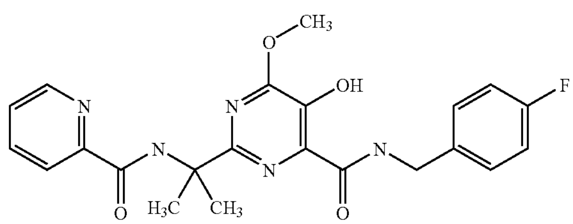 | N-(4-fluorobenzyl)-5-hydroxy-6-methoxy-2-{1-methyl-1-[(pyridin-2-ylcarbonyl)amino]ethyl}pyrimidine-4-carboxamide (TFA salt) | 440 | I |
| 7 | 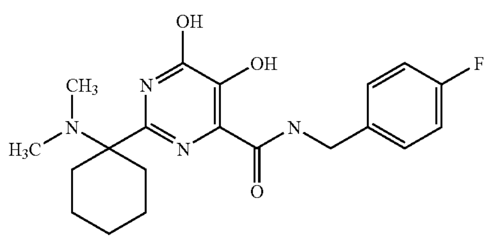 | 2-[1-(dimethylamino)cyclohexyl]-N-(4-fluorobenzyl)-5,6-dihydroxypyrimidine-4-carboxamide (TFA salt) | 389 | E |
| 8 | 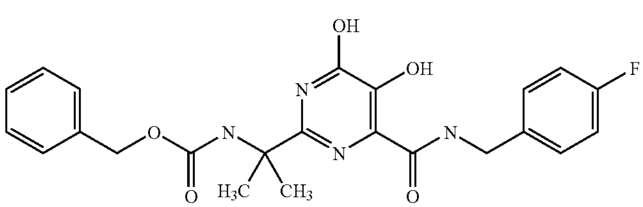 | benzyl 1-(4-{[(4-fluoro-benzyl)amino]carbonyl}-5,6-dihydroxypyrimidin-2-yl)-1-methylethylcarbamate | 455 | A |
| 9 | 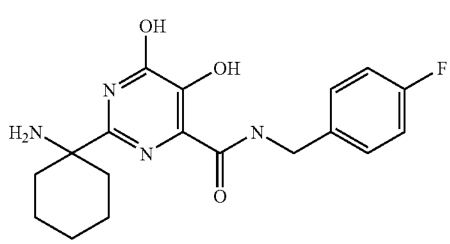 | 2-(1-aminocyclohexyl)-N-(4-fluorobenzyl)-5,6-dihydroxypyrimidine-4-carbaxamide (TFA salt) | 361 | A* |

TABLE 15-continued

| | Structure | Name | MW | Activity |
|---|---|---|---|---|
| 10 | 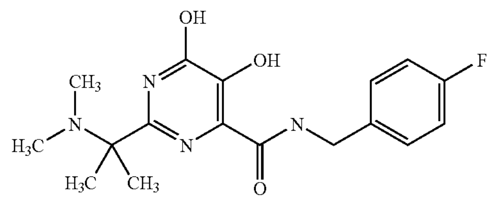 | 2-[1-(dimethylamino)-1-methylethyl]-N-(4-fluorobenzyl)-5,6-dihydroxypyrimidine-4-carboxamide (TFA salt) | 349 | E |
| 11 | 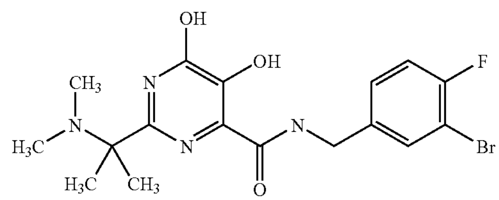 | N-(3-bromo-4-fluorobenzyl)-2-[1-(dimethylamino)-1-methylethyl]-5,6-dihydroxypyrimidine-4-carboxamide (TFA salt) | 428 | E |
| 12 | 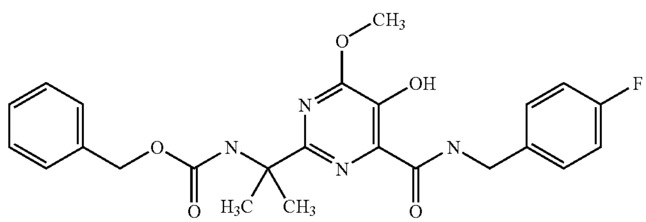 | benzyl 1-(4-{[(4-fluorobenzyl)amino]carbonyl}-5-hydroxy-6-methoxypyrimidin-2-yl)-1-methylethylcarbamate | 469 | J |
| 13 | 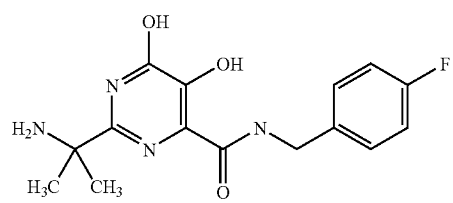 | 2-(1-amino-1-methylethyl)-N-(4-fluorobenzyl)-5,6-dihydroxypyrimidine-4-carboxamide | 321 | A* |
| 14 | 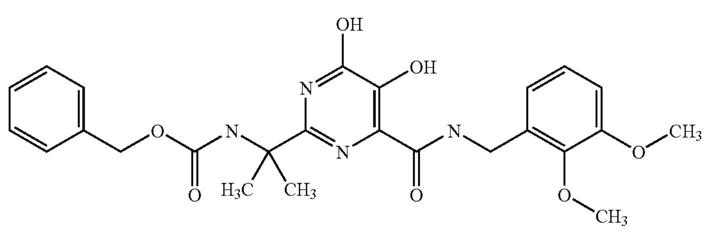 | benzyl 1-(4-{[(2,3-dimethoxybenzyl)amino]carbonyl}-5,6-dihydroxypyrimidin-2-yl)-1-methylethylcarbamate | 497 | A |
| 15 | 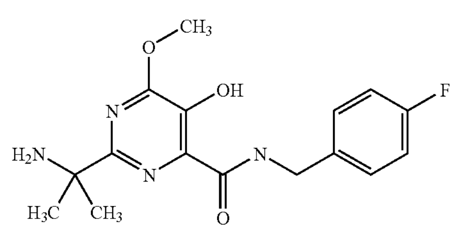 | 2-(1-amino-1-methylethyl)-N-(4-fluorobenzyl)-5-hydroxy-6-methoxypyrimidine-4-carboxamide | 335 | A* |
| 16 | 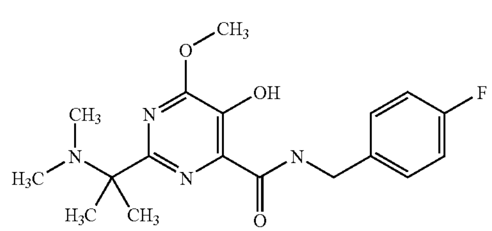 | 2-[1-(dimethylamino)-1-methylethyl]-N-(4-fluorobenzyl)-5-hydroxy-6-methoxypyrimidine-4-carboxamide | 363 | A |

TABLE 16

| | | | | |
|---|---|---|---|---|
| 1 | | N-(4-fluorobenzyl)-5,6-dihydroxy-2-(1-methyl-2,3-dihydro-1H-indol-2-yl)pyrimidine-4-carboxamide (TFA salt) | 395 | C |
| 2 | | N-(4-fluorobenzyl)-5,6-dihydroxy-2-{2-phenyl-1-[(pyridin-2-ylcarbonyl)amino]ethyl}pyrimidine-4-carboxamide (TFA salt) | 488 | I |
| 3 | | N-(4-fluorobenzyl)-5,6-dihydroxy-2-(2-methyl-1,2,3,4-tetrahydro-isoquinolin-3-yl)pyrimidine-4-carboxamide (TFA salt) | 409 | C |
| 4 | | 2-(2-benzoyl-1,2,3,4-tetrahydro-isoquinolin-3-yl)-N-(4-fluoro-benzyl)-5,6-dihydroxypyrimidine-4-carboxamide | 499 | I |
| 5 | | 2-[1-(N,N-dimethylglycyl)-2,3-dihydro-1H-indol-2-yl]-N-(4-fluorobenzyl)-5,6-dihydroxy-pyrimidine-4-carboxamide (TFA salt) | 466 | I |

TABLE 16-continued

| # | Structure | Name | MW | Act |
|---|---|---|---|---|
| 6 | 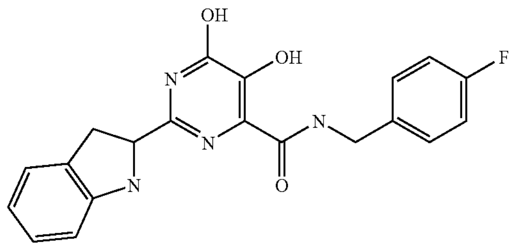 | 2-(2,3-dihydro-1H-indol-2-yl)-N-(4-fluorobenzyl)-5,6-dihydroxy-pyrimidine-4-carboxamide (TFA salt) | 381 | A* |
| 7 | 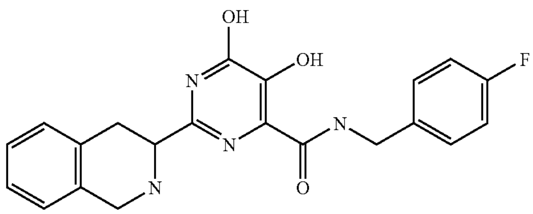 | N-(4-fluorobenzyl)-5,6-dihydroxy-2-(1,2,3,4-tetrahydroisoquinolin-3-yl)pyrimidine-4-carboxamide | 395 | A* |
| 8 | 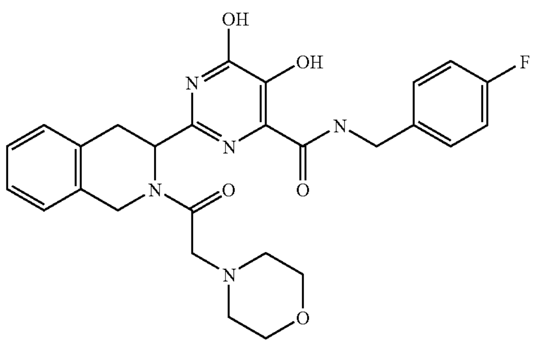 | N-(4-fluorobenzyl)-5,6-dihydroxy-2-[2-(morpholin-4-ylacetyl)-1,2,3,4-tetrahydroisoquinolin-3-yl]pyrimidine-4-carboxamide (TFA salt) | 522 | I |
| 9 | 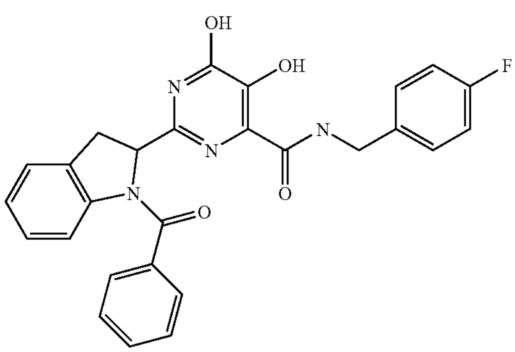 | 2-(1-benzoyl-2,3-dihydro-1H-indol-2-yl)-N-(4-fluorobenzyl)-5,6-dihydroxypyrimidine-4-carboxamide | 485 | I |
| 10 | 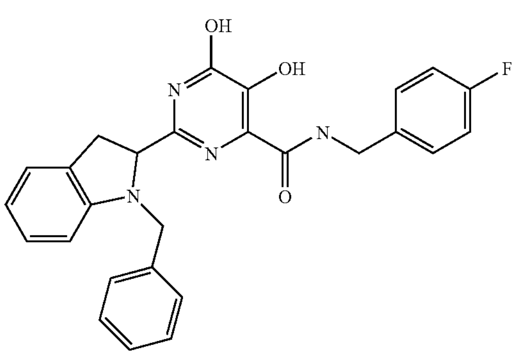 | 2-(1-benzyl-2,3-dihydro-1H-indol-2-yl)-N-(4-fluorobenzyl)-5,6-dihydroxypyrimidine-4-carboxamide (TFA salt) | 471 | C |

TABLE 16-continued

| 11 | 2-[1-(dimethylamino)-2-phenylethyl]-N-(4-fluorobenzyl)-5,6-dihydroxypyrimidine-4-carboxamide (TFA salt) | 411 | C |
| 12 | benzyl 2-(4-{[(4-fluorobenzyl)amino]carbonyl}-5,6-dihydroxy-pyrimidin-2-yl)indoline-1-carboxylate | 515 | A |
| 13 | 2-[2-(N,N-dimethylglycyl)-1,2,3,4-tetrahydroisoquinolin-3-yl]-N-(4-fluorobenzyl)-5,6-dihydroxy-pyrimidine-4-carboxamide (TFA salt) | 480 | I |
| 14 | tert-butyl 1-(4-{[(4-fluoro-benzyl)amino]carbonyl}-5,6-dihydroxypyrimidin-2-yl)-2-phenylethylcarbamate | 483 | A |

TABLE 16-continued

| 15 | | 2-{1-[(N,N-dimethylglycyl)amino]-2-phenylethyl}-N-(4-fluorobenzyl)-5,6-dihydroxypyrimidine-4-carboxamide | 468 | I |
|---|---|---|---|---|
| 16 | | 2-(1-amino-2-phenylethyl)-N-(4-fluorobenzyl)-5,6-dihydroxy-pyrimidine-4-carboxamide (TFA salt) | 383 | A* |

TABLE 17

| 1 | | benzyl 2-(4-{[(4-fluorobenzyl)-amino]carbonyl}-5,6-dihydroxy-pyrimidin-2-yl)piperidine-1-carboxylate | 481 | A |
|---|---|---|---|---|
| 2 | | N-(4-fluorobenzyl)-5,6-dihydroxy-2-[1-(methylsulfonyl)piperidin-2-yl]pyrimidine-4-carboxamide | 425 | I |
| 3 | | N-(4-fluorobenzyl)-5,6-dihydroxy-2-{1-[(4-methyl-1,2,3-thiadiazol-5-yl)carbonyl]piperidin-2-yl}pyrimidine-4-carboxamide (TFA salt) | 473 | I |

TABLE 17-continued

| | | | | |
|---|---|---|---|---|
| 4 | 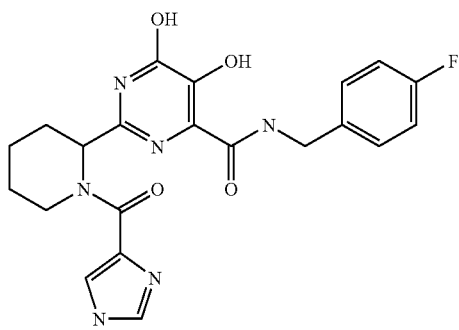 | N-(4-fluorobenzyl)-5,6-dihydroxy-2-[1-(1H-imidazol-4-ylcarbonyl)-piperidin-2-yl]pyrimidine-4-carboxamide (TFA salt) | 441 | I |
| 5 | 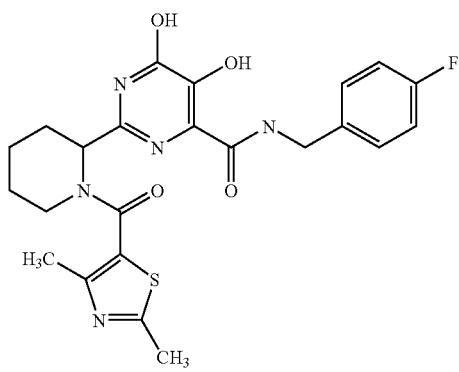 | 2-{1-[(2,4-dimethyl-1,3-thiazol-5-yl)carbonyl]piperidin-2-yl}-N-(4-fluorobenzyl)-5,6-dihydroxypyrimidine-4-carboxamide (TFA salt) | 486 | I |
| 6 | 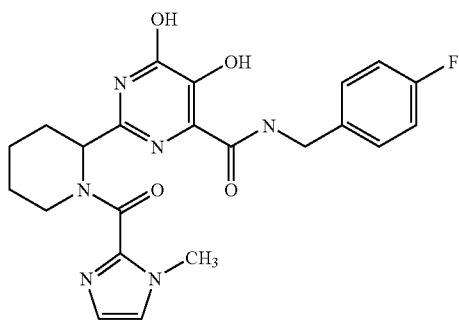 | N-(4-fluorobenzyl)-5,6-dihydroxy-2-{1-[(1-methyl-1H-imidazol-2-yl)carbonyl]piperidin-2-yl}pyrimidine-4-carboxamide (TFA salt) | 455 | I |
| 7 | 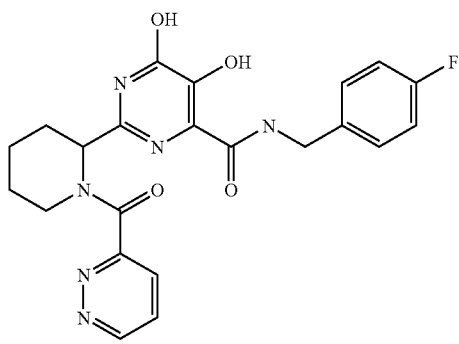 | N-(4-fluorobenzyl)-5,6-dihydroxy-2-[1-(pyridazin-3-ylcarbonyl)piperidin-2-yl]pyrimidine-4-carboxamide | 453 | I |

TABLE 17-continued
| | | | | |
|---|---|---|---|---|
| 8 | 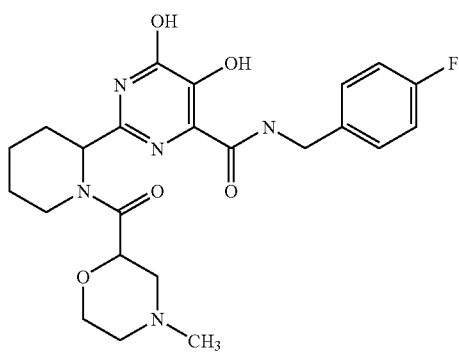 | N-(4-fluorobenzyl)-5,6-dihydroxy-2-{1-[(4-methylmorpholin-2-yl)carbonyl]piperidin-2-yl}pyrimidine-4-carboxamide | 474 | I |
| 9 | 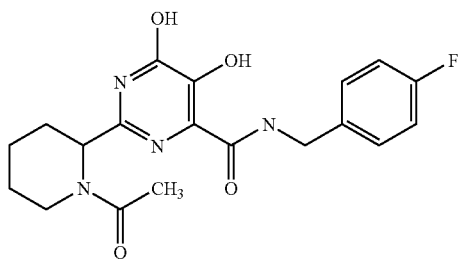 | 2-(1-acetylpiperidin-2-yl)-N-(4-fluorobenzyl)-5,6-dihydroxypyrimidine-4-carboxamide | 389 | I |
| 10 | 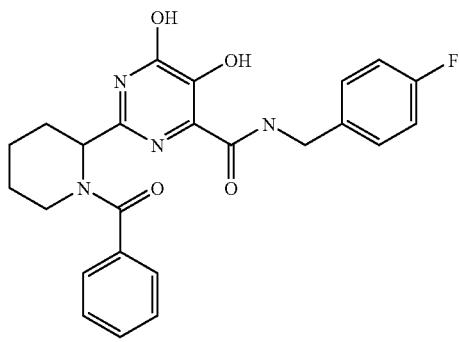 | 2-(1-benzoylpiperidin-2-yl)-N-(4-fluorobenzyl)-5,6-dihydroxypyrimidine-4-carboxamide | 451 | I |
| 11 | 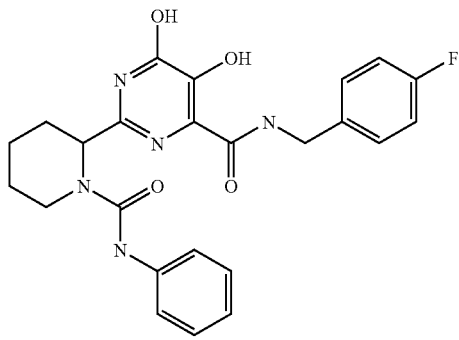 | 2-[1-(anilinocarbonyl)piperidin-2-yl]-N-(4-fluorobenzyl)-5,6-dihydroxypyrimidine-4-carboxamide | 466 | G |

TABLE 17-continued

| | | | | |
|---|---|---|---|---|
| 12 | (structure) | N-(4-fluorobenzyl)-5,6-dihydroxy-2-[1-(pyridin-2-ylcarbonyl)-piperidin-2-yl]pyrimidine-4-carboxamide (TFA salt) | 452 | I |
| 13 | (structure) | 2-[1-(1H-benzimidazol-5-ylcarbonyl)piperidin-2-yl]-N-(4-fluorobenzyl)-5,6-dihydroxypyrimidine-4-carboxamide (TFA salt) | 491 | I |
| 14 | (structure) | 2-{1-[(ethylamino)carbonyl]-piperidin-2-yl}-N-(4-fluorobenzyl)-5,6-dihydroxy-pyrimidine-4-carboxamide | 418 | G |
| 15 | (structure) | N-(4-fluorobenzyl)-2-(1-formylpiperidin-2-yl)-5,6-dihydroxypyrimidine-4-carboxamide | 375 | I |
| 16 | (structure) | N-(4-fluorobenzyl)-5,6-dihydroxy-2-piperidin-2-ylpyrimidine-4-carboxamide | 347 | A* |

TABLE 17-continued

| | | | | |
|---|---|---|---|---|
| 17 | 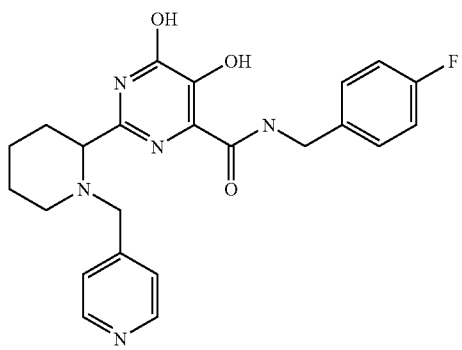 | N-(4-fluorobenzyl)-5,6-dihydroxy-2-[1-(pyridin-4-ylmethyl)piperidin-2-yl]pyrimidine-4-carboxamide (TFA salt) | 438 | D |
| 18 | 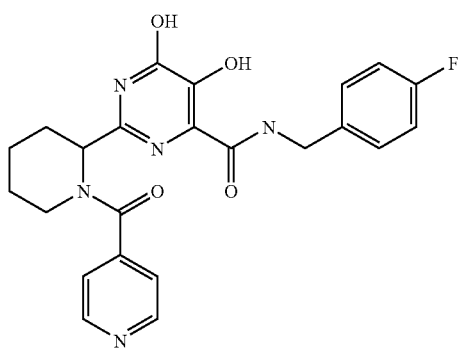 | N-(4-fluorobenzyl)-5,6-dihydroxy-2-(1-isonicotinoylpiperidin-2-yl)pyrimidine-4-carboxamide (TFA salt) | 452 | I |
| 19 | 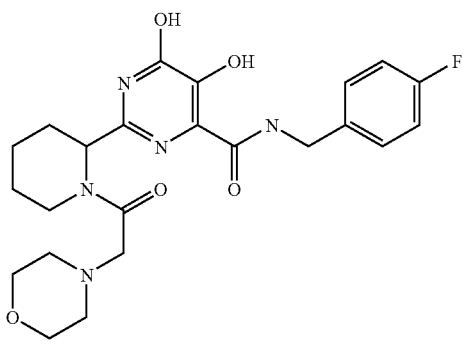 | N-(4-fluorobenzyl)-5,6-dihydroxy-2-[1-(morpholin-4-ylacetyl)piperidin-2-yl]pyrimidine-4-carboxamide (TFA salt) | 474 | I |
| 20 | 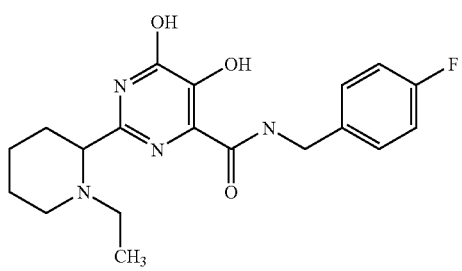 | 2-(1-ethylpiperidin-2-yl)-N-(4-fluorobenzyl)-5,6-dihydroxypyrimidine-4-carboxamide (TFA salt) | 375 | C |

TABLE 17-continued

| | | | | |
|---|---|---|---|---|
| 21 | 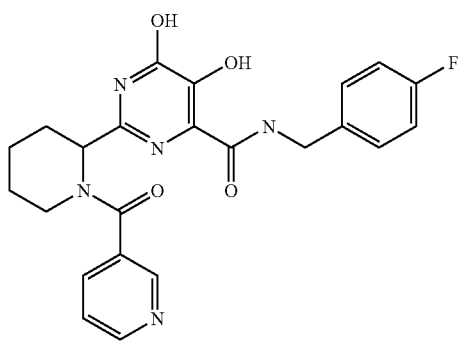 | N-(4-fluorobenzyl)-5,6-dihydroxy-2-[1-(pyridin-3-ylcarbonyl)piperidin-2-yl]pyrimidine-4-carboxamide (TFA salt) | 452 | I |
| 22 | 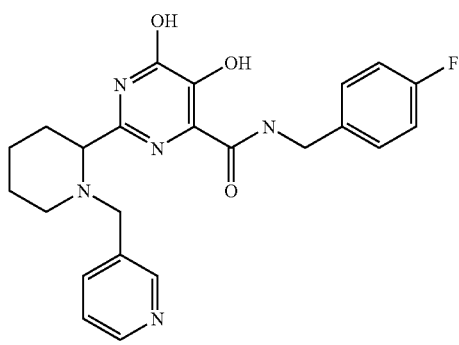 | N-(4-fluorobenzyl)-5,6-dihydroxy-2-[1-(pyridin-3-ylmethyl)piperidin-2-yl]pyrimidine-4-carboxamide (TFA salt) | 438 | D |
| 23 | 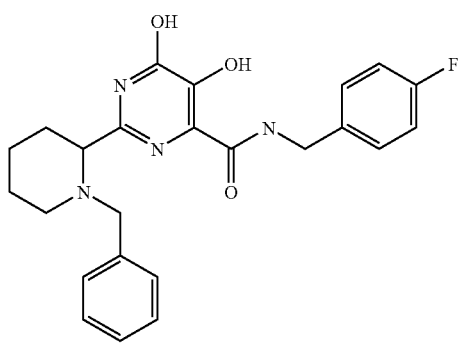 | 2-(1-benzylpiperidin-2-yl)-N-(4-fluorobenzyl)-5,6-dihydroxypyrimidine-4-carboxamide (TFA salt) | 437 | D |
| 24 | 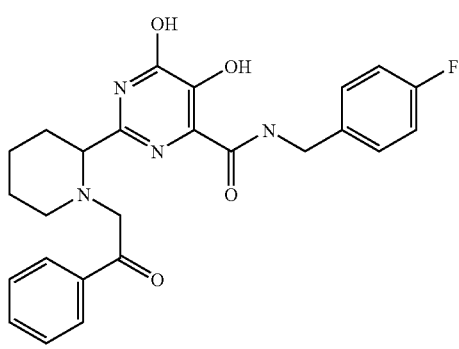 | N-(4-fluorobenzyl)-5,6-dihydroxy-2-[1-(2-oxo-2-phenylethyl)-piperidin-2-yl]pyrimidine-4-carboxamide (TFA salt) | 465 | D |

TABLE 17-continued

| | Structure | Name | MW | Cat |
|---|---|---|---|---|
| 25 | 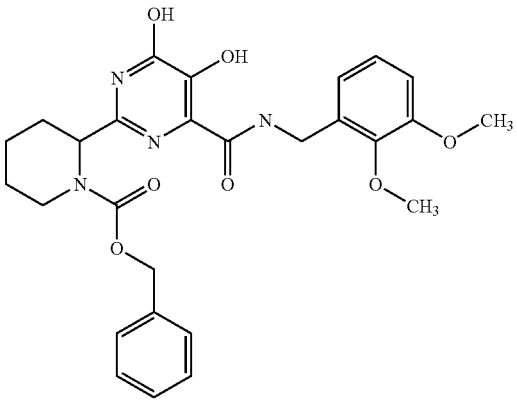 | benzyl 2-(4-{[(2,3-dimethoxybenzyl)amino]carbonyl}-5,6-dihydroxypyrimidin-2-yl)piperidine-1-carboxylate | 523 | A |
| 26 | 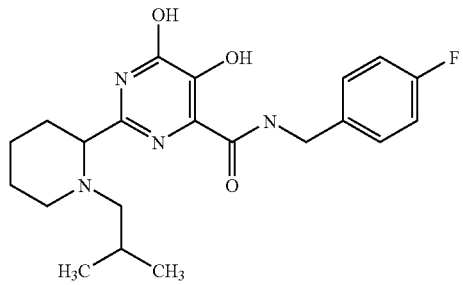 | N-(4-fluorobenzyl)-5,6-dihydroxy-2-(1-isobutylpiperidin-2-yl)-pyrimidine-4-carboxamide (TFA salt) | 403 | C |
| 27 | 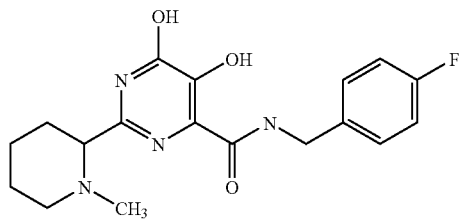 | N-(4-fluorobenzyl)-5,6-dihydroxy-2-(1-methylpiperidin-2-yl)pyrimidine-4-carboxamide (TFA salt) | 361 | D |
| 28 | 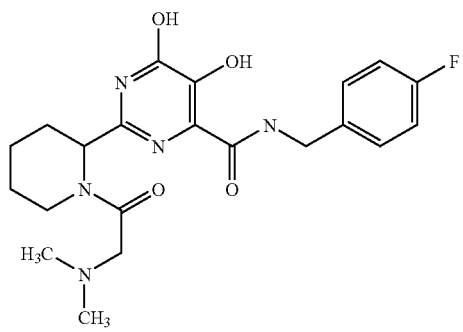 | 2-[1-(N,N-dimethylglycyl)piperidin-2-yl]-N-(4-fluorobenzyl)-5,6-dihydroxypyrimidine-4-carboxamide (TFA salt) | 432 | I |
| 29 | 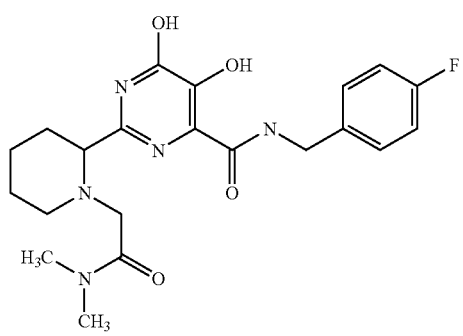 | 2-{1-[2-(dimethylamino)-2-oxoethyl]piperidin-2-yl}-N-(4-fluorobenzyl)-5,6-dihydroxy-pyrimidine-4-carboxamide (TFA salt) | 432 | D |

TABLE 17-continued

| | | | | |
|---|---|---|---|---|
| 30 | 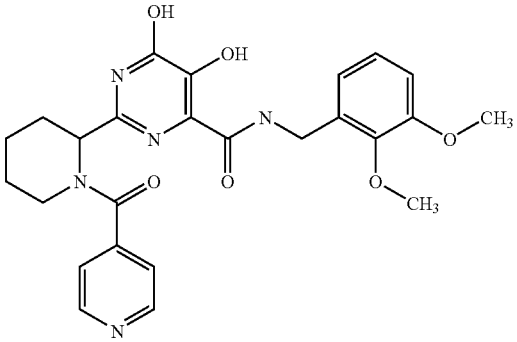 | N-(2,3-dimethoxybenzyl)-5,6-dihydroxy-2-(1-isonicotinoyl-piperidin-2-yl)pyrimidine-4-carboxamide (TFA salt) | 494 | I |
| 31 | 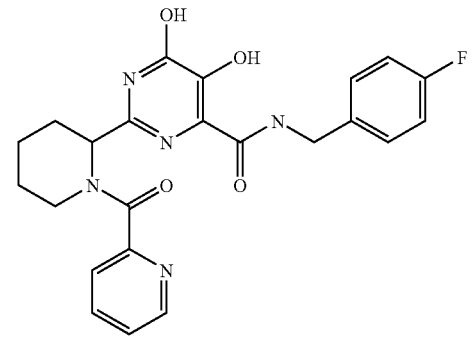 | N-(4-fluorobenzyl)-5,6-dihydroxy-2-[1-(pyridin-2-ylmethyl)piperidin-2-yl]pyrimidine-4-carboxamide (TFA salt) | 438 | D |
| 32 | 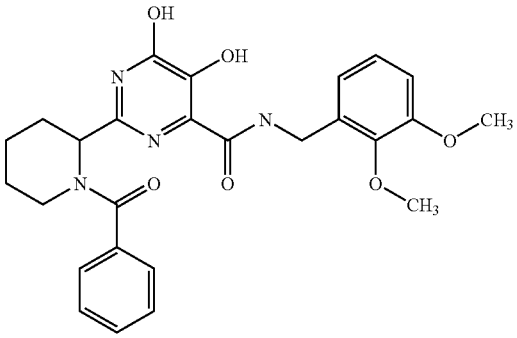 | 2-(1-benzylpiperidin-2-yl)-N-(2,3-dimethoxybenzyl)-5,6-dihydroxypyrimidine-4-carboxamide (TFA salt) | 479 | D |
| 33 | 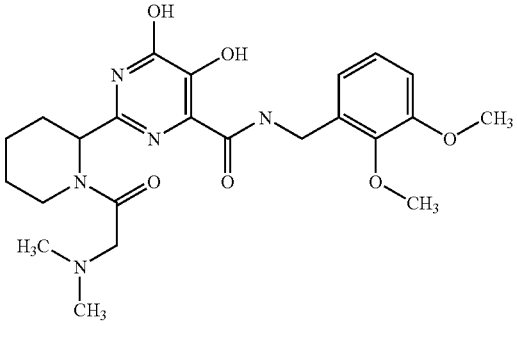 | N-(2,3-dimethoxybenzyl)-2-[1-(N,N-dimethylglycyl)piperidin-2-yl]-5,6-dihydroxypyrimidine-4-carboxamide (TFA salt) | 474 | I |
| 34 | 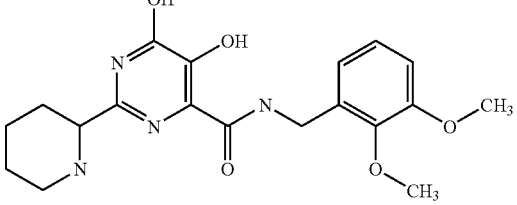 | N-(2,3-dimethoxybenzyl)-5,6-dihydroxy-2-piperidin-2-ylpyrimidine-4-carboxamide | 389 | A* |

TABLE 18

| | Structure | Name | MW | Activity |
|---|---|---|---|---|
| 1 | 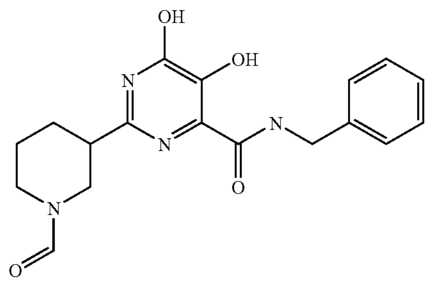 | N-benzyl-2-(1-formylpiperidin-3-yl)-5,6-dihydroxypyrimidine-4-carboxamide | 357 | I |
| 2 | 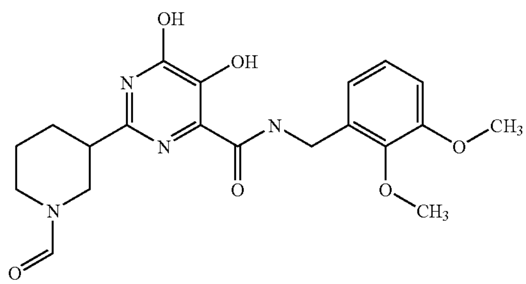 | N-(2,3-dimethoxybenzyl)-2-(1-formylpiperidin-3-yl)-5,6-dihydroxypyrimidine-4-carboxamide | 417 | I |
| 3 | 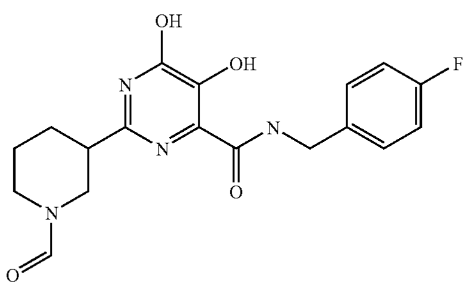 | N-(4-fluorobenzyl)-2-(1-formylpiperidin-3-yl)-5,6-dihydroxypyrimidine-4-carboxamide | 375 | I |
| 4 | 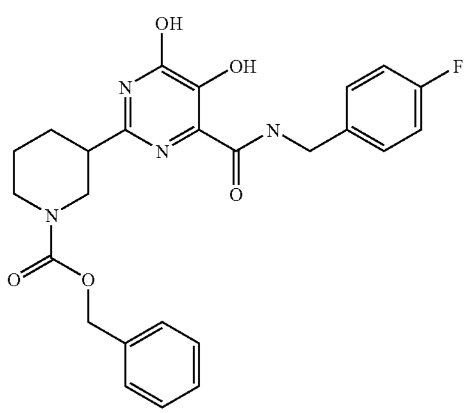 | benzyl 3-(4-{[(4-fluorobenzyl)amino]carbonyl}-5,6-dihydroxy-pyrimidin-2-yl)piperidine-1-carboxylate | 481 | A |
| 5 | 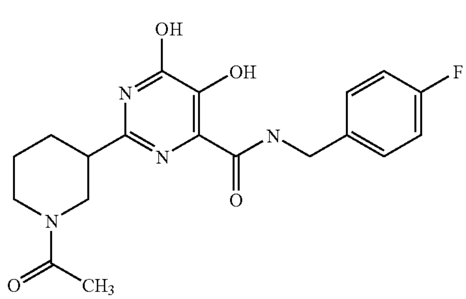 | 2-(1-acetylpiperidin-3-yl)-N-(4-fluorobenzyl)-5,6-dihydroxy-pyrimidine-4-carboxamide | 389 | I |

TABLE 18-continued

| 6 | 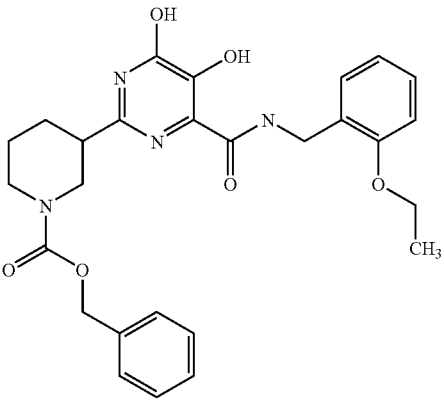 | benzyl 3-(4-{[(2-ethoxybenzyl)amino]carbonyl}-5,6-dihydroxy-pyrimidin-2-yl)piperidine-1-carboxylate | 507 | A |
| 7 | 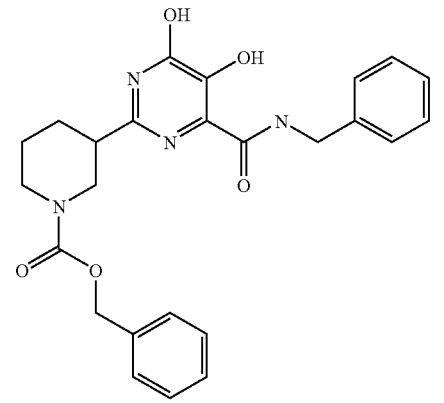 | benzyl 3-{4-[(benzylamino)carbonyl]-5,6-dihydroxypyrimidin-2-yl}piperidine-1-carboxylate | 463 | A |
| 8 | 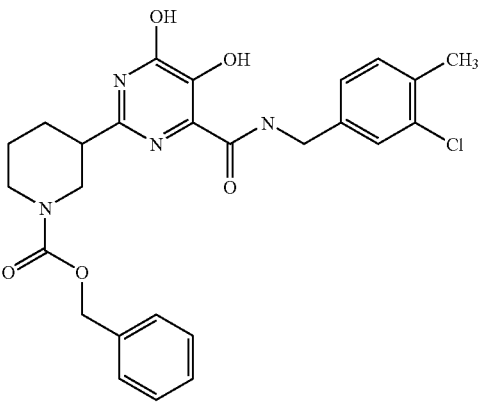 | benzyl 3-(4-{[(3-chloro-4-methylbenzyl)amino]carbonyl}-5,6-dihydroxypyrimidin-2-yl)piperidine-1-carboxylate | 511 | A |
| 9 | 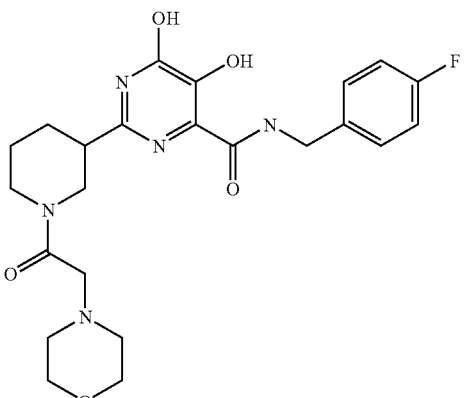 | N-(4-fluorobenzyl)-5,6-dihydroxy-2-[1-(morpholin-4-ylacetyl)piperidin-3-yl]pyrimidine-4-carboxamide (TFA salt) | 474 | I |

TABLE 18-continued
| 10 | 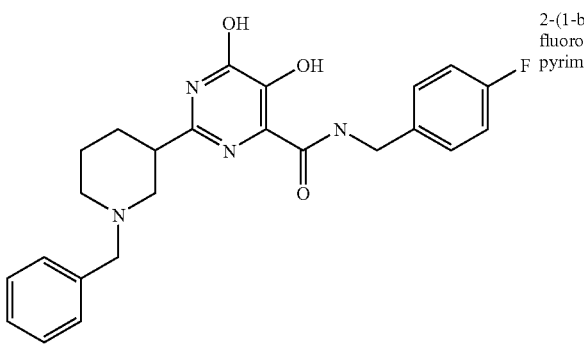 | 2-(1-benzylpiperidin-3-yl)-N-(4-fluorobenzyl)-5,6-dihydroxy-pyrimidine-4-carboxamide (TFA salt) | 437 | C |
| 11 | 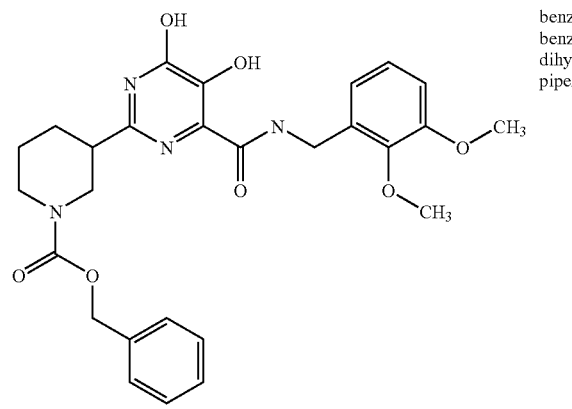 | benzyl 3-(4-{[(2,3-dimethoxy-benzyl)amino]carbonyl}-5,6-dihydroxypyrimidin-2-yl)piperidine-1-carboxylate | 523 | A |
| 12 | 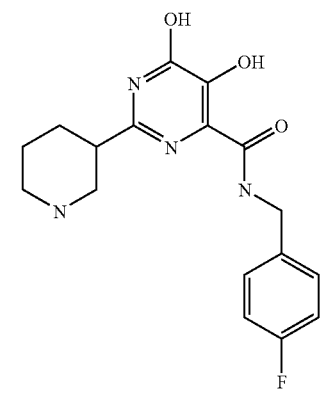 | N-(4-fluorobenzyl)-5,6-dihydroxy-2-piperidin-3-ylpyrimidine-4-carboxamide (TFA salt) | 347 | A* |
| 13 | 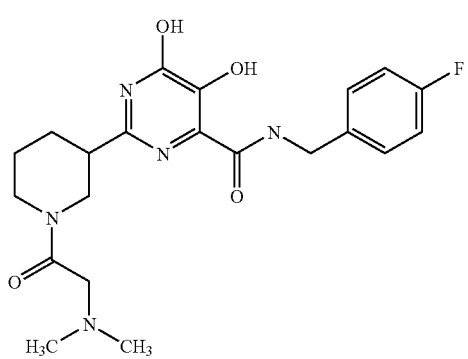 | 2-[1-(N,N-dimethylglycyl)piperidin-3-yl]-N-(4-fluorobenzyl)-5,6-dihydroxypyrimidine-4-carboxamide (TFA salt) | 432 | I |

TABLE 18-continued

| | | | | |
|---|---|---|---|---|
| 14 | 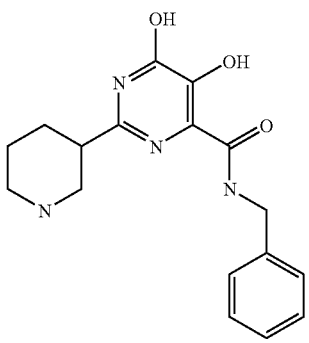 | N-benzyl-5,6-dihydroxy-2-piperidin-3-ylpyrimidine-4-carboxamide (TFA salt) | 329 | A* |
| 15 | 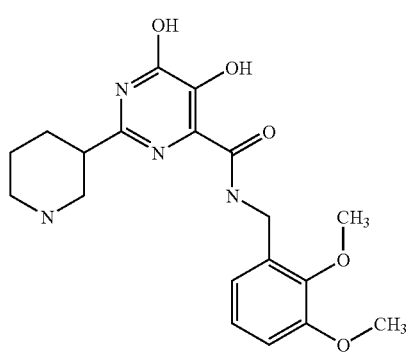 | N-(2,3-dimethoxybenzyl)-5,6-dihydroxy-2-piperidin-3-ylpyrimidine-4-carboxamide (TFA salt) | 389 | A* |

TABLE 19

| | | | | |
|---|---|---|---|---|
| 1 | 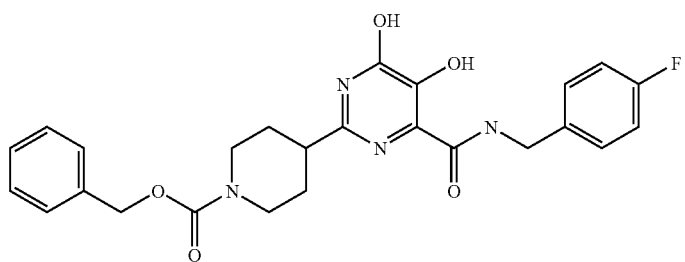 | benzyl 4-(4-{[(4-fluorobenzyl)amino]carbonyl}-5,6-dihydroxypyrimidin-2-yl)piperidine-1-carboxylate | 481 | A |
| 2 | 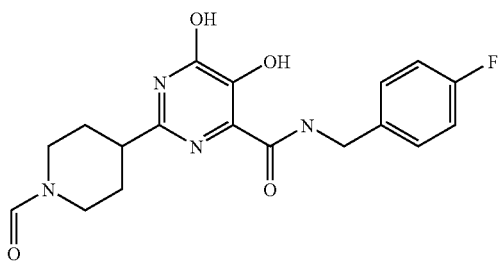 | N-(4-fluorobenzyl)-2-(1-formylpiperidin-4-yl)-5,6-dihydroxypyrimidine-4-carboxamide | 375 | I |
| 3 | 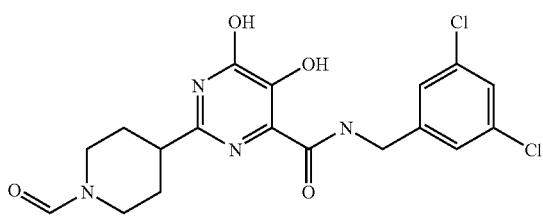 | N-(3,5-dichlorobenzyl)-2-(1-formylpiperidin-4-yl)-5,6-dihydroxypyrimidine-4-carboxamide | 425 | I |

TABLE 19-continued

| # | Structure | Name | MW | Cat |
|---|---|---|---|---|
| 4 | 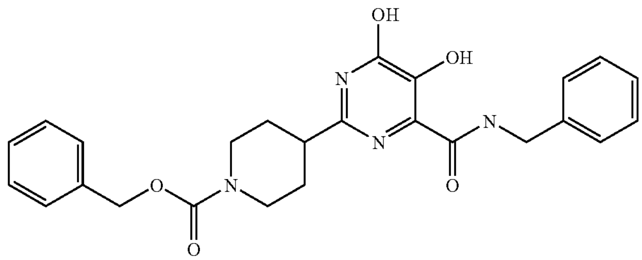 | benzyl 4-{4-[(benzylamino)carbonyl]-5,6-dihydroxypyrimidin-2-yl}piperidine-1-carboxylate | 463 | A |
| 5 | 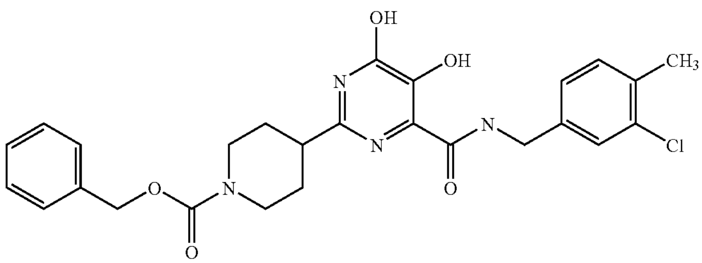 | benzyl 4-(4-{[(3-chloro-4-methylbenzyl)amino]carbonyl}-5,6-dihydroxypyrimidin-2-yl)piperidine-1-carboxylate | 511 | A |
| 6 | 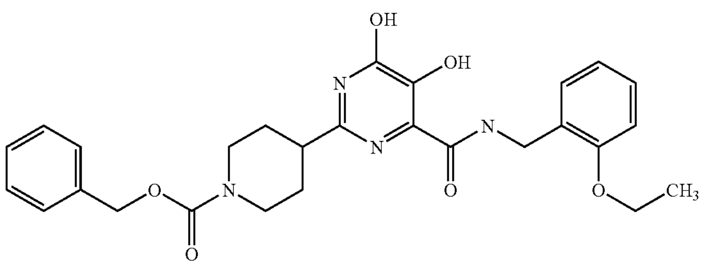 | benzyl 4-(4-{[(2-ethoxybenzyl)amino]carbonyl}-5,6-dihydroxy-pyrimidin-2-yl)piperidine-1-carboxylate | 507 | A |
| 7 | 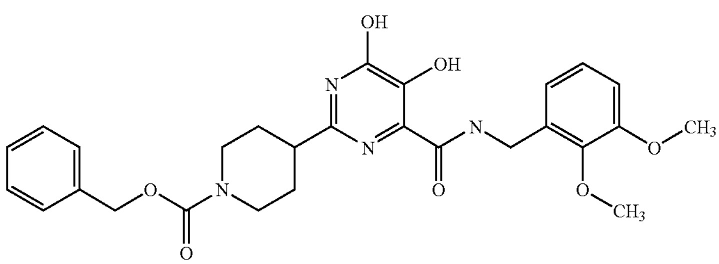 | benzyl 4-(4-{[(2,3-dimethoxybenzyl)amino]carbonyl}-5,6-dihydroxypyrimidin-2-yl)piperidine-1-carboxylate | 523 | A |
| 8 | 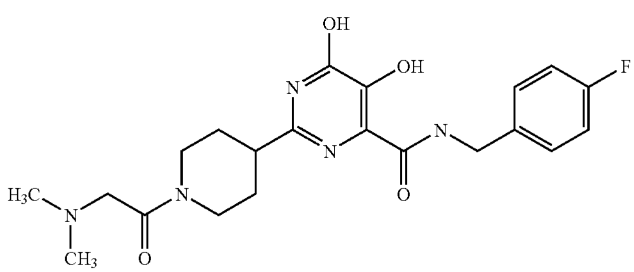 | 2-[1-(N,N-dimethylglycyl)piperidin-4-yl]-N-(4-fluorobenzyl)-5,6-dihydroxypyrimidine-4-carboxamide (TFA salt) | 432 | I |
| 9 | 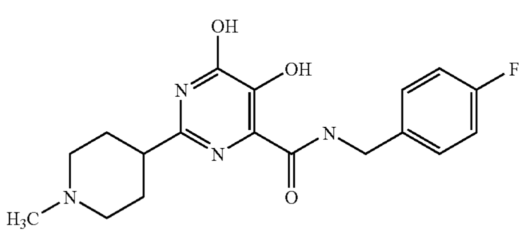 | N-(4-fluorobenzyl)-5,6-dihydroxy-2-(1-methylpiperidin-4-yl)pyrimidine-4-carboxamide (TFA salt) | 361 | C |

TABLE 19-continued

| 10 | [structure] | N-(4-fluorobenzyl)-5,6-dihydroxy-2-piperidin-4-ylpyrimidine-4-carboxamide (TFA salt) | 347 | A* |
| 11 | [structure] | N-(2,3-dimethoxybenzyl)-5,6-dihydroxy-2-piperidin-4-yl-pyrimidine-4-carboxamide (TFA salt) | 389 | A* |
| 12 | [structure] | N-benzyl-5,6-dihydroxy-2-piperidin-4-ylpyrimidine-4-carboxamide (TFA salt) | 329 | A* |

TABLE 20

| 1 | [structure] | N-(4-fluorobenzyl)-5,6-dihydroxy-2-(1,2,3,4-tetrahydroquinolin-2-yl)pyrimidine-4-carboxamide (TFA salt) | 395 | A* |

TABLE 20-continued

| 2 | [structure] | benzyl 2-(4-{[(4-fluorobenzyl)amino]carbonyl}-5,6-dihydroxy-pyrimidin-2-yl)-3,4-dihydro-quinoline-1(2H)-carboxylate | 529 | A |
| --- | --- | --- | --- | --- |
| 3 | [structure] | 2-(1-benzoyl-1,2,3,4-tetrahydro-quinolin-2-yl)-N-(4-fluorobenzyl)-5,6-dihydroxypyrimidine-4-carboxamide | 499 | I |
| 4 | [structure] | N-(4-fluorobenzyl)-5,6-dihydroxy-2-(1-methyl-1,2,3,4-tetrahydro-quinolin-2-yl)pyrimidine-4-carboxamide (TFA salt) | 409 | C |
| 5 | [structure] | N-(4-fluorobenzyl)-5,6-dihydroxy-2-[1-(pyridin-2-ylcarbonyl)-1,2,3,4-tetrahydroquinolin-2-yl]pyrimidine-4-carboxamide (TFA salt) | 500 | I |

TABLE 20-continued

| | Structure | Name | MW | Activity |
|---|---|---|---|---|
| 6 | 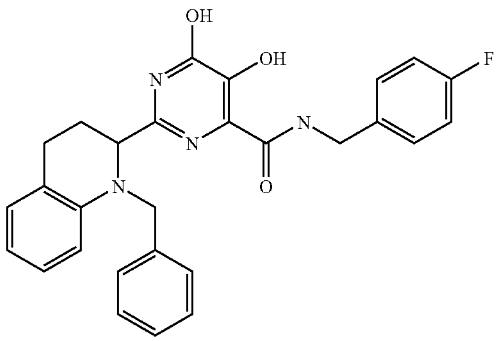 | 2-(1-benzyl-1,2,3,4-tetrahydro-quinolin-2-yl)-N-(4-fluorobenzyl)-5,6-dihydroxypyrimidine-4-carboxamide (TFA salt) | 485 | C |

TABLE 21

| | Structure | Name | MW | Activity |
|---|---|---|---|---|
| 1 | 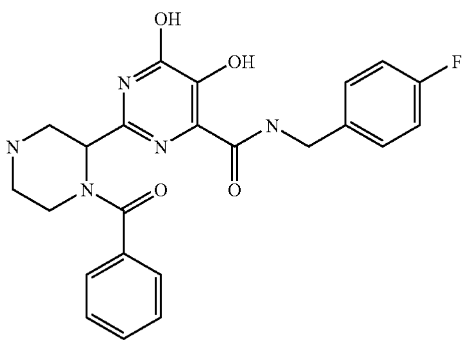 | 2-(1-benzoylpiperazin-2-yl)-N-(4-fluorobenzyl)-5,6-dihydroxy-pyrimidine-4-carboxamide (TFA salt) | 452 | A* |
| 2 | 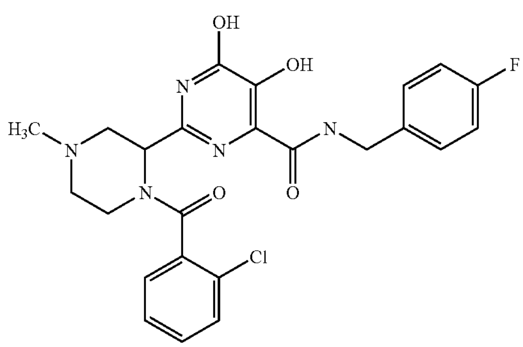 | 2-[1-(2-chlorobenzoyl)-4-methylpiperazin-2-yl]-N-(4-fluorobenzyl)-5,6-dihydroxy-pyrimidine-4-carboxamide (HCl salt) | 500 | I |
| 3 | 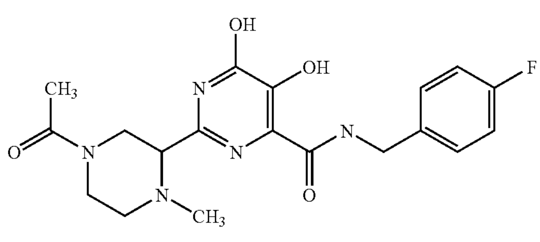 | 2-(4-acetyl-1-methylpiperazin-2-yl)-N-(4-fluorobenzyl)-5,6-dihydroxy-pyrimidine-4-carboxamide (TFA salt) | 404 | I |
| 4 | 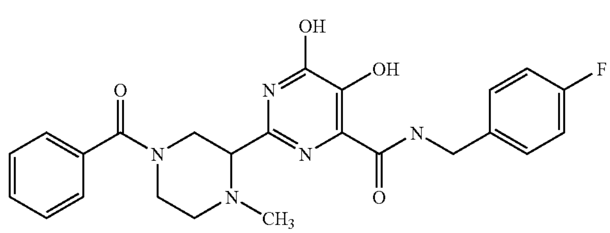 | 2-(4-benzoyl-1-methylpiperazin-2-yl)-N-(4-fluorobenzyl)-5,6-dihydroxypyrimidine-4-carboxamide (TFA salt) | 466 | I |

TABLE 21-continued

| | Structure | Name | MW | Class |
|---|---|---|---|---|
| 5 | 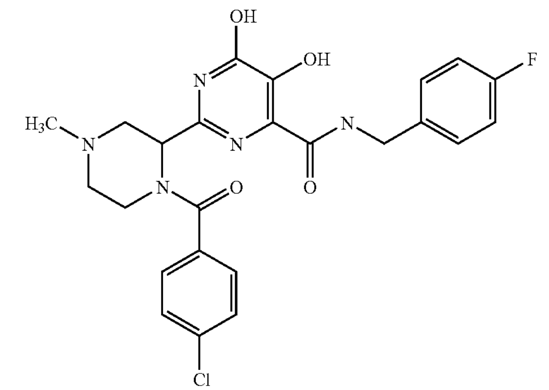 | 2-[1-(4-chlorobenzoyl)-4-methylpiperazin-2-yl]-N-(4-fluorobenzyl)-5,6-dihydroxy-pyrimidine-4-carboxamide (TFA salt) | 500 | I |
| 6 | 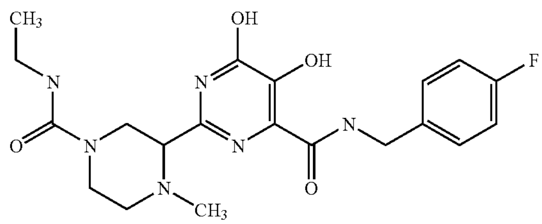 | 2-{4-[(ethylamino)carbonyl]-1-methylpiperazin-2-yl}-N-(4-fluorobenzyl)-5,6-dihydroxy-pyrimidine-4-carboxamide (TFA salt) | 433 | G |
| 7 | 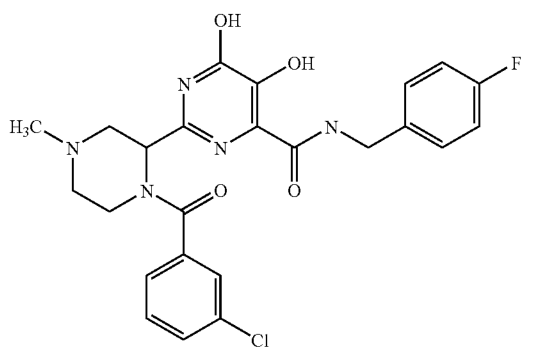 | 2-[1-(3-chlorobenzoyl)-4-methyl-piperazin-2-yl]-N-(4-fluorobenzyl)-5,6-dihydroxypyrimidine-4-carboxamide (TFA salt) | 500 | I |
| 8 | 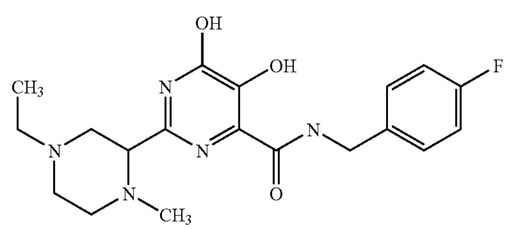 | 2-(4-ethyl-1-methylpiperazin-2-yl)-N-(4-fluorobenzyl)-5,6-dihydroxy-pyrimidine-4-carboxamide (TFA salt) | 390 | C |
| 9 | 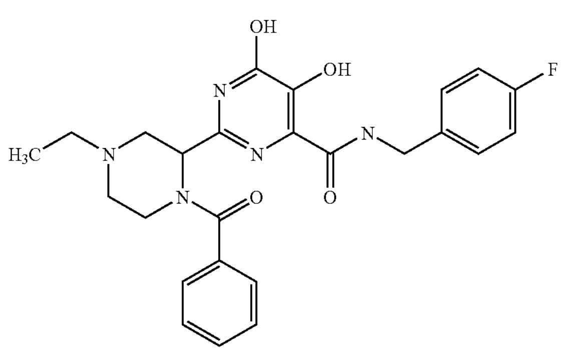 | 2-(1-benzoyl-4-ethylpiperazin-2-yl)-N-(4-fluorobenzyl)-5,6-dihydroxy-pyrimidine-4-carboxamide (TFA salt) | 480 | C |

TABLE 21-continued

| # | Structure | Name | MW | Class |
|---|---|---|---|---|
| 10 | 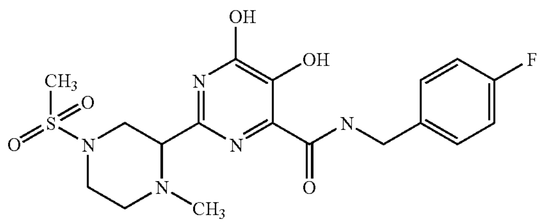 | N-(4-fluorobenzyl)-5,6-dihydroxy-2-[1-methyl-4-(methylsulfonyl)piperazin-2-yl]pyrimidine-4-carboxamide (TFA salt) | 440 | I |
| 11 | 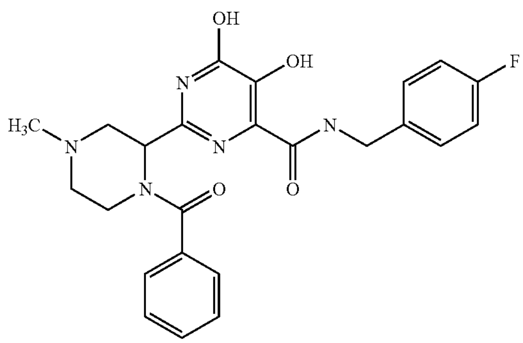 | 2-(1-benzoyl-4-methylpiperazin-2-yl)-N-(4-fluorobenzyl)-5,6-dihydroxypyrimidine-4-carboxamide (TFA salt) | 466 | I |
| 12 | 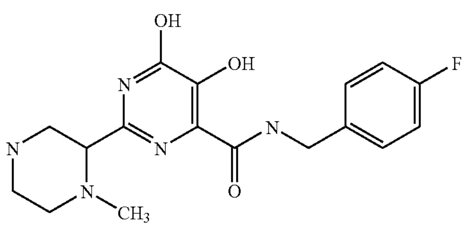 | N-(4-fluorobenzyl)-5,6-dihydroxy-2-(1-methylpiperazin-2-yl)pyrimidine-4-carboxamide (TFA salt) | 362 | A* |
| 13 | 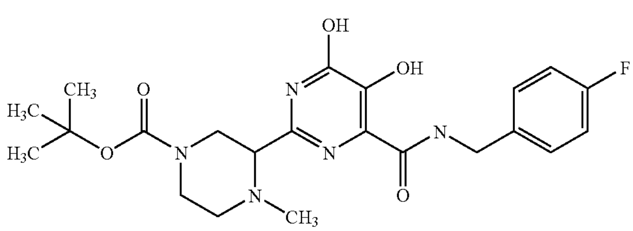 | tert-butyl 3-(4-{[(4-fluorobenzyl)amino]carbonyl}-5,6-dihydroxy-pyrimidin-2-yl)-4-methylpiperazine-1-carboxylate (TFA salt) | 462 | C |
| 14 | 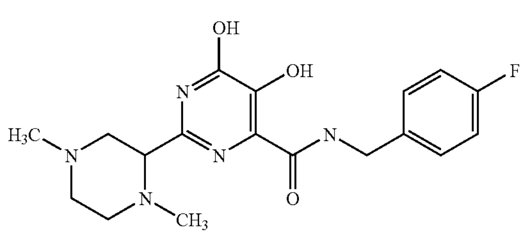 | 2-(1,4-dimethylpiperazin-2-yl)-N-(4-fluorobenzyl)-5,6-dihydroxy-pyrimidine-4-carboxamide (TFA salt) | 376 | C |
| 15 | 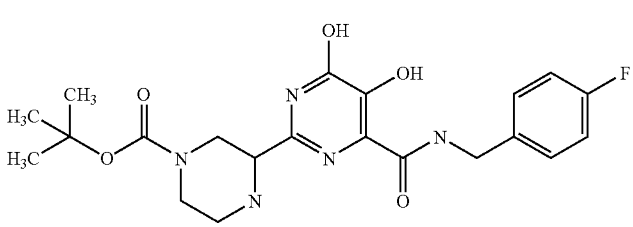 | tert-butyl 3-(4-{[(4-fluorobenzyl)amino]carbonyl}-5,6-dihydroxy-pyrimidin-2-yl)piperazine-1-carboxylate (TFA salt) | 448 | A* |

| | | | | |
|---|---|---|---|---|
| 16 | | 2-[1-benzoyl-4-(N,N-dimethyl-glycyl)piperazin-2-yl]-N-(4-fluoro-benzyl)-5,6-dihydroxypyrimidine-4-carboxamide (TFA salt) | 537 | I |
| 17 | | 2-(4-benzyl-1-methylpiperazin-2-yl)-N-(4-fluorobenzyl)-5,6-dihydroxy-pyrimidine-4-carboxamide (TFA salt) | 452 | C |
| 18 | | 2-(1-benzoyl-4-isopropylpiperazin-2-yl)-N-(4-fluorobenzyl)-5,6-dihydroxypyrimidine-4-carboxamide (TFA salt) | 494 | C |
| 19 | | N-(4-fluorobenzyl)-5,6-dihydroxy-2-(1-isopropyl-4-methylpiperazin-2-yl)pyrimidine-4-carboxamide (TFA salt) | 404 | C |
| 20 | | benzyl 2-(4-{[(4-fluorobenzyl)amino]carbonyl}-5,6-dihydroxy-pyrimidin-2-yl)piperazine-1-carboxylate (TFA salt) | 482 | A* |

TABLE 21-continued

| # | Structure | Name | MS | |
|---|---|---|---|---|
| 21 | 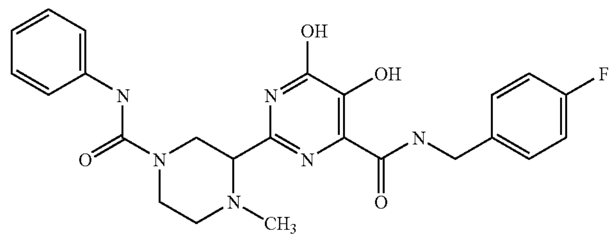 | 2-[4-(anilinocarbonyl)-1-methyl-piperazin-2-yl]-N-(4-fluorobenzyl)-5,6-dihydroxypyrimidine-4-carboxamide (TFA salt) | 481 | G |
| 22 | 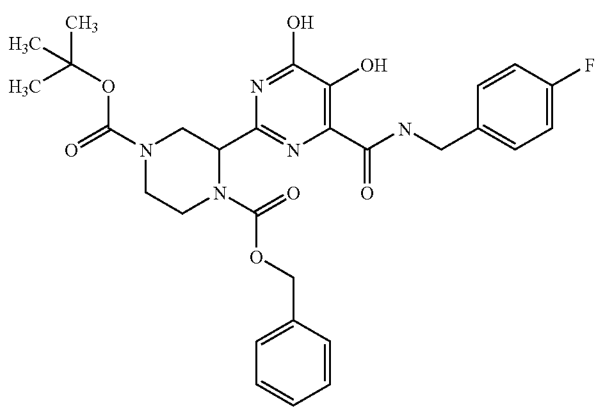 | 1-benzyl 4-tert-butyl 2-(4-{[(4-fluorobenzyl)amino]carbonyl}-5,6-dihydroxypyrimidin-2-yl)piperazine-1,4-dicarboxylate | 580 (M−) | A |
| 23 | 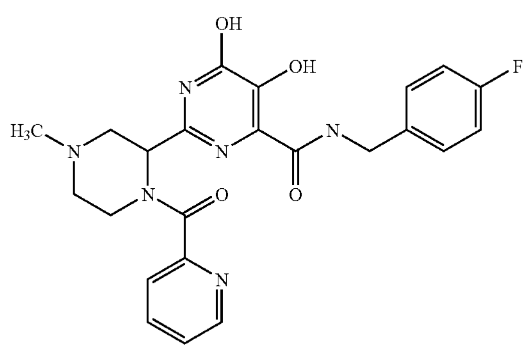 | N-(4-fluorobenzyl)-5,6-dihydroxy-2-[4-methyl-1-(pyridin-2-ylcarbonyl)piperazin-2-yl]pyrimidine-4-carboxamide (TFA salt) | 467 | C |
| 24 | 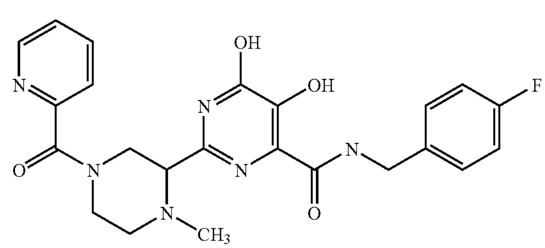 | N-(4-fluorobenzyl)-5,6-dihydroxy-2-[1-methyl-4-(pyridin-2-ylcarbonyl)piperazin-2-yl]pyrimidine-4-carboxamide (TFA salt) | 467 | I |
| 25 | 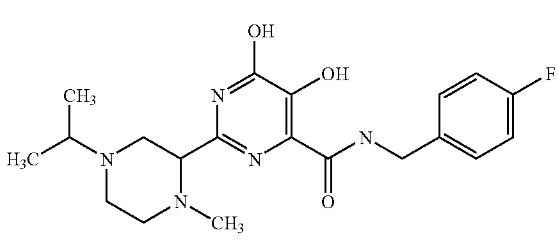 | N-(4-fluorobenzyl)-5,6-dihydroxy-2-(4-isopropyl-1-methylpiperazin-2-yl)pyrimidine-4-carboxamide (TFA salt) | 404 | C |

TABLE 21-continued

| # | Structure | Name | MW | Activity |
|---|---|---|---|---|
| 26 | 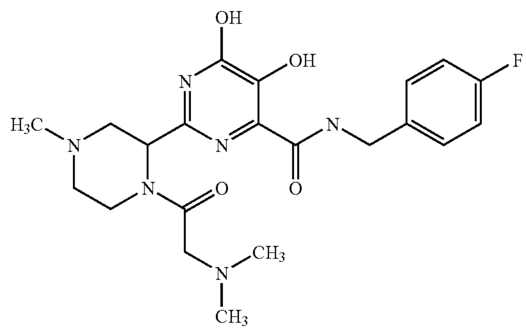 | 2-[1-(N,N-dimethylglycyl)-4-methylpiperazin-2-yl]-N-(4-fluorobenzyl)-5,6-dihydroxy-pyrimidine-4-carboxamide (TFA salt) | 447 | I |
| 27 | 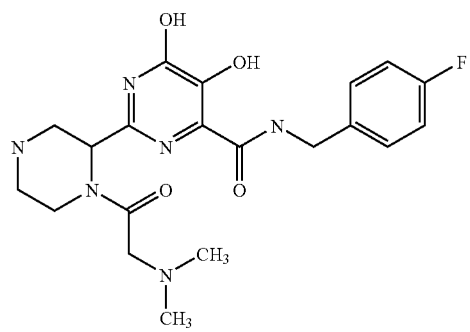 | 2-[1-(N,N-dimethylglycyl)piperazin-2-yl]-N-(4-fluorobenzyl)-5,6-dihydroxypyrimidine-4-carboxamide (TFA salt) | 433 | A* |
| 28 | 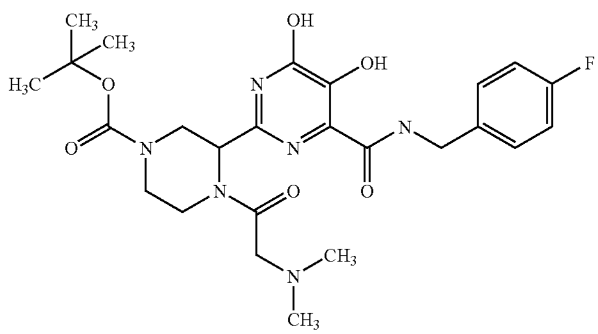 | tert-butyl 4-(N,N-dimethylglycyl)-3-(4-{[(4-fluorobenzyl)amino]carbonyl}-5,6-dihydroxypyrimidin-2-yl)piperazine-1-carboxylate (TFA salt) | 533 | I |
| 29 | 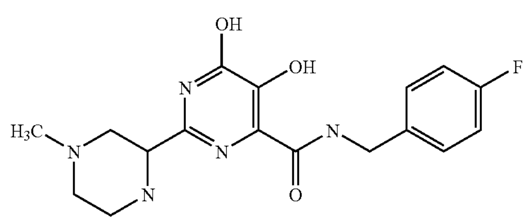 | N-(4-fluorobenzyl)-5,6-dihydroxy-2-(4-methylpiperazin-2-yl)pyrimidine-4-carboxamide (TFA salt) | 362 | A* |
| 30 | 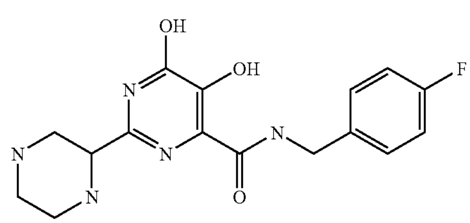 | N-(4-fluorobenzyl)-5,6-dihydroxy-2-piperazin-2-ylpyrimidine-4-carboxamide (TFA salt) | 348 | A* |

TABLE 22

| | Structure | Name | MW | Activity |
|---|---|---|---|---|
| 1 | 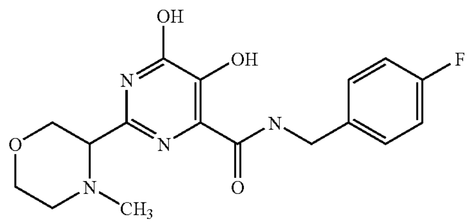 | N-(4-fluorobenzyl)-5,6-dihydroxy-2-(4-methylmorpholin-3-yl)pyrimidine-4-carboxamide (TFA salt) | 363 | C |
| 2 | 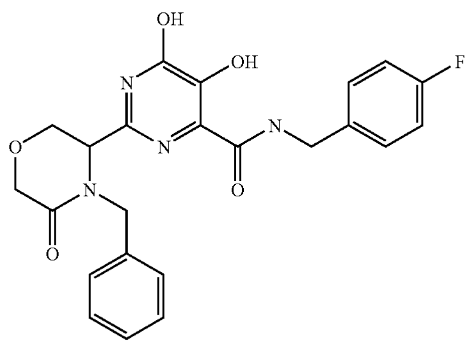 | 2-(4-benzyl-5-oxomorpholin-3-yl)-N-(4-fluorobenzyl)-5,6-dihydroxypyrimidine-4-carboxamide | 453 | A |
| 3 | 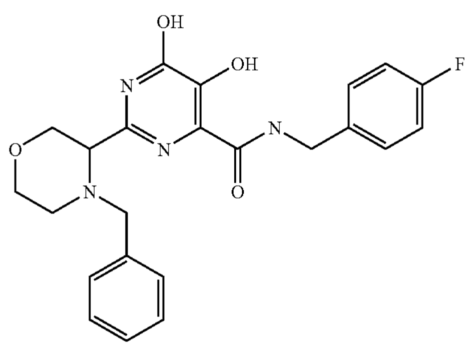 | 2-(4-benzylmorpholin-3-yl)-N-(4-fluorobenzyl)-5,6-dihydroxy-pyrimidine-4-carboxamide (TFA salt) | 439 | C |
| 4 | 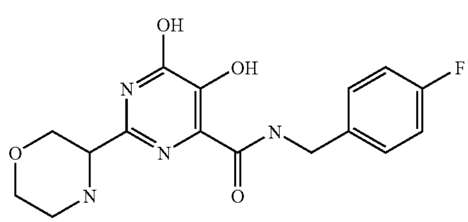 | N-(4-fluorobenzyl)-5,6-dihydroxy-2-morpholin-3-ylpyrimidine-4-carboxamide (TFA salt) | 349 | A* |

TABLE 23

| | Structure | Name | MW | Activity |
|---|---|---|---|---|
| 1 | Chiral | 2-[(2S,4R)-4-(benzyloxy)-1-methylpyrrolidin-2-yl]-N-(4-fluorobenzyl)-5,6-dihydroxy-pyrimidine-4-carboxamide (TFA salt) | 453 | A |

TABLE 23-continued

| # | Structure | | Name | MW | Activity |
|---|---|---|---|---|---|
| 2 | (structure) | Chiral | 2-[(2S,4R)-1-benzoyl-4-hydroxy-pyrrolidin-2-yl]-N-(4-fluorobenzyl)-5,6-dihydroxy-pyrimidine-4-carboxamide | 453 | I |
| 3 | (structure) | Chiral | N-(4-fluorobenzyl)-5,6-dihydroxy-2-[(2S,4R)-4-hydroxy-1-methyl-pyrrolidin-2-yl]pyrimidine-4-carboxamide (TFA salt) | 363 | A* |
| 4 | (structure) | Chiral | 2-[(2S,4R)-1-benzyl-4-(benzyloxy)-pyrrolidin-2-yl]-N-(4-fluorobenzyl)-5,6-dihydroxypyrimidine-4-carboxamide | 529 | C |
| 5 | (structure) | | 2-(1-benzoylpyrrolidin-2-yl)-N-(4-fluorobenzyl)-5,6-dihydroxy-pyrimidine-4-carboxamide | 437 | I |

TABLE 23-continued

| | Structure | | Name | MW | Activity |
|---|---|---|---|---|---|
| 6 | 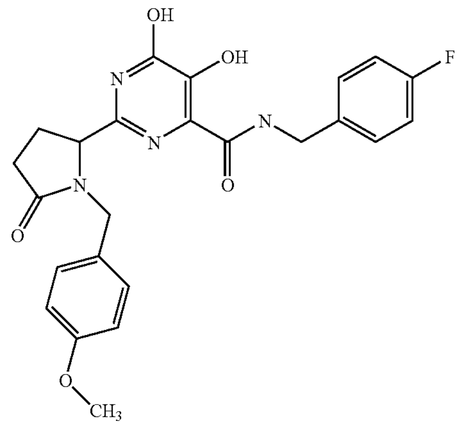 | | N-(4-fluorobenzyl)-5,6-dihydroxy-2-[1-(4-methoxybenzyl)-5-oxo-pyrrolidin-2-yl]pyrimidine-4-carboxamide | 467 | A |
| 7 | 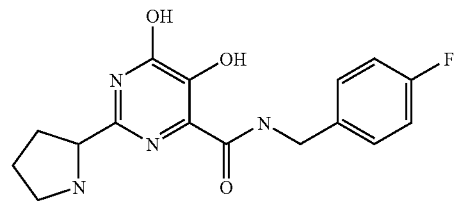 | | N-(4-fluorobenzyl)-5,6-dihydroxy-2-pyrrolidin-2-ylpyrimidine-4-carboxamide (TFA salt) | 333 | A* |
| 8 | 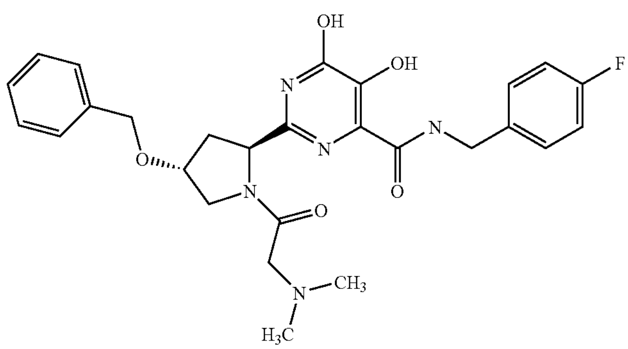 | Chiral | 2-[(2S,4R)-4-(benzyloxy)-1-(N,N-dimethylglycyl)pyrrolidin-2-yl]-N-(4-fluorobenzyl)-5,6-dihydroxy-pyrimidine-4-carboxamide (TFA salt) | 524 | I |
| 9 | 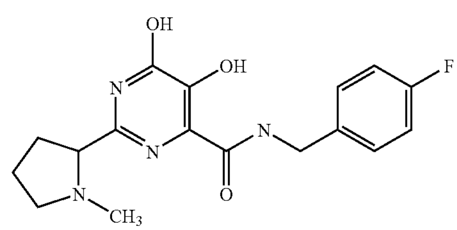 | | N-(4-fluorobenzyl)-5,6-dihydroxy-2-(1-methylpyrrolidin-2-yl)pyrimidine-4-carboxamide (TFA salt) | 347 | D |
| 10 | 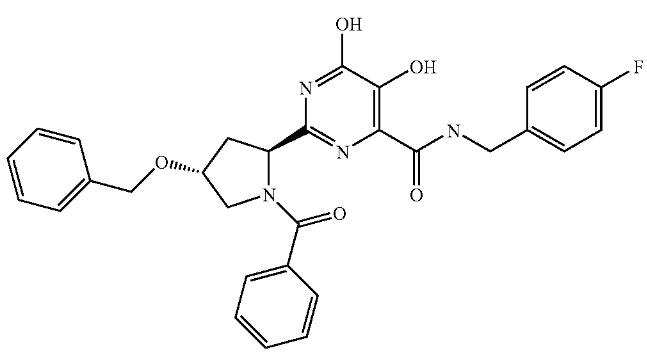 | Chiral | 2-[(2S,4R)-1-benzoyl-4-(benzyloxy)pyrrolidin-2-yl]-N-(4-fluorobenzyl)-5,6-dihydroxypyrimidine-4-carboxamide | 543 | I |

TABLE 23-continued

| 11 | 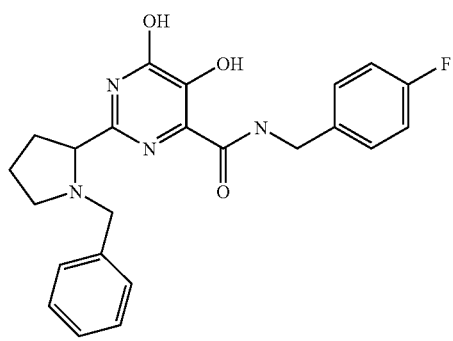 | 2-(1-benzylpyrrolidin-2-yl)-N-(4-fluorobenzyl)-5,6-dihydroxy-pyrimidine-4-carboxamide (TFA salt) | 423 | D |
| --- | --- | --- | --- | --- |
| 12 | 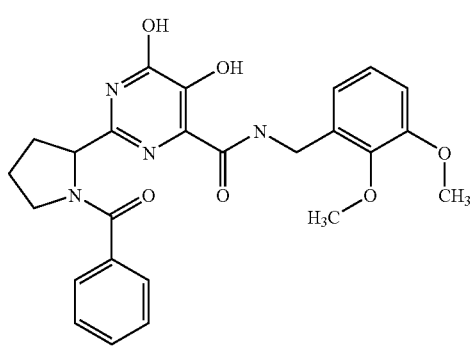 | 2-(1-benzoylpyrrolidin-2-yl)-N-(2,3-dimethoxybenzyl)-5,6-dihydroxy-pyrimidine-4-carboxamide | 479 | I |
| 13 | 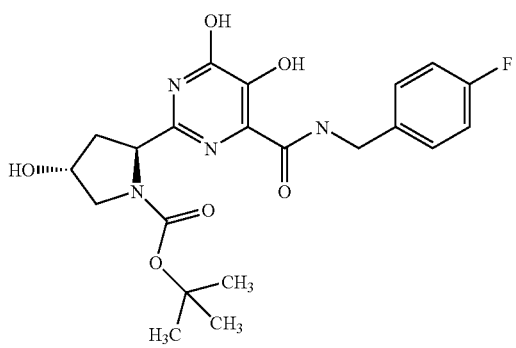 | tert-butyl (2S,4R)-2-(4-{[(4-fluorobenzyl)amino]carbonyl}-5,6-dihydroxypyrimidin-2-yl)-4-hydroxypyrrolidine-1-carboxylate | 449 | A* |
| 14 | 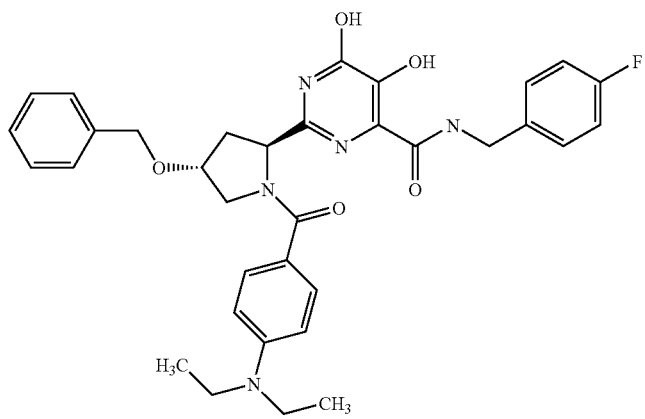 | Chiral 2-{(2S,4R)-4-(benzyloxy)-1-[4-(diethylamino)benzoyl]pyrrolidin-2-yl}-N-(4-fluorobenzyl)-5,6-dihydroxypyrimidine-4-carboxamide | 614 | I |

TABLE 23-continued

| | Structure | Name | MW | Activity |
|---|---|---|---|---|
| 15 | | N-(4-fluorobenzyl)-5,6-dihydroxy-2-[(2S,4R)-4-hydroxypyrrolidin-2-yl]-pyrimidine-4-carboxamide (TFA salt) | 349 | A* |
| 16 | | 2-[1-(N,N-dimethylglycyl)pyrrolidin-2-yl]-N-(4-fluorobenzyl)-5,6-dihydroxypyrimidine-4-carboxamide (TFA salt) | 418 | I |
| 17 | | 2-{1-[2-(dimethylamino)-2-oxo-ethyl]pyrrolidin-2-yl}-N-(4-fluorobenzyl)-5,6-dihydroxy-pyrimidine-4-carboxamide (TFA salt) | 418 | D |
| 18 | Chiral | tert-butyl (2S,4R)-4-(benzyloxy)-2-(4-{[(4-fluorobenzyl)amino]carbonyl}-5,6-dihydroxypyrimidin-2-yl)pyrrolidine-1-carboxylate | 539 | A |
| 19 | Chiral | 2-[(2S,4R)-4-(benzyloxy)pyrrolidin-2-yl]-N-(4-fluorobenzyl)-5,6-dihydroxypyrimidine-4-carboxamide (HCl salt) | 439 | A* |

TABLE 24

| # | Structure | Name | MW | Grade |
|---|---|---|---|---|
| 1 | 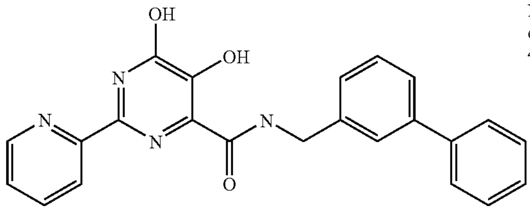 | N-(1,1'-biphenyl-3-ylmethyl)-5,6-dihydroxy-2-pyridin-2-ylpyrimidine-4-carboxamide (HCl salt) | 399 | A |
| 2 | 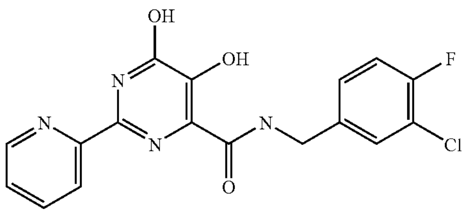 | N-(3-chloro-4-fluorobenzyl)-5,6-dihydroxy-2-pyridin-2-ylpyrimidine-4-carboxamide (HCl salt) | 375 | A |
| 3 | 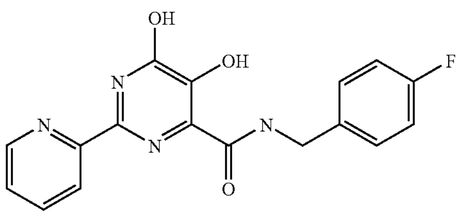 | N-(4-fluorobenzyl)-5,6-dihydroxy-2-pyridin-2-ylpyrimidine-4-carboxamide (HCl salt) | 341 | A |
| 4 | 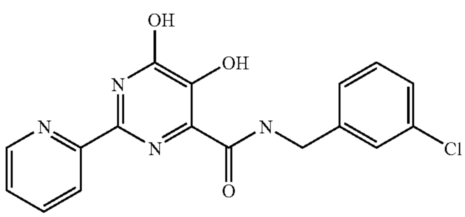 | N-(3-chlorobenzyl)-5,6-dihydroxy-2-pyridin-2-ylpyrimidine-4-carboxamide (HCl salt) | 357 | A |
| 5 | 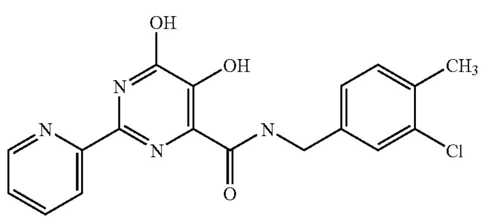 | N-(3-chloro-4-methylbenzyl)-5,6-dihydroxy-2-pyridin-2-ylpyrimidine-4-carboxamide (HCl salt) | 371 | A |
| 6 | 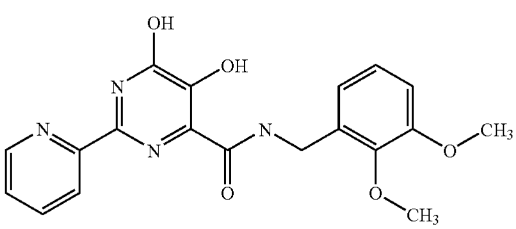 | N-(2,3-dimethoxybenzyl)-5,6-dihydroxy-2-pyridin-2-ylpyrimidine-4-carboxamide (HCl salt) | 383 | A |
| 7 | 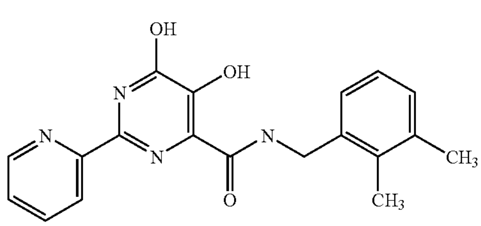 | N-(2,3-dimethylbenzyl)-5,6-dihydroxy-2-pyridin-2-ylpyrimidine-4-carboxamide (HCl salt) | 351 | A |

TABLE 24-continued

| # | Structure | Name | M+1 | Procedure |
|---|---|---|---|---|
| 8 | 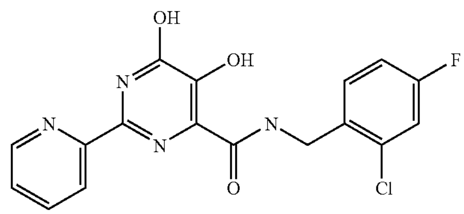 | N-(2-chloro-4-fluorobenzyl)-5,6-dihydroxy-2-pyridin-2-ylpyrimidine-4-carboxamide (HCl salt) | 375 | A |
| 9 | 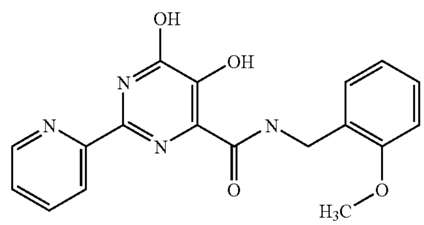 | 5,6-dihydroxy-N-(2-methoxybenzyl)-2-pyridin-2-ylpyrimidine-4-carboxamide (HCl salt) | 353 | A |
| 10 | 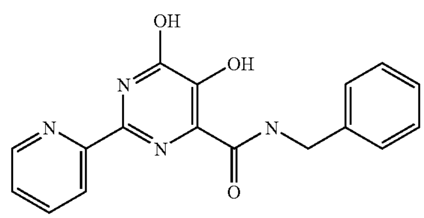 | N-benzyl-5,6-dihydroxy-2-pyridin-2-ylpyrimidine-4-carboxamide (HCl salt) | 323 | A |
| 11 | 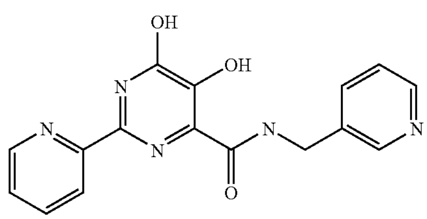 | 5,6-dihydroxy-2-pyridin-2-yl-N-(pyridin-3-ylmethyl)pyrimidine-4-carboxamide (TFA salt) | 324 | A |
| 12 | 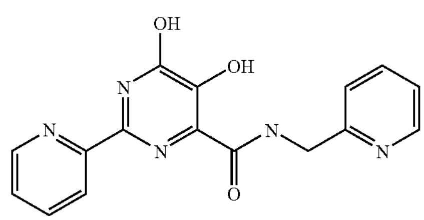 | 5,6-dihydroxy-2-pyridin-2-yl-N-(pyridin-2-ylmethyl)pyrimidine-4-carboxamide (TFA salt) | 324 | A |

TABLE 15B

| Structuture | name | M + 1 | Procedure |
|---|---|---|---|
| | benzyl 1-[4-({[4-fluoro-2-(methylsulfonyl)benzyl]amino}carbonyl)-5,6-dihydroxypyrimidin-2-yl]-1-methylethylcarbamate | 533 | A |

TABLE 15B-continued

| Structure | name | M + 1 | Procedure |
|---|---|---|---|
| | 2-(1-amino-1-methylethyl)-N-[4-fluoro-2-(methylsulfonyl)benzyl]-5,6-dihydroxypyrimidine-4-carboxamide | 399 | A* |
| | 2-[1-(dimethylamino)-1-methylethyl]-N-[4-fluoro-2-(methylsulfonyl)benzyl]-5,6-dihydroxypyrimidine-4-carboxamide | 427 | C |
| | 2-(1-aminocyclopropyl)-N-(4-fluorobenzyl)-5,6-dihydroxypyrimidine-4-carboxamide | 319 | A* |
| | 2-[1-(dimethylamino)cyclopropyl]-N-(4-fluorobenzyl)-5,6-dihydroxypyrimidine-4-carboxamide | 347 | C |
| | N-(4-fluorobenzyl)-5,6-dihydroxy-2-{1-[(pyrazin-2-ylcarbonyl)amino]cyclopropyl}pyrimidine-4-carboxamide | 425 | I |
| | benzyl 1-(4-{[(4-fluorobenzyl)amino]carbonyl}-5,6-dihydroxypyrimidin-2-yl)cyclopentylcarbamate | 481 | A |
| | 2-(1-aminocyclopentyl)-N-(4-fluorobenzyl)-5,6-dihydroxypyrimidine-4-carboxamide | 347 | A* |

TABLE 15B-continued

| Strucuture | name | M + 1 | Procedure |
|---|---|---|---|
|  | 2-[1-(dimethylamino)cyclopentyl]-N-(4-fluorobenzyl)-5,6-dihydroxypyrimidine-4-carboxamide | 375 | C |
|  | 2-(1-{[(ethylamino)carbonyl]amino}-1-methylethyl)-N-(4-fluorobenzyl)-5,6-dihydroxypyrimidine-4-carboxamide | 392 | G |
|  | 2-[1-(benzylamino)-1-methylethyl]-N-(4-fluorobenzyl)-5,6-dihydroxypyrimidine-4-carboxamide | 411 | C |
|  | 2-[1-(benzoylamino)-1-methylethyl]-N-(4-fluorobenzyl)-5,6-dihydroxypyrimidine-4-carboxamide | 425 | I |
|  | 2-{1-[benzyl(methyl)amino]-1-methylethyl}-N-(4-fluorobenzyl)-5,6-dihydroxypyrimidine-4-carboxamide | 425 | C |
|  | 2-[1-(dimethylamino)-1-methylethyl]-N-(2-ethoxybenzyl)-5,6-dihydroxypyrimidine-4-carboxamide | 375 | A |
|  | N-(2-chlorobenzyl)-2-[1-(dimethylamino)-1-methylethyl]-5,6-dihydroxypyrimidine-4-carboxamide | 365 | A |

TABLE 15B-continued

| Structure | name | M + 1 | Procedure |
|---|---|---|---|
| | N-(2-chlorobenzyl)-2-[1-(dimethylamino)-1-methylethyl]-5,6-dihydroxypyrimidine-4-carboxamide | 383 | A |
| | N-(5-chloro-2-methylbenzyl)-2-[1-(dimethylamino)-1-methylethyl]-5,6-dihydroxypyrimidine-4-carboxamide | 379 | A |
| | N-(4-fluorobenzyl)-5,6-dihydroxy-2-{1-methyl-1-[(pyrazin-2-ylcarbonyl)amino]ethyl}pyrimidine-4-carboxamide | 427 | I |
| | 2-[1-(diethylamino)-1-methylethyl]-N-(4-fluorobenzyl)-5,6-dihydroxypyrimidine-4-carboxamide | 377 | K |
| | N-(4-fluorobenzyl)-5,6-dihydroxy-2-(1-methyl-1-morpholin-4-ylethyl)pyrimidine-4-carboxamide | 391 | K |
| | N-(4-fluorobenzyl)-5,6-dihydroxy-2-(1-methyl-1-piperidin-1-ylethyl)pyrimidine-4-carboxamide | 389 | K |
| | N-(4-fluorobenzyl)-5,6-dihydroxy-2-(1-methyl-1-pyrrolidin-1-ylethyl)pyrimidine-4-carboxamide | 375 | K |

TABLE 15B-continued

| Strucuture | name | M + 1 | Procedure |
|---|---|---|---|
| | N-(4-fluorobenzyl)-5,6-dihydroxy-2-{1-methyl-1-[methyl(pyridin-4-ylmethyl)amino]ethyl}pyrimidine-4-carboxamide | 426 | C |
| | 2-[1-(dimethylamino)-1-methylethyl]-5,6-dihydroxy-N-[2-(methylthio)benzyl]pyrimidine-4-carboxamide | 377 | A |
| | N1,N1-diethyl-N2-[1-(4-{[(4-fluorobenzyl)amino]carbonyl}-5,6-dihydroxypyrimidin-2-yl)-1-methylethyl]ethanediamide | 448 | |
| | 2-[1-(1,4-dioxa-8-azaspiro[4.5]dec-8-yl]-1-methylethyl]-N-(4-fluorobenzyl)-5,6-dihydroxypyrimidine-4-carboxamide | 447 | K |
| | N-(4-fluorobenzyl)-5,6-dihydroxy-2-(1-methyl-1-{[(1-methyl-1H-imidazol-2-yl)carbonyl]amino}ethyl)pyrimidine-4-carboxamide | 429 | I |
| | N-(4-fluorobenzyl)-5,6-dihydroxy-2-[1-methyl-1-(4-oxopiperidin-1-yl)ethyl]pyrimidine-4-carboxamide | 403 | K |
| | N-(4-fluorobenzyl)-5,6-dihydroxy-2-{1-methyl-1-[methyl(pyridin-2-ylmethyl)amino]ethyl}pyrimidine-4-carboxamide | 426 | C |

TABLE 15B-continued

| Strucuture | name | M + 1 | Procedure |
|---|---|---|---|
| | N-[1-(4-{[(4-fluorobenzyl)amino]-carbonyl}-5,6-dihydroxypyrimidin-2-yl)-1-methylethyl]-4-methylmorpholine-2-carboxamide | 448 | I |
| | 2-{1-[acetyl(methyl)amino]-1-methylethyl}-N-(4-fluorobenzyl)-5,6-dihydroxypyrimidine-4-carboxamide | 377 | I |
| | 2-[1-(acetylamino)-1-methylethyl]-N-(4-fluorobenzyl)-5,6-dihydroxypyrimidine-4-carboxamide | 363 | I |
| | 2-{1-[4-(dimethylamino)piperidin-1-yl]-1-methylethyl}-N-(4-fluorobenzyl)-5,6-dihydroxypyrimidine-4-carboxamide | | E |
| | N-(2,3-dimethoxybenzyl)-2-[1-(dimethylamino)-1-methylethyl]-5,6-dihydroxypyrimidine-4-carboxamide | 391 | A |
| | 2-[4-(dimethylamino)tetrahydro-2H-pyran-4-yl]-N-(4-fluorobenzyl)-5,6-dihydroxypyrimidine-4-carboxamide | | C |
| | N-(4-fluorobenzyl)-5,6-dihydroxy-2-(7-methyl-7-azabicyclo[2.2.1]hept-1-yl)pyrimidine-4-carboxamide | 373 | C |

TABLE 15B-continued

| Strucuture | name | M + 1 | Procedure |
|---|---|---|---|
| | 2-(7-acetyl-7-azabicyclo[2.2.1]hept-1-yl)-N-(4-fluorobenzyl)-5,6-dihydroxypyrimidine-4-carboxamide | 401 | A |
| | 2-(2-acetyl-2-azabicyclo[2.1.1]hex-1-yl)-N-(4-fluorobenzyl)-5,6-dihydroxypyrimidine-4-carboxamide | 387 | A |
| | N-(4-fluorobenzyl)-5,6-dihydroxy-2-(2-methyl-2-azabicyclo[2.1.1]hex-1-yl)pyrimidine-4-carboxamide | 359 | C |

TABLE 17B

| Structure | Name | M + 1 | Procedure |
|---|---|---|---|
| 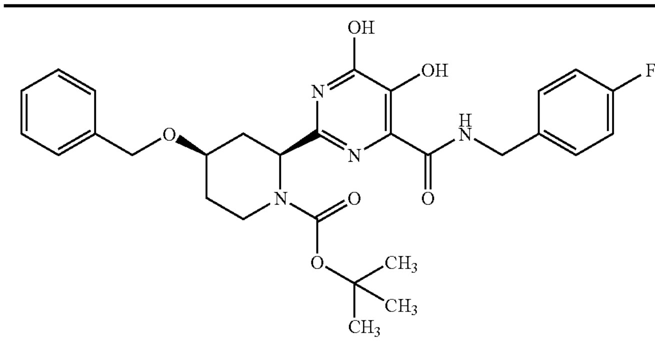 | tert-butyl (2S,4R)-4-(benzyloxy)-2-(4-{[(4-fluorobenzyl)amino]carbonyl}-5,6-dihydroxypyrimidin-2-yl)piperidine-1-carboxylate | 553 | A |
| 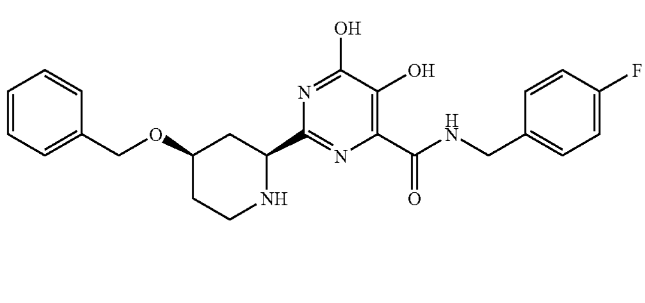 | 2-[(2S,4R)-4-(benzyloxy)piperidin-2-yl]-N-(4-fluorobenzyl)-5,6-dihydroxypyrimidine-4-carboxamide | 453 | A* |

TABLE 17B-continued

| Structure | Name | M + 1 | Procedure |
|---|---|---|---|
| 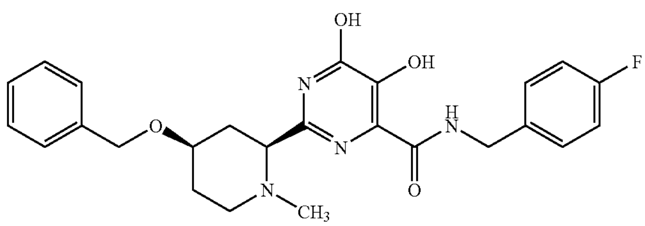 | 2-[(2S,4R)-4-(benzyloxy)-1-methylpiperidin-2-yl]-N-(4-fluorobenzyl)-5,6-dihydroxypyrimidine-4-carboxamide | 467 | C |
| 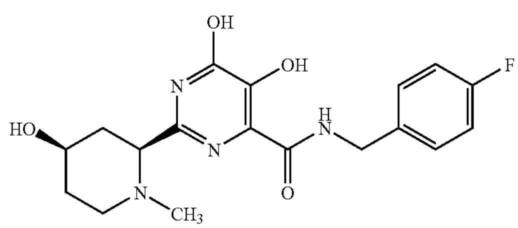 | N-(4-fluorobenzyl)-5,6-dihydroxy-2-[(2S,4R)-4-hydroxy-1-methylpiperidin-2-yl]pyrimidine-4-carboxamide | 377 | A* |
| 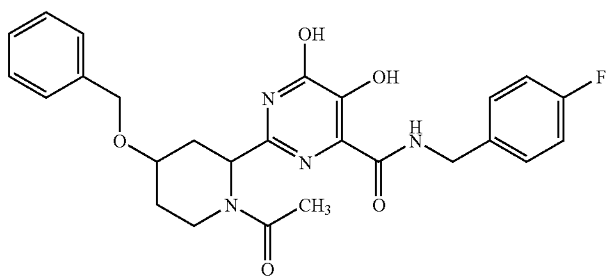 | 2-[1-acetyl-4-(benzyloxy)piperidin-2-yl]-N-(4-fluorobenzyl)-5,6-dihydroxypyrimidine-4-carboxamide | 495 | I |

TABLE 21B

| Structure | Name | M + 1 | Procedure |
|---|---|---|---|
| 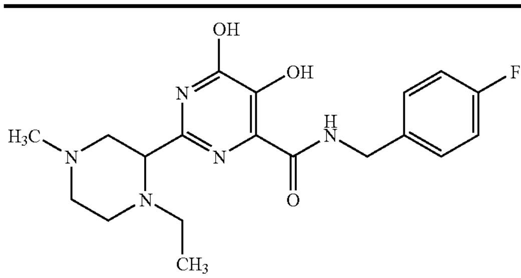 | 2-(1-ethyl-4-methylpiperazin-2-yl)-N-(4-fluorobenzyl)-5,6-dihydroxypyrimidine-4-carboxamide | 390 | A |
| 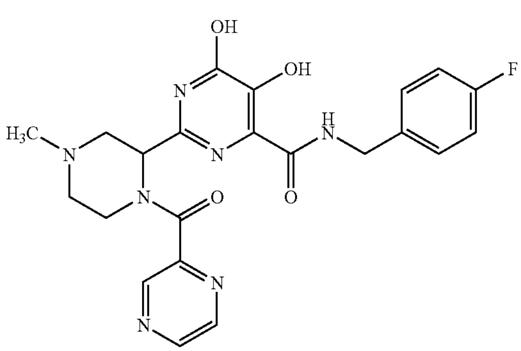 | N-(4-fluorobenzyl)-5,6-dihydroxy-2-[4-methyl-1-(pyrazin-2-ylcarbonyl)piperazin-2-yl]pyrimidine-4-carboxamide | 468 | A |

TABLE 22B

| Structure | Name | M+1 | Procedure |
|---|---|---|---|
| 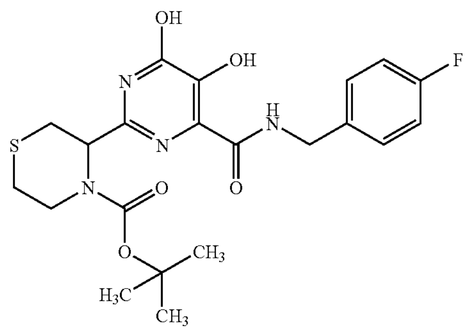 | tert-butyl 3-(4-{[(4-fluorobenzyl)amino]carbonyl}-5,6-dihydroxypyrimidin-2-yl)thiomorpholine-4-carboxylate | 465 | A |
| 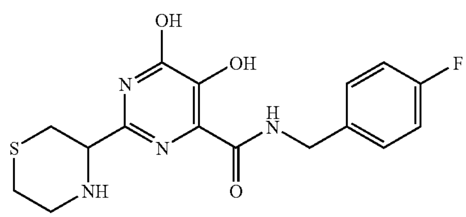 | N-(4-fluorobenzyl)-5,6-dihydroxy-2-thiomorpholin-3-ylpyrimidine-4-carboxamide | 365 | A* |
| 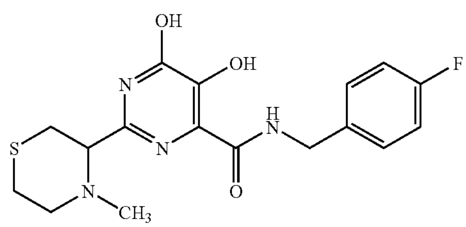 | N-(4-fluorobenzyl)-5,6-dihydroxy-2-(4-methylthiomorpholin-3-yl)pyrimidine-4-carboxamide | 379 | C |
| 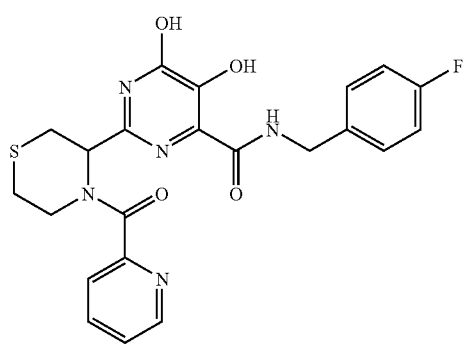 | N-(4-fluorobenzyl)-5,6-dihydroxy-2-[4-(pyridin-2-ylcarbonyl)thiomorpholin-3-yl]pyrimidine-4-carboxamide | 470 | I |
| 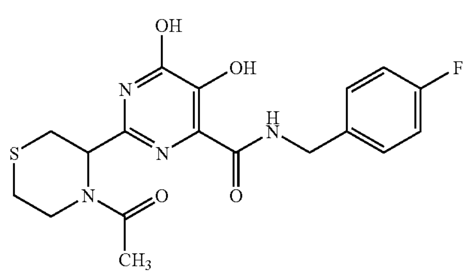 | 2-(4-acetylthiomorpholin-3-yl)-N-(4-fluorobenzyl)-5,6-dihydroxypyrimidine-4-carboxamide | 407 | I |

TABLE 22B-continued

| Structure | Name | M+1 | Procedure |
|---|---|---|---|
| 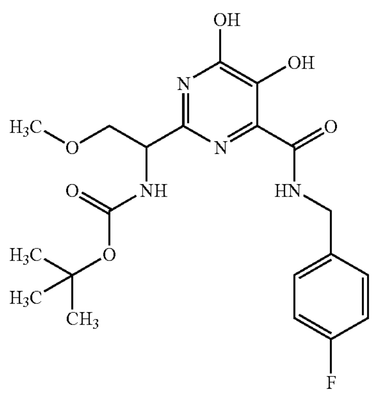 | tert-butyl 1-(4-{[(4-fluorobenzyl)amino]carbonyl}-5,6-dihydroxypyrimidin-2-yl)-2-methoxyethylcarbamate | 437 | A |
| 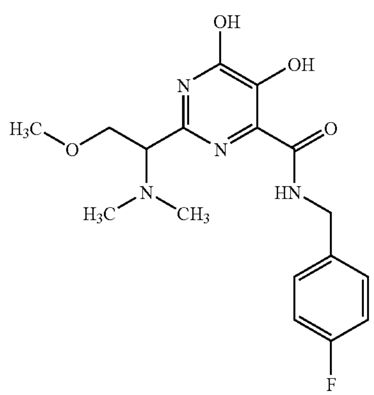 | 2-[1-(dimethylamino)-2-methoxyethyl]-N-(4-fluorobenzyl)-5,6-dihydroxypyrimidine-4-carboxamide | 365 | C |
| 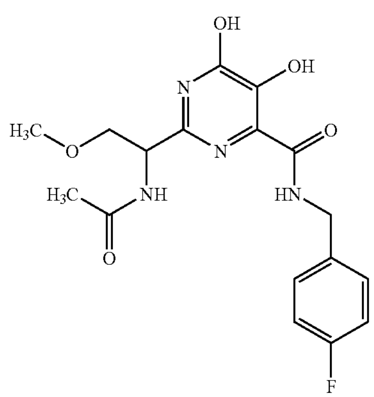 | 2-[1-(acetylamino)-2-methoxyethyl]-N-(4-fluorobenzyl)-5,6-dihydroxypyrimidine-4-carboxamide | 379 | I |
| 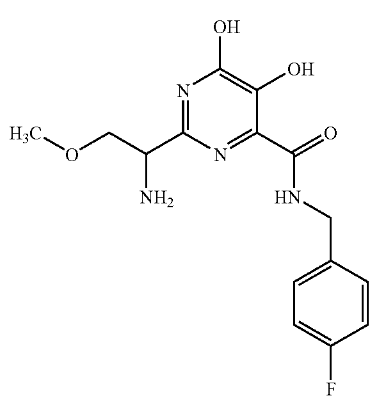 | 2-(1-amino-2-methoxyethyl)-N-(4-fluorobenzyl)-5,6-dihydroxypyrimidine-4-carboxamide | 337 | A* |

TABLE 22B-continued

| Structure | Name | M+1 | Procedure |
|---|---|---|---|
| 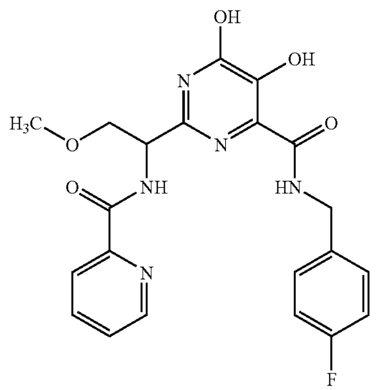 | N-(4-fluorobenzyl)-5,6-dihydroxy-2-{2-methoxy-1-[(pyridin-2-ylcarbonyl)amino]ethyl}pyrimidine-4-carboxamide | 442 | I |
| 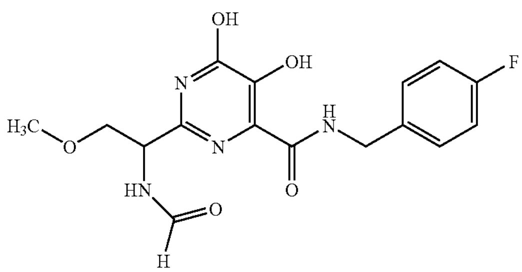 | N-(4-fluorobenzyl)-2-[1-(formylamino)-2-methoxyethyl]-5,6-dihydroxypyrimidine-4-carboxamide | 365 | A |
| 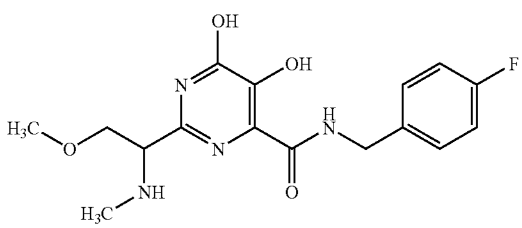 | N-(4-fluorobenzyl)-5,6-dihydroxy-2-[2-methoxy-1-(methylamino)ethyl]pyrimidine-4-carboxamide | 352 | A |
| 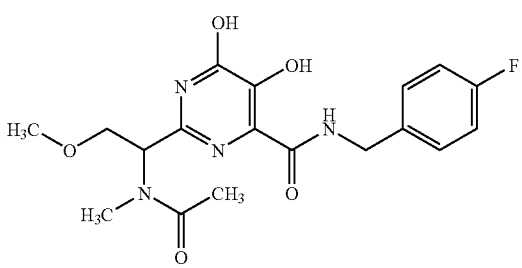 | 2-{1-[acetyl(methyl)amino]-2-methoxyethyl}-N-(4-fluorobenzyl)-5,6-dihydroxypyrimidine-4-carboxamide | 393 | I |
| 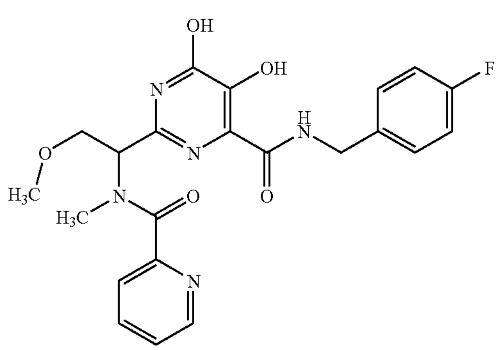 | N-(4-fluorobenzyl)-5,6-dihydroxy-2-{2-methoxy-1-[methyl(pyridin-2-ylcarbonyl)amino]ethyl}pyrimidine-4-carboxamide | 456 | I |

TABLE 23B

| Structure | Name | M+1 | Procedure |
|---|---|---|---|
| 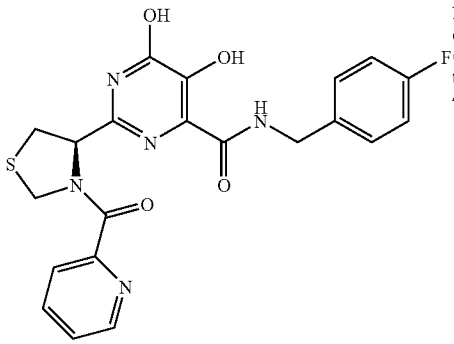 | N-(4-fluorobenzyl)-5,6-dihydroxy-2-[(4R)-3-(pyridin-2-ylcarbonyl)-1,3-thiazolidin-4-yl]pyrimidine-4-carboxamide | 456 | I |
| 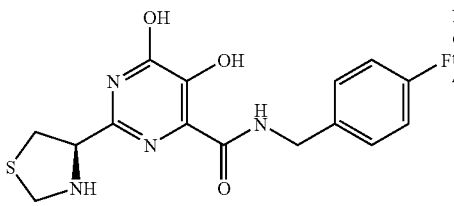 | N-(4-fluorobenzyl)-5,6-dihydroxy-2-[(4R)-1,3-thiazolidin-4-yl]pyrimidine-4-carboxamide | 351 | A* |
| 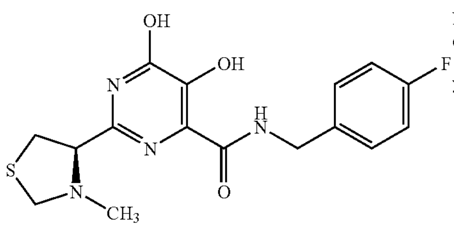 | N-(4-fluorobenzyl)-5,6-dihydroxy-2-[(4R)-3-methyl-1,3-thiazolidin-4-yl]pyrimidine-4-carboxamide | 365 | C |
| 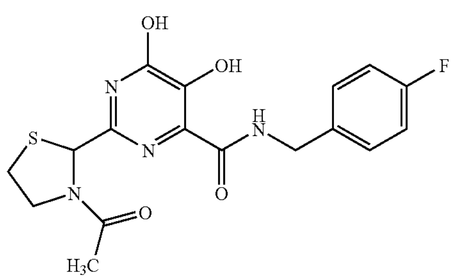 | 2-(3-acetyl-1,3-thiazolidin-2-yl)-N-(4-fluorobenzyl)-5,6-dihydroxypyrimidine-4-carboxamide | 393 | I |
| 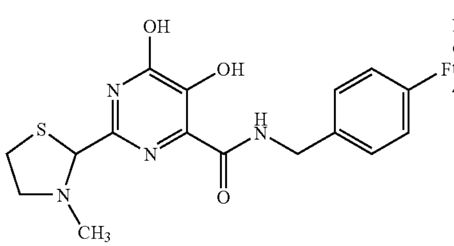 | N-(4-fluorobenzyl)-5,6-dihydroxy-2-(3-methyl-1,3-thiazolidin-2-yl)pyrimidine-4-carboxamide | 365 | C |

TABLE 25B

| Structure | Name | M+1 | Procedure |
|---|---|---|---|
| 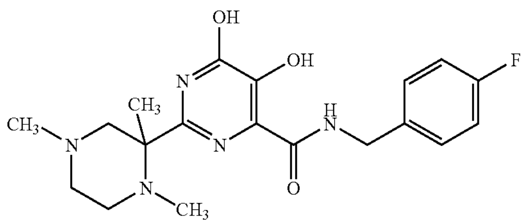 | N-(4-fluorobenzyl)-5,6-dihydroxy-2-(1,2,4-trimethylpiperazin-2-yl)pyrimidine-4-carboxamide | 390 | C |
| 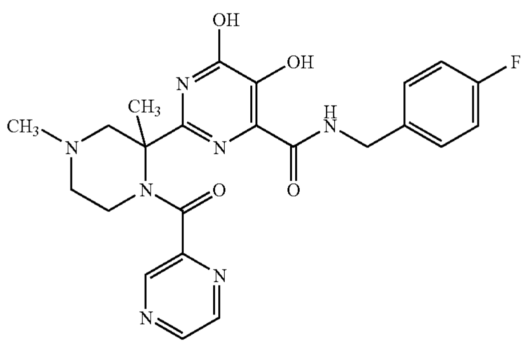 | 2-[2,4-dimethyl-1-(pyrazin-2-ylcarbonyl)piperazin-2-yl]-N-(4-fluorobenzyl)-5,6-dihydroxypyrimidine-4-carboxamide | 482 | C |
| 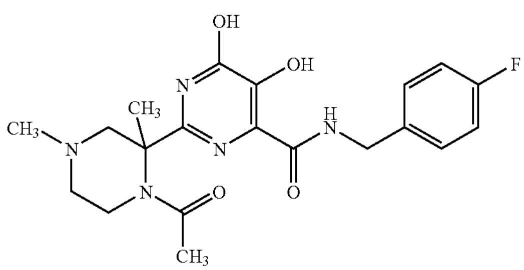 | 2-(1-acetyl-2,4-dimethylpiperazin-2-yl)-N-(4-fluorobenzyl)-5,6-dihydroxypyrimidine-4-carboxamide | 418 | C |
| 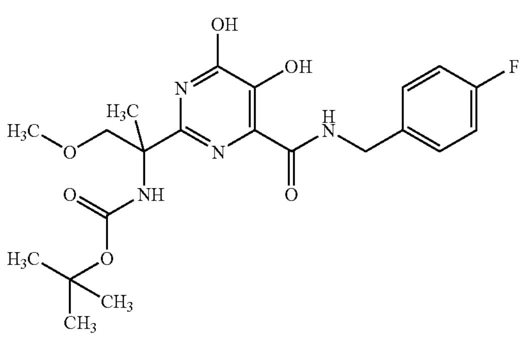 | tert-butyl 1-(4-{[(4-fluorobenzyl)amino]carbonyl}-5,6-dihydroxypyrimidin-2-yl)-2-methoxy-1-methylethylcarbamate | 451 | A |
| 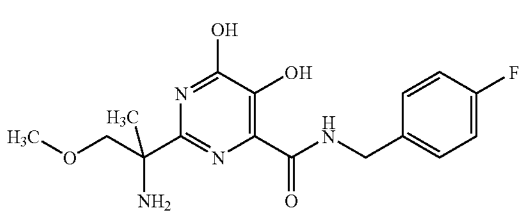 | 2-(1-amino-2-methoxy-1-methylethyl)-N-(4-fluorobenzyl)-5,6-dihydroxypyrimidine-4-carboxamide | 351 | A* |

TABLE 25B-continued

| Structure | Name | M+1 | Procedure |
|---|---|---|---|
| 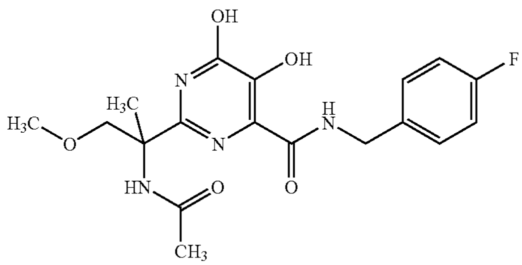 | 2-[1-(acetylamino)-2-methoxy-1-methylethyl]-N-(4-fluorobenzyl)-5,6-dihydroxypyrimidine-4-carboxamide | 393 | I |
| 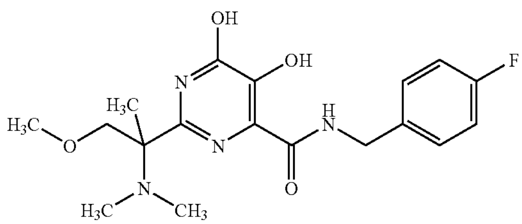 | 2-[1-(dimethylamino)-2-methoxy-1-methylethyl]-N-(4-fluorobenzyl)-5,6-dihydroxypyrimidine-4-carboxamide | 379 | C |
| 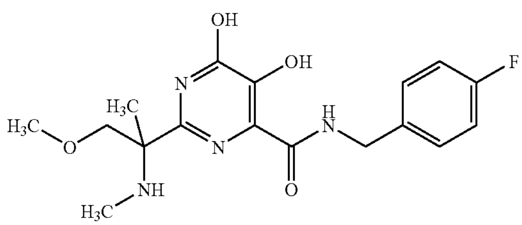 | N-(4-fluorobenzyl)-5,6-dihydroxy-2-[2-methoxy-1-methyl-1-(methylamino)ethyl]pyrimidine-4-carboxamide | 365 | C |
| 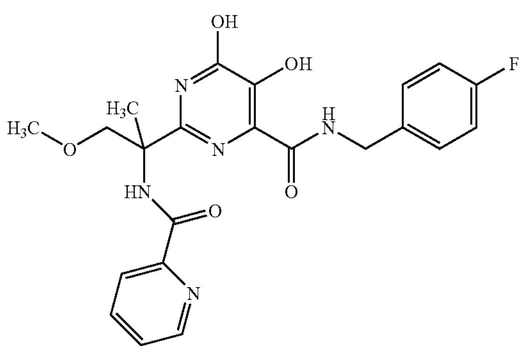 | N-(4-fluorobenzyl)-5,6-dihydroxy-2-{2-methoxy-1-methyl-1-[(pyridin-2-ylcarbonyl)amino]ethyl}pyrimidine-4-carboxamide | 456 | G |
| 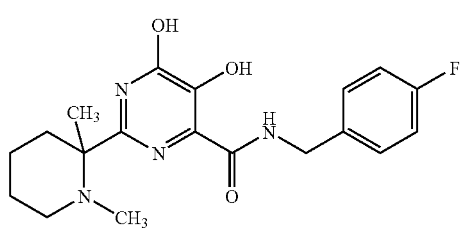 | 2-(1,2-dimethylpiperidin-2-yl)-N-(4-fluorobenzyl)-5,6-dihydroxypyrimidine-4-carboxamide | 375 | C |
| 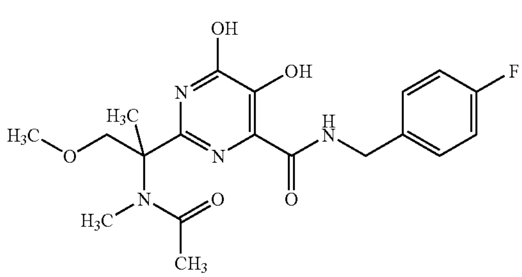 | 2-{1-[acetyl(methyl)amino]-2-methoxy-1-methylethyl}-N-(4-fluorobenzyl)-5,6-dihydroxypyrimidine-4-carboxamide | 407 | I |

TABLE 25B-continued

| Structure | Name | M+1 | Procedure |
|---|---|---|---|
| 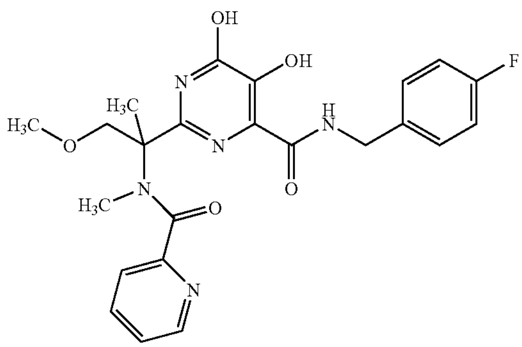 | N-(4-fluorobenzyl)-5,6-dihydroxy-2-{2-methoxy-1-methyl-1-[methyl(pyridin-2-ylcarbonyl)amino]ethyl}pyrimidine-4-carboxamide | 470 | I |
| 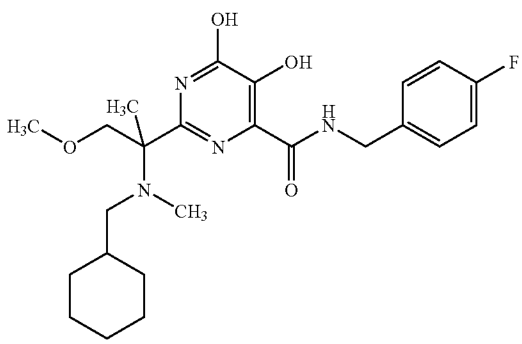 | 2-{1-[(cyclohexylmethyl)(methyl)amino]-2-methoxy-1-methylethyl}-N-(4-fluorobenzyl)-5,6-dihydroxypyrimidine-4-carboxamide | 461 | C |
| | 2-{1-[(cyclohexylmethyl)amino]-2-methoxy-1-methylethyl}-N-(4-fluorobenzyl)-5,6-dihydroxypyrimidine-4-carboxamide | 447 | C |
| | 2-{1-[(cyclohexylmethyl)amino]-2-methoxy-1-methylethyl}-N-(4-fluorobenzyl)-5,6-dihydroxypyrimidine-4-carboxamide | 361 | A* |
| 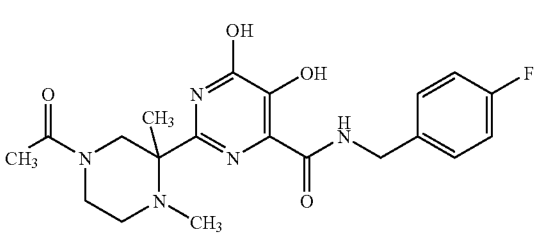 | 2-(4-acetyl-1,2-dimethylpiperazin-2-yl)-N-(4-fluorobenzyl)-5,6-dihydroxypyrimidine-4-carboxamide | 418 | A |

TABLE 25B-continued

| Structure | Name | M+1 | Procedure |
|---|---|---|---|
| 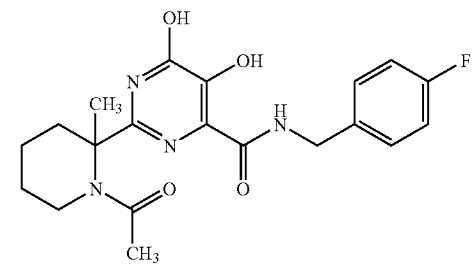 | 2-(1-acetyl-2-methylpiperidin-2-yl)-N-(4-fluorobenzyl)-5,6-dihydroxypyrimidine-4-carboxamide | 403 | A |
| 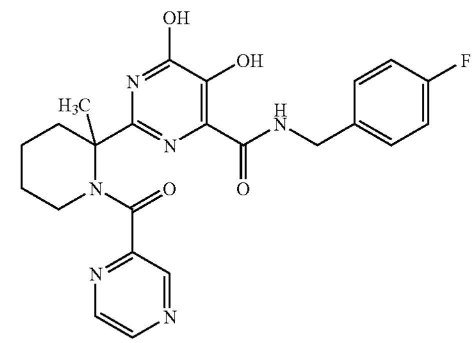 | N-(4-fluorobenzyl)-5,6-dihydroxy-2-[2-methyl-1-(pyrazin-2-ylcarbonyl)piperidin-2-yl]pyrimidine-4-carboxamide | 467 | A |
| 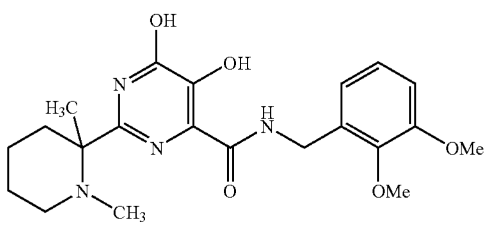 | N-(2,3-dimethoxybenzyl)-2-(1,2-dimethylpiperidin-2-yl)-5,6-dihydroxypyrimidine-4-carboxamide | 417 | C |
| 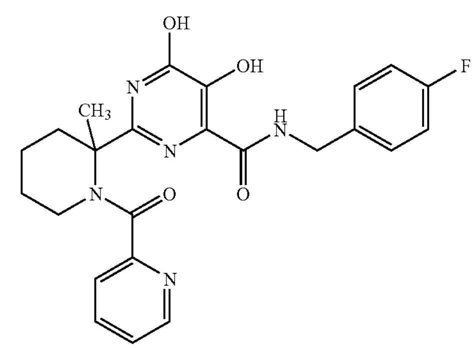 | N-(4-fluorobenzyl)-5,6-dihydroxy-2-[2-methyl-1-(pyridin-2-ylcarbonyl)piperidin-2-yl]pyrimidine-4-carboxamide | 466 | A |
| 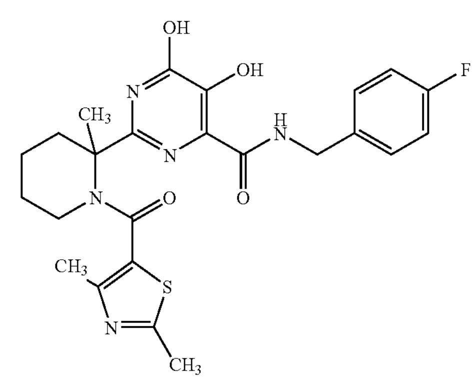 | 2-{1-[(2,4-dimethyl-1,3-thiazol-5-yl)carbonyl]-2-methylpiperidin-2-yl}-N-(4-fluorobenzyl)-5,6-dihydroxypyrimidine-4-carboxamide | 500 | A |

TABLE 25B-continued

| Structure | Name | M+1 | Procedure |
|---|---|---|---|
| 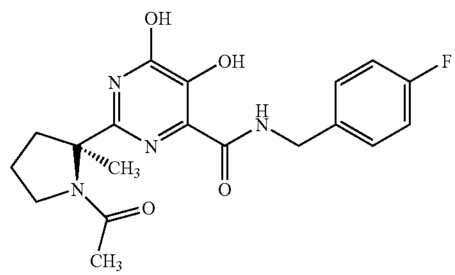 | 2-[(2S)-1-acetyl-2-methylpyrrolidin-2-yl]-N-(4-fluorobenzyl)-5,6-dihydroxypyrimidine-4-carboxamide | 389 | A |

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of Formula (I):

(I)

wherein
$R^1$ is
(1) —$C_{1-6}$ alkyl, which is substituted with one or more substituents each of which is independently halogen, —OH, —CN, —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —C(=O) —$C_{0-6}$ alkyl-N($R^aR^b$), N($R^a$) —C(=O) —$C_{0-6}$ alkyl-N($R^bR^c$), —$SO_2R^a$, —N($R^a$)$SO_2R^b$, —$SO_2$N($R^aR^b$), —N($R^a$) —C(=O)$R^b$, —N($R^a$)C(=O)N($R^bR^c$), —N($R^a$)C(=O)C(=O)N($R^bR^c$), or —N($R^a$)C(=O)O$R^b$, (2) —O—$C_{1-6}$ alkyl, which is substituted with one or more substituents each of which is independently halogen, —OH, —CN, —O—$C_{1-6}$ alkyl, —O—$C_{1-6}$ haloalkyl, —C(=O)$R^a$, —$CO_2R^a$, —$SR^a$, —S(=O)$R^a$, —N($R^aR^b$), —C(=O) —$C_{0-6}$ alkyl-N($R^aR^b$), N($R^a$) —C(=O) —$C_{0-6}$ alkyl-N($R^bR^c$), —$SO_2R^a$, —N($R^a$)$SO_2R^b$, —$SO_2$N($R^aR^b$), or —N($R^a$) —C($R^b$)=O, (3) —$R^k$, (4) —$C_{1-6}$ alkyl-$R^k$, wherein the alkyl is optionally substituted with one or more substituents each of which is independently halogen, —OH, —CN, —O—$C_{1-6}$ alkyl, —O—$C_{1-6}$ haloalkyl, —N($R^aR^b$), —N($R^a$)$CO_2R^b$, —N($R^a$)C(=O) —$C_{0-6}$ alkyl-N($R^bR^c$), or —N($R^a$) —$C_{2-6}$ alkyl-OH with the proviso that the —OH is not attached to the carbon alpha to N($R^a$), (5) —$C_{2-5}$ alkenyl-$R^k$,
(6) —$C_{2-5}$ alkynyl-$R^k$,
(7) —$C_{0-6}$ alkyl-O—$C_{0-6}$ alkyl-$R^k$,
(8) —$C_{0-6}$ alkyl-S(O)$_n$—$C_{0-6}$ alkyl-$R^k$,
(9) —O—$C_{1-6}$ alkyl-O$R^k$,
(10) —O—$C_{1-6}$ alkyl-O—$C_{1-6}$ alkyl-$R^k$,
(11) —O—$C_{1-6}$ alkyl-S(O)$_n$$R^k$,
(12) —$C_{0-6}$ alkyl-N($R^a$) —$R^k$,
(13) —$C_{0-6}$ alkyl-N($R^a$) —$C_{1-6}$ alkyl-$R^k$,
(14) —$C_{0-6}$ alkyl-N($R^a$) —$C_{1-6}$ alkyl-O$R^k$,
(15) —$C_{0-6}$ alkyl-C(=O) —$R^k$,
(16) —$C_{0-6}$ alkyl-C(=O)N($R^a$) —$C_{0-6}$ alkyl-$R^k$,
(17) —$C_{1-6}$ alkyl-N($R^a$)C(=O) —$C_{0-6}$ alkyl-$R^k$,
(18) —$C_{0-6}$ alkyl-N($R^a$)C(=O) —O—$C_{0-6}$ alkyl-$R^k$,
(19) —$C_{1-6}$ alkyl which is:
  (i) substituted with aryl or —O-aryl, wherein the aryl is optionally substituted with one or more substituents each of which is independently halogen, —OH, —$C_{1-6}$ alkyl, —$C_{1-6}$ alkyl-O$R^a$, —$C_{1-6}$ haloalkyl, —O—$C_{1-6}$ alkyl, —O—$C_{1-6}$ haloalkyl, methylenedioxy attached to two adjacent carbon atoms, or aryl;
  (ii) substituted with —$R^k$, —$C_{1-6}$ alkyl-$R^k$, —N($R^a$) —C(=O) —$C_{0-6}$ alkyl-$R^k$, —$C_{0-6}$ alkyl-N($R^a$) —$C_{0-6}$ alkyl-$R^k$, —$C_{0-6}$ alkyl-O—$C_{0-6}$ alkyl-$R^k$, or —$C_{0-6}$ alkyl-N($R^a$) —C(=O) —$C_{0-6}$ alkyl-$R^k$; and
  (iii) optionally substituted with one or more substituents each of which is independently halogen, —OH, —CN, —O—$C_{1-6}$ alkyl, —O—$C_{1-6}$ haloalkyl, or —N($R^aR^b$), or
(20) —$C_{1-6}$ alkyl, substituted with —O—$C_{1-6}$ alkyl, and with a substituent selected from the group consisting of —N($R^a$)C(=O)$R^k$ and —N($R^a$)$C_{1-6}$ alkyl-$R^k$, $R^2$ is —H or —$C_{1-6}$ alkyl which is optionally substituted with one or more substituents each of which is independently
(1) halogen,
(2) —OH,
(3) —CN,
(4) —O—$C_{1-6}$ alkyl,
(5) —O—$C_{1-6}$ haloalkyl,
(6) —C(=O)$R^a$, (7) —CO$_2$R$^a$,
(8) —SR$^a$,
(9) —S(=O)R$^a$,
(10) —N(R$^a$R$^b$),
(11) —C(=O)N(R$^a$R$^b$),
(12) —N(R$^a$)—C(=O)—C$_{1-6}$ alkyl-N(R$^b$R$^c$),
(13) —SO$_2$R$^a$,
(14) —N(R$^a$)SO$_2$R$^b$,
(15) —SO$_2$N(R$^a$R$^b$),
(16) —N(R$^a$)—C(R$^b$)=O,
(17) —C$_{3-8}$ cycloalkyl,
(18) aryl, wherein the aryl is optionally substituted with one or more substituents each of which is independently halogen, —C$_{1-6}$ alkyl, —C$_{1-6}$ haloalkyl, —O—C$_{1-6}$ alkyl, —O—C$_{1-6}$ haloalkyl, —C$_{0-6}$ alkyl-N(R$^a$R$^b$), or —C$_{1-6}$ alkyl substituted with a 5- or 6-membered saturated heterocyclic ring containing from 1 to 4 heteroatoms independently selected from N, O and S; wherein the saturated heterocyclic ring is optionally substituted with from 1 to 3 substituents each of which is independently —C$_{1-6}$ alkyl, oxo, or a 5- or 6-membered heteroaromatic ring containing from 1 to 4 heteroatoms independently selected from N, O and S; or
(19) a 5- to 8-membered monocyclic heterocycle which is saturated or unsaturated and contains from 1 to 4 heteroatoms independently selected from N, O and S; wherein the heterocycle is optionally substituted with one or more substituents each of which is independently —C$_{1-6}$ alkyl, —O—C$_{1-6}$ alkyl, oxo, phenyl, or naphthyl;

R$^3$ is —H or —C$_{1-6}$ alkyl;
R$^4$ is
(1) H,
(2) C$_{1-6}$ alkyl which is optionally substituted with one or more substituents each of which is independently halogen, —OH, O—C$_{1-6}$ alkyl, —O—C$_{1-6}$ haloalkyl, —NO$_2$, —N(R$^a$R$^b$), —C(=O)R$^a$, —CO$_2$R$^a$, —SR$^a$, —S(=O)R$^a$, —SO$_2$R$^a$, or —N(R$^a$)CO$_2$R$^b$,
(3) C$_{1-6}$ alkyl which is optionally substituted with one or more substituents each of which is independently halogen, —OH, or O—C$_{1-4}$ alkyl, and which is substituted with 1 or 2 substituents each of which is independently:
 (i) C$_{3-8}$ cycloalkyl,
 (ii) aryl,
 (iii) a fused bicyclic carbocycle consisting of a benzene ring fused to a C$_{5-7}$ cycloalkyl,
 (iv) a 5- or 6-membered saturated heterocyclic ring containing from 1 to 4 heteroatoms independently selected from N, O and S,
 (v) a 5- or 6-membered heteroaromatic ring containing from 1 to 4 heteroatoms independently selected from N, O and S, or
 (vi) a 9- or 10-membered fused bicyclic heterocycle containing from 1 to 4 heteroatoms independently selected from N, O and S, wherein at least one of the rings is aromatic,
(4) C$_{2-5}$ alkynyl optionally substituted with aryl,
(5) C$_{3-8}$ cycloalkyl optionally substituted with aryl,
(6) aryl,
(7) a fused bicyclic carbocycle consisting of a benzene ring fused to a C$_{5-7}$ cycloalkyl,
(8) a 5- or 6-membered saturated heterocyclic ring containing from 1 to 4 heteroatoms independently selected from N, O and S,
(9) a 5- or 6-membered heteroaromatic ring containing from 1 to 4 heteroatoms independently selected from N, O and S, or
(10) a 9- or 10-membered fused bicyclic heterocycle containing from 1 to 4 heteroatoms independently selected from N, O and S, wherein at least one of the rings is aromatic;

wherein
each aryl in (3)(ii) or the aryl (4), (5) or (6) or each fused carbocycle in (3)(iii) or the fused carbocycle in (7) is optionally substituted with one or more substituents each of which is independently halogen, —OH, —C$_{1-6}$ alkyl, —C$_{1-6}$ alkyl-OR$^a$, —C$_{1-6}$ haloalkyl, —O—C$_{1-6}$ alkyl, —O—C$_{1-6}$ haloalkyl, —CN, —NO$_2$, —N(R$^a$R$^b$), —C$_{1-6}$ alkyl-N(R$^a$R$^b$), —C(=O)N(R$^a$R$^b$), —C(=O)R$^a$, —CO$_2$R$^a$, —C$_{1-6}$ alkyl-CO$_2$R$^a$, —OCO$_2$R$^a$, —SR$^a$, —S(=O)R$^a$, —SO$_2$R$^a$, —N(R$^a$)SO$_2$R$^b$, —SO$_2$N(R$^a$R$^b$), —N(R$^a$)C(=O)R$^b$, —N(R$^a$)CO$_2$R$^b$, —C$_{1-6}$ alkyl-N(R$^a$)CO$_2$R$^b$, aryl, —C$_{1-6}$ alkyl-aryl, —O-aryl, or —C$_{0-6}$ alkyl-het wherein het is a 5- or 6-membered heteroaromatic ring containing from 1 to 4 heteroatoms independently selected from N, O and S, and het is optionally fused with a benzene ring, and is optionally substituted with one or more substituents each of which is independently —C$_{1-6}$ alkyl, —C$_{1-6}$ haloalkyl, —O—C$_{1-6}$ alkyl, —O—C$_{1-6}$ haloalkyl, oxo, or —CO$_2$R$^a$;

each saturated heterocyclic ring in (3)(iv) or the saturated heterocyclic ring in (8) is optionally substituted with one or more substituents each of which is independently halogen, —C$_{1-6}$ alkyl, —C$_{1-6}$ haloalkyl, —O—C$_{1-6}$ alkyl, —O—C$_{1-6}$ haloalkyl, oxo, aryl, or a 5- or 6-membered heteroaromatic ring containing from 1 to 4 heteroatoms independently selected from N, —O and S; and each heteroaromatic ring in (3)(v) or the heteroaromatic ring in (9) or each fused bicyclic heterocycle in (3)(vi) or the fused bicyclic heterocycle in (10) is optionally substituted with one or more substituents each of which is independently halogen, —C$_{1-6}$ alkyl, —C$_{1-6}$ haloalkyl, —O—C$_{1-6}$ alkyl, —O—C$_{1-6}$ haloalkyl, oxo, aryl, or —C$_{1-6}$ alkyl-aryl;

or alternatively R$^3$ and R$^4$ together with the N to which both are attached form a C$_{3-7}$ azacycloalkyl which is optionally substituted with one or more substituents each of which is independently —C$_{1-6}$ alkyl or oxo;

each R$^a$, R$^b$, R$^c$, and R$^d$ is independently —H or —C$_{1-6}$ alkyl;

R$^k$ is carbocycle or heterocycle, wherein the carbocycle or heterocycle is optionally substituted with one or more substituents each of which is independently
(1) halogen,
(2) —OH,
(3) —CN,
(4) —C$_{1-6}$ alkyl, which is optionally substituted with one or more substituents each of which is independently halogen, —OH, —CN, —O—C$_{1-6}$ alkyl, —O—C$_{1-6}$ haloalkyl, —C(=O)R$^a$, —CO$_2$R$^a$, —SR$^a$, —S(=O)R$^a$, —N(R$^a$R$^b$), —C(=O)

—(CH$_2$)$_{0-2}$N(R$^a$R$^b$), N(R$^a$) —C(=O) —(CH$_2$)$_{0-2}$N(R$^b$R$^c$), —SO$_2$R$^a$, —N(R$^a$)SO$_2$R$^b$, —SO$_2$N(R$^a$R$^b$), or —N(R$^a$) —C(R$^b$)=O, (5) —O—C$_{1-6}$ alkyl, which is optionally substituted with one or more substituents each of which is independently halogen, —OH, —CN, —O—C$_{1-6}$ alkyl, —O—C$_{1-6}$ haloalkyl, —C(=O)R$^a$, —CO$_2$R$^a$, —SR$^a$, —S(=O)R$^a$, —N(R$^a$R$^b$), —C(=O) —(CH$_2$)$_{0-2}$N(R$^a$R$^b$), N(R$^a$) —C(=O) —(CH$_2$)$_{0-2}$N(R$^b$R$^c$), —SO$_2$R$^a$, —N(R$^a$)SO$_2$R$^b$, —SO$_2$N(R$^a$R$^b$), or —N(R$^a$) —C(R$^b$)=O, (6) —NO$_2$, (7) oxo, (8) ethylenedioxy, spiro substituted on a ring carbon in a saturated ring of R$^k$;

(9) —C(=O)R$^a$,

(10) —CO$_2$R$^a$,

(11) —SR$^a$,

(12) —S(=O)R$^a$,

(13) —N(R$^a$R$^b$),

(14) —C(=O)N(R$^a$R$^b$),

(15) —C(=O) —C$_{1-6}$ alkyl-N(R$^a$R$^b$),

(16) —N(R$^a$)C(=O)R$^b$,

(17) —SO$_2$R$^a$,

(18) —SO$_2$N(R$^a$R$^b$),

(19) —N(R$^a$)SO$_2$R$^b$,

(20) —R$^m$,

(21) —C$_{1-6}$ alkyl-R$^m$, wherein the alkyl is optionally substituted with one or more substituents each of which is independently halogen, —OH, —CN, —C$_{1-6}$ haloalkyl, —O—C$_{1-6}$ alkyl, —O—C$_{1-6}$ haloalkyl, —C(=O)R$^a$, —CO$_2$R$^a$, —SR$^a$, —S(=O)R$^a$, —N(R$^a$R$^b$), —N(R$^a$)CO$_2$R$^b$, —SO$_2$R$^a$, —N(R$^a$)SO$_2$R$^b$, —SO$_2$N(R$^a$R$^b$), or —N(R$^a$) —C(R$^b$)=O,

(22) —C$_{0-6}$ alkyl-N(R$^a$) —C$_{0-6}$ alkyl-R$^m$,

(23) —C$_{0-6}$ alkyl-O—C$_{0-6}$ alkyl-R$^m$,

(24) —C$_{0-6}$ alkyl-S—C$_{0-6}$ alkyl-R$^m$,

(25) —C$_{0-6}$ alkyl-C(=O) —C$_{0-6}$ alkyl-R$^m$,

(26) —C(=O) —O—C$_{0-6}$ alkyl-R$^m$,

(27) —C(=O)N(R$^a$) —C$_{0-6}$ alkyl-R$^m$,

(28) —N(R$^a$)C(=O) —R$^m$,

(29) —N(R$^a$)C(=O) —C$_{1-6}$ alkyl-R$^m$, wherein the alkyl is optionally substituted with one or more substituents each of which is independently halogen, —OH, —CN, —C$_{1-6}$ haloalkyl, —O—C$_{1-6}$ alkyl, —O—C$_{1-6}$ haloalkyl, —C(=O)R$^a$, —CO$_2$R$^a$, —SR$^a$, —S(=O)R$^a$, —N(R$^a$R$^b$), —N(R$^a$)CO$_2$R$^b$, —SO$_2$R$^a$, —N(R$^a$)SO$_2$R$^b$, —SO$_2$N(R$^a$R$^b$), or —N(R$^a$) —C(R$^b$)=O,

(30) —N(R$^a$) —C(=O) —N(R$^b$) —C$_{0-6}$ alkyl-R$^m$,

(31) —N(R$^a$) —C(=O) —O—C$_{0-6}$ alkyl-R$^m$, or

(32) —N(R$^a$) —C(=O) —N(R$^b$) —SO$_2$—C$_{0-6}$ alkyl-R$^m$;

carbocycle in R$^k$ is (i) a C$_3$ to C$_8$ monocyclic, saturated or unsaturated ring, (ii) a C$_7$ to C$_{12}$ bicyclic ring system, or (iii) a C$_{11}$ to C$_{16}$ tricyclic ring system, wherein each ring in (ii) or (iii) is independent of or fused to the other ring or rings and each ring is saturated or unsaturated;

heterocycle in R$^k$ is (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of or fused to or bridged with or spiro to the other ring or rings and each ring is saturated or unsaturated; the monocyclic ring, bicyclic ring system, or tricyclic ring system contains from 1 to 6 heteroatoms selected from N, O and S and a balance of carbon atoms; and wherein any one or more of the nitrogen and sulfur heteroatoms is optionally be oxidized, and any one or more of the nitrogen heteroatoms is optionally quaternized;

each R$^m$ is independently C$_{3-8}$ cycloalkyl; aryl; a 5- to 8-membered monocyclic heterocycle which is saturated or unsaturated and contains from 1 to 4 heteroatoms independently selected from N, O and S; or a 9- to 10-membered bicyclic heterocycle which is saturated or unsaturated and contains from 1 to 4 heteroatoms independently selected from N, O and S; wherein any one or more of the nitrogen and sulfur heteroatoms in the monocyclic or bicyclic heterocycle is optionally oxidized and any one or more of the nitrogen heteroatoms is optionally quaternized; and wherein the cycloalkyl or the aryl is optionally substituted with one or more substituents each of which is independently halogen, —C$_{1-6}$ alkyl, —C$_{1-6}$ haloalkyl, —O—C$_{1-6}$ alkyl, —O—C$_{1-6}$ haloalkyl, —N(R$^a$R$^b$), aryl, or —C$_{1-6}$ alkyl-aryl; and the monocyclic or bicyclic heterocycle is optionally substituted with one or more substituents each of which is independently halogen, —C$_{1-6}$ alkyl optionally substituted with —O—C$_{1-6}$ alkyl, —C$_{1-6}$ haloalkyl, —O—C$_{1-6}$ alkyl, —O—C$_{1-6}$ haloalkyl, oxo, aryl, —C$_{1-6}$ alkyl-aryl, —C(=O)-aryl, —CO$_2$-aryl, —CO$_2$—C$_{1-6}$ alkyl-aryl, a 5- or 6-membered saturated heterocyclic ring containing from 1 to 4 heteroatoms independently selected from N, O and S, or a 5- or 6-membered heteroaromatic ring containing from 1 to 4 heteroatoms independently selected from N, O and S; and each n is independently an integer equal to zero, 1 or 2; or a pharmaceutically acceptable salt thereof.

2. The compound according to claim 1, wherein R$^1$ is:

(1) —C$_{1-6}$ alkyl, which is substituted with from 1 to 5 substituents each of which is independently halogen, —OH, —CN, —O—C$_{1-4}$ alkyl, —O—C$_{1-4}$ haloalkyl, —C(=O)R$^a$, —CO$_2$R$^a$, —SR$^a$, —S(=O)R$^a$, —N(R$^a$R$^b$), —C(=O) —(CH$_2$)$_{0-2}$N(R$^a$R$^b$), N(R$^a$) —C(=O) —(CH$_2$)$_{0-2}$N(R$^b$R$^c$), —SO$_2$R$^a$, —N(R$^a$)SO$_2$R$^b$, —SO$_2$N(R$^a$R$^b$), —N(R$^a$) —C(=O)R$^b$,

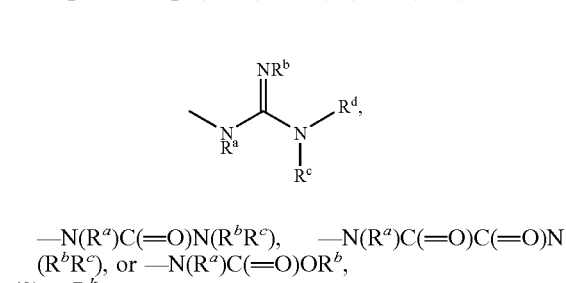

—N(R$^a$)C(=O)N(R$^b$R$^c$), —N(R$^a$)C(=O)C(=O)N(R$^b$R$^c$), or —N(R$^a$)C(=O)OR$^b$, (2) —R$^k$, (3) —C$_{1-4}$ alkyl-R$^k$, wherein the alkyl is optionally substituted with 1 or 2 substituents each of which is independently halogen, —OH, —CN, —O—C$_{1-4}$ alkyl, —O—C$_{1-4}$ haloalkyl, —N(R$^a$R$^b$), or —N(R$^a$) —(CH$_2$)$_{2-4}$—OH, (4) —O—(CH$_2$)$_{0-3}$—R$^k$, (5) —C$_{1-4}$ alkyl-O—(CH$_2$)$_{0-3}$—R$^k$, (6) —(CH$_2$)$_{0-3}$—S(O)$_n$—(CH$_2$)$_{0-3}$—R$^k$, (7) —O—(CH$_2$)$_{1-3}$—OR$^k$, (8) —O—(CH$_2$)$_{1-3}$—O—(CH$_2$)$_{1-3}$—R$^k$, (9) —O—(CH$_2$)$_{1-3}$—S(O)$_n$R$^k$,

(10) —(CH$_2$)$_{0-3}$—N(R$^a$) —R$^k$,

(11) —(CH$_2$)$_{0-3}$—N(R$^a$) —(CH$_2$)$_{1-3}$—R$^k$,

(12) —(CH$_2$)$_{0-3}$—N(R$^a$) —(CH$_2$)$_{1-3}$—OR$^k$,

(13) —(CH$_2$)$_{0-3}$—C(=O) —R$^k$,

(14) —(CH$_2$)$_{0-3}$—C(=O)N(R$^a$) —(CH$_2$)$_{0-3}$—R$^k$,

(15) —(CH$_2$)$_{1-3}$—N(R$^a$)C(=O) —(CH$_2$)$_{0-3}$—R$^k$,
(16) —(CH$_2$)$_{0-3}$—N(R$^a$)C(=O) —O—(CH$_2$)$_{0-3}$—R$^k$,
(17) —C$_{1-6}$ alkyl which is:
   (i) substituted with aryl or —O-aryl, wherein the aryl is optionally substituted with from 1 to 3 substituents each of which is independently halogen, —OH, —C$_{1-4}$ alkyl, —C$_{1-4}$ alkyl-OR$^a$, —C$_{1-4}$ haloalkyl, —O—C$_{1-4}$ alkyl, —O—C$_{1-4}$ haloalkyl, methylenedioxy attached to two adjacent carbon atoms, or aryl;
   (ii) substituted with —R$^k$, —(CH$_2$)$_{1-3}$—R$^k$, —N(R$^a$) —C(=O) —(CH$_2$)$_{0-3}$—R$^k$, —(CH$_2$)$_{0-3}$—N(R$^a$) —(CH$_2$)$_{0-3}$—R$^k$, or —(CH$_2$)$_{0-3}$—O—(CH$_2$)$_{0-3}$—R$^k$, or —(CH$_2$)$_{0-3}$—N(R$^a$) —C(=O) —(CH$_2$)$_{0-3}$—R$^k$; and
   (iii) optionally substituted with from 1 to 4 substituents each of which is independently halogen, —OH, —CN, —O—C$_{1-4}$ alkyl, —O—C$_{1-4}$ haloalkyl, or —N(R$^a$R$^b$),
(18) —C(CH$_3$)$_2$N(R$^a$)C(=O)OCH$_2$R$^k$,
(19) —C(CH$_3$)$_2$N(R$^a$)CH$_2$R$^k$,
(20) —C(CH$_3$)$_2$N(R$^a$)C(=O)R$^k$,
(21) —C(R$^b$)(N(R$^a$)C(=O)R$^k$)(CH$_2$OR$^c$), or
(22) —C(R$^b$)(N(R$^a$)(CH$_2$) —R$^k$)(CH$_2$OR$_c$),
or a pharmaceutically acceptable salt thereof.

3. The compound according to claim 2, wherein R$^1$ is:
(1) —C$_{1-4}$ alkyl, which is substituted with from 1 to 3 substituents each of which is independently halogen, —OH, —CN, —O—C$_{1-4}$ alkyl, —O—C$_{1-4}$ haloalkyl, —C(=O)R$^a$, —CO$_2$R$^a$, —SR$^a$, —S(=O)R$^a$, —N(R$^a$R$^b$), —C(=O) —(CH$_2$)$_{0-2}$N(R$^a$R$^b$), N(R$^a$) —C(=O) —(CH$_2$)$_{0-2}$N(R$^b$R$^c$), —SO$_2$R$^a$, —N(R$^a$)SO$_2$R$^b$, —SO$_2$N(R$^a$R$^b$), —N(R$^a$) —C(=O)R$^b$,

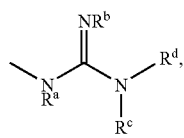

—N(R$^a$)C(=O)N(R$^b$R$^c$), —N(R$^a$)C(=O)C(=O)N(R$^b$R$^c$), or —N(R$^a$)C(=O)OR$^b$,
(2) —R$^k$,
(3) —CH(CH$_3$) —R$^k$,
(4) —(CH$_2$)$_{1-4}$—R$^k$, wherein the —(CH$_2$)$_{1-4}$— moiety is optionally substituted with one of —N(R$^a$R$^b$) or —N(R$^a$) —(CH$_2$)$_2$—OH,
(5) —(CH$_2$)$_{1-2}$—O—(CH$_2$)$_{0-1}$—R$^k$,
(6) —(CH$_2$)$_{1-2}$—S(O)$_n$—(CH$_2$)$_{0-1}$—R$^k$,
(7) —O—(CH$_2$)$_{1-2}$—OR$^k$,
(8) —O—(CH$_2$)$_{1-2}$—O—(CH$_2$)$_{1-2}$—R$^k$,
(9) —O—(CH$_2$)$_{1-2}$—S(O)$_n$R$^k$,
(10) —(CH$_2$)$_{1-2}$—N(R$^a$) —R$^k$,
(11) —(CH$_2$)$_{1-2}$—N(R$^a$) —(CH$_2$)$_{1-3}$—R$^k$,
(12) —(CH$_2$)$_{1-2}$—N(R$^a$) —(CH$_2$)$_{1-3}$—OR$^k$,
(13) —(CH$_2$)$_{0-2}$—C(=O) —R$^k$,
(14) —C(=O)N(R$^a$) —(CH$_2$)$_{1-2}$—R$^k$,
(15) —(CH$_2$)$_{0-2}$—C(=O)N(R$^a$) —(CH$_2$)$_{0-2}$—R$^k$,
(16) —(CH$_2$)$_{1-2}$—N(R$^a$)C(=O) —(CH$_2$)$_{0-1}$—R$^k$,
(17) —(CH$_2$)$_{1-2}$—N(R$^a$)C(=O) —O—(CH$_2$)$_{0-1}$—R$^k$,
(18) —C$_{1-4}$ alkyl which is:
   (i) substituted with aryl or —O-aryl wherein the aryl is optionally substituted with from 1 to 3 substituents each of which is independently fluoro, chloro, —C$_{1-4}$ alkyl, —C$_{1-4}$ fluoroalkyl, —O—C$_{1-4}$ alkyl, —O—C$_{1-4}$ fluoroalkyl, methylenedioxy attached to two adjacent carbon atoms, or phenyl;
   (ii) substituted with —R$^k$, —(CH$_2$)$_{1-3}$—R$^k$, —N(R$^a$) —C(=O) —(CH$_2$)$_{0-3}$—R$^k$, —N(R$^a$) —(CH$_2$)$_{1-3}$—R$^k$, —O—(CH$_2$)$_{1-2}$—R$^k$, or —N(R$^a$) —C(=O) —(CH$_2$)$_{0-2}$—R$^k$; and
   (iii) optionally substituted with from 1 to 4 substituents each of which is independently halogen, —OH, —CN, —O—C$_{1-4}$ alkyl, —O—C$_{1-4}$ haloalkyl, or —N(R$^a$R$^b$),
(19) —C(CH$_3$)$_2$N(R$^a$)C(=O)OCH$_2$R$^k$,
(20) —C(CH$_3$)$_2$N(R$^a$)CH$_2$R$^k$,
(21) —C(CH$_3$)$_2$N(R$^a$)C(=O)R$^k$,
(22) —C(R$^b$)(N(R$^a$)C(=O)R$^k$)(CH$_2$OR$^c$), or
(23) —C(R$^b$)(N(R$^a$)(CH$_2$) —R$^k$)(CH$_2$OR$^c$),
or a pharmaceutically acceptable salt thereof.

4. The compound according to claim 1, wherein R$^k$ is C$_{3-8}$ cycloalkyl; aryl selected from phenyl and naphthyl; a bicyclic carbocycle selected from indanyl and tetrahydronaphthyl; a 5- or 6-membered saturated heterocyclic ring containing from 1 to 4 heteroatoms independently selected from N, O and S; a 5- or 6-membered heteroaromatic ring containing from 1 to 4 heteroatoms independently selected from N, O and S; or a bicyclic heterocycle which is a benzene ring fused to a 5- or 6-membered saturated or unsaturated heterocyclic ring containing from 1 to 3 heteroatoms independently selected from N, O and S;
wherein the cycloalkyl, aryl, bicyclic carbocycle, saturated heterocyclic ring, heteroaromatic ring, or bicyclic heterocycle is optionally substituted with from 1 to 4 substituents each of which is independently
(1) halogen,
(2) —OH,
(3) —CN,
(4) —C$_{1-4}$ haloalkyl,
(5) —C$_{1-4}$ alkyl, which is optionally substituted with from 1 to 3 substituents each of which is independently —OH, —CN, —O—C$_{1-4}$ alkyl, —O—C$_{1-4}$ haloalkyl, —C(=O)R$^a$, —CO$_2$R$^a$, —SR$^a$, —S(=O)R$^a$, —N(R$^a$R$^b$), —C(=O) —(CH$_2$)$_{0-2}$N(R$^a$R$^b$), N(R$^a$) —C(=O) —(CH$_2$)$_{0-2}$N(R$^b$R$^c$), —SO$_2$R$^a$, —N(R$^a$)SO$_2$R$^b$, —SO$_2$N(R$^a$R$^b$), or —N(R$^a$) —C(R$^b$)=O,
(6) —O—C$_{1-4}$ haloalkyl
(7) —O—C$_{1-4}$ alkyl, which is optionally substituted with from 1 to 3 substituents each of which is independently —OH, —CN, —O—C$_{1-6}$ alkyl, —O—C$_{1-6}$ haloalkyl, —C(=O)R$^a$, —CO$_2$R$^a$, —SR$^a$, —S(=O)R$^a$, —N(R$^a$R$^b$), —C(=O) —(CH$_2$)$_{0-2}$N(R$^a$R$^b$), N(R$^a$) —C(=O) —(CH$_2$)$_{0-2}$N(R$^b$R$^c$), —SO$_2$R$^a$, —N(R$^a$)SO$_2$R$^b$, —SO$_2$N(R$^a$R$^b$), or —N(R$^a$) —C(R$^b$)=O,
(8) —NO$_2$,
(9) oxo,
(10) —C(=O)R$^a$,
(11) —CO$_2$R$^a$,
(12) —SR$^a$,
(13) —S(=O)R$^a$,
(14) —N(R$^a$R$^b$),
(15) —C(=O)N(R$^a$R$^b$),
(16) —C(=O) —C$_{1-6}$ alkyl-N(R$^a$R$^b$),
(17) —N(R$^a$)C(=O)R$^b$,
(18) —SO$_2$R$^a$,
(18) —SO$_2$N(R$^a$R$^b$),
(19) —N(R$^a$)SO$_2$R$^b$,
(20) —R$^m$,

(21) —CH(CH$_3$)—R$^m$,
(22) —(CH$_2$)$_{1-4}$—R$^m$,
(23) —(CH$_2$)$_{0-2}$—N(R$^a$)—(CH$_2$)$_{0-2}$—R$^m$,
(24) —(CH$_2$)$_{0-2}$—O—(CH$_2$)$_{0-2}$—R$^m$,
(25) —(CH$_2$)$_{0-2}$—S—(CH$_2$)$_{0-2}$—R$^m$,
(26) —(CH$_2$)$_{0-2}$—C(=O)—(CH$_2$)$_{0-2}$—R$^m$,
(27) —C(=O)—O—(CH$_2$)$_{0-2}$—R$^m$,
(28) —C(=O)N(R$^a$)—R$^m$,
(29) —N(R$^a$)C(=O)—R$^m$,
(30) —N(R$^a$)C(=O)—(CH$_2$)$_{1-3}$—R$^m$, wherein the —(CH$_2$)$_{1-3}$— moiety is optionally substituted with one of —N(R$^a$R$^b$), —N(R$^a$)CO$_2$R$^b$, —SO$_2$R$^a$, —N(R$^a$)SO$_2$R$^b$, —SO$_2$N(R$^a$R$^b$), or —N(R$^a$)—C(R$^b$)=O,
(31) —N(R$^a$)—C(=O)—N(R$^b$)—(CH$_2$)$_{1-2}$—R$^m$,
(32) —N(R$^a$)—C(=O)—O—(CH$_2$)$_{1-2}$—R$^m$, or
(33) —N(R$^a$)—C(=O)—N(R$^b$)SO$_2$—R$^m$;

or a pharmaceutically acceptable salt thereof.

5. The compound according to claim 4, wherein
each R$^m$ is independently C$_{5-7}$ cycloalkyl; aryl selected from phenyl and naphthyl; a 5- or 6-membered saturated heterocyclic ring containing from 1 to 4 heteroatoms independently selected from N, O and S; a 5- or 6-membered heteroaromatic ring containing from 1 to 4 heteroatoms independently selected from N, O and S; or a bicyclic heterocycle which is a benzene ring fused to a 5- or 6-membered, saturated or unsaturated heterocyclic ring containing from 1 to 3 heteroatoms selected from N, O and S; wherein
the cycloalkyl or the aryl is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, —N(R$^a$R$^b$), phenyl, or —(CH$_2$)$_{1-2}$-phenyl;
the saturated heterocyclic ring is optionally substituted with from 1 to 4 substituents each of which is independently —C$_{1-4}$ alkyl optionally substituted with —O—C$_{1-4}$ alkyl, —C$_{1-4}$ haloalkyl, —O—C$_{1-4}$ alkyl, —O—C$_{1-4}$ haloalkyl, oxo, phenyl, —(CH$_2$)$_{1-2}$-phenyl, —C(=O)-phenyl, —CO$_2$-phenyl, —CO$_2$—(CH$_2$)$_{1-2}$-phenyl, a 5- or 6-membered saturated heterocyclic ring containing from 1 to 4 heteroatoms independently selected from N, O and S, or a 5- or 6-membered heteroaromatic ring containing from 1 to 4 heteroatoms independently selected from N, O and S; and
the heteroaromatic ring or the bicyclic heterocycle is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, oxo, phenyl, or —(CH$_2$)$_{1-2}$-phenyl;

or a pharmaceutically acceptable salt thereof.

6. The compound according to claim 4, wherein
R$^k$ is cycloalkyl selected from cyclopropyl, cyclopentyl and cyclohexyl; aryl selected from phenyl and naphthyl; a bicyclic carbocycle selected from indanyl and tetrahydronaphthyl; a 5- or 6-membered saturated heterocyclic ring selected from pyrrolidinyl, piperidinyl, piperazinyl, morpholinyl, pyranyl, tetrahydrofuranyl, imidazolidinyl, thiomorpholinyl, thiazolidinyl, isothiazolidinyl, oxazolidinyl, isooxazolidinyl, and pyrazolidinyl; a 5- or 6-membered heteroaromatic ring selected from thienyl, pyridyl, imidazolyl, pyrrolyl, pyrazolyl, thiazolyl, isothiazolyl, thiadiazolyl, oxopiperidinyl, oxazolyl, isooxazolyl, oxadiazolyl, pyrazinyl, pyrimidinyl, triazolyl, tetrazolyl, furanyl, and pyridazinyl; or a bicyclic heterocycle selected from indolyl, indolinyl, tetrahydroquinolinyl, quinolinyl, 1,4-dioxa-8-azaspiro[4.5]decyl, azabicyclo[2.2.1]heptyl, azabicyclo[2.1.1]hexyl, tetrahydroisoquinolinyl, isoquinolinyl, 2,3-dihydrobenzofuranyl, 2,3-dihydrobenzo-1,4-dioxinyl, and benzo-1,3-dioxolyl;
wherein the cycloalkyl, aryl, bicyclic carbocycle, saturated heterocyclic ring, heteroaromatic ring, or bicyclic heterocycle is optionally substituted with from 1 to 3 substituents each of which is independently
(1) fluoro,
(2) chloro,
(3) bromo,
(4) —CF$_3$,
(5) —C$_{1-4}$ alkyl, which is optionally substituted with 1 or 2 substituents each of which is independently —OH, —CN, —O—C$_{1-4}$ alkyl, —OCF$_3$, —N(R$^a$R$^b$), —C(=O)N(R$^a$R$^b$), or N(R$^a$)—C(=O)—(CH$_2$)$_{0-2}$N(R$^b$R$^c$),
(6) —OCF$_3$,
(7) —O—C$_{1-4}$ alkyl
(8) —NO$_2$,
(9) oxo,
(10) —C(=O)R$^a$,
(11) —CO$_2$R$^a$,
(12) —SR$^a$,
(13) —S(=O)R$^a$,
(14) —N(R$^a$R$^b$),
(15) —C(=O)N(R$^a$R$^b$),
(16) —C(=O)—(CH$_2$)$_{1-2}$—N(R$^a$R$^b$),
(17) —N(R$^a$)C(=O)R$^b$,
(18) —SO$_2$R$^a$,
(19) —R$^m$,
(20) —CH(CH$_3$)—R$^m$,
(21) —CH$_2$—R$^m$,
(22) —(CH$_2$)$_{0-2}$—N(R$^a$)—(CH$_2$)$_{0-2}$—R$^m$,
(23) —O—(CH$_2$)$_{1-2}$—R$^m$,
(24) —(CH$_2$)$_{0-1}$—S—(CH$_2$)$_{0-2}$—R$^m$,
(25) —(CH$_2$)$_{0-1}$—C(=O)—(CH$_2$)$_{0-2}$—R$^m$,
(26) —(CH$_2$)$_{0-1}$—C(=O)—O—(CH$_2$)$_{0-2}$—R$^m$,
(27) —C(=O)N(R$^a$)—R$^m$,
(28) —N(R$^a$)C(=O)R$^m$,
(29) —N(R$^a$)C(=O)—(CH$_2$)$_{1-2}$—R$^m$, wherein the —(CH$_2$)$_{1-2}$— moiety is optionally substituted with —N(R$^a$R$^b$),
(30) —N(R$^a$)—C(=O)—N(R$^b$)—(CH$_2$)$_{1-2}$—R$^m$,
(31) —N(R$^a$)—C(=O)—O—(CH$_2$)$_{1-2}$—R$^m$,
(32) —N(R$^a$)—C(=O)—N(R$^b$)SO$_2$—R$^m$,
(33) —OH;

or a pharmaceutically acceptable salt thereof.

7. The compound according to claim 6, wherein
each R$^m$ is independently aryl selected from phenyl and naphthyl; a 5- or 6-membered saturated heterocyclic ring selected from pyrrolidinyl, imidazolidinyl, pyrazolidinyl, piperidinyl, piperazinyl, thiazolidinyl, and morpholinyl; or a 5- or 6-membered heteroaromatic ring selected from thienyl, pyridyl, imidazolyl, pyrrolyl, pyrazolyl, thiazolyl, isothiazolyl, oxazolyl, isooxazolyl, oxadiazolyl, thiadiazolyl, pyrazinyl, pyrimidinyl, triazolyl, tetrazolyl, furanyl, and pyridazinyl; wherein
the aryl is optionally substituted with from 1 to 3 substituents each of which is independently halogen, —C$_{1-4}$ alkyl, —CF$_3$, —O—C$_{1-4}$ alkyl, —OCF$_3$, or —N(R$^a$R$^b$);
the saturated heterocyclic ring is optionally substituted with 1 or 2 substituents each of which is independently —C$_{1-4}$ alkyl, —CF$_3$, —O—C$_{1-4}$ alkyl, —OCF$_3$, oxo, phenyl, —(CH$_2$)$_{1-2}$-phenyl, —C(=O)-phenyl, —CO$_2$-phenyl, or —CO$_2$—CH$_2$-phenyl; and the heteroaromatic ring is optionally substituted with 1 or 2 substituents each of which is independently —C$_{1-4}$ alkyl, —CF$_3$, —O—C$_{1-4}$ alkyl, —OCF$_3$, oxo, phenyl, or —(CH$_2$)$_{1-2}$-phenyl;

or a pharmaceutically acceptable salt thereof.

8. The compound according to claim 1, wherein R$^2$ is —H or —C$_{1-6}$ alkyl which is optionally substituted with one of:
(1) —N(R$^a$R$^b$),
(2) phenyl which is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, or —C$_{0-6}$ alkyl-N(R$^a$R$^b$), or
(3) a 5- or 6-membered saturated monocyclic heterocycle which contains from 1 to 4 heteroatoms independently selected from N, O and S; wherein the heterocycle is optionally substituted with from 1 to 4 substituents each of which is independently —C$_{1-6}$ alkyl, —O—C$_{1-6}$ alkyl, oxo, or phenyl;

or a pharmaceutically acceptable salt thereof.

9. The compound according to claim 8, wherein R$^2$ is
(1) —H,
(2) —C$_{1-4}$ alkyl,
(3) —(CH$_2$)$_{1-3}$—N(R$^a$R$^b$),
(4) —(CH$_2$)$_{1-3}$-phenyl, wherein the phenyl is optionally substituted with from 1 to 3 substituents each of which is independently fluoro, chloro, bromo, —C$_{1-4}$ alkyl, —C$_{1-4}$ fluoroalkyl, —O—C$_{1-4}$ alkyl, —O—C$_{1-4}$ fluoroalkyl, or —(CH$_2$)$_{1-3}$—N(R$^a$R$^b$); or
(5) —(CH$_2$)$_{1-3}$R$^t$, wherein R$^t$ is a 6-membered saturated heterocyclic ring containing from 1 to 3 heteroatoms independently selected from N, O and S;

or a pharmaceutically acceptable salt thereof.

10. The compound according to claim 9, wherein R$^2$ is —H or methyl; or a pharmaceutically acceptable salt thereof.

11. The compound according to claim 10, wherein R$^2$ is —H; or a pharmaceutically acceptable salt thereof.

12. The compound according to claim 1, wherein R$^3$ is —H or —C$_{1-4}$ alkyl; or a pharmaceutically acceptable salt thereof.

13. The compound according to claim 12, wherein R$^3$ is —H or methyl; or a pharmaceutically acceptable salt thereof.

14. The compound according to claim 13, wherein R$^3$ is —H; or a pharmaceutically acceptable salt thereof.

15. The compound according to claim 1, wherein R$^4$ is
(1) C$_{1-4}$ alkyl,
(2) C$_{1-4}$ alkyl substituted with from 1 to 3 substituents each of which is independently —OH, O—C$_{1-4}$ alkyl, or —O—C$_{1-4}$ haloalkyl,
(3) C$_{1-4}$ alkyl which is substituted with an aryl or with two aryls which are the same or different, and is optionally substituted with —OH,
(4) C$_{1-4}$ alkyl substituted with one of:
(i) C$_{5-7}$ cycloalkyl,
(ii) a fused bicyclic carbocycle consisting of a benzene ring fused to a C$_{5-7}$ cycloalkyl,
(iii) a 5- or 6-membered saturated heterocyclic ring containing from 1 to 4 heteroatoms independently selected from N, O and S,
(iv) a 5- or 6-membered heteroaromatic ring containing from 1 to 4 heteroatoms independently selected from N, O and S, or
(v) a 9- or 10-membered fused bicyclic heterocycle containing from 1 to 4 heteroatoms independently selected from N, O and S, wherein at least one of the rings is aromatic;
(5) C$_{2-4}$ alkynyl optionally substituted with aryl,
(6) C$_{3-7}$ cycloalkyl optionally substituted with aryl,
(7) aryl,
(8) a fused bicyclic carbocycle consisting of a benzene ring fused to a C$_{5-7}$ cycloalkyl,
(9) a 5- or 6-membered saturated heterocyclic ring containing from 1 to 4 heteroatoms independently selected from N, O and S,
(10) a 5- or 6-membered heteroaromatic ring containing from 1 to 4 heteroatoms independently selected from N, O and S, or
(11) a 9- or 10-membered fused bicyclic heterocycle containing from 1 to 4 heteroatoms independently selected from N, O and S, wherein at least one of the rings is aromatic;

wherein each aryl in (3) or the aryl in (5), (6) or (7) or the fused carbocycle in (4)(ii) or (8) is optionally substituted with from 1 to 4 substituents each of which is independently halogen, —OH, —C$_{1-4}$ alkyl, —C$_{1-4}$ alkyl-OR$^a$, —C$_{1-4}$ haloalkyl, —O—C$_{1-4}$ alkyl, —O—C$_{1-4}$ haloalkyl, —CN, —NO$_2$, —N(R$^a$R$^b$), —C$_{1-4}$ alkyl-N(R$^a$R$^b$), —C(=O)N(R$^a$R$^b$), —C(=O)R$^a$, —CO$_2$R$^a$, —C$_{1-4}$ alkyl-CO$_2$R$^a$, —OCO$_2$R$^a$, —SR$^a$, —S(=O)R$^a$, —SO$_2$R$^a$, —N(R$^a$)SO$_2$R$^b$, —SO$_2$N(R$^a$R$^b$), —N(R$^a$)C(=O)R$^b$, —N(R$^a$)CO$_2$R$^b$, —C$_{1-4}$ alkyl-N(R$^a$)CO$_2$R$^b$, phenyl, —C$_{1-4}$ alkyl-phenyl, —O-phenyl, or —(CH$_2$)$_{0-2}$-het wherein het is a 5- or 6-membered heteroaromatic ring containing from 1 to 4 heteroatoms independently selected from N, O and S, and het is optionally fused with a benzene ring, and is optionally substituted with 1 or 2 substituents each of which is independently —C$_{1-4}$ alkyl, —C$_{1-4}$ haloalkyl, —O—C$_{1-4}$ alkyl, —O—C$_{1-4}$ haloalkyl, or —CO$_2$R$^a$;

the saturated heterocyclic ring in (4)(iii) or (9) is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, oxo, phenyl, or a 5- or 6-membered heteroaromatic ring containing from 1 to 4 heteroatoms independently selected from N, O and S; and the heteroaromatic ring in (4)(iv) or (10) or the fused bicyclic heterocycle in (4)(v) or (11) is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, oxo, or phenyl;

or a pharmaceutically acceptable salt thereof.

16. The compound according to claim 15, wherein R$^4$ is:
(1) C$_{1-3}$ alkyl substituted with 1 or 2 phenyls, and is optionally substituted with an —OH,
(2) C$_{1-4}$ alkyl substituted with one of:
(i) cyclohexyl,
(ii) naphthyl,
(iii) a fused bicyclic carbocycle selected from

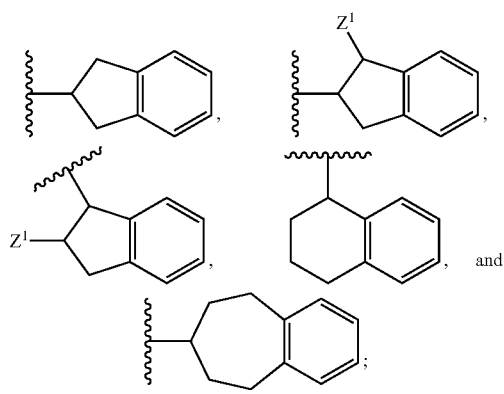

(iv) a saturated heterocyclic ring containing from zero to 1 oxygen atoms and from 1 to 3 nitrogen atoms,
(v) a 5- or 6-membered heteroaromatic ring containing from zero to 1 heteroatoms selected from O and S and from 1 to 3 nitrogen atoms, or
(vi) a fused bicyclic heterocycle selected from

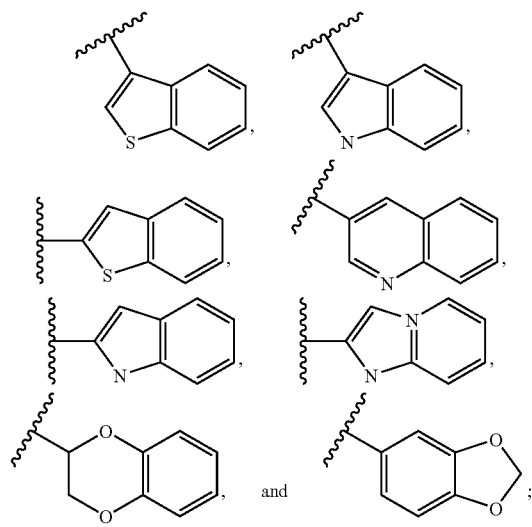

(3)

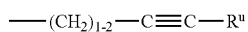

wherein $R^u$ is H or phenyl,
(4) $C_{3-6}$ cycloalkyl optionally substituted with phenyl,
(5) phenyl or naphthyl,
(6) a fused bicyclic carbocycle selected from

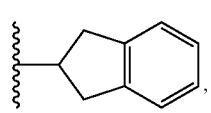

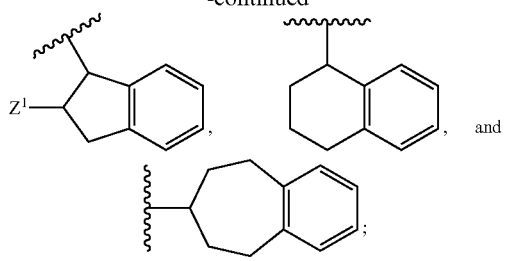

(7) a saturated heterocyclic ring containing from zero to 1 oxygen atoms and from 1 to 3 nitrogen atoms,
(8) a 5- or 6-membered heteroaromatic ring containing from zero to 1 heteroatoms selected from O and S and from 1 to 3 nitrogen atoms, or
(9) a fused bicyclic heterocycle selected from

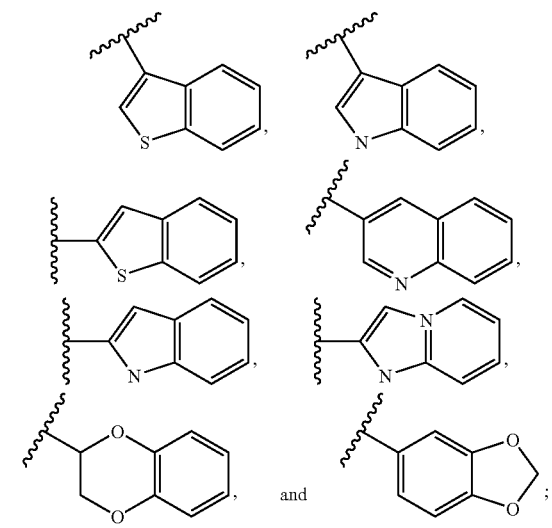

wherein $Z^1$ is —H or —OH;
each phenyl in (1) or the phenyl in (3) or (4) or (5) or the naphthyl in (2)(ii) or (5) is optionally substituted with from 1 to 3 substituents each of which is independently fluoro, bromo, chloro, —OH, —$C_{1-4}$ alkyl, —$CF_3$, —O—$C_{1-4}$ alkyl, —$OCF_3$, —CN, —$NO_2$, —$(CH_2)_{1-2}$—$N(R^aR^b)$, —C(=O)$R^a$, —$CO_2R^a$, —$SR^a$, —S(=O)$R^a$, —$SO_2R^a$, —$N(R^a)SO_2R^b$, —$SO_2N(R^aR^b)$, or —$N(R^a)CO_2R^b$; and is additionally and optionally mono-substituted with phenyl, —$(CH_2)_{1-2}$-phenyl, —O-phenyl, or —$(CH_2)_{0-2}$-het wherein het is thiadiazolyl or indolyl, and het is optionally substituted with —$C_{1-4}$ alkyl, —$CF_3$, —O—$C_{1-6}$ alkyl, —$OCF_3$, or —$CO_2R^a$;
the saturated heterocyclic ring in (2)(iv) or (7) is optionally substituted with from 1 to 3 substituents each of which is independently halogen, —$C_{1-4}$ alkyl, —$CF_3$, —O—$C_{1-4}$ alkyl, —$OCF_3$, oxo; and is additionally and optionally mono-substituted with phenyl or a heteroaromatic ring selected from pyridyl, pyrimidinyl, and pyrazinyl; and
the heteroaromatic ring in (2)(v) or (8) is optionally substituted with from 1 to 3 substituents each of which is independently halogen, —$C_{1-4}$ alkyl, —$CF_3$, —O—C$_{1-4}$ alkyl, —OCF$_3$, or oxo; and is additionally and optionally mono-substituted with phenyl;
or a pharmaceutically acceptable salt thereof.

17. The compound according to claim 15, wherein R$^4$ is:

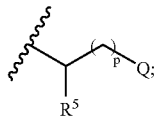

wherein
Q is
(1) ethynyl optionally substituted with aryl,
(2) C$_{5-7}$ cycloalkyl,
(3) aryl,
(4) a fused bicyclic carbocycle consisting of a benzene ring fused to a C$_{5-7}$ cycloalkyl,
(5) a 5- or 6-membered saturated heterocyclic ring containing from 1 to 4 heteroatoms independently selected from N, O and S,
(6) a 5- or 6-membered heteroaromatic ring containing from 1 to 4 heteroatoms independently selected from N, O and S, or
(7) a 9- or 10-membered fused bicyclic heterocycle containing from 1 to 4 heteroatoms independently selected from N, O and S, wherein at least one of the rings is aromatic;
wherein
aryl in (1) or (3) or the fused carbocycle in (4) is optionally substituted with from 1 to 4 substituents each of which is independently halogen, —OH, —C$_{1-4}$ alkyl, —C$_{1-4}$ alkyl-OR$^a$, —C$_{1-4}$ haloalkyl, —O—C$_{1-4}$ alkyl, —O—C$_{1-4}$ haloalkyl, —CN, —NO$_2$, —N(R$^a$R$^b$), —C$_{1-4}$ alkyl-N(R$^a$R$^b$), —C(=O)N(R$^a$R$^b$), —C(=O)R$^a$, —CO$_2$R$^a$, —C$_{1-4}$ alkyl-CO$_2$R$^a$, —OCO$_2$R$^a$, —SR$^a$, —S(=O)R$^a$, —SO$_2$R$^a$, —N(R$^a$)SO$_2$R$^b$, —SO$_2$N(R$^a$R$^b$), —N(R$^a$)C(=O)R$^b$, —N(R$^a$)CO$_2$R$^b$, —C$_{1-4}$ alkyl-N(R$^a$)CO$_2$R$^b$, phenyl, —C$_{1-4}$ alkyl-phenyl, —O-phenyl, or —(CH$_2$)$_{0-2}$-het wherein het is a 5- or 6-membered heteroaromatic ring containing from 1 to 4 heteroatoms independently selected from N, O and S, and het is optionally fused with a benzene ring, and is optionally substituted with —C$_{1-4}$ alkyl, —C$_{1-4}$ haloalkyl, —O—C$_{1-4}$ alkyl, —O—C$_{1-4}$ haloalkyl, or —CO$_2$R$^a$;
the saturated heterocyclic ring in (5) is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, oxo, phenyl, or a 5- or 6-membered heteroaromatic ring containing from 1 to 4 heteroatoms independently selected from N, O and S; and
the heteroaromatic ring in (6) or the fused bicyclic heterocycle in (7) is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, oxo, or phenyl;
R$^5$ is H, methyl, or CH$_2$OH, with the proviso that when R$^5$ is CH$_2$OH, then Q is aryl; and
p is an integer equal to zero, 1 or 2;
or a pharmaceutically acceptable salt thereof.

18. The compound according to claim 17, wherein Q is
(1) —C≡C—R$^u$ wherein R$^u$ is H or phenyl,
(2) phenyl or naphthyl,
(3) cyclopentyl or cyclohexyl,
(4) a fused bicyclic carbocycle selected from the group consisting of indanyl, tetrahydronaphthalenyl, and benzocycloheptyl,
(5) a saturated heterocyclic ring selected from the group consisting of tetrahydrofuranyl, pyrrolidinyl, imidazolidinyl, piperidinyl, piperazinyl, morpholinyl, thiomorpholinyl, thiazolidinyl, isothiazolidinyl, oxazolidinyl, isooxazolidinyl, and pyrazolidinyl,
(6) a heteroaromatic ring selected from the group consisting of thienyl, pyridyl, imidazolyl, pyrrolyl, pyrazolyl, thiazolyl, isothiazolyl, oxazolyl, isooxazolyl, oxadiazolyl, pyrazinyl, pyrimidinyl, triazolyl, tetrazolyl, furanyl, and pyridazinyl, or
(7) a fused bicyclic heterocycle selected from the group consisting of benzothiophenyl, indolyl, pyridoimidazolyl, indazolyl, 2,3-dihydrobenzo-1,4-dioxinyl, dihydrobenzofuranyl, benzo-1,3-dioxolyl, quinolinyl, and isoquinolinyl;
wherein
the phenyl in (1) or the phenyl or naphthyl in (2) is optionally substituted with from 1 to 4 substituents each of which is independently halogen, —OH, —C$_{1-4}$ alkyl, —C$_{1-4}$ haloalkyl, —O—C$_{1-4}$ alkyl, —O—C$_{1-4}$ haloalkyl, —CN, —NO$_2$, —C$_{1-4}$ alkyl-N(R$^a$R$^b$), —C(=O)R$^a$, —CO$_2$R$^a$, —C$_{1-4}$ alkyl-CO$_2$R$^a$, —SR$^a$, —S(=O)R$^a$, —SO$_2$R$^a$, —N(R$^a$)SO$_2$R$^b$, —SO$_2$N(R$^a$R$^b$), —N(R$^a$)CO$_2$R$^b$, —C$_{1-4}$ alkyl-N(R$^a$)CO$_2$R$^b$, phenyl, —(CH$_2$)$_{1-2}$-phenyl, —O-phenyl, or —(CH$_2$)$_{0-2}$-het wherein het is pyrrolyl, pyrazolyl, imidazolyl, triazolyl, thiazolyl, oxazolyl, isothiazolyl, isooxazolyl, pyridyl, pyrazinyl, thiadiazolyl or indolyl, and het is optionally substituted with —C$_{1-4}$ alkyl, —CF$_3$, —O—C$_{1-6}$ alkyl, —OCF$_3$, oxo, or —CO$_2$R$^a$;
the fused carbocycle in (4) is optionally substituted with from 1 to 4 substituents each of which is independently halogen, —OH, —C$_{1-4}$ alkyl, —C$_{1-4}$ haloalkyl, —O—C$_{1-4}$ alkyl, —O—C$_{1-4}$ haloalkyl, —C$_{1-4}$ alkyl-N(R$^a$R$^b$), —C(=O)R$^a$, —CO$_2$R$^a$, —SR$^a$, —S(=O)R$^a$, —SO$_2$R$^a$, —N(R$^a$)CO$_2$R$^b$, phenyl, —(CH$_2$)$_{1-2}$-phenyl, or —O-phenyl;
the saturated heterocyclic ring in (5) is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, oxo, phenyl, pyridyl, pyrazinyl, or pyrimidinyl; and
the heteroaromatic ring in (6) or the fused bicyclic heterocycle in (7) is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, oxo, or phenyl;
or a pharmaceutically acceptable salt thereof.

19. The compound according to claim 18, wherein Q is phenyl, which is optionally substituted with from 1 to 3 substituents each of which is independently fluoro, bromo, chloro, —OH, —C$_{1-4}$ alkyl, —C$_{1-4}$ fluoroalkyl, —O—C$_{1-4}$ alkyl, —O—C$_{1-4}$ fluoroalkyl, —CN, —SR$^a$, —(CH$_2$)$_{1-2}$—N(R$^a$R$^b$), —SO$_2$R$^a$, —N(R$^a$)SO$_2$R$^b$, —SO$_2$N(R$^a$R$^b$), —(CH$_2$)$_{0-2}$—CO$_2$R$^{a*}$, —(CH$_2$)$_{0-2}$—N(R$^a$)CO$_2$R$^{b*}$, —NO$_2$, or phenyl;
each R$^a$ is independently H, methyl, or ethyl;
each R$^b$ is independently H, methyl, or ethyl; and
each R$^{a*}$ and R$^{b*}$ is independently H or —C$_{1-4}$ alkyl;
or a pharmaceutically acceptable salt thereof.

20. The compound according to claim 19, wherein $R^5$ is H and p is zero; or a pharmaceutically acceptable salt thereof.

21. The compound according to claim 20, wherein Q is phenyl which is optionally substituted with from 1 to 3 substituents, each of which is independently —F, —Br, —Cl, —OH, —$C_{1-4}$ alkyl, —$C_{1-4}$ fluoroalkyl, —O—$C_{1-4}$ alkyl, —O—$C_{1-4}$ fluoroalkyl, —CN, —$SR^a$ or —$SO_2R^a$;
or a pharmaceutically acceptable salt thereof.

22. The compound according to claim 21, wherein Q is p-fluorophenyl or 2,3-dimethoxyphenyl;
or a pharmaceutically acceptable salt thereof.

23. The compound according to claim 1, wherein
$R^1$ is —$R^k$;
$R^k$ is a 5- or 6-membered heteroaromatic ring containing from 1 to 3 heteroatoms independently selected from N, O and S;
wherein the heteroaromatic ring is optionally substituted with from 1 to 3 substituents each of which is independently
(1) halogen,
(2) —$C_{1-6}$ alkyl, which is optionally substituted with from 1 to 5 substituents each of which is independently halogen, —O—$C_{1-4}$ alkyl, —O—$C_{1-4}$ haloalkyl, —C(=O)$R^a$, —$CO_2R^a$, —$SR^a$, —S(=O)$R^a$, —N($R^a R^b$), —C(=O)—$(CH_2)_{0-2}$N($R^a R^b$), N($R^a$)—C(=O)—$(CH_2)_{0-2}$N($R^b R^c$), —$SO_2R^a$, —N($R^a$)$SO_2R^b$, —$SO_2$N($R^a R^b$), or —N($R^a$)—C($R^b$)=O,
(3) —$NO_2$,
(4) oxo,
(5) —C(=O)$R^a$,
(6) —$CO_2R^a$,
(7) —C(=O)N($R^a R^b$),
(8) —C(=O)—$C_{1-4}$ alkyl—N($R^a R^b$),
(9) —$R^m$,
(10) —$C_{1-6}$ alkyl-$R^m$, wherein the alkyl is optionally substituted with from 1 to 5 substituents each of which is independently halogen, —OH, —CN, —$C_{1-4}$ haloalkyl, —O—$C_{1-4}$ alkyl, —O—$C_{1-4}$ haloalkyl, —C(=O)$R^a$, —$CO_2R^a$, —$SR^a$, —S(=O)$R^a$, —N($R^a R^b$), —N($R^a$)$CO_2R^b$, —$SO_2R^a$, —N($R^a$)$SO_2R^b$, —$SO_2$N($R^a R^b$), or —N($R^a$)—C($R^b$)=O,
(11) —$C_{0-4}$ alkyl-N($R^a$)—$C_{0-4}$ alkyl-$R^m$,
(12) —$C_{0-4}$ alkyl-O—$C_{0-4}$ alkyl-$R^m$,
(13) —$C_{0-4}$ alkyl-S—$C_{0-4}$ alkyl-$R^m$,
(14) —$C_{0-4}$ alkyl-C(=O)—$C_{0-4}$ alkyl-$R^m$,
(15) —C(=O)—O—$C_{0-4}$ alkyl-$R^m$,
(16) —C(=O)N($R^a$)—$C_{0-4}$ alkyl-$R^m$,
(17) —N($R^a$)C(=O)—$R^m$,
(18) —N($R^a$)C(=O)—$C_{1-6}$ alkyl-$R^m$, wherein the alkyl is optionally substituted with from 1 to 5 substituents each of which is independently halogen, —OH, —CN, —$C_{1-4}$ haloalkyl, —O—$C_{1-4}$ alkyl, —O—$C_{1-4}$ haloalkyl, —C(=O)$R^a$, —$CO_2R^a$, —$SR^a$, —S(=O)$R^a$, —N($R^a R^b$), —N($R^a$)$CO_2R^b$, —$SO_2R^a$, —N($R^a$)$SO_2R^b$, —$SO_2$N($R^a R^b$), or —N($R^a$)—C($R^b$)=O,
(19) —N($R^a$)—C(=O)—N($R^b$)—$C_{0-4}$ alkyl-$R^m$,
(20) —N($R^a$)—C(=O)—O—$C_{0-4}$ alkyl-$R^m$, or
(21) —N($R^a$)—C(=O)—N($R^b$)$SO_2$—$C_{0-4}$ alkyl-$R^m$;
wherein each $R^m$ is independently aryl selected from phenyl and naphthyl or a 5- or 6-membered heteroaromatic ring containing from 1 to 3 heteroatoms independently selected from N, O and S; wherein the aryl is optionally substituted with from 1 to 3 substituents each of which is independently halogen, —$C_{1-4}$ alkyl, —$CF_3$, —O—$C_{1-4}$ alkyl, —$OCF_3$, or —N($R^a R^b$); and
the heteroaromatic ring is optionally substituted with 1 or 2 substituents each of which is independently —$C_{1-4}$ alkyl or oxo; and
each $R^a$ and $R^b$ is independently —H or —$C_{1-4}$ alkyl;
or a pharmaceutically acceptable salt thereof.

24. The compound according to claim 23, wherein $R^1$ is:

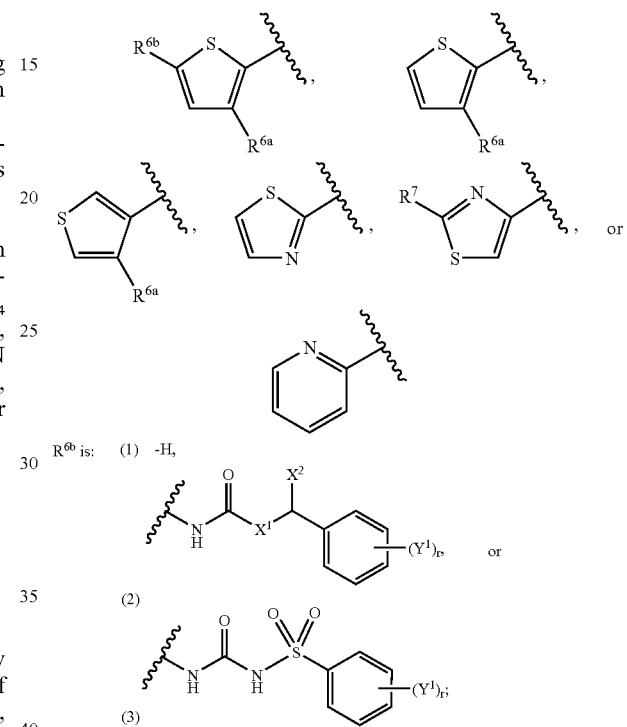

$R^{6b}$ is —H or —$NO_2$; and
$R^7$ is —H or —$C_{1-4}$ alkyl;
or a pharmaceutically acceptable salt thereof.

wherein $X^1$ is a single bond connecting the carbonyl carbon to the carbon substituted with $X^2$, —O—, or —NH—;
$X^2$ is —H, —$NH_2$, or —N(H)$CO_2R^a$;
$Y^1$ is —H, halo or —$C_{1-4}$ alkyl; and
r is an integer equal to zero, 1 or 2; and 25. The compound according to claim 24, wherein
$R^{6a}$ and $R^{6b}$ are both —H; and
$R^7$ is —H or —$CH_3$;
or a pharmaceutically acceptable salt thereof.

26. The compound according to claim 25, wherein
$R^2$ is —H or methyl;
$R^3$ is —H; and
$R^4$ is —$CH_2$-Q; wherein Q is phenyl optionally substituted with from 1 to 3 substituents each of which is independently —F, —Cl, —Br, —OH, —$C_{1-4}$ alkyl, —$CF_3$, —O—$C_{1-4}$ alkyl, —$OCF_3$, —CN, or —$SO_2R^a$; and is additionally and optionally mono-substituted with methylenedioxy attached to two adjacent ring carbon atoms, phenyl, or —O-phenyl;
or a pharmaceutically acceptable salt thereof.

27. The compound according to claim 1, wherein:
$R^1$ is —$R^k$;
$R^k$ is phenyl which is optionally substituted with from 1 to 3 substituents each of which is independently:
(1) halogen,
(2) —$C_{1-6}$ alkyl, which is optionally substituted with from 1 to 5 substituents each of which is independently halogen, —OH, —O—$C_{1-4}$ alkyl, —O—$C_{1-4}$ haloalkyl, —C(=O)$R^a$, —$CO_2R^a$, —$SR^a$, —S(=O)$R^a$, —N($R^aR^b$), —C(=O)—$(CH_2)_{0-2}$N($R^aR^b$), N($R^a$)—C(=O)—$(CH_2)_{0-2}$N($R^bR^c$), —$SO_2R^a$, —N($R^a$)$SO_2R^b$, —$SO_2$N($R^aR^b$), or —N($R^a$)—C($R^b$)=O,
(3) —$NO_2$,
(4) —C(=O)$R^a$,
(5) —$CO_2R^a$,
(6) —C(=O)N($R^aR^b$),
(7) —C(=O)—$C_{1-4}$ alkyl-N($R^aR^b$),
(8) —$R^m$,
(9) —$C_{1-6}$ alkyl-$R^m$, wherein the alkyl is optionally substituted with from 1 to 5 substituents each of which is independently halogen, —OH, —CN, —$C_{1-4}$ haloalkyl, —O—$C_{1-4}$ alkyl, —O—$C_{1-4}$ haloalkyl, —C(=O)$R^a$, —$CO_2R^a$, —$SR^a$, —S(=O)$R^a$, —N($R^aR^b$), —N($R^a$)$CO_2R^b$, —$SO_2R^a$, —N($R^a$)$SO_2R^b$, —$SO_2$N($R^aR^b$), or —N($R^a$)—C($R^b$)=O,
(10) —$C_{0-4}$ alkyl-N($R^a$)—$C_{0-4}$ alkyl-$R^m$,
(11) —$C_{0-4}$ alkyl-O—$C_{0-4}$ alkyl-$R^m$,
(12) —$C_{0-4}$ alkyl-S—$C_{0-4}$ alkyl-$R^m$,
(13) —$C_{0-4}$ alkyl-C(=O)—$C_{0-4}$ alkyl-$R^m$,
(14) —C(=O)—O—$C_{0-4}$ alkyl-$R^m$,
(15) —C(=O)N($R^a$)$C_{0-4}$ alkyl-$R^m$,
(16) —N($R^a$)C(=O)—$R^m$,
(17) —N($R^a$)C(=O)—$C_{1-6}$ alkyl-$R^m$, wherein the alkyl is optionally substituted with from 1 to 5 substituents each of which is independently halogen, —OH, —CN, —$C_{1-4}$ haloalkyl, —O—$C_{1-4}$ alkyl, —O—$C_{1-4}$ haloalkyl, —C(=O)$R^a$, —$CO_2R^a$, —$SR^a$, —S(=O)$R^a$, —N($R^aR^b$), —N($R^a$)$CO_2R^b$, —$SO_2R^a$, —N($R^a$)$SO_2R^b$, —$SO_2$N($R^aR^b$), or —N($R^a$)—C($R^b$)=O,
(18) —N($R^a$)—C(=O)—N($R^b$)—$C_{0-4}$ alkyl-$R^m$,
(19) —N($R^a$)—C(=O)—O—$C_{0-4}$ alkyl-$R^m$, or
(20) —N($R^a$)—C(=O)—N($R^b$)$SO_2$—$C_{0-4}$ alkyl-$R^m$;
wherein each $R^m$ is independently aryl selected from phenyl and naphthyl; a 5- or 6-membered saturated heterocyclic ring containing from 1 to 3 heteroatoms independently selected from N, O and S; or a 5- or 6-membered heteroaromatic ring containing from 1 to 3 heteroatoms independently selected from N, O and S; wherein
the aryl is optionally substituted with from 1 to 3 substituents each of which is independently halogen, —$C_{1-4}$ alkyl, —$CF_3$, —O—$C_{1-4}$ alkyl, —$OCF_3$, or —N($R^aR^b$);
the saturated heterocyclic ring is optionally substituted with from 1 to 3 substituents each of which is independently —$C_{1-4}$ alkyl or oxo, and is additionally optionally mono-substituted with phenyl, —$(CH_2)_{1-2}$-phenyl, —C(=O)-phenyl, —$CO_2$-phenyl, or —$CO_2$—$(CH_2)_{1-2}$-phenyl; and
the heteroaromatic ring is optionally substituted with 1 or 2 substituents each of which is independently —$C_{1-4}$ alkyl or oxo;
or a pharmaceutically acceptable salt thereof.

28. The compound according to claim 27, wherein $R^1$ is phenyl which is mono-substituted with one of:
(1) fluoro, chloro, or bromo,
(2) —$C_{1-4}$ alkyl, which is optionally substituted with 1 or 2 substituents each of which is independently —OH, —O—$C_{1-4}$ alkyl, —$OCF_3$, —C(=O)$R^a$, —$CO_2R^a$, —$SR^a$, —N($R^aR^b$), or —C(=O)N($R^aR^b$),
(3) —$NO_2$,
(4) —$C_{1-4}$ alkyl-$R^m$,
(5) —O—$(CH_2)_{1-2}$—$R^m$,
(6) —$(CH_2)_{0-2}$—S—$(CH_2)_{0-2}$—$R^m$
(7) —N($R^a$)C(=O)—$R^m$,
(8) —N($R^a$)C(=O)—$(CH_2)_{1-2}$—$R^m$, wherein the $(CH_2)_{1-2}$ moiety is optionally mono-substituted with —N($R^aR^b$) or —N($R^a$)$CO_2R^b$, or
(9) —N($R^a$)—C(=O)—N($R^b$)—$(CH_2)_{1-2}$—$R^m$;
wherein $R^m$ is aryl selected from phenyl and naphthyl; a 5- or 6-membered saturated heterocyclic ring containing 1 or 2 heteroatoms independently selected from N and O; or a 5- or 6-membered heteroaromatic ring containing from 1 or 2 nitrogens; wherein
the aryl is optionally substituted with from 1 to 3 substituents each of which is independently halogen, —$C_{1-4}$ alkyl, —$CF_3$, —O—$C_{1-4}$ alkyl, —$OCF_3$, or —N($R^aR^b$); and
the saturated heterocyclic ring is optionally substituted with from 1 to 3 substituents each of which is independently —$C_{1-4}$ alkyl or oxo; and is additionally and optionally mono-substituted with phenyl, —$(CH_2)_{1-2}$-phenyl, —C(=O)-phenyl, —$CO_2$-phenyl, or —$CO_2$—$(CH_2)_{1-2}$-phenyl; and
the heteroaromatic ring is optionally substituted with 1 or 2 substituents each of which is independently —$C_{1-4}$ alkyl or oxo; and
each $R^a$ and $R^b$ is each independently —H or —$C_{1-4}$ alkyl; or a pharmaceutically acceptable salt thereof.

29. The compound according to claim 28, wherein
$R^2$ is —H or methyl;
$R^3$ is —H; and
$R^4$ is —$CH_2$-Q; wherein Q is phenyl optionally substituted with from 1 to 3 substituents each of which is independently —F, —Cl, —Br, —OH, —$C_{1-4}$ alkyl, —$CF_3$, —O—$C_{1-4}$ alkyl, —$OCF_3$, —CN, or —$SO_2R^a$; and is additionally and optionally mono-substituted with methylenedioxy attached to two adjacent ring carbon atoms, phenyl, or —O-phenyl;
or a pharmaceutically acceptable salt thereof.

30. The compound according to claim 1, wherein
$R^1$ is —$R^k$;
$R^k$ is a 5- or 6-membered saturated heterocyclic ring containing from 0 to 1 oxygen atoms and from 1 to 3 nitrogen atoms or a bicyclic heterocycle which is a benzene ring fused to a 5- or 6-membered saturated heterocyclic ring containing from 0 to 1 oxygen atoms and from 1 to 3 nitrogen atoms;
wherein the saturated heterocyclic ring or bicyclic heterocycle is optionally substituted with from 1 to 3 substituents each of which is independently
(1) halogen,
(2) —$C_{1-6}$ alkyl, which is optionally substituted with from 1 to 5 substituents each of which is independently halogen, —O—$C_{1-4}$ alkyl, —O—$C_{1-4}$ haloalkyl, —C(=O)$R^a$, —$CO_2R^a$, —$SR^a$, —S(=O)$R^a$, —N($R^aR^b$), —C(=O)—$(CH_2)_{0-2}$N($R^aR^b$), N($R^a$)—C(=O)—$(CH_2)_{0-2}$N($R^bR^c$), —$S_2R^a$, —N($R^a$)$SO_2R^b$, —$SO_2$N($R^aR^b$), or —N($R^a$)—C($R^b$)=O, (3) —NO₂,
(4) oxo,
(5) —C(=O)Rᵃ,
(6) —CO₂Rᵃ,
(7) —C(=O)N(RᵃRᵇ),
(8) —C(=O) —C₁₋₄ alkyl-N(RᵃRᵇ),
(9) —SRᵃ,
(10) —S(=O)Rᵃ,
(11) —SO₂Rᵃ,
(12) —N(RᵃRᵇ),
(13) —Rᵐ,
(14) —C₁₋₆ alkyl-Rᵐ, wherein the alkyl is optionally substituted with from 1 to 5 substituents each of which is independently halogen, —OH, —CN, —C₁₋₄ haloalkyl, —O—C₁₋₄ alkyl, —O—C₁₋₄ haloalkyl, —C(=O)Rᵃ, —CO₂Rᵃ, —SRᵃ, —S(=O)Rᵃ, —N(RᵃRᵇ), —N(Rᵃ)CO₂Rᵇ, —SO₂Rᵃ, —N(Rᵃ)SO₂Rᵇ, —SO₂N(RᵃRᵇ), or —N(Rᵃ) —C(Rᵇ)=O,
(15) —C₀₋₄ alkyl-N(Rᵃ) —C₀₋₄ alkyl-Rᵐ,
(16) —C₀₋₄ alkyl-O—C₀₋₄ alkyl-Rᵐ,
(17) —C₀₋₄ alkyl-S—C₀₋₄ alkyl-Rᵐ,
(18) —C₀₋₄ alkyl-C(=O)C₀₋₄ alkyl-Rᵐ,
(19) —C(=O) —O—C₀₋₄ alkyl-Rᵐ,
(20) —C(=O)N(Rᵃ) —C₀₋₄ alkyl-Rᵐ,
(21) —N(Rᵃ)C(=O) —Rᵐ,
(22) —N(Rᵃ)C(=O) —C₁₋₆ alkyl-Rᵐ, wherein the alkyl is optionally substituted with from 1 to 5 substituents each of which is independently halogen, —OH, —CN, —C₁₋₄ haloalkyl, —O—C₁₋₄ alkyl, —O—C₁₋₄ haloalkyl, —C(=O)Rᵃ, —CO₂Rᵃ, —SRᵃ, —S(=O)Rᵃ, —N(RᵃRᵇ), —N(Rᵃ)CO₂Rᵇ, —SO₂Rᵃ, —N(Rᵃ)SO₂Rᵇ, —SO₂N(RᵃRᵇ), or —N(Rᵃ) —C(Rᵇ)=O,
(23) —N(Rᵃ) —C(=O) —N(Rᵇ) —C₀₋₄ alkyl-Rᵐ,
(24) —N(Rᵃ) —C(=O) —O—C₀₋₄ alkyl-Rᵐ, or
(25) —N(Rᵃ) —C(=O) —N(Rᵇ)SO₂—C₀₋₄ alkyl-Rᵐ;

wherein each Rᵐ is independently aryl selected from phenyl and naphthyl; a 5- or 6-membered saturated heterocyclic ring containing from 1 to 3 heteroatoms independently selected from N, O and S; a 5- or 6-membered heteroaromatic ring containing from 1 to 3 heteroatoms independently selected from N, O and S; or a 9- to 10-membered bicyclic heterocycle which is saturated or unsaturated and contains from 1 to 3 heteroatoms independently selected from N, O and S; wherein the aryl is optionally substituted with from 1 to 3 substituents each of which is independently halogen, —C₁₋₄ alkyl, —CF₃, —O—C₁₋₄ alkyl, —OCF₃, or —N(RᵃRᵇ);

the saturated heterocyclic ring is optionally substituted with from 1 to 3 substituents each of which is independently —C₁₋₄ alkyl or oxo, and is additionally optionally mono-substituted with phenyl, —(CH₂)₁₋₂-phenyl, —C(=O)-phenyl, —CO₂-phenyl, or —CO₂—(CH₂)₁₋₂-phenyl; and the heteroaromatic ring or the bicyclic heterocycle is optionally substituted with 1 or 2 substituents each of which is independently —C₁₋₄ alkyl or oxo;

or a pharmaceutically acceptable salt thereof.

31. The compound according to claim 30, wherein

R¹ is:

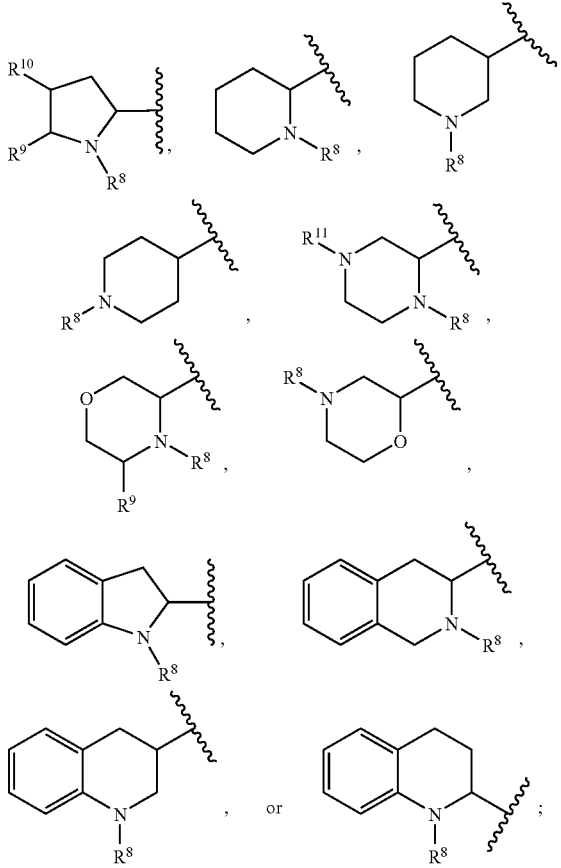

R⁸ is:
(1) —H
(2) —C₁₋₄ alkyl, which is optionally substituted with 1 or 2 substituents each of which is independently —OH, —O—C₁₋₄ alkyl, —OCF₃, —C(=O)Rᵃ, —CO₂Rᵃ, —SRᵃ, —N(RᵃRᵇ), or —C(=O)N(RᵃRᵇ),
(3) —C(=O)Rᵃ,
(4) —CO₂Rᵃ,
(5) —C(=O) —(CH₂)₁₋₂—N(RᵃRᵇ),
(6) —SO₂Rᵃ,
(7) —(CH₂)₁₋₂—Rᵐ,
(8) —(CH₂)₀₋₂—C(=O) —(CH₂)₀₋₂—Rᵐ,
(9) —C(=O) —O—(CH₂)₀₋₂—Rᵐ, or
(10) —C(=O)N(Rᵃ) —(CH₂)₀₋₂—Rᵐ;

R⁹ is —H, —C₁₋₄ alkyl, or oxo;
R¹⁰ is —H, —OH, —C₁₋₄ alkyl, —O—C₁₋₄ alkyl, oxo, or —O—(CH₂)₁₋₂—Rᵐ;
R¹¹ is
(1) —H,
(2) —C₁₋₄ alkyl, which is optionally substituted with 1 or 2 substituents each of which is independently —OH, —O—C₁₋₄ alkyl, —OCF₃, —C(=O)Rᵃ, —CO₂Rᵃ, —SRᵃ, —N(RᵃRᵇ), or —C(=O)N(RᵃRᵇ),
(3) —C(=O)Rᵃ,
(4) —CO₂Rᵃ,
(5) —C(=O) —(CH₂)₁₋₂—N(RᵃRᵇ),
(6) —SO₂Rᵃ, (7) —(CH$_2$)$_{1-2}$—R$^m$,
(8) —(CH$_2$)$_{0-2}$—C(=O) —(CH$_2$)$_{0-2}$—R$^m$,
(9) —C(=O) —O—(CH$_2$)$_{0-2}$—R$^m$, or
(10) —C(=O)N(R$^a$) —(CH$_2$)$_{0-2}$—R$^m$;
with the proviso that when one of R$^8$ and R$^{11}$ is —(CH$_2$)$_{1-2}$—R$^m$, —(CH$_2$)$_{0-2}$—C(=O) —(CH$_2$)$_{0-2}$—R$^m$, —C(=O) —O—(CH$_2$)$_{0-2}$—R$^m$, or —C(=O)N(R$^a$) —(CH$_2$)$_{0-2}$—R$^m$, then the other of R$^8$ and R$^{11}$ is other than —(CH$_2$)$_{1-2}$—R$^m$, —(CH$_2$)$_{0-2}$—C(=O) —(CH$_2$)$_{0-2}$R$^m$, —C(=O) —O—(CH$_2$)$_{0-2}$—R$^m$, or —C(=O)N(R$^a$) —(CH$_2$)$_{0-2}$—R$^m$;

R$^m$ is aryl selected from phenyl and naphthyl; a 5- or 6-membered saturated heterocyclic ring containing 1 or 2 heteroatoms independently selected from N and O; a 5- or 6-membered heteroaromatic ring containing from 1 to 3 heteroatoms selected from N, O and S; or a bicyclic heterocycle which is a benzene ring fused to a saturated or unsaturated heterocycle containing from 1 to 3 nitrogen atoms; wherein
the aryl is optionally substituted with from 1 to 3 substituents each of which is independently halogen, —C$_{1-4}$ alkyl, —CF$_3$, —O—C$_{1-4}$ alkyl, —OCF$_3$, or —N(R$^a$R$^b$); and
the saturated heterocyclic ring is optionally substituted with from 1 to 3 substituents each of which is independently —C$_{1-4}$ alkyl or oxo; and is additionally and optionally mono-substituted with phenyl, —(CH$_2$)$_{1-2}$-phenyl, —C(=O)-phenyl, —CO$_2$-phenyl, or —CO$_2$—(CH$_2$)$_{1-2}$-phenyl; and
the heteroaromatic ring or the bicyclic heterocycle is optionally substituted with 1 or 2 substituents each of which is independently —C$_{1-4}$ alkyl or oxo; and
each R$^a$ and R$^b$ is independently —H or —C$_{1-4}$ alkyl;
or a pharmaceutically acceptable salt thereof.

32. The compound according to claim 31, wherein
R$^2$ is —H or methyl;
R$^3$ is —H; and
R$^4$ is —CH$_2$-Q; wherein Q is phenyl optionally substituted with from 1 to 3 substituents each of which is independently —F, —Cl, —Br, —OH, —C$_{1-4}$ alkyl, —CF$_3$, —O—C$_{1-4}$ alkyl, —OCF$_3$, —CN, or —SO$_2$R$^a$; and is additionally and optionally mono-substituted with methylenedioxy attached to two adjacent ring carbon atoms, phenyl, or —O-phenyl;
or a pharmaceutically acceptable salt thereof.

33. The compound according to claim 1, which is a compound of Formula (II):

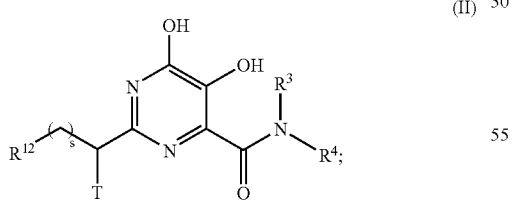

(II)

wherein T is:
(1) —H,
(2) —OH,
(3) —C$_{1-4}$ haloalkyl,
(4) —C$_{1-3}$ alkyl, optionally substituted with —OH or —O—C$_{1-4}$ alkyl,
(5) —O—C$_{1-4}$ haloalkyl,
(6) —O—C$_{1-4}$ alkyl (7) —N(R$^a$R$^b$),
(8) —N(R$^a$) —(CH$_2$)$_2$—OH,
(9) —N(R$^a$) —CO$_2$R$^b$,
(10) —N(R$^a$) —C(=O) —(CH$_2$)$_{1-2}$—N(R$^a$R$^b$),
(11) —R$^k$,
(12) —(CH$_2$)$_{1-4}$—R$^k$,
(13) —(CH$_2$)$_{2-0}$—(CH$_2$)$_{0-2}$—R$^k$,
(14) —(CH$_2$)$_{0-2}$—N(R$^a$) —(CH$_2$)$_{0-3}$—R$^k$, or
(15) —(CH$_2$)$_{0-2}$—N(R$^a$) —C(=O) —(CH$_2$)$_{0-2}$—R$^k$;

R$^k$ is aryl selected from phenyl and naphthyl; a 5- or 6-membered saturated heterocyclic ring containing from 1 to 3 heteroatoms independently selected from N, O and S; a 5- or 6-membered heteroaromatic ring containing from 1 to 3 heteroatoms independently selected from N, O and S; or a bicyclic heterocycle which is a benzene ring fused to a 5- or 6-membered saturated or unsaturated heterocyclic ring containing from 1 to 3 heteroatoms independently selected from N, O and S; wherein
the aryl is optionally substituted with from 1 to 4 substituents each of which is independently halogen, —C$_{1-4}$ alkyl, —C$_{1-4}$ alkyl-OR$^a$, —C$_{1-4}$ haloalkyl, —O—C$_{1-4}$ alkyl, —O—C$_{1-4}$ haloalkyl, or —N(R$^a$R$^b$); and
the saturated heterocyclic ring is optionally substituted with from 1 to 4 substituents each of which is independently —C$_{1-4}$ alkyl; —C$_{1-4}$ alkyl-OR$^a$; —C$_{1-4}$ haloalkyl; —O—C$_{1-4}$ alkyl; —O—C$_{1-4}$ haloalkyl; —C(=O)R$^a$; oxo; ethylenedioxy spiro substituted on a ring carbon; phenyl; —CH$_2$-phenyl; a 5- or 6-membered saturated heterocyclic ring containing from 1 to 4 heteroatoms independently selected from N, O and S; —CH$_2$-saturated heterocycle which is a a 5- or 6-membered ring containing from 1 to 4 heteroatoms independently selected from N, O and S; or a 5- or 6-membered heteroaromatic ring containing from 1 to 4 heteroatoms independently selected from N, O and S;
the heteroaromatic ring is optionally substituted with from 1 to 4 substituents each of which is independently —C$_{1-4}$ alkyl, —C$_{1-4}$ alkyl-OR$^a$, —C$_{1-4}$ haloalkyl, —O—C$_{1-4}$ alkyl, —O—C$_{1-4}$ haloalkyl, or oxo; and
the bicyclic heterocycle is optionally substituted with from 1 to 4 substituents each of which is independently —C$_{1-4}$ alkyl or oxo;

R$^{12}$ is phenyl which is optionally substituted with from 1 to 3 substituents each of which is independently —F, —Cl, Br, —C$_{1-4}$ alkyl, —CF$_3$, —O—C$_{1-4}$ alkyl, —OCF$_3$, methylenedioxy attached to two adjacent carbon atoms, or phenyl;
each R$^a$ and R$^b$ is independently —H or —C$_{1-4}$ alkyl; and
s is an integer equal to zero, 1, 2, or 3;
or a pharmaceutically acceptable salt thereof.

34. The compound according to claim 33, wherein
R$^3$ is —H; and
R$^4$ is —CH$_2$-Q; wherein Q is phenyl optionally substituted with from 1 to 3 substituents each of which is independently —F, —Cl, —Br, —OH, —C$_{1-4}$ alkyl, —CF$_3$, —O—C$_{1-4}$ alkyl, —OCF$_3$, —CN, —SR$^a$, or —SO$_2$R$^a$; and is additionally and optionally mono-substituted with methylenedioxy attached to two adjacent ring carbon atoms, phenyl, or —O-phenyl;
or a pharmaceutically acceptable salt thereof.

35. The compound according to claim 33, wherein
s is zero, 1 or 2;
and with the proviso that when s is 1 or 2, T is —H;
or a pharmaceutically acceptable salt thereof.

36. A compound of Formula (III):

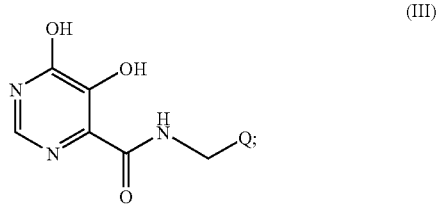

wherein Q is phenyl optionally substituted with from 1 to 3 substituents each of which is independently —F, —Cl, —Br, —OH, —C$_{1-4}$ alkyl, —CF$_3$, —O—C$_{1-4}$ alkyl, —OCF$_3$, —CN, —SR$^a$, or —SO$_2$R$^a$; and is additionally and optionally mono-substituted with methylenedioxy attached to two adjacent ring carbon atoms, phenyl, or —O-phenyl; and
each R$^a$ is independently —H or —C$_{1-6}$alkyl;
or a pharmaceutically acceptable salt thereof.

37. The compound according to claim 1, wherein R$^1$ is
(1) —C$_{1-4}$ alkyl, which is substituted with 1 to 3 substituents each of which is independently fluoro, chloro, —OH, —O—C$_{1-4}$ alkyl, —O—C$_{1-4}$ haloalkyl, —C(=O)R$^a$, —CO$_2$R$^a$, —SR$^a$, —S(=O)R$^a$, —N(R$^a$R$^b$), —C(=O) —(CH$_2$)$_{0-2}$N(R$^a$R$^b$), —N(R$^a$) —C(=O) —(CH$_2$)$_{1-2}$N(R$^b$R$^c$), —SO$_2$R$^a$, —N(R$^a$)SO$_2$R$^b$, —SO$_2$N(R$^a$R$^b$), —N(R$^a$) —C(R$^b$)=O,

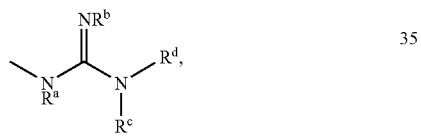

—N(R$^a$)C(=O)N(R$^b$R$^c$), —N(R$^a$)C(=O)C(=O)N(R$^b$R$^c$), or —N(R$^a$)C(=O)OR$^b$,
(2) —(CH$_2$)$_{1-3}$—R$^k$,
(3) —(CH$_2$)$_{1-3}$—O —(CH$_2$)$_{0-2}$—R$^k$,
(4) —(CH$_2$)$_{1-3}$—N—(CH$_2$)$_{0-2}$—R$^k$,
(5) —(CH$_2$)$_{1-3}$—N(R$^a$)C(=O) —(CH$_2$)$_{0-2}$—R$^k$,
(6) —(CH$_2$)$_{1-3}$—N(R$^a$)C(=O) —O—(CH$_2$)$_{0-2}$—R$^k$,
(7) —(CH$_2$)$_{0-3}$—C(=O)N(R$^a$) —(CH$_2$)$_{0-2}$—R$^k$, or
(8) —C(=O) —(CH$_2$)$_{0-2}$—R$^k$,
(9) —C(CH$_3$)$_2$N(R$^a$)C(=O)OCH$_2$R$^k$,
(10) —C(CH$_3$)$_2$N(R$^a$)CH$_2$R$^k$,
(11) —C(CH$_3$)$_2$N(R$^a$)C(=O)R$^k$,
(12) —C(R$^b$)(N(R$^a$)C(=O)R$^k$)(CH$_2$OR$^c$), or
(13) —C(R$^b$)(N(R$^a$)(CH$_2$) —R$^k$)(CH$_2$OR$^c$),
R$^k$ is aryl selected from phenyl and naphthyl, with the proviso that when R$^1$ is —(CH$_2$)$_{1-3}$—R$^k$, then R$^k$ is not phenyl; a bicyclic carbocycle selected from indanyl and tetrahydronaphthyl; a 5- or 6-membered saturated heterocyclic ring containing from 1 to 4 heteroatoms independently selected from N, O and S; a 5- or 6-membered heteroaromatic ring containing from 1 to 4 heteroatoms independently selected from N, O and S; or a bicyclic heterocycle which is a benzene ring fused to a 5- or 6-membered saturated or unsaturated heterocyclic ring containing from 1 to 3 heteroatoms independently selected from N, O and S, with the proviso that the bicyclic heterocycle is not benzo-1,3-dioxolyl; wherein the aryl, bicyclic carbocycle, saturated heterocyclic ring, heteroaromatic ring, or bicyclic heterocycle is optionally substituted with from 1 to 3 substituents each of which is independently
(1) fluoro, chloro, or bromo,
(2) —OH,
(3) —CN,
(4) —CF$_3$,
(4) —C$_{1-4}$ alkyl, which is optionally substituted with 1 or 2 substituents each of which is independently —OH, —O—C$_{1-4}$ alkyl, —OCF$_3$, —C(=O)R$^a$, —CO$_2$R$^a$, —SR$^a$, or —N(R$^a$R$^b$),
(5) —OCF$_3$,
(5) —O—C$_{1-4}$ alkyl,
(8) oxo,
(9) methylenedioxy attached to two adjacent ring carbon atoms,
(10) —C(=O)R$^a$,
(11) —CO$_2$R$^a$,
(12) —SR$^a$,
(13) —S(=O)R$^a$,
(14) —N(R$^a$R$^b$),
(15) —(CH$_2$)$_{0-2}$—C(=O)N(R$^a$R$^b$),
(16) —C(=O) —(CH$_2$)$_{1-2}$—N(R$^a$R$^b$), or
(17) —SO$_2$R$^a$;
or a pharmaceutically acceptable salt thereof.

38. The compound according to claim 37, wherein
R$^2$ is —H; and
R$^4$ is —CH$_2$-Q; wherein Q is phenyl optionally substituted with from 1 to 3 substituents each of which is independently —F, —Cl, —Br, —OH, —C$_{1-4}$ alkyl, —CF$_3$, —O—C$_{1-4}$ alkyl, —OCF$_3$, —CN, or —SO$_2$R$^a$; and is additionally and optionally mono-substituted with methylenedioxy attached to two adjacent ring carbon atoms, phenyl, or —O-phenyl;
each R$^a$ and R$^b$ is independently —H or —C$_{1-4}$ alkyl;
R$^k$ is aryl selected from phenyl and naphthyl, with the proviso that when R$^1$ is —(CH$_2$)$_{1-3}$—R$^k$, then R$^k$ is not phenyl; a bicyclic carbocycle selected from indanyl and tetrahydronaphthyl; a 5- or 6-membered saturated heterocyclic ring containing from 1 to 4 heteroatoms independently selected from N, O and S; a 5- or 6-membered heteroaromatic ring containing from 1 to 4 heteroatoms independently selected from N, O and S; or a bicyclic heterocycle which is a benzene ring fused to a 5- or 6-membered saturated or unsaturated heterocyclic ring containing from 1 to 3 heteroatoms independently selected from N, O and S, with the proviso that the bicyclic heterocycle is not benzo-1,3-dioxolyl; wherein the aryl, bicyclic carbocycle, saturated heterocyclic ring, heteroaromatic ring, or bicyclic heterocycle is optionally substituted with from 1 to 3 substituents each of which is independently
(1) fluoro, chloro, or bromo,
(2) —OH,
(3) —CN,
(4) —CF$_3$,
(4) —C$_{1-4}$ alkyl, which is optionally substituted with 1 or 2 substituents each of which is independently —OH, —O—C$_{1-4}$ alkyl, —OCF$_3$, —C(=O)R$^a$, —CO$_2$R$^a$, —SR$^a$, or —N(R$^a$R$^b$),
(5) —OCF$_3$,
(5) —O—C$_{1-4}$ alkyl,
(8) oxo,
(9) methylenedioxy attached to two adjacent ring carbon atoms,
(10) —C(=O)R$^a$,

(11) —CO$_2$R$^a$,
(12) —SR$^a$,
(13) —S(=O)R$^a$,
(14) —N(R$^a$R$^b$),
(15) —(CH$_2$)$_{0-2}$—C(=O)N(R$^a$R$^b$),
(16) —C(=O) —(CH$_2$)$_{1-2}$—N(R$^a$R$^b$), or
(17) —SO$_2$R$^a$;

or a pharmaceutically acceptable salt thereof.

39. The compound according to claim 1, which is a compound of Formula (IV):

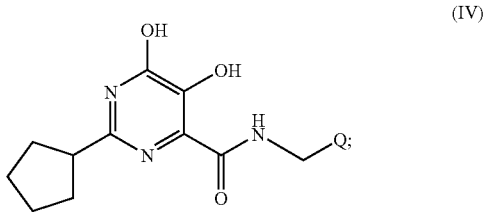

(IV)

wherein Q is phenyl optionally substituted with from 1 to 3 substituents each of which is independently —F, —Cl, —Br, —OH, —C$_{1-4}$ alkyl, —CF$_3$, —O—C$_{1-4}$ alkyl, —OCF$_3$, —CN, —SR$^a$, or —SO$_2$R$^a$; and is additionally and optionally mono-substituted with methylenedioxy attached to two adjacent ring carbon atoms, phenyl, or —O-phenyl;

or a pharmaceutically acceptable salt thereof.

40. The compound according to claim 1, which is a compound of Formula (V):

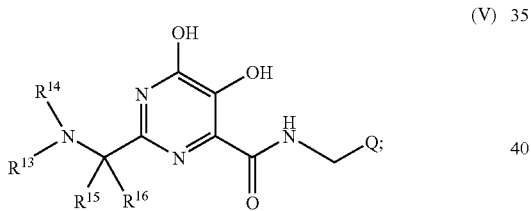

(V)

wherein
R$^{13}$ is —H or —C$_{1-6}$ alkyl;
R$^{14}$ is —H, —C$_{1-6}$ alkyl, —C(=O) —C$_{1-6}$ alkyl, —C(=O) —(CH$_2$)$_{0-2}$-J, or —C(=O) —O—(CH$_2$)$_{0-2}$-J; wherein J is aryl selected from phenyl and naphthyl; a 5- or 6-membered saturated heterocyclic ring containing from 1 to 4 heteroatoms independently selected from N, O and S; or a 5- or 6-membered heteroaromatic ring containing from 1 to 4 heteroatoms independently selected from N, O and S; and wherein the aryl is optionally substituted with from 1 to 3 substituents each of which is independently fluoro, chloro, bromo, —CF$_3$, —C$_{1-4}$ alkyl, —OCF$_3$, or —O—C$_{1-4}$ alkyl; and wherein the saturated heterocyclic ring or heteroaromatic ring is optionally substituted with from 1 to 3 substituents each of which is independently fluoro, chloro, bromo, —CF$_3$, —C$_{1-4}$ alkyl, —OCF$_3$, —O—C$_{1-4}$ alkyl, or oxo;

R$^{15}$ and R$^{16}$ are each independently —C$_{1-6}$ alkyl; or alternatively R$^{15}$ and R$^{16}$ together with the carbon atom to which they are both attached form C$_{3-8}$ cycloalkyl; and Q is phenyl optionally substituted with from 1 to 3 substituents each of which is independently —F, —Cl, —Br, —OH, —C$_{1-4}$ alkyl, —CF$_3$, —O—C$_{1-4}$ alkyl, —OCF$_3$, —CN, —SR$^a$, or —SO$_2$R$^a$; and is additionally and optionally mono-substituted with methylenedioxy attached to two adjacent ring carbon atoms, phenyl, or —O-phenyl;

or a pharmaceutically acceptable salt thereof.

41. The compound according to claim 40, wherein R$^{15}$ and R$^{16}$ are both methyl; or alternatively R$^{15}$ and R$^{16}$ together with the carbon atom to which they are both attached form cyclohexyl;

or a pharmaceutically acceptable salt thereof.

42. A compound selected from the group consisting of
N-(4-fluorobenzyl)-5,6-dihydroxy-2-[1-methyl-1-(methylamino)ethyl]pyrimidine-4-carboxamide;
N-(4-fluorobenzyl)-5,6-dihydroxy-2-(4-methylmorpholin-3-yl)pyrimidine-4-carboxamide;
2-[1-benzoyl-4-(N,N-dimethylglycyl)piperazin-2-yl]-N-(4-fluorobenzyl)-5,6-dihydroxypyrimidine-4-carboxamide;
2-(1-benzoyl-4-methylpiperazin-2-yl)-N-(4-fluorobenzyl)-5,6-dihydroxypyrimidine-4-carboxamide;
N-(4-fluorobenzyl)-5,6-dihydroxy-2-(1-methylpiperidin-2-yl)pyrimidine-4-carboxamide;
N-(4-fluorobenzyl)-5,6-dihydroxy-2-[1-(pyridin-2-ylcarbonyl)-1,2,3,4-tetrahydroquinolin-2-yl]pyrimidine-4-carboxamide;
N-(4-fluorobenzyl)-5,6-dihydroxy-2-[4-methyl-1-(pyridin-2-ylcarbonyl)piperazin-2-yl]pyrimidine-4-carboxamide;
N-(4-fluorobenzyl)-5,6-dihydroxy-2-[1-methyl-4-(pyridin-2-ylcarbonyl)piperazin-2-yl]pyrimidine-4-carboxamide;
2-(1-ethylpiperidin-2-yl)-N-(4-fluorobenzyl)-5,6-dihydroxypyrimdine-4-carboxamide;
N-(4-fluorobenzyl)-5,6-dihydroxy-2-(4-isopropyl-1-methylpiperazin-2-yl)pyrimidine-4-carboxamide;
2-[1-(acetylamino)cyclohexyl]-N-(4-fluorobenzyl)-5,6-dihydroxypyrimidine-4-carboxamide;
N-(4-fluorobenzyl)-5,6-dihydroxy-2-[1-(morpholin-4-ylacetyl)piperidin-2-yl]pyrimidine-4-carboxamide;
N-(4-fluorobenzyl)-5,6-dihydroxy-2-(pyrrolidin-1-ylmethyl)pyrimidine-4-carboxamide;
N-(4-fluorobenzyl)-5,6-dihydroxy-2-(1-methylpyrrolidin-2-yl)pyrimidine-4-carboxamide;
2-[1-(N,N-dimethylglycyl)piperidin-2-yl]-N-(4-fluorobenzyl)-5,6-dihydroxypyrimidine-4-carboxamide;
N-(4-fluorobenzyl)-5,6-dihydroxy-2-{1-methyl-1-[(pyridin-2-lcarbonyl)amino]ethyl}pyrimidine-4-carboxamide;
2-[1-(dimethylamino)-2-phenylethyl]-N-(4-fluorobenzyl)-5,6-dihydroxypyrimidine-4-carboxamide;
2-{1-[(2,4-dimethyl-1,3-thiazol-5-yl)carbonyl]piperidin-2-yl}-N-(4-fluorobenzyl)-5,6-dihydroxypyrimidine-4-carboxamide;
2-[1-(3-chlorobenzoyl)-4-methylpiperazin-2-yl]-N-(4-fluorobenzyl)-5,6-dihydroxypyrimidine-4-carboxamide;
N-(4-fluorobenzyl)-5,6-dihydroxy-2-[1-methyl-4-(methylsulfonyl)piperazin-2-yl]pyrimidine-4-carboxamide;
N-(4-fluorobenzyl)-5,6-dihydroxy-2-(1-isopropyl-4-methylpiperazin-2-yl)pyrimidine-4-carboxamide;
N-(3-bromo-4-fluorobenzyl)-2-[1-(dimethylamino)-1-methylethyl]-5,6-dihydroxypyrimidine-4-carboxamide;

2-[1-(dimethylamino)cyclohexyl]-N-(4-fluorobenzyl)-5,6-dihydroxypyrimidine-4-carboxamide;
N-(4-fluorobenzyl)-5,6-dihydroxy-2-{1-[(pyridin-2-ylcarbonyl)amino]cyclohexyl}pyrimidine-4-carboxamide;
2-(4-benzyl-1-methylpiperazin-2-yl)-N-(4-fluorobenzyl)-5,6-dihydroxypyrimidine-4-carboxamide;
N-(2,3-dimethoxybenzyl)-5,6-dihydroxy-2-[4-(1-piperidin-1-ylethyl)phenyl]pyrimidine-4-carboxamide;
N-(4-fluorobenzyl)-5,6-dihydroxy-2-(2-methyl-1,2,3,4-tetrahydroisoquinolin-3-yl)pyrimidine-4-carboxamide;
N-(2,3-dimethoxybenzyl)-2-[1-(N,N-dimethylglycyl)piperidin-2-yl]-5,6-dihydroxypyrimidine-4-carboxamide;
2-[1-(anilinocarbonyl)piperidin-2-yl]-N-(4-fluorobenzyl)-5,6-dihydroxypyrimidine-4-carboxamide;
2-[(2S,4R)-1-benzoyl-4-(benzyloxy)pyrrolidin-2-yl]-N-(4-fluorobenzyl)-5,6-dihydroxypyrimidine-4-carboxamide;
N-(4-fluorobenzyl)-5,6-dihydroxy-2-[1-(pyridin-2-ylcarbonyl)piperidin-2-yl]pyrimidine-4-carboxamide;
N-(4-fluorobenzyl)-5,6-dihydroxy-2-[2-(morpholin-4-ylacetyl)-1,2,3,4-tetrahydroisoquinolin-3-yl]pyrimidine-4-carboxamide;
N-(4-fluorobenzyl)-5,6-dihydroxy-2-{2-phenyl-1-[(pyridin-2-lcarbonyl)amino]ethyl}pyrimidine-4-carboxamide;
2-(1-benzoylpiperidin-2-yl)-N-(4-fluorobenzyl)-5,6-dihydroxypyrimidine-4-carboxamide;
2-(1-benzylpiperidin-2-yl)-N-(4-fluorobenzyl)-5,6-dihydroxypyrimidine-4-carboxamide;
2-(1-benzoylpyrrolidin-2-yl)-N-(4-fluorobenzyl)-5,6-hydroxypyrimidine-4-carboxamide;
N-(4-fluorobenzyl)-5,6-dihydroxy-2-(1-isonicotinoylpiperidin-2-yl)pyrimidine-4-carboxamide;
N-(2,3-dimethoxybenzyl)-5,6-dihydroxy-2-(1-isonicotinoylpiperidin-2-yl)pyrimidine-4-carboxamide;
N-(4-fluorobenzyl)-5,6-dihydroxy-2-[1-(methylsulfonyl)piperidin-2-yl]pyrimidine-4-carboxamide;
2-(1-benzoyl-1,2,3,4-tetrahydroquinolin-2-yl)-N-(4-fluorobenzyl)-5,6-dihydroxypyrimidine-4-carboxamide;
2-{1-[(N,N-dimethylglycyl)amino]-2-phenylethyl}-N-(4-fluorobenzyl)-5,6-dihydroxypyrimidine-4-carboxamide;
N-(2,3-dimethoxybenzyl)-5,6-dihydroxy-2-[4-(piperidin-1-ylmethyl)phenyl]pyrimidine-4-carboxamide;
2-{4-[(diethylamino)methyl]phenyl}-N-(2,3-dimethoxybenzyl)-5,6-dihydroxypyrimidine-4-carboxamide;
N-(4-fluorobenzyl)-5,6-dihydroxy-2-[1-(pyridin-4-ylmethyl)piperidin-2-yl]pyrimidine-4-carboxamide;
2-(1-benzoylpyrrolidin-2-yl)-N-(2,3-dimethoxybenzyl)-5,6-dihydroxypyrimidine-4-carboxamide;
tert-butyl 2-(4-{[(4-fluorobenzyl)amino]carbonyl}-5,6-dihydroxypyrimidin-2-yl)morpholine-4-carboxylate;
N-(4-fluorobenzyl)-5,6-dihydroxy-2-[1-(pyridin-3-ylcarbonyl)piperidin-2-yl]pyrimidine-4-carboxamide;
2-[2-(N,N-dimethylglycyl)-1,2,3,4-tetrahydroisoquinolin-3-yl]-N-(4-fluorobenzyl)-5,6-dihydroxypyrimidine-4-carboxamide;
2-(1-benzoyl-2,3-dihydro-1H-indol-2-yl)-N-(4-fluorobenzyl)-5,6-dihydroxypyrimidine-4-carboxamide;
2-(2-benzoyl-1,2,3,4-tetrahydroisoquinolin-3-yl)-N-(4-fluorobenzyl)-5,6-dihydroxypyrimidine-4-carboxamide;
2-(1-amino-2-phenylethyl)-N-(4-fluorobenzyl)-5,6-dihydroxypyrimidine-4-carboxamide;
2-(4-benzylmorpholin-3-yl)-N-(4-fluorobenzyl)-5,6-dihydroxypyrimidine-4-carboxamide;
N-(4-fluorobenzyl)-5,6-dihydroxy-2-{1-[(1-methyl-1H-imidazol-2-yl)carbonyl]piperidin-2-yl}pyrimidine-4-carboxamide;
N-(2,3-dimethoxybenzyl)-5,6-dihydroxy-2-[4-(morpholin-4-ylmethyl)phenyl]pyrimidine-4-carboxamide;
N-(4-fluorobenzyl)-5,6-dihydroxy-2-(morpholin-4-ylmethyl)pyrimidine-4-carboxamide;
N-(4-Fluorobenzyl)-5,6-dihydroxypyrimidine-4-carboxamide;
2-{4-[({[(2-chlorophenyl)sulfonyl]amino}carbonyl)amino]thien-3-yl}-N-(2,3-dimethoxybenzyl)-5,6-dihydroxypyrimidine-4 carboxamide;
$N^4$-(4-fluorobenzyl)-5,6-dihydroxy-$N^2$-(pyridin-2-ylmethyl)pyrimidine-2,4-dicarboxamide;
2-Benzyl-N-(4-fluorobenzyl)-5-hydroxy-6-(2-morpholin-4-ylethoxy)pyrimidine-4-carboxamide;
and pharmaceutically acceptable salts thereof.

43. A compound according to claim 42, which is a compound selected from the group consisting of
N-(4-fluorobenzyl)-5,6-dihydroxy-2-(1-methylpiperidin-2-yl)pyrimidine-4-carboxamide;
2-[1-(dimethylamino)-1-methylethyl]-N-(4-fluorobenzyl)-5,6-dihydroxypyrimidine-4-carboxamide;
N-(4-fluorobenzyl)-5,6-dihydroxy-2-(4-methylmorpholin-3-yl)pyrimidine-4-carboxamide;
2-[(dimethylamino)(phenyl)methyl]-N-(4-fluorobenzyl)-5,6-dihydroxypyrimidine-4-carboxamide;
2-{4-[(diethylamino)methyl]phenyl}-N-(2,3-dimethoxybenzyl)-5,6-dihydroxypyrimidine-4-carboxamide;
N-benzyl-5,6-dihydroxy-2-(3-phenylpropyl)pyrimidine-4-carboxamide;
N-(4-fluorobenzyl)-5,6-dihydroxy-2-[1-(pyridin-2-ylcarbonyl)-1,2,3,4-tetrahydroquinolin-2-yl]pyrimidine-4-carboxamide;
and pharmaceutically acceptable salts thereof.

44. A compound selected from the group consisting of
benzyl 1-[4-({[4-fluoro-2-(methylsulfonyl)benzyl]amino}carbonyl)-5,6-dihydroxypyrimidin-2-yl]-1-methylethylcarbamate;
2-(1-amino-1-methylethyl)-N-[4-fluoro-2-(methylsulfonyl)benzyl]-5,6-dihydroxypyrimidine-4-carboxamide;
2-[1-(dimethylamino)-1-methylethyl]-N-[4-fluoro-2-(methylsulfonyl)benzyl]-5,6-dihydroxypyrimidine-4-carboxamide;
2-(1-aminocyclopropyl)-N-(4-fluorobenzyl)-5,6-dihydroxypyrimidine-4-carboxamide;
2-[1-(dimethylamino)cyclopropyl]-N-(4-fluorobenzyl)-5,6-dihydroxypyrine-4-carboxamide;
N-(4-fluorobenzyl)-5,6-dihydroxy-2-{1-[(pyrazin-2-ylcarbonyl)amino]cyclopropyl}pyrimidine-4-carboxamide;
benzyl 1-(4-{[(4-fluorobenzyl)amino]carbonyl}-5,6-dihydroxypyrimidin-2-yl)cyclopentylcarbamate;
2-(1-aminocyclopentyl)-N-(4-fluorobenzyl)-5,6-dihydroxypyrimidine-4-carboxamide;
2-[1-(dimethylamino)cyclopentyl]-N-(4-fluorobenzyl)-5,6-dihydroxypyrimidine-4-carboxamide;
2-(1-{[(ethylamino)carbonyl]amino}-1-methylethyl)-N-(4-fluorobenzyl)-5,6-dihydroxypyrimidine-4-carboxamide;
2-[1-(benzylamino)-1-methylethyl]-N-(4-fluorobenzyl)-5,6-dihydroxypyrimidine-4-carboxamide;
2-[1-(benzoylamino)-1-methylethyl]-N-(4-fluorobenzyl)-5,6-dihydroxypyrimidine-4-carboxamide;
2-{1-[benzyl(methyl)amino]-1-methylethyl}-N-(4-fluorobenzyl)-5,6-dihydroxypyrimdine-4-carboxamide;

2-[1-(dimethylamino)-1-methylethyl]-N-(2-ethoxybenzyl)-5,6-dihydroxypyrimidine-4-carboxamide;
N-(2-chlorobenzyl)-2-[1-(dimethylamino)-1-methylethyl]-5,6-dihydroxypyrimidine-4-carboxamide;
N-(2-chlorobenzyl)-2-[1-(dimethylamino)-1-methylethyl]-5,6-dihydroxypyrimidine-4-carboxamide;
N-(5-chloro-2-methylbenzyl)-2-[1-(dimethylamino)-1-methylethyl]-5,6-dihydroxypyrimidine-4-carboxamide;
N-(4-fluorobenzyl)-5,6-dihydroxy-2-{1-methyl-1-[(pyrazin-2-ylcarbonyl)amino]ethyl}pyrimidine-4-carboxamide;
2-[1-(diethylamino)-1-methylethyl]-N-(4-fluorobenzyl)-5,6-dihydroxypyrimidine-4-carboxamide;
N-(4-fluorobenzyl)-5,6-dihydroxy-2-(1-methyl-1-morpholin-4-ylethyl)pyrimidine-4-carboxamide;
N-(4-fluorobenzyl)-5,6-dihydroxy-2-(1-methyl-1-piperidin-1-ylethyl)pyrimidine-4-carboxamide;
N-(4-fluorobenzyl)-5,6-dihydroxy-2-(1-methyl-1-pyrrolidin-1-ylethyl)pyrimidine-4-carboxamide;
N-(4-fluorobenzyl)-5,6-dihydroxy-2-{1-methyl-1-[methyl(pyridin-4-ylmethyl)amino]ethyl}pyrimidine-4-carboxamide;
2-[1-(dimethylamino)-1-methylethyl]-5,6-dihydroxy-N-[2-(methylthio)benzyl]pyrimidine-4-carboxamide;
$N^1,N^1$-diethyl-$N^2$-[1-(4-{[(4-fluorobenzyl)amino]carbonyl}-5,6-dihydroxypyrimidin-2-yl)-1-methylethyl]ethanediamide;
2-[1-(1,4-dioxa-8-azaspiro[4.5]dec-8-yl)-1-methylethyl]-N-(4-fluorobenzyl)-5,6-dihydroxypyrimidine-4-carboxamide;
N-(4-fluorobenzyl)-5,6-dihydroxy-2-(1-methyl-1-{[(1-methyl-1H-imidazol-2-yl)carbonyl]amino}ethyl)pyrimidine-4-carboxamide;
N-(4-fluorobenzyl)-5,6-dihydroxy-2-[1-methyl-1-(4-oxopiperidin-1-yl)ethyl]pyrimidine-4-carboxamide;
N-(4-fluorobenzyl)-5,6-dihydroxy-2-{1-methyl-1-[methyl(pyridin-2-ylmethyl)amino]ethyl}pyrimidine-4-carboxamide;
N-[1-(4-{[(4-fluorobenzyl)amino]carbonyl}-5,6-dihydroxypyrimidin-2-yl)-1-methylethyl]-4-methylmorpholine-2-carboxamide;
2-{1-[acetyl(methyl)amino]-1-methylethyl}-N-(4-fluorobenzyl)-5,6-dihydroxypyrimidine-4-carboxamide;
2-[1-(acetylamino)-1-methylethyl]-N-(4-fluorobenzyl)-5,6-dihydroxypyrimidine-4-carboxamide;
2-{1-[4-(dimethylamino)piperidin-1-yl]-1-methylethyl}-N-(4-fluorobenzyl)-5,6-dihydroxypyrimidine-4-carboxamide;
N-(2,3-dimethoxybenzyl)-2-[1-(dimethylamino)-1-methylethyl]-5,6-dihydroxypyrimidine-4-carboxamide;
2-[4-(dimethylamino)tetrahydro-2H-pyran-4-yl]-N-(4-fluorobenzyl)-5,6-dihydroxypyrimidine-4-carboxamide;
N-(4-fluorobenzyl)-5,6-dihydroxy-2-(7-methyl-7-azabicyclo[2.2.1]hept-1-yl)pyrimidine-4-carboxamide;
2-(7-acetyl-7-azabicyclo[2.2.1]hept-1-yl)-N-(4-fluorobenzyl)-5,6-dihydroxypyrimidine-4-carboxamide;
2-(2-acetyl-2-azabicyclo[2.1.1]hex-1-yl)-N-(4-fluorobenzyl)-5,6-dihydroxypyrimidine-4-carboxamide;
N-(4-fluorobenzyl)-5,6-dihydroxy-2-(2-methyl-2-azabicyclo[2.1.1]hex-1-yl)pyrimidine-4-carboxamide;
tert-butyl (2S,4R)-4-(benzyloxy)-2-(4-{[(4-fluorobenzyl)amino]carbonyl}-5,6-dihydroxypyrimidin-2-yl)piperidine-1-carboxylate;
2-[(2S,4R)-4-(benzyloxy)piperidin-2-yl]-N-(4-fluorobenzyl)-5,6-dihydroxypyrimidine-4-carboxamide;
2-[(2S,4R)-4-(benzyloxy)-1-methylpiperidin-2-yl]-N-(4-fluorobenzyl)-5,6-dihydroxypyrimdine-4-carboxamide;
N-(4-fluorobenzyl)-5,6-dihydroxy-2-[(2S,4R)-4-hydroxy-1-methylpiperidin-2-yl]pyrimidine-4-carboxamide;
2-[1-acetyl-4-(benzyloxy)piperidin-2-yl]-N-(4-fluorobenzyl)-5,6-dihydroxypyrimidine-4-carboxamide;
2-(1-ethyl-4-methylpiperazin-2-yl)-N-(4-fluorobenzyl)-5,6-dihydroxypyrimidine-4-carboxamide;
N-(4-fluorobenzyl)-5,6-dihydroxy-2-[4-methyl-1-(pyrazin-2-ylcarbonyl)piperazin-2-yl]pyrimidine-4-carboxamide;
tert-butyl 3-(4-{[(4-fluorobenzyl)amino]carbonyl}-5,6-dihydroxypyrimidin-2-yl)thiomorpholine-4-carboxylate;
N-(4-fluorobenzyl)-5,6-dihydroxy-2-thiomorpholin-3-ylpyrimidine-4-carboxamide;
N-(4-fluorobenzyl)-5,6-dihydroxy-2-(4-methylthiomorpholin-3-yl)pyrimidine-4-carboxamide;
N-(4-fluorobenzyl)-5,6-dihydroxy-2-[4-(pyridin-2-ylcarbonyl)thiomorpholin-3-yl]pyrimidine-4-carboxamide;
2-(4-acetylthiomorpholin-3-yl)-N-(4-fluorobenzyl)-5,6-dihydroxypyrimidine-4-carboxamide;
tert-butyl 1-(4-{[(4-fluorobenzyl)amino]carbonyl}-5,6-dihydroxypyrimidin-2-yl)-2-methoxyethylcarbamate;
2-[1-(dimethylamino)-2-methoxyethyl]-N-(4-fluorobenzyl)-5,6-dihydroxypyrimidine-4-carboxamide;
2-[1-(acetylamino)-2-methoxyethyl]-N-(4-fluorobenzyl)-5,6-dihydroxypyrimidine-4-carboxamide;
2-(1-amino-2-methoxyethyl)-N-(4-fluorobenzyl)-5,6-dihydroxypyrimidine-4-carboxamide;
N-(4-fluorobenzyl)-5,6-dihydroxy-2-{2-methoxy-1-[(pyridin-2-ylcarbonyl)amino]ethyl}pyrimidine-4-carboxamide;
N-(4-fluorobenzyl)-2-[1-(formylamino)-2-methoxyethyl]-5,6-dihydroxypyrimidine-4-carboxamide;
N-(4-fluorobenzyl)-5,6-dihydroxy-2-[2-methoxy-1-(methylamino)ethyl]pyrimidine-4-carboxamide;
2-{1-[acetyl(methyl)amino]-2-methoxyethyl}-N-(4-fluorobenzyl)-5,6-dihydroxypyrimidine-4-carboxamide;
N-(4-fluorobenzyl)-5,6-dihydroxy-2-{2-methoxy-1-[methyl(pyridin-2-ylcarbonyl)amino]ethyl}pyrimidine-4-carboxamide;
N-(4-fluorobenzyl)-5,6-dihydroxy-2-[(4R)-3-(pyridin-2-ylcarbonyl)-1,3-thiazolidin-4-yl]pyrimidine-4-carboxamide;
N-(4-fluorobenzyl)-5,6-dihydroxy-2-[(4R)-1,3-thiazolidin-4-yl]pyrimidine-4-carboxamide;
N-(4-fluorobenzyl)-5,6-dihydroxy-2-[(4R)-3-methyl-1,3-thiazolidin4-yl]pyrimidine-4-carboxamide;
2-(3-acetyl-1,3-thiazolidin-2-yl)-N-(4-fluorobenzyl)-5,6-dihydroxypyrimidine-4-carboxamide;
N-(4-fluorobenzyl)-5,6-dihydroxy-2-(3-methyl-1,3-thiazolidin-2-yl)pyrimidine-4-carboxamide;
N-(4-fluorobenzyl)-5,6-dihydroxy-2-(1,2,4-trimethylpiperazin-2-yl)pyrimidine-4-carboxamide;
2-[2,4-methyl-1-(pyrazin-2-ylcarbonyl)piperazin-2-yl]-N-(4-fluorobenzyl)-5,6-dihydroxypyrimidine-4-carboxamide;
2-(1-acetyl-2,4-dimethylpiperazin-2-yl)-N-(4-fluorobenzyl)-5,6-dihydroxypyrimidine-4-carboxamide;
tert-butyl 1-(4-{[(4-fluorobenzyl)amino]carbonyl}-5,6-dihydroxypyrimidin-2-yl)-2-methoxy-1-methylethylcarbamate;
2-(1-amino-2-methoxy-1-methylethyl)-N-(4-fluorobenzyl)-5,6-dihydroxypyrimidine-4-carboxamide;

2-[1-(acetylamino)-2-methoxy-1-methylethyl]-N-(4-fluorobenzyl)-5,6-dihydroxypyrimidine-4-carboxamide;

2-[1-(dimethylamino)-2-methoxy-1-methylethyl]-N-(4-fluorobenzyl)-5,6-dihydroxypyrimidine-4-carboxamide;

N-(4-fluorobenzyl)-5,6-dihydroxy-2-[2-methoxy-1-methyl-1-(methylamino)ethyl]pyrimidine-4-carboxamide;

N-(4-fluorobenzyl)-5,6-dihydroxy-2-{2-methoxy-1-methyl-1-[(pyridin-2-ylcarbonyl)amino]ethyl}pyrimidine-4-carboxamide;

2-(1,2-dimethylpiperidin-2-yl)-N-(4-fluorobenzyl)-5,6-dihydroxypyrimidine-4-carboxamide;

2-{1-[acetyl(methyl)amino]-2-methoxy-1-methylethyl}-N-(4-fluorobenzyl)-5,6-dihydroxypyrimidine-4-carboxamide;

N-(4-fluorobenzyl)-5,6-dihydroxy-2-{2-methoxy-1-methyl-1-[methyl(pyridin-2-ylcarbonyl)amino]ethyl}pyrimidine-4-carboxamide;

2-{1-[(cyclohexylmethyl)(methyl)amino]-2-methoxy-1-methylethyl}-N-(4-fluorobenzyl)-5,6-dihydroxypyrimidine-4-carboxamide;

2-{1-[(cyclohexylmethyl)amino]-2-methoxy-1-methylethyl}-N-(4-fluorobenzyl)-5,6-dihydroxypyrimidine-4-carboxamide;

2-{1-[(cyclohexylmethyl)amino]-2-methoxy-1-methylethyl}-N-(4-fluorobenzyl)-5,6-dihydroxypyrimidine-4-carboxamide;

2-(4-acetyl-1,2-dimethylpiperazin-2-yl)-N-(4-fluorobenzyl)-5,6-dihydroxypyrimidine-4-carboxamide;

2-(1-acetyl-2-methylpiperidin-2-yl)-N-(4-fluorobenzyl)-5,6-dihydroxypyrimidine-4-carboxamide;

N-(4-fluorobenzyl)-5,6-dihydroxy-2-[2-methyl-1-(pyrazin-2-ylcarbonyl)piperidin-2-yl]pyrimidine-4-carboxamide;

N-(2,3-dimethoxybenzyl)-2-(1,2-dimethylpiperidin-2-yl-)-5,6-dihydroxypyrimidine-4-carboxamide;

N-(4-fluorobenzyl)-5,6-dihydroxy-2-[2-methyl-1-(pyridin-2-ylcarbonyl)piperidin-2-yl]pyrimidine-4-carboxamide;

2-{1-[(2,4-dimethyl-1,3-thiazol-5-yl)carbonyl]-2-methylpiperidin-2-yl}-N-(4-fluorobenzyl)-5,6-dihydroxypyrimidine-4-carboxamide;

2-[(2S)-1-acetyl-2-methylpyrrolidin-2-yl]-N-(4-fluorobenzyl)-5,6-dihydroxypyrimidine-4-carboxamide;

and pharmaceutically acceptable salts thereof.

45. A pharmaceutical composition comprising a therapeutically effective amount of a compound according to claim 1, or a pharmaceutically acceptable salt thereof, and a pharmaceutically acceptable carrier.

46. A pharmaceutical composition which comprises the product prepared by combining an effective amount of a compound according to claim 1, or a pharmaceutically acceptable salt thereof, and a pharmaceutically acceptable carrier.

\* \* \* \* \*